United States Patent
KC et al.

(10) Patent No.: US 10,526,347 B2
(45) Date of Patent: *Jan. 7, 2020

(54) 3-(3H-IMIDAZO[4,5-B]PYRIDIN-2-YL)-1H-PYRAZOLO[3,4-B]PYRIDINE AND THERAPEUTIC USES THEREOF

(71) Applicant: Samumed, LLC, San Diego, CA (US)

(72) Inventors: Sunil Kumar KC, San Diego, CA (US); David Mark Wallace, San Diego, CA (US); Jianguo Cao, San Diego, CA (US); Chandramouli Chiruta, San Diego, CA (US); John Hood, San Diego, CA (US)

(73) Assignee: Samumed, LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/162,155

(22) Filed: Oct. 16, 2018

(65) Prior Publication Data

US 2019/0119303 A1 Apr. 25, 2019

Related U.S. Application Data

(63) Continuation of application No. 15/668,992, filed on Aug. 4, 2017, now Pat. No. 10,131,677, which is a continuation of application No. 14/847,379, filed on Sep. 8, 2015, now Pat. No. 9,758,531.

(60) Provisional application No. 62/051,567, filed on Sep. 17, 2014, provisional application No. 62/047,575, filed on Sep. 8, 2014.

(51) Int. Cl.
*A61K 31/437* (2006.01)
*C07D 519/00* (2006.01)

(52) U.S. Cl.
CPC .................................. *C07D 519/00* (2013.01)

(58) Field of Classification Search
CPC .......................... C07D 401/14; A61K 31/437
USPC ......................................... 514/303; 546/119
See application file for complete search history.

(56) References Cited

U.S. PATENT DOCUMENTS

| | | | |
|---|---|---|---|
| 4,164,559 A | 8/1979 | Miyata et al. | |
| 4,474,752 A | 10/1984 | Haslam et al. | |
| 4,603,139 A | 7/1986 | King | |
| 5,922,733 A | 7/1999 | Forbes et al. | |
| 6,120,484 A | 9/2000 | Silverstein | |
| 6,358,978 B1 | 3/2002 | Ritzeler et al. | |
| 6,377,849 B1 | 4/2002 | Lenarz et al. | |
| 6,440,102 B1 | 8/2002 | Arenberg et al. | |
| 6,555,539 B2 | 4/2003 | Reich et al. | |
| 6,648,873 B2 | 11/2003 | Arenberg et al. | |
| 6,831,175 B2 | 12/2004 | Li et al. | |
| 6,884,890 B2 | 4/2005 | Kania et al. | |
| 6,897,208 B2 | 5/2005 | Edwards et al. | |
| 6,911,211 B2 | 6/2005 | Eini et al. | |
| 6,919,461 B2 | 7/2005 | Reich et al. | |
| 7,008,953 B2 | 3/2006 | Kephart et al. | |
| 7,064,215 B2 | 6/2006 | Renhowe et al. | |
| 7,232,912 B2 | 6/2007 | Reich et al. | |
| 7,285,565 B2 | 10/2007 | Zhu et al. | |
| 7,390,815 B2 | 6/2008 | Davies et al. | |
| 7,429,609 B2 | 9/2008 | Ohi et al. | |
| 7,452,993 B2 | 11/2008 | Arnold et al. | |
| 7,468,376 B2 | 12/2008 | Rosales et al. | |
| 7,482,342 B2 | 1/2009 | D'Orchymont et al. | |
| 7,488,737 B2 | 2/2009 | Xie et al. | |
| 7,491,710 B2 | 2/2009 | Cherrier et al. | |
| 7,541,367 B2 | 6/2009 | Chin et al. | |
| 7,626,021 B2 | 12/2009 | Arnold et al. | |
| 7,642,278 B2 | 1/2010 | Jansen et al. | |
| 7,666,867 B2 | 2/2010 | Makriyannis et al. | |
| 7,812,043 B2 | 10/2010 | Lau et al. | |
| 7,829,558 B2 | 11/2010 | Arnold et al. | |
| 7,842,711 B2 | 11/2010 | D'Orchymont et al. | |
| 7,902,217 B2 | 3/2011 | Xie et al. | |
| 7,943,616 B2 | 5/2011 | Cox et al. | |
| 8,008,481 B2 | 8/2011 | Ericsson et al. | |
| 8,088,772 B2 | 1/2012 | Garcia et al. | |
| 8,129,519 B2 | 3/2012 | Cholody et al. | |

(Continued)

FOREIGN PATENT DOCUMENTS

| | | |
|---|---|---|
| CN | 1394205 | 1/2003 |
| CN | 1671710 | 9/2005 |

(Continued)

OTHER PUBLICATIONS

"Application of Hamish Christopher Swan Wood, Norman Whittaker, Irene Stirling and Kyuji Ohta.," 582 F.2d 638 (Fed. Cir. 1978), 2 pages.
Adaimy et al., "Mutation in WNT10A Is Associated with an Autosomal Recessive Ectodermal Dysplasia: The Odonto-onychodermal Dysplasia," *Am. J. Hum. Genet.*, (Oct. 2007), 81(4), 821-828.
Anastas and Moon, "WNT signalling pathways as therapeutic targets in cancer," *Nat Rev Cancer*, 13(1):11-26, Jan. 2013.
Andres, "Molecular genetics and animal models in autistic disorder," *Brain Research Bulletin*, (2002), 57(1), 109-119.
Barker and Clevers, "Mining the Wnt pathway for cancer therapeutics," *Nat Rev Drug Discov.*, 5(12):997-1014, Dec. 2006.

(Continued)

*Primary Examiner* — Niloofar Rahmani
(74) *Attorney, Agent, or Firm* — Fish & Richardson P.C.

(57) ABSTRACT

Azaindazole compounds for treating various diseases and pathologies are disclosed. More particularly, the present invention concerns the use of an azaindazole compound or analogs thereof, in the treatment of disorders characterized by the activation of Wnt pathway signaling (e.g., cancer, abnormal cellular proliferation, angiogenesis, fibrotic disorders, bone or cartilage diseases, and osteoarthritis), the modulation of cellular events mediated by Wnt pathway signaling, as well as genetic diseases and neurological conditions/disorders/diseases due to mutations or dysregulation of the Wnt pathway and/or of one or more of Wnt signaling components. Also provided are methods for treating Wnt-related disease states.

34 Claims, No Drawings

(56) References Cited

U.S. PATENT DOCUMENTS

| | | |
|---|---|---|
| 8,158,647 B2 | 4/2012 | Blaney et al. |
| 8,252,812 B2 | 8/2012 | Hood et al. |
| 8,288,425 B2 | 10/2012 | Edwards et al. |
| 8,304,408 B2 | 11/2012 | Wrasidlo et al. |
| 8,450,340 B2 * | 5/2013 | Hood .................. A61K 31/415 514/300 |
| 8,604,052 B2 | 12/2013 | Hood et al. |
| 8,618,128 B1 | 12/2013 | Hood et al. |
| 8,637,508 B2 | 1/2014 | Badiger et al. |
| 8,664,241 B2 | 3/2014 | Hood et al. |
| 8,673,936 B2 | 3/2014 | Hood et al. |
| 8,697,887 B2 | 4/2014 | Hood et al. |
| 8,703,794 B2 | 4/2014 | Hood et al. |
| 8,815,897 B2 * | 8/2014 | Hood .................. A61K 31/415 514/303 |
| 8,822,478 B2 | 9/2014 | Hood et al. |
| 8,846,714 B2 * | 9/2014 | Hood .................. A61K 31/415 514/303 |
| 8,883,822 B2 | 11/2014 | Hood et al. |
| 8,901,150 B2 * | 12/2014 | Hood .................. A61K 31/415 514/300 |
| 8,987,298 B2 | 3/2015 | Hood et al. |
| 9,012,472 B2 | 4/2015 | Hood et al. |
| 9,056,874 B2 | 6/2015 | Adams et al. |
| 9,067,939 B2 * | 6/2015 | Hood .................. A61K 31/415 |
| 9,090,613 B2 | 7/2015 | Hood et al. |
| 9,174,967 B2 | 11/2015 | Körber et al. |
| 9,199,991 B2 | 12/2015 | Hood et al. |
| 9,221,793 B2 | 12/2015 | Hood et al. |
| 9,233,104 B2 | 1/2016 | Hood et al. |
| 9,381,192 B2 | 7/2016 | Hood et al. |
| 9,538,272 B2 | 1/2017 | Auclair et al. |
| 9,586,977 B2 | 3/2017 | Hood et al. |
| 9,745,271 B2 | 8/2017 | Hood et al. |
| 9,763,927 B2 | 9/2017 | Hood et al. |
| 9,763,951 B2 | 9/2017 | Kumar KC et al. |
| 9,802,916 B2 | 10/2017 | Hood et al. |
| 9,815,854 B2 | 11/2017 | Kumar KC et al. |
| 9,828,372 B2 | 11/2017 | Kumar KC et al. |
| 9,844,536 B2 | 12/2017 | Kumar KC et al. |
| 9,855,272 B2 | 1/2018 | Hood et al. |
| 10,131,677 B2 * | 11/2018 | KC ....................... C07D 519/00 |
| 2002/0103229 A1 | 8/2002 | Bhagwat et al. |
| 2002/0161022 A1 | 10/2002 | Reich et al. |
| 2003/0199516 A1 | 10/2003 | Moser et al. |
| 2004/0048868 A1 | 3/2004 | Edwards et al. |
| 2004/0077681 A1 | 4/2004 | Rawlings et al. |
| 2004/0176325 A1 | 9/2004 | Munson et al. |
| 2004/0236101 A1 | 11/2004 | Makriyannis et al. |
| 2005/0009894 A1 | 1/2005 | Babin et al. |
| 2005/0026960 A1 | 2/2005 | Kephart et al. |
| 2005/0090529 A1 | 4/2005 | McAlpine et al. |
| 2005/0192262 A1 | 9/2005 | Hagstrom et al. |
| 2005/0208582 A1 | 9/2005 | Ohi et al. |
| 2005/0261339 A1 | 11/2005 | Ohi et al. |
| 2006/0004000 A1 | 1/2006 | D'Orchymont et al. |
| 2006/0014756 A1 | 1/2006 | Edwards et al. |
| 2006/0079564 A1 | 4/2006 | Jansen et al. |
| 2006/0094706 A1 | 5/2006 | Paruch et al. |
| 2006/0111322 A1 | 5/2006 | Reich et al. |
| 2006/0116519 A1 | 6/2006 | Ma et al. |
| 2006/0135589 A1 | 6/2006 | Berdino et al. |
| 2006/0142345 A1 | 6/2006 | Kephart et al. |
| 2006/0167056 A1 | 7/2006 | Rynberg et al. |
| 2006/0264897 A1 | 11/2006 | Lobl |
| 2007/0027140 A1 | 2/2007 | Lau et al. |
| 2007/0049598 A1 | 3/2007 | Billedeau et al. |
| 2007/0060616 A1 | 3/2007 | Bennett et al. |
| 2007/0078147 A1 | 4/2007 | Schumacher et al. |
| 2007/0185187 A1 | 8/2007 | D'Orchymont et al. |
| 2007/0219257 A1 | 9/2007 | Beachy et al. |
| 2007/0282101 A1 | 12/2007 | Ericsson et al. |
| 2008/0004270 A1 | 1/2008 | Gill et al. |
| 2008/0255085 A1 | 10/2008 | Arvidsson et al. |
| 2008/0262205 A1 | 10/2008 | Haar et al. |
| 2008/0287452 A1 | 11/2008 | Bursavich et al. |
| 2009/0005356 A1 | 1/2009 | Blaney et al. |
| 2009/0005377 A1 | 1/2009 | Almansa Rosales et al. |
| 2009/0048249 A1 | 2/2009 | Chiu et al. |
| 2009/0054397 A1 | 2/2009 | Ohi et al. |
| 2009/0099062 A1 | 4/2009 | Lee et al. |
| 2009/0203690 A1 | 8/2009 | Akritopoulou-Zanze et al. |
| 2009/0247504 A1 | 10/2009 | Churcher et al. |
| 2009/0264446 A9 | 10/2009 | Rosales et al. |
| 2009/0286983 A1 | 11/2009 | Almansa Rosales et al. |
| 2010/0298377 A1 | 11/2010 | Aletru et al. |
| 2011/0009353 A1 | 1/2011 | Chen-Kiang et al. |
| 2011/0021467 A1 | 1/2011 | D'Orchymont et al. |
| 2011/0034441 A1 | 2/2011 | Hood et al. |
| 2011/0082144 A1 | 4/2011 | Lau et al. |
| 2011/0178075 A1 | 7/2011 | Xie et al. |
| 2012/0053345 A1 | 3/2012 | Ericson et al. |
| 2012/0059047 A1 | 3/2012 | Prins et al. |
| 2012/0129837 A1 | 5/2012 | Cholody et al. |
| 2012/0277229 A1 | 11/2012 | Bearss et al. |
| 2013/0039906 A1 | 2/2013 | Do et al. |
| 2013/0267548 A1 | 10/2013 | Follmann et al. |
| 2014/0194441 A1 | 7/2014 | Kumar KC et al. |
| 2015/0087687 A1 | 3/2015 | Brown et al. |
| 2016/0068529 A1 | 3/2016 | KC et al. |
| 2016/0068547 A1 | 3/2016 | KC et al. |
| 2016/0068548 A1 | 3/2016 | KC et al. |
| 2016/0068549 A1 | 3/2016 | KC et al. |
| 2016/0068550 A1 | 3/2016 | KC et al. |
| 2016/0068551 A1 | 3/2016 | KC et al. |
| 2016/0075701 A1 | 3/2016 | Kumar KC |
| 2016/0090380 A1 | 3/2016 | Kumar KC |
| 2016/0101092 A1 | 4/2016 | Hood et al. |
| 2016/0297812 A1 | 10/2016 | Hood et al. |
| 2017/0224697 A1 | 8/2017 | Kumar KC et al. |
| 2017/0333409 A1 | 11/2017 | Hood et al. |
| 2017/0349584 A1 | 12/2017 | Kumar KC et al. |
| 2018/0086754 A1 | 3/2018 | Kumar KC et al. |
| 2018/0133199 A1 | 5/2018 | Dellamary |
| 2018/0148444 A1 | 5/2018 | Kumar KC et al. |
| 2018/0318292 A1 | 11/2018 | Hood et al. |
| 2019/0071440 A1 | 3/2019 | Hood et al. |

FOREIGN PATENT DOCUMENTS

| | | |
|---|---|---|
| CN | 1829713 | 9/2006 |
| CN | 101440092 | 5/2009 |
| KZ | 20122 | 1/2010 |
| RU | 2331640 | 8/2008 |
| WO | WO1987005297 | 9/1987 |
| WO | WO1996002537 | 2/1996 |
| WO | WO2001002369 | 1/2001 |
| WO | WO2001053268 | 7/2001 |
| WO | WO2003004488 | 1/2003 |
| WO | WO2003035005 | 5/2003 |
| WO | WO2003035065 | 5/2003 |
| WO | WO2003035644 | 5/2003 |
| WO | WO2003051366 | 6/2003 |
| WO | WO2003070236 | 8/2003 |
| WO | WO2003070706 | 8/2003 |
| WO | WO2003097610 | 11/2003 |
| WO | WO2003101968 | 12/2003 |
| WO | WO2003101993 | 12/2003 |
| WO | WO2004014864 | 2/2004 |
| WO | WO2004031158 | 4/2004 |
| WO | WO2004076450 | 9/2004 |
| WO | WO2005009997 | 2/2005 |
| WO | WO2005012301 | 2/2005 |
| WO | WO2005014554 | 2/2005 |
| WO | WO2005047266 | 5/2005 |
| WO | WO2005049019 | 6/2005 |
| WO | WO2005092890 | 10/2005 |
| WO | WO2005099703 | 10/2005 |
| WO | WO2005110410 | 11/2005 |
| WO | WO2006001894 | 1/2006 |
| WO | WO2006015124 | 2/2006 |
| WO | WO2006024945 | 3/2006 |
| WO | WO2006054143 | 5/2006 |
| WO | WO2006054151 | 5/2006 |

(56) References Cited

FOREIGN PATENT DOCUMENTS

| WO | WO2006063302 | 6/2006 |
|---|---|---|
| WO | WO2006063841 | 6/2006 |
| WO | WO2006130673 | 12/2006 |
| WO | WO2007061360 | 5/2007 |
| WO | WO2007107346 | 9/2007 |
| WO | WO2007117465 | 10/2007 |
| WO | WO2007147874 | 12/2007 |
| WO | WO2008061109 | 5/2008 |
| WO | WO2008071397 | 6/2008 |
| WO | WO2008071398 | 6/2008 |
| WO | WO2008071451 | 6/2008 |
| WO | WO2008124848 | 10/2008 |
| WO | WO2008137408 | 11/2008 |
| WO | WO2008140792 | 11/2008 |
| WO | WO2008147713 | 12/2008 |
| WO | WO2008150914 | 12/2008 |
| WO | WO2008154241 | 12/2008 |
| WO | WO2008156757 | 12/2008 |
| WO | WO2009011850 | 1/2009 |
| WO | WO2009016072 | 2/2009 |
| WO | WO2009029609 | 3/2009 |
| WO | WO2009061345 | 5/2009 |
| WO | WO2010064875 | 6/2010 |
| WO | WO2010107765 | 9/2010 |
| WO | WO2010111060 | 9/2010 |
| WO | WO2010132725 | 11/2010 |
| WO | WO2011011722 | 1/2011 |
| WO | WO2011019648 | 2/2011 |
| WO | WO2011019651 | 2/2011 |
| WO | WO2011050245 | 4/2011 |
| WO | WO2011079076 | 6/2011 |
| WO | WO2011084486 | 7/2011 |
| WO | WO2011123890 | 10/2011 |
| WO | WO2012068589 | 5/2012 |
| WO | WO2012104388 | 8/2012 |
| WO | WO2012129562 | 9/2012 |
| WO | WO2013024011 | 2/2013 |
| WO | WO2013030138 | 3/2013 |
| WO | WO2013113722 | 8/2013 |
| WO | WO2017079765 | 5/2017 |

OTHER PUBLICATIONS

Beyer et al., "Extended report: β-catenin is a central mediator of pro-fibrotic Wnt signaling in systemic sclerosis," *Ann Rheum Dis*, 71:761-767, online Feb. 2012.
Biason-Lauber et al., "A WNT4 Mutation Associated with Mullerian-Duct Regression and Virilization in a 46,XX Woman," *N. Engl. J. Med.*, (Aug. 2004), 351(8), 792-798.
Blaydon et al., "The gene encoding R-spondin 4 (RSPO4), a secreted protein implicated in Wnt signaling, is mutated in inherited anonychia," *Nat. Genet.*, (Nov. 2006), 38(11), 1245-1247.
Blom et al., "Involvement of the Wnt signaling pathway in experimental and human osteoarthritis: prominent role of Wnt-induced signaling protein 1," *Arthritis Rheum.*, 60(2):501-512, Feb. 2009.
Boyden et al., "High Bone Density Due to a Mutation in LDL-Receptor-Related Protein 5," *N. Engl. J. Med.*, (May 2002), 346(20):1513-1521.
Brack et al., "Increased Wnt signaling during aging alters muscle stem cell fate and increases fibrosis" *Science.*, 317(5839):807-810, Aug. 2007.
Brown et al., "Toxicity and toxicokinetics of the cyclin-dependent kinase inhibitor AG-024322 in cynomolgus monkeys following intravenous infusion," *Cancer Chemother Pharmacol.*, 62(6):1091-1101, Epub May 2008.
Chilosi et al., "The pathogenesis of COPD and IPF: Distinct horns of the same devil?," *Respiratory Research*, 13:3, 2012.
Bendele, "Animal Models of Arthritis: Relevance to Human Disease" Toxicol Pathol 1999 27: 134-142.
Chockalingam et al., "Elevated aggrecanase activity in a rat model of joint injury is attenuated by an aggrecanase specific inhibitor," Osteoarthritis Cartilage, Mar. 2011, 19(3): 315-323.

Chou and Talalay, "Quantitative analysis of dose-effect relationships: the combined effects of multiple drugs or enzyme inhibitors," *Advances in Enzyme Regulation* (1984), 22, 27-55.
Chou, "Drug combination studies and their synergy quantification using the Chou-Talalay method," *Cancer Res.*, 70(2):440-446, Jan 2010.
Chou, "Graphic rule for drug metabolism systems," *Current Drug Metabolism*, (May 2010) 11(4): 369-378.
Christodoulides et al., "WNT10B mutations in human obesity," *Diabetologia*, (2006) 49(4):678-684.
Clevers and Nusse, "Wnt/β-catenin signaling and disease," *Cell*, (Jun. 2012), 149(6):1192-1205.
Clevers, "Wnt/beta-catenin signaling in development and disease," *Cell*, (Nov. 2006), 127(3), 469- 480.
Corr, "Wnt-beta-catenin signaling in the pathogenesis of osteoarthritis," *Nat Clin Pract Rheumatol.*, 4(10):550-556, Oct. 2008.
D'Alessio et al., "Benzodipyrazoles: a new class of potent CDK2 inhibitors," *Bioorganic & Medicinal Chemistry Letters* (2005), 15(5), 1315-1319.
Damia "Contemporary pre-clinical development of anticancer agents—What are the optimal preclinical models?" European Journal of Cancer 2009, 45, 2768-2781 p. 2778.
Dann et al., "Insights into Wnt binding and signaling from the structures of two Frizzled cysteine-rich domains," Nature, (Jul. 2001), 412, pp. 86-90.
Datta et al., "Novel therapeutic approaches for pulmonary fibrosis," *Br J Pharmacol.*, 163(1):141-172, May 2011.
Davidson et al., "Emerging links between CDK cell cycle regulators and Wnt signaling," Trends Cell Biol., Aug. 2010, 20(8):453-460.
De Ferrari and Inestrosa, "Wnt signaling function in Alzheimer's disease," *Brain Research Reviews*, (2000), 33(1): 1-12.
De Ferrari and Moon, "The ups and downs of Wnt signaling in prevalent neurological disorders," Oncogene, (2006) 25(57): 7545-7553.
De Ferrari et al., "Common genetic variation within the Low-Density Lipoprotein Receptor-Related Protein 6 and late-onset Alzheimer's disease," Proc. Natl. Acad. Sci. USA, (May 2007), 104(22):9434-9439.
Dermer, "Another Anniversary for the War on Cancer," *Nature Biotechnology*, 12:320 (1994).
Dessalew et al., "3D-QSAR CoMFA and CoMSIA study on benzodipyrazoles as cyclin dependent kinase 2 inhibitors," *Medicinal Chemistry*, (2008), 4(4), 313-321.
Dong et al., "QSAR study of Akt/protein kinase B (PKB) inhibitors using support vector machine," *European Journal of Medicinal Chemistry*, (Oct. 2009), pp. 44(10): 4090-4097.
Doumpas et al., "TCF/LEF dependent and independent transcriptional regulation of Wnt/b-catenin target genes" The EMBO Journal Nov. 13, 2018 1-14.
Du Bois, "Strategies for treating idiopathic pulmonary fibrosis," *Nature Reviews Drug Discovery*, 9(2): 129-140 (Feb. 2010).
Edamoto et al., "Alterations of RB1, p53 and Wnt pathways in hepatocellular carcinomas associated with hepatitis C, hepatitis B and alcoholic liver cirrhosis," *Int J Cancer.*, 106(3):334-341, Sep. 1, 2003.
Egloff et al., "Gastrin-releasing peptide receptor expression in non-cancerous bronchial epithelia is associated with lung cancer: a case-control study," *Respiratory Research*, 13:9, Feb. 2012.
Espada et al., "Wnt signalling and cancer stem cells," *Clin. Transl. Oncol.*, (2009), 11(7), 411-27.
European Search Report for Application No. 13772420.9 dated Mar. 19, 2015, 4 pages.
Ewan et al., "A useful approach to identify novel small-molecule inhibitors of Wnt-dependent transcription," *Cancer Res.* (2010), 70(14), 5963-5973.
Exhibit A: *Otsuka Pharmaceutical Co., Ltd., v. Sandoz, Inc., Sun Pharmaceutical Industries, Ltd., Synton BV, Synthon Holding BV, Synthon Laboratories, Inc., and Synton Pharmaceuticals, Inc., and Apotex Inc. and Apotex Corp., and Teva Pharmaceuticals USA, Inc., Barr Laboratories, Inc., and Barr Pharmaceuticals, Inc.*, Decision on Appeal, 2011-1126, -1127, May 7, 2012, 33 pages.

(56) References Cited

OTHER PUBLICATIONS

Florez et al., "TCF7L2 Polymorphisms and Progression to Diabetes in the Diabetes Prevention Program," *N. Engl. J. Med.*, (Jul. 2006), 355(3):241-250.
Freese et al., "Wnt signaling in development and disease," *Neurobiology of Disease*, (2010) 38(2): 148-153.
Fujii et al., "An antagonist of dishevelled protein-protein interaction suppresses beta-catenin-dependent tumor cell growth," *Cancer Res.*, 67(2):573-579, Jan. 2007.
Fukuzawa et al., "Beckwith-Wiedemann Syndrome-associated Hepatoblastoma: Wnt Signal Activation Occurs Later in Tumorigenesis in Patients with 11p15.5 Uniparental Disomy," *Pediatric and Developmental Pathology* (2003), 6(4): 299-306.
Giles et al., "Caught up in a Wnt storm: Wnt signaling in cancer," *Biochim Biophys Acta.*, 1653(1):1-24, Jun. 2003.
Handeli and Simon, "A small-molecule inhibitor of Tcf/beta-catenin signaling down-regulates PPARgamma and PPARdelta activities," *Mol Cancer Ther.*, 7(3):521-529, Mar. 2008.
Henderson Jr. et al., "Inhibition of Wnt/beta-catenin/CREB binding protein (CBP) signaling reverses pulmonary fibrosis," Proc Natl Acad Sci U S A., 107(32):14309-14314, Epub Jul. 2010.
Hu et al., "Discovery of indazoles as inhibitors of Tpl2 kinase," *Bioorganic & Medicinal Chemistry Letters*, (Aug. 2011) 21(16): 4758-4761.
Huang et al., "Tankyrase inhibition stabilizes axin and antagonizes Wnt signaling," *Nature*, (Oct. 2009), 461(7264): 614-620.
Huang et al., "Synthesis of 3-(1H-benzimidazol-2-yl)-5-isoquinolin-4-ylpyrazolo[1,2-b]pyridine, a potent cyclin dependent kinase 1 (CDK1) inhibitor," *Bioorganic & Medicinal Chemistry Letters*, (2007) 17(5): 1243-1245.
Hübner et al., "Standardized quantification of pulmonary fibrosis in histological samples," *Biotechniques*, 44(4):507-511, 514-517, Apr. 2008.
Im et al., "Wnt inhibitors enhance chondrogenesis of human mesenchymal stem cells in a long-term pellet culture," *Biotechnol Lett.*, 33(5):1061-1068, Epub Jan. 2011.
Inestrosa and Toledo, "The role of Wnt signaling in neuronal dysfunction in Alzheimer's Disease," *Mol Neurodegener*, 3:9, doi:10.1186/1750-1326-3-9, 13 pages, Jul. 2008.
International Preliminary Report on Patentability for Application No. PCT/US2015/048705, dated Mar. 23, 2017, 9 pages.
International Search Report and Written Opinion for PCT/US2015/048705, dated Dec. 15, 2015, 14 pages.
Janssens et al., "The Wnt-dependent signaling pathways as target in oncology drug discovery," *Invest New Drugs.*, 24(4):263-280, Jul. 2006.
Jenkins et al., "Germline mutations in WTX cause a sclerosing skeletal dysplasia but do not predispose to tumorigenesis," *Nat. Genet.* (Jan. 2009), 41(1), 95-100.
Jessen et al., "Peripheral white blood cell toxicity induced by broad spectrum cyclin-dependent kinase inhibitors," *Journal of Applied Toxicology* (Jan. 2007), 27(2), 133-142.
Johnson et al., "A stem cell-based approach to cartilage repair," *Science.*, 336(6082):717-721, Epub Apr. 5, 2012.
Johnson, et. al. "Relationships between drug activity in NCI preclinical in vitro and in vivo models and early clinical trials." British Journal of Cancer 2001, 84, 1424-1431.
Kanazawa et al., "Association of the Gene Encoding Wingless-Type Mammary Tumor Virus Integration-Site Family Member 5B (WNT5B) with Type 2 Diabetes," *Am. J. Hum. Genet.* (2004), 75(5), 832-843.
Karlberg et al., "Structural basis for the interaction between tankyrase-2 and a potent Wnt-signaling inhibitor," *J. Med. Chem.* (2010), 53(14), 5352-5.
Kibar et al., "Mutations in VANGL1 Associated with Neural-Tube Defects," *N. Engl. J. Med.*, (Apr. 2007), 356(14):1432-1437.
King et al., "BUILD-3: a randomized, controlled trial of bosentan in idiopathic pulmonary fibrosis," *Am J Respir Crit Care Med.*, 184(1):92-99, Epub Apr. 2011.

Kishimoto et al: "Wnt/Beta-Catenin Signaling Suppresses Expressions of Ses, Mkx and Tnmd in Tendon-Derived Cells," PLOS One, Jul. 27, 2017, 12(7), E0182051, pp. 1-17.
Kuwajima et al., "Necdin Promotes GABAergic Neuron Differentiation in Cooperation with Dlx Homeodomain Proteins," *Journal of Neuroscience* (May 2006), 26(20), 5383-5392.
Lacy et al., "Generation and characterization of ABT-981, a dual variable domain immunoglobulin (DVD-Ig(TM)) molecule that specifically and potently neutralizes both IL-1α and IL-1β," Mabs, May 2015, 7(3): 605-619.
Lala and Orucevic, "Role of nitric oxide in tumor progression: lessons from experimental tumors," Cancer and Metastasi Review, vol. 17, Mar. 1998, pp. 91-106.
Lammi et al., "Mutations in AXIN2 Cause Familial Tooth Agenesis and Predispose to Colorectal Cancer," *Am. J. Hum. Genet.* (2004), 74(5), 1043-1050.
Ledford "US cancer institute overhauls cell lines" Nature Feb. 25, 2016 vol. 530 p. 391.
Leyns et al., "Frzb-1 Is a Secreted Antagonist of Wnt Signaling Expressed in the Spemann Organizer," *Cell* (Mar. 1997), 88(6), 747-756.
Li et al., "Artesunate attenuates the growth of human colorectal carcinoma and inhibits hyperactive Wnt/beta-catenin pathway," *Int J Cancer.*, 121(6):1360-1365, Sep. 2007.
Lin et al., "Synthesis and evaluation of pyrazolo[3,4-b]pyridine CDK1 inhibitors as anti-tumor agents," *Bioorganic & Medicinal Chemistry Letters*, (Aug. 2007), 17(15): 4297-4302.
Liu, et.al., "Fibrotic lung fibroblasts show blunted inhibition by cAMP due to deficient cAMP response element-binding protein phosphorylation," *J Pharmacol Exp Ther.*, 315(2):678-687, Epub Aug. 3, 2005.
Lories et al., "To Wnt or not to Wnt: the bone and joint health dilemma," *Nat Rev Rheumatol.*, 9(6):328-339, Epub Mar. 2013.
Low et al., "Phenotypic fingerprinting of small molecule cell cycle kinase inhibitors for drug discovery," *Curr Chem Genomics.*, 3:13-21, Mar. 2009.
Lu et al., "Structure-activity relationship studies of small-molecule inhibitors of Wnt response," *Bioorganic & Medicinal Chemistry Letters*, (Jul. 2009), 19(14):3825-3827.
Lui: "Histopathological Changes in Tendinopathypotential Roles of BMPs?" Rheumatology, May 2013, 52:2116-2126.
Luo et al., "Fragile X Mental Retardation Protein Regulates Proliferation and Differentiation of Adult Neural Stem/Progenitor Cells," *PLoS Genetics*, (Apr. 2010), 6(4):e1000898, 15 pages.
Luu et al., "Wnt/beta-catenin signaling pathway as a novel cancer drug target," *Curr Cancer Drug Targets.*, 4(8):653-671, Dec. 2004.
Luyten et al., "Wnt signaling and osteoarthritis," *Bone*, 44(4):522-527, Epub Dec. 14, 2008.
MacDonald et al., "Wnt/beta-catenin signaling: components, mechanisms, and diseases," *Dev. Cell* (Jul. 2009), 17(1), 9-26.
Mandel et al., "SERKAL Syndrome: An Autosomal-Recessive Disorder Caused by a Loss-of-Function Mutation in WNT4," *Am. J. Hum. Genet.*, (Jan. 2008), 82(1), 39-47.
Mani, et al., "LRP6 Mutation in a Family with Early Coronary Disease and Metabolic Risk Factors," *Science*, (Mar. 2007), 315(5816), 1278-1282.
McBride, et al. "Design and structure-activity relationship of 3-benzimidazol-2-yl-1H-indazoles as inhibitors of receptor tyrosine kinases," *Bioorganic & Medicinal Chemistry Letters* (2006), 16(13), 3595-3599.
MedlinePlus, [online] "Cancer," [retrieved on Jul. 6, 2007]. Retrieved from the internet, URL http://www.nlnn.nih.govinnedlineplus/cancer.html>.
Misra et al., "1H-Pyrazolo[3,4-b]pyridine inhibitors of cyclin-dependent kinases highly potent 2,6-Difluorophenacyl analogues," *Bioorganic & Medicinal Chemistry Letters*, (2003), 13:2405-2408.
Mora et al, "Emerging therapies for idiopathic pulmonary fibrosis, a progressive age-related disease," Nat Rev Drug Discov. Oct. 30, 2017; 16(11): 810.
Morrisey, "Wnt signaling and pulmonary fibrosis," *Am J Pathol.*, 162(5):1393-1397, May 2003.
Muddassar et al., "Elucidation of binding mode and three dimensional quantitative structure-activity relationship studies of a novel

(56) References Cited

OTHER PUBLICATIONS series of protein kinase B/Akt inhibitors ," *Journal of Molecular Modeling*, (2009), 15(2): 183-192.
Niemann et al., "Homozygous WNT3 Mutation Causes Tetra-Amelia in a Large Consanguineous Family," *Am. J. Hum. Genet.* (2004), 74(3), 558-563.
Nishisho et al., "Mutations of chromosome 5q21 genes in FAP and colorectal cancer patients," *Science*, (Aug. 1991), 253(5020):665-669.
Nusse, "Wnt signaling in disease and in development," *Cell Res.*, 15(1):28-32, Jan. 2005.
Oates et al., "Increased DNA Methylation at the AXIN1 Gene in a Monozygotic Twin from a Pair Discordant for a Caudal Duplication Anomaly," *Am. J. Hum. Genet.* (2006 ), 79(1), 155-162.
Ocana, A. "Preclinical development of molecular targeted agents for cancel" Nat. Rev. Clin. Oncol. 2011, 8, 200-209.
Oduor et al., "Trypanosoma brucei glycogen synthase kinase-3, a target for anti-trypanosomal drug development: a public-private partnership to identify novel leads," *PLoS Negl Trop Dis.*, 5(4):e1017, Apr. 2011.
Okerlund and Cheyette, "Synaptic Wnt signaling-a contributor to major psychiatric disorders?" *J Neurodev Disord.*, (2011) 3(2):162-174.
Parsons et al., "Benzo[d]imidazole Transient Receptor Potential Vanilloid 1 Antagonists for the Treatment of Pain: Discovery of trans-2-(2-{2-[2-(4-Trifluoromethyl-phenyl)-vinyl]-1H-benzimidazol-5-yl}-phenyl)-propan-2-ol (Mavatrep)," J Med Chem, May 2015, 58(9): 3859-3874.
Piersanti et al., "Synthesis of benzo[1,2-d;3,4-d']diimidazole and 1 H-pyrazolo[4,3-b]pyridine as putative A2A receptor antagonists," Organic and Biomolecular Chemistry, Aug. 2007, 5(16):2567-2571.
Polakis, "Wnt signaling and cancer," *Genes Dev.*, 14: 1837-1851, 2000.
Pubchem. Substance Record for SID 164345938. Deposit Date: Nov. 4, 2013. [retrieved on Nov. 16, 2015]. Retrieved from the Internet. <URL: https://pubchem.ncbi.nlm.nih.gov/substance/164345938#section=Top>, 5 pages.
Qin et al. "Complexity of the genotype-phenotype correlation in familial exudative vitreoretinopathy with mutations in the LRP5 and/or FZD4 genes," *Hum. Mutat.* (2005), 26(2), 104-112.
Reya and Clevers, "Wnt signalling in stem cells and cancer," *Nature* 434: 843-850, Apr. 2005.
Richards et al., "Peripheral blood proteins predict mortality in idiopathic pulmonary fibrosis," *Am J Respir Crit Care Med.*, 185(1):67-76, Jan. 2012.
Rivera et al., "An X Chromosome Gene, WTX, Is Commonly Inactivated in Wilms Tumor," *Science*, (Feb. 2007), 315(5812):642-645, published online Jan. 4, 2007.
Robitaille et al., "Mutant frizzled-4 disrupts retinal angiogenesis in familial exudative vitreoretinopathy," *Nat. Genet.*, (Sep. 2002), 32(2):326-330.
Rother et al., "Efficacy and safety of epicutaneous ketoprofen in Transfersome (IDEA-033) versus oral celecoxib and placebo in osteoarthritis of the knee: multicentre randomised controlled trial," Annals of the Rheumatic Diseases, Sep. 2007, 66(9): 1178-1183.
Ryu et al., "Natural derivatives of curcumin attenuate the Wnt/beta-catenin pathway through down-regulation of the transcriptional coactivator p300," *Biochem Biophys Res Commun.*, 377(4):1304-1308, print Dec. 2008, Epub Nov. 2008.
Salinas, "Wnt signaling in the vertebrate central nervous system: from axon guidance to synaptic function," *Cold Spring Harb Perspect Biol.*, (2012) 4(2). pii: a008003, 15 pages.
Sato, "Upregulation of the Wnt/beta-catenin pathway induced by transforming growth factor-beta in hypertrophic scars and keloids," *Acta Derm Venereol.*, 86(4):300-307, 2006.
Seah et al., "Neuronal Death Resulting from Targeted Disruption of the Snf2 Protein ATRX Is Mediated by p53," *Journal of Neuroscience* (Nov. 2008), 28(47), 12570-12580.

Shih et al., "Pharmacophore modeling and virtual screening to identify potential RET kinase inhibitors," *Bioorg Med Chem Lett.*, 21(15):4490-4497, Epub Jun. 2011.
Shruster et al., "Wnt signaling enhances neurogenesis and improves neurological function after focal ischemic injury," *PLoS One*, (Jul. 2012), 7(7):e40843, 11 pages.
Silva et al, "Advances in Prodrug Design," *Mini-Revs. In Med. Chem.* (2005), 5: 893-914.
Solowiej et al., "Characterizing the Effects of the Juxtamembrane Domain on Vascular Endothelial Growth Factor Receptor-2 Enzymatic Activity, Autophosphorylation, and Inhibition by Axitinib," *Biochemistry*, (2009), 48(29), 7019-7031.
Staines et al., "Cartilage development and degeneration: a Wnt situation," *Cell Biochem Funct.*, 30(8):633-642, Epub Jun. 2012.
Sutherland et al., "A robust high-content imaging approach for probing the mechanism of action and phenotypic outcomes of cell-cycle modulators," *Molecular Cancer Therapeutics*, (Feb. 2011), 10(2): 242-254.
Swaney et al., "A novel, orally active LPA(1) receptor antagonist inhibits lung fibrosis in the mouse bleomycin model," *Br J Pharmacol.*, 160(7):1699-1713, Aug. 2010.
Takahashi-Yanaga et al., "Celecoxib-induced degradation of T-cell factors-1 and -4 in human colon cancer cells," *Biochem Biophys Res Commun.*, 377(4):1185-1190, print Dec. 2008, Epub Nov. 2008.
Tamamura et al., "Developmental regulation of Wnt/beta-catenin signals is required for growth plate assembly, cartilage integrity, and endochondral ossification," *J Biol Chem.*, 280(19):19185-95. Epub Mar. 2005.
Thompson et al., "WNT/beta-catenin signaling in liver health and disease," *Hepatology.*, 45(5):1298-1305, May 2007.
Trujillo et al., "2-(6-Phenyl-1H-indazol-3-yl)-1H-benzo[d]imidazoles: design and synthesis of a potent and isoform selective PKC-zeta inhibitor," *Bioorg Med Chem Lett.*, 19(3):908-911, Epub Dec. 6, 2008.
Ugur et al., "Homozygous WNT10b mutation and complex inheritance in Split-Hand/Foot Malformation," *Hum. Mol. Genet.* (2008), 17(17), 2644-2653.
Vulpetti et al., "Structure-Based Approaches to Improve Selectivity: CDK2-GSK3β Binding Site Analysis," *Journal of Chemical Information and Modeling* (2005), 45(5), 1282-1290.
Wagner et al., "The therapeutic potential of the Wnt signaling pathway in bone disorders," *Curr Mol Pharmacol.*, 4(1):14-25, Jan. 2011.
Walters and Kleeberger, "Mouse models of bleomycin-induced pulmonary fibrosis," *Current Protocols in Pharmacology*, (2008) Chapter 5: Unit 5.46, 1-17.
Wang, et al., "Mutations in X-linked PORCN, a putative regulator of Wnt signaling, cause focal dermal hypoplasia," *Nat. Genet.* (Jul. 2007), 39(7), 836-838.
Wantanabe and Dai, "Winning WNT: race to Wnt signaling inhibitors," *Proc Natl Acad Sci U S A.* 108(15):5929-5930, Epub Mar. 2011.
Watts et.al., "RhoA signaling modulates cyclin D1 expression in human lung fibroblasts; implications foridiopathic pulmonary fibrosis," *Respir Res.*, 7:88, Jun. 15, 2006.
Weng et al., "Control of Dkk-1 ameliorates chondrocyte apoptosis, cartilage destruction, and subchondral bone deterioration in osteoarthritic knees," *Arthritis Rheum.*, 62(5):1393-1402, May 2010.
Witherington et al., "5-Aryl-pyrazolo[3,4-b]pyridazines: potent inhibitors of glycogen synthase kinase-3 (GSK-3)," *Bioorganic & Medicinal Chemistry Letters*, (May 2003), 13(9):1581-1584.
Woods, S. et al., "Mutations in WNT7A Cause a Range of Limb Malformations, Including Fuhrmann Syndrome and Al-Awadi/Raas-Rothschild/Schinzel Phocomelia Syndrome," *Am. J. Hum. Genet.* (Aug. 2006), 79(2), 402-408.
Yan et al., "Discovery of small molecule inhibitors of the Wnt/b-catenin signaling pathway by targeting b-catenin/Tcf4 interactions" Experimental Biology and Medicine vol. 242 Jun. 2017 1185-1197.
Yardy and Brewster, "Wnt signalling and prostate cancer," *Prostate Cancer Prostatic Dis*, 8(2):119-126, 2005.
Zhan et al., "Wnt signaling in cancer" Oncogene (2017) 36, 1461-1473.

(56) References Cited

OTHER PUBLICATIONS

Zhang et al., "Small-molecule synergist of the Wnt/beta-catenin signaling pathway," *Proc Natl Acad Sci U S A.*, 104(18):7444-7448, Epub Apr. 2007 and correction 104(30):12581, Jul. 2007.
Zheng "Small-molecule inhibitors of Wnt signaling pathway: towards novel anticancer therapeutics" Future Med. Chem. (2015) 7(18), 2485-2505.
Zhong et al., "Characterization of in vitro and in vivo metabolism of AG-024322, a novel cyclin-dependent kinase (CDK) inhibitor," *Health* (2009), 1(4): 249-262.
Zhu et al. "Design and synthesis of pyridine-pyrazolopyridine-based inhibitors of protein kinase B/Akt," Bioorganic & Medicinal Chemistry, Mar. 2007, 15(6):2441-2452.
U.S. Appl. No. 15/773,737, filed May 4, 2018, Hood et al.
U.S. Appl. No. 15/773,951, filed May 4, 2018, Hood et al.
U.S. Appl. No. 15/889,403, filed Feb. 6, 2018, Kumar KC et al.
U.S. Appl. No. 15/968,555, filed May 1, 2018, Hood et al.
U.S. Appl. No. 16/115,222, filed Aug. 28, 2018, Kumar KC.
U.S. Appl. No. 14/939,434, filed Nov. 12, 2015, Hood et al.
U.S. Appl. No. 15/257,398, filed Sep. 6, 2016, Kumar KC et al.
U.S. Appl. No. 15/611,150, filed Jun. 1, 2017, Kumar KC.
U.S. Appl. No. 15/668,992, filed Aug. 4, 2017, Kumar KC et al.
U.S. Appl. No. 15/681,035, filed Aug. 18, 2017, Hood et al.
U.S. Appl. No. 15/709,057, filed Sep. 19, 2017, Hood et al.
U.S. Appl. No. 15/716,803, filed Sep. 27, 2017, Kumar KC et al.
U.S. Appl. No. 15/716,894, filed Sep. 27, 2017, Kumar KC et al.
U.S. Appl. No. 15/749,586, filed Feb. 1, 2018, Kumar KC et al.
U.S. Appl. No. 15/749,587, filed Feb. 1, 2018, Kumar KC et al.
U.S. Appl. No. 15/749,592, filed Feb. 1, 2018, Kumar KC et al.
U.S. Appl. No. 15/749,606, filed Feb. 1, 2018, Kumar KC et al.
U.S. Appl. No. 15/749,701, filed Feb. 1, 2018, Kumar KC et al.
U.S. Appl. No. 15/749,706, filed Feb. 1, 2018, Kumar KC et al.
U.S. Appl. No. 15/749,718, filed Feb. 1, 2018, Kumar KC et al.
U.S. Appl. No. 15/749,721, filed Feb. 1, 2018, Kumar KC et al.
U.S. Appl. No. 15/749,727, filed Feb. 1, 2018, Kumar KC et al.
U.S. Appl. No. 15/749,737, filed Feb. 1, 2018, Kumar KC et al.
U.S. Appl. No. 15/749,739, filed Feb. 1, 2018, Kumar KC et al.
U.S. Appl. No. 15/749,741, filed Feb. 1, 2018, Kumar KC et al.
U.S. Appl. No. 15/749,742, filed Feb. 1, 2018, Kumar KC et al.
U.S. Appl. No. 15/749,922, filed Feb. 2, 2018, Kumar KC et al.
U.S. Appl. No. 15/749,929, filed Feb. 2, 2018, Kumar KC et al.
U.S. Appl. No. 15/790,544, filed Oct. 23, 2017, Deshmukh.
U.S. Appl. No. 15/806,321, filed Nov. 7, 2017, Dellamary.
U.S. Appl. No. 15/808,602, filed Nov. 9, 2017, Kumar KC et al.
U.S. Appl. No. 15/812,629, filed Nov. 14, 2017, Hood et al.
U.S. Appl. No. 16/032,905, filed Jul. 11, 2018, Hood et al.
U.S. Appl. No. 16/015,996, filed Jun. 22, 2018, Kumar KC et al.
U.S. Appl. No. 15/591,566, filed May 10, 2017, Kumar KC et al.
U.S. Appl. No. 15/749,713, filed Feb. 1, 2018, Kumar KC et al.
U.S. Appl. No. 14/149,948, filed Jan. 8, 2014, Kumar KC et al.
U.S. Appl. No. 12/968,505, filed Dec. 15, 2010, Hood et al.
U.S. Appl. No. 13/552,188, filed Jul. 18, 2012, Hood et al.
U.S. Appl. No. 13/614,296, filed Sep. 13, 2012, Hood et al.
U.S. Appl. No. 13/800,963, filed Mar. 13, 2013, Hood et al.
U.S. Appl. No. 13/855,874, filed Apr. 3, 2013, Hood et al.
U.S. Appl. No. 13/887,177, filed May 3, 2013, Hood et al.
U.S. Appl. No. 13/938,691, filed Jul. 10, 2013, Hood et al.
U.S. Appl. No. 13/938,692, filed Jul. 10, 2013, Hood et al.
U.S. Appl. No. 14/019,103, filed Sep. 5, 2013, Hood et al.
U.S. Appl. No. 14/019,147, filed Sep. 5, 2013, Hood et al.
U.S. Appl. No. 14/019,229, filed Sep. 5, 2013, Hood et al.
U.S. Appl. No. 14/019,940, filed Sep. 6, 2013, Hood et al.
U.S. Appl. No. 14/178,749, filed Feb. 12, 2014, Hood et al.
U.S. Appl. No. 14/331,427, filed Jul. 15, 2014, Hood et al.
U.S. Appl. No. 14/334,005, filed Jul. 17, 2014, Hood et al.
U.S. Appl. No. 14/454,279, filed Aug. 7, 2014, Hood et al.
U.S. Appl. No. 14/465,056, filed Aug. 21, 2014, Hood et al.
U.S. Appl. No. 14/621,195, filed Feb. 12, 2015, Hood et al.
U.S. Appl. No. 14/621,222, filed Feb. 12, 2015, Hood et al.
U.S. Appl. No. 14/718,354, filed May 21, 2015, Hood et al.
U.S. Appl. No. 14/847,259, filed Sep. 8, 2015, Kumar KC et al.
U.S. Appl. No. 14/847,287, filed Sep. 8, 2015, Kumar KC et al.
U.S. Appl. No. 14/847,299, filed Sep. 8, 2015, Kumar KC et al.
U.S. Appl. No. 14/847,336, filed Sep. 8, 2015, Kumar KC et al.
U.S. Appl. No. 14/847,344, filed Sep. 8, 2015, Kumar KC et al.
U.S. Appl. No. 14/847,379, filed Sep. 8, 2015, Kumar KC et al.
U.S. Appl. No. 14/847,394, filed Sep. 8, 2015, Kumar KC et al.
U.S. Appl. No. 14/940,958, filed Nov. 13, 2015, Hood et al.
U.S. Appl. No. 14/962,681, filed Dec. 8, 2015, Hood et al.
U.S. Appl. No. 15/184,553, filed Jun. 16, 2016, Hood et al.
U.S. Appl. No. 15/244,687, filed Aug. 23, 2016, Hood et al.
U.S. Appl. No. 15/267,939, filed Sep. 16, 2016, Kumar KC et al.
U.S. Appl. No. 15/298,346, filed Oct. 20, 2016, Kumar KC et al.
U.S. Appl. No. 15/357,494, filed Nov. 21, 2016, Kumar KC et al.
U.S. Appl. No. 15/363,086, filed Nov. 29, 2016, Kumar KC et al.
U.S. Appl. No. 15/420,398, filed Jan. 31, 2017, Hood et al.
U.S. Appl. No. 15/661,231, filed Jul. 27, 2017, Kumar KC et al.
U.S. Appl. No. 15/673,834, filed Aug. 10, 2017, Kumar KC et al.
U.S. Appl. No. 15/749,608, filed Feb. 1, 2018, Kumar KC et al.
U.S. Appl. No. 15/749,868, filed Feb. 2, 2018, Kumar KC et al.
U.S. Appl. No. 15/749,923, filed Feb. 2, 2018, Kumar KC et al.
U.S. Appl. No. 15/843,818, filed Dec. 15, 2017, Kumar KC et al.
U.S. Appl. No. 14/847,371, filed Sep. 8, 2015, Kumar KC et al.
U.S. Appl. No. 14/741,645, filed Jun. 17, 2015, Hood et al.
U.S. Appl. No. 12/852,681, filed Aug. 9, 2010, Hood et al.
U.S. Appl. No. 12/852,706, filed Aug. 9, 2010, Hood et al.
U.S. Appl. No. 15/749,910, filed Feb. 2, 2018, Kumar KC et al.
U.S. Appl. No. 16/162,155, filed Oct. 16, 2018, Kumar et al.
Bharath et al, "Evaluation of Myofibroblasts by Expression of Alpha Smooth Muscle Actin: A Marker in Fibrosis, Dysplasia and Carcinoma," Journal of Clinical and Diagnostic Research, 2014, 8(4):ZC14-ZC17.
Bollong et al, "Small molecule-mediated in inhibition of myofibroblast trans differentiation for the treatment of fibrosis," PNAS, 2017, 114:18:4679-4684.
Caira, "Crystalline Polymorphism of Organic Compounds," Topics in Current Chemistry, Jan. 1998, 198:163-208.
Carpino et al, "Alpha-SMA expression in hepatic stellate cells and quantitative analysis of hepatic fibrosis in cirrhosis and in recurrent chronic hepatitis after liver transplantation," Digestive and Liver Disease, 2005, 37:349-356.
Guo et al, "Wnt/β-Catenin Signaling: a Promising New Target for Fibrosis Diseases," Physiol. Res., 2012, 61:337-346.
Kim et al, "Blockade of the Wnt/β-Catenin Pathway Attenuates Bleomycin-Induced Pulmonary Fibrosis," Tohoku J. Exp. Med., 2011, 223:45-54.
United States Court of Appeals for the Federal Circuit, *Eli Lilly and Company*, Plaintiff-Appellant, v. *Actavis Elizabeth LLC*, Defendant-Appellee, *and Sun Pharmaceutical Industries, Ltd.*, Defendant-Appellee, *and Sandoz, Inc.*, Defendant-Appellee, *and Mylan Pharmaceuticals Inc.*, Defendant-Appellee, *and Apotex Inc.*, Defendant-Appellee, *and Aurobindo Pharma Ltd.*, Defendant-Appellee, *and Teva Pharmaceuticals USA, Inc.*, Defendant-Appellee, Appeal from the United States District Court for the District of New Jersey in Case No. 07-CV-3770, Judge Dennis M. Cavanaugh, decided on Jul. 29, 2011, 20 pages.

\* cited by examiner

3-(3H-IMIDAZO[4,5-B]PYRIDIN-2-YL)-1H-PYRAZOLO[3,4-B]PYRIDINE AND THERAPEUTIC USES THEREOF

RELATED APPLICATIONS

This application is a continuation application of U.S. application Ser. No. 15/668,992, filed Aug. 4, 2017, which is a continuation application of U.S. application Ser. No. 14/847,379, filed Sep. 8, 2015, and claims the benefit of U.S. Provisional Application Nos. 62/051,567, filed Sep. 17, 2014, and 62/047,575, filed Sep. 8, 2014, all of which are incorporated herein by reference in their entirety.

BACKGROUND

Technical Field

This disclosure relates to inhibitors of one or more proteins in the Wnt pathway, including inhibitors of one or more Wnt proteins, and compositions comprising the same. More particularly, it concerns the use of an azaindazole compound or salts or analogs thereof, in the treatment of disorders characterized by the activation of Wnt pathway signaling (e.g., cancer, abnormal cellular proliferation, angiogenesis, fibrotic disorders, bone or cartilage diseases, and osteoarthritis), the modulation of cellular events mediated by Wnt pathway signaling, as well as genetic diseases and neurological conditions/disorders/diseases due to mutations or dysregulation of the Wnt pathway and/or of one or more of Wnt signaling components. Also provided are methods for treating Wnt-related disease states.

Background

The Wnt growth factor family includes more than 10 genes identified in the mouse and at least 19 genes identified in the human. Members of the Wnt family of signaling molecules mediate many short- and long-range patterning processes during invertebrate and vertebrate development. The Wnt signaling pathway is known for its role in the inductive interactions that regulate growth and differentiation, and it also plays roles in the homeostatic maintenance of post-embryonic tissue integrity. Wnt stabilizes cytoplasmic β-catenin, which stimulates the expression of genes including c-myc, c jun, fra-1, and cyclin D1. In addition, misregulation of Wnt signaling can cause developmental defects and is implicated in the genesis of several human cancers. The Wnt pathway has also been implicated in the maintenance of stem or progenitor cells in a growing list of adult tissues including skin, blood, gut, prostate, muscle, and the nervous system.

SUMMARY

The present disclosure provides methods and reagents, involving contacting a cell with an agent, such as an azaindazole compound, in a sufficient amount to antagonize a Wnt activity, e.g., to reverse or control an aberrant growth state or correct a genetic disorder due to mutations in Wnt signaling components.

Some embodiments disclosed herein include Wnt inhibitors containing an azaindazole core. Other embodiments disclosed herein include pharmaceutical compositions and methods of treatment using these compounds.

One embodiment disclosed herein includes a compound having the structure of Formula I:

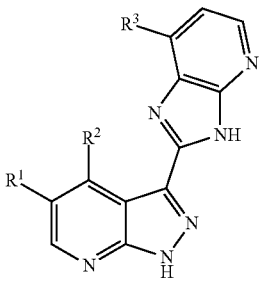

as well as prodrugs and pharmaceutically acceptable salts thereof.

In some embodiments of Formula (I):
$R^1$ is selected from the group consisting of -heteroaryl $(R^4)_q$ and -heterocyclyl$(R^5)_h$;
$R^2$ is selected from the group consisting of H and halide;
$R^3$ is selected from the group consisting of H, -heteroaryl $(R^6)_q$, -heterocyclyl$(R^7)_h$, and -aryl$(R^8)_k$;
each $R^4$ is one substituent attached to the heteroaryl and is independently selected from the group consisting of halide, —($C_{1-6}$ alkyl), —($C_{1-4}$ alkylene)$_p$heterocyclyl $(R^9)_h$, —($C_{1-4}$ alkylene)$_p$carbocyclyl$(R^{10})_j$, —($C_{1-4}$ alkylene)$_p$aryl$(R^{11})_k$, —NHC(=O)$R^{12}$, —$NR^{13}R^{14}$, —($C_{1-6}$ alkylene)$NR^{15}R^{16}$, and —$OR^{22}$;
each $R^5$ is one substituent attached to the heterocyclyl and is independently selected from the group consisting of —($C_{1-4}$ alkyl), halide, —$CF_3$, and —CN;
each $R^6$ is one substituent attached to the heteroaryl and is independently selected from the group consisting of —($C_{1-6}$ alkyl), halide, —$CF_3$, —$OCH_3$, —CN, and —C(=O)$R^{17}$;
each $R^7$ is one substituent attached to the heterocyclyl and is independently selected from the group consisting of —($C_{1-6}$ alkyl), halide, —$CF_3$, —CN, and —$OCH_3$;
each $R^8$ is one substituent attached to the aryl and is independently selected from the group consisting of —($C_{1-6}$ alkyl), halide, —$CF_3$, —CN, —$OCH_3$, —($C_{1-6}$ alkylene)$_p$$NHSO_2R^{17}$, —$NR^{13}$($C_{1-6}$ alkylene)$NR^{13}R^{14}$, —($C_{1-6}$ alkylene)$_p$$NR^{13}R^{14}$, and —$OR^{25}$;
each $R^9$ is one substituent attached to the heterocyclyl and is independently selected from the group consisting of amino, —($C_{1-4}$ alkyl), halide, —$CF_3$, and —CN;
each $R^{10}$ is one substituent attached to the carbocyclyl and is independently selected from the group consisting of —($C_{1-4}$ alkyl), halide, —$CF_3$, and —CN;
each $R^{11}$ is one substituent attached to the aryl and is independently selected from the group consisting of —($C_{1-4}$ alkyl), halide, —$CF_3$, and —CN;
each $R^{12}$ is independently selected from the group consisting of —($C_{1-9}$ alkyl), -heteroaryl$(R^{18})_q$, -aryl$(R^{19})_k$, —$CH_2$aryl$(R^{19})_k$, -carbocyclyl$(R^{20})_j$, —$CH_2$carbocyclyl$(R^{20})_j$, —($C_{1-4}$ alkylene)$_p$$NR^{23}R^{24}$, -heterocyclyl$(R^{21})_h$, and —$CH_2$heterocyclyl$(R^{21})_h$;
each $R^{13}$ is independently selected from the group consisting of H and —($C_{1-6}$ alkyl);
each $R^{14}$ is independently selected from the group consisting of H, —($C_{1-6}$ alkyl), —$CH_2$aryl$(R^{19})_k$, and —$CH_2$carbocyclyl$(R^{20})_j$;
each $R^{15}$ is independently selected from the group consisting of H and —($C_{1-6}$ alkyl);
each $R^{16}$ is independently selected from the group consisting of H, —($C_{1-6}$ alkyl), —$CH_2$aryl$(R^{19})_k$, and —$CH_2$carbocyclyl$(R^{20})_j$;

each $R^{17}$ is a —($C_{1-6}$ alkyl);

each $R^{18}$ is one substituent attached to the heteroaryl and is independently selected from the group consisting of —($C_{1-4}$ alkyl), halide, —$CF_3$, and —CN;

each $R^{19}$ is one substituent attached to the aryl and is independently selected from the group consisting of —($C_{1-4}$ alkyl), halide, —$CF_3$, and —CN;

each $R^{20}$ is one substituent attached to the carbocyclyl and is independently selected from the group consisting of —($C_{1-4}$ alkyl), halide, —$CF_3$, and —CN;

each $R^{21}$ is one substituent attached to the heterocyclyl and is independently selected from the group consisting of —($C_{1-4}$ alkyl), halide, —$CF_3$, and —CN;

each $R^{22}$ is independently selected from the group consisting of H, —($C_{1-6}$ alkyl), —($C_{1-4}$ alkylene)$_p$heterocyclyl($R^{21}$)$_h$, —($C_{1-4}$ alkylene)$_p$carbocyclyl($R^{20}$)$_j$, —($C_{1-4}$ alkylene)$_p$aryl($R^{19}$)$_k$, and —($C_{1-6}$ alkylene)$_p$NR$^{23}$R$^{24}$;

each $R^{23}$ is independently selected from the group consisting of H and —($C_{1-6}$ alkyl);

each $R^{24}$ is independently selected from the group consisting of H and —($C_{1-6}$ alkyl);

each $R^{25}$ is independently selected from the group consisting of H, —($C_{1-6}$ alkyl), —($C_{1-4}$ alkylene)$_p$heterocyclyl($R^{21}$)$_h$, and —($C_{1-6}$ alkylene)$_p$NR$^{23}$R$^{24}$;

each p is independently 0 or 1;

each q is independently 0 to 4;

each h is independently 0 to 10;

each k is independently 0 to 5; and each j is independently 0 to 12.

Some embodiments include stereoisomers and pharmaceutically acceptable salts of a compound of Formula (I).

Some embodiments include pro-drugs of a compound of Formula (I).

Some embodiments of the present disclosure include pharmaceutical compositions comprising a compound of Formula (I) and a pharmaceutically acceptable carrier, diluent, or excipient.

Other embodiments disclosed herein include methods of inhibiting one or more members of the Wnt pathway, including one or more Wnt proteins by administering to a patient affected by a disorder or disease in which aberrant Wnt signaling is implicated, such as cancer and other diseases associated with abnormal angiogenesis, cellular proliferation, cell cycling and mutations in Wnt signaling components, a compound according to Formula (I). Accordingly, the compounds and compositions provided herein can be used to treat cancer, to reduce or inhibit angiogenesis, to reduce or inhibit cellular proliferation and correct a genetic disorder due to mutations in Wnt signaling components.

Non-limiting examples of diseases which can be treated with the compounds and compositions provided herein include a variety of cancers, diabetic retinopathy, pulmonary fibrosis, rheumatoid arthritis, sepsis, anklyosing spondylitis, psoriasis, scleroderma, mycotic and viral infections, osteochondrodysplasia, Alzheimer's disease, lung disease, bone/osteoporotic (wrist, spine, shoulder and hip) fractures, articular cartilage (chondral) defects, degenerative disc disease (or intervertebral disc degeneration), polyposis coli, osteoporosis-pseudoglioma syndrome, familial exudative vitreoretinopathy, retinal angiogenesis, early coronary disease, tetra-Amelia syndrome, Müllerian-duct regression and virilization, SERKAL syndrome, diabetes mellitus type 2, Fuhrmann syndrome, Al-Awadi/Raas-Rothschild/Schinzel phocomelia syndrome, odonto-onycho-dermal dysplasia, obesity, split-hand/foot malformation, caudal duplication syndrome, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease, and Rett syndrome.

Some embodiments of the present disclosure include methods to prepare compounds of Formula (I).

It is to be understood that both the foregoing general description and the following detailed description are exemplary and explanatory only and are not restrictive of the invention, as claimed.

DETAILED DESCRIPTION

Provided herein are compositions and methods for inhibiting one or more members of the Wnt pathway, including one or more Wnt proteins. Other Wnt inhibitors and methods for using the same are disclosed in U.S. application Ser. Nos. 12/852,706; 12/968,505; 13/552,188; 13/800,963; 13/855,874; 13/887,177 13/938,691; 13/938,692; 14/019,103; 14/019,147; 14/019,940; 14/149,948; 14/178,749; 14/331,427; and Ser. No. 14/334,005; and U.S. Provisional Application Ser. Nos. 61/232,603; 61/288,544; 61/305,459; 61/620,107; 61/642,915; and 61/750,221, all of which are incorporated by reference in their entirety herein.

Some embodiments provided herein relate to a method for treating a disease or disorder including, but not limited to, cancers, diabetic retinopathy, pulmonary fibrosis, rheumatoid arthritis, sepsis, anklyosing spondylitis, psoriasis, scleroderma, mycotic and viral infections, bone and cartilage diseases, Alzheimer's disease, lung disease, osteoarthritis, bone/osteoporotic (wrist, spine, shoulder and hip) fractures, articular cartilage (chondral) defects, degenerative disc disease (or intervertebral disc degeneration), polyposis coli, bone density and vascular defects in the eye (Osteoporosis-pseudoglioma Syndrome, OPPG) and other eye diseases or syndromes associated with defects or damaged photoreceptors, familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman's syndrome, Prader-Willi syndrome, Beckwith-Wiedemann Syndrome, Norrie disease, and Rett syndrome.

In some embodiments, non-limiting examples of bone and cartilage diseases which can be treated with the compounds and compositions provided herein include bone spur (osteophytes), craniosynostosis, fibrodysplasia ossificans progressive, fibrous dysplasia, giant cell tumor of bone, hip labral tear, meniscal tears, bone/osteoporotic (wrist, spine, shoulder and hip) fractures, articular cartilage (chondral) defects, degenerative disc disease (or intervertebral disc degeneration), osteochondritis dissecans, osteochondroma (bone tumor), osteopetrosis, relapsing polychondritis, and Salter-Harris fractures.

In some embodiments, pharmaceutical compositions are provided that are effective for treatment of a disease of an animal, e.g., a mammal, caused by the pathological activation or mutations of the Wnt pathway. The composition includes a pharmaceutically acceptable carrier and a compound as described herein.

Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

As used herein, "alkyl" means a branched, or straight chain chemical group containing only carbon and hydrogen, such as methyl, ethyl, n-propyl, iso-propyl, n-butyl, iso-butyl, sec-butyl, tert-butyl, n-pentyl, iso-pentyl, sec-pentyl and neo-pentyl. Alkyl groups can either be unsubstituted or substituted with one or more substituents. Alkyl groups can be saturated or unsaturated (e.g., containing —C=C— or —C≡C— subunits), at one or several positions. In some embodiments, alkyl groups include 1 to 9 carbon atoms (for example, 1 to 6 carbon atoms, 1 to 4 carbon atoms, or 1 to 2 carbon atoms).

As used herein, "alkylene" means a bivalent branched, or straight chain chemical group containing only carbon and hydrogen, such as methylene, ethylene, n-propylene, iso-propylene, n-butylene, iso-butylene, sec-butylene, tert-butylene, n-pentylene, iso-pentylene, sec-pentylene and neo-pentylene. Alkylene groups can either be unsubstituted or substituted with one or more substituents. Alkylene groups can be saturated or unsaturated (e.g., containing —C=C— or —C≡C— subunits), at one or several positions. In some embodiments, alkylene groups include 1 to 9 carbon atoms (for example, 1 to 6 carbon atoms, 1 to 4 carbon atoms, or 1 to 2 carbon atoms).

As used herein, "carbocyclyl" means a cyclic ring system containing only carbon atoms in the ring system backbone, such as cyclopropyl, cyclobutyl, cyclopentyl, cyclohexyl, and cyclohexenyl. Carbocyclyls may include multiple fused rings. Carbocyclyls may have any degree of saturation provided that at least one ring in the ring system is not aromatic. Carbocyclyl groups can either be unsubstituted or substituted with one or more substituents. In some embodiments, carbocyclyl groups include 3 to 10 carbon atoms, for example, 3 to 6 carbon atoms.

As used herein, "lower alkyl" means a subset of alkyl having 1 to 3 carbon atoms, which is linear or branched. Examples of lower alkyls include methyl, ethyl, n-propyl and isopropyl. Likewise, radicals using the terminology "lower" refer to radicals having 1 to about 3 carbons in the alkyl portion of the radical.

As used herein, "aryl" means a mono-, bi-, tri- or polycyclic group with only carbon atoms present in the ring backbone having 5 to 14 ring atoms, alternatively 5, 6, 9, or 10 ring atoms; and having 6, 10, or 14 pi electrons shared in a cyclic array; wherein at least one ring in the system is aromatic. Aryl groups can either be unsubstituted or substituted with one or more substituents. Examples of aryl include phenyl, naphthyl, tetrahydronaphthyl, 2,3-dihydro-1H-indenyl, and others. In some embodiments, the aryl is phenyl.

As used herein, "arylalkyl" means an aryl-alkyl-group in which the aryl and alkyl moieties are as previously described. In some embodiments, arylalkyl groups contain a $C_{1-4}$alkyl moiety. Exemplary arylalkyl groups include benzyl and 2-phenethyl.

As used herein, the term "heteroaryl" means a mono-, bi-, tri- or polycyclic group having 5 to 14 ring atoms, alternatively 5, 6, 9, or 10 ring atoms; and having 6, 10, or 14 pi electrons shared in a cyclic array; wherein at least one ring in the system is aromatic, and at least one ring in the system contains one or more heteroatoms independently selected from the group consisting of N, O, and S. Heteroaryl groups can either be unsubstituted or substituted with one or more substituents. Examples of heteroaryl include thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido[2,3-d]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c]pyridine, pyrazolo[4,3-b]pyridinyl, tetrazolyl, chromane, 2,3-dihydrobenzo[b][1,4]dioxine, benzo[d][1,3]dioxole, 2,3-dihydrobenzofuran, 2,3-dihydrobenzo[b][1,4]oxathiine, and others. In some embodiments, the heteroaryl is selected from thienyl, pyridinyl, furyl, pyrazolyl, imidazolyl, pyranyl, pyrazinyl, and pyrimidinyl.

As used herein, "halo", "halide" or "halogen" is a chloro, bromo, fluoro, or iodo atom radical. In some embodiments, a halo is a chloro, bromo or fluoro. For example, a halide can be fluoro.

As used herein, "haloalkyl" means a hydrocarbon substituent, which is a linear or branched, alkyl, alkenyl or alkynyl substituted with one or more chloro, bromo, fluoro, and/or iodo atom(s). In some embodiments, a haloalkyl is a fluoroalkyls, wherein one or more of the hydrogen atoms have been substituted by fluoro. In some embodiments, haloalkyls are of 1 to about 3 carbons in length (e.g., 1 to about 2 carbons in length or 1 carbon in length). The term "haloalkylene" means a diradical variant of haloalkyl, and such diradicals may act as spacers between radicals, other atoms, or between a ring and another functional group.

As used herein, "heterocyclyl" means a nonaromatic cyclic ring system comprising at least one heteroatom in the ring system backbone. Heterocyclyls may include multiple fused rings. Heterocyclyls may be substituted or unsubstituted with one or more substituents. In some embodiments, heterocycles have 5-7 members. In six membered monocyclic heterocycles, the heteroatom(s) are selected from one to three of O, N or S, and wherein when the heterocycle is five membered, it can have one or two heteroatoms selected from O, N, or S. Examples of heterocyclyl include azirinyl, aziridinyl, azetidinyl, oxetanyl, thietanyl, 1,4,2-dithiazolyl, dihydropyridinyl, 1,3-dioxanyl, 1,4-dioxanyl, 1,3-dioxolanyl, morpholinyl, thiomorpholinyl, piperazinyl, pyranyl, pyrrolidinyl, tetrahydrofuryl, tetrahydropyridinyl, oxazinyl, thiazinyl, thiinyl, thiazolidinyl, isothiazolidinyl, oxazolidinyl, isoxazolidinyl, piperidinyl, pyrazolidinyl imidazolidinyl, thiomorpholinyl, and others. In some embodiments, the heterocyclyl is selected from azetidinyl, morpholinyl, piperazinyl, pyrrolidinyl, and tetrahydropyridinyl.

As used herein, "monocyclic heterocyclyl" means a single nonaromatic cyclic ring comprising at least one heteroatom in the ring system backbone. Heterocyclyls may be substituted or unsubstituted with one or more substituents. In some embodiments, heterocycles have 5-7 members. In six membered monocyclic heterocycles, the heteroatom(s) are selected from one to three of O, N or S, and wherein when the heterocycle is five membered, it can have one or two heteroatoms selected from O, N, or S. Examples of heterocyclyl include azirinyl, aziridinyl, azetidinyl, oxetanyl, thietanyl, 1,4,2-dithiazolyl, dihydropyridinyl, 1,3-dioxanyl, 1,4-dioxanyl, 1,3-dioxolanyl, morpholinyl, thiomorpholinyl, piperazinyl, pyranyl, pyrrolidinyl, tetrahydrofuryl, tetrahydropyridinyl, oxazinyl, thiazinyl, thiinyl, thiazolidinyl, isothiazolidinyl, oxazolidinyl, isoxazolidinyl, piperidinyl, pyrazolidinyl imidazolidinyl, thiomorpholinyl, and others.

The term "substituted" refers to moieties having substituents replacing a hydrogen on one or more non-hydrogen atoms of the molecule. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. Substituents can include, for example, —($C_{1-9}$ alkyl) optionally substituted with one or more of hydroxyl, —$NH_2$, —$NH(C_{1-3}$ alkyl), and —$N(C_{1-3}$ alkyl)$_2$; —($C_{1-9}$ haloalkyl); a halide; a hydroxyl; a carbonyl [such as —C(O)OR, and —C(O)R]; a thiocarbonyl [such as —C(S)OR, —C(O)SR, and —C(S)R]; —($C_{1-9}$ alkoxyl) optionally substituted with one or more of halide, hydroxyl, —$NH_2$, —$NH(C_{1-3}$ alkyl), and —$N(C_{1-3}$ alkyl)$_2$; —$OPO(OH)_2$; a phosphonate [such as —$PO(OH)_2$ and —$PO(OR')_2$]; —OPO(OR')R"; —NRR'; —C(O)NRR'; —C(NR)NR'R"; —C(NR')R"; a cyano; a nitro; an azido; —SH; —S—R; —$SO_2(OR)$; a sulfonate [such as —$SO_2$(OH) and —$SO_2(OR)$]; —$SO_2NR'R$"; and —$SO_2R$; in which each occurrence of R, R' and R" are independently selected from H; —($C_{1-9}$ alkyl); $C_{6-10}$ aryl optionally substituted with from 1-3R'''; 5-10 membered heteroaryl having from 1-4 heteroatoms independently selected from N, O, and S and optionally substituted with from 1-3 R'''; $C_{3-7}$ carbocyclyl optionally substituted with from 1-3 R'''; and 3-8 membered heterocyclyl having from 1-4 heteroatoms independently selected from N, O, and S and optionally substituted with from 1-3 R'''; wherein each R''' is independently selected from —($C_{1-6}$ alkyl), —($C_{1-6}$ haloalkyl), a halide (e.g., F), a hydroxyl, —C(O)OR, —C(O)R, —($C_{1-6}$ alkoxyl), —NRR', —C(O)NRR', and a cyano, in which each occurrence of R and R' is independently selected from H and —($C_{1-6}$ alkyl). In some embodiments, the substituent is selected from —($C_{1-6}$ alkyl), —($C_{1-6}$ haloalkyl), a halide (e.g., F), a hydroxyl, —C(O)OR, —C(O)R, —($C_{1-6}$ alkoxyl), —NRR', —C(O)NRR', and a cyano, in which each occurrence of R and R' is independently selected from H and —($C_{1-6}$ alkyl).

As used herein, when two groups are indicated to be "linked" or "bonded" to form a "ring", it is to be understood that a bond is formed between the two groups and may involve replacement of a hydrogen atom on one or both groups with the bond, thereby forming a carbocyclyl, heterocyclyl, aryl, or heteroaryl ring. The skilled artisan will recognize that such rings can and are readily formed by routine chemical reactions. In some embodiments, such rings have from 3-7 members, for example, 5 or 6 members.

The skilled artisan will recognize that some structures described herein may be resonance forms or tautomers of compounds that may be fairly represented by other chemical structures, even when kinetically, the artisan recognizes that such structures are only a very small portion of a sample of such compound(s). Such compounds are clearly contemplated within the scope of this disclosure, though such resonance forms or tautomers are not represented herein.

The compounds provided herein may encompass various stereochemical forms. The compounds also encompass diastereomers as well as optical isomers, e.g., mixtures of enantiomers including racemic mixtures, as well as individual enantiomers and diastereomers, which arise as a consequence of structural asymmetry in certain compounds. Separation of the individual isomers or selective synthesis of the individual isomers is accomplished by application of various methods which are well known to practitioners in the art. Unless otherwise indicated, when a disclosed compound is named or depicted by a structure without specifying the stereochemistry and has one or more chiral centers, it is understood to represent all possible stereoisomers of the compound.

The term "administration" or "administering" refers to a method of providing a dosage of a compound or pharmaceutical composition to a vertebrate or invertebrate, including a mammal, a bird, a fish, or an amphibian, where the method is, e.g., orally, subcutaneously, intravenously, intralymphatic, intranasally, topically, transdermally, intraperitoneally, intramuscularly, intrapulmonarilly, vaginally, rectally, ontologically, neuro-otologically, intraocularly, subconjuctivally, via anterior eye chamber injection, intravitreally, intraperitoneally, intrathecally, intracystically, intrapleurally, via wound irrigation, intrabuccally, intraabdominally, intra-articularly, intra-aurally, intrabronchially, intracapsularly, intrameningeally, via inhalation, via endotracheal or endobronchial instillation, via direct instillation into pulmonary cavities, intraspinally, intrasynovially, intrathoracically, via thoracostomy irrigation, epidurally, intratympanically, intracisternally, intravascularly, intraventricularly, intraosseously, via irrigation of infected bone, or via application as part of any admixture with a prosthetic device. The method of administration can vary depending on various factors, e.g., the components of the pharmaceutical composition, the site of the disease, the disease involved, and the severity of the disease.

A "diagnostic" as used herein is a compound, method, system, or device that assists in the identification or characterization of a health or disease state. The diagnostic can be used in standard assays as is known in the art.

The term "mammal" is used in its usual biological sense. Thus, it specifically includes humans, cattle, horses, monkeys, dogs, cats, mice, rats, cows, sheep, pigs, goats, and non-human primates, but also includes many other species.

The term "pharmaceutically acceptable carrier", "pharmaceutically acceptable diluent" or "pharmaceutically acceptable excipient" includes any and all solvents, co-solvents, complexing agents, dispersion media, coatings, isotonic and absorption delaying agents and the like which are not biologically or otherwise undesirable. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (2010); *Goodman and Gilman's: The Pharmacological Basis of Therapeutics, 12th Ed.,* The McGraw-Hill Companies.

The term "pharmaceutically acceptable salt" refers to salts that retain the biological effectiveness and properties of the compounds provided herein and, which are not biologically or otherwise undesirable. In many cases, the compounds provided herein are capable of forming acid and/or base salts by virtue of the presence of amino and/or carboxyl groups or groups similar thereto. Many such salts are known in the art, for example, as described in WO 87/05297. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium, and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine.

"Solvate" refers to the compound formed by the interaction of a solvent and a compound as provided herein or a salt thereof. Suitable solvates are pharmaceutically acceptable solvates including hydrates.

"Patient" as used herein, means a human or a non-human mammal, e.g., a dog, a cat, a mouse, a rat, a cow, a sheep, a pig, a goat, a non-human primate, or a bird, e.g., a chicken, as well as any other vertebrate or invertebrate. In some embodiments, the patient is a human.

A "therapeutically effective amount" or "pharmaceutically effective amount" of a compound as provided herein is one which is sufficient to achieve the desired physiological effect and may vary according to the nature and severity of the disease condition, and the potency of the compound. "Therapeutically effective amount" is also intended to include one or more of the compounds of Formula I in combination with one or more other agents that are effective to treat the diseases and/or conditions described herein. The combination of compounds can be a synergistic combination. Synergy, as described, for example, by Chou and Talalay, *Advances in Enzyme Regulation* (1984), 22, 27-55, occurs when the effect of the compounds when administered in combination is greater than the additive effect of the compounds when administered alone as a single agent. In general, a synergistic effect is most clearly demonstrated at sub-optimal concentrations of the compounds. It will be appreciated that different concentrations may be employed for prophylaxis than for treatment of an active disease. This amount can further depend upon the patient's height, weight, sex, age and medical history.

A therapeutic effect relieves, to some extent, one or more of the symptoms of the disease.

"Treat," "treatment," or "treating," as used herein refers to administering a compound or pharmaceutical composition as provided herein for therapeutic purposes. The term "therapeutic treatment" refers to administering treatment to a patient already suffering from a disease thus causing a therapeutically beneficial effect, such as ameliorating existing symptoms, ameliorating the underlying metabolic causes of symptoms, postponing or preventing the further development of a disorder, and/or reducing the severity of symptoms that will or are expected to develop.

"Drug-eluting" and/or controlled release as used herein refers to any and all mechanisms, e.g., diffusion, migration, permeation, and/or desorption by which the drug(s) incorporated in the drug-eluting material pass therefrom over time into the surrounding body tissue.

"Drug-eluting material" and/or controlled release material as used herein refers to any natural, synthetic or semi-synthetic material capable of acquiring and retaining a desired shape or configuration and into which one or more drugs can be incorporated and from which incorporated drug(s) are capable of eluting over time.

"Elutable drug" as used herein refers to any drug or combination of drugs having the ability to pass over time from the drug-eluting material in which it is incorporated into the surrounding areas of the body.

The term "comprising" as used herein is synonymous with "including," "containing," or "characterized by," and is inclusive or open-ended and does not exclude additional, unrecited elements or method steps.

Compounds

The compounds and compositions described herein can be used as anti-proliferative agents, e.g., anti-cancer and anti-angiogenesis agents, and/or as inhibitors of the Wnt signaling pathway, e.g., for treating diseases or disorders associated with aberrant Wnt signaling. In addition, the compounds can be used as inhibitors of one or more kinases, kinase receptors, or kinase complexes. Such compounds and compositions are also useful for controlling cellular proliferation, differentiation, and/or apoptosis.

Some embodiments of the present disclosure include compounds of Formula I:

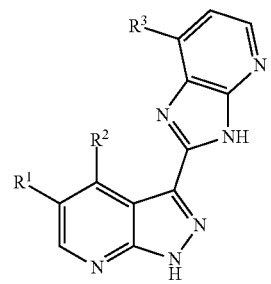

or salts, pharmaceutically acceptable salts, or prodrugs thereof.

In some embodiments, $R^1$ is selected from the group consisting of -pyridinyl($R^4$) and -pyrimidinyl($R^5$).

In some embodiments, $R^1$ is selected from the group consisting of -heteroaryl($R^4$)$_q$ and -heterocyclyl($R^5$)$_h$.

In some embodiments, $R^1$ is selected from the group consisting of -piperidinyl($R^5$)$_h$ and -tetrahydropyridinyl ($R^5$)$_h$.

In some embodiments, $R^1$ is selected from the group consisting of -pyridinyl($R^4$)$_q$, -pyrimidinyl($R^4$)$_q$, -pyrazinyl ($R^4$)$_q$, -pyrazolyl($R^4$)$_q$, and -imidazolyl($R^4$)$_q$.

In some embodiments, $R^2$ is selected from the group consisting of H and halide.

In some embodiments, $R^3$ is selected from the group consisting of -heteroaryl($R^6$)$_q$, -heterocyclyl($R^7$)$_h$, and -aryl ($R^8$)$_k$.

In some embodiments, $R^3$ is selected from the group consisting of H, -heteroaryl($R^6$)$_q$, -heterocyclyl($R^7$)$_h$, and -aryl($R^8$)$_k$.

In some embodiments, $R^3$ is selected from the group consisting of -pyridinyl($R^6$)$_q$, -imidazolyl($R^6$)$_q$, -furanyl ($R^6$)$_q$, -thiophenyl($R^6$)$_q$, -piperidinyl($R^7$)$_h$, -piperazinyl ($R^7$)$_h$, and -phenyl($R^8$)$_k$.

In some embodiments, $R^4$ is one substituent attached to the pyridinyl and is independently selected from the group consisting of H, halide, —($C_{1-6}$ alkyl), —($C_{1-4}$ alkylene)$_p$heterocyclyl($R^9$)$_h$, —($C_{1-4}$ alkylene)$_p$carbocyclyl ($R^{10}$)$_j$, —($C_{1-4}$ alkylene)$_p$aryl($R^{11}$)$_k$, —NHC(=O)$R^{12}$, —$NR^{13}R^{14}$, and —($C_{1-6}$ alkylene)$NR^{15}R^{16}$.

In some embodiments, each $R^4$ is one substituent attached to the heteroaryl and is independently selected from the group consisting of halide, —($C_{1-6}$ alkyl), —($C_{1-4}$ alkylene)$_p$heterocyclyl($R^9$)$_h$, —($C_{1-4}$ alkylene)$_p$carbocyclyl ($R^{10}$)$_j$, —($C_{1-4}$ alkylene)$_p$aryl($R^{11}$)$_k$, —NHC(=O)$R^{12}$, —$NR^{13}R^{14}$, —($C_{1-6}$ alkylene)$NR^{15}R^{16}$, and —$OR^{22}$.

In some embodiments, each $R^4$ is one substituent attached to the heteroaryl and is independently selected from the group consisting of F, -Me, -Et, —(CH$_2$)heterocyclyl($R^9$)$_h$, -heterocyclyl($R^9$)$_h$, —(CH$_2$)carbocyclyl($R^{10}$)$_j$, —(CH$_2$)aryl ($R^{11}$)$_k$, —NHC(=O)($C_{1-5}$ alkyl), —NHC(=O)phenyl($R^{19}$)$_k$, —NHC(=O)(CH$_2$)phenyl($R^{19}$)$_k$, —NHC(=O)carbocyclyl($R^{20}$)$_j$, —NHC(=O)(CH$_2$)heterocyclyl ($R^{21}$)$_h$, —NH$_2$, —N($C_{1-3}$ alkyl)$_2$, —NH($C_{1-4}$ alkyl), —(CH$_2$)N($C_{1-3}$ alkyl)$_2$, —(CH$_2$)NH($C_{1-4}$ alkyl), —OH, —O($C_{1-3}$ alkyl), —Ocarbocyclyl($R^{20}$)$_j$, —Oheterocyclyl ($R^2$)$_h$, —O(CH$_2$CH$_2$)heterocyclyl($R^{21}$)$_h$, —O(CH$_2$CH$_2$)N ($C_{1-3}$ alkyl)$_2$, and —O(CH$_2$)phenyl($R^{19}$)$_k$.

In some embodiments, $R^5$ is one substituent attached to the pyrimidinyl and is independently selected from the group consisting of H, halide, —($C_{1-6}$ alkyl), —($C_{1-4}$ alkylene)$_p$heterocyclyl($R^9$)$_h$, —($C_{1-4}$ alkylene)$_p$carbocyclyl ($R^{10}$)$_j$, —($C_{1-4}$ alkylene)$_p$aryl($R^{11}$)$_k$, —NHC(=O)$R^{12}$, —$NR^{13}R^{14}$, and —($C_{1-6}$ alkylene)$NR^{15}R^{16}$.

In some embodiments, each $R^5$ is one substituent attached to the heterocyclyl and is independently selected from the group consisting of —($C_{1-4}$ alkyl), halide, —CF$_3$, and —CN.

In some embodiments, each $R^6$ is one substituent attached to the heteroaryl and is independently selected from the group consisting of H, —($C_{1-6}$ alkyl), halide, —CF$_3$, —OCH$_3$, —CN, and —C(=O)$R^{17}$.

In some embodiments, each $R^6$ is one substituent attached to the heteroaryl and is independently selected from the group consisting of —($C_{1-6}$ alkyl), halide, —CF$_3$, —OCH$_3$, —CN, and —C(=O)$R^{17}$.

In some embodiments, each $R^6$ is one substituent attached to the heteroaryl and is independently selected from the group consisting of -Me, -Et, F, —CF$_3$, —OCH$_3$, —CN, and —C(=O)($C_{1-3}$ alkyl).

In some embodiments, each $R^7$ is one substituent attached to the heterocyclyl and is independently selected from the group consisting of H, —($C_{1-6}$ alkyl), halide, —CF$_3$, —CN, and —OCH$_3$.

In some embodiments, each $R^7$ is one substituent attached to the heterocyclyl and is independently selected from the group consisting of —($C_{1-6}$ alkyl), halide, —CF$_3$, —CN, and —OCH$_3$.

In some embodiments, each $R^8$ is one substituent attached to the aryl and is independently selected from the group consisting of H, —($C_{1-6}$ alkyl), halide, —CF$_3$, —CN, —OCH$_3$, —($C_{1-6}$ alkylene)$_p$NHSO$_2R^{17}$, —$NR^{13}$($C_{1-6}$ alkylene)$NR^{13}R^{14}$, and —($C_{1-6}$ alkylene)$_p$$NR^{13}R^{14}$.

In some embodiments, each $R^8$ is one substituent attached to the aryl and is independently selected from the group consisting of —($C_{1-6}$ alkyl), halide, —CF$_3$, —CN, —OCH$_3$, —($C_{1-6}$ alkylene)$_p$NHSO$_2R^{17}$, —$NR^{13}$($C_{1-6}$ alkylene)$NR^{13}R^{14}$, —($C_{1-6}$ alkylene)$_p$$NR^{13}R^{14}$, and —$OR^{25}$.

In some embodiments, each $R^8$ is one substituent attached to the aryl and is independently selected from the group consisting of -Me, -Et, F, —CF$_3$, —CN, —OCH$_3$, —(CH$_2$CH$_2$)NHSO$_2$($C_{1-3}$ alkyl), —NH(CH$_2$CH$_2$)N($C_{1-3}$ alkyl)$_2$, —OH, —O($C_{1-3}$ alkyl), —O(CH$_2$CH$_2$)heterocyclyl ($R^{21}$)$_h$, and —O(CH$_2$CH$_2$)N($C_{1-3}$ alkyl)$_2$.

In some embodiments, each $R^9$ is one substituent attached to the heterocyclyl and is independently selected from the group consisting of H, —($C_{1-4}$ alkyl), halide, —CF$_3$, and —CN.

In some embodiments, each $R^9$ is one substituent attached to the heterocyclyl and is independently selected from the group consisting of amino, —($C_{1-4}$ alkyl), halide, —CF$_3$, and —CN.

In some embodiments, each $R^9$ is one substituent attached to the heterocyclyl and is independently selected from the group consisting of amino, Me, Et, F, Cl, and —CF$_3$.

In some embodiments, each $R^{10}$ is one substituent attached to the carbocyclyl and is independently selected from the group consisting of H, —($C_{1-4}$ alkyl), halide, —CF$_3$, and —CN.

In some embodiments, each $R^{10}$ is one substituent attached to the carbocyclyl and is independently selected from the group consisting of —($C_{1-4}$ alkyl), halide, —CF$_3$, and —CN.

In some embodiments, each $R^{10}$ is one substituent attached to the carbocyclyl and is independently selected from the group consisting of Me, Et, F, Cl, and —CF$_3$.

In some embodiments, each $R^{11}$ is one substituent attached to the aryl and is independently selected from the group consisting of H, —($C_{1-4}$ alkyl), halide, —CF$_3$, and —CN.

In some embodiments, each $R^{11}$ is one substituent attached to the aryl and is independently selected from the group consisting of —($C_{1-4}$ alkyl), halide, —CF$_3$, and —CN.

In some embodiments, each $R^{11}$ is one substituent attached to the aryl and is independently selected from the group consisting of Me, Et, F, Cl, and —CF$_3$.

In some embodiments, each $R^{12}$ is independently selected from the group consisting of —($C_{1-9}$ alkyl), -heteroaryl ($R^{18}$)$_q$, -aryl($R^{19}$)$_k$, —CH$_2$aryl($R^{19}$)$_k$, -carbocyclyl($R^{20}$)$_j$, and —CH$_2$carbocyclyl($R^{20}$)$_j$.

In some embodiments, each $R^{12}$ is independently selected from the group consisting of —($C_{1-9}$ alkyl), -heteroaryl ($R^{18}$)$_q$, -aryl($R^{19}$)$_k$, —CH$_2$aryl($R^{19}$)$_k$, -carbocyclyl($R^{20}$)$_j$, —CH$_2$carbocyclyl($R^{20}$)$_j$, —($C_{1-4}$ alkylene)$_p$$NR^{23}R^{24}$, -heterocyclyl($R^{21}$)$_h$, and —CH$_2$heterocyclyl($R^{21}$)$_h$.

In some embodiments, each $R^{12}$ is independently selected from the group consisting of —($C_{1-5}$ alkyl), -phenyl($R^{19}$)$_k$, —(CH$_2$)phenyl($R^{19}$)$_k$, -carbocyclyl($R^{20}$)$_j$, —(CH$_2$)carbocyclyl($R^{20}$)$_j$, —(CH$_2$)N($C_{1-3}$ alkyl)$_2$, and —(CH$_2$)heterocyclyl ($R^{21}$)$_h$.

In some embodiments, each $R^{13}$ is independently selected from the group consisting of H and —($C_{1-6}$ alkyl).

In some embodiments, each $R^{13}$ is independently selected from the group consisting of H and —($C_{1-3}$ alkyl).

In some embodiments, each $R^{14}$ is independently selected from the group consisting of H, —($C_{1-6}$ alkyl), —CH$_2$aryl ($R^{19}$)$_k$, and —CH$_2$carbocyclyl($R^{20}$)$_j$.

In some embodiments, each $R^{14}$ is independently selected from the group consisting of H, —($C_{1-3}$ alkyl), —CH$_2$phenyl($R^{19}$)$_k$, and —CH$_2$carbocyclyl($R^{20}$)$_j$.

In some embodiments, each $R^{15}$ is independently selected from the group consisting of H and —($C_{1-6}$ alkyl).

In some embodiments, each $R^{15}$ is independently selected from the group consisting of H and —($C_{1-3}$ alkyl).

In some embodiments, each $R^{16}$ is independently selected from the group consisting of H, —($C_{1-6}$ alkyl), —CH$_2$aryl ($R^{19}$)$_k$, and —CH$_2$carbocyclyl($R^{20}$)$_j$.

In some embodiments, each $R^{16}$ is independently selected from the group consisting of H, —($C_{1-3}$ alkyl), —$CH_2$phenyl($R^{19}$)$_k$, and —$CH_2$carbocyclyl($R^{20}$)$_j$.

In some embodiments, each $R^{17}$ is independently a —($C_{1-6}$ alkyl).

In some embodiments, each $R^{17}$ is independently a —($C_{1-3}$ alkyl).

In some embodiments, each $R^{18}$ is one substituent attached to the heteroaryl and is independently selected from the group consisting of H, —($C_{1-4}$ alkyl), halide, —$CF_3$, and —CN.

In some embodiments, each $R^{18}$ is one substituent attached to the heteroaryl and is independently selected from the group consisting of —($C_{1-4}$ alkyl), halide, —$CF_3$, and —CN.

In some embodiments, each $R^{18}$ is one substituent attached to the heteroaryl and is independently selected from the group consisting of Me, Et, F, Cl, and —$CF_3$.

In some embodiments, each $R^{19}$ is one substituent attached to the aryl and is independently selected from the group consisting of H, —($C_{1-4}$ alkyl), halide, —$CF_3$, and —CN.

In some embodiments, each $R^{19}$ is one substituent attached to the aryl and is independently selected from the group consisting of —($C_{1-4}$ alkyl), halide, —$CF_3$, and —CN.

In some embodiments, each $R^{19}$ is one substituent attached to the aryl and is independently selected from the group consisting of Me, Et, F, Cl, and —$CF_3$.

In some embodiments, each $R^{20}$ is one substituent attached to the carbocyclyl and is independently selected from the group consisting of H, —($C_{1-4}$ alkyl), halide, —$CF_3$, and —CN.

In some embodiments, each $R^{20}$ is one substituent attached to the carbocyclyl and is independently selected from the group consisting of —($C_{1-4}$ alkyl), halide, —$CF_3$, and —CN.

In some embodiments, each $R^{20}$ is one substituent attached to the carbocyclyl and is independently selected from the group consisting of Me, Et, F, Cl, and —$CF_3$.

In some embodiments, each $R^{21}$ is one substituent attached to the heterocyclyl and is independently selected from the group consisting of —($C_{1-4}$ alkyl), halide, —$CF_3$, and —CN.

In some embodiments, each $R^{21}$ is one substituent attached to the heterocyclyl and is independently selected from the group consisting of Me, Et, F, Cl, and —$CF_3$.

In some embodiments, $R^{22}$ is selected from the group consisting of H, —($C_{1-6}$ alkyl), —($C_{1-4}$ alkylene)$_p$heterocyclyl($R^{21}$)$_h$, —($C_{1-4}$ alkylene)$_p$carbocyclyl($R^{20}$)$_j$, —($C_{1-4}$ alkylene)$_p$aryl($R^{19}$)$_k$, and —($C_{1-6}$ alkylene)$_p$N$R^{23}R^{24}$.

In some embodiments, $R^{22}$ is selected from the group consisting of H, -Me, -Et, -iPr, -heterocyclyl($R^{21}$)$_h$, —($CH_2CH_2$)heterocyclyl($R^{21}$)$_h$, -carbocyclyl($R^{20}$)$_j$, —($CH_2$)phenyl($R^{19}$)$_k$, and —($CH_2CH_2$)N($C_{1-3}$ alkyl)$_2$.

In some embodiments, each $R^{23}$ is independently selected from the group consisting of H and —($C_{1-6}$ alkyl).

In some embodiments, each $R^{23}$ is independently selected from the group consisting of Me and Et.

In some embodiments, each $R^{24}$ is independently selected from the group consisting of H and —($C_{1-6}$ alkyl).

In some embodiments, each $R^{24}$ is independently selected from the group consisting of Me and Et.

In some embodiments, $R^{25}$ is selected from the group consisting of H, —($C_{1-6}$ alkyl), —($C_{1-4}$ alkylene)$_p$heterocyclyl($R^{21}$)$_h$, and —($C_{1-6}$ alkylene)$_p$N$R^{23}R^{24}$.

In some embodiments, $R^{25}$ is selected from the group consisting of H, -Me, -Et, -iPr, —($CH_2CH_2$)heterocyclyl($R^{21}$)$_h$, and —($CH_2CH_2$)N($C_{1-3}$ alkyl)$_2$.

In some embodiments, each p is independently 0 or 1.

In some embodiments, each q is independently 1 to 4.

In some embodiments, each h is independently 1 to 10.

In some embodiments, each k is independently 1 to 5.

In some embodiments, each j is independently 1 to 12.

In some embodiments, each p is independently 0 or 1; in some embodiments, each p is 0; in some embodiments, each p 1.

In some embodiments, each q is independently 0 to 4; in some embodiments, each q is 0; in some embodiments, each q is 1; in some embodiments, each q is 2; in some embodiments, each q is 3; in some embodiments, each q is 4.

In some embodiments, each h is independently 0 to 10; in some embodiments, each h is 0; in some embodiments, each h is 1; in some embodiments, each h is 2; in some embodiments, each h is 3; in some embodiments, each h is 4.

In some embodiments, each k is independently 0 to 5; in some embodiments, each k is 0; in some embodiments, each k is 1; in some embodiments, each k is 2; in some embodiments, each k is 3.

In some embodiments, each j is independently 0 to 12; in some embodiments, each j is 0; in some embodiments, each j is 1; in some embodiments, each j is 2; in some embodiments, each j is 3; in some embodiments, each j is 4.

In some embodiments, there is the proviso that the compound of Formula I is not a structure selected from the group consisting of:

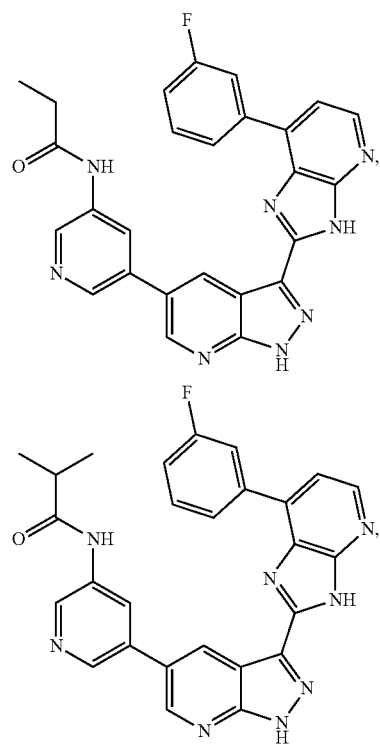

15
-continued
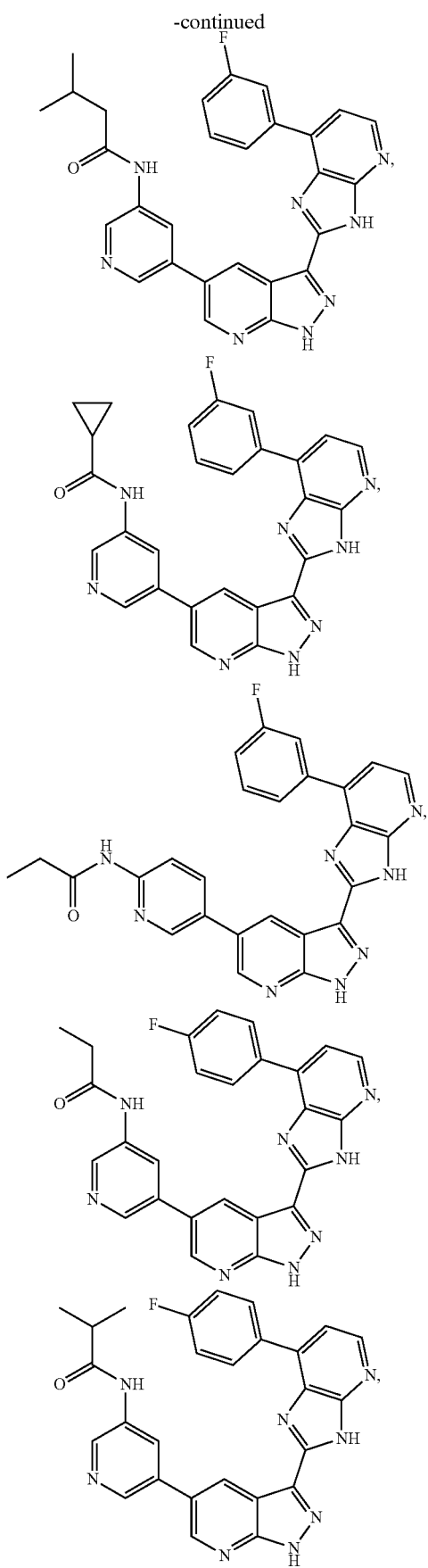
16
-continued
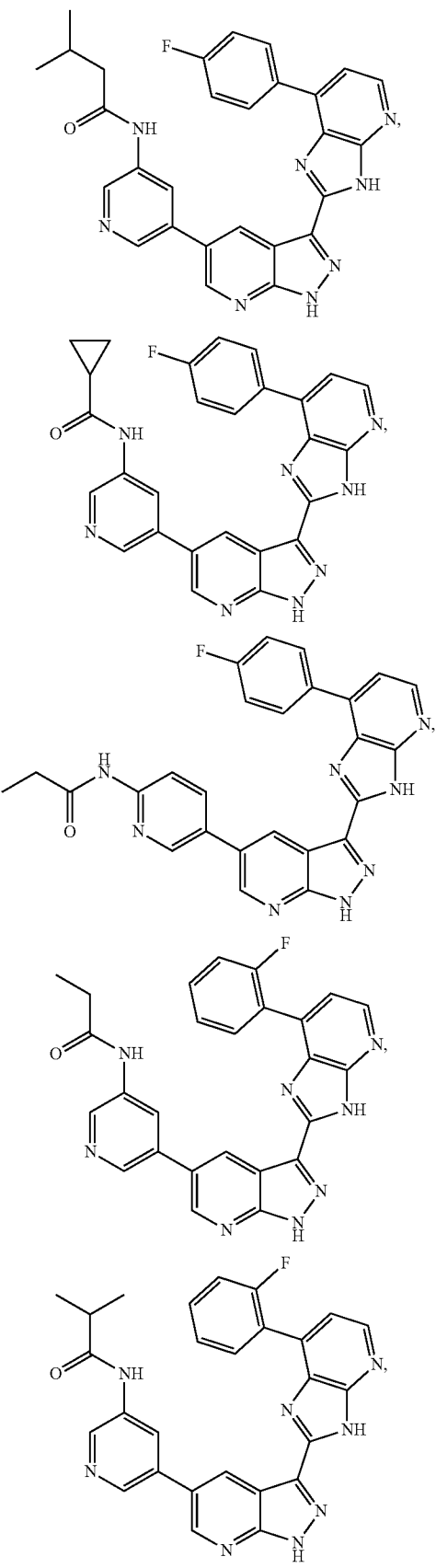

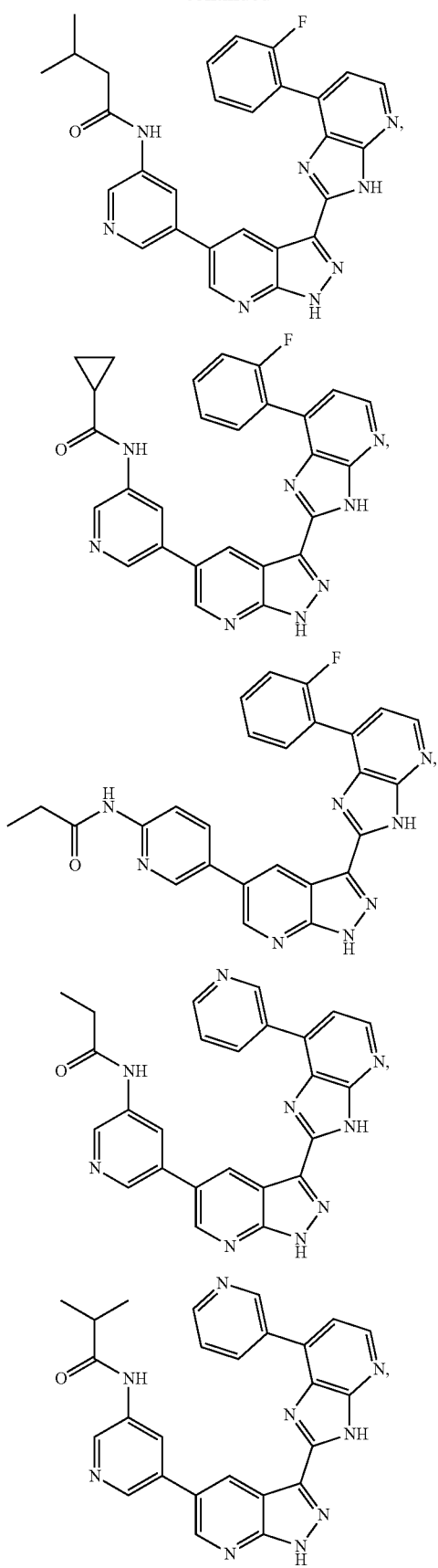
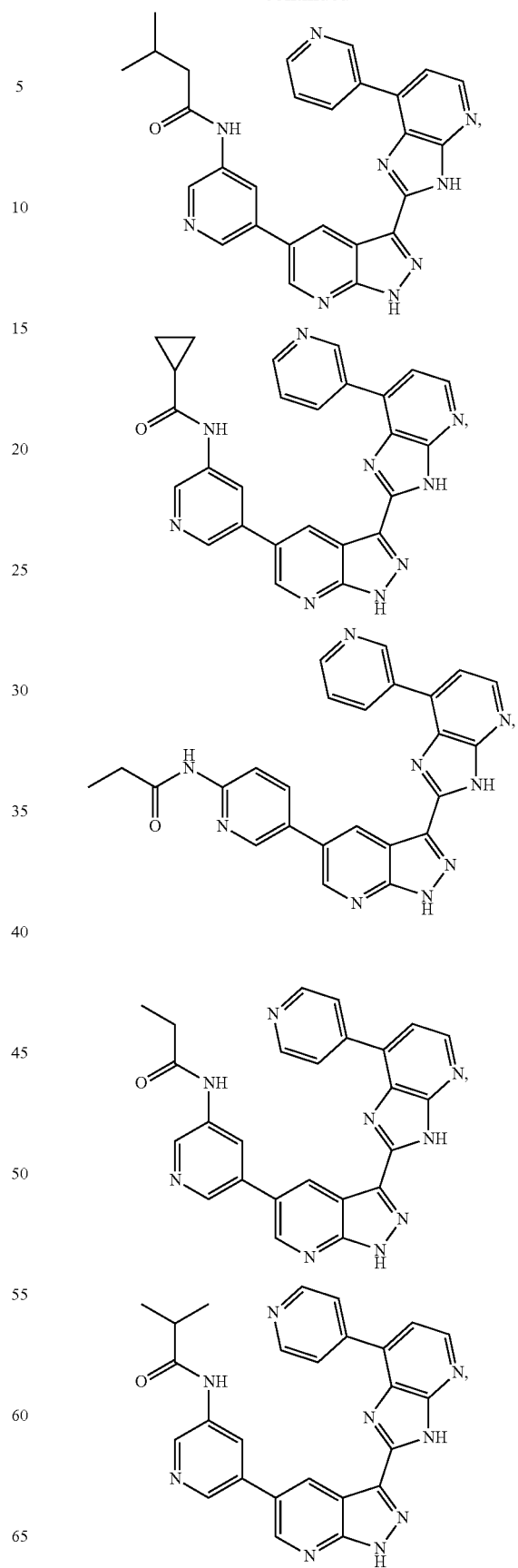

-continued
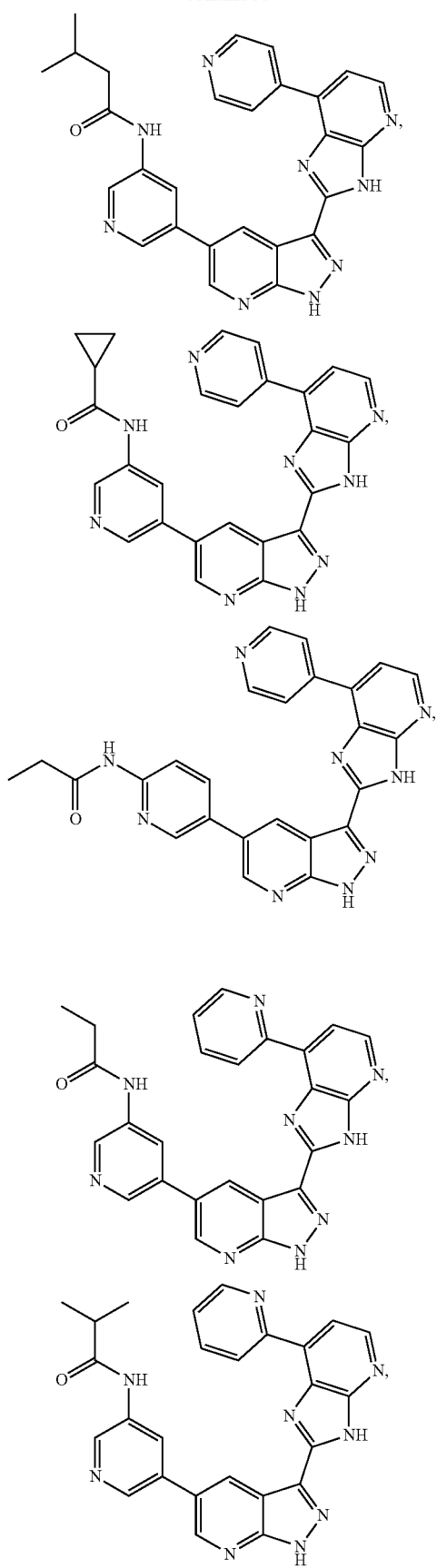
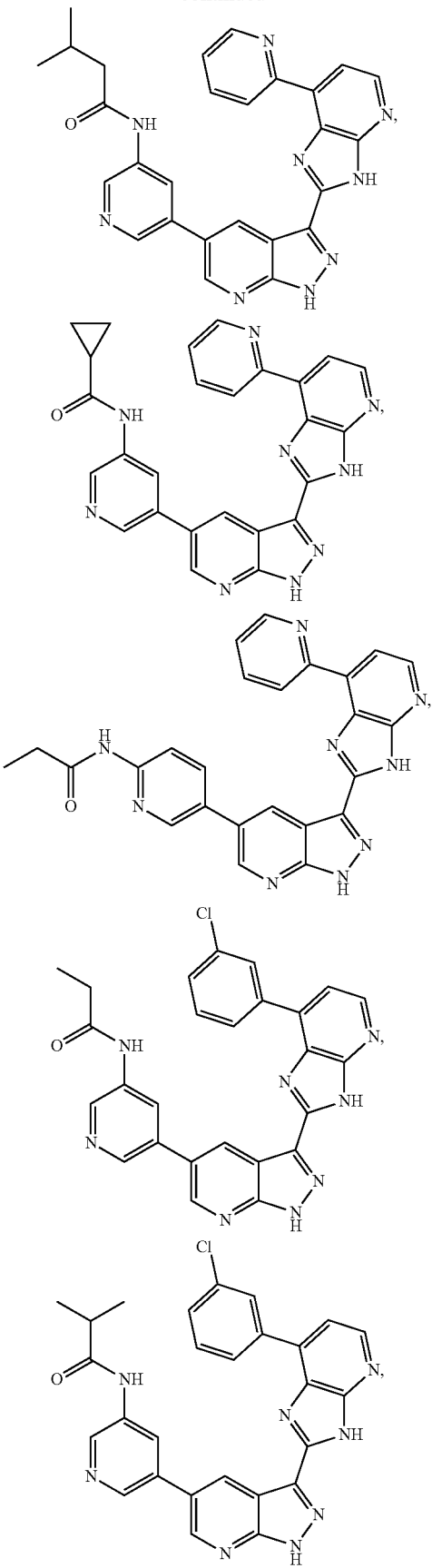

-continued

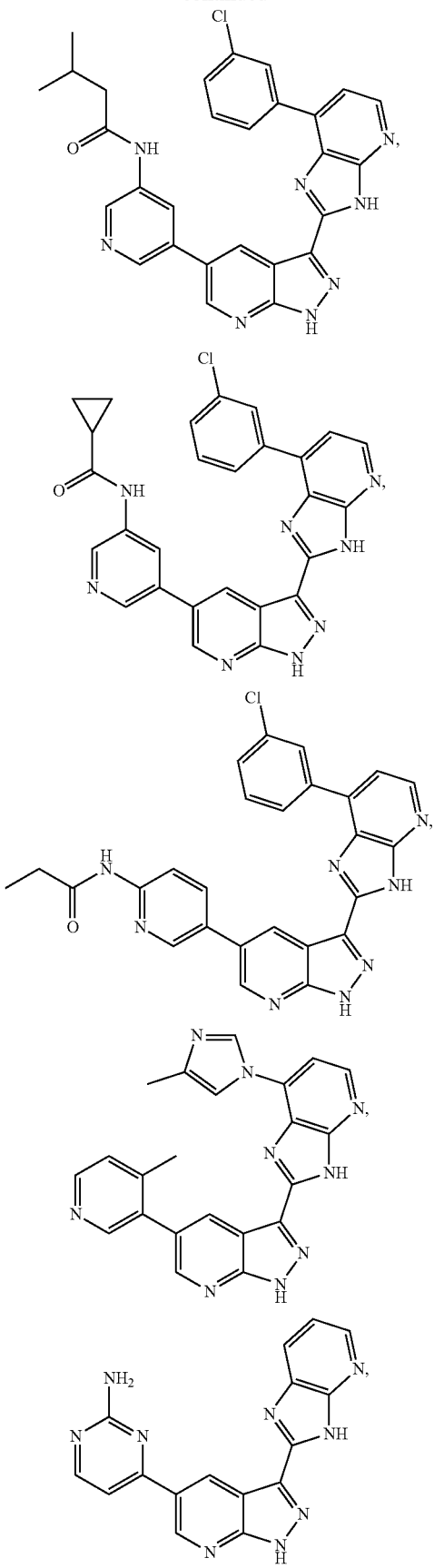

-continued

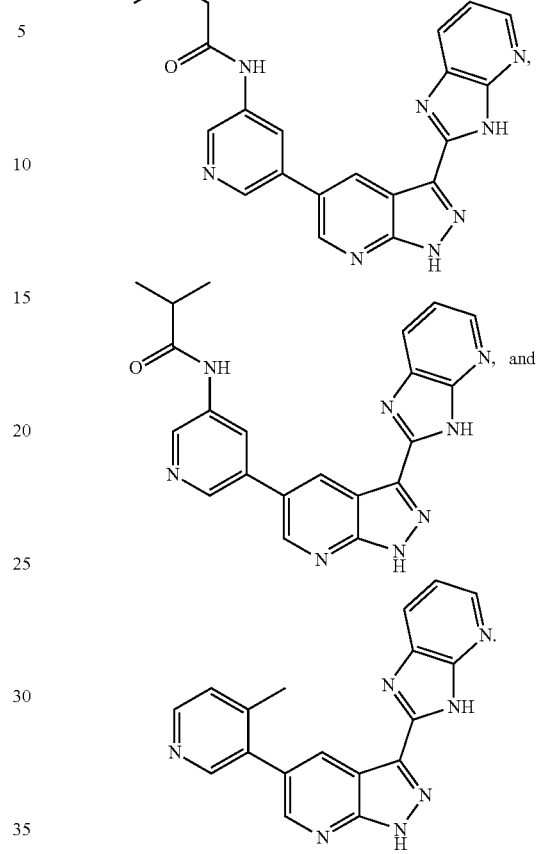

In some embodiments, each R⁴ is one substituent attached to the heteroaryl ring and is selected from the group consisting of —($C_{1-3}$ alkyl), —$CH_2$heterocyclyl($R^9)_h$, —NHC(=O)$R^{12}$, —$NR^{13}R^{14}$, and $CH_2NR^{15}R^{16}$.

In some embodiments, at least one $R^9$ is halide.

In some embodiments, $R^{12}$ is selected from the group consisting of —($C_{1-5}$ alkyl), -phenyl($R^{19})_k$, —$CH_2$phenyl($R^{19})_k$, and -carbocyclyl($R^{20})_j$.

In some embodiments, $R^{13}$ and $R^{14}$ are independently selected from H and —($C_{1-5}$ alkyl).

In some embodiments, $R^{15}$ and $R^{16}$ are independently selected from H and —($C_{1-5}$ alkyl).

In some embodiments, k is 1 or 2 and each $R^8$ is independently a halide.

In some embodiments, k is 2, one $R^8$ is halide and the other $R^8$ is —$CH_2NHSO_2R^{17}$.

In some embodiments, $R^{17}$ is —($C_{1-3}$ alkyl).

In some embodiments, k is 2, one $R^8$ is halide and the other $R^8$ is —$NHCH_2CH_2NR^{13}R^{14}$.

In some embodiments, $R^{13}$ and $R^{14}$ are independently selected from H and —($C_{1-3}$ alkyl).

In some embodiments, $R^3$ is selected from the group consisting of -pyridinyl($R^6)_q$, -imidazolyl($R^6)_q$, -furanyl($R^6)_q$, and -thiophenyl($R^6)_q$.

In some embodiments, q is 0 or 1, $R^6$ is selected from the group consisting of halide, —($C_{1-3}$ alkyl), and —C(=O)$R^{17}$, wherein $R^{17}$ is —($C_{1-2}$ alkyl).

In some embodiments, $R^3$ is selected from the group consisting of -piperidinyl($R^7)_h$ and -piperazinyl($R^7)_h$.

In some embodiments, q is 1, and $R^7$ is selected from the group consisting of H and —($C_{1-3}$ alkyl).

In some embodiments, $R^2$ is H; in other embodiments, $R^2$ is halide, e.g. F.

In some embodiments, $R^1$ is -heteroaryl$(R^4)_q$.
In some embodiments, $R^1$ is -pyridinyl$(R^4)_q$.
In some embodiments, $R^1$ is -pyridin-3-yl$(R^4)_q$.
In some embodiments, $R^1$ is -pyrimidinyl$(R^4)_q$.
In some embodiments, $R^1$ is -pyrimidin-5-yl$(R^4)_q$.
In some embodiments, $R^1$ is -pyrimidin-5-yl$(R^4)_q$ and q is 0.
In some embodiments, $R^1$ is -pyrazinyl$(R^4)_q$.
In some embodiments, $R^1$ is -pyrazolyl$(R^4)_q$.
In some embodiments, $R^1$ is -pyrazol-4-yl$(R^4)_q$, q is 1, and $R^4$ is Me.
In some embodiments, $R^1$ is -pyrazol-4-yl$(R^4)_q$ and q is 0.
In some embodiments, $R^1$ is -imidazolyl$(R^4)_q$.
In some embodiments, $R^1$ is -imidazol-5-yl$(R^4)_q$, q is 1, and $R^4$ is Me.
In some embodiments, $R^1$ is -imidazol-5-yl$(R^4)_q$, q is 2, and both $R^4$ are Me.
In some embodiments, $R^1$ is -heterocyclyl$(R^5)_h$.
In some embodiments, $R^1$ is -piperidinyl$(R^5)_h$.
In some embodiments, $R^1$ is -piperidin-4-yl$(R^5)_h$.
In some embodiments, $R^1$ is -piperidin-4-yl$(R^5)_h$, and h is 0.
In some embodiments, $R^1$ is -tetrahydropyridinyl$(R^5)_h$.
In some embodiments, $R^1$ is -1,2,3,6-tetrahydropyridinyl$(R^5)_h$.
In some embodiments, $R^1$ is -1,2,3,6-tetrahydropyridinyl$(R^5)_h$, and h is 0.
In some embodiments, $R^3$ is H.
In some embodiments, $R^3$ is -heteroaryl$(R^6)_q$.
In some embodiments, $R^3$ is -heterocyclyl$(R^7)_h$.
In some embodiments, $R^3$ is -piperidinyl$(R^7)_h$.
In some embodiments, $R^3$ is -piperazinyl$(R^7)_h$.
In some embodiments, $R^3$ is -aryl$(R^8)_k$.
In some embodiments, $R^3$ is -pyridinyl$(R^6)_q$.
In some embodiments, $R^3$ is -pyridin-3-yl$(R^6)_q$.
In some embodiments, $R^3$ is -pyridin-4-yl$(R^6)_q$.
In some embodiments, $R^3$ is -pyridin-5-yl$(R^6)_q$.
In some embodiments, $R^3$ is -pyridin-3-yl$(R^6)_q$, q is 0.
In some embodiments, $R^3$ is -pyridin-4-yl$(R^6)_q$, q is 0.
In some embodiments, $R^3$ is -pyridin-5-yl$(R^6)_q$, q is 0.
In some embodiments, $R^3$ is -imidazolyl$(R^6)_q$.
In some embodiments, $R^3$ is -imidazol-1-yl$(R^6)_q$, q is 1, and $R^6$ is —($C_{1-3}$ alkyl).
In some embodiments, $R^3$ is -imidazol-1-yl$(R^6)_q$, q is 1, and $R^6$ is methyl.
In some embodiments, $R^3$ is -furanyl$(R^6)_q$.
In some embodiments, $R^3$ is -furan-2-yl$(R^6)_q$.
In some embodiments, $R^3$ is -furan-2-yl$(R^6)_q$ and q is 0.
In some embodiments, $R^3$ is -furan-3-yl$(R^6)_q$.
In some embodiments, $R^3$ is -furan-3-yl$(R^6)_q$ and q is 0.
In some embodiments, $R^3$ is -thiophenyl$(R^6)_q$.
In some embodiments, $R^3$ is -thiophen-2-yl$(R^6)_q$.
In some embodiments, $R^3$ is -thiophen-2-yl$(R^6)_q$ and q is 0.
In some embodiments, $R^3$ is -thiophen-2-yl$(R^6)_q$, q is 1 or 2, and each $R^6$ is independently a halide.
In some embodiments, $R^3$ is -thiophen-2-yl$(R^6)_q$, q is 1 or 2, and $R^6$ is F.
In some embodiments, $R^3$ is -thiophen-2-yl$(R^6)_q$, q is 1 or 2, and each $R^6$ is independently —($C_{1-6}$ alkyl).
In some embodiments, $R^3$ is -thiophen-2-yl$(R^6)_q$, q is 1 or 2, and each $R^6$ is independently —($C_{1-2}$ alkyl).
In some embodiments, $R^3$ is -thiophen-2-yl$(R^6)_q$, q is 1 or 2, and $R^6$ is methyl.
In some embodiments, $R^3$ is -thiophen-2-yl$(R^6)_q$, q is 1 or 2, and $R^6$ is —$CF_3$.
In some embodiments, $R^3$ is -thiophen-2-yl$(R^6)_q$, q is 1 or 2, and $R^6$ is CN.
In some embodiments, $R^3$ is -thiophen-2-yl$(R^6)_q$, q is 1, and $R^6$ is —C(=O)$R^{17}$.
In some embodiments, $R^3$ is -thiophen-2-yl$(R^6)_q$, q is 1, $R^6$ is —C(=O)$R^{17}$, and $R^{17}$ is —($C_{1-6}$ alkyl).
In some embodiments, $R^3$ is -thiophen-2-yl$(R^6)_q$, q is 1, $R^6$ is —C(=O)$R^{17}$, and $R^{17}$ is —($C_{1-4}$ alkyl).
In some embodiments, $R^3$ is -thiophen-2-yl$(R^6)_q$, q is 1, $R^6$ is —C(=O)$R^{17}$, and $R^{17}$ is —($C_{1-2}$ alkyl).
In some embodiments, $R^3$ is -thiophen-2-yl$(R^6)_q$, q is 1, $R^6$ is —C(=O)$R^{17}$, and $R^{17}$ is methyl.
In some embodiments, $R^3$ is -thiophen-3-yl$(R^6)_q$.
In some embodiments, $R^3$ is -thiophen-3-yl$(R^6)_q$ and q is 0.
In some embodiments, $R^3$ is -thiophen-3-yl$(R^6)_q$, q is 1 or 2, and each $R^6$ is independently halide.
In some embodiments, $R^3$ is -thiophen-3-yl$(R^6)_q$, q is 1 or 2, and $R^6$ is F.
In some embodiments, $R^3$ is -thiophen-3-yl$(R^6)_q$, q is 1 or 2, and each $R^6$ is independently —($C_{1-6}$ alkyl).
In some embodiments, $R^3$ is -thiophen-3-yl$(R^6)_q$, q is 1 or 2, and each $R^6$ is independently —($C_{1-2}$ alkyl).
In some embodiments, $R^3$ is -thiophen-3-yl$(R^6)_q$, q is 1 or 2, and $R^6$ is methyl.
In some embodiments, $R^3$ is -thiophen-3-yl$(R^6)_q$, q is 1 or 2, and $R^6$ is —$CF_3$.
In some embodiments, $R^3$ is -thiophen-3-yl$(R^6)_q$, q is 1 or 2, and $R^6$ is CN.
In some embodiments, $R^3$ is -thiophen-3-yl$(R^6)_q$, q is 1, and $R^6$ is —C(=O)$R^{17}$.
In some embodiments, $R^3$ is -thiophen-3-yl$(R^6)_q$, q is 1, $R^6$ is —C(=O)$R^{17}$, and $R^{17}$ is —($C_{1-4}$ alkyl).
In some embodiments, $R^3$ is -thiophen-3-yl$(R^6)_q$, q is 1, $R^6$ is —C(=O)$R^{17}$, and $R^{17}$ is —($C_{1-2}$ alkyl).
In some embodiments, $R^3$ is -thiophen-3-yl$(R^6)_q$, q is 1, $R^6$ is —C(=O)$R^{17}$, and $R^{17}$ is methyl.

In some embodiments, $R^3$ is selected from the group consisting of:

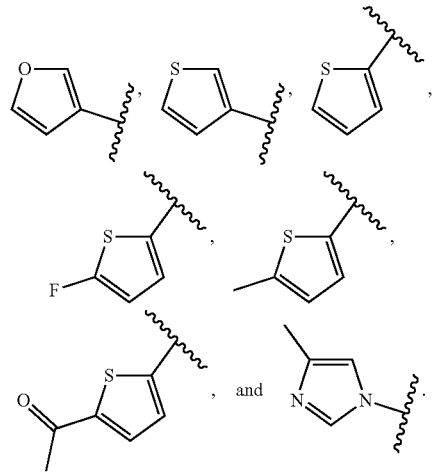

In some embodiments, $R^3$ is -phenyl$(R^8)_k$.
In some embodiments, $R^3$ is -phenyl$(R^8)_k$ and k is 0.

In some embodiments, $R^3$ is -phenyl$(R^8)_k$, k is 1 or 2, and each $R^8$ is independently a halide.

In some embodiments, $R^3$ is -phenyl$(R^8)_k$, k is 1 or 2, and $R^8$ is F.

In some embodiments, $R^3$ is -phenyl$(R^8)_k$, k is 1, and $R^8$ is F.

In some embodiments, $R^3$ is -phenyl$(R^8)_k$, k is 2, one $R^8$ is a halide and the other $R^8$ is —$(C_{1-6}$ alkylene$)_p$NHSO$_2$R$^{17}$.

In some embodiments, $R^3$ is -phenyl$(R^8)_k$, k is 2, one $R^8$ is a halide and the other $R^8$ is —$(C_{1-4}$ alkylene$)_p$NHSO$_2$R$^{17}$, and p is 1.

In some embodiments, $R^3$ is -phenyl$(R^8)_k$, k is 2, one $R^8$ is a halide and the other $R^8$ is —$(C_{1-2}$ alkylene$)_p$NHSO$_2$R$^{17}$, and p is 1.

In some embodiments, $R^3$ is -phenyl$(R^8)_k$, k is 2, one $R^8$ is a halide and the other $R^8$ is —CH$_2$NHSO$_2$R$^{17}$.

In some embodiments, $R^3$ is -phenyl$(R^8)_k$, k is 2, one $R^8$ is a halide and the other $R^8$ is —CH$_2$NHSO$_2$R$^{17}$, and $R^{17}$ is —$(C_{1-4}$ alkyl).

In some embodiments, $R^3$ is -phenyl$(R^8)_k$, k is 2, one $R^8$ is a halide and the other $R^8$ is —CH$_2$NHSO$_2$R$^{17}$, and $R^{17}$ is —$(C_{1-2}$ alkyl).

In some embodiments, $R^3$ is -phenyl$(R^8)_k$, k is 2, one $R^8$ is a halide and the other $R^8$ is —CH$_2$NHSO$_2$R$^{17}$, and $R^{17}$ is methyl.

In some embodiments, $R^3$ is -phenyl$(R^8)_k$, k is 2, one $R^8$ is F and the other $R^8$ is —CH$_2$NHSO$_2$R$^{17}$, and $R^{17}$ is —$(C_{1-2}$ alkyl).

In some embodiments, $R^3$ is -phenyl$(R^8)_k$, k is 2, one $R^8$ is F and the other $R^8$ is —CH$_2$NHSO$_2$R$^{17}$, and $R^{17}$ is methyl.

In some embodiments, $R^3$ is -phenyl$(R^8)_k$, k is 2, one $R^8$ is halide and the other $R^8$ is —NR$^{13}$(C$_{1-6}$ alkylene)NR$^{13}$R$^{14}$.

In some embodiments, $R^3$ is -phenyl$(R^8)_k$, k is 2, one $R^8$ is halide and the other $R^8$ is —NR$^{13}$(C$_{1-5}$ alkylene)NR$^{13}$R$^{14}$.

In some embodiments, $R^3$ is -phenyl$(R^8)_k$, k is 2, one $R^8$ is halide and the other $R^8$ is —NR$^{13}$(C$_{1-4}$ alkylene)NR$^{13}$R$^{14}$.

In some embodiments, $R^3$ is -phenyl$(R^8)_k$, k is 2, one $R^8$ is halide and the other $R^8$ is —NR$^{13}$(C$_{1-3}$ alkylene)NR$^{13}$R$^{14}$.

In some embodiments, $R^3$ is -phenyl$(R^8)_k$, k is 2, one $R^8$ is halide and the other $R^8$ is —NR$^{13}$CH$_2$CH$_2$NR$^{13}$R$^{14}$.

In some embodiments, $R^3$ is -phenyl$(R^8)_k$, k is 2, $R^8$ is halide and the other $R^8$ is —NHCH$_2$CH$_2$NR$^{13}$R$^{14}$, and $R^{13}$ and $R^{14}$ are independently selected from —$(C_{1-6}$ alkyl).

In some embodiments, $R^3$ is -phenyl$(R^8)_k$, k is 2, one $R^8$ is halide and the other $R^8$ is —NHCH$_2$CH$_2$NR$^{13}$R$^{14}$, and $R^{13}$ and $R^{14}$ are independently selected from —$(C_{1-4}$ alkyl).

In some embodiments, $R^3$ is -phenyl$(R^8)_k$, k is 2, one $R^8$ is halide and the other $R^8$ is —NHCH$_2$CH$_2$NR$^{13}$R$^{14}$, and $R^{13}$ and $R^{14}$ are independently selected from —$(C_{1-2}$ alkyl).

In some embodiments, $R^3$ is -phenyl$(R^8)_k$, k is 2, one $R^8$ is halide and the other $R^8$ is —NHCH$_2$CH$_2$NR$^{13}$R$^{14}$, and $R^{13}$ and $R^{14}$ are both methyl.

In some embodiments, $R^3$ is -phenyl$(R^8)_k$, k is 2, one $R^8$ is F and the other $R^8$ is —NHCH$_2$CH$_2$NR$^{13}$R$^{14}$, and $R^{13}$ and $R^{14}$ are independently selected from —$(C_{1-2}$ alkyl).

In some embodiments, $R^3$ is -phenyl$(R^8)_k$, k is 2, one $R^8$ is F and the other $R^8$ is —NHCH$_2$CH$_2$NR$^{13}$R$^{14}$, and $R^{13}$ and $R^{14}$ are both methyl.

In some embodiments, $R^3$ is -phenyl$(R^8)_k$, k is 2, one $R^8$ is halide and the other $R^8$ is —OCH$_2$CH$_2$NR$^{23}$R$^{24}$.

In some embodiments, $R^3$ is -phenyl$(R^8)_k$, k is 2, one $R^8$ is halide and the other $R^8$ is —OCH$_2$CH$_2$NR$^{23}$R$^{24}$, and $R^{23}$ and $R^{24}$ are independently a —$(C_{1-2}$ alkyl).

In some embodiments, $R^3$ is -phenyl$(R^8)_k$, k is 2, one $R^8$ is halide and the other $R^8$ is —OCH$_2$CH$_2$NR$^{23}$R$^{24}$, and $R^{23}$ and $R^{24}$ are both methyl.

In some embodiments, $R^3$ is -phenyl$(R^8)_k$, k is 2, one $R^8$ is F and the other $R^8$ is —OCH$_2$CH$_2$NR$^{23}$R$^{24}$, and $R^{23}$ and $R^{24}$ are both methyl.

In some embodiments, $R^3$ is -phenyl$(R^8)_k$, k is 2, one $R^8$ is halide and the other $R^8$ is —CH$_2$NHSO$_2$R$^{17}$, and $R^{17}$ is —$(C_{1-4}$ alkyl).

In some embodiments, $R^3$ is -phenyl$(R^8)_k$, k is 2, one $R^8$ is halide and the other $R^8$ is —CH$_2$NHSO$_2$R$^{17}$, and $R^{17}$ is —$(C_{1-2}$ alkyl).

In some embodiments, $R^3$ is -phenyl$(R^8)_k$, k is 2, one $R^8$ is halide and the other $R^8$ is —CH$_2$NHSO$_2$R$^{17}$, and $R^{17}$ is methyl.

In some embodiments, $R^3$ is -phenyl$(R^8)_k$, k is 2, one $R^8$ is F and the other $R^8$ is —CH$_2$NHSO$_2$R$^{17}$, and $R^{17}$ is —$(C_{1-2}$ alkyl).

In some embodiments, $R^3$ is -phenyl$(R^8)_k$, k is 2, one $R^8$ is F and the other $R^8$ is —CH$_2$NHSO$_2$R$^{17}$, and $R^{17}$ is methyl.

In some embodiments, $R^3$ is selected from the group consisting of:

In some embodiments, $R^3$ is -piperidinyl$(R^7)_h$.

In some embodiments, $R^3$ is -piperidin-1-yl$(R^7)_h$.

In some embodiments, $R^3$ is -piperidin-1-yl$(R^7)_h$ and h is 0.

In some embodiments, $R^3$ is -piperidin-1-yl$(R^7)_h$, h is 1 or 2, and each $R^7$ is independently selected from a halide.

In some embodiments, $R^3$ is -piperazinyl($R^7$)$_h$.
In some embodiments, $R^3$ is -piperazin-1-yl($R^7$)$_h$.
In some embodiments, $R^3$ is -piperazin-1-yl($R^7$)$_h$, h is 1, and $R^7$ is $C_{1-3}$ alkyl.
In some embodiments, $R^3$ is -piperazin-1-yl($R^7$)$_h$, h is 1, and $R^7$ is methyl.
In some embodiments, $R^3$ is -morpholinyl($R^7$)$_h$.
In some embodiments, $R^3$ is -morpholin-1-yl($R^7$)$_h$.
In some embodiments, $R^3$ is -morpholin-1-yl($R^7$)$_h$ and h is 0.
In some embodiments, $R^3$ is selected from the group consisting of:

[Structures: piperidinyl, piperazinyl (NH), 4,4-difluoropiperidinyl, morpholinyl], and

[Structure: piperazinyl with N-substitution].

In some embodiments, q is 0.
In some embodiments, at least one $R^4$ is a halide.
In some embodiments, at least one $R^4$ is a F.
In some embodiments, $R^4$ is F.
In some embodiments, at least one $R^4$ is —($C_{1-6}$ alkyl).
In some embodiments, at least one $R^4$ is —($C_{1-5}$ alkyl).
In some embodiments, at least one $R^4$ is —($C_{1-4}$ alkyl).
In some embodiments, at least one $R^4$ is —($C_{1-3}$ alkyl).
In some embodiments, at least one $R^4$ is —($C_{1-2}$ alkyl).
In some embodiments, $R^4$ is a methyl.
In some embodiments, at least one $R^4$ is —($C_{1-4}$ alkylene)$_p$heterocyclyl($R^9$)$_h$ and p is 0 or 1.
In some embodiments, at least one $R^4$ is —($C_{1-3}$ alkylene)$_p$heterocyclyl($R^9$)$_h$ and p is 0 or 1.
In some embodiments, at least one $R^4$ is —($C_{1-2}$ alkylene)$_p$heterocyclyl($R^9$)$_h$ and p is 0 or 1.
In some embodiments, at least one $R^4$ is —CH$_2$pyrrolidinyl($R^9$)$_h$.
In some embodiments, at least one $R^4$ is —CH$_2$pyrrolidinyl($R^9$)$_h$ and h is 0.
In some embodiments, $R^4$ is a —CH$_2$pyrrolidinyl($R^9$)$_h$ and h is 0.
In some embodiments, at least one $R^4$ is —CH$_2$pyrrolidinyl($R^9$)$_h$, h is 1 or 2, and at least one $R^9$ is halide.
In some embodiments, at least one $R^4$ is —CH$_2$pyrrolidinyl($R^9$)$_h$, h is 1 or 2, and at least one $R^9$ is F.
In some embodiments, $R^4$ is a —CH$_2$pyrrolidinyl($R^9$)$_h$, h is 1 or 2, and at least one $R^9$ is halide.
In some embodiments, $R^4$ is —CH$_2$pyrrolidinyl($R^9$)$_h$, h is 1 or 2, and at least one $R^9$ is F.
In some embodiments, $R^4$ is a —CH$_2$pyrrolidinyl($R^9$)$_h$, h is 1 or 2, and each $R^9$ is F.
In some embodiments, at least one $R^4$ is —CH$_2$piperidinyl($R^9$)$_h$.
In some embodiments, at least one $R^4$ is —CH$_2$piperidinyl($R^9$)$_h$ and h is 0.
In some embodiments, $R^4$ is a —CH$_2$piperidinyl($R^9$)$_h$ and h is 0.
In some embodiments, at least one $R^4$ is —CH$_2$piperidinyl($R^9$)$_h$ and at least one $R^9$ is halide.
In some embodiments, at least one $R^4$ is —CH$_2$piperidinyl($R^9$)$_h$ and at least one $R^9$ is F.
In some embodiments, at least one $R^4$ is —CH$_2$piperidinyl($R^9$)$_h$, h is 1 or 2, and at least one $R^9$ is halide.
In some embodiments, at least one $R^4$ is —CH$_2$piperidinyl($R^9$)$_h$, h is 1 or 2, and at least one $R^9$ is F.
In some embodiments, $R^4$ is —CH$_2$piperidinyl($R^9$)$_h$, h is 1 or 2, and each $R^9$ is a halide.
In some embodiments, $R^4$ is —CH$_2$piperidinyl($R^9$)$_h$, h is 1 or 2, and each $R^9$ is F.
In some embodiments, $R^4$ is a —CH$_2$piperidinyl($R^9$)$_h$, h is 1 or 2, and each $R^9$ is F.
In some embodiments, $R^4$ is a

[Structure: 3,3-difluoropyrrolidinyl-CH$_2$-].

In some embodiments, at least one $R^4$ is —($C_{1-4}$ alkylene)$_p$carbocyclyl($R^{10}$)$_j$.
In some embodiments, at least one $R^4$ is —($C_{1-4}$ alkylene)$_p$carbocyclyl($R^{10}$)$_j$ and j is 0 or 1.
In some embodiments, at least one $R^4$ is —($C_{1-3}$ alkylene)$_p$carbocyclyl($R^{10}$)$_j$ and j is 0 or 1.
In some embodiments, at least one $R^4$ is —($C_{1-2}$ alkylene)$_p$carbocyclyl($R^{10}$)$_j$ and j is 0 or 1.
In some embodiments, at least one $R^4$ is —CH$_2$carbocyclyl($R^{10}$)$_j$.
In some embodiments, $R^4$ is a —CH$_2$carbocyclyl($R^{10}$)$_j$.
In some embodiments, at least one $R^4$ is —($C_{1-4}$ alkylene)$_p$aryl($R^{11}$)$_k$ and k is 0 or 1.
In some embodiments, at least one $R^4$ is —($C_{1-3}$ alkylene)$_p$aryl($R^{11}$)$_k$ and k is 0 or 1.
In some embodiments, at least one $R^4$ is —($C_{1-2}$ alkylene)$_p$aryl($R^{11}$)$_k$ and k is 0 or 1.
In some embodiments, at least one $R^4$ is —CH$_2$aryl($R^{11}$)$_k$.
In some embodiments, at least one $R^4$ is —CH$_2$phenyl($R^{11}$)$_k$.
In some embodiments, $R^4$ is a —CH$_2$phenyl($R^{11}$)$_k$.
In some embodiments, at least one $R^4$ is —NHC(=O)$R^{12}$.
In some embodiments, $R^4$ is a —NHC(=O)$R^{12}$.
In some embodiments, at least one $R^4$ is —NHC(=O)$R^{12}$ and $R^{12}$ is —($C_{1-9}$ alkyl).
In some embodiments, at least one $R^4$ is —NHC(=O)$R^{12}$ and $R^{12}$ is —($C_{1-8}$ alkyl).
In some embodiments, at least one $R^4$ is —NHC(=O)$R^{12}$ and $R^{12}$ is —($C_{1-7}$ alkyl).
In some embodiments, at least one $R^4$ is —NHC(=O)$R^{12}$ and $R^{12}$ is —($C_{1-6}$ alkyl).
In some embodiments, at least one $R^4$ is —NHC(=O)$R^{12}$ and $R^{12}$ is —($C_{1-5}$ alkyl).
In some embodiments, $R^4$ is a —NHC(=O)$R^{12}$ and $R^{12}$ is —($C_{1-5}$ alkyl).
In some embodiments, at least one $R^4$ is —NHC(=O)$R^{12}$ and $R^{12}$ is —($C_{1-4}$ alkyl).

In some embodiments, $R^4$ is a —NHC(=O)$R^{12}$ and $R^{12}$ is —($C_{1-4}$ alkyl).

In some embodiments, at least one $R^4$ is —NHC(=O)$R^{12}$ and $R^{12}$ is —($C_{1-3}$ alkyl).

In some embodiments, $R^4$ is a —NHC(=O)$R^{12}$ and $R^{12}$ is —($C_{1-3}$ alkyl).

In some embodiments, at least one $R^4$ is —NHC(=O)$R^{12}$ and $R^{12}$ is —($C_{1-2}$ alkyl).

In some embodiments, at least one $R^4$ is —NHC(=O)$R^{12}$ and $R^{12}$ is —($C_{2-5}$ alkyl).

In some embodiments, $R^4$ is a —NHC(=O)$R^{12}$ and $R^{12}$ is —($C_{2-5}$ alkyl).

In some embodiments, at least one $R^4$ is —NHC(=O)$R^{12}$ and $R^{12}$ is —($C_{3-4}$ alkyl).

In some embodiments, at least one $R^4$ is —NHC(=O)$R^{12}$ and $R^{12}$ is -aryl($R^{19}$)$_k$.

In some embodiments, at least one $R^4$ is —NHC(=O)$R^{12}$, $R^{12}$ is -phenyl($R^{19}$)$_k$, and k is 0.

In some embodiments, $R^4$ is a —NHC(=O)$R^{12}$, $R^{12}$ is -phenyl($R^{19}$)$_k$, and k is 0.

In some embodiments, at least one $R^4$ is —NHC(=O)$R^{12}$ and $R^{12}$ is —CH$_2$aryl($R^{19}$)$_k$.

In some embodiments, at least one $R^4$ is —NHC(=O)$R^{12}$, $R^{12}$ is —CH$_2$phenyl($R^{19}$)$_k$, and k is 0.

In some embodiments, $R^4$ is —NHC(=O)$R^{12}$, $R^{12}$ is —CH$_2$phenyl($R^{19}$)$_k$, and k is 0.

In some embodiments, at least one $R^4$ is —NHC(=O)$R^{12}$ and $R^{12}$ is -heteroaryl($R^{18}$)$_q$.

In some embodiments, at least one $R^4$ is —NHC(=O)$R^{12}$ and $R^{12}$ is -carbocyclyl($R^{20}$)$_j$.

In some embodiments, at least one $R^4$ is —NHC(=O)$R^{12}$, $R^{12}$ is -carbocyclyl($R^{20}$)$_j$, and j is 0.

In some embodiments, at least one $R^4$ is —NHC(=O)$R^{12}$, $R^{12}$ is -cyclopropyl($R^{20}$)$_j$, and j is 0.

In some embodiments, $R^4$ is a —NHC(=O)$R^{12}$, $R^{12}$ is -cyclopropyl($R^{20}$)$_j$, and j is 0.

In some embodiments, at least one $R^4$ is —NHC(=O)$R^{12}$, $R^{12}$ is -cyclobutyl($R^{20}$)$_j$, and j is 0.

In some embodiments, $R^4$ is a —NHC(=O)$R^{12}$, $R^{12}$ is -cyclobutyl($R^{20}$)$_j$, and j is 0.

In some embodiments, at least one $R^4$ is —NHC(=O)$R^{12}$, $R^{12}$ is -cyclopentyl($R^{20}$)$_j$, and j is 0.

In some embodiments, $R^4$ is a —NHC(=O)$R^{12}$, $R^{12}$ is -cyclopentyl($R^{20}$)$_j$, and j is 0.

In some embodiments, at least one $R^4$ is —NHC(=O)$R^{12}$, $R^{12}$ is -cyclohexyl($R^{20}$)$_j$, and j is 0.

In some embodiments, $R^4$ is a —NHC(=O)$R^{12}$, $R^{12}$ is -cyclohexyl($R^{20}$)$_j$, and j is 0.

In some embodiments, at least one $R^4$ is —NHC(=O)$R^{12}$, $R^{12}$ is —CH$_2$carbocyclyl($R^{20}$)$_j$, and j is 0.

In some embodiments, at least one $R^4$ is —NHC(=O)$R^{12}$, $R^{12}$ is —CH$_2$cyclopropyl($R^{20}$)$_j$, and j is 0.

In some embodiments, at least one $R^4$ is —NR$^{13}$R$^{14}$.

In some embodiments, at least one $R^4$ is —NR$^{13}$R$^{14}$, and $R^{13}$ and $R^{14}$ are independently selected from the group consisting of H and —($C_{1-6}$ alkyl).

In some embodiments, at least one $R^4$ is —NR$^{13}$R$^{14}$, and $R^{13}$ and $R^{14}$ are independently selected from the group consisting of H and —($C_{1-5}$ alkyl).

In some embodiments, at least one $R^4$ is —NR$^{13}$R$^{14}$, and $R^{13}$ and $R^{14}$ are independently selected from the group consisting of H and —($C_{1-4}$ alkyl).

In some embodiments, at least one $R^4$ is —NR$^{13}$R$^{14}$, and $R^{13}$ and $R^{14}$ are independently selected from the group consisting of H and —($C_{1-3}$ alkyl).

In some embodiments, at least one $R^4$ is —NR$^{13}$R$^{14}$, and $R^{13}$ and $R^{14}$ are independently selected from the group consisting of H and —($C_{1-2}$ alkyl).

In some embodiments, at least one $R^4$ is —NR$^{13}$R$^{14}$, and $R^{13}$ and $R^{14}$ are independently selected from the group consisting of H and methyl.

In some embodiments, at least one $R^4$ is —NH$_2$.

In some embodiments, $R^4$ is a —NH$_2$.

In some embodiments, at least one $R^4$ is —NHR$^{14}$ and $R^{14}$ is —($C_{1-4}$ alkyl).

In some embodiments, at least one $R^4$ is —NHR$^{14}$ and $R^{14}$ is —($C_{1-3}$ alkyl).

In some embodiments, at least one $R^4$ is —NHR$^{14}$ and $R^{14}$ is —($C_{1-2}$ alkyl).

In some embodiments, $R^4$ is a —NHR$^{14}$ and $R^{14}$ is —($C_{1-2}$ alkyl).

In some embodiments, at least one $R^4$ is —NHR$^{14}$ and $R^{14}$ is —CH$_2$aryl($R^{19}$)$_k$.

In some embodiments, at least one $R^4$ is —NHR$^4$, $R^{14}$ is —CH$_2$phenyl($R^{19}$)$_k$, and k is 0.

In some embodiments, $R^4$ is —NHR$^4$, $R^{14}$ is —CH$_2$phenyl($R^{19}$)$_k$, and k is 0.

In some embodiments, at least one $R^4$ is —NHR$^{14}$ and $R^{14}$ is —CH$_2$carbocyclyl($R^{20}$)$_j$.

In some embodiments, at least one $R^4$ is —NHR$^{14}$, $R^{14}$ is —CH$_2$cyclopropyl($R^{20}$)$_j$, and j is 0.

In some embodiments, $R^4$ is a —NHR$^4$, $R^{14}$ is —CH$_2$cyclopropyl($R^{20}$)$_j$, and j is 0.

In some embodiments, at least one $R^4$ is —NHR$^4$, $R^{14}$ is —CH$_2$cyclobutyl($R^{20}$)$_j$, and j is 0.

In some embodiments, $R^4$ is a —NHR$^4$, $R^{14}$ is —CH$_2$cyclobutyl($R^{20}$)$_j$, and j is 0.

In some embodiments, at least one $R^4$ is —NHR$^4$, $R^{14}$ is —CH$_2$cyclopentyl($R^{20}$)$_j$, and j is 0.

In some embodiments, $R^4$ is a —NHR$^{14}$, $R^{14}$ is —CH$_2$cyclopentyl($R^{20}$)$_j$, and j is 0.

In some embodiments, at least one $R^4$ is —NHR$^{14}$, $R^{14}$ is —CH$_2$cyclohexyl($R^{20}$)$_j$, and j is 0.

In some embodiments, $R^4$ is a —NHR$^{14}$, $R^{14}$ is —CH$_2$cyclohexyl($R^{20}$)$_j$, and j is 0.

In some embodiments, at least one $R^4$ is —($C_{1-6}$ alkylene)NR$^{15}$R$^{16}$.

In some embodiments, at least one $R^4$ is —($C_{1-5}$ alkylene)NR$^{15}$R$^{16}$.

In some embodiments, at least one $R^4$ is —($C_{1-4}$ alkylene)NR$^{15}$R$^{16}$.

In some embodiments, at least one $R^4$ is —($C_{1-3}$ alkylene)NR$^{15}$R$^{16}$.

In some embodiments, at least one $R^4$ is —($C_{1-2}$ alkylene)NR$^{15}$R$^{16}$.

In some embodiments, at least one $R^4$ is —CH$_2$NR$^{15}$R$^{16}$.

In some embodiments, $R^4$ is a —CH$_2$NR$^{15}$R$^{16}$.

In some embodiments, at least one $R^4$ is —CH$_2$NR$^{15}$R$^{16}$, and $R^{15}$ and $R^{16}$ are independently selected from the group consisting of H and —($C_{1-6}$ alkyl).

In some embodiments, at least one $R^4$ is —CH$_2$NR$^{15}$R$^{16}$, and $R^{15}$ and $R^{16}$ are independently selected from the group consisting of H and —($C_{1-5}$ alkyl).

In some embodiments, at least one $R^4$ is —CH$_2$NR$^{15}$R$^{16}$, and $R^{15}$ and $R^{16}$ are independently selected from the group consisting of H and —($C_{1-4}$ alkyl).

In some embodiments, at least one $R^4$ is —CH$_2$NR$^{15}$R$^{16}$, and $R^{15}$ and $R^{16}$ are independently selected from the group consisting of H and —($C_{1-3}$ alkyl).

In some embodiments, at least one $R^4$ is —CH$_2$NR$^{15}$R$^{16}$, and $R^{15}$ and $R^{16}$ are independently selected from the group consisting of H and —($C_{1-2}$ alkyl).

In some embodiments, at least one $R^4$ is —$CH_2NR^{15}R^{16}$, and $R^{15}$ and $R^{16}$ are independently selected from the group consisting of H and methyl.

In some embodiments, $R^4$ is a —$CH_2NR^{15}R^{16}$, and $R^{15}$ and $R^{16}$ are independently selected from the group consisting of H and methyl.

In some embodiments, at least one $R^4$ is —$CH_2NH_2$.

In some embodiments, $R^4$ is a —$CH_2NH_2$.

In some embodiments, at least one $R^4$ is —$CH_2NMe_2$.

In some embodiments, $R^4$ is —$CH_2NMe_2$.

In some embodiments, at least one $R^4$ is —$CH_2NHR^{16}$ and $R^{16}$ is —($C_{1-4}$ alkyl).

In some embodiments, at least one $R^4$ is —$CH_2NHR^{16}$ and $R^{16}$ is —($C_{1-3}$ alkyl).

In some embodiments, at least one $R^4$ is —$CH_2NHR^{16}$ and $R^{16}$ is —($C_{1-2}$ alkyl).

In some embodiments, $R^4$ is a —$CH_2NHR^{16}$ and $R^{16}$ is —($C_{1-2}$ alkyl).

In some embodiments, at least one $R^4$ is —$CH_2NHR^{16}$ and $R^{16}$ is —$CH_2$aryl$(R^{19})_k$.

In some embodiments, at least one $R^4$ is —$CH_2NHR^{16}$, $R^{16}$ is —$CH_2$phenyl$(R^{19})_k$, and k is 0.

In some embodiments, $R^4$ is a —$CH_2NHR^{16}$, $R^{16}$ is —$CH_2$phenyl$(R^{19})_k$, and k is 0.

In some embodiments, at least one $R^4$ is —$CH_2NHR^{16}$ and $R^{16}$ is —$CH_2$carbocyclyl$(R^{20})_j$.

In some embodiments, at least one $R^4$ is —$CH_2NHR^{16}$, $R^{16}$ is —$CH_2$cyclopropyl$(R^{20})_j$, and j is 0.

In some embodiments, $R^4$ is a —$CH_2NHR^{16}$, $R^{16}$ is —$CH_2$cyclopropyl$(R^{20})_j$, and j is 0.

In some embodiments, at least one $R^4$ is —$CH_2NHR^{16}$, $R^{16}$ is —$CH_2$cyclobutyl$(R^{20})_j$, and j is 0.

In some embodiments, $R^4$ is a —$CH_2NHR^{16}$, $R^{16}$ is —$CH_2$cyclobutyl$(R^{20})_j$, and j is 0.

In some embodiments, at least one $R^4$ is —$CH_2NHR^{16}$, $R^{16}$ is —$CH_2$cyclopentyl$(R^{20})_j$, and j is 0.

In some embodiments, $R^4$ is a —$CH_2NHR^{16}$, $R^{16}$ is —$CH_2$cyclopentyl$(R^{20})_j$, and j is 0.

In some embodiments, at least one $R^4$ is —$CH_2NHR^{16}$, $R^{16}$ is —$CH_2$cyclohexyl$(R^{20})_j$, and j is 0.

In some embodiments, $R^4$ is a —$CH_2NHR^{16}$, $R^{16}$ is —$CH_2$cyclohexyl$(R^{20})_j$, and j is 0.

In some embodiments, at least one $R^4$ is —$OR^{22}$.

In some embodiments, at least one $R^4$ is —OH.

In some embodiments, $R^4$ is a —OH.

In some embodiments, at least one $R^4$ is —$OR^{22}$ and $R^{22}$ is —($C_{1-3}$ alkyl).

In some embodiments, at least one $R^4$ is —$OR^{22}$ and $R^{22}$ is —($C_{1-2}$ alkyl).

In some embodiments, at least one $R^4$ is —OMe.

In some embodiments, $R^4$ is a —OMe.

In some embodiments, at least one $R^4$ is —$OR^{22}$, $R^{22}$ is -heterocyclyl$(R^{21})_h$, and h is 0.

In some embodiments, $R^4$ is a —$OR^{22}$, $R^{22}$ is -heterocyclyl$(R^{21})_h$, and h is 0.

In some embodiments, at least one $R^4$ is —$OR^{22}$, $R^{22}$ is -carbocyclyl$(R^{20})_j$, and j is 0.

In some embodiments, $R^4$ is a —$OR^{22}$, $R^{22}$ is -carbocyclyl$(R^{20})_j$, and j is 0.

In some embodiments, at least one $R^4$ is —$OR^{22}$, $R^{22}$ is —($C_{1-4}$ alkylene)heterocyclyl$(R^{21})_h$, and h is 0.

In some embodiments, at least one $R^4$ is —$OR^{22}$, $R^{22}$ is —($CH_2CH_2$)heterocyclyl$(R^{21})_h$, and h is 0.

In some embodiments, $R^4$ is a —$OR^{22}$, $R^{22}$ is —($CH_2CH_2$)heterocyclyl$(R^{21})_h$, and h is 0.

In some embodiments, at least one $R^4$ is —$OR^{22}$, $R^{22}$ is —($C_{1-4}$ alkylene)$NR^{23}R^{24}$ and $R^{23}$ and $R^{24}$ are independently a —($C_{1-4}$ alkyl).

In some embodiments, at least one $R^4$ is —$OR^{22}$, $R^{22}$ is —($CH_2CH_2$)$NR^{23}R^{24}$ and $R^{23}$ and $R^{24}$ are independently a —($C_{1-2}$ alkyl).

In some embodiments, at least one $R^4$ is —$OR^{22}$, and $R^{22}$ is —($CH_2CH_2$)$NMe_2$.

In some embodiments, $R^4$ is a —$OR^{22}$, and $R^{22}$ is —($CH_2CH_2$)$NMe_2$.

In some embodiments, at least one $R^4$ is —$OR^{22}$, $R^{22}$ is —($C_{1-4}$ alkylene)aryl$(R^{19})_k$, k is 0 or 1 and $R^{19}$ is halide.

In some embodiments, at least one $R^4$ is —$OR^{22}$, $R^{22}$ is —($CH_2CH_2$)phenyl$(R^{19})_k$, k is 0 or 1 and $R^{19}$ is a halide.

In some embodiments, $R^4$ is a —$OR^{22}$, $R^{22}$ is —($CH_2CH_2$)phenyl$(R^{19})_k$, k is 0 or 1 and $R^{19}$ is a halide.

In some embodiments, at least one $R^4$ is —$OR^{22}$, $R^{22}$ is —($CH_2$)phenyl$(R^{19})_k$, k is 0 or 1 and $R^{19}$ is a halide.

In some embodiments, $R^4$ is a —$OR^{22}$, $R^{22}$ is —($CH_2$)phenyl$(R^{19})_k$, k is 0 or 1 and $R^{19}$ is a halide.

In some embodiments, h is 0.

In some embodiments, at least one $R^5$ is a halide.

In some embodiments, at least one $R^5$ is a F.

In some embodiments, at least one $R^5$ is —($C_{1-6}$ alkyl).

In some embodiments, at least one $R^5$ is —($C_{1-5}$ alkyl).

In some embodiments, at least one $R^5$ is —($C_{1-4}$ alkyl).

In some embodiments, at least one $R^5$ is —($C_{1-3}$ alkyl).

In some embodiments, at least one $R^5$ is —($C_{1-2}$ alkyl).

In some embodiments, at least one $R^5$ is methyl.

In some embodiments, at least one $R^6$ is a halide.

In some embodiments, at least one $R^6$ is a F.

In some embodiments, at least one $R^6$ is —($C_{1-4}$ alkyl).

In some embodiments, at least one $R^6$ is —($C_{1-3}$ alkyl).

In some embodiments, at least one $R^6$ is —($C_{1-2}$ alkyl).

In some embodiments, at least one $R^6$ is methyl.

In some embodiments, $R^6$ is a methyl.

In some embodiments, at least one $R^6$ is —C(=O)($C_{1-3}$ alkyl).

In some embodiments, at least one $R^6$ is —C(=O)Me.

In some embodiments, $R^6$ is a —C(=O)Me.

In some embodiments, at least one $R^8$ is F.

In some embodiments, at least one $R^8$ is Cl.

In some embodiments, at least one $R^8$ is Br.

In some embodiments, at least one $R^8$ is I.

In some embodiments, at least one $R^{12}$ is —($C_{1-9}$ alkyl).

In some embodiments, at least one $R^{12}$ is methyl.

In some embodiments, at least one $R^{12}$ is ethyl.

In some embodiments, at least one $R^{12}$ is propyl.

In some embodiments, at least one $R^{12}$ is —($C_{1-2}$ alkyl).

In some embodiments, at least one $R^{12}$ is —($C_{1-3}$ alkyl).

In some embodiments, at least one $R^{12}$ is —($C_{1-4}$ alkyl).

In some embodiments, at least one $R^{12}$ is —($C_{1-5}$ alkyl).

In some embodiments, at least one $R^{12}$ is —($C_{2-9}$ alkyl).

In some embodiments, at least one $R^{12}$ is —($C_{3-9}$ alkyl).

In some embodiments, at least one $R^{12}$ is —($C_{4-9}$ alkyl).

In some embodiments, at least one $R^{12}$ is —($C_{5-9}$ alkyl).

In some embodiments, at least one $R^{12}$ is —($C_{6-9}$ alkyl).

In some embodiments, at least one $R^{12}$ is —($C_{7-9}$ alkyl).

In some embodiments, at least one $R^{12}$ is —($C_{8-9}$ alkyl).

In some embodiments, at least one $R^{12}$ is -carbocyclyl$(R^{20})_j$.

In some embodiments, at least one $R^{12}$ is cyclopropyl.

In some embodiments, at least one $R^{12}$ is cyclobutyl.

In some embodiments, at least one $R^{12}$ is cyclopentyl.

In some embodiments, at least one $R^{12}$ is cyclohexyl.

In some embodiments, at least one $R^{12}$ is —($C_{3-6}$ carbocyclyl)$(R^{20})_j$.

In some embodiments, at least one $R^{12}$ is —($C_{4-6}$ carbocyclyl)($R^{20}$)$_j$.

In some embodiments, at least one $R^{12}$ is —($C_{5-6}$ carbocyclyl)($R^{20}$)$_j$.

In some embodiments:
$R^1$ is -pyridinyl($R^4$)$_q$, wherein q is 1;
$R^2$ is H;
$R^3$ is selected from the group consisting of -pyridinyl($R^6$)$_q$, wherein q is 0; and -aryl($R^8$)$_k$;
$R^4$ is one substituent attached to the pyridinyl and is —NHC(=O)$R^{12}$;
each $R^8$ is one substituent attached to the aryl and is independently selected from the group consisting of Cl and F;
$R^{12}$ is independently selected from the group consisting of methyl, —($C_{5-9}$ alkyl), -heteroaryl($R^{18}$)$_q$, -aryl($R^{19}$)$_k$, —CH$_2$aryl($R^{19}$)$_k$, —($C_{4-6}$ carbocyclyl)($R^{20}$)$_j$, and —CH$_2$carbocyclyl($R^{20}$)$_j$;
each $R^{18}$ is one substituent attached to the heteroaryl and is independently selected from the group consisting of —($C_{1-4}$ alkyl), halide, —CF$_3$, and —CN;
each $R^{19}$ is one substituent attached to the aryl and is independently selected from the group consisting of —($C_{1-4}$ alkyl), halide, —CF$_3$, and —CN;
each $R^{20}$ is one substituent attached to the carbocyclyl and is independently selected from the group consisting of —($C_{1-4}$ alkyl), halide, —CF$_3$, and —CN;
each q is independently 0 to 4;
each k is independently 0 to 5; and
each j is independently 0 to 12.

In some embodiments:
$R^1$ is -pyridinyl($R^4$)$_q$, wherein q is 1;
$R^2$ is H;
$R^3$ is selected from the group consisting of -pyridinyl($R^6$)$_q$ and -aryl($R^8$)$_k$;
$R^4$ is one substituent attached to the pyridinyl and is —NHC(=O)$R^{12}$;
each $R^6$ is one substituent attached to the pyridinyl and is independently selected from the group consisting of —($C_{1-6}$ alkyl), halide, —CF$_3$, —OCH$_3$, —CN, and —C(=O)$R^{17}$;
each $R^8$ is one substituent attached to the aryl and is independently selected from the group consisting of —($C_{1-6}$ alkyl), Br, I, —CF$_3$, —CN, —OCH$_3$, —($C_{1-6}$ alkylene)$_p$NHSO$_2$R$^{17}$, —NR$^{13}$($C_{1-6}$ alkylene)NR$^{13}$R$^{14}$, —($C_{1-6}$ alkylene)$_p$NR$^{13}$R$^{14}$, and —OR$^{25}$;
$R^{12}$ is selected from the group consisting of —($C_{1-9}$ alkyl), -heteroaryl($R^{18}$)$_q$, -aryl($R^{19}$)$_k$, —CH$_2$aryl($R^{19}$)$_k$, -carbocyclyl($R^{20}$)$_j$, and —CH$_2$carbocyclyl($R^{20}$)$_j$;
each $R^{13}$ is independently selected from the group consisting of H and —($C_{1-6}$ alkyl);
each $R^{14}$ is independently selected from the group consisting of H, —($C_{1-6}$ alkyl), —CH$_2$aryl($R^{19}$)$_k$, and —CH$_2$carbocyclyl($R^{20}$)$_j$;
each $R^{17}$ is a —($C_{1-6}$ alkyl);
each $R^{18}$ is one substituent attached to the heteroaryl and is independently selected from the group consisting of —($C_{1-4}$ alkyl), halide, —CF$_3$, and —CN;
each $R^{19}$ is one substituent attached to the aryl and is independently selected from the group consisting of —($C_{1-4}$ alkyl), halide, —CF$_3$, and —CN;
each $R^{20}$ is one substituent attached to the carbocyclyl and is independently selected from the group consisting of —($C_{1-4}$ alkyl), halide, —CF$_3$, and —CN;
each $R^{21}$ is one substituent attached to the heterocyclyl and is independently selected from the group consisting of —($C_{1-4}$ alkyl), halide, —CF$_3$, and —CN;
each $R^{23}$ is independently selected from the group consisting of H and —($C_{1-6}$ alkyl);
each $R^{24}$ is independently selected from the group consisting of H and —($C_{1-6}$ alkyl);
$R^{25}$ is selected from the group consisting of H, —($C_{1-6}$ alkyl), —($C_{1-4}$ alkylene)$_p$heterocyclyl($R^{21}$)$_h$, and —($C_{1-6}$ alkylene)$_p$NR$^{23}$R$^{24}$;
each p is independently 0 or 1;
each q is independently 0 to 4;
each k is independently 0 to 5; and
each j is independently 0 to 12.

In some embodiments:
$R^1$ is -pyridinyl($R^4$)$_q$, wherein q is 0 or 1;
$R^2$ is H;
$R^3$ is selected from the group consisting of -pyridinyl($R^6$)$_q$ and -aryl($R^8$)$_k$;
$R^4$ is one substituent attached to the pyridinyl and is selected from the group consisting of halide, —($C_{1-6}$ alkyl), —($C_{1-4}$ alkylene)$_p$heterocyclyl($R^9$)$_h$, —($C_{1-4}$ alkylene)$_p$carbocyclyl($R^{10}$)$_j$, —($C_{1-4}$ alkylene)$_p$aryl($R^{11}$)$_k$, —NR$^{13}$R$^{14}$, —($C_{1-6}$ alkylene)NR$^{15}$R$^{16}$, and —OR$^{22}$;
each $R^6$ is one substituent attached to the pyridinyl and is independently selected from the group consisting of —($C_{1-6}$ alkyl), halide, —CF$_3$, —OCH$_3$, —CN, and —C(=O)$R^{17}$;
each $R^8$ is one substituent attached to the aryl and is independently selected from the group consisting of —($C_{1-6}$ alkyl), halide, —CF$_3$, —CN, —OCH$_3$, —($C_{1-6}$ alkylene)$_p$NHSO$_2$R$^{17}$, —NR$^{13}$($C_{1-6}$ alkylene)NR$^{13}$R$^{14}$, —($C_{1-6}$ alkylene)$_p$NR$^{13}$R$^{14}$, and —OR$^{25}$;
each $R^9$ is one substituent attached to the heterocyclyl and is independently selected from the group consisting of —($C_{1-4}$ alkyl), halide, —CF$_3$, and —CN;
each $R^{10}$ is one substituent attached to the carbocyclyl and is independently selected from the group consisting of —($C_{1-4}$ alkyl), halide, —CF$_3$, and —CN;
each $R^{11}$ is one substituent attached to the aryl and is independently selected from the group consisting of —($C_{1-4}$ alkyl), halide, —CF$_3$, and —CN;
each $R^{13}$ is independently selected from the group consisting of H and —($C_{1-6}$ alkyl);
each $R^{14}$ is independently selected from the group consisting of H, —($C_{1-6}$ alkyl), —CH$_2$aryl($R^{19}$)$_k$, and —CH$_2$carbocyclyl($R^{20}$)$_j$;
each $R^{15}$ is independently selected from the group consisting of H and —($C_{1-6}$ alkyl);
each $R^{16}$ is independently selected from the group consisting of H, —($C_{1-6}$ alkyl), —CH$_2$aryl($R^{19}$)$_k$, and —CH$_2$carbocyclyl($R^{20}$)$_j$;
each $R^{17}$ is a —($C_{1-6}$ alkyl);
each $R^{18}$ is one substituent attached to the heteroaryl and is independently selected from the group consisting of —($C_{1-4}$ alkyl), halide, —CF$_3$, and —CN;
each $R^{19}$ is one substituent attached to the aryl and is independently selected from the group consisting of —($C_{1-4}$ alkyl), halide, —CF$_3$, and —CN;
each $R^{20}$ is one substituent attached to the carbocyclyl and is independently selected from the group consisting of —($C_{1-4}$ alkyl), halide, —CF$_3$, and —CN;
each $R^{21}$ is one substituent attached to the heterocyclyl and is independently selected from the group consisting of —($C_{1-4}$ alkyl), halide, —CF$_3$, and —CN;
$R^{22}$ is selected from the group consisting of H, —($C_{1-6}$ alkyl), —($C_{1-4}$ alkylene)$_p$heterocyclyl($R^{21}$)$_h$, —($C_{1-4}$ alkylene)$_p$carbocyclyl($R^{20}$)$_j$, —($C_{1-4}$ alkylene)$_p$aryl($R^{19}$)$_k$, and —($C_{1-6}$ alkylene)$_p$NR$^{23}$R$^{24}$;

each $R^{23}$ is independently selected from the group consisting of H and —($C_{1-6}$ alkyl);

each $R^{24}$ is independently selected from the group consisting of H and —($C_{1-6}$ alkyl);

$R^{25}$ is selected from the group consisting of H, —($C_{1-6}$ alkyl), —($C_{1-4}$ alkylene)$_p$heterocyclyl($R^{21}$)$_h$, and —($C_{1-6}$ alkylene)$_p$NR$^{23}$R$^{24}$;

each p is independently 0 or 1;

each q is independently 0 to 4;

each h is independently 0 to 10;

each k is independently 0 to 5; and each j is independently 0 to 12.

In some embodiments:

$R^1$ is -pyridinyl($R^4$)$_q$, wherein q is 0 or 1;

$R^2$ is H;

$R^3$ is selected from the group consisting of -pyridinyl($R^6$)$_q$ and -aryl($R^8$)$_k$;

$R^4$ is one substituent attached to the pyridinyl and is selected from the group consisting of halide, —($C_{1-6}$ alkyl), —($C_{1-4}$ alkylene)$_p$heterocyclyl($R^9$)$_h$, —($C_{1-4}$ alkylene)$_p$carbocyclyl($R^{10}$)$_j$, —($C_{1-4}$ alkylene)$_p$aryl($R^{11}$)$_k$, —NR$^{13}$R$^{14}$, —($C_{1-6}$ alkylene)NR$^{15}$R$^{16}$, and —OR$^{22}$;

each $R^6$ is one substituent attached to the pyridinyl and is independently selected from the group consisting of —($C_{1-6}$ alkyl), halide, —CF$_3$, —OCH$_3$, —CN, and —C(=O)R$^{17}$;

each $R^8$ is one substituent attached to the aryl and is independently selected from the group consisting of —($C_{1-6}$ alkyl), halide, —CF$_3$, —CN, —OCH$_3$, —($C_{1-6}$ alkylene)$_p$NHSO$_2$R$^{17}$, —NR$^{13}$($C_{1-6}$ alkylene)NR$^{13}$R$^{14}$, —($C_{1-6}$ alkylene)$_p$NR$^{13}$R$^{14}$, and —OR$^{25}$;

each $R^9$ is one substituent attached to the heterocyclyl and is independently selected from the group consisting of —($C_{1-4}$ alkyl), halide, —CF$_3$, and —CN;

each $R^{10}$ is one substituent attached to the carbocyclyl and is independently selected from the group consisting of —($C_{1-4}$ alkyl), halide, —CF$_3$, and —CN;

each $R^{11}$ is one substituent attached to the aryl and is independently selected from the group consisting of —($C_{1-4}$ alkyl), halide, —CF$_3$, and —CN;

each $R^{13}$ is independently selected from the group consisting of H and —($C_{1-6}$ alkyl);

each $R^{14}$ is independently selected from the group consisting of H, —($C_{1-6}$ alkyl), —CH$_2$aryl($R^{19}$)$_k$, and —CH$_2$carbocyclyl($R^{20}$)$_j$;

each $R^{15}$ is independently selected from the group consisting of H and —($C_{1-6}$ alkyl);

each $R^{16}$ is independently selected from the group consisting of H, —($C_{1-6}$ alkyl), —CH$_2$aryl($R^{19}$)$_k$, and —CH$_2$carbocyclyl($R^{20}$)$_j$;

each $R^{17}$ is a —($C_{1-6}$ alkyl);

each $R^{18}$ is one substituent attached to the heteroaryl and is independently selected from the group consisting of —($C_{1-4}$ alkyl), halide, —CF$_3$, and —CN;

each $R^{19}$ is one substituent attached to the aryl and is independently selected from the group consisting of —($C_{1-4}$ alkyl), halide, —CF$_3$, and —CN;

each $R^{20}$ is one substituent attached to the carbocyclyl and is independently selected from the group consisting of —($C_{1-4}$ alkyl), halide, —CF$_3$, and —CN;

each $R^{21}$ is one substituent attached to the heterocyclyl and is independently selected from the group consisting of —($C_{1-4}$ alkyl), halide, —CF$_3$, and —CN;

$R^{22}$ is selected from the group consisting of H, —($C_{1-6}$ alkyl), —($C_{1-4}$ alkylene)$_p$heterocyclyl($R^{21}$)$_h$, —($C_{1-4}$ alkylene)$_p$carbocyclyl($R^{20}$)$_j$, —($C_{1-4}$ alkylene)$_p$aryl($R^{19}$)$_k$, and —($C_{1-6}$ alkylene)$_p$NR$^{23}$R$^{24}$;

each $R^{23}$ is independently selected from the group consisting of H and —($C_{1-6}$ alkyl);

each $R^{24}$ is independently selected from the group consisting of H and —($C_{1-6}$ alkyl);

$R^{25}$ is selected from the group consisting of H, —($C_{1-6}$ alkyl), —($C_{1-4}$ alkylene)$_p$heterocyclyl($R^{21}$)$_h$, and —($C_{1-6}$ alkylene)$_p$NR$^{23}$R$^{24}$;

each p is independently 0 or 1;

each q is independently 0 to 4;

each h is independently 0 to 10;

each k is independently 0 to 5; and each j is independently 0 to 12.

In some embodiments:

$R^1$ is -pyridinyl($R^4$)$_q$, wherein q is 0 or 1;

$R^2$ is H;

$R^3$ is H;

$R^4$ is one substituent attached to the pyridinyl and is selected from the group consisting of halide, —($C_{2-6}$ alkyl), —($C_{1-4}$ alkylene)$_p$heterocyclyl($R^9$)$_h$, —($C_{1-4}$ alkylene)$_p$carbocyclyl($R^{10}$)$_j$, —($C_{1-4}$ alkylene)$_p$aryl($R^{11}$)$_k$, —NHC(=O)R$^{12}$, —NR$^{13}$R$^{14}$, —($C_{1-6}$ alkylene)NR$^{15}$R$^{16}$, and —OR$^{22}$;

each $R^9$ is one substituent attached to the heterocyclyl and is independently selected from the group consisting of —($C_{1-4}$ alkyl), halide, —CF$_3$, and —CN;

each $R^{10}$ is one substituent attached to the carbocyclyl and is independently selected from the group consisting of —($C_{1-4}$ alkyl), halide, —CF$_3$, and —CN;

each $R^{11}$ is one substituent attached to the aryl and is independently selected from the group consisting of —($C_{1-4}$ alkyl), halide, —CF$_3$, and —CN;

$R^{12}$ is selected from the group consisting of —($C_{1-2}$ alkyl), —($C_{5-9}$ alkyl), -heteroaryl($R^{18}$)$_q$, -aryl($R^{19}$)$_k$, —CH$_2$aryl($R^{19}$)$_k$, -carbocyclyl($R^{20}$)$_j$, and —CH$_2$carbocyclyl($R^{20}$)$_j$;

each $R^{13}$ is independently selected from the group consisting of H and —($C_{1-6}$ alkyl);

each $R^{14}$ is independently selected from the group consisting of H, —($C_{1-6}$ alkyl), —CH$_2$aryl($R^{19}$)$_k$, and —CH$_2$carbocyclyl($R^{20}$)$_j$;

each $R^{15}$ is independently selected from the group consisting of H and —($C_{1-6}$ alkyl);

each $R^{16}$ is independently selected from the group consisting of H, —($C_{1-6}$ alkyl), —CH$_2$aryl($R^{19}$)$_k$, and —CH$_2$carbocyclyl($R^{20}$)$_j$;

each $R^{18}$ is one substituent attached to the heteroaryl and is independently selected from the group consisting of —($C_{1-4}$ alkyl), halide, —CF$_3$, and —CN;

each $R^{19}$ is one substituent attached to the aryl and is independently selected from the group consisting of —($C_{1-4}$ alkyl), halide, —CF$_3$, and —CN;

each $R^{20}$ is one substituent attached to the carbocyclyl and is independently selected from the group consisting of —($C_{1-4}$ alkyl), halide, —CF$_3$, and —CN;

each $R^{21}$ is one substituent attached to the heterocyclyl and is independently selected from the group consisting of —($C_{1-4}$ alkyl), halide, —CF$_3$, and —CN;

$R^{22}$ is selected from the group consisting of H, —($C_{1-6}$ alkyl), —($C_{1-4}$ alkylene)$_p$heterocyclyl($R^{21}$)$_h$, —($C_{1-4}$ alkylene)$_p$carbocyclyl($R^{20}$)$_j$, —($C_{1-4}$ alkylene)$_p$aryl($R^{19}$)$_k$, and —($C_{1-6}$ alkylene)$_p$NR$^{23}$R$^{24}$;

$R^{23}$ is selected from the group consisting of H and —($C_{1-6}$ alkyl);

$R^{24}$ is selected from the group consisting of H and —($C_{1-6}$ alkyl);

each p is independently 0 or 1;
each q is independently 0 to 4;
each h is independently 0 to 10;
each k is independently 0 to 5; and
each j is independently 0 to 12.

In some embodiments:
$R^1$ is -pyridinyl$(R^4)_q$, wherein q is 0 or 1;
$R^2$ is H;
$R^3$ is -imidazolyl$(R^6)_q$;
$R^4$ is one substituent attached to the pyridinyl and is selected from the group consisting of halide, —($C_{2-6}$ alkyl), —($C_{1-4}$ alkylene)$_p$heterocyclyl$(R^9)_h$, —($C_{1-4}$ alkylene)$_p$carbocyclyl$(R^{10})_j$, —($C_{1-4}$ alkylene)$_p$aryl $(R^{11})_k$, —NHC(=O)$R^{12}$, —NR$^{13}$R$^{14}$, —($C_{1-6}$ alkylene)NR$^{15}$R$^{16}$, and —OR$^{22}$;
each $R^6$ is one substituent attached to the imidazolyl and is independently selected from the group consisting of —($C_{1-6}$ alkyl), halide, —$CF_3$, —$OCH_3$, —CN, and —C(=O)$R^{17}$;
each $R^9$ is one substituent attached to the heterocyclyl and is independently selected from the group consisting of —($C_{1-4}$ alkyl), halide, —$CF_3$, and —CN;
each $R^{10}$ is one substituent attached to the carbocyclyl and is independently selected from the group consisting of —($C_{1-4}$ alkyl), halide, —$CF_3$, and —CN;
each $R^{11}$ is one substituent attached to the aryl and is independently selected from the group consisting of —($C_{1-4}$ alkyl), halide, —$CF_3$, and —CN;
$R^{12}$ is selected from the group consisting of —($C_{1-9}$ alkyl), -heteroaryl$(R^{18})_q$, -aryl$(R^{19})_k$, —CH$_2$aryl$(R^{19})_k$, -carbocyclyl$(R^{20})_j$, and —CH$_2$carbocyclyl$(R^{20})_j$;
$R^{13}$ is selected from the group consisting of H and —($C_{1-6}$ alkyl);
$R^{14}$ is selected from the group consisting of H, —($C_{1-6}$ alkyl), —CH$_2$aryl$(R^{19})_k$, and —CH$_2$carbocyclyl$(R^{20})_j$;
$R^{15}$ is selected from the group consisting of H and —($C_{1-6}$ alkyl);
$R^{16}$ is selected from the group consisting of H, —($C_{1-6}$ alkyl), —CH$_2$aryl$(R^{19})_k$, and —CH$_2$carbocyclyl$(R^{20})_j$;
each $R^{17}$ is a —($C_{1-6}$ alkyl);
each $R^{18}$ is one substituent attached to the heteroaryl and is independently selected from the group consisting of —($C_{1-4}$ alkyl), halide, —$CF_3$, and —CN;
each $R^{19}$ is one substituent attached to the aryl and is independently selected from the group consisting of —($C_{1-4}$ alkyl), halide, —$CF_3$, and —CN;
each $R^{20}$ is one substituent attached to the carbocyclyl and is independently selected from the group consisting of —($C_{1-4}$ alkyl), halide, —$CF_3$, and —CN;
each $R^{21}$ is one substituent attached to the heterocyclyl and is independently selected from the group consisting of —($C_{1-4}$ alkyl), halide, —$CF_3$, and —CN;
$R^{22}$ is selected from the group consisting of H, —($C_{1-6}$ alkyl), —($C_{1-4}$ alkylene)$_p$heterocyclyl$(R^{21})_h$, —($C_{1-4}$ alkylene)$_p$carbocyclyl$(R^{20})_j$, —($C_{1-4}$ alkylene)$_p$aryl $(R^{19})_k$, and —($C_{1-6}$ alkylene)$_p$NR$^{23}$R$^{24}$;
$R^{23}$ is selected from the group consisting of H and —($C_{1-6}$ alkyl);
$R^{24}$ is selected from the group consisting of H and —($C_{1-6}$ alkyl);
each p is independently an integer of 0 or 1;
each q is independently 0 to 4;
each h is independently 0 to 10;
each k is independently 0 to 5; and
each j is independently 0 to 12.

In some embodiments:
$R^1$ is -pyridinyl$(R^4)_q$, wherein q is 0 or 1;
$R^2$ is H;
$R^3$ is selected from the group consisting of -heteroaryl $(R^6)_q$ and -heterocyclyl$(R^7)_h$, with the proviso that heteroaryl does not include pyridinyl and imidazolyl.
$R^4$ is one substituent attached to the pyridinyl and is selected from the group consisting of halide, —($C_{1-6}$ alkyl), —($C_{1-4}$ alkylene)$_p$heterocyclyl$(R^9)_h$, —($C_{1-4}$ alkylene)$_p$carbocyclyl$(R^{10})_j$, —($C_{1-4}$ alkylene)$_p$aryl $(R^{11})_k$, —NHC(=O)$R^{12}$, —NR$^{13}$R$^{14}$, —($C_{1-6}$ alkylene)NR$^{15}$R$^{16}$, and —OR$^{22}$;
each $R^6$ is one substituent attached to the heteroaryl and is independently selected from the group consisting of —($C_{1-6}$ alkyl), halide, —$CF_3$, —$OCH_3$, —CN, and —C(=O)$R^{17}$;
each $R^7$ is one substituent attached to the heterocyclyl and is independently selected from the group consisting of —($C_{1-6}$ alkyl), halide, —$CF_3$, —CN, and —$OCH_3$;
each $R^9$ is one substituent attached to the heterocyclyl and is independently selected from the group consisting of —($C_{1-4}$ alkyl), halide, —$CF_3$, and —CN;
each $R^{10}$ is one substituent attached to the carbocyclyl and is independently selected from the group consisting of —($C_{1-4}$ alkyl), halide, —$CF_3$, and —CN;
each $R^{11}$ is one substituent attached to the aryl and is independently selected from the group consisting of —($C_{1-4}$ alkyl), halide, —$CF_3$, and —CN;
$R^{12}$ is selected from the group consisting of —($C_{1-9}$ alkyl), -heteroaryl$(R^{18})_q$, -aryl$(R^{19})_k$, —CH$_2$aryl$(R^{19})_k$, -carbocyclyl$(R^{20})_j$, and —CH$_2$carbocyclyl$(R^{20})_j$;
$R^{13}$ is selected from the group consisting of H and —($C_{1-6}$ alkyl);
$R^{14}$ is selected from the group consisting of H, —($C_{1-6}$ alkyl), —CH$_2$aryl$(R^{19})_k$, and —CH$_2$carbocyclyl$(R^{20})_j$;
$R^{15}$ is selected from the group consisting of H and —($C_{1-6}$ alkyl);
$R^{16}$ is selected from the group consisting of H, —($C_{1-6}$ alkyl), —CH$_2$aryl$(R^{19})_k$, and —CH$_2$carbocyclyl$(R^{20})_j$;
each $R^{17}$ is a —($C_{1-6}$ alkyl);
each $R^{18}$ is one substituent attached to the heteroaryl and is independently selected from the group consisting of —($C_{1-4}$ alkyl), halide, —$CF_3$, and —CN;
each $R^{19}$ is one substituent attached to the aryl and is independently selected from the group consisting of —($C_{1-4}$ alkyl), halide, —$CF_3$, and —CN;
each $R^{20}$ is one substituent attached to the carbocyclyl and is independently selected from the group consisting of —($C_{1-4}$ alkyl), halide, —$CF_3$, and —CN;
each $R^{21}$ is one substituent attached to the heterocyclyl and is independently selected from the group consisting of —($C_{1-4}$ alkyl), halide, —$CF_3$, and —CN;
$R^{22}$ is selected from the group consisting of H, —($C_{1-6}$ alkyl), —($C_{1-4}$ alkylene)$_p$heterocyclyl$(R^{21})_h$, —($C_{1-4}$ alkylene)$_p$carbocyclyl$(R^{20})_j$, —($C_{1-4}$ alkylene)$_p$aryl $(R^{19})_k$, and —($C_{1-6}$ alkylene)$_p$NR$^{23}$R$^{24}$;
$R^{23}$ is selected from the group consisting of H and —($C_{1-6}$ alkyl);
$R^{24}$ is selected from the group consisting of H and —($C_{1-6}$ alkyl);
each p is independently 0 or 1;
each q is independently 0 to 4;
each h is independently 0 to 10;
each k is independently 0 to 5; and
each j is independently 0 to 12.

In some embodiments:
$R^1$ is selected from the group consisting of -pyrimidinyl $(R^4)_q$, -pyrazinyl$(R^4)_q$, -pyrazolyl$(R^4)_q$, -imidazolyl $(R^4)_q$, and -heterocyclyl$(R^5)_h$;

$R^2$ is H;

$R^3$ is selected from the group consisting of H, -heteroaryl$(R^6)_q$, -heterocyclyl$(R^7)_h$, and -aryl$(R^8)_k$;

each $R^4$ is one substituent attached to the heteroaryl and is independently selected from the group consisting of halide, —($C_{1-6}$ alkyl), —($C_{1-4}$ alkylene)$_p$heterocyclyl$(R^9)_h$, —($C_{1-4}$ alkylene)$_p$carbocyclyl$(R^{10})_j$, —($C_{1-4}$ alkylene)$_p$aryl$(R^{11})_k$, —NHC(=O)$R^{12}$, —NR$^{13}$R$^{14}$, —($C_{1-6}$ alkylene)NR$^{15}$R$^{16}$, and —OR$^{22}$;

each $R^5$ is one substituent attached to the heterocyclyl and is independently selected from the group consisting of —($C_{1-4}$ alkyl), halide, —$CF_3$, and —CN;

each $R^6$ is one substituent attached to the heteroaryl and is independently selected from the group consisting of —($C_{1-6}$ alkyl), halide, —$CF_3$, —$OCH_3$, —CN, and —C(=O)$R^{17}$;

each $R^7$ is one substituent attached to the heterocyclyl and is independently selected from the group consisting of —($C_{1-6}$ alkyl), halide, —$CF_3$, —CN, and —$OCH_3$;

each $R^8$ is one substituent attached to the aryl and is independently selected from the group consisting of —($C_{1-6}$ alkyl), halide, —$CF_3$, —CN, —$OCH_3$, —($C_{1-6}$ alkylene)$_p$NHSO$_2$R$^{17}$, —NR$^{13}$($C_{1-6}$ alkylene)NR$^{13}$R$^{14}$, —($C_{1-6}$ alkylene)$_p$NR$^{13}$R$^{14}$, and —OR$^{25}$;

each $R^9$ is one substituent attached to the heterocyclyl and is independently selected from the group consisting of amino, —($C_{1-4}$ alkyl), halide, —$CF_3$, and —CN;

each $R^{10}$ is one substituent attached to the carbocyclyl and is independently selected from the group consisting of —($C_{1-4}$ alkyl), halide, —$CF_3$, and —CN;

each $R^{11}$ is one substituent attached to the aryl and is independently selected from the group consisting of —($C_{1-4}$ alkyl), halide, —$CF_3$, and —CN;

each $R^{12}$ is independently selected from the group consisting of —($C_{1-9}$ alkyl), -heteroaryl$(R^{18})_q$, -aryl$(R^{19})_k$, —CH$_2$aryl$(R^{19})_k$, -carbocyclyl$(R^{20})_j$, —CH$_2$carbocyclyl$(R^{20})_j$, —($C_{1-4}$ alkylene)$_p$NR$^{23}$R$^{24}$, -heterocyclyl$(R^{21})_h$, and —CH$_2$heterocyclyl$(R^{21})_h$;

each $R^{13}$ is independently selected from the group consisting of H and —($C_{1-6}$ alkyl);

each $R^{14}$ is independently selected from the group consisting of H, —($C_{1-6}$ alkyl), —CH$_2$aryl$(R^{19})_k$, and —CH$_2$carbocyclyl$(R^{20})_j$;

each $R^{15}$ is independently selected from the group consisting of H and —($C_{1-6}$ alkyl);

each $R^{16}$ is independently selected from the group consisting of H, —($C_{1-6}$ alkyl), —CH$_2$aryl$(R^{19})_k$, and —CH$_2$carbocyclyl$(R^{20})_j$;

each $R^{17}$ is a —($C_{1-6}$ alkyl);

each $R^{18}$ is one substituent attached to the heteroaryl and is independently selected from the group consisting of —($C_{1-4}$ alkyl), halide, —$CF_3$, and —CN;

each $R^{19}$ is one substituent attached to the aryl and is independently selected from the group consisting of —($C_{1-4}$ alkyl), halide, —$CF_3$, and —CN;

each $R^{20}$ is one substituent attached to the carbocyclyl and is independently selected from the group consisting of —($C_{1-4}$ alkyl), halide, —$CF_3$, and —CN;

each $R^{21}$ is one substituent attached to the heterocyclyl and is independently selected from the group consisting of —($C_{1-4}$ alkyl), halide, —$CF_3$, and —CN;

$R^{22}$ is selected from the group consisting of H, —($C_{1-6}$ alkyl), —($C_{1-4}$ alkylene)$_p$heterocyclyl$(R^{21})_h$, —($C_{1-4}$ alkylene)$_p$carbocyclyl$(R^{20})_j$, —($C_{1-4}$ alkylene)$_p$aryl$(R^{19})_k$, and —($C_{1-6}$ alkylene)$_p$NR$^{23}$R$^{24}$;

each $R^{23}$ is independently selected from the group consisting of H and —($C_{1-6}$ alkyl);

each $R^{24}$ is independently selected from the group consisting of H and —($C_{1-6}$ alkyl);

$R^{25}$ is selected from the group consisting of H, —($C_{1-6}$ alkyl), —($C_{1-4}$ alkylene)$_p$heterocyclyl$(R^{21})_h$, and —($C_{1-6}$ alkylene)$_p$NR$^{23}$R$^{24}$;

each p is independently 0 or 1;

each q is independently 0 to 4;

each h is independently 0 to 10;

each k is independently 0 to 5; and each j is independently 0 to 12.

In some embodiments:

$R^1$ is selected from the group consisting of -heteroaryl$(R^4)_q$ and -heterocyclyl$(R^5)_h$;

$R^2$ is a halide;

$R^3$ is selected from the group consisting of H, -heteroaryl$(R^6)_q$, -heterocyclyl$(R^7)_h$, and -aryl$(R^8)_k$;

each $R^4$ is one substituent attached to the heteroaryl and is independently selected from the group consisting of halide, —($C_{1-6}$ alkyl), —($C_{1-4}$ alkylene)$_p$heterocyclyl$(R^9)_h$, —($C_{1-4}$ alkylene)$_p$carbocyclyl$(R^{10})_j$, —($C_{1-4}$ alkylene)$_p$aryl$(R^{11})_k$, —NHC(=O)$R^{12}$, —NR$^{13}$R$^{14}$, —($C_{1-6}$ alkylene)NR$^{15}$R$^{16}$, and —OR$^{22}$;

each $R^5$ is one substituent attached to the heterocyclyl and is independently selected from the group consisting of —($C_{1-4}$ alkyl), halide, —$CF_3$, and —CN;

each $R^6$ is one substituent attached to the heteroaryl and is independently selected from the group consisting of —($C_{1-6}$ alkyl), halide, —$CF_3$, —$OCH_3$, —CN, and —C(=O)$R^{17}$;

each $R^7$ is one substituent attached to the heterocyclyl and is independently selected from the group consisting of —($C_{1-6}$ alkyl), halide, —$CF_3$, —CN, and —$OCH_3$;

each $R^8$ is one substituent attached to the aryl and is independently selected from the group consisting of —($C_{1-6}$ alkyl), halide, —$CF_3$, —CN, —$OCH_3$, —($C_{1-6}$ alkylene)$_p$NHSO$_2$R$^{17}$, —NR$^{13}$($C_{1-6}$ alkylene)NR$^{13}$R$^{14}$, —($C_{1-6}$ alkylene)$_p$NR$^{13}$R$^{14}$, and —OR$^{25}$;

each $R^9$ is one substituent attached to the heterocyclyl and is independently selected from the group consisting of amino, —($C_{1-4}$ alkyl), halide, —$CF_3$, and —CN;

each $R^{10}$ is one substituent attached to the carbocyclyl and is independently selected from the group consisting of —($C_{1-4}$ alkyl), halide, —$CF_3$, and —CN;

each $R^{11}$ is one substituent attached to the aryl and is independently selected from the group consisting of —($C_{1-4}$ alkyl), halide, —$CF_3$, and —CN;

each $R^{12}$ is independently selected from the group consisting of —($C_{1-9}$ alkyl), -heteroaryl$(R^{18})_q$, -aryl$(R^{19})_k$, —CH$_2$aryl$(R^{19})_k$, -carbocyclyl$(R^{20})_j$, —CH$_2$carbocyclyl$(R^{20})_j$, —($C_{1-4}$ alkylene)$_p$NR$^{23}$R$^{24}$, -heterocyclyl$(R^{21})_h$, and —CH$_2$heterocyclyl$(R^{21})_h$;

each $R^{13}$ is independently selected from the group consisting of H and —($C_{1-6}$ alkyl);

each $R^{14}$ is independently selected from the group consisting of H, —($C_{1-6}$ alkyl), —CH$_2$aryl$(R^{19})_k$, and —CH$_2$carbocyclyl$(R^{20})_j$;

each $R^{15}$ is independently selected from the group consisting of H and —($C_{1-6}$ alkyl);

each $R^{16}$ is independently selected from the group consisting of H, —($C_{1-6}$ alkyl), —CH$_2$aryl$(R^{19})_k$, and —CH$_2$carbocyclyl$(R^{20})_j$;

each $R^{17}$ is a —($C_{1-6}$ alkyl);

each $R^{18}$ is one substituent attached to the heteroaryl and is independently selected from the group consisting of —($C_{1-4}$ alkyl), halide, —$CF_3$, and —CN;

each $R^{19}$ is one substituent attached to the aryl and is independently selected from the group consisting of —($C_{1-4}$ alkyl), halide, —$CF_3$, and —CN;

each $R^{20}$ is one substituent attached to the carbocyclyl and is independently selected from the group consisting of —($C_{1-4}$ alkyl), halide, —$CF_3$, and —CN;

each $R^{21}$ is one substituent attached to the heterocyclyl and is independently selected from the group consisting of —($C_{1-4}$ alkyl), halide, —$CF_3$, and —CN;

$R^{22}$ is selected from the group consisting of H, —($C_{1-6}$ alkyl), —($C_{1-4}$ alkylene)$_p$heterocyclyl($R^{21}$)$_h$, —($C_{1-4}$ alkylene)$_p$carbocyclyl($R^{20}$)$_j$, —($C_{1-4}$ alkylene)$_p$aryl($R^{19}$)$_k$, and —($C_{1-6}$ alkylene)$_p$NR$^{23}$R$^{24}$;

each $R^{23}$ is independently selected from the group consisting of H and —($C_{1-6}$ alkyl);

each $R^{24}$ is independently selected from the group consisting of H and —($C_{1-6}$ alkyl);

$R^{25}$ is selected from the group consisting of H, —($C_{1-6}$ alkyl), —($C_{1-4}$ alkylene)$_p$heterocyclyl($R^{21}$)$_h$, and —($C_{1-6}$ alkylene)$_p$NR$^{23}$R$^{24}$;

each p is independently 0 or 1;
each q is independently 0 to 4;
each h is independently 0 to 10;
each k is independently 0 to 5; and
each j is independently 0 to 12.

In some embodiments, $R^2$ is H; $R^1$ is -pyridin-3-yl($R^4$)$_q$; q is 1; $R^4$ is —NHC(=O)$R^{12}$; $R^{12}$ is —($C_{2-5}$ alkyl); $R^3$ is -phenyl($R^8$)$_k$; k is 1 or 2; and $R^8$ is F.

In some embodiments, $R^2$ is H; $R^1$ is -pyridin-3-yl($R^4$)$_q$; q is 1; $R^4$ is —NHC(=O)$R^{12}$; $R^{12}$ is —($C_{2-5}$ alkyl); $R^3$ is -phenyl($R^8$)$_k$; k is 2; one $R^8$ is F and the other $R^8$ is —($C_{1-2}$ alkylene)$_p$NHSO$_2$R$^{17}$; p is 1; and $R^{17}$ is —($C_{1-3}$ alkyl).

In some embodiments, $R^2$ is H; $R^1$ is -pyridin-3-yl($R^4$)$_q$; q is 1; $R^4$ is —NHC(=O)$R^{12}$; $R^{12}$ is —($C_{2-5}$ alkyl); $R^3$ is -phenyl($R^8$)$_k$; k is 2; one $R^8$ is F and the other $R^8$ is —NH($C_{1-6}$alkylene)NR$^{13}$R$^{14}$; and $R^{13}$ and $R^{14}$ are independently selected from —($C_{1-3}$ alkyl).

In some embodiments, $R^2$ is H; $R^1$ is -pyridin-3-yl($R^4$)$_q$, wherein q is 1; $R^4$ is —NHC(=O)$R^{12}$; $R^{12}$ is —($C_{2-5}$ alkyl); $R^3$ is -heteroaryl($R^6$)$_q$, wherein q is 1; $R^6$ is selected from the group consisting of halide, —($C_{1-2}$ alkyl), and —C(=O)$R^{17}$; $R^{17}$ is —($C_{1-3}$ alkyl); and the heteroaryl is selected from the group consisting of pyridine, furan, thiophene, and imidazole.

In some embodiments, $R^2$ is H; $R^1$ is -pyridin-3-yl($R^4$)$_q$; q is 1; $R^4$ is —NHC(=O)$R^{12}$; $R^{12}$ is —($C_{2-5}$ alkyl); $R^3$ is -heterocyclyl($R^7$)$_h$; h is 1 or 2; and $R^7$ is selected from the group consisting of halide and —($C_{1-2}$ alkyl).

In some embodiments, $R^2$ is H; $R^1$ is -pyridin-3-yl($R^4$)$_q$; q is 1; $R^4$ is —NHC(=O)$R^{12}$; $R^{12}$ is -carbocyclyl($R^{20}$)$_j$; j is 0; $R^3$ is -phenyl($R^8$)$_k$; k is 1 or 2; $R^8$ is F; and the carbocyclyl is selected from the group consisting of cyclopropyl, cyclobutyl, cyclopentyl, and cyclohexyl.

In some embodiments, $R^2$ is H; $R^1$ is -pyridin-3-yl($R^4$)$_q$; q is 1; $R^4$ is —NHC(=O)$R^{12}$; $R^{12}$ is -carbocyclyl($R^{20}$)$_j$; j is 0; $R^3$ is -phenyl($R^8$)$_k$; k is 2; one $R^8$ is F and the other $R^8$ is —($C_{1-2}$ alkylene)$_p$NHSO$_2$R$^{17}$; p is 1; $R^{17}$ is —($C_{1-3}$ alkyl); and the carbocyclyl is selected from the group consisting of cyclopropyl, cyclobutyl, cyclopentyl, and cyclohexyl.

In some embodiments, $R^2$ is H; $R^1$ is -pyridin-3-yl($R^4$)$_q$; q is 1; $R^4$ is —NHC(=O)$R^{12}$; $R^{12}$ is -carbocyclyl($R^{20}$)$_j$; j is 0; $R^3$ is -phenyl($R^8$)$_k$; k is 2; one $R^8$ is F and the other $R^8$ is —NH($C_{1-6}$ alkylene)NR$^{13}$R$^{14}$; $R^{13}$ and $R^{14}$ are independently selected from —($C_{1-3}$ alkyl); and the carbocyclyl is selected from the group consisting of cyclopropyl, cyclobutyl, cyclopentyl, and cyclohexyl.

In some embodiments, $R^2$ is H; $R^1$ is -pyridin-3-yl($R^4$)$_q$, wherein q is 1; $R^4$ is —NHC(=O)$R^{12}$; $R^{12}$ is -carbocyclyl($R^{20}$)$_j$; j is 0; $R^3$ is -heteroaryl($R^6$)$_q$, wherein q is 1; $R^6$ is selected from the group consisting of halide, —($C_{1-2}$ alkyl), and —C(=O)$R^{17}$; $R^{17}$ is $C_{1-3}$ alkyl; the heteroaryl is selected from the group consisting of pyridine, furan, thiophene, and imidazole; and the carbocyclyl is selected from the group consisting of cyclopropyl, cyclobutyl, cyclopentyl, and cyclohexyl.

In some embodiments, $R^2$ is H; $R^1$ is -pyridin-3-yl($R^4$)$_q$; q is 1; $R^4$ is —NHC(=O)$R^{12}$; $R^{12}$ is -carbocyclyl($R^{20}$)$_j$; j is 0; $R^3$ is -heterocyclyl($R^7$)$_h$; h is 1 or 2; $R^7$ is selected from the group consisting of halide and —($C_{1-2}$ alkyl); and the carbocyclyl is selected from the group consisting of cyclopropyl, cyclobutyl, cyclopentyl, and cyclohexyl.

In some embodiments, $R^2$ is H; $R^1$ is -pyridin-3-yl($R^4$)$_q$; q is 1; $R^4$ is selected from the group consisting of —NR$^{13}$R$^{14}$ and —CH$_2$NR$^{15}$R$^{16}$; $R^{13}$ and $R^{15}$ are independently selected from the group consisting of H and —($C_{1-3}$ alkyl); $R^{14}$ and $R^{16}$ are independently selected from the group consisting of H, —($C_{1-3}$ alkyl), —CH$_2$phenyl($R^{19}$)$_k$, and —CH$_2$carbocyclyl($R^{20}$)$_j$, wherein j and k are 0; $R^3$ is -phenyl($R^8$)$_k$, wherein k is 1 or 2; $R^8$ is F; and the carbocyclyl is selected from the group consisting of cyclopropyl, cyclobutyl, cyclopentyl, and cyclohexyl.

In some embodiments, $R^2$ is H; $R^1$ is -pyridin-3-yl($R^4$)$_q$; q is 1; $R^4$ is selected from the group consisting of —NR$^{13}$R$^{14}$ and —CH$_2$NR$^{15}$R$^{16}$; $R^{13}$ and $R^{15}$ are independently selected from the group consisting of H and —($C_{1-3}$ alkyl); $R^{14}$ and $R^{16}$ are independently selected from the group consisting of H, —($C_{1-3}$ alkyl), —CH$_2$phenyl($R^{19}$)$_k$, and —CH$_2$carbocyclyl($R^{20}$)$_j$, wherein j and k are 0; $R^3$ is -phenyl($R^8$)$_k$, wherein k is 2; one $R^8$ is F and the other $R^8$ is —($C_{1-2}$ alkylene)$_p$NHSO$_2$R$^{17}$; p is 1; $R^{17}$ is —($C_{1-3}$ alkyl); and the carbocyclyl is selected from the group consisting of cyclopropyl, cyclobutyl, cyclopentyl, and cyclohexyl.

In some embodiments, $R^2$ is H; $R^1$ is -pyridin-3-yl($R^4$)$_q$; q is 1; $R^4$ is selected from the group consisting of —NR$^{13}$R$^{14}$ and —CH$_2$NR$^{15}$R$^{16}$, wherein $R^{13}$ and $R^{15}$ are independently selected from the group consisting of H and —($C_{1-3}$ alkyl), and $R^{14}$ and $R^{16}$ are independently selected from the group consisting of H, —($C_{1-3}$ alkyl), —CH$_2$phenyl($R^{19}$)$_k$, and —CH$_2$carbocyclyl($R^{20}$)$_j$, wherein k and j are 0; $R^3$ is -phenyl($R^8$)$_k$, wherein k is 2; one $R^8$ is F and the other $R^8$ is —NH($C_{1-6}$ alkylene)NR$^{13}$R$^{14}$, wherein $R^{13}$ and $R^{14}$ are independently selected from —($C_{1-3}$ alkyl); and the carbocyclyl is selected from the group consisting of cyclopropyl, cyclobutyl, cyclopentyl, and cyclohexyl.

In some embodiments, $R^2$ is H; $R^1$ is -pyridin-3-yl($R^4$)$_q$, wherein q is 1; $R^4$ is selected from the group consisting of —NR$^{13}$R$^{14}$ and —CH$_2$NR$^{15}$R$^{16}$; $R^{13}$ and $R^{15}$ are independently selected from the group consisting of H and —($C_{1-3}$ alkyl); $R^{14}$ and $R^{16}$ are independently selected from the group consisting of H, —($C_{1-3}$ alkyl), —CH$_2$phenyl($R^{19}$)$_k$, and —CH$_2$carbocyclyl($R^{20}$)$_j$; k and j are 0; $R^3$ is -heteroaryl($R^6$)$_q$, wherein q is 1; $R^6$ is selected from the group consisting of halide, —($C_{1-2}$ alkyl), and —C(=O)$R^{17}$; $R^{17}$ is —($C_{1-3}$ alkyl); the heteroaryl is selected from the group consisting of pyridine, furan, thiophene, and imidazole; and the carbocyclyl is selected from the group consisting of cyclopropyl, cyclobutyl, cyclopentyl, and cyclohexyl.

In some embodiments, $R^2$ is H; $R^1$ is -pyridin-3-yl($R^4$)$_q$; q is 1; $R^4$ is selected from the group consisting of —NR$^{13}$R$^{14}$ and —CH$_2$NR$^{15}$R$^{16}$; $R^{13}$ and $R^{15}$ are independently selected from the group consisting of H and —($C_{1-3}$ alkyl); $R^{14}$ and $R^{16}$ are independently selected from the group consisting of H, —($C_{1-3}$ alkyl), —CH$_2$phenyl($R^{19}$)$_k$, and —CH$_2$carbocyclyl(R$^{20}$)$_j$; k and j are 0; R$^3$ is -heterocyclyl(R$^7$)$_h$; h is 1 or 2; R$^1$ is selected from the group consisting of halide and —(C$_{1-2}$ alkyl); and the carbocyclyl is selected from the group consisting of cyclopropyl, cyclobutyl, cyclopentyl, and cyclohexyl.

In some embodiments, R$^2$ is H; R$^1$ is -pyridin-3-yl(R$^4$)$_q$; q is 1; R$^4$ is —CH$_2$heterocyclyl(R$^9$)$_h$; h is 0-2; R$^9$ is F; R$^3$ is -phenyl(R$^8$)$_k$; k is 1 or 2; R$^8$ is F; and the heterocyclyl is selected from the group consisting of pyrrolidine and piperidine.

In some embodiments, R$^2$ is H; R$^1$ is -pyridin-3-yl(R$^4$)$_q$; q is 1; R$^4$ is —CH$_2$heterocyclyl(R$^9$)$_h$; h is 0-2; R$^9$ is F; R$^3$ is -phenyl(R$^8$)$_k$; k is 2; one R$^8$ is F and the other R$^8$ is —(C$_{1-2}$ alkylene)$_p$NHSO$_2$R$^{17}$; p is 1; R$^{17}$ is —(C$_{1-3}$ alkyl); and the heterocyclyl is selected from the group consisting of pyrrolidine and piperidine.

In some embodiments, R$^2$ is H; R$^1$ is -pyridin-3-yl(R$^4$)$_q$; q is 1; R$^4$ is —CH$_2$heterocyclyl(R$^9$)$_h$; h is 0-2; R$^9$ is F; R$^3$ is -phenyl(R$^8$)$_k$; k is 2; and R$^8$ is one F and the other R$^8$—NH(C$_{1-6}$ alkylene)NR$^{13}$R$^{14}$; R$^{13}$ and R$^{14}$ are independently selected from —(C$_{1-3}$ alkyl); and the heterocyclyl is selected from the group consisting of pyrrolidine and piperidine.

In some embodiments, R$^2$ is H; R$^1$ is -pyridin-3-yl(R$^4$)$_q$, wherein q is 1; R$^4$ is —CH$_2$heterocyclyl(R$^9$)$_h$; h is 0-2; R$^9$ is F; R$^3$ is -heteroaryl(R$^6$)$_q$, wherein q is 1; R$^6$ is selected from the group consisting of halide, —(C$_{1-2}$ alkyl), and —C(=O)R$^{17}$; R$^{17}$ is —(C$_{1-3}$ alkyl); the heteroaryl is selected from the group consisting of pyridine, furan, thiophene, and imidazole; and the heterocyclyl is selected from the group consisting of pyrrolidine and piperidine.

In some embodiments, R$^2$ is H; R$^1$ is -pyridin-3-yl(R$^4$)$_q$; q is 1; R$^4$ is —CH$_2$heterocyclyl(R$^9$)$_h$; h is 0-2; R$^9$ is F; R$^3$ is -heterocyclyl(R$^7$)$_h$; h is 1 or 2; R$^7$ is selected from the group consisting of halide and —(C$_{1-2}$ alkyl); and the heterocyclyl is selected from the group consisting of pyrrolidine and piperidine.

In some embodiments, R$^2$ is H; R$^1$ is -pyrimidinyl(R$^4$)$_q$; q is 0; R$^3$ is -phenyl(R$^8$)$_k$; k is 1 or 2; and R$^8$ is F.

In some embodiments, R$^2$ is H; R$^1$ is -pyrimidinyl(R$^4$)$_q$; q is 0; R$^3$ is -phenyl(R$^8$)$_k$; k is 2; one R$^8$ is F and the other R$^8$ is —(C$_{1-2}$ alkylene)$_p$NHSO$_2$R$^{17}$; p is 1; and R$^{17}$ is —(C$_{1-3}$ alkyl).

In some embodiments, R$^2$ is H; R$^1$ is -pyrimidinyl(R$^4$)$_q$; q is 0; R$^3$ is -phenyl(R$^8$)$_k$; k is 2; one R$^8$ is F and the other R$^8$ is —NH(C$_{1-6}$ alkylene)NR$^{13}$R$^{14}$; and R$^{13}$ and R$^{14}$ are independently selected from —(C$_{1-3}$ alkyl).

In some embodiments, R$^2$ is H; R$^1$ is -pyrimidinyl(R$^4$)$_q$, wherein q is 0; R$^3$ is -heteroaryl(R$^6$)$_q$, wherein q is 1; R$^6$ is selected from the group consisting of halide, —(C$_{1-2}$ alkyl), and —C(=O)R$^{17}$; R$^{17}$ is —(C$_{1-3}$ alkyl); and the heteroaryl is selected from the group consisting of pyridine, furan, thiophene, and imidazole.

In some embodiments, R$^2$ is H; R$^1$ is -pyrimidinyl(R$^4$)$_q$; q is 0; R$^3$ is -heterocyclyl(R$^7$)$_h$; h is 1 or 2; R$^7$ is selected from the group consisting of halide and —(C$_{1-2}$ alkyl).

In some embodiments, R$^2$ is F; R$^1$ is -pyridin-3-yl(R$^4$)$_q$; q is 1; R$^4$ is —NHC(=O)R$^{12}$; R$^{12}$ is —(C$_{2-5}$ alkyl); R$^3$ is -phenyl(R$^8$)$_k$; k is 1 or 2; and R$^8$ is F.

In some embodiments, R$^2$ is F; R$^1$ is -pyridin-3-yl(R$^4$)$_q$; q is 1; R$^4$ is —NHC(=O)R$^{12}$; R$^{12}$ is —(C$_{2-5}$ alkyl); R$^3$ is -phenyl(R$^8$)$_k$; k is 2; one R$^8$ is F and the other R$^8$ is —(C$_{1-2}$ alkylene)$_p$NHSO$_2$R$^{17}$; p is 1; and R$^{17}$ is —(C$_{1-3}$ alkyl).

In some embodiments, R$^2$ is F; R$^1$ is -pyridin-3-yl(R$^4$)$_q$; q is 1; R$^4$ is —NHC(=O)R$^{12}$; R$^{12}$ is —(C$_{2-5}$ alkyl); R$^3$ is -phenyl(R$^8$)$_k$; k is 2; one R$^8$ is F and the other R$^8$ is —NH(C$_{1-6}$ alkylene)NR$^{13}$R$^{14}$; and R$^{13}$ and R$^{14}$ are independently selected from —(C$_{1-3}$ alkyl).

In some embodiments, R$^2$ is F; R$^1$ is -pyridin-3-yl(R$^4$)$_q$, wherein q is 1; R$^4$ is —NHC(=O)R$^{12}$; R$^{12}$ is —(C$_{2-5}$ alkyl); R$^3$ is -heteroaryl(R$^6$)$_q$, wherein q is 1; R$^6$ is selected from the group consisting of halide, —(C$_{1-2}$ alkyl), and —C(=O)R$^{17}$; R$^{17}$ is —(C$_{1-3}$ alkyl); and the heteroaryl is selected from the group consisting of pyridine, furan, thiophene, and imidazole.

In some embodiments, R$^2$ is F; R$^1$ is -pyridin-3-yl(R$^4$)$_q$; q is 1; R$^4$ is —NHC(=O)R$^{12}$; R$^{12}$ is —(C$_{2-5}$ alkyl); R$^3$ is -heterocyclyl(R$^7$)$_h$; h is 1 or 2; and R$^7$ is selected from the group consisting of halide and —(C$_{1-2}$ alkyl).

In some embodiments, R$^2$ is F; R$^1$ is -pyridin-3-yl(R$^4$)$_q$; q is 1; R$^4$ is —NHC(=O)R$^{12}$; R$^{12}$ is -carbocyclyl(R$^{20}$)$_j$; j is 0; R$^3$ is -phenyl(R$^8$)$_k$; k is 1 or 2; R$^8$ is F; and the carbocyclyl is selected from the group consisting of cyclopropyl, cyclobutyl, cyclopentyl, and cyclohexyl.

In some embodiments, R$^2$ is F; R$^1$ is -pyridin-3-yl(R$^4$)$_q$; q is 1; R$^4$ is —NHC(=O)R$^{12}$; R$^{12}$ is -carbocyclyl(R$^{20}$)$_j$; j is 0; R$^3$ is -phenyl(R$^8$)$_k$; k is 2; one R$^8$ is F and the other R$^8$ is —(C$_{1-2}$ alkylene)$_p$NHSO$_2$R$^{17}$; p is 1; R$^{17}$ is —(C$_{1-3}$ alkyl); and the carbocyclyl is selected from the group consisting of cyclopropyl, cyclobutyl, cyclopentyl, and cyclohexyl.

In some embodiments, R$^2$ is F; R$^1$ is -pyridin-3-yl(R$^4$)$_q$; q is 1; R$^4$ is —NHC(=O)R$^{12}$; R$^{12}$ is -carbocyclyl(R$^{20}$)$_j$; j is 0; R$^3$ is -phenyl(R$^8$)$_k$; k is 2; one R$^8$ is F and the other R$^8$ is —NH(C$_{1-6}$ alkylene)NR$^{13}$R$^{14}$; R$^{13}$ and R$^{14}$ are independently selected from —(C$_{1-3}$ alkyl); and the carbocyclyl is selected from the group consisting of cyclopropyl, cyclobutyl, cyclopentyl, and cyclohexyl.

In some embodiments, R$^2$ is F; R$^1$ is -pyridin-3-yl(R$^4$)$_q$, wherein q is 1; R$^4$ is —NHC(=O)R$^{12}$; R$^{12}$ is -carbocyclyl(R$^{20}$)$_j$; j is 0; R$^3$ is -heteroaryl(R$^6$)$_q$, wherein q is 1; R$^6$ is selected from the group consisting of halide, —(C$_{1-2}$ alkyl), and —C(=O)R$^{17}$; R$^{17}$ is C$_{1-3}$ alkyl; the heteroaryl is selected from the group consisting of pyridine, furan, thiophene, and imidazole; and the carbocyclyl is selected from the group consisting of cyclopropyl, cyclobutyl, cyclopentyl, and cyclohexyl.

In some embodiments, R$^2$ is F; R$^1$ is -pyridin-3-yl(R$^4$)$_q$; q is 1; R$^4$ is —NHC(=O)R$^{12}$; R$^{12}$ is -carbocyclyl(R$^{20}$)$_j$; j is 0; R$^3$ is -heterocyclyl(R$^7$)$_h$; h is 1 or 2; R is selected from the group consisting of halide and —(C$_{1-2}$ alkyl); and the carbocyclyl is selected from the group consisting of cyclopropyl, cyclobutyl, cyclopentyl, and cyclohexyl.

In some embodiments, R$^2$ is F; R$^1$ is -pyridin-3-yl(R$^4$)$_q$; q is 1; R$^4$ is selected from the group consisting of —NR$^{13}$R$^{14}$ and —CH$_2$NR$^{15}$R$^{16}$; R$^{13}$ and R$^{15}$ are independently selected from the group consisting of H and —(C$_{1-3}$ alkyl); R$^{14}$ and R$^{16}$ are independently selected from the group consisting of H, —(C$_{1-3}$ alkyl), —CH$_2$phenyl(R$^{19}$)$_k$, and —CH$_2$carbocyclyl(R$^{20}$)$_j$, wherein k and j are 0; R$^3$ is -phenyl(R$^8$)$_k$, wherein k is 1 or 2; R$^8$ is F; and the carbocyclyl is selected from the group consisting of cyclopropyl, cyclobutyl, cyclopentyl, and cyclohexyl.

In some embodiments, R$^2$ is F; R$^1$ is -pyridin-3-yl(R$^4$)$_q$; q is 1; R$^4$ is selected from the group consisting of —NR$^{13}$R$^{14}$ and —CH$_2$NR$^{15}$R$^{16}$; R$^{13}$ and R$^{15}$ are independently selected from the group consisting of H and —(C$_{1-3}$ alkyl); R$^{14}$ and R$^{16}$ are independently selected from the group consisting of H, —(C$_{1-3}$ alkyl), —CH$_2$phenyl(R$^{19}$)$_k$, and —CH$_2$carbocyclyl(R$^{20}$)$_j$, wherein k and j are 0; R$^3$ is -phenyl(R$^8$)$_k$, wherein k is 2; one R$^8$ is F and the other R$^8$ is —(C$_{1-2}$ alkylene)$_p$NHSO$_2$R$^{17}$; p is 1; R$^{17}$ is —(C$_{1-3}$ alkyl); and the carbocyclyl is selected from the group consisting of cyclopropyl, cyclobutyl, cyclopentyl, and cyclohexyl.

In some embodiments, $R^2$ is F; $R^1$ is -pyridin-3-yl$(R^4)_q$; q is 1; $R^4$ is selected from the group consisting of —$NR^{13}R^{14}$ and —$CH_2NR^{15}R^{16}$, wherein $R^{13}$ and $R^{15}$ are independently selected from the group consisting of H and —($C_{1-3}$ alkyl), and $R^{14}$ and $R^{16}$ are independently selected from the group consisting of H, —($C_{1-3}$ alkyl), —$CH_2$phenyl$(R^{19})_k$, and —$CH_2$carbocyclyl$(R^{20})_j$, wherein k and j are 0; $R^3$ is -phenyl $(R^8)_k$, wherein k is 2; one $R^8$ is F and the other $R^8$ is —$NH(C_{1-6}$ alkylene)$NR^{13}R^{14}$, wherein $R^{13}$ and $R^{14}$ are independently selected from —($C_{1-3}$ alkyl); and the carbocyclyl is selected from the group consisting of cyclopropyl, cyclobutyl, cyclopentyl, and cyclohexyl.

In some embodiments, $R^2$ is F; $R^1$ is -pyridin-3-yl$(R^4)_q$, wherein q is 1; $R^4$ is selected from the group consisting of —$NR^{13}R^{14}$ and —$CH_2NR^{15}R^{16}$; $R^{13}$ and $R^{15}$ are independently selected from the group consisting of H and —($C_{1-3}$ alkyl); $R^{14}$ and $R^{16}$ are independently selected from the group consisting of H, —($C_{1-3}$ alkyl), —$CH_2$phenyl$(R^{19})_k$, and —$CH_2$carbocyclyl$(R^{20})_j$; k and j are 0; $R^3$ is -heteroaryl $(R^6)_q$, wherein q is 1; $R^6$ is selected from the group consisting of halide, —($C_{1-2}$ alkyl), and —C(=O)$R^{17}$; $R^{17}$ is —($C_{1-3}$ alkyl); the heteroaryl is selected from the group consisting of pyridine, furan, thiophene, and imidazole; and the carbocyclyl is selected from the group consisting of cyclopropyl, cyclobutyl, cyclopentyl, and cyclohexyl.

In some embodiments, $R^2$ is F; $R^1$ is -pyridin-3-yl$(R^4)_q$; q is 1; $R^4$ is selected from the group consisting of —$NR^3R^4$ and —$CH_2NR^{15}R^{16}$; $R^{13}$ and $R^{15}$ are independently selected from the group consisting of H and —($C_{1-3}$ alkyl); $R^{14}$ and $R^{16}$ are independently selected from the group consisting of H, —($C_{1-3}$ alkyl), —$CH_2$phenyl$(R^{19})_k$, and —$CH_2$carbocyclyl$(R^{20})_j$; k and j are 0; $R^3$ is -heterocyclyl $(R^7)_h$; h is 1 or 2; $R^7$ is selected from the group consisting of halide and —($C_{1-2}$ alkyl); and the carbocyclyl is selected from the group consisting of cyclopropyl, cyclobutyl, cyclopentyl, and cyclohexyl.

In some embodiments, $R^2$ is F; $R^1$ is -pyridin-3-yl$(R^4)_q$; q is 1; $R^4$ is —$CH_2$heterocyclyl$(R^9)_h$; h is 0-2; $R^9$ is F; $R^3$ is -phenyl$(R^8)_k$; k is 1 or 2; $R^8$ is F; and the heterocyclyl is selected from the group consisting of pyrrolidine and piperidine.

In some embodiments, $R^2$ is F; $R^1$ is -pyridin-3-yl$(R^4)_q$; q is 1; $R^4$ is —$CH_2$heterocyclyl$(R^9)_h$; h is 0-2; $R^9$ is F; $R^3$ is -phenyl$(R^8)_k$; k is 2; one $R^8$ is F and the other $R^8$ is —($C_{1-2}$ alkylene)$_p$NHSO$_2R^{17}$; p is 1; $R^{17}$ is —($C_{1-3}$ alkyl); and the heterocyclyl is selected from the group consisting of pyrrolidine and piperidine.

In some embodiments, $R^2$ is F; $R^1$ is -pyridin-3-yl$(R^4)_q$; q is 1; $R^4$ is —$CH_2$heterocyclyl$(R^9)_h$; h is 0-2; $R^9$ is F; $R^3$ is -phenyl$(R^8)_k$; k is 2; and $R^8$ is one F and the other $R^8$ is —$NH(C_{1-6}$ alkylene)$NR^{13}R^{14}$; $R^{13}$ and $R^{14}$ are independently selected from —($C_{1-3}$ alkyl); and the heterocyclyl is selected from the group consisting of pyrrolidine and piperidine.

In some embodiments, $R^2$ is F; $R^1$ is -pyridin-3-yl$(R^4)_q$, wherein q is 1; $R^4$ is —$CH_2$heterocyclyl$(R^9)_h$; h is 0-2; $R^9$ is F; $R^3$ is -heteroaryl$(R^6)_q$, wherein q is 1; $R^6$ is selected from the group consisting of halide, —($C_{1-2}$ alkyl), and —C(=O)$R^{17}$; $R^{17}$ is —($C_{1-3}$ alkyl); the heteroaryl is selected from the group consisting of pyridine, furan, thiophene, and imidazole; and the heterocyclyl is selected from the group consisting of pyrrolidine and piperidine.

In some embodiments, $R^2$ is F; $R^1$ is -pyridin-3-yl$(R^4)_q$; q is 1; $R^4$ is —$CH_2$heterocyclyl$(R^9)_h$, wherein h is 0-2; $R^9$ is F; $R^3$ is -heterocyclyl$(R^7)_h$, wherein h is 1 or 2; $R^7$ is selected from the group consisting of halide and —($C_{1-2}$ alkyl); and the heterocyclyl is selected from the group consisting of pyrrolidine and piperidine.

In some embodiments, $R^2$ is F; $R^1$ is -pyrimidinyl$(R^4)_q$; q is 0; $R^3$ is -phenyl$(R^8)_k$; k is 1 or 2; and $R^8$ is F.

In some embodiments, $R^2$ is F; $R^1$ is -pyrimidinyl$(R^4)_q$; q is 0; $R^3$ is -phenyl$(R^8)_k$; k is 2; one $R^8$ is F and the other $R^8$ is —($C_{1-2}$ alkylene)$_p$NHSO$_2R^{17}$; p is 1; and $R^{17}$ is —($C_{1-3}$ alkyl).

In some embodiments, $R^2$ is F; $R^1$ is -pyrimidinyl$(R^4)_q$; q is 0; $R^3$ is -phenyl$(R^8)_k$; k is 2; one $R^8$ is F and the other $R^8$ is —$NH(C_{1-6}$ alkylene)$NR^{13}R^{14}$; and $R^{13}$ and $R^{14}$ are independently selected from —($C_{1-3}$ alkyl).

In some embodiments, $R^2$ is F; $R^1$ is -pyrimidinyl$(R^4)_q$, wherein q is 0; $R^3$ is -heteroaryl$(R^6)_q$, wherein q is 1; $R^6$ is selected from the group consisting of halide, —($C_{1-2}$ alkyl), and —C(=O)$R^{17}$; $R^{17}$ is —($C_{1-3}$ alkyl); and the heteroaryl is selected from the group consisting of pyridine, furan, thiophene, and imidazole.

In some embodiments, $R^2$ is F; $R^1$ is -pyrimidinyl$(R^4)_q$; q is 0; $R^3$ is -heterocyclyl$(R^7)_h$; h is 1 or 2; $R^7$ is selected from the group consisting of halide and —($C_{1-2}$ alkyl).

In some embodiments, $R^2$ is H; $R^1$ is -pyrazol-4-yl$(R^4)_q$; q is 0 or 1; $R^4$ is —($C_{1-3}$ alkyl); $R^3$ is -phenyl$(R^8)_k$; k is 1 or 2; and $R^8$ is F.

In some embodiments, $R^2$ is H; $R^1$ is -imidazol-5-yl$(R^4)_q$; q is 1 or 2; each $R^4$ is independently selected from —($C_{1-3}$ alkyl); $R^3$ is -phenyl$(R^8)_k$; k is 1 or 2; and $R^8$ is F.

In some embodiments, $R^2$ is H; $R^1$ is -pyridin-3-yl$(R^4)_q$; q is 1; $R^4$ is —$OR^{22}$; $R^{22}$ is selected from the group consisting of H and —($C_{1-3}$ alkyl); $R^3$ is -phenyl$(R^8)_k$; k is 1 or 2; and $R^8$ is F.

Illustrative compounds of Formula (I) are shown in Table 1.

TABLE 1

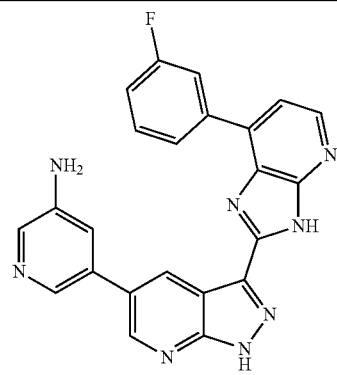

1

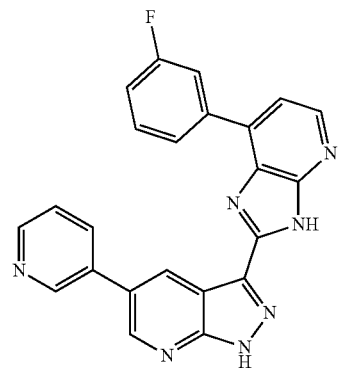 [SMILES: Fc1cccc(-c2ccnc3[nH]c(-c4n[nH]c5ncc(-c6cccnc6)cc45)nc23)c1]

2

TABLE 1-continued
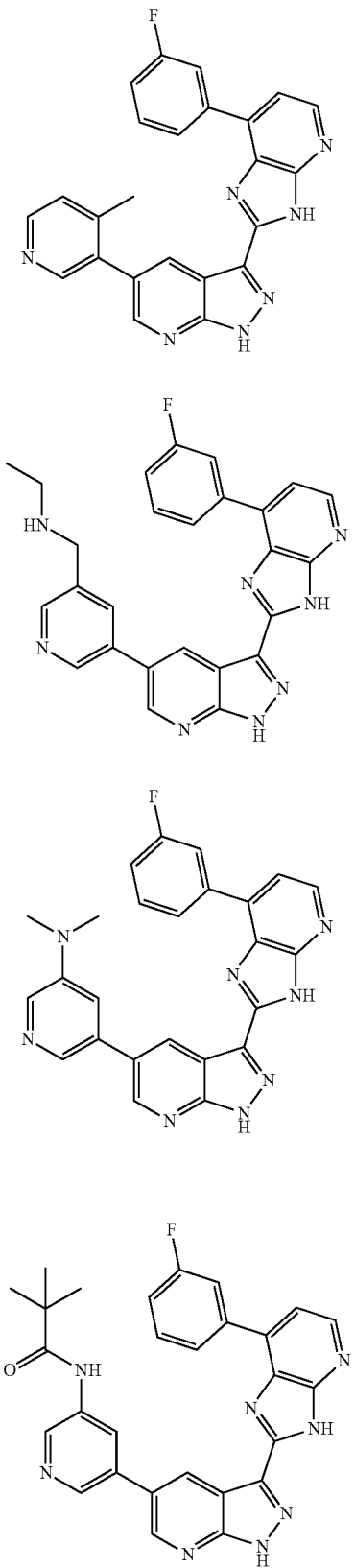
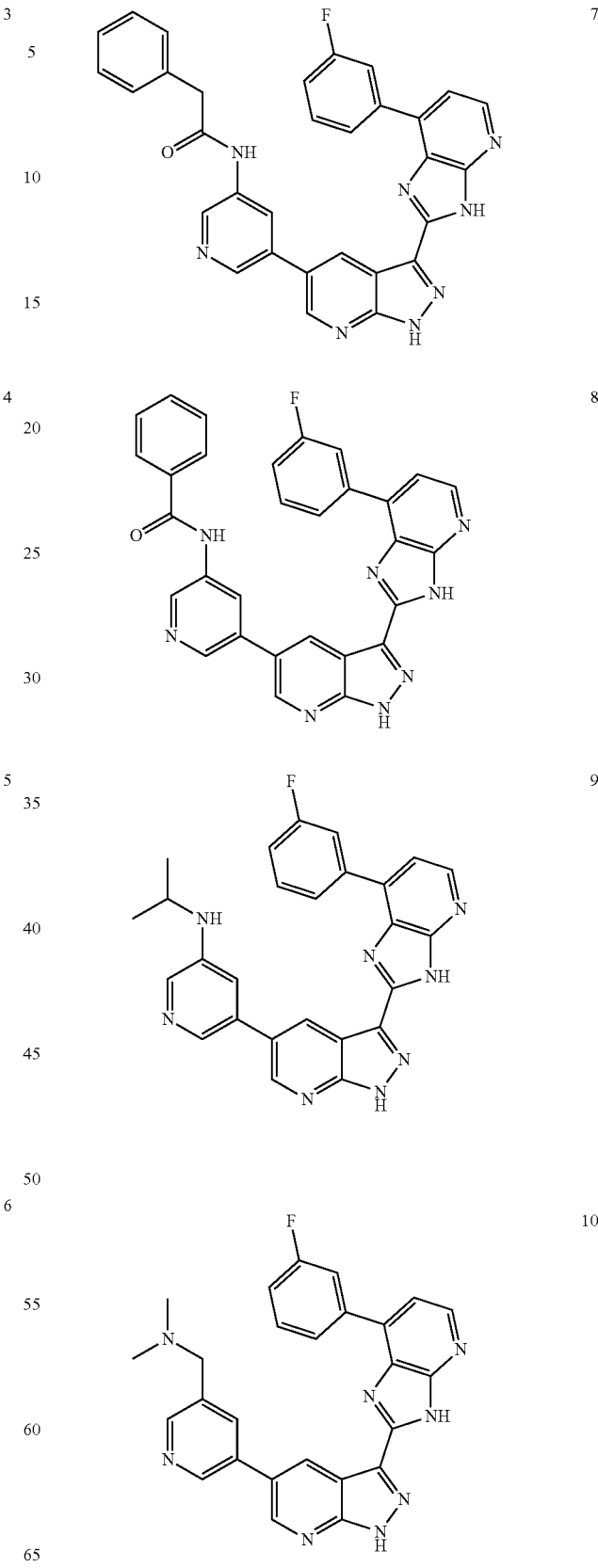

TABLE 1-continued
| | |
|---|---|
| 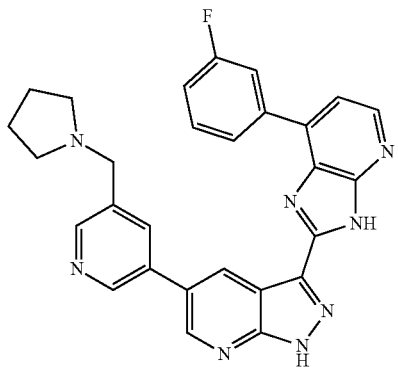 [SMILES: Fc1cccc(-c2ccnc3[nH]c(-c4n[nH]c5ncc(-c6cncc(CN7CCCC7)c6)cc45)nc23)c1] 11 | 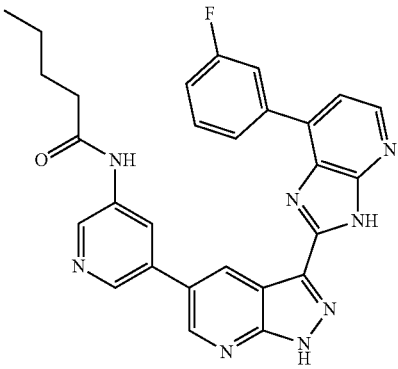 15 |
| 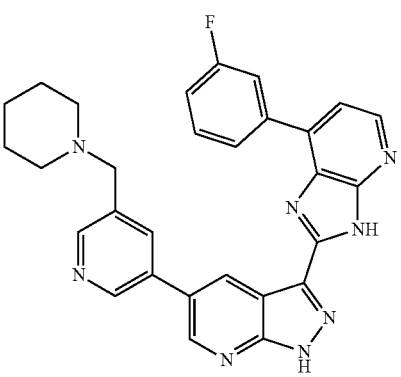 [SMILES: Fc1cccc(-c2ccnc3[nH]c(-c4n[nH]c5ncc(-c6cncc(CN7CCCCC7)c6)cc45)nc23)c1] 12 | 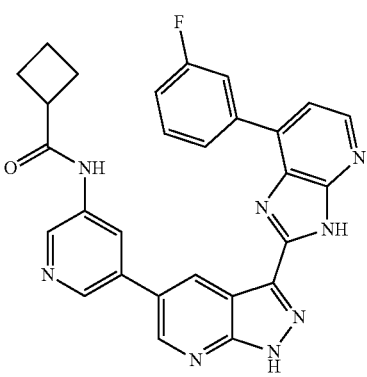 16 |
| 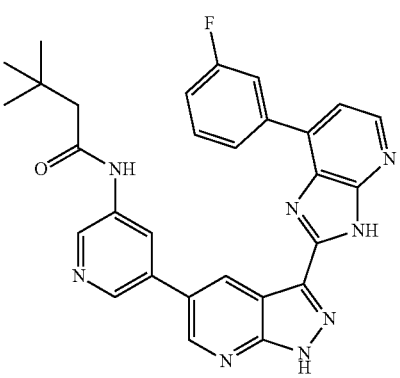 [SMILES: CC(C)(C)CC(=O)Nc1cncc(-c2cnc3[nH]nc(-c4nc5c(-c6cccc(F)c6)ccnc5[nH]4)c3c2)c1] 13 | 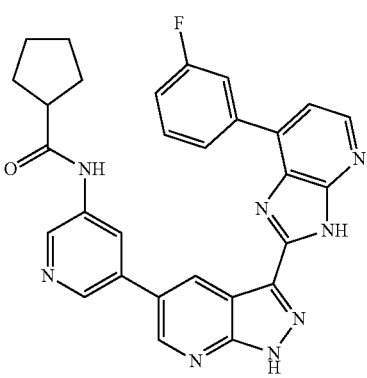 17 |
| 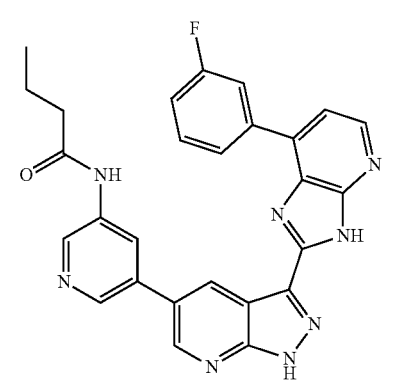 [SMILES: CCCC(=O)Nc1cncc(-c2cnc3[nH]nc(-c4nc5c(-c6cccc(F)c6)ccnc5[nH]4)c3c2)c1] 14 | 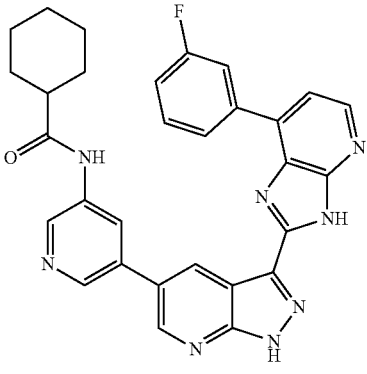 [SMILES: O=C(Nc1cncc(-c2cnc3[nH]nc(-c4nc5c(-c6cccc(F)c6)ccnc5[nH]4)c3c2)c1)C1CCCCC1] 18 |

TABLE 1-continued
19
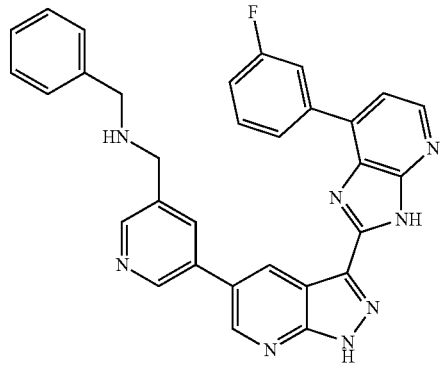 [SMILES: Fc1cccc(-c2ccnc3[nH]c(-c4n[nH]c5ncc(-c6cncc(CNCc7ccccc7)c6)cc45)nc23)c1]
20
23
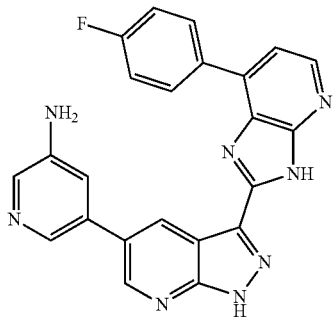
24
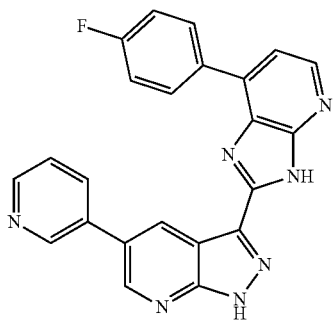
21
25
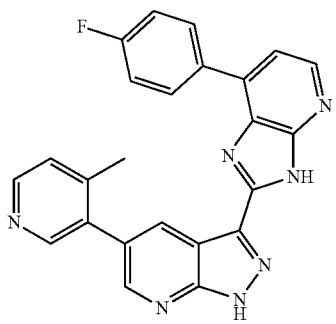 [SMILES: Cc1ccncc1-c1cnc2[nH]nc(-c3nc4c(-c5ccc(F)cc5)ccnc4[nH]3)c2c1]
26
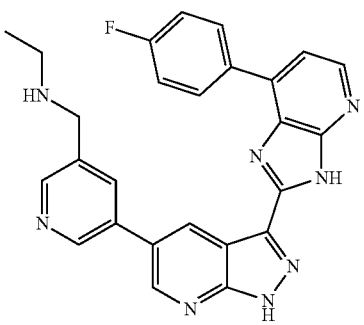 [SMILES: CCNCc1cncc(-c2cnc3[nH]nc(-c4nc5c(-c6ccc(F)cc6)ccnc5[nH]4)c3c2)c1]
22
27
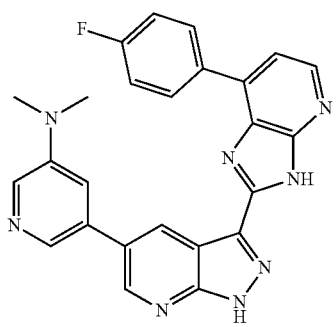 [SMILES: CN(C)c1cncc(-c2cnc3[nH]nc(-c4nc5c(-c6ccc(F)cc6)ccnc5[nH]4)c3c2)c1]

TABLE 1-continued
28
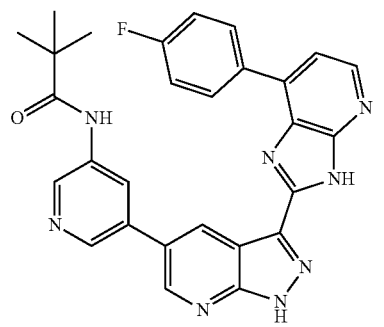 [SMILES: CC(C)(C)C(=O)Nc1cncc(-c2cnc3[nH]nc(-c4nc5c(-c6ccc(F)cc6)ccnc5[nH]4)c3c2)c1]
29
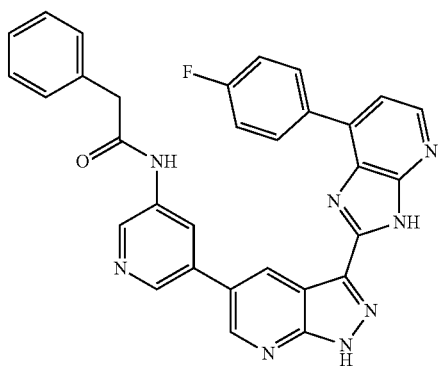 [SMILES: O=C(Cc1ccccc1)Nc1cncc(-c2cnc3[nH]nc(-c4nc5c(-c6ccc(F)cc6)ccnc5[nH]4)c3c2)c1]
30
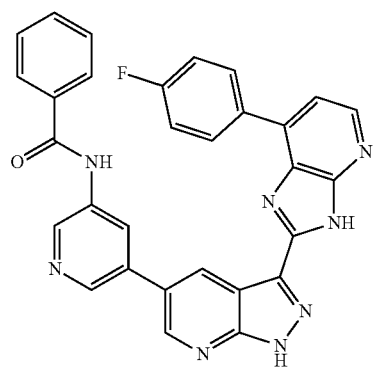 [SMILES: O=C(Nc1cncc(-c2cnc3[nH]nc(-c4nc5c(-c6ccc(F)cc6)ccnc5[nH]4)c3c2)c1)c1ccccc1]
31
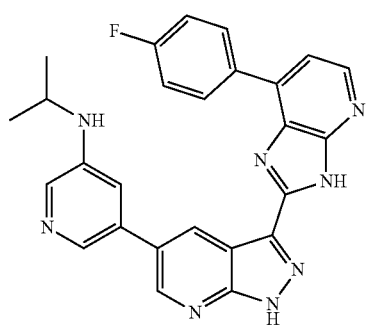 [SMILES: CC(C)Nc1cncc(-c2cnc3[nH]nc(-c4nc5c(-c6ccc(F)cc6)ccnc5[nH]4)c3c2)c1]
TABLE 1-continued
32
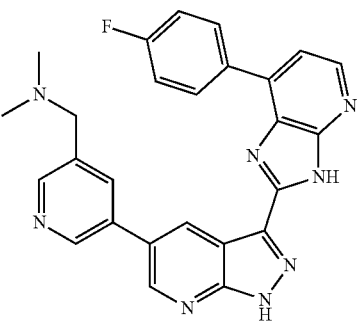 [SMILES: CN(C)Cc1cncc(-c2cnc3[nH]nc(-c4nc5c(-c6ccc(F)cc6)ccnc5[nH]4)c3c2)c1]
33
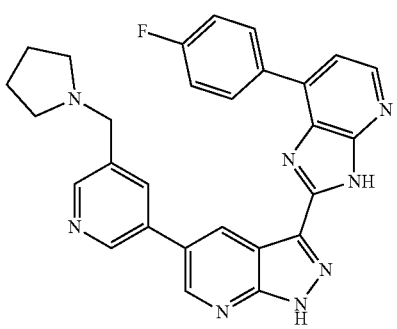 [SMILES: Fc1ccc(-c2ccnc3[nH]c(-c4n[nH]c5ncc(-c6cncc(CN7CCCC7)c6)cc45)nc23)cc1]
34
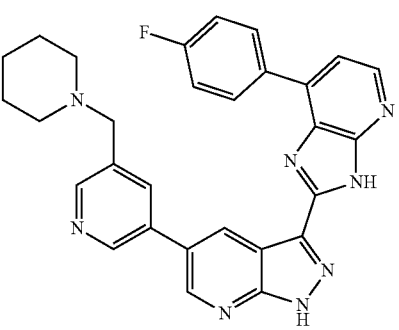 [SMILES: Fc1ccc(-c2ccnc3[nH]c(-c4n[nH]c5ncc(-c6cncc(CN7CCCCC7)c6)cc45)nc23)cc1]
35
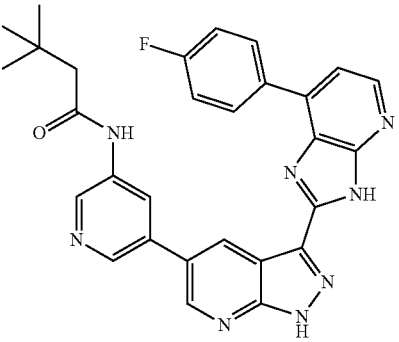 [SMILES: CC(C)(C)CC(=O)Nc1cncc(-c2cnc3[nH]nc(-c4nc5c(-c6ccc(F)cc6)ccnc5[nH]4)c3c2)c1]

TABLE 1-continued
36 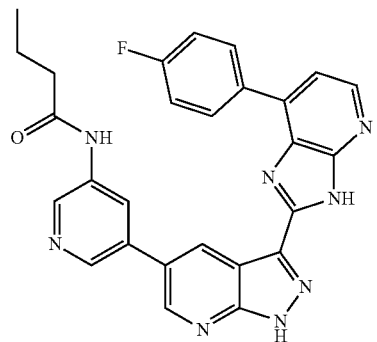 [SMILES: CCCC(=O)Nc1cncc(-c2cnc3[nH]nc(-c4nc5c(-c6ccc(F)cc6)ccnc5[nH]4)c3c2)c1]
37 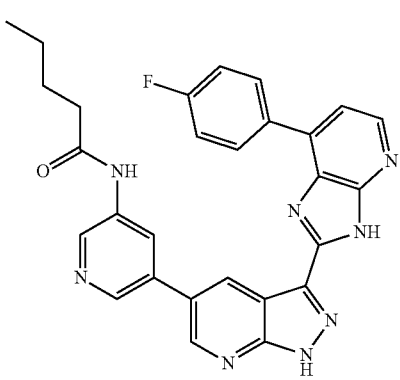 [SMILES: CCCCC(=O)Nc1cncc(-c2cnc3[nH]nc(-c4nc5c(-c6ccc(F)cc6)ccnc5[nH]4)c3c2)c1]
38 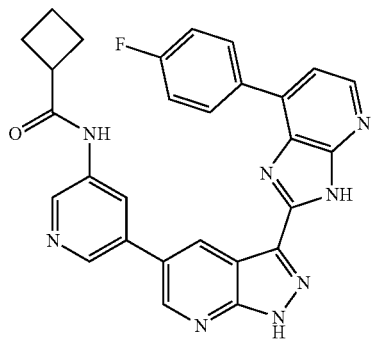 [SMILES: O=C(Nc1cncc(-c2cnc3[nH]nc(-c4nc5c(-c6ccc(F)cc6)ccnc5[nH]4)c3c2)c1)C1CCC1]
39 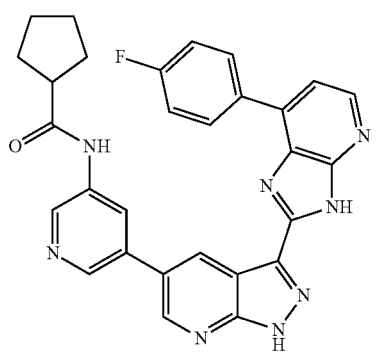 [SMILES: O=C(Nc1cncc(-c2cnc3[nH]nc(-c4nc5c(-c6ccc(F)cc6)ccnc5[nH]4)c3c2)c1)C1CCCC1]
TABLE 1-continued
40 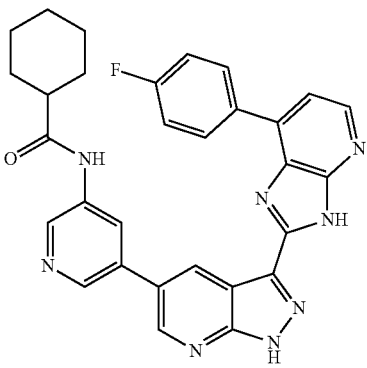 [SMILES: O=C(Nc1cncc(-c2cnc3[nH]nc(-c4nc5c(-c6ccc(F)cc6)ccnc5[nH]4)c3c2)c1)C1CCCCC1]
41 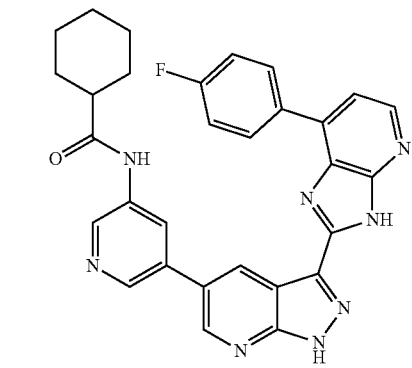
42 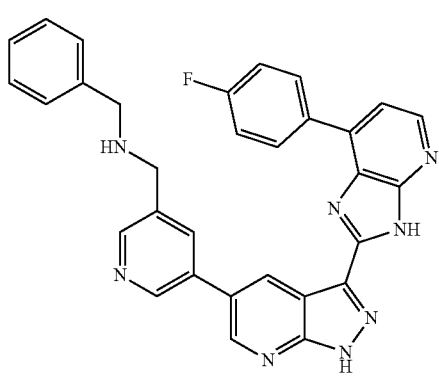 [SMILES: Fc1ccc(-c2ccnc3[nH]c(-c4n[nH]c5ncc(-c6cncc(CNCc7ccccc7)c6)cc45)nc23)cc1]
43 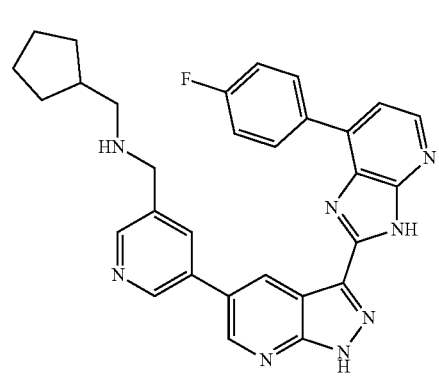 [SMILES: Fc1ccc(-c2ccnc3[nH]c(-c4n[nH]c5ncc(-c6cncc(CNCC7CCCC7)c6)cc45)nc23)cc1]

TABLE 1-continued
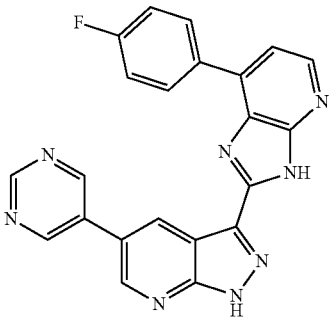 [SMILES: Fc1ccc(-c2ccnc3[nH]c(-c4n[nH]c5ncc(-c6cncnc6)cc45)nc23)cc1]
44
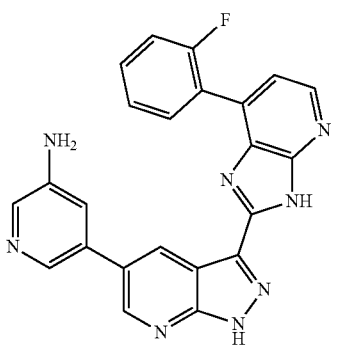 [SMILES: Nc1cncc(-c2cnc3[nH]nc(-c4nc5c(-c6ccccc6F)ccnc5[nH]4)c3c2)c1]
45
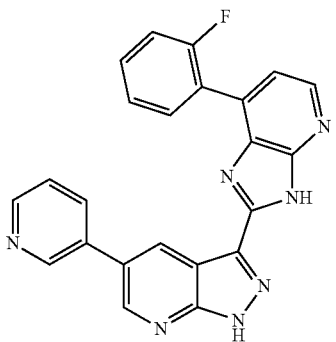 [SMILES: Fc1ccccc1-c1ccnc2[nH]c(-c3n[nH]c4ncc(-c5cccnc5)cc34)nc12]
46
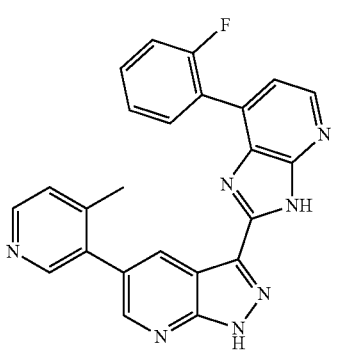 [SMILES: Cc1ccncc1-c1cnc2[nH]nc(-c3nc4c(-c5ccccc5F)ccnc4[nH]3)c2c1]
47
TABLE 1-continued
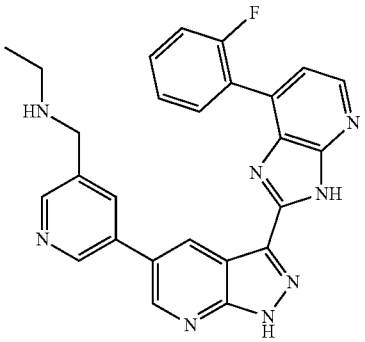 [SMILES: CCNCc1cncc(-c2cnc3[nH]nc(-c4nc5c(-c6ccccc6F)ccnc5[nH]4)c3c2)c1]
48
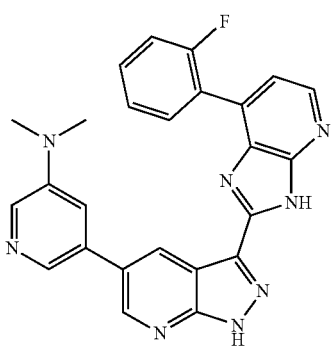 [SMILES: CN(C)c1cncc(-c2cnc3[nH]nc(-c4nc5c(-c6ccccc6F)ccnc5[nH]4)c3c2)c1]
49
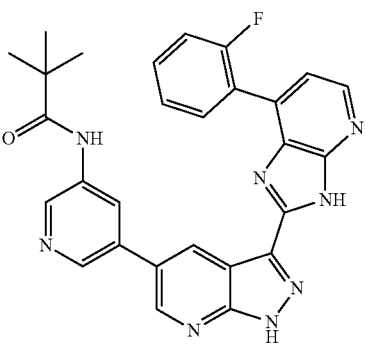 [SMILES: CC(C)(C)C(=O)Nc1cncc(-c2cnc3[nH]nc(-c4nc5c(-c6ccccc6F)ccnc5[nH]4)c3c2)c1]
50
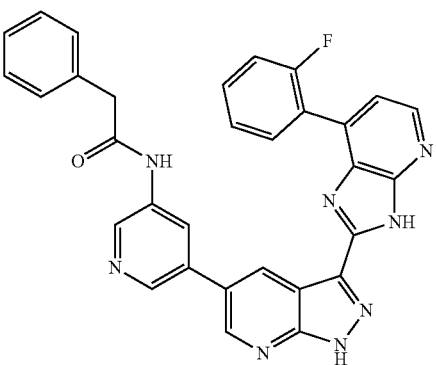 [SMILES: O=C(Cc1ccccc1)Nc1cncc(-c2cnc3[nH]nc(-c4nc5c(-c6ccccc6F)ccnc5[nH]4)c3c2)c1]
51

TABLE 1-continued
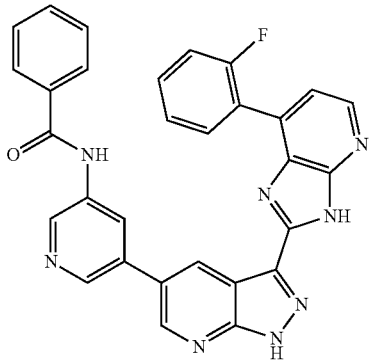 [SMILES: O=C(Nc1cncc(-c2cnc3[nH]nc(-c4nc5c(-c6ccccc6F)ccnc5[nH]4)c3c2)c1)c1ccccc1]
52
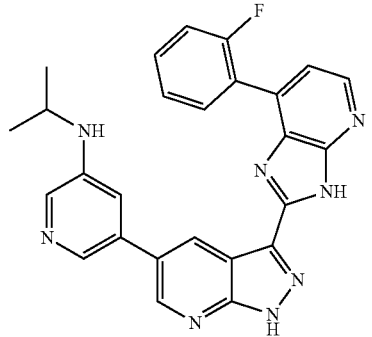 [SMILES: CC(C)Nc1cncc(-c2cnc3[nH]nc(-c4nc5c(-c6ccccc6F)ccnc5[nH]4)c3c2)c1]
53
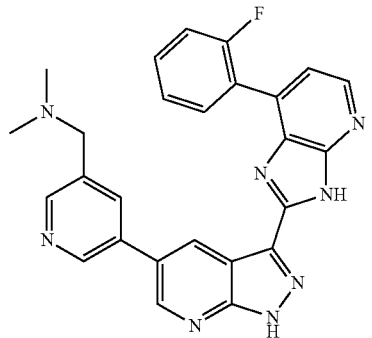 [SMILES: CN(C)Cc1cncc(-c2cnc3[nH]nc(-c4nc5c(-c6ccccc6F)ccnc5[nH]4)c3c2)c1]
54
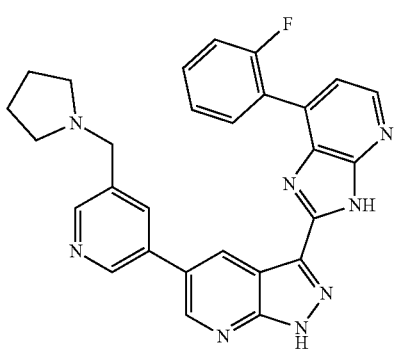 [SMILES: Fc1ccccc1-c1ccnc2[nH]c(-c3n[nH]c4ncc(-c5cncc(CN6CCCC6)c5)cc34)nc12]
55
TABLE 1-continued
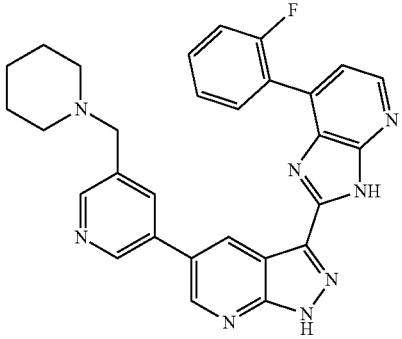 [SMILES: Fc1ccccc1-c1ccnc2[nH]c(-c3n[nH]c4ncc(-c5cncc(CN6CCCCC6)c5)cc34)nc12]
56
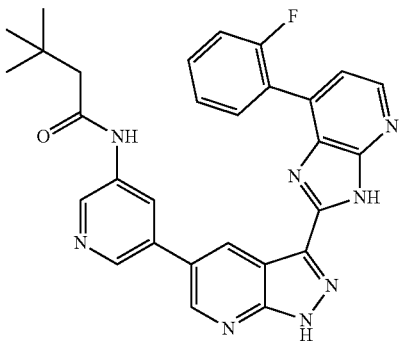 [SMILES: CC(C)(C)CC(=O)Nc1cncc(-c2cnc3[nH]nc(-c4nc5c(-c6ccccc6F)ccnc5[nH]4)c3c2)c1]
57
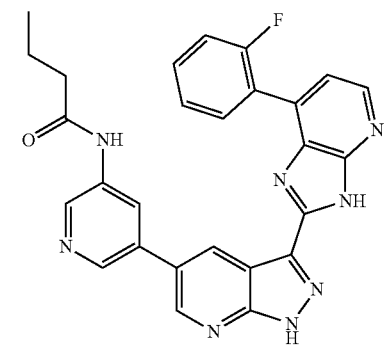 [SMILES: CCCC(=O)Nc1cncc(-c2cnc3[nH]nc(-c4nc5c(-c6ccccc6F)ccnc5[nH]4)c3c2)c1]
58
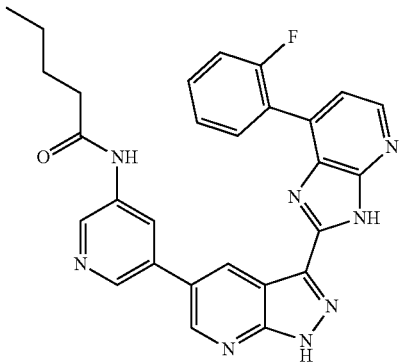 [SMILES: CCCCC(=O)Nc1cncc(-c2cnc3[nH]nc(-c4nc5c(-c6ccccc6F)ccnc5[nH]4)c3c2)c1]
59

TABLE 1-continued
| 60 | 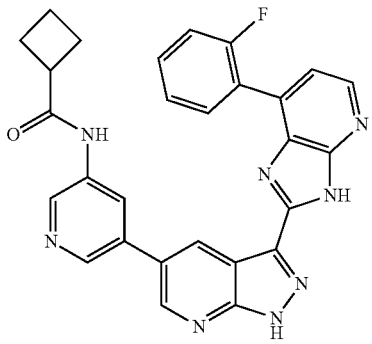 [SMILES: O=C(Nc1cncc(-c2cnc3[nH]nc(-c4nc5c(-c6ccccc6F)ccnc5[nH]4)c3c2)c1)C1CCC1] |
| 61 | 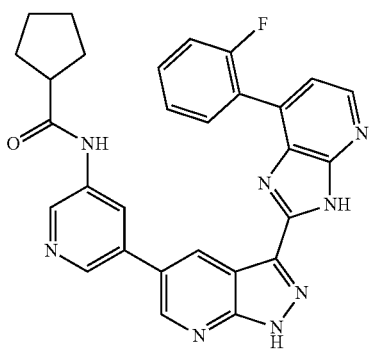 [SMILES: O=C(Nc1cncc(-c2cnc3[nH]nc(-c4nc5c(-c6ccccc6F)ccnc5[nH]4)c3c2)c1)C1CCCC1] |
| 62 | 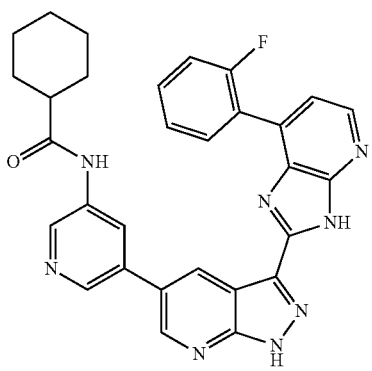 [SMILES: O=C(Nc1cncc(-c2cnc3[nH]nc(-c4nc5c(-c6ccccc6F)ccnc5[nH]4)c3c2)c1)C1CCCCC1] |
| 63 | 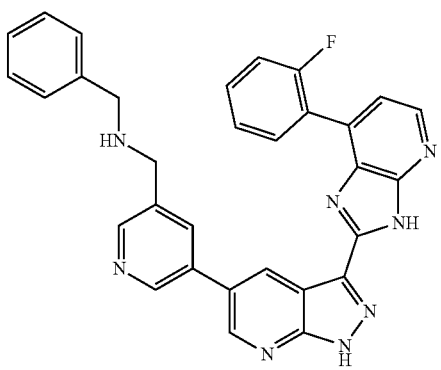 [SMILES: Fc1ccccc1-c1ccnc2[nH]c(-c3n[nH]c4ncc(-c5cncc(CNCc6ccccc6)c5)cc34)nc12] |
| 64 | |
| 65 | |
| 66 | |
| 67 | |

TABLE 1-continued
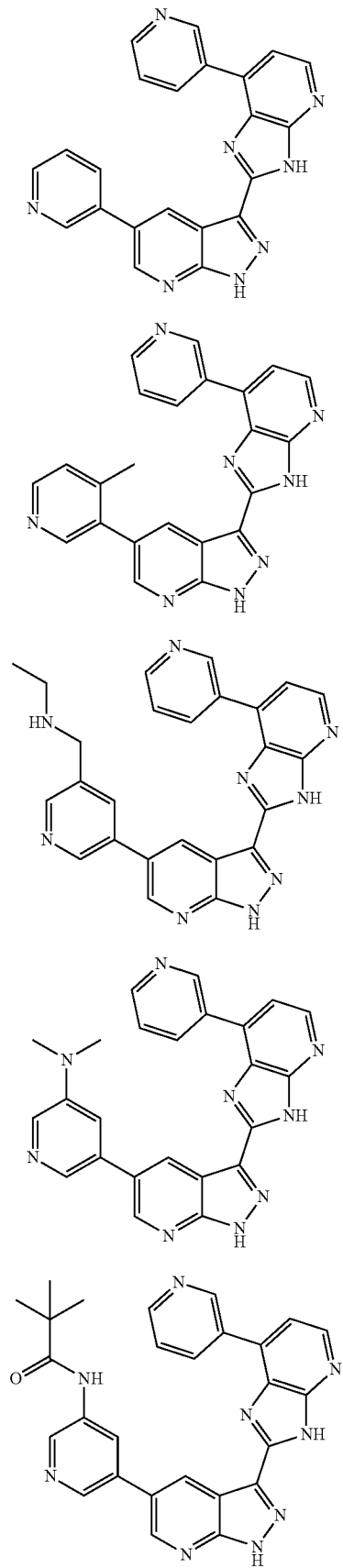
TABLE 1-continued
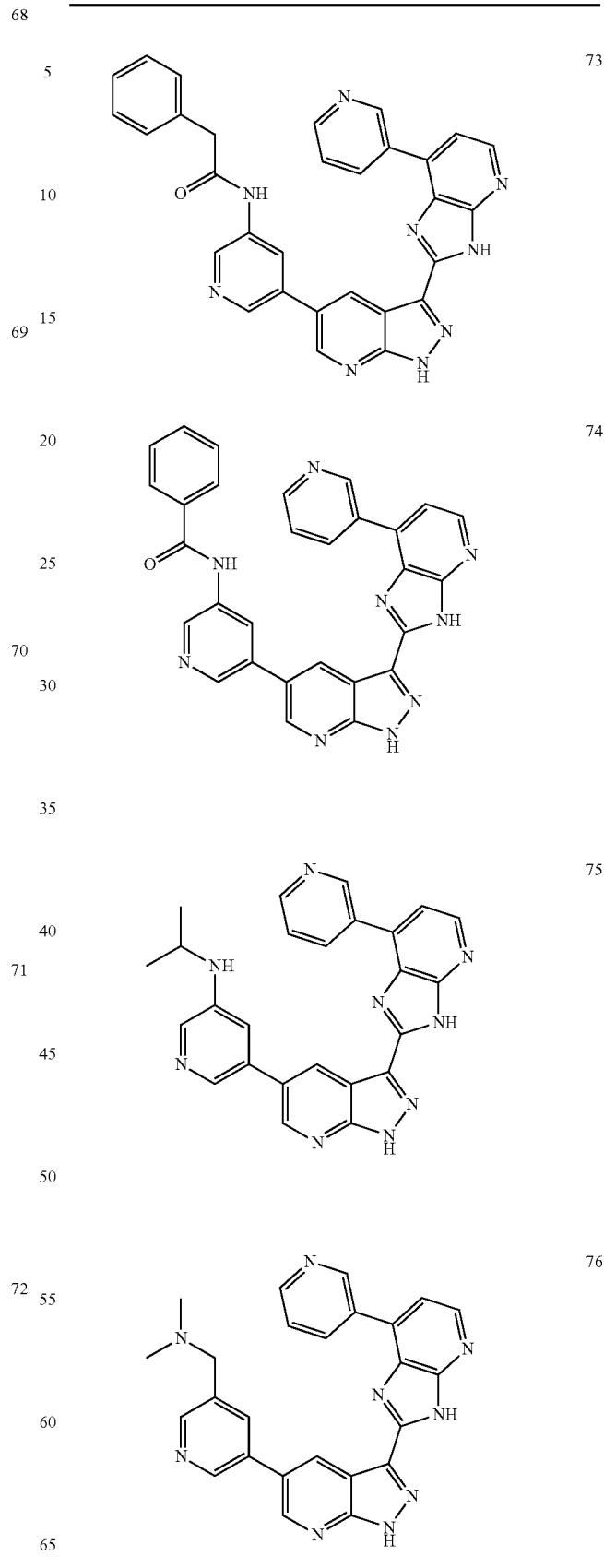

TABLE 1-continued
77 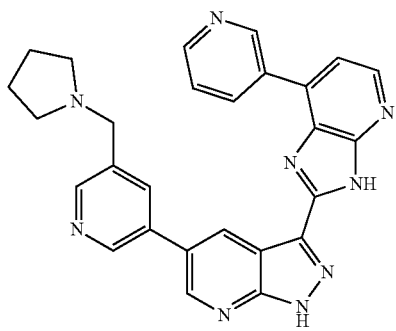 [SMILES: c1cncc(-c2ccnc3[nH]c(-c4n[nH]c5ncc(-c6cncc(CN7CCCC7)c6)cc45)nc23)c1]
78 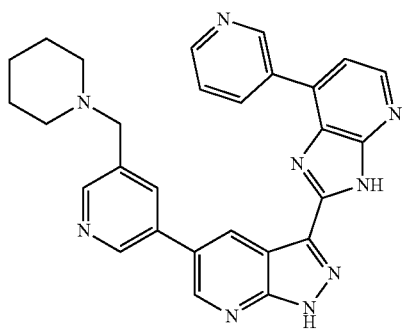 [SMILES: c1cncc(-c2ccnc3[nH]c(-c4n[nH]c5ncc(-c6cncc(CN7CCCCC7)c6)cc45)nc23)c1]
79 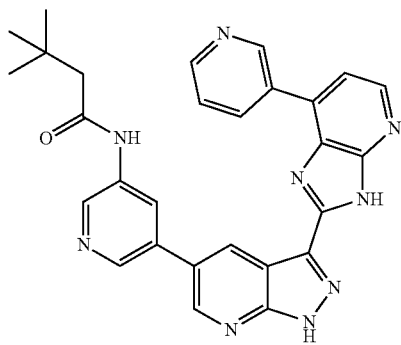
80 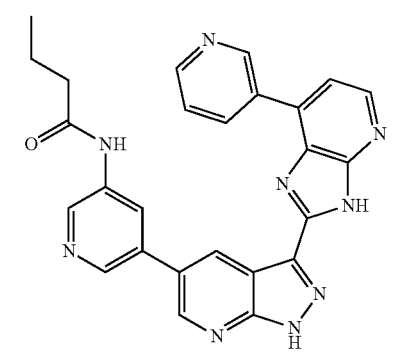 [SMILES: CCCC(=O)Nc1cncc(-c2cnc3[nH]nc(-c4nc5c(-c6cccnc6)ccnc5[nH]4)c3c2)c1]
TABLE 1-continued
81 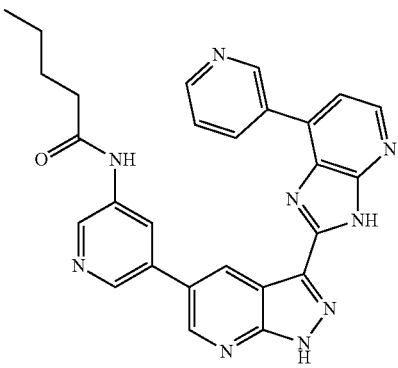 [SMILES: CCCCC(=O)Nc1cncc(-c2cnc3[nH]nc(-c4nc5c(-c6cccnc6)ccnc5[nH]4)c3c2)c1]
82 
83 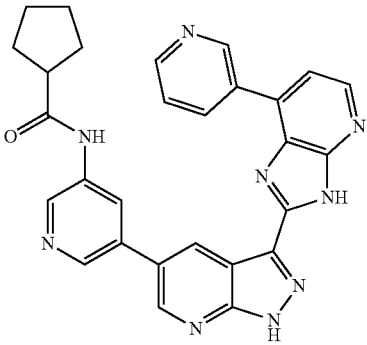 [SMILES: O=C(Nc1cncc(-c2cnc3[nH]nc(-c4nc5c(-c6cccnc6)ccnc5[nH]4)c3c2)c1)C1CCCC1]
84 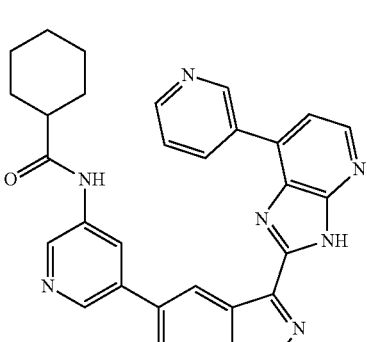

TABLE 1-continued
| | |
|---|---|
| 85 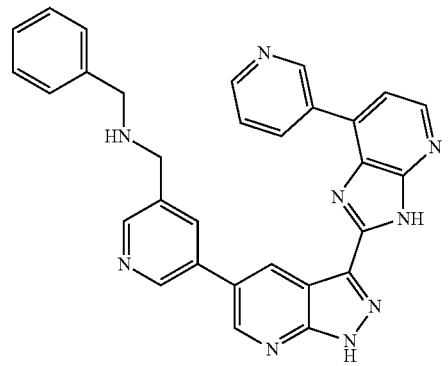 [SMILES: c1ccc(CNCc2cncc(-c3cnc4[nH]nc(-c5nc6c(-c7cccnc7)ccnc6[nH]5)c4c3)c2)cc1] | 89 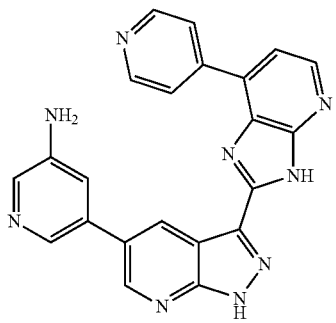 |
| 86 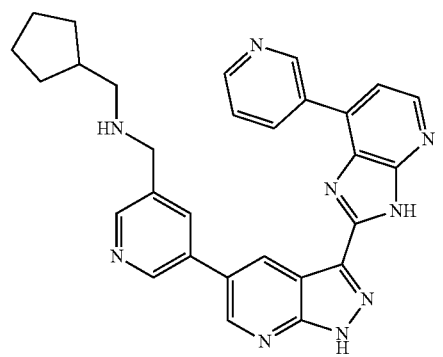 [SMILES: c1cncc(-c2ccnc3[nH]c(-c4n[nH]c5ncc(-c6cncc(CNCC7CCCC7)c6)cc45)nc23)c1] | 90 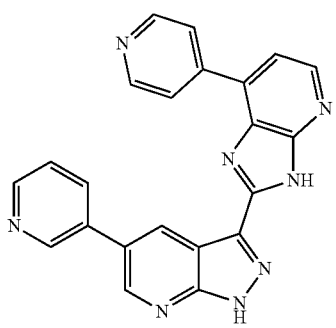 |
| 87 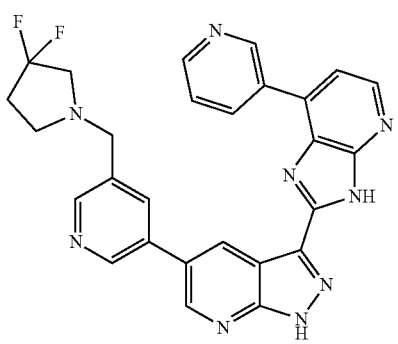 [SMILES: FC1(F)CCN(Cc2cncc(-c3cnc4[nH]nc(-c5nc6c(-c7cccnc7)ccnc6[nH]5)c4c3)c2)C1] | 91 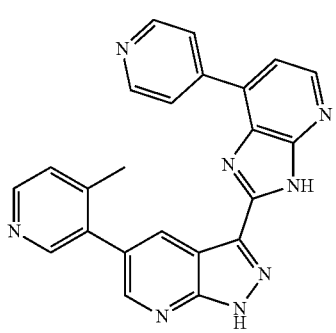 |
| 88 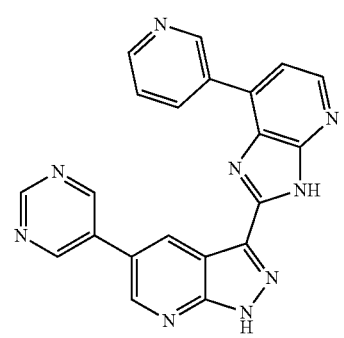 [SMILES: c1cncc(-c2ccnc3[nH]c(-c4n[nH]c5ncc(-c6cncnc6)cc45)nc23)c1] | 92 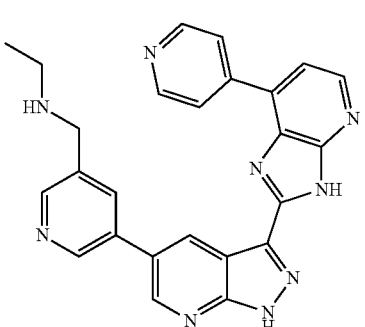 |
| | 93 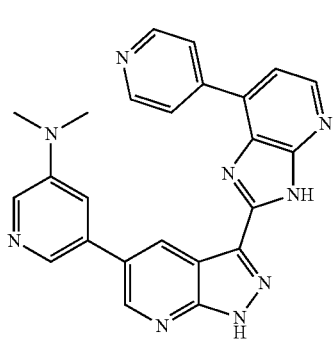 [SMILES: CN(C)c1cncc(-c2cnc3[nH]nc(-c4nc5c(-c6ccncc6)ccnc5[nH]4)c3c2)c1] |

TABLE 1-continued
94 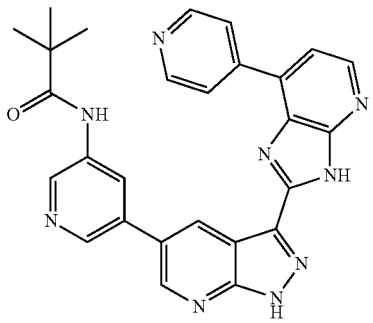 [SMILES: CC(C)(C)C(=O)Nc1cncc(-c2cnc3[nH]nc(-c4nc5c(-c6ccncc6)ccnc5[nH]4)c3c2)c1]
95 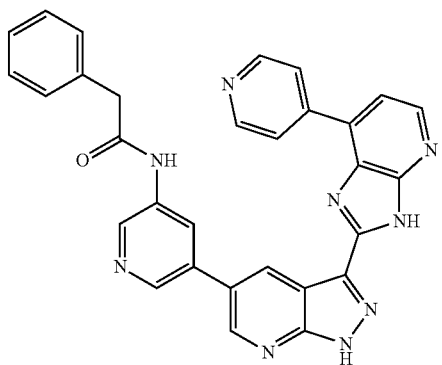 [SMILES: O=C(Cc1ccccc1)Nc1cncc(-c2cnc3[nH]nc(-c4nc5c(-c6ccncc6)ccnc5[nH]4)c3c2)c1]
96 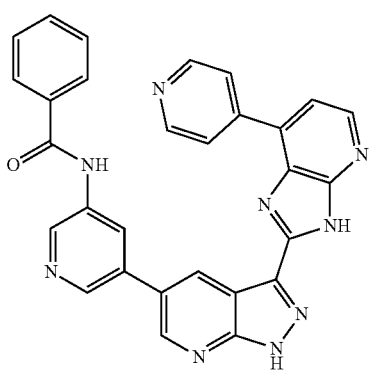 [SMILES: O=C(Nc1cncc(-c2cnc3[nH]nc(-c4nc5c(-c6ccncc6)ccnc5[nH]4)c3c2)c1)c1ccccc1]
97 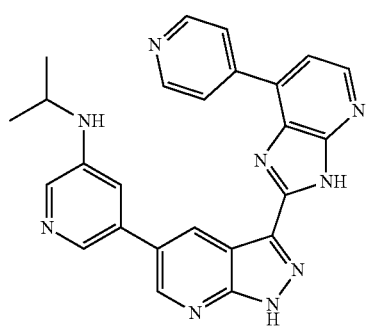 [SMILES: CC(C)Nc1cncc(-c2cnc3[nH]nc(-c4nc5c(-c6ccncc6)ccnc5[nH]4)c3c2)c1]
TABLE 1-continued
98 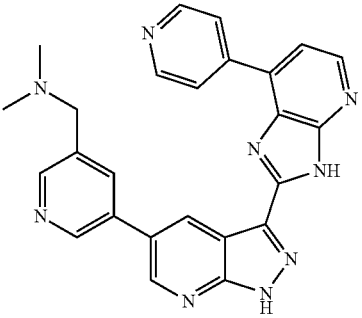 [SMILES: CN(C)Cc1cncc(-c2cnc3[nH]nc(-c4nc5c(-c6ccncc6)ccnc5[nH]4)c3c2)c1]
99 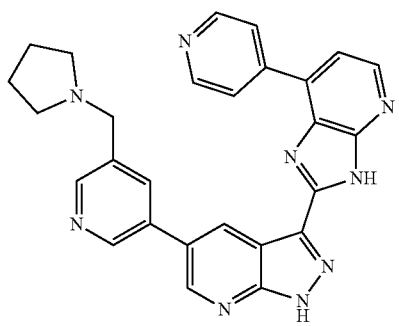 [SMILES: c1cc(-c2ccnc3[nH]c(-c4n[nH]c5ncc(-c6cncc(CN7CCCC7)c6)cc45)nc23)ccn1]
100 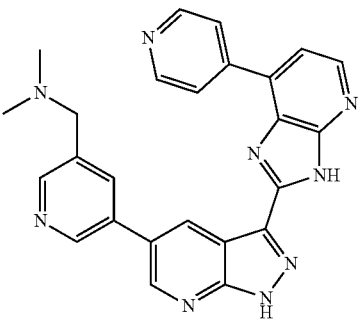 [SMILES: CN(C)Cc1cncc(-c2cnc3[nH]nc(-c4nc5c(-c6ccncc6)ccnc5[nH]4)c3c2)c1]
101 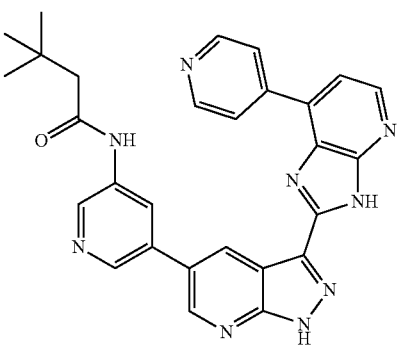 [SMILES: CC(C)(C)CC(=O)Nc1cncc(-c2cnc3[nH]nc(-c4nc5c(-c6ccncc6)ccnc5[nH]4)c3c2)c1]

TABLE 1-continued
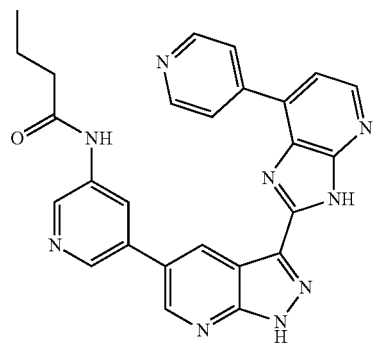 [SMILES: CCCC(=O)Nc1cncc(-c2cnc3[nH]nc(-c4nc5c(-c6ccncc6)ccnc5[nH]4)c3c2)c1]
102
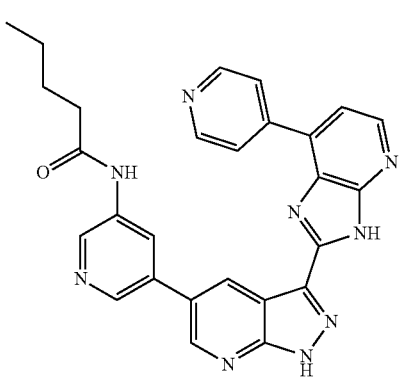 [SMILES: CCCCC(=O)Nc1cncc(-c2cnc3[nH]nc(-c4nc5c(-c6ccncc6)ccnc5[nH]4)c3c2)c1]
103
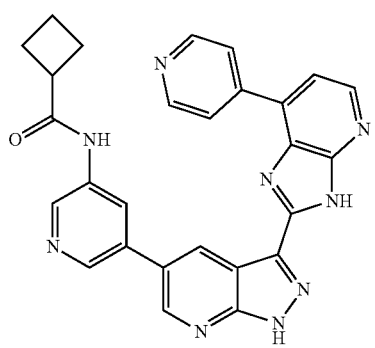 [SMILES: O=C(Nc1cncc(-c2cnc3[nH]nc(-c4nc5c(-c6ccncc6)ccnc5[nH]4)c3c2)c1)C1CCC1]
104
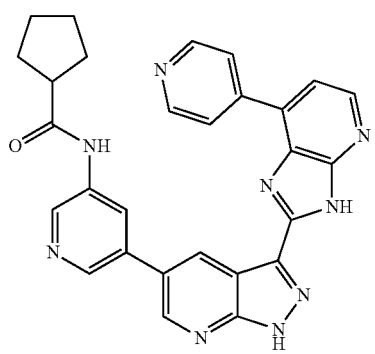 [SMILES: O=C(Nc1cncc(-c2cnc3[nH]nc(-c4nc5c(-c6ccncc6)ccnc5[nH]4)c3c2)c1)C1CCCC1]
105
TABLE 1-continued
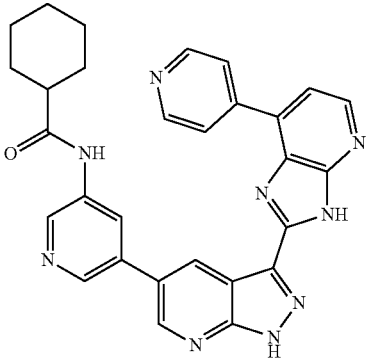 [SMILES: O=C(Nc1cncc(-c2cnc3[nH]nc(-c4nc5c(-c6ccncc6)ccnc5[nH]4)c3c2)c1)C1CCCCC1]
106
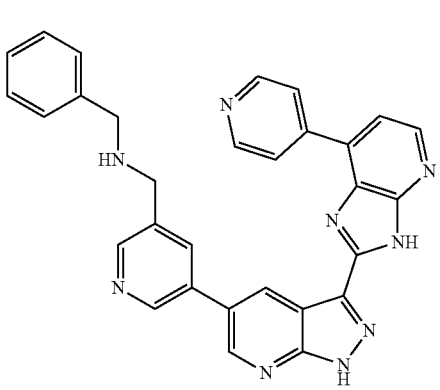 [SMILES: c1ccc(CNCc2cncc(-c3cnc4[nH]nc(-c5nc6c(-c7ccncc7)ccnc6[nH]5)c4c3)c2)cc1]
107
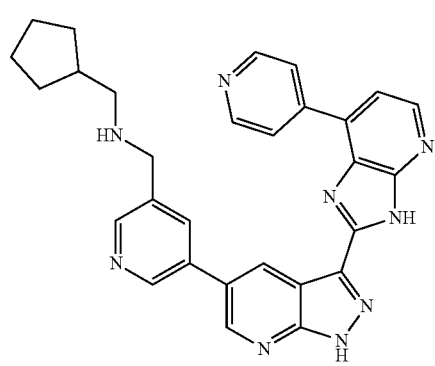 [SMILES: c1cc(-c2ccnc3[nH]c(-c4n[nH]c5ncc(-c6cncc(CNCC7CCCC7)c6)cc45)nc23)ccn1]
108
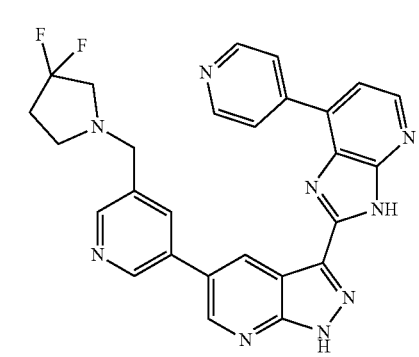 [SMILES: FC1(F)CCN(Cc2cncc(-c3cnc4[nH]nc(-c5nc6c(-c7ccncc7)ccnc6[nH]5)c4c3)c2)C1]
109

TABLE 1-continued
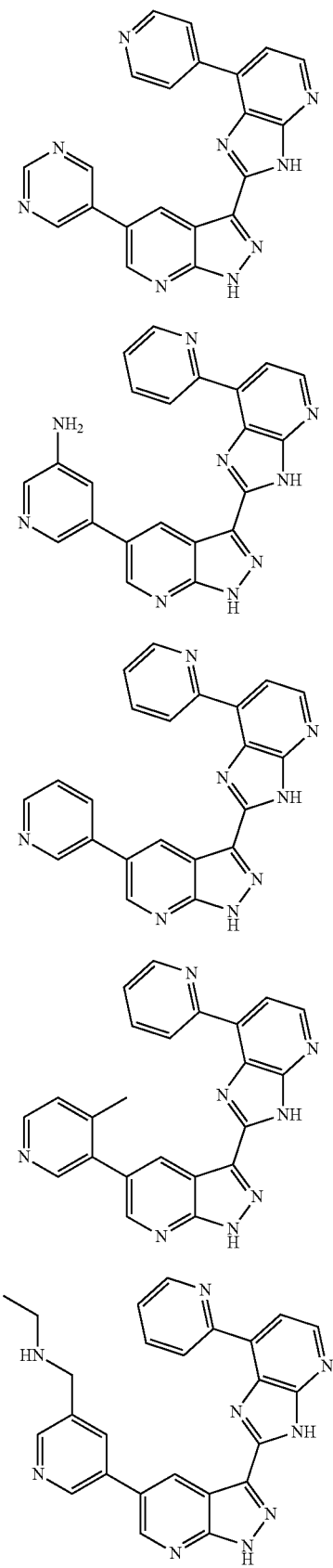
110
111
112
113
114
TABLE 1-continued
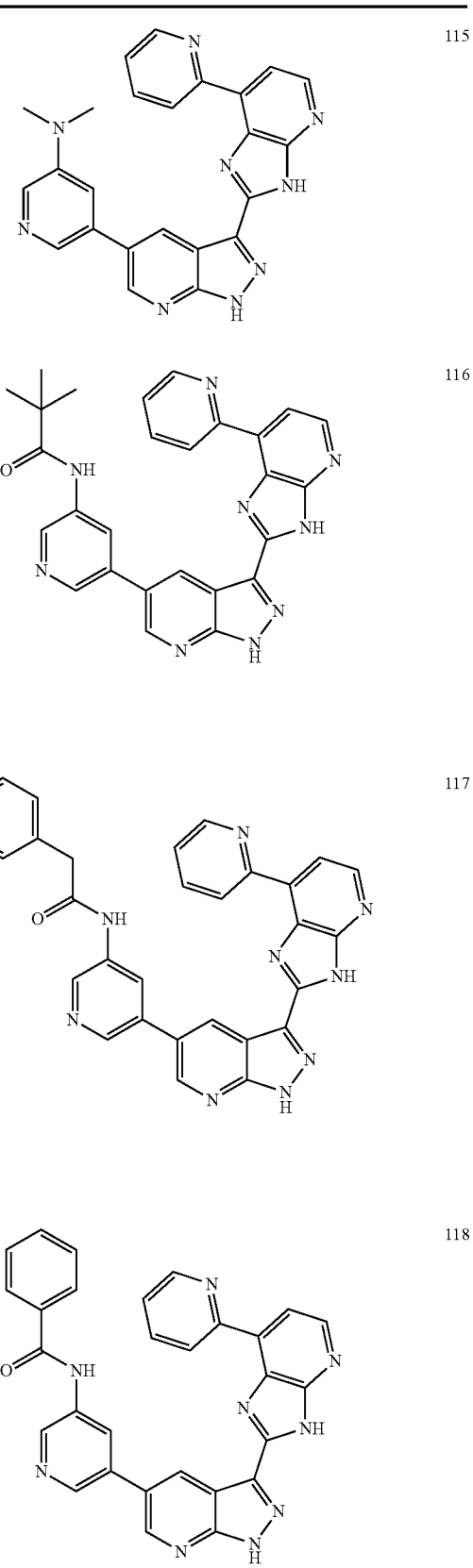
115
116
117
118

TABLE 1-continued
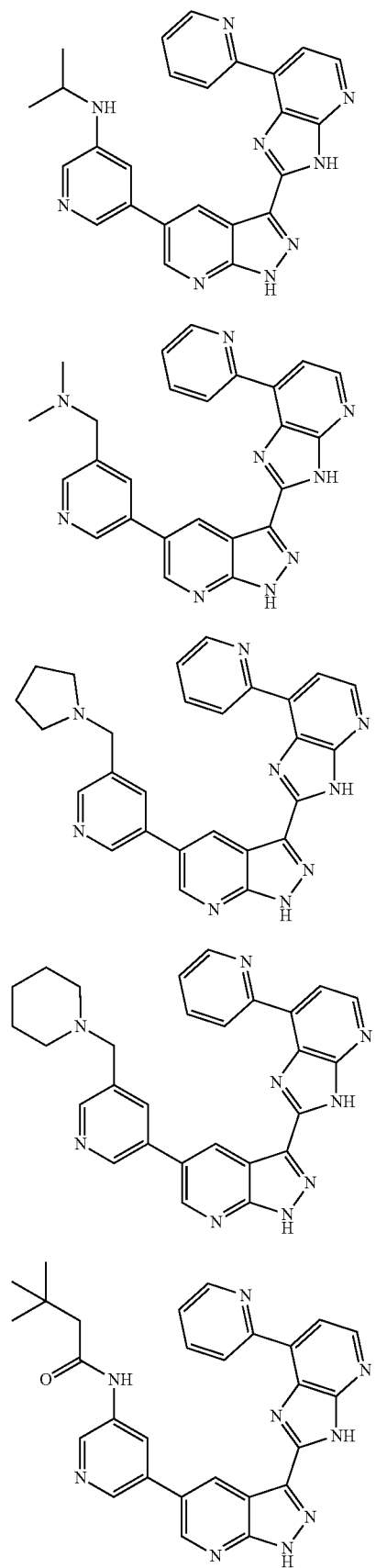
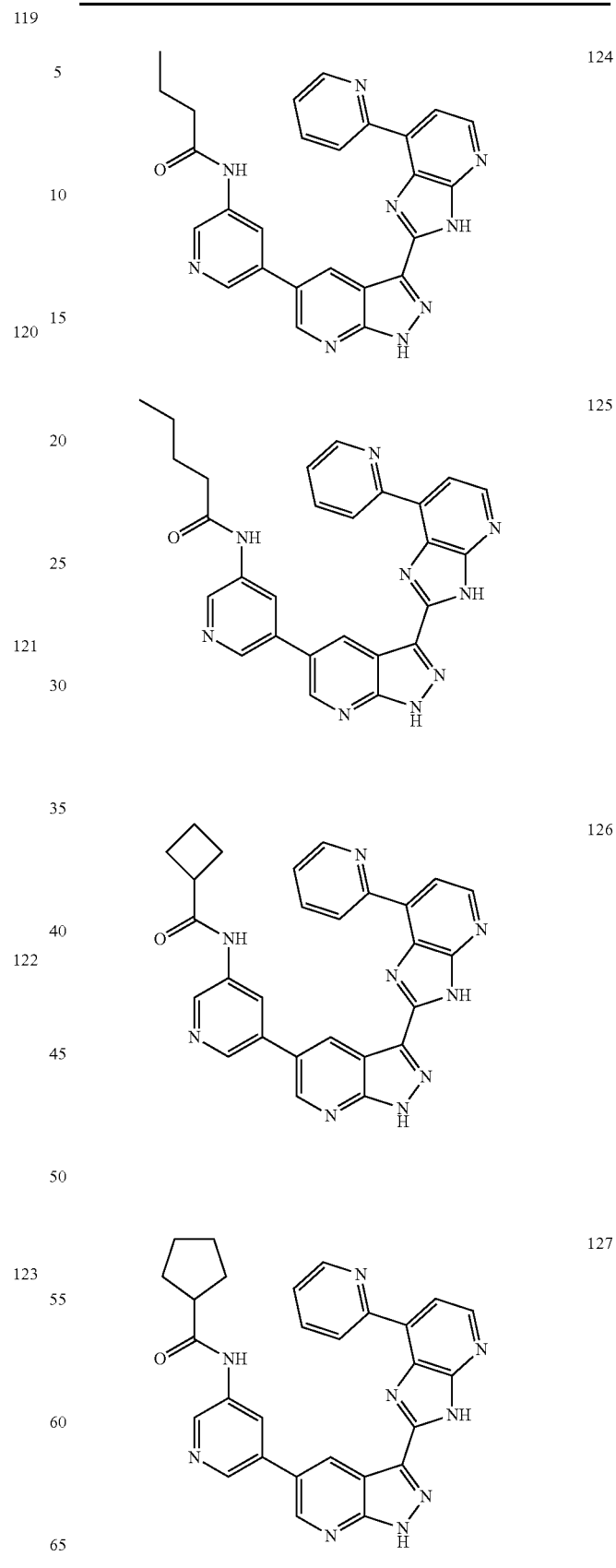

TABLE 1-continued
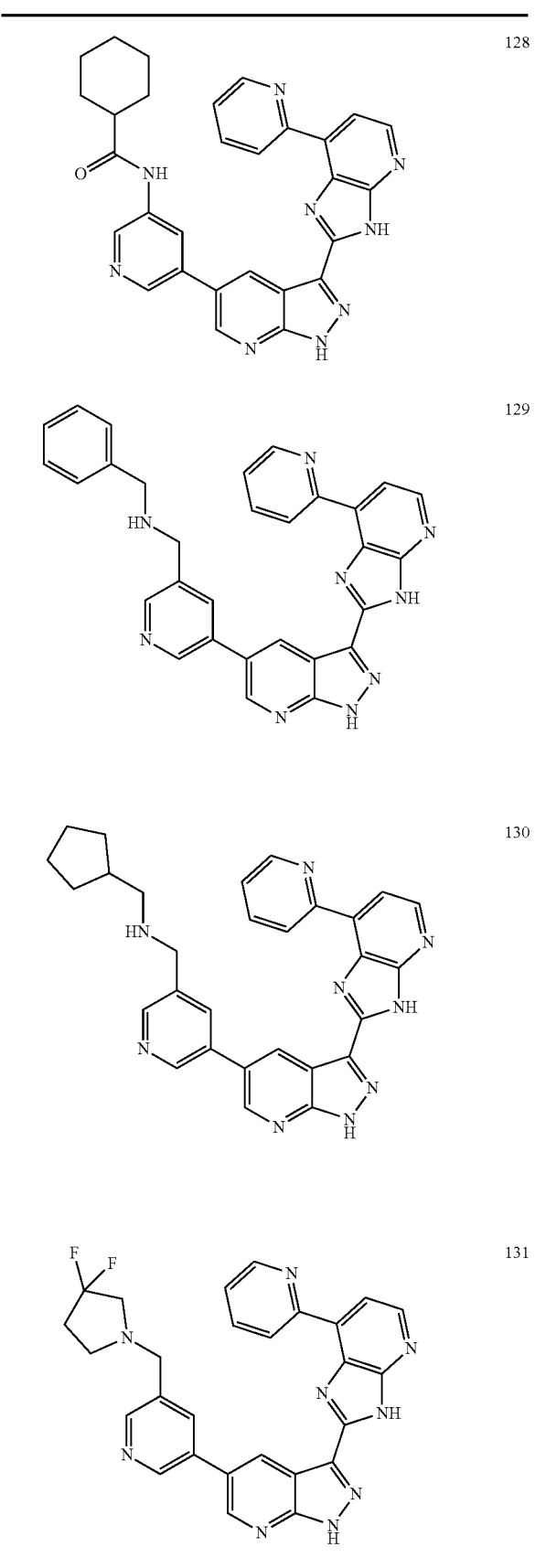
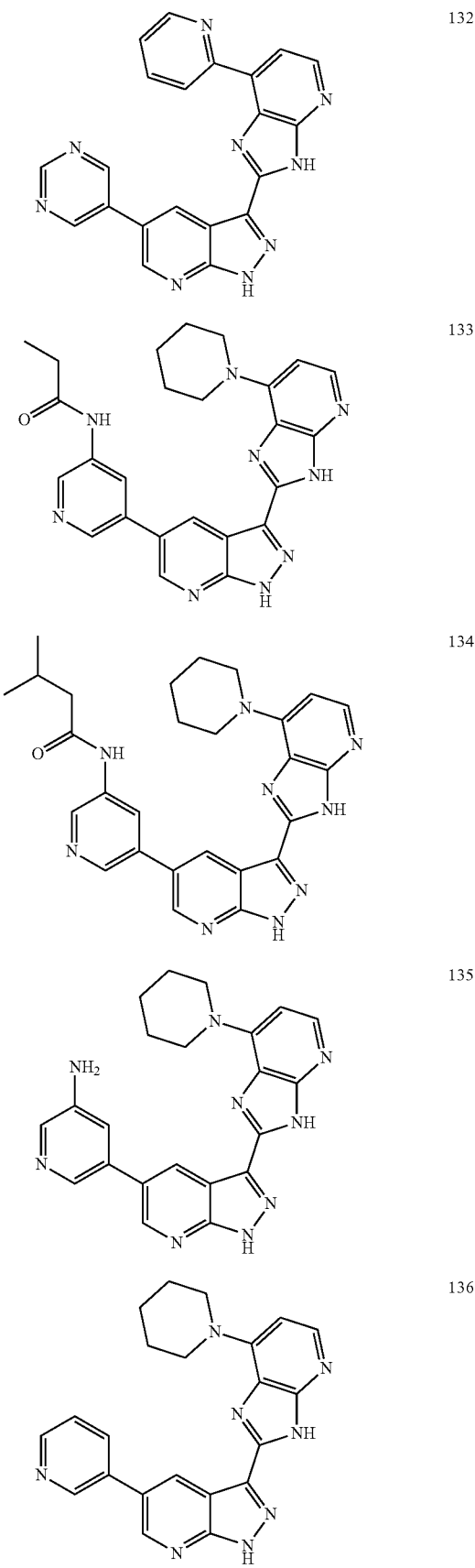

TABLE 1-continued
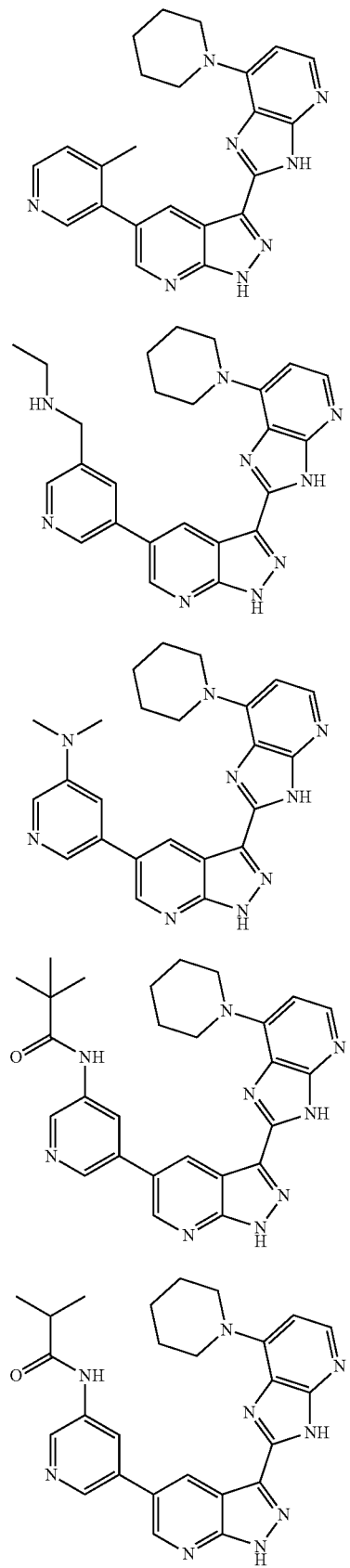
137
138
139
140
141
TABLE 1-continued
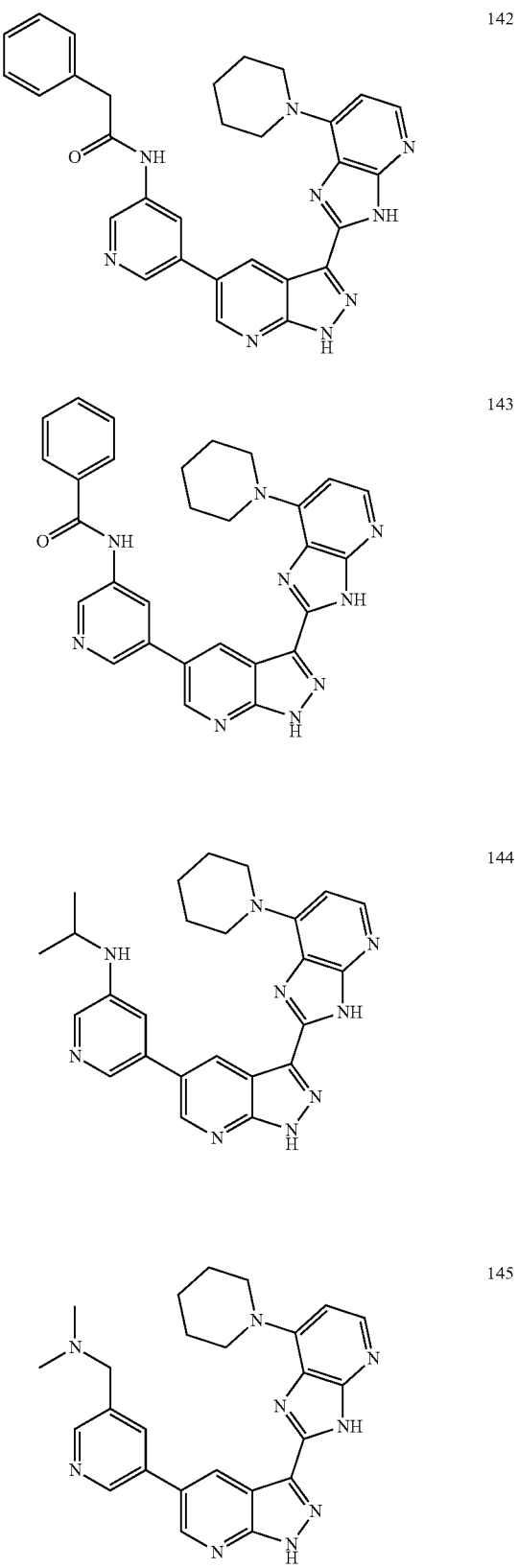
142
143
144
145

TABLE 1-continued
146
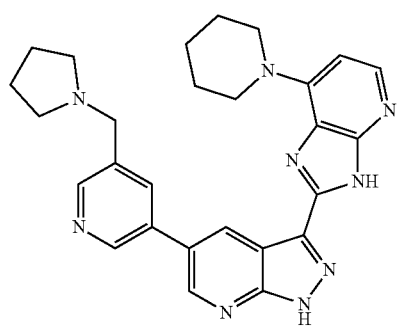 [SMILES: c1cc(N2CCCCC2)c2nc(-c3n[nH]c4ncc(-c5cncc(CN6CCCC6)c5)cc34)[nH]c2n1]
147
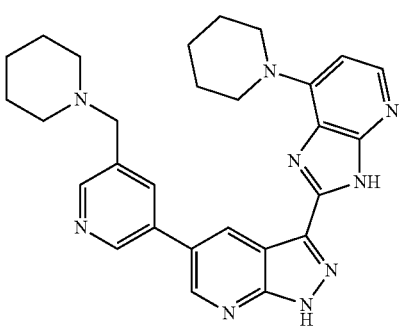 [SMILES: c1cc(N2CCCCC2)c2nc(-c3n[nH]c4ncc(-c5cncc(CN6CCCCC6)c5)cc34)[nH]c2n1]
148
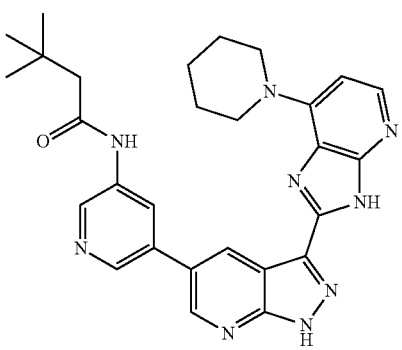 [SMILES: CC(C)(C)CC(=O)Nc1cncc(-c2cnc3[nH]nc(-c4nc5c(N6CCCCC6)ccnc5[nH]4)c3c2)c1]
149
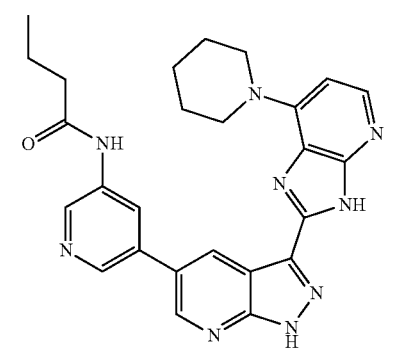 [SMILES: CCCC(=O)Nc1cncc(-c2cnc3[nH]nc(-c4nc5c(N6CCCCC6)ccnc5[nH]4)c3c2)c1]
TABLE 1-continued
150
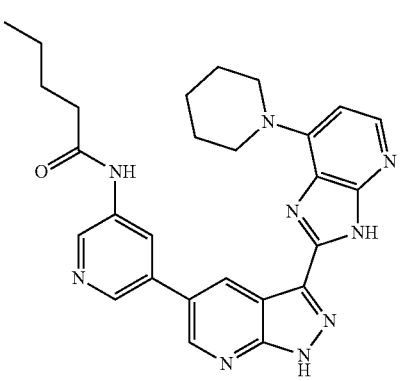 [SMILES: CCCCC(=O)Nc1cncc(-c2cnc3[nH]nc(-c4nc5c(N6CCCCC6)ccnc5[nH]4)c3c2)c1]
151
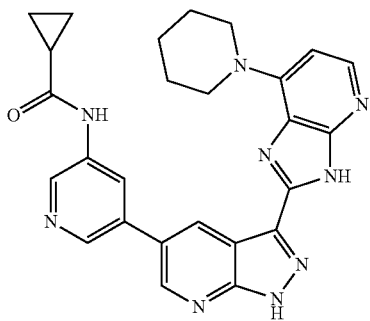 [SMILES: O=C(Nc1cncc(-c2cnc3[nH]nc(-c4nc5c(N6CCCCC6)ccnc5[nH]4)c3c2)c1)C1CC1]
152
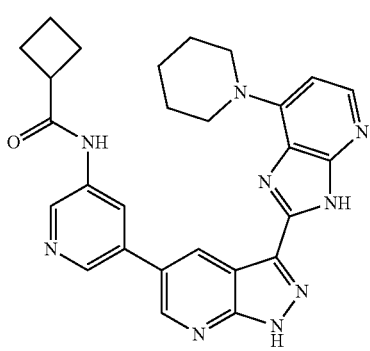 [SMILES: O=C(Nc1cncc(-c2cnc3[nH]nc(-c4nc5c(N6CCCCC6)ccnc5[nH]4)c3c2)c1)C1CCC1]
153
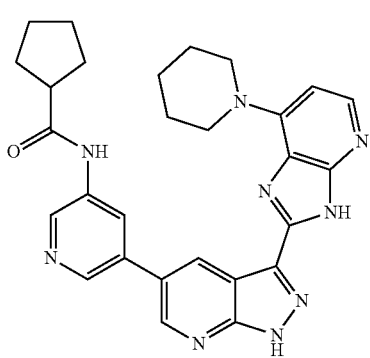 [SMILES: O=C(Nc1cncc(-c2cnc3[nH]nc(-c4nc5c(N6CCCCC6)ccnc5[nH]4)c3c2)c1)C1CCCC1]

TABLE 1-continued
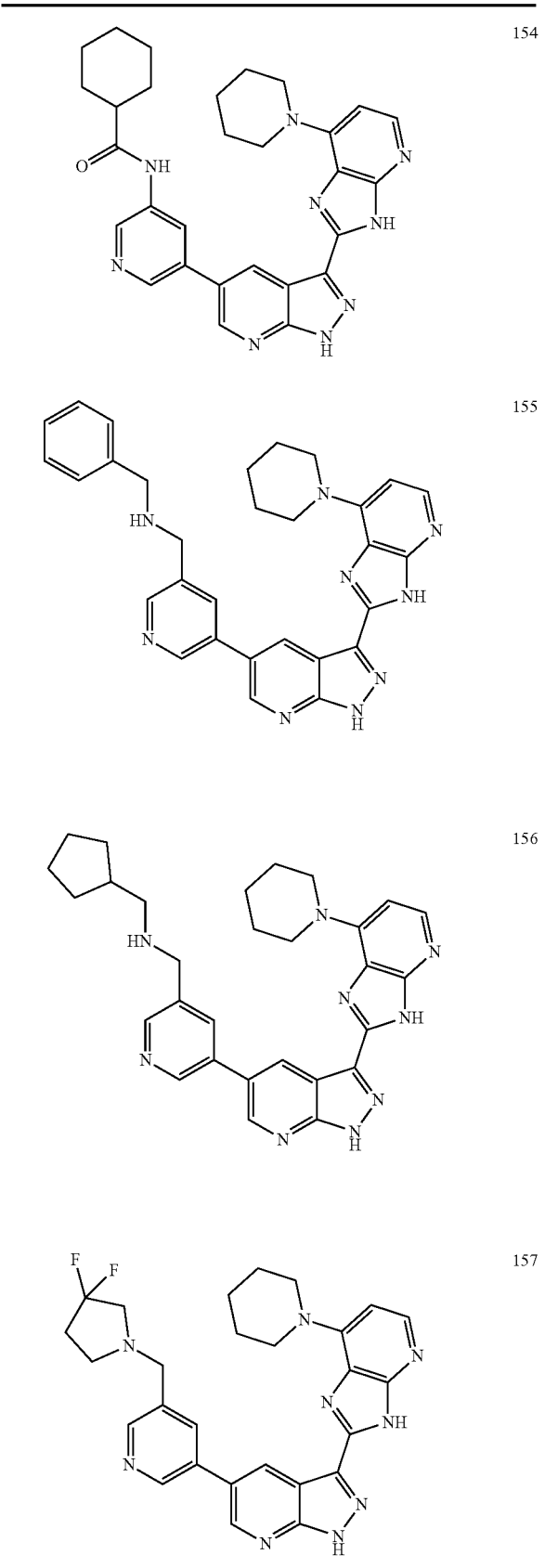
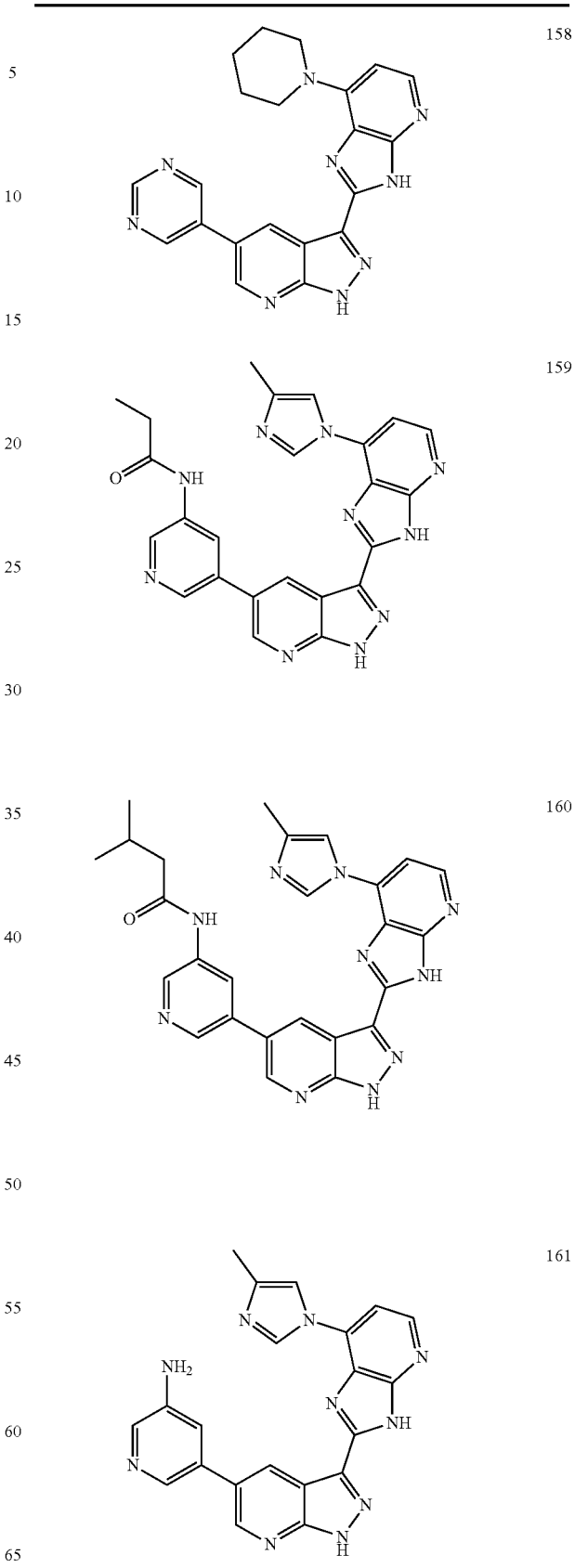

TABLE 1-continued
162 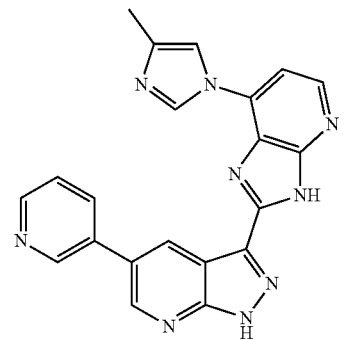 [SMILES: Cc1cn(-c2ccnc3[nH]c(-c4n[nH]c5ncc(-c6cccnc6)cc45)nc23)cn1]
163 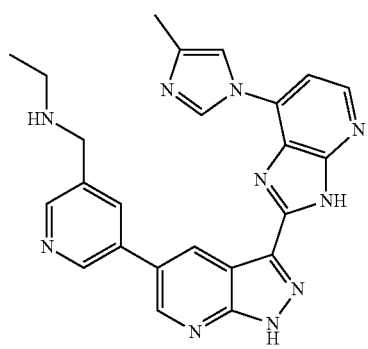 [SMILES: CCNCc1cncc(-c2cnc3[nH]nc(-c4nc5c(-n6cnc(C)c6)ccnc5[nH]4)c3c2)c1]
164 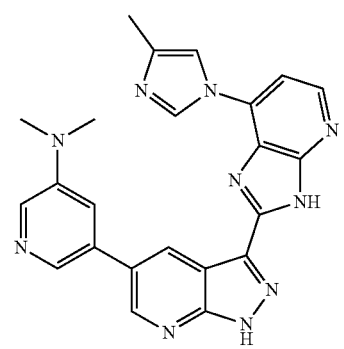 [SMILES: Cc1cn(-c2ccnc3[nH]c(-c4n[nH]c5ncc(-c6cncc(N(C)C)c6)cc45)nc23)cn1]
165 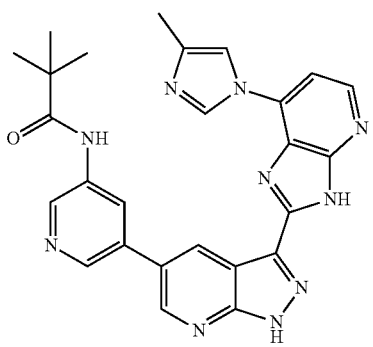 [SMILES: Cc1cn(-c2ccnc3[nH]c(-c4n[nH]c5ncc(-c6cncc(NC(=O)C(C)(C)C)c6)cc45)nc23)cn1]
TABLE 1-continued
166 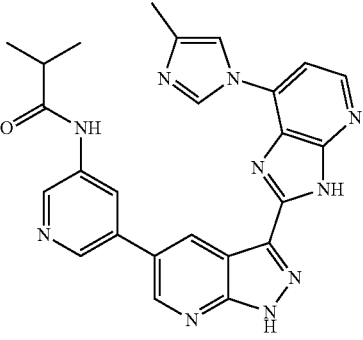 [SMILES: Cc1cn(-c2ccnc3[nH]c(-c4n[nH]c5ncc(-c6cncc(NC(=O)C(C)C)c6)cc45)nc23)cn1]
167 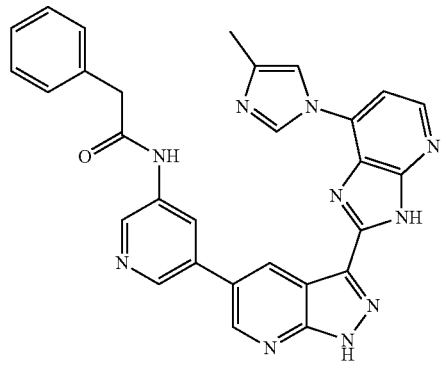 [SMILES: Cc1cn(-c2ccnc3[nH]c(-c4n[nH]c5ncc(-c6cncc(NC(=O)Cc7ccccc7)c6)cc45)nc23)cn1]
168 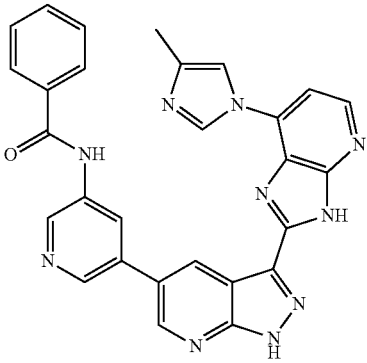 [SMILES: Cc1cn(-c2ccnc3[nH]c(-c4n[nH]c5ncc(-c6cncc(NC(=O)c7ccccc7)c6)cc45)nc23)cn1]
169 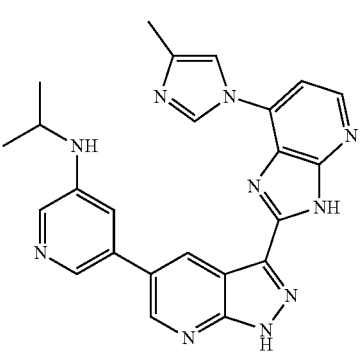 [SMILES: Cc1cn(-c2ccnc3[nH]c(-c4n[nH]c5ncc(-c6cncc(NC(C)C)c6)cc45)nc23)cn1]

TABLE 1-continued
| | |
|---|---|
| 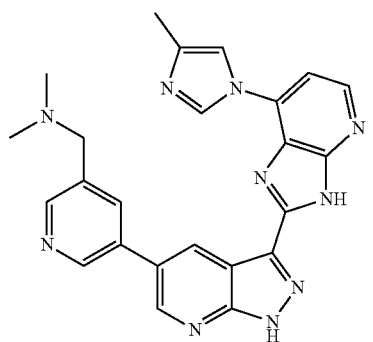 [SMILES: Cc1cn(-c2ccnc3[nH]c(-c4n[nH]c5ncc(-c6cncc(CN(C)C)c6)cc45)nc23)cn1] 170 | 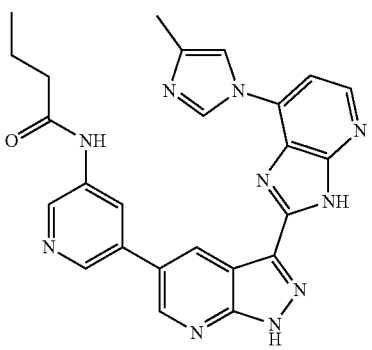 174 |
| 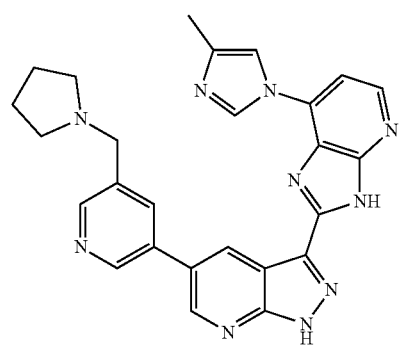 171 | 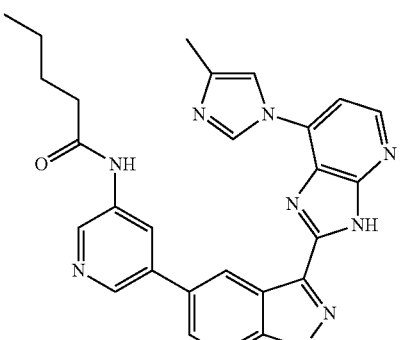 175 |
| 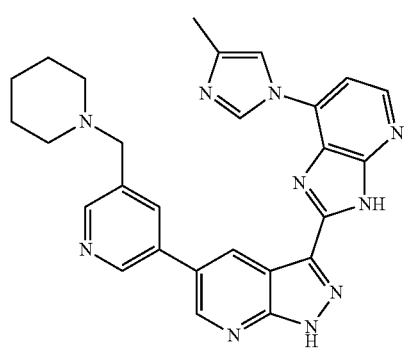 [SMILES: Cc1cn(-c2ccnc3[nH]c(-c4n[nH]c5ncc(-c6cncc(CN7CCCCC7)c6)cc45)nc23)cn1] 172 | 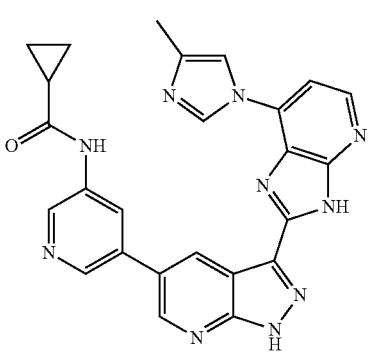 176 |
| 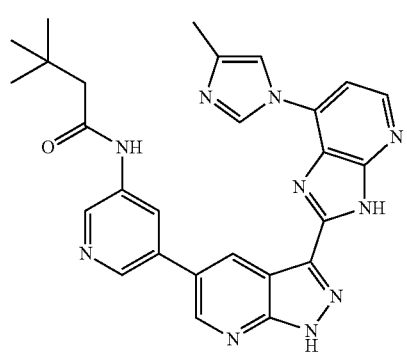 [SMILES: Cc1cn(-c2ccnc3[nH]c(-c4n[nH]c5ncc(-c6cncc(NC(=O)CC(C)(C)C)c6)cc45)nc23)cn1] 173 | 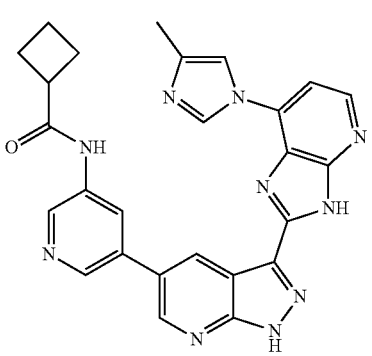 [SMILES: Cc1cn(-c2ccnc3[nH]c(-c4n[nH]c5ncc(-c6cncc(NC(=O)C7CCC7)c6)cc45)nc23)cn1] 177 |

TABLE 1-continued
| | |
|---|---|
| 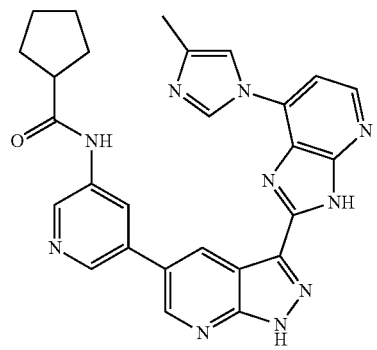 [SMILES: Cc1cn(-c2ccnc3[nH]c(-c4n[nH]c5ncc(-c6cncc(NC(=O)C7CCCC7)c6)cc45)nc23)cn1] 178 | 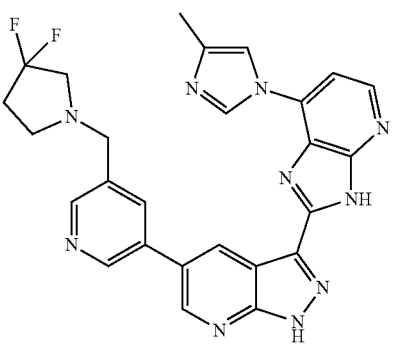 182 |
| 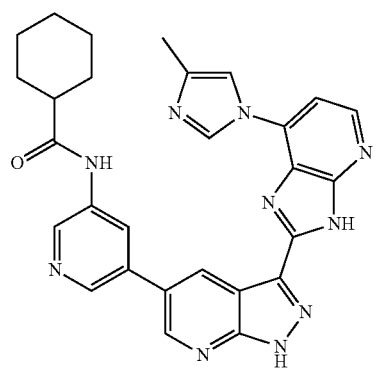 [SMILES: Cc1cn(-c2ccnc3[nH]c(-c4n[nH]c5ncc(-c6cncc(NC(=O)C7CCCCC7)c6)cc45)nc23)cn1] 179 | 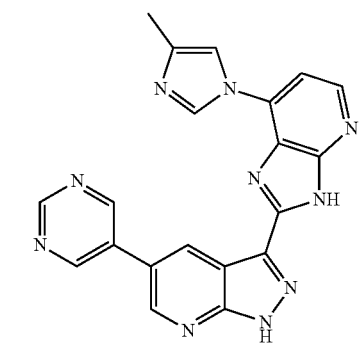 183 |
| 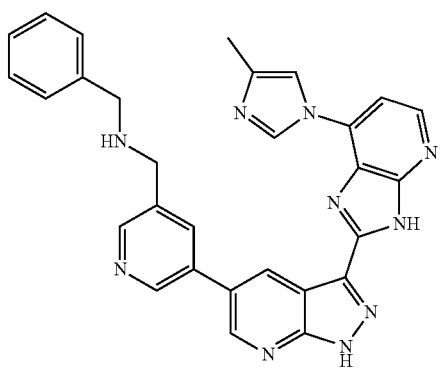 [SMILES: Cc1cn(-c2ccnc3[nH]c(-c4n[nH]c5ncc(-c6cncc(CNCc7ccccc7)c6)cc45)nc23)cn1] 180 | 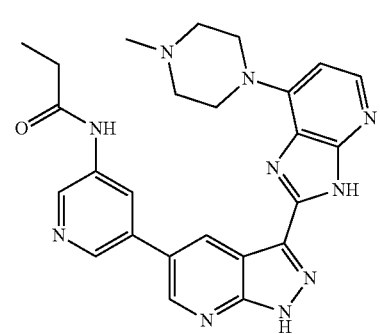 184 |
| 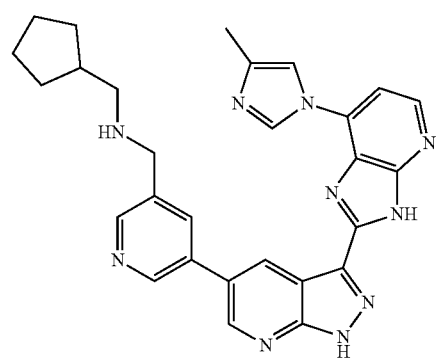 [SMILES: Cc1cn(-c2ccnc3[nH]c(-c4n[nH]c5ncc(-c6cncc(CNCC7CCCC7)c6)cc45)nc23)cn1] 181 | 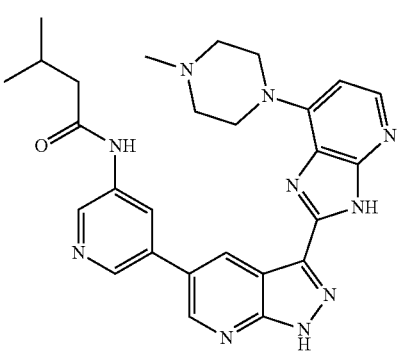 [SMILES: CC(C)CC(=O)Nc1cncc(-c2cnc3[nH]nc(-c4nc5c(N6CCN(C)CC6)ccnc5[nH]4)c3c2)c1] 185 |

TABLE 1-continued
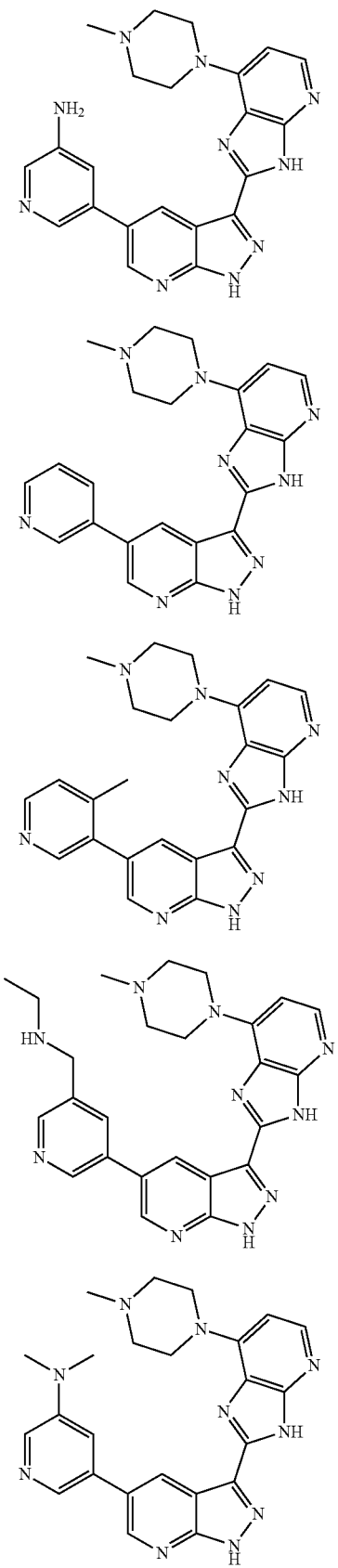
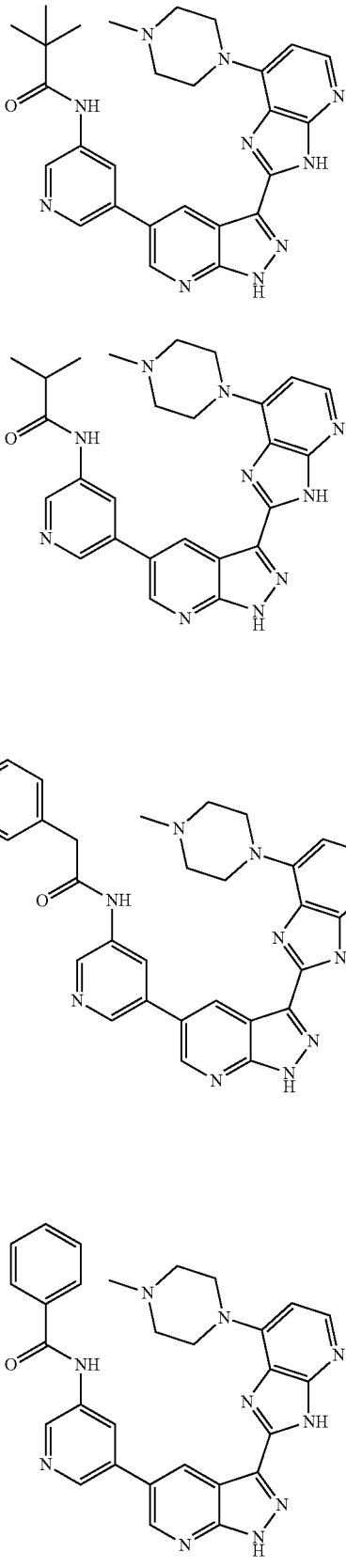

TABLE 1-continued
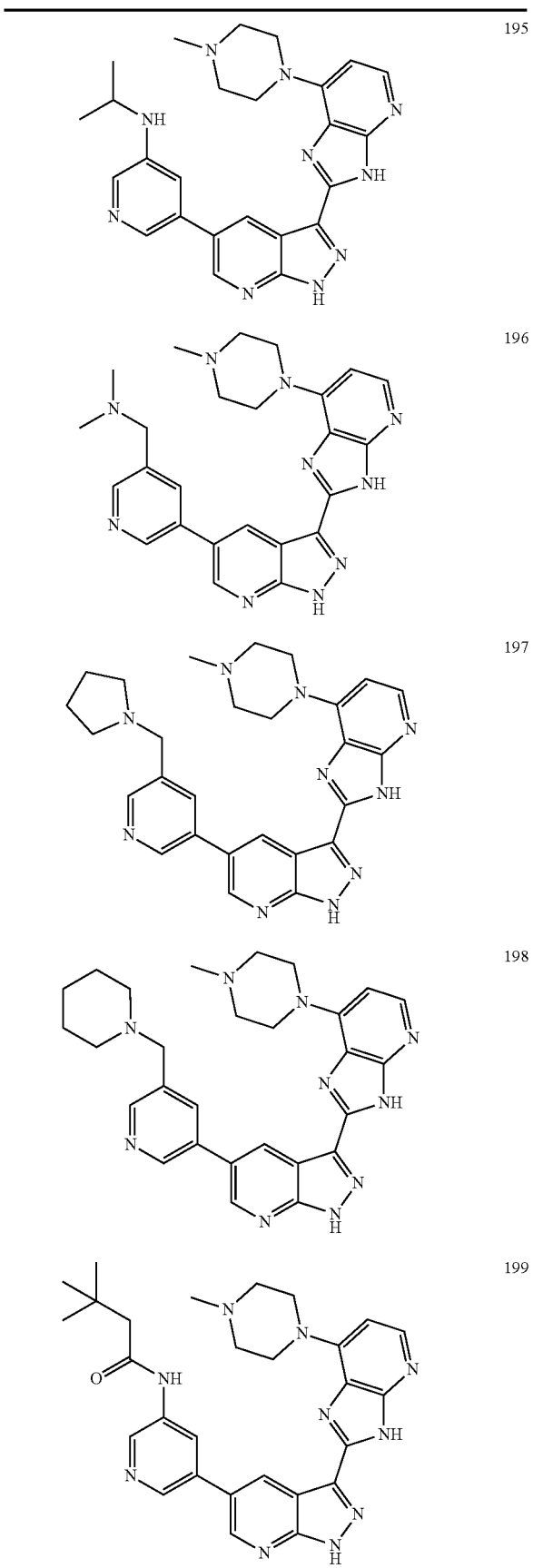
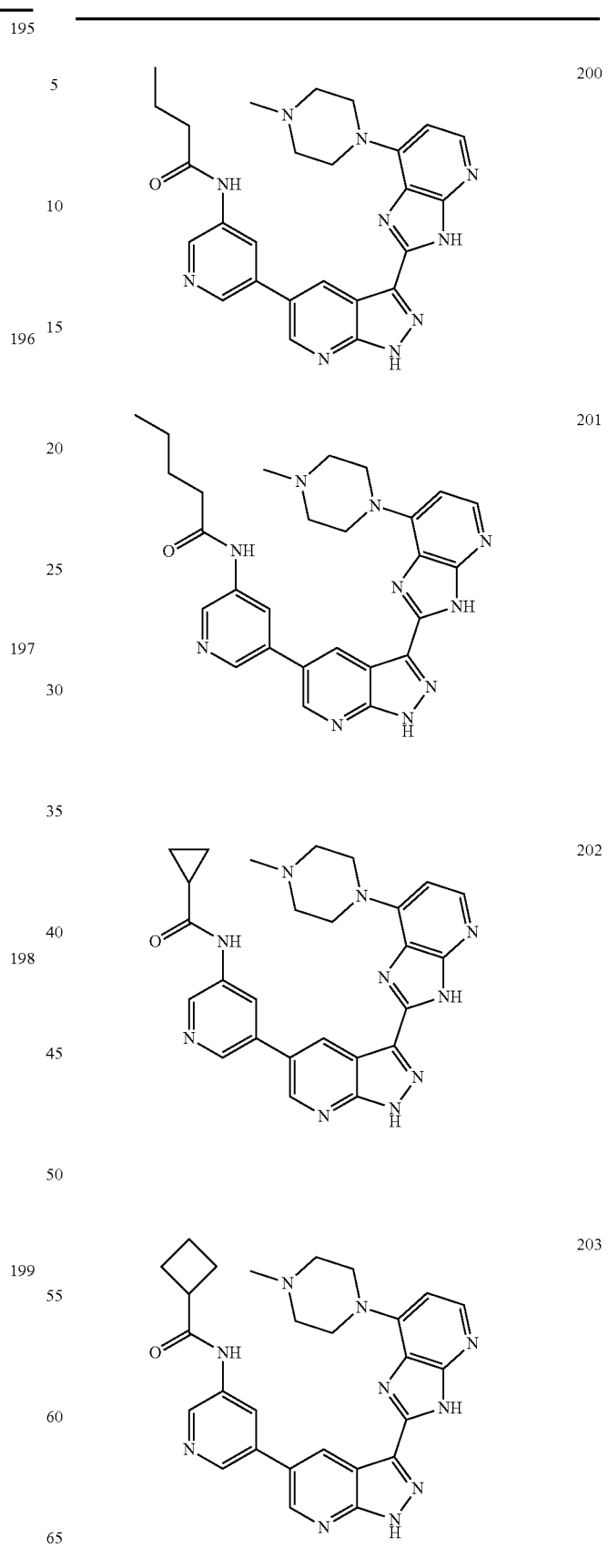

TABLE 1-continued
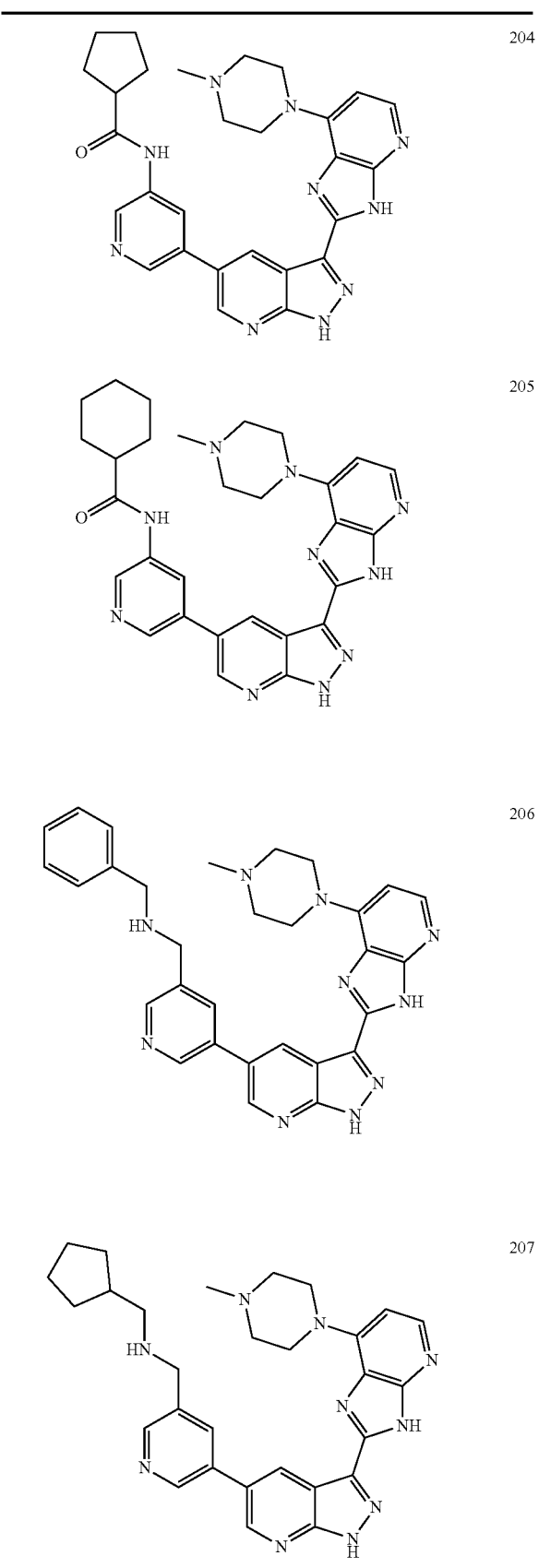
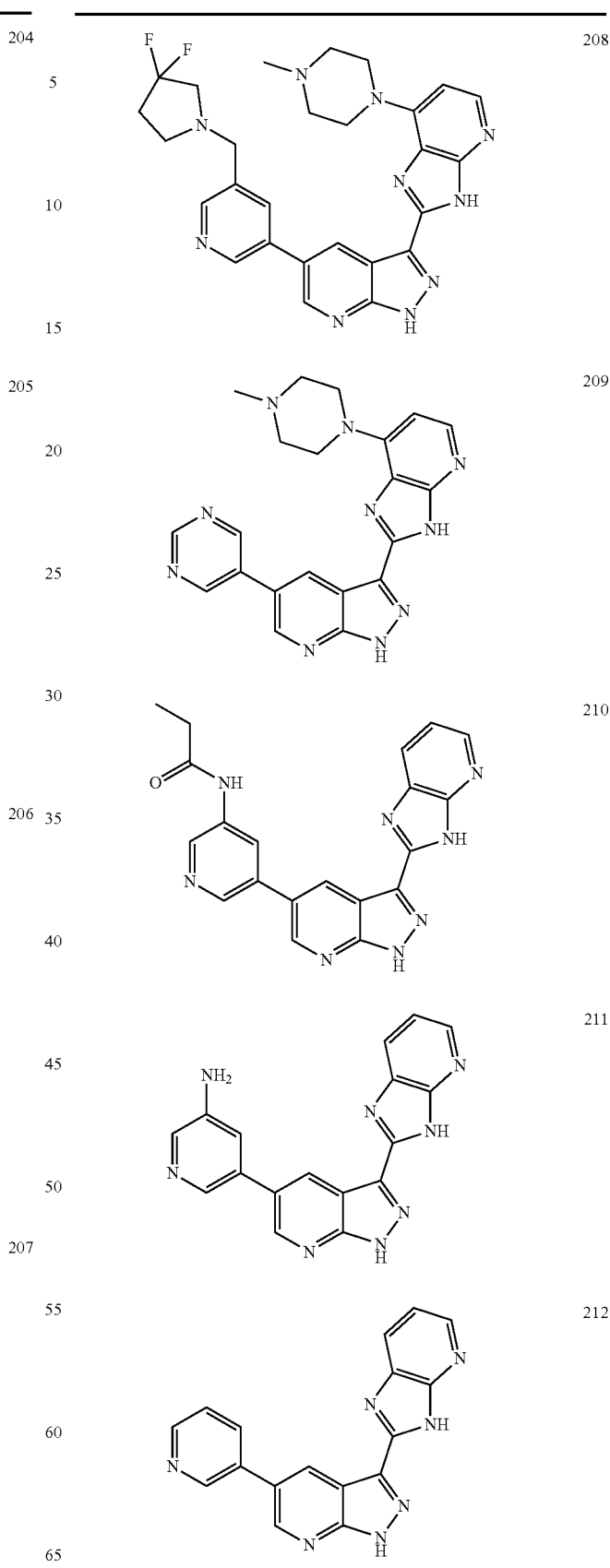

TABLE 1-continued
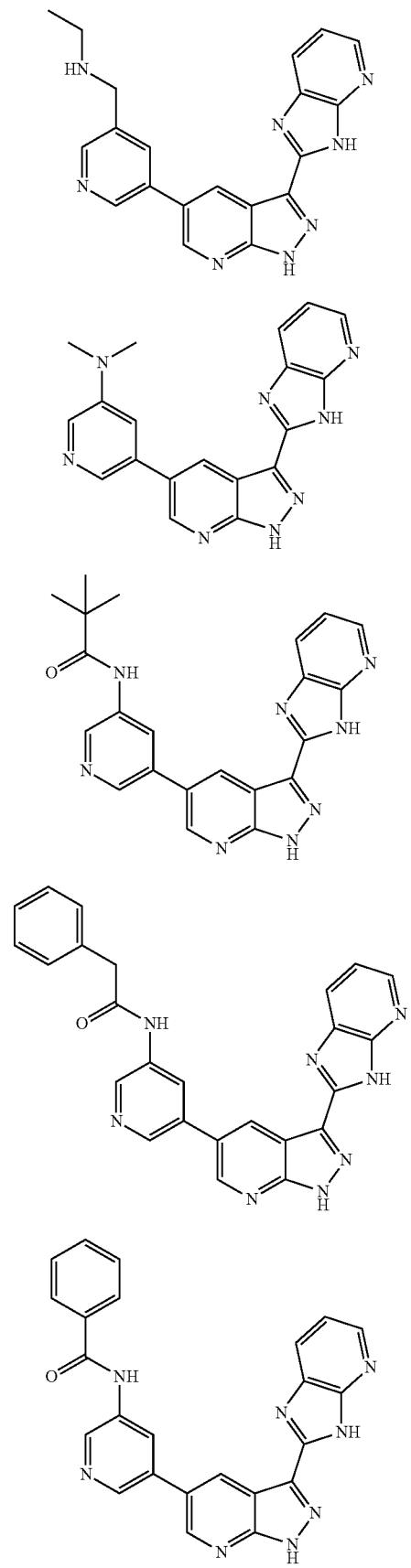
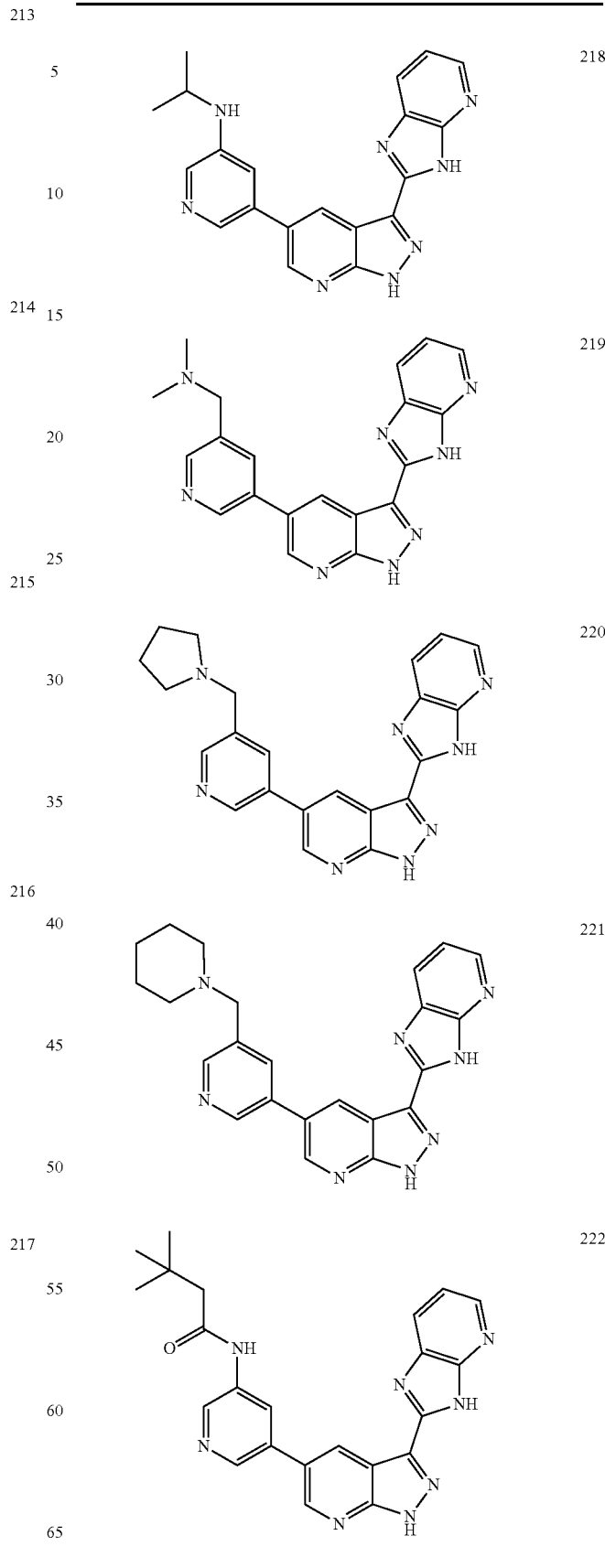

TABLE 1-continued
223
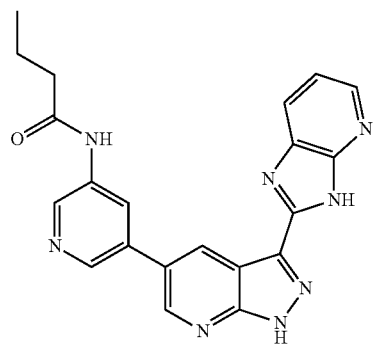 [SMILES: CCCC(=O)Nc1cncc(-c2cnc3[nH]nc(-c4nc5cccnc5[nH]4)c3c2)c1]
224
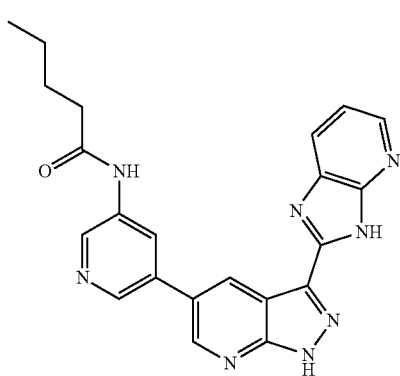 [SMILES: CCCCC(=O)Nc1cncc(-c2cnc3[nH]nc(-c4nc5cccnc5[nH]4)c3c2)c1]
225
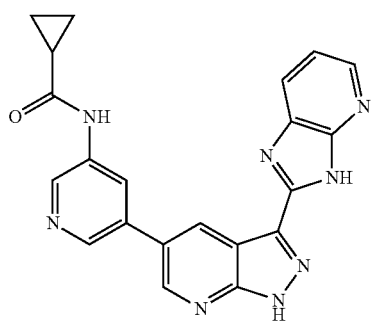 [SMILES: O=C(Nc1cncc(-c2cnc3[nH]nc(-c4nc5cccnc5[nH]4)c3c2)c1)C1CC1]
226
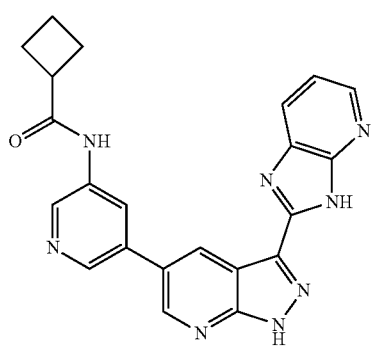 [SMILES: O=C(Nc1cncc(-c2cnc3[nH]nc(-c4nc5cccnc5[nH]4)c3c2)c1)C1CCC1]
TABLE 1-continued
227
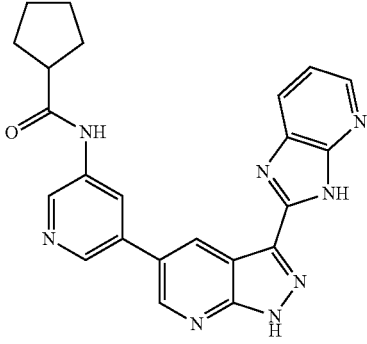 [SMILES: O=C(Nc1cncc(-c2cnc3[nH]nc(-c4nc5cccnc5[nH]4)c3c2)c1)C1CCCC1]
228
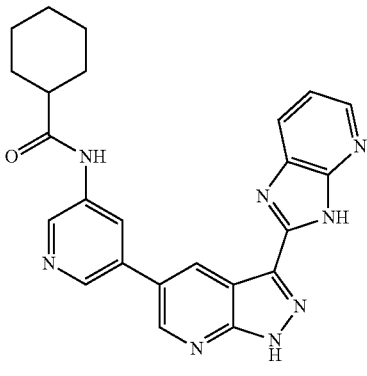 [SMILES: O=C(Nc1cncc(-c2cnc3[nH]nc(-c4nc5cccnc5[nH]4)c3c2)c1)C1CCCCC1]
229
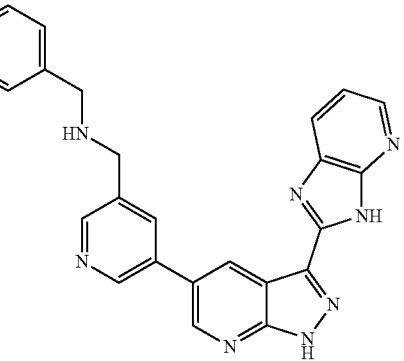
230
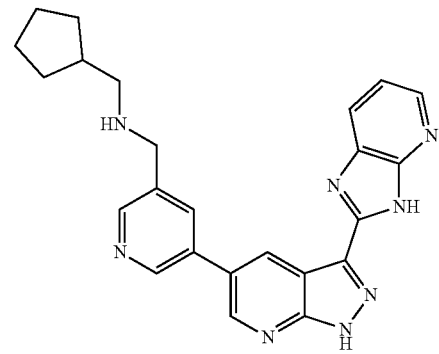 [SMILES: c1cnc2[nH]c(-c3n[nH]c4ncc(-c5cncc(CNCC6CCCC6)c5)cc34)nc2c1]

TABLE 1-continued
| | |
|---|---|
| 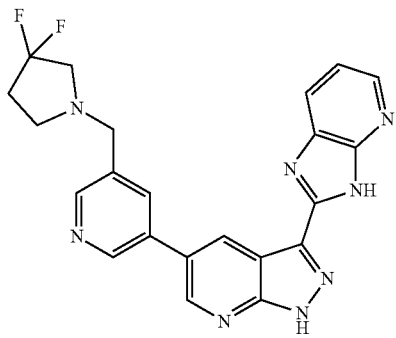 [SMILES: FC1(F)CCN(Cc2cncc(-c3cnc4[nH]nc(-c5nc6cccnc6[nH]5)c4c3)c2)C1] 231 | 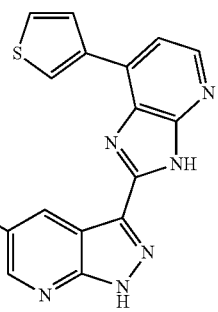 236 |
| 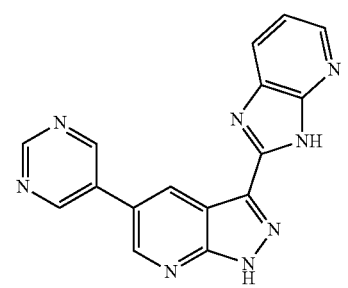 [SMILES: c1cnc2[nH]c(-c3n[nH]c4ncc(-c5cncnc5)cc34)nc2c1] 232 | 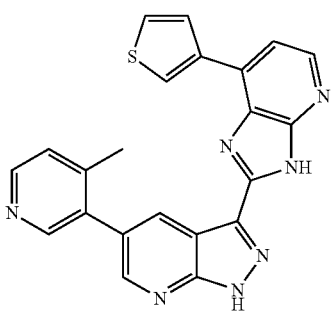 237 |
| 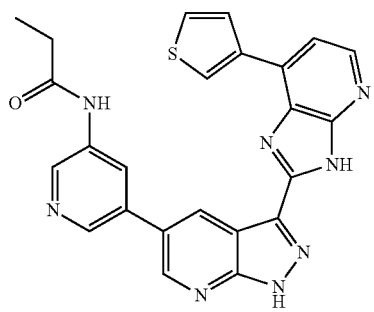 233 | 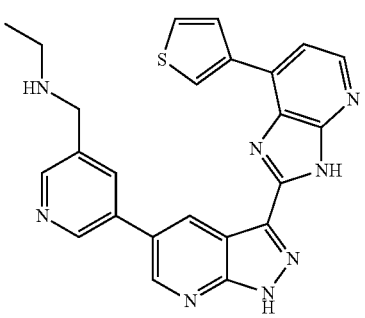 238 |
| 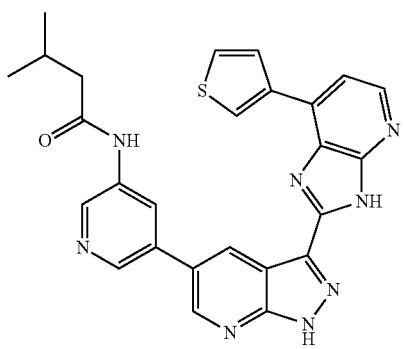 234 | 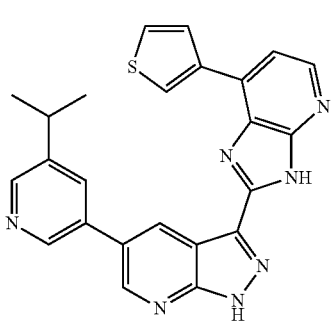 [SMILES: CC(C)c1cncc(-c2cnc3[nH]nc(-c4nc5c(-c6ccsc6)ccnc5[nH]4)c3c2)c1] 239 |
| 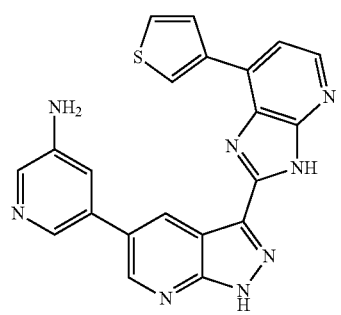 235 | 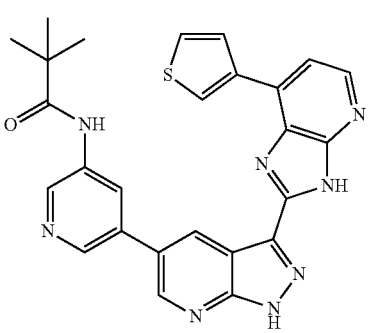 240 |

TABLE 1-continued
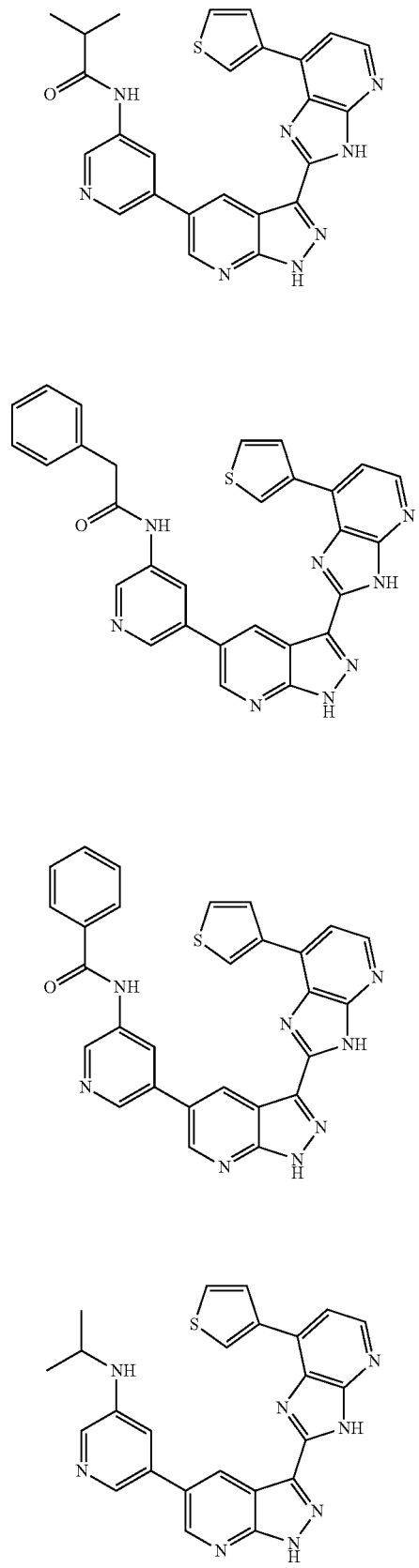
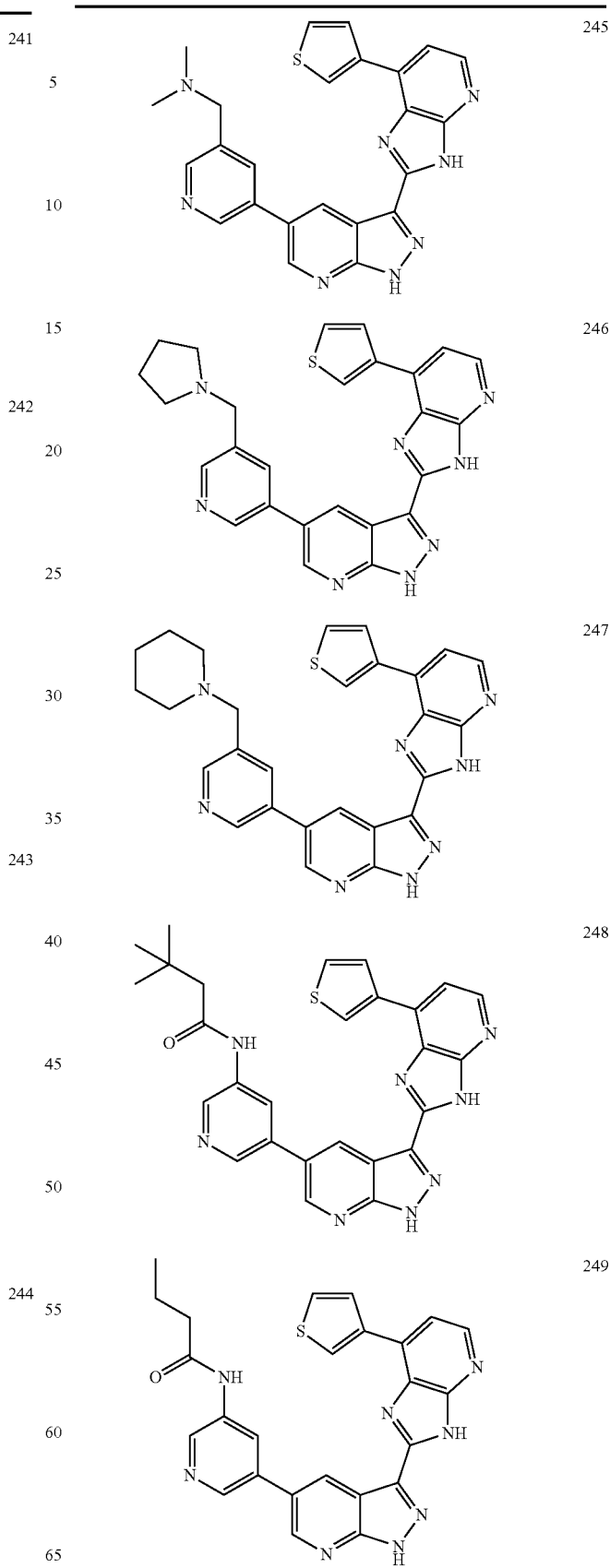

TABLE 1-continued
250 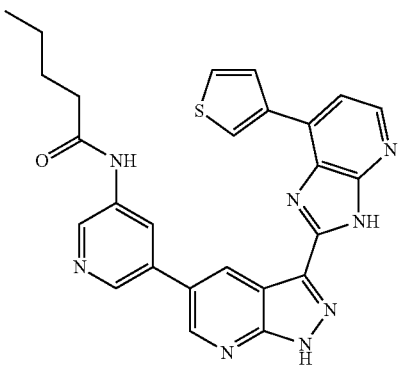 [SMILES: CCCCC(=O)Nc1cncc(-c2cnc3[nH]nc(-c4nc5c(-c6ccsc6)ccnc5[nH]4)c3c2)c1]
251 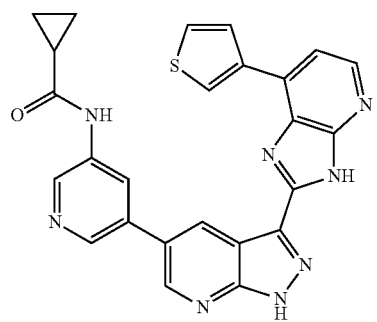 [SMILES: O=C(Nc1cncc(-c2cnc3[nH]nc(-c4nc5c(-c6ccsc6)ccnc5[nH]4)c3c2)c1)C1CC1]
252 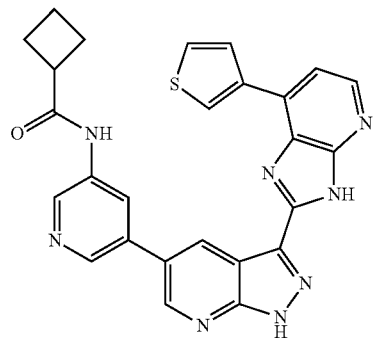 [SMILES: O=C(Nc1cncc(-c2cnc3[nH]nc(-c4nc5c(-c6ccsc6)ccnc5[nH]4)c3c2)c1)C1CCC1]
253 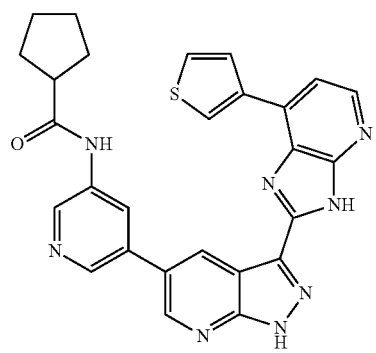
TABLE 1-continued
254 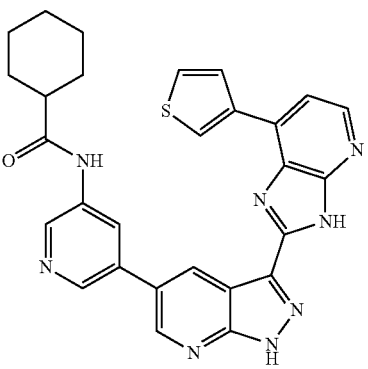 [SMILES: O=C(Nc1cncc(-c2cnc3[nH]nc(-c4nc5c(-c6ccsc6)ccnc5[nH]4)c3c2)c1)C1CCCCC1]
255 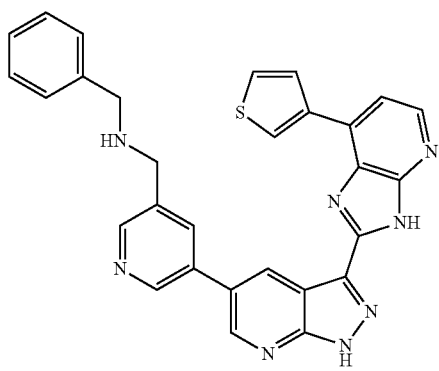 [SMILES: c1ccc(CNCc2cncc(-c3cnc4[nH]nc(-c5nc6c(-c7ccsc7)ccnc6[nH]5)c4c3)c2)cc1]
256 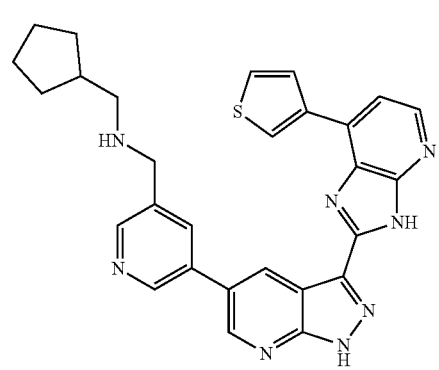 [SMILES: c1cc(-c2ccsc2)c2nc(-c3n[nH]c4ncc(-c5cncc(CNCC6CCCC6)c5)cc34)[nH]c2n1]
257 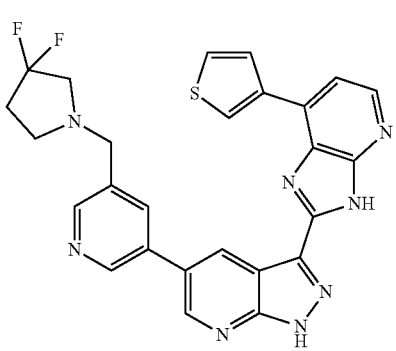 [SMILES: FC1(F)CCN(Cc2cncc(-c3cnc4[nH]nc(-c5nc6c(-c7ccsc7)ccnc6[nH]5)c4c3)c2)C1]

TABLE 1-continued
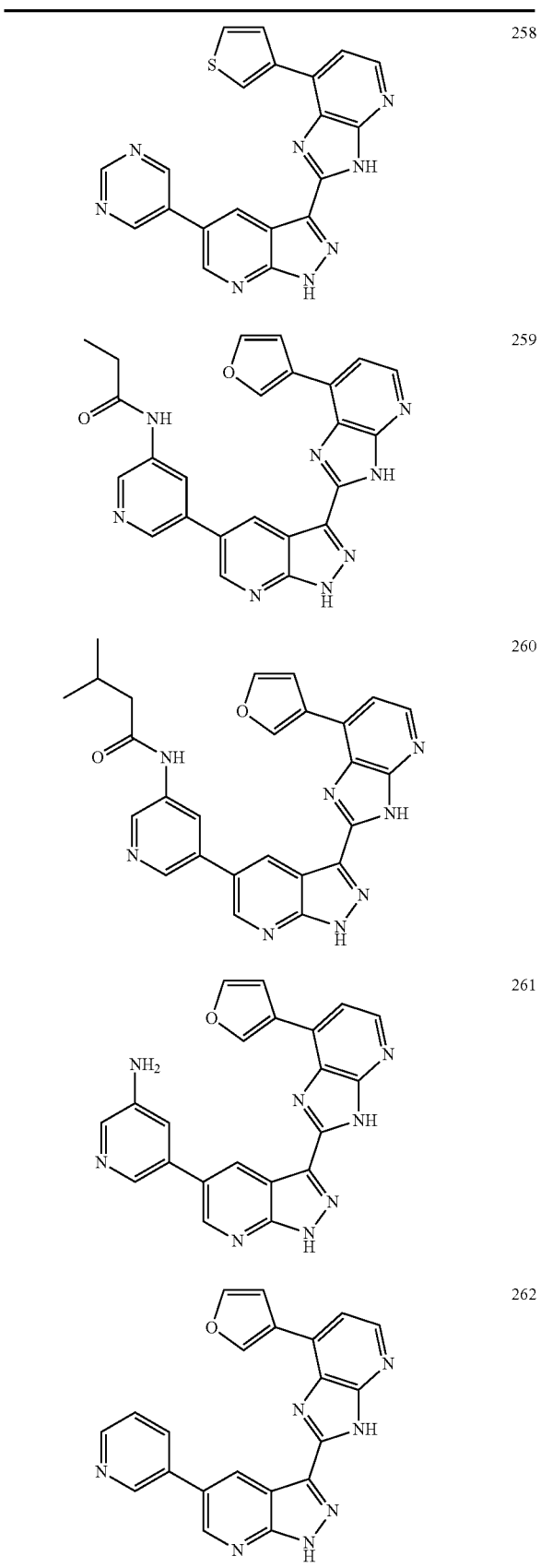
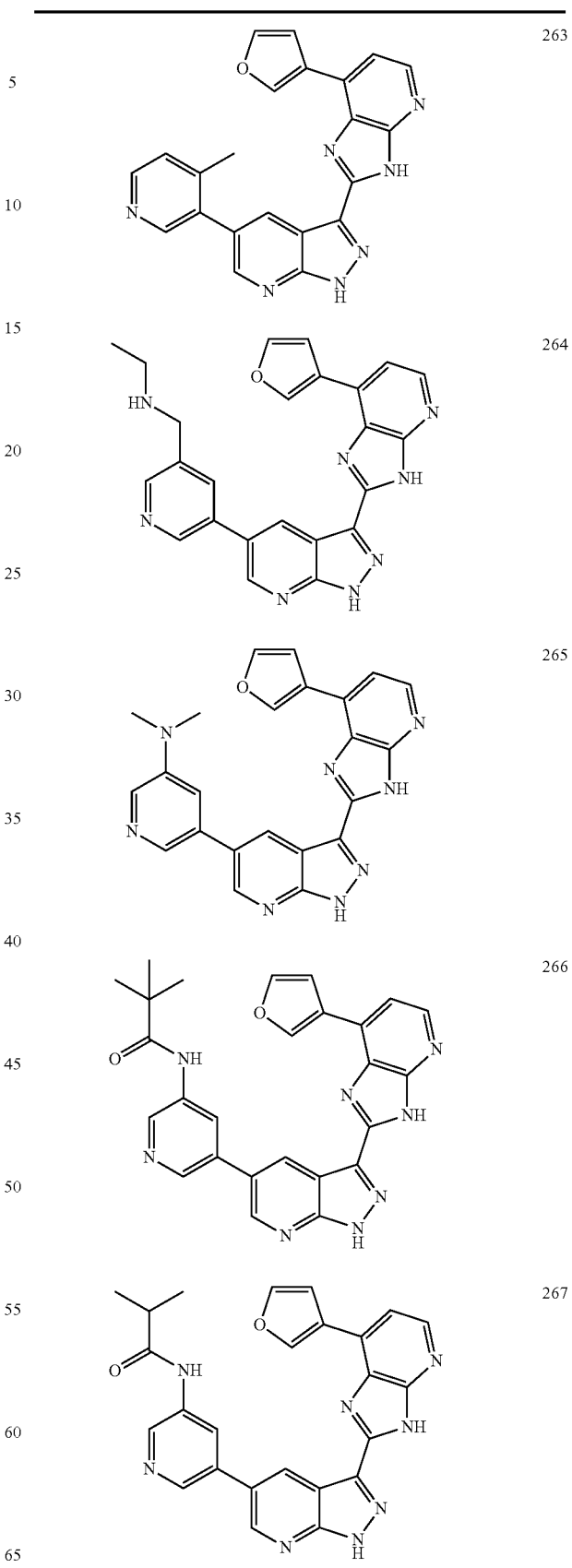

TABLE 1-continued
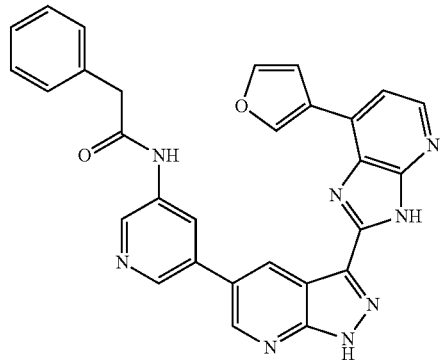 [SMILES: O=C(Cc1ccccc1)Nc1cncc(-c2cnc3[nH]nc(-c4nc5c(-c6ccoc6)ccnc5[nH]4)c3c2)c1]
268
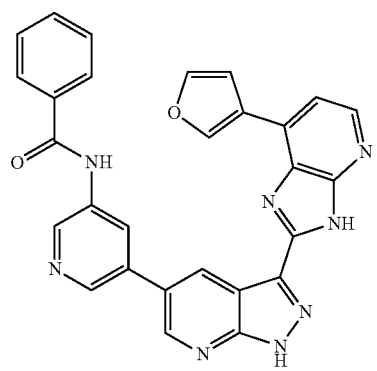 [SMILES: O=C(Nc1cncc(-c2cnc3[nH]nc(-c4nc5c(-c6ccoc6)ccnc5[nH]4)c3c2)c1)c1ccccc1]
269
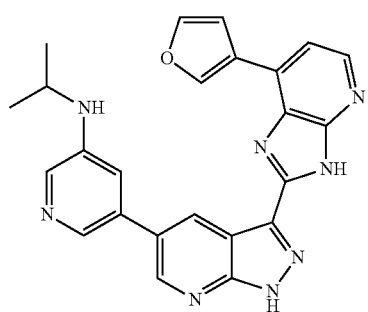 [SMILES: CC(C)Nc1cncc(-c2cnc3[nH]nc(-c4nc5c(-c6ccoc6)ccnc5[nH]4)c3c2)c1]
270
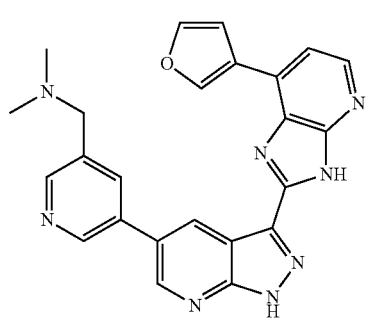 [SMILES: CN(C)Cc1cncc(-c2cnc3[nH]nc(-c4nc5c(-c6ccoc6)ccnc5[nH]4)c3c2)c1]
271
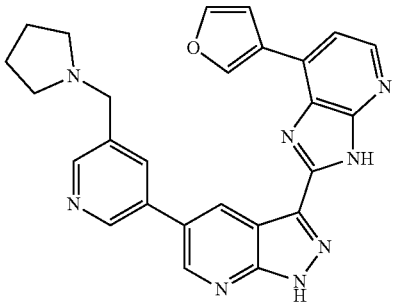 [SMILES: c1cc(-c2ccoc2)c2nc(-c3n[nH]c4ncc(-c5cncc(CN6CCCC6)c5)cc34)[nH]c2n1]
272
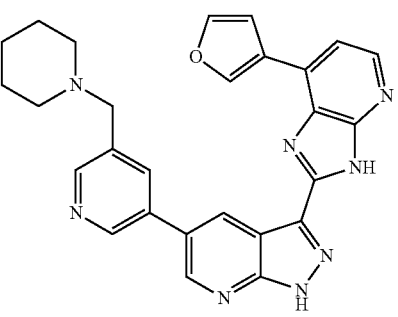
273
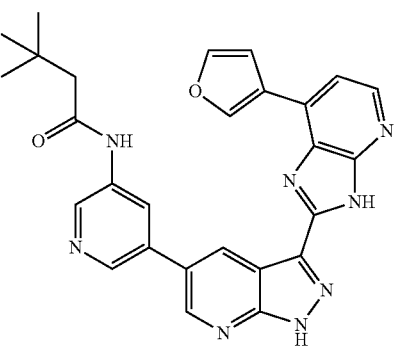
274
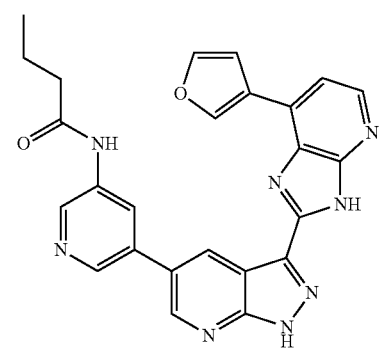 [SMILES: CCCC(=O)Nc1cncc(-c2cnc3[nH]nc(-c4nc5c(-c6ccoc6)ccnc5[nH]4)c3c2)c1]
275

TABLE 1-continued
| 276 | 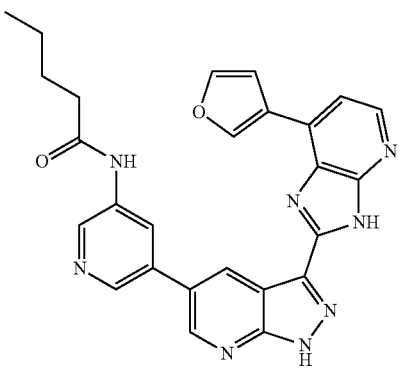 |
| 277 | 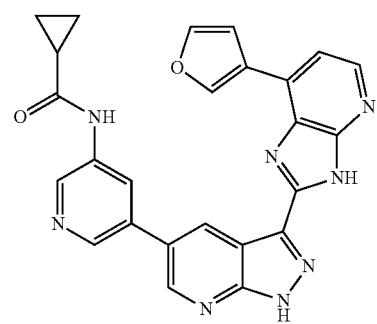 |
| 278 | 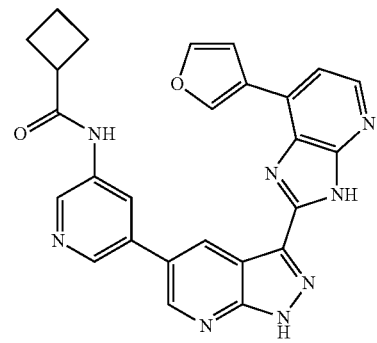 [SMILES: O=C(Nc1cncc(-c2cnc3[nH]nc(-c4nc5c(-c6ccoc6)ccnc5[nH]4)c3c2)c1)C1CCC1] |
| 279 | 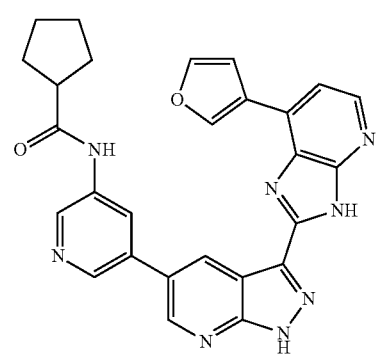 |
TABLE 1-continued
| 280 | 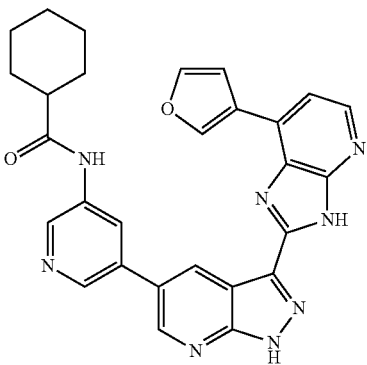 [SMILES: O=C(Nc1cncc(-c2cnc3[nH]nc(-c4nc5c(-c6ccoc6)ccnc5[nH]4)c3c2)c1)C1CCCCC1] |
| 281 | 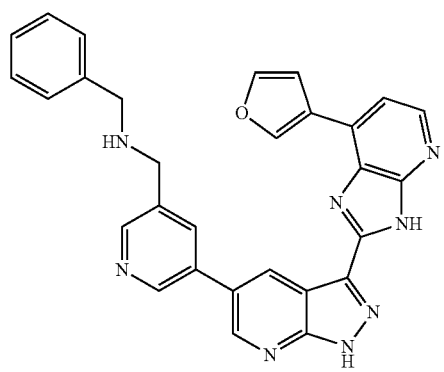 |
| 282 | 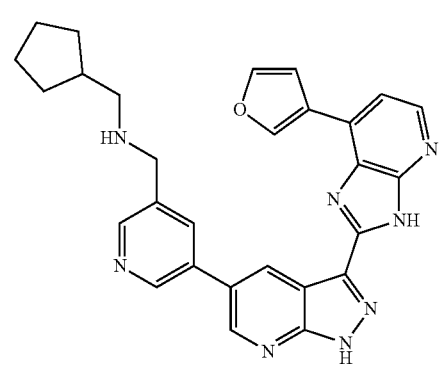 [SMILES: c1cc(-c2ccoc2)c2nc(-c3n[nH]c4ncc(-c5cncc(CNCC6CCCC6)c5)cc34)[nH]c2n1] |
| 283 | 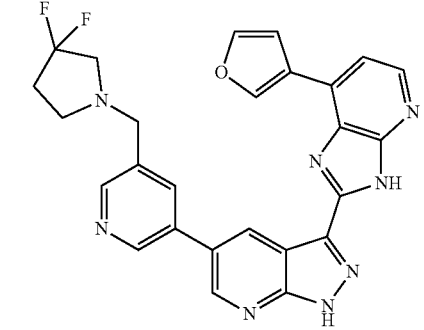 [SMILES: FC1(F)CCN(Cc2cncc(-c3cnc4[nH]nc(-c5nc6c(-c7ccoc7)ccnc6[nH]5)c4c3)c2)C1] |

TABLE 1-continued
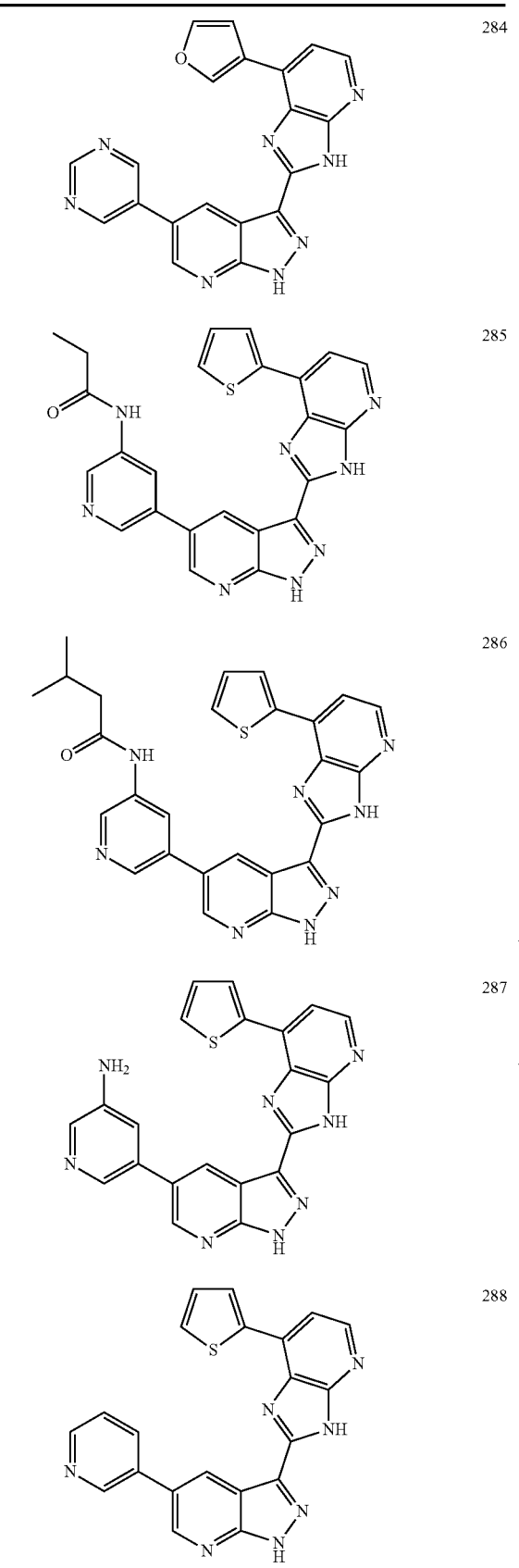
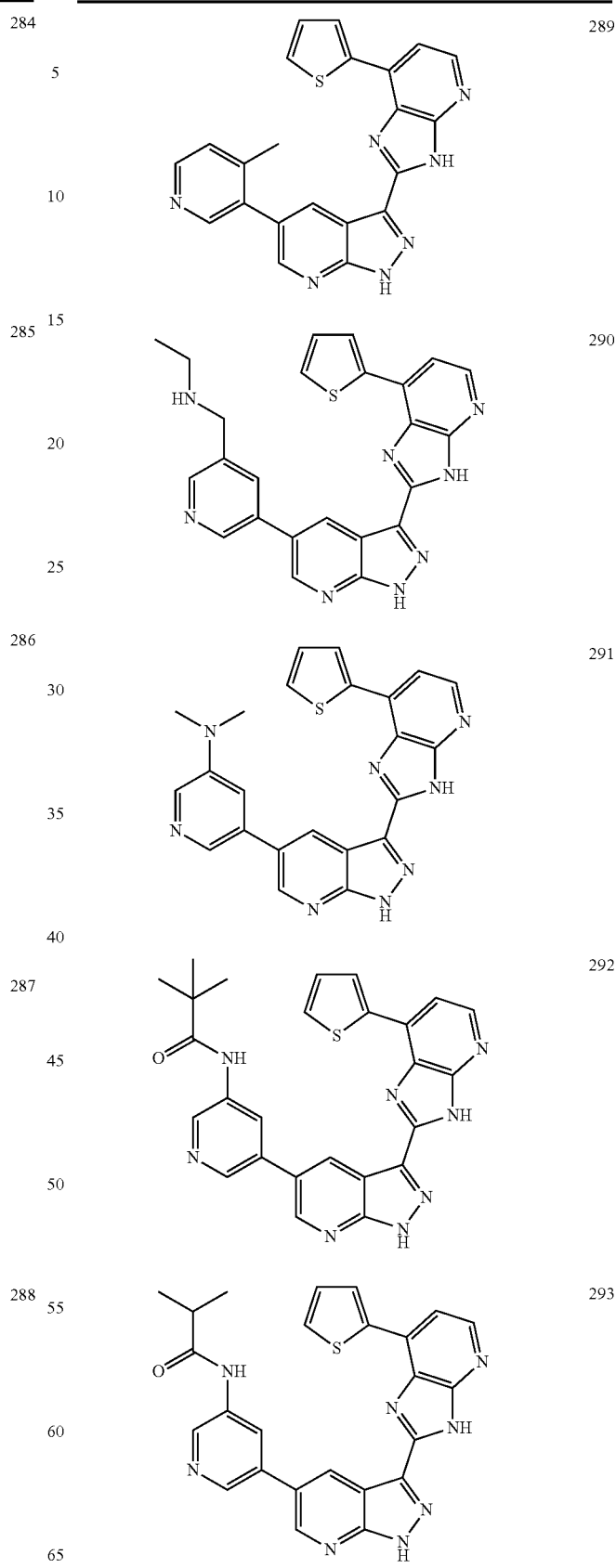

TABLE 1-continued
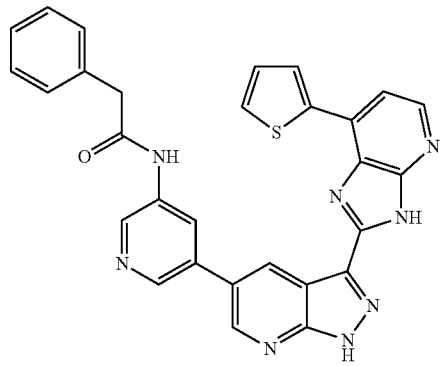 [SMILES: O=C(Cc1ccccc1)Nc1cncc(-c2cnc3[nH]nc(-c4nc5c(-c6cccs6)ccnc5[nH]4)c3c2)c1]
294
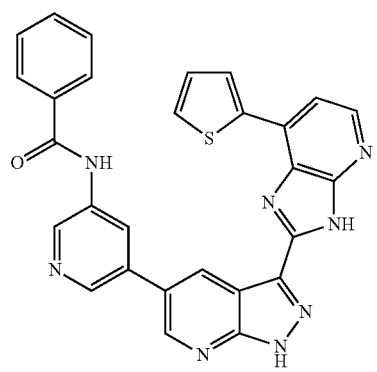 [SMILES: O=C(Nc1cncc(-c2cnc3[nH]nc(-c4nc5c(-c6cccs6)ccnc5[nH]4)c3c2)c1)c1ccccc1]
295
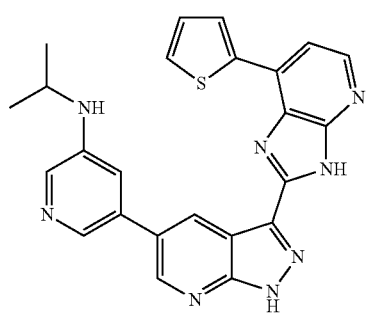 [SMILES: CC(C)Nc1cncc(-c2cnc3[nH]nc(-c4nc5c(-c6cccs6)ccnc5[nH]4)c3c2)c1]
296
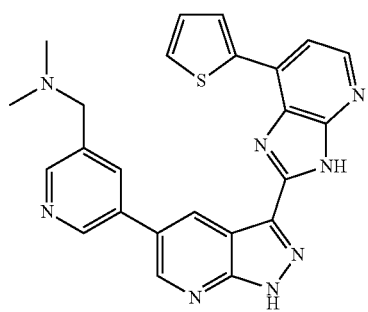 [SMILES: CN(C)Cc1cncc(-c2cnc3[nH]nc(-c4nc5c(-c6cccs6)ccnc5[nH]4)c3c2)c1]
297
TABLE 1-continued
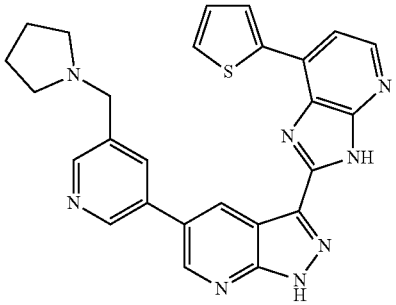 [SMILES: c1csc(-c2ccnc3[nH]c(-c4n[nH]c5ncc(-c6cncc(CN7CCCC7)c6)cc45)nc23)c1]
298
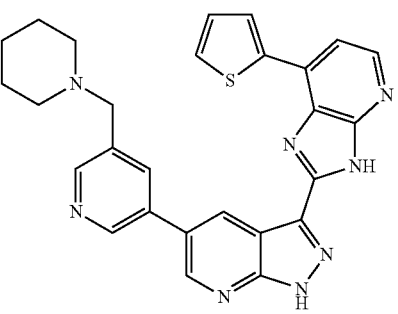 [SMILES: c1csc(-c2ccnc3[nH]c(-c4n[nH]c5ncc(-c6cncc(CN7CCCCC7)c6)cc45)nc23)c1]
299
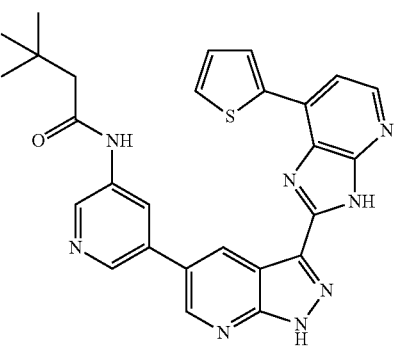 [SMILES: CC(C)(C)CC(=O)Nc1cncc(-c2cnc3[nH]nc(-c4nc5c(-c6cccs6)ccnc5[nH]4)c3c2)c1]
300
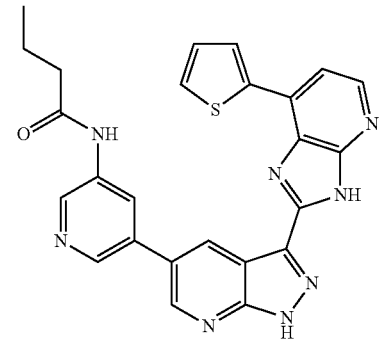 [SMILES: CCCC(=O)Nc1cncc(-c2cnc3[nH]nc(-c4nc5c(-c6cccs6)ccnc5[nH]4)c3c2)c1]
301

TABLE 1-continued
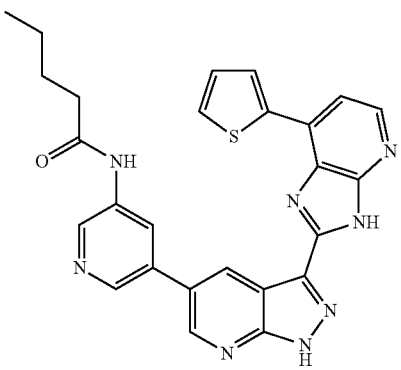 [SMILES: CCCCC(=O)Nc1cncc(-c2cnc3[nH]nc(-c4nc5c(-c6cccs6)ccnc5[nH]4)c3c2)c1]
302
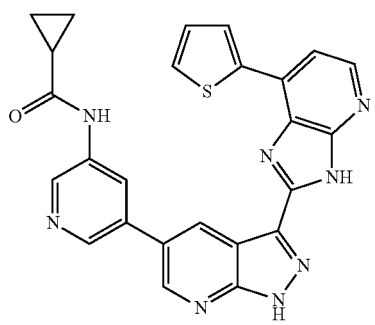 [SMILES: O=C(Nc1cncc(-c2cnc3[nH]nc(-c4nc5c(-c6cccs6)ccnc5[nH]4)c3c2)c1)C1CC1]
303
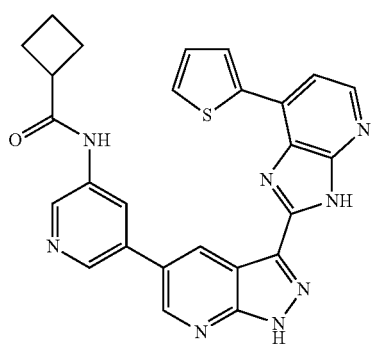 [SMILES: O=C(Nc1cncc(-c2cnc3[nH]nc(-c4nc5c(-c6cccs6)ccnc5[nH]4)c3c2)c1)C1CCC1]
304
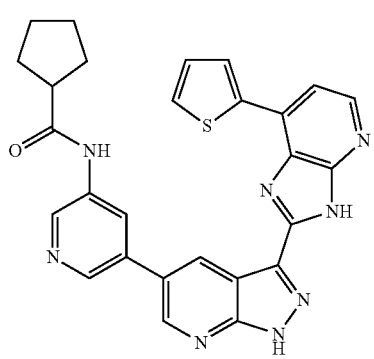 [SMILES: O=C(Nc1cncc(-c2cnc3[nH]nc(-c4nc5c(-c6cccs6)ccnc5[nH]4)c3c2)c1)C1CCCC1]
305
TABLE 1-continued
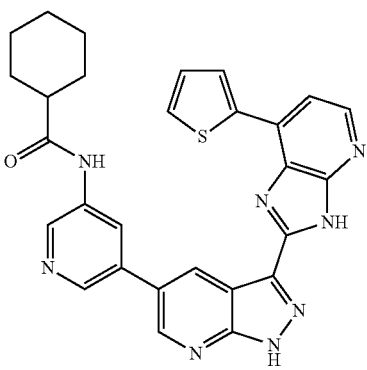 [SMILES: O=C(Nc1cncc(-c2cnc3[nH]nc(-c4nc5c(-c6cccs6)ccnc5[nH]4)c3c2)c1)C1CCCCC1]
306
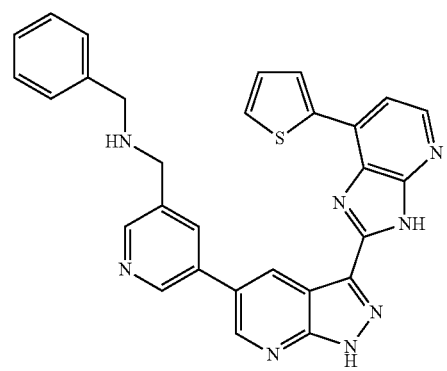 [SMILES: c1ccc(CNCc2cncc(-c3cnc4[nH]nc(-c5nc6c(-c7cccs7)ccnc6[nH]5)c4c3)c2)cc1]
307
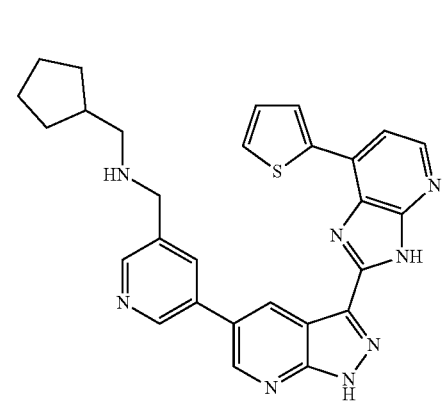 [SMILES: c1csc(-c2ccnc3[nH]c(-c4n[nH]c5ncc(-c6cncc(CNCC7CCCC7)c6)cc45)nc23)c1]
308
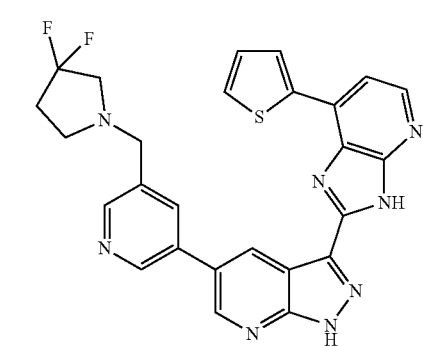 [SMILES: FC1(F)CCN(Cc2cncc(-c3cnc4[nH]nc(-c5nc6c(-c7cccs7)ccnc6[nH]5)c4c3)c2)C1]
309

TABLE 1-continued
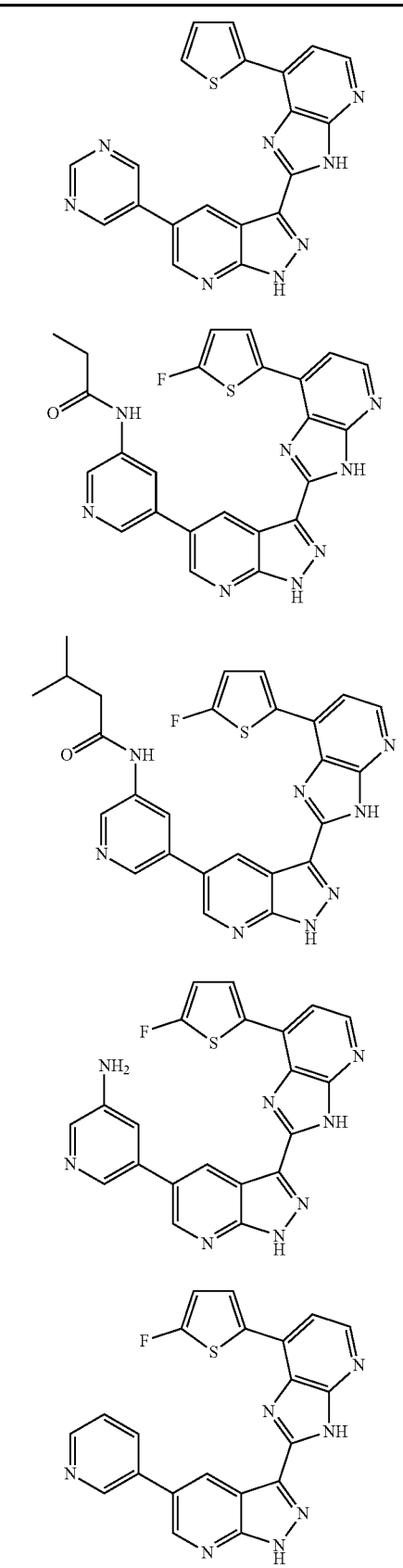
310
311
312
313
314
TABLE 1-continued
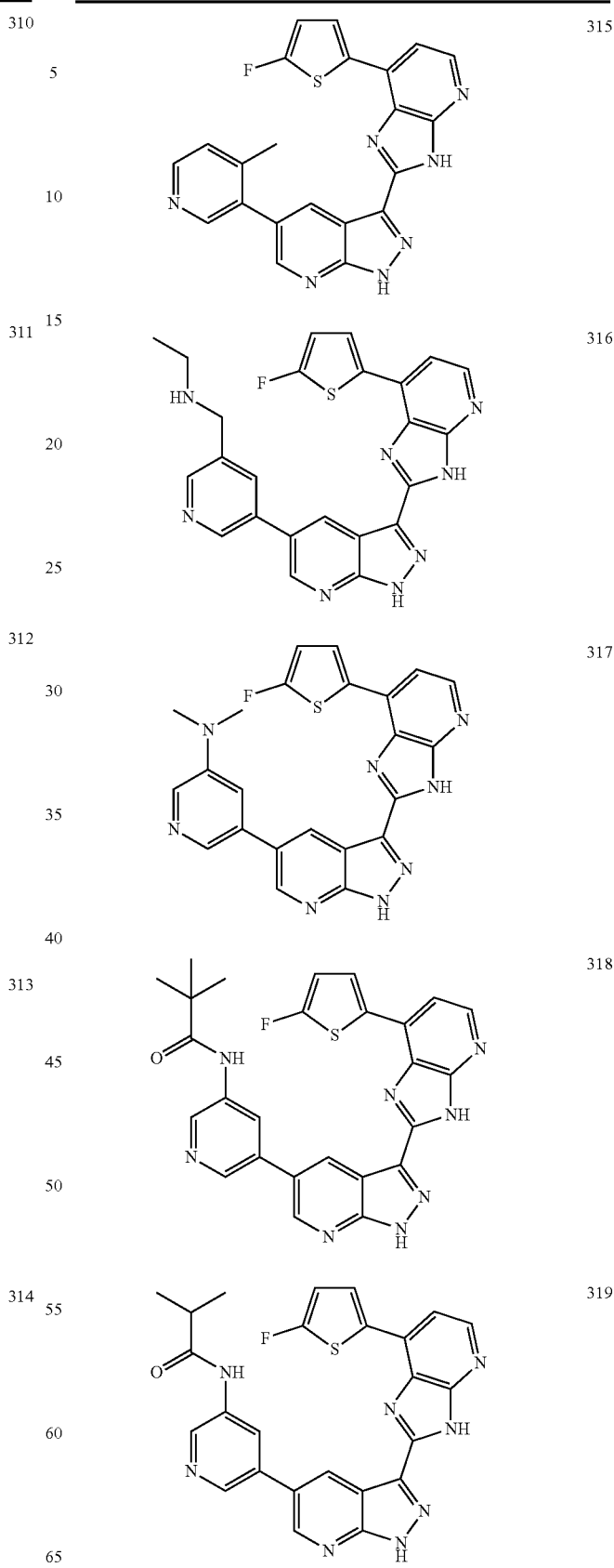
315
316
317
318
319

TABLE 1-continued
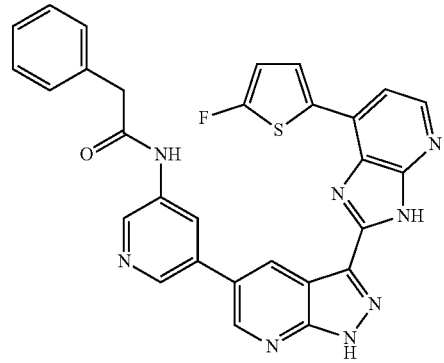 [SMILES: O=C(Cc1ccccc1)Nc1cncc(-c2cnc3[nH]nc(-c4nc5c(-c6ccc(F)s6)ccnc5[nH]4)c3c2)c1] 320
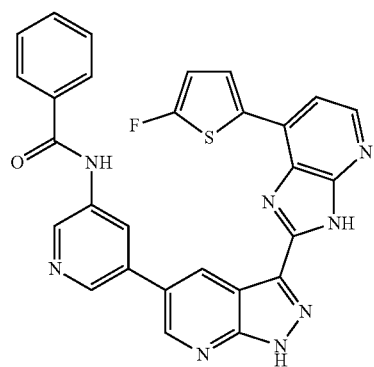 321
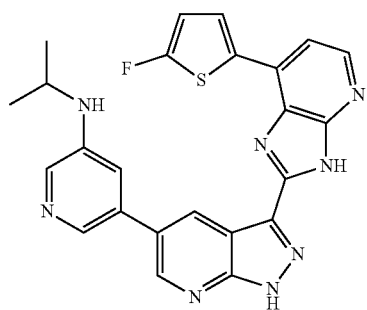 322
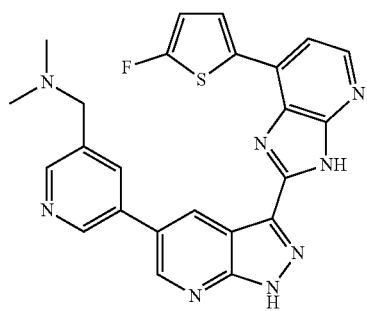 [SMILES: CN(C)Cc1cncc(-c2cnc3[nH]nc(-c4nc5c(-c6ccc(F)s6)ccnc5[nH]4)c3c2)c1] 323
TABLE 1-continued
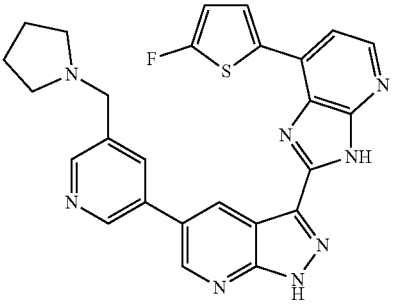 [SMILES: Fc1ccc(-c2ccnc3[nH]c(-c4n[nH]c5ncc(-c6cncc(CN7CCCC7)c6)cc45)nc23)s1] 324
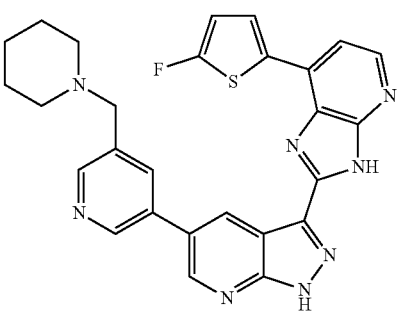 325
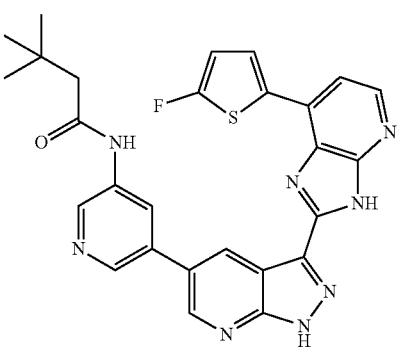 [SMILES: CC(C)(C)CC(=O)Nc1cncc(-c2cnc3[nH]nc(-c4nc5c(-c6ccc(F)s6)ccnc5[nH]4)c3c2)c1] 326
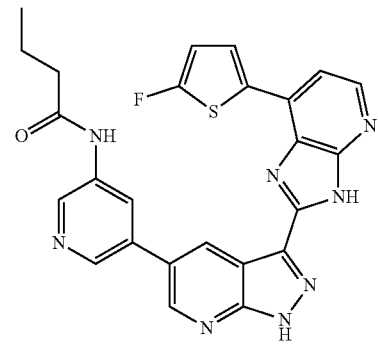 [SMILES: CCCC(=O)Nc1cncc(-c2cnc3[nH]nc(-c4nc5c(-c6ccc(F)s6)ccnc5[nH]4)c3c2)c1] 327

TABLE 1-continued
328 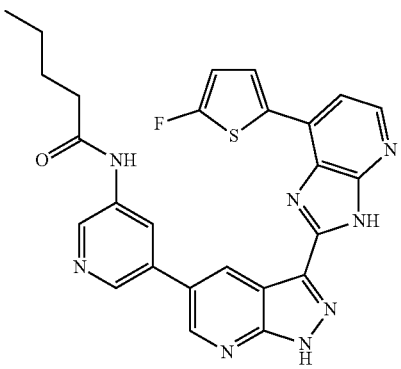
329 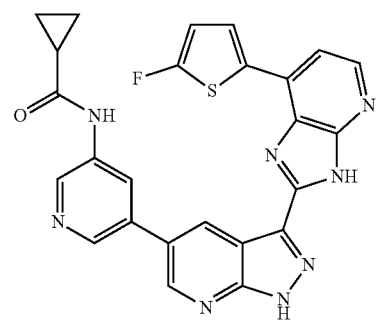
330 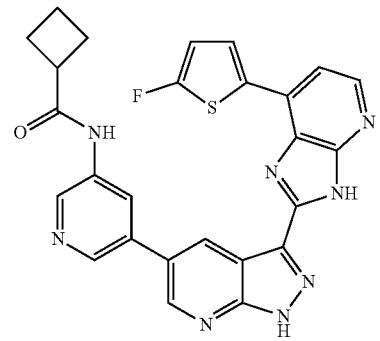 [SMILES: O=C(Nc1cncc(-c2cnc3[nH]nc(-c4nc5c(-c6ccc(F)s6)ccnc5[nH]4)c3c2)c1)C1CCC1]
331 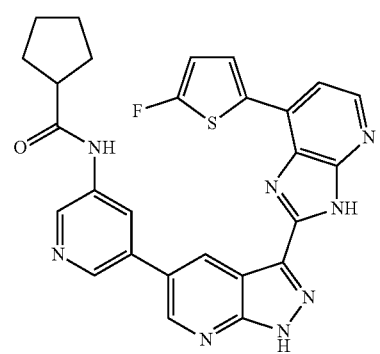
TABLE 1-continued
332 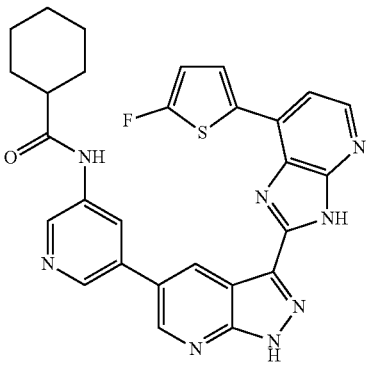 [SMILES: O=C(Nc1cncc(-c2cnc3[nH]nc(-c4nc5c(-c6ccc(F)s6)ccnc5[nH]4)c3c2)c1)C1CCCCC1]
333 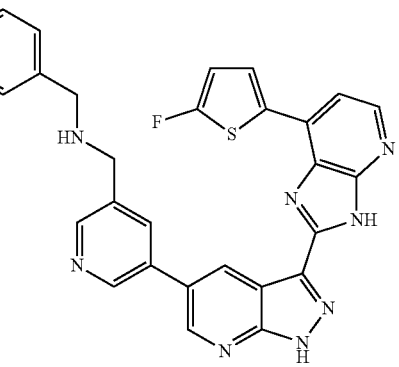
334 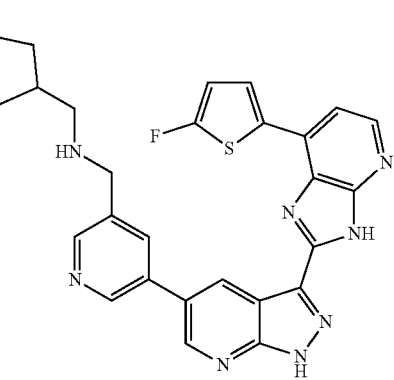
335 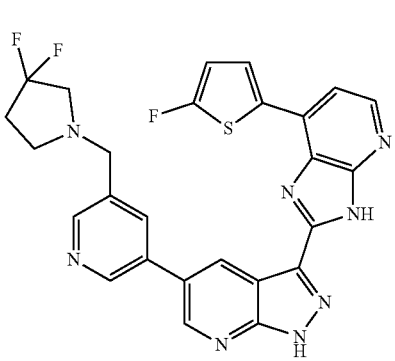 [SMILES: Fc1ccc(-c2ccnc3[nH]c(-c4n[nH]c5ncc(-c6cncc(CN7CCC(F)(F)C7)c6)cc45)nc23)s1]

TABLE 1-continued

TABLE 1-continued
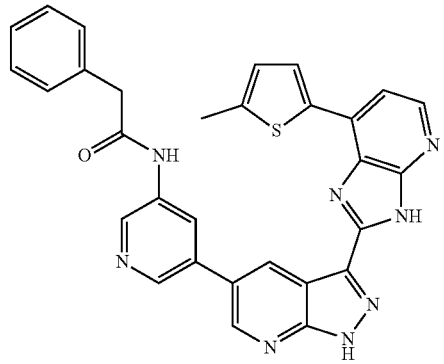 [SMILES: Cc1ccc(-c2ccnc3[nH]c(-c4n[nH]c5ncc(-c6cncc(NC(=O)Cc7ccccc7)c6)cc45)nc23)s1] 346
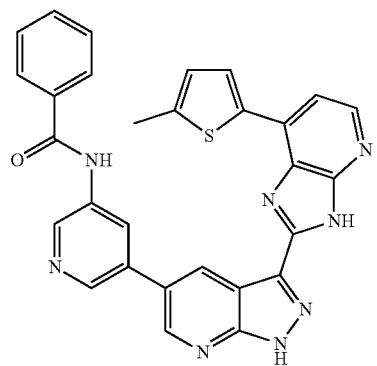 [SMILES: Cc1ccc(-c2ccnc3[nH]c(-c4n[nH]c5ncc(-c6cncc(NC(=O)c7ccccc7)c6)cc45)nc23)s1] 347
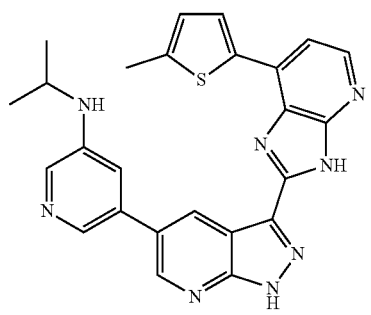 [SMILES: Cc1ccc(-c2ccnc3[nH]c(-c4n[nH]c5ncc(-c6cncc(NC(C)C)c6)cc45)nc23)s1] 348
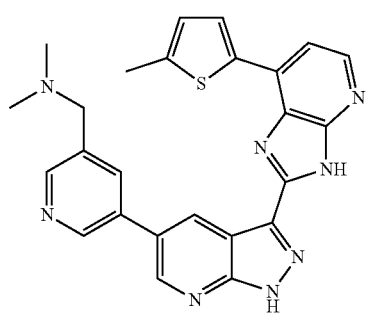 [SMILES: Cc1ccc(-c2ccnc3[nH]c(-c4n[nH]c5ncc(-c6cncc(CN(C)C)c6)cc45)nc23)s1] 349
TABLE 1-continued
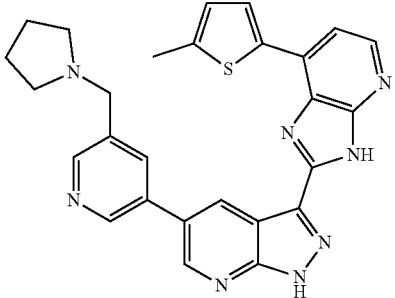 [SMILES: Cc1ccc(-c2ccnc3[nH]c(-c4n[nH]c5ncc(-c6cncc(CN7CCCC7)c6)cc45)nc23)s1] 350
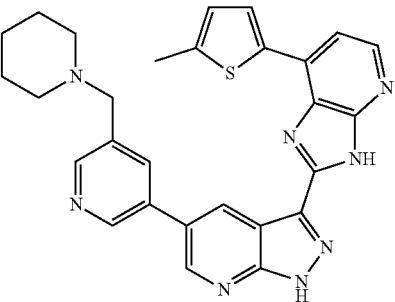 351
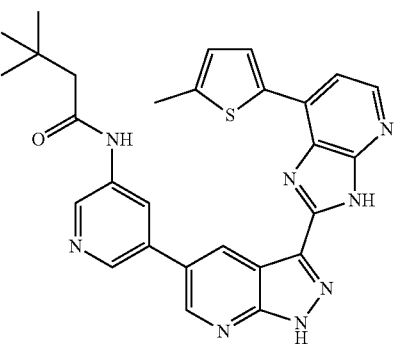 352
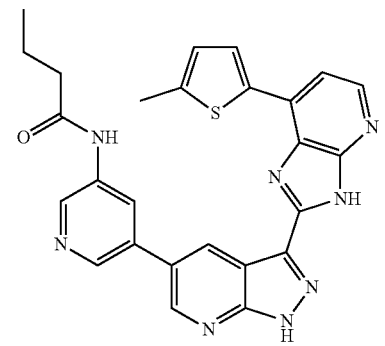 [SMILES: CCCC(=O)Nc1cncc(-c2cnc3[nH]nc(-c4nc5c(-c6ccc(C)s6)ccnc5[nH]4)c3c2)c1] 353

TABLE 1-continued
354 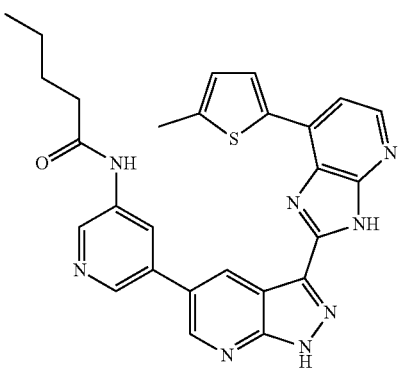 [SMILES: CCCCC(=O)Nc1cncc(-c2cnc3[nH]nc(-c4nc5c(-c6ccc(C)s6)ccnc5[nH]4)c3c2)c1]
355 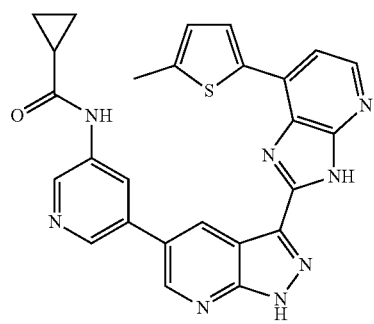 [SMILES: Cc1ccc(-c2ccnc3[nH]c(-c4n[nH]c5ncc(-c6cncc(NC(=O)C7CC7)c6)cc45)nc23)s1]
356 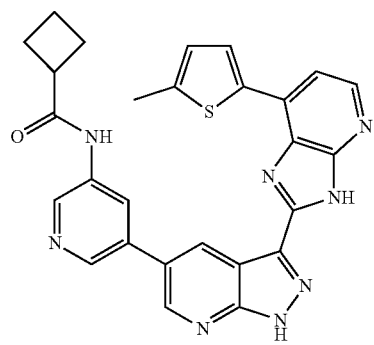
357 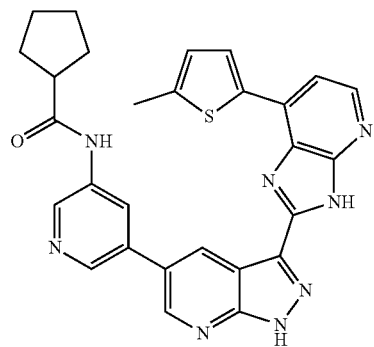 [SMILES: Cc1ccc(-c2ccnc3[nH]c(-c4n[nH]c5ncc(-c6cncc(NC(=O)C7CCCC7)c6)cc45)nc23)s1]
358 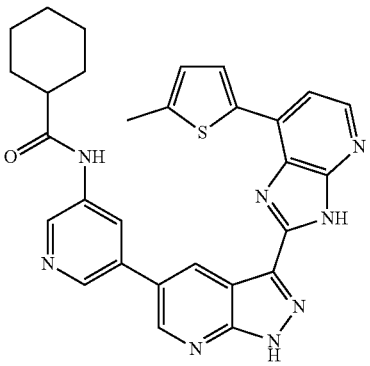 [SMILES: Cc1ccc(-c2ccnc3[nH]c(-c4n[nH]c5ncc(-c6cncc(NC(=O)C7CCCCC7)c6)cc45)nc23)s1]
359 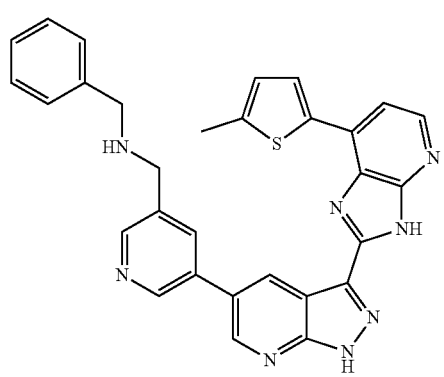 [SMILES: Cc1ccc(-c2ccnc3[nH]c(-c4n[nH]c5ncc(-c6cncc(CNCc7ccccc7)c6)cc45)nc23)s1]
360 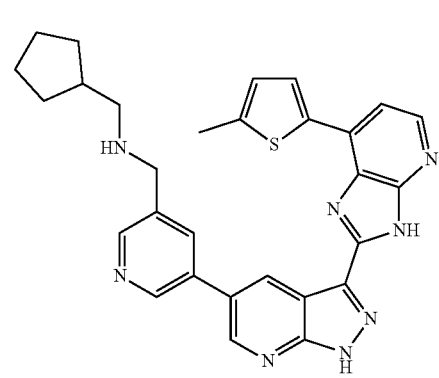
361 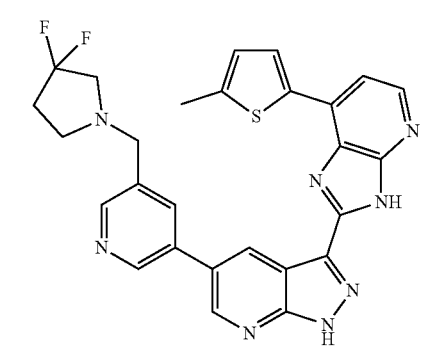 [SMILES: Cc1ccc(-c2ccnc3[nH]c(-c4n[nH]c5ncc(-c6cncc(CN7CCC(F)(F)C7)c6)cc45)nc23)s1]

TABLE 1-continued
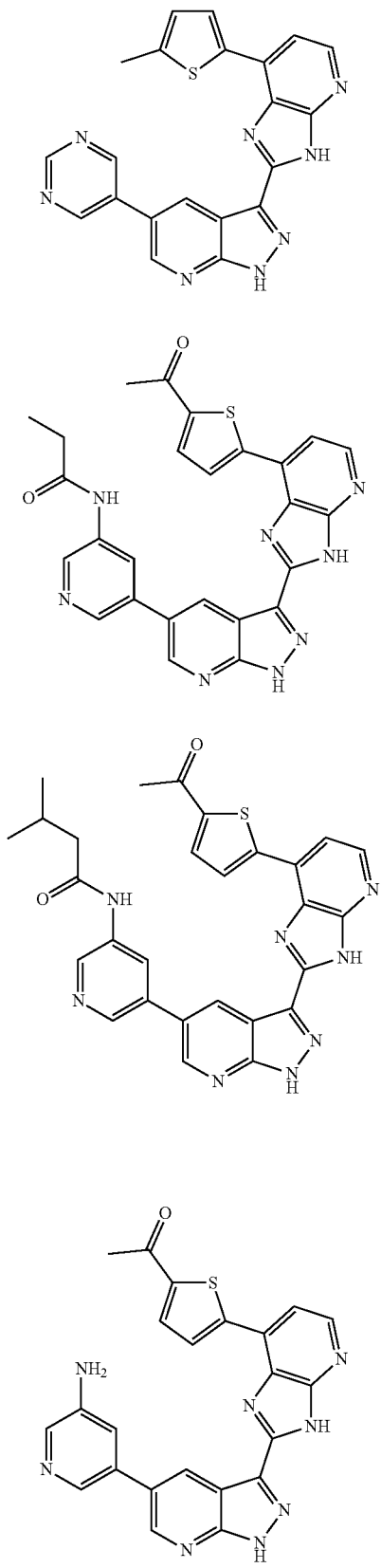
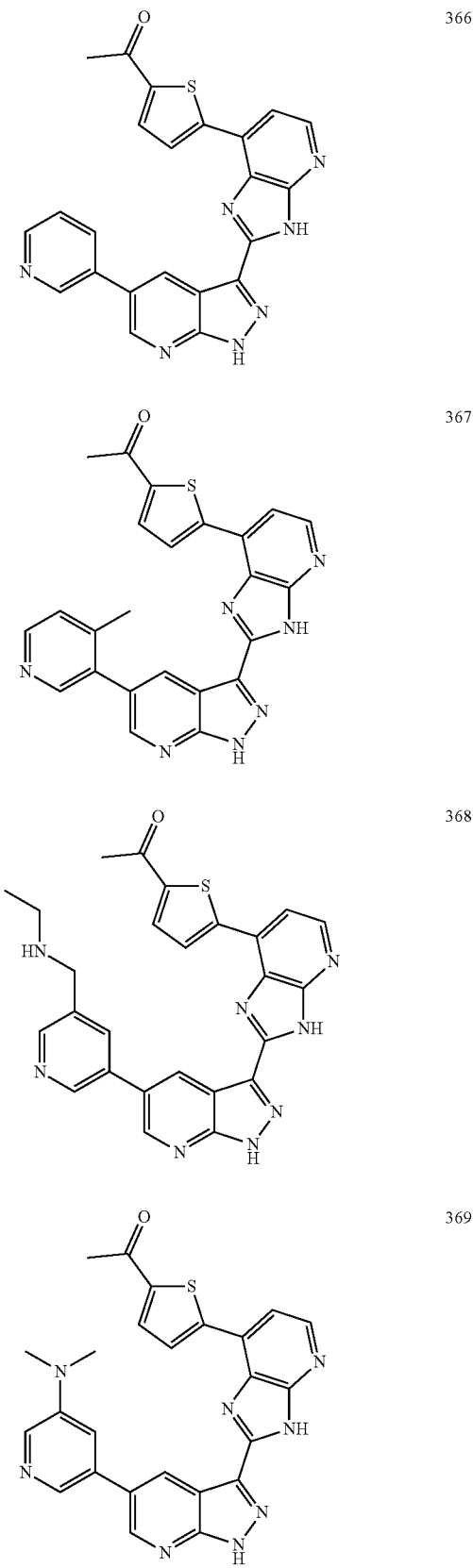

TABLE 1-continued
| | |
|---|---|
| 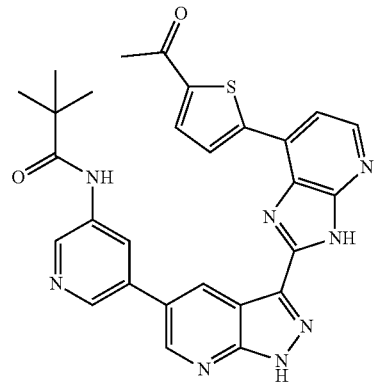 [SMILES: CC(=O)c1ccc(-c2ccnc3[nH]c(-c4n[nH]c5ncc(-c6cncc(NC(=O)C(C)(C)C)c6)cc45)nc23)s1] 370 | 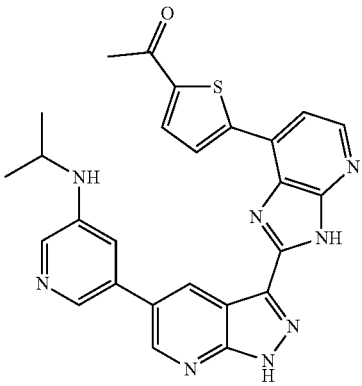 374 |
| 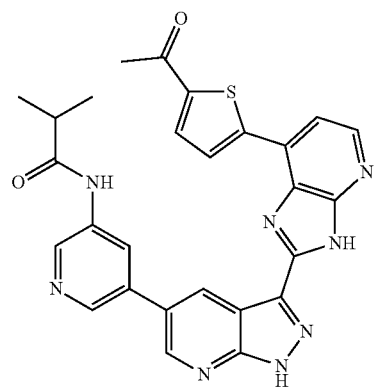 [SMILES: CC(=O)c1ccc(-c2ccnc3[nH]c(-c4n[nH]c5ncc(-c6cncc(NC(=O)C(C)C)c6)cc45)nc23)s1] 371 | 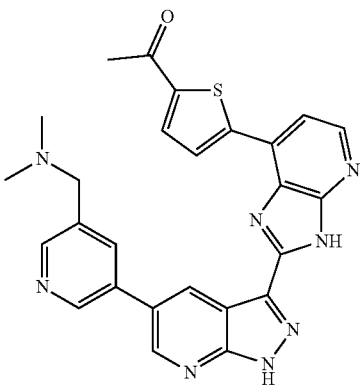 375 |
| 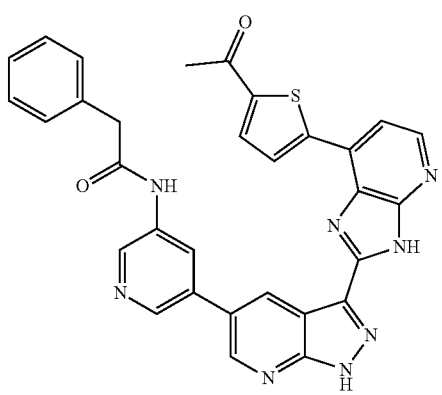 [SMILES: CC(=O)c1ccc(-c2ccnc3[nH]c(-c4n[nH]c5ncc(-c6cncc(NC(=O)Cc7ccccc7)c6)cc45)nc23)s1] 372 | 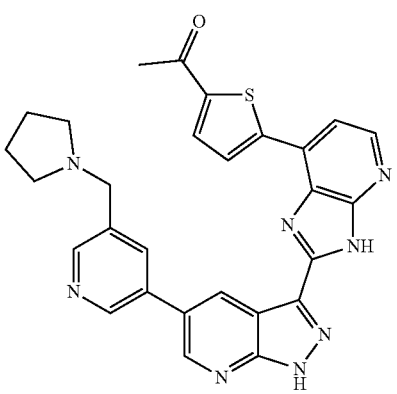 376 |
| 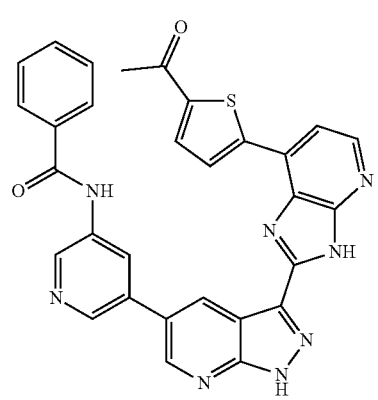 [SMILES: CC(=O)c1ccc(-c2ccnc3[nH]c(-c4n[nH]c5ncc(-c6cncc(NC(=O)c7ccccc7)c6)cc45)nc23)s1] 373 | 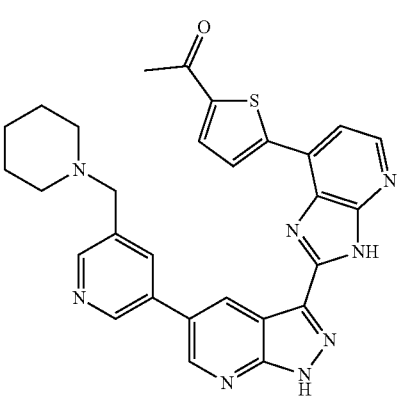 [SMILES: CC(=O)c1ccc(-c2ccnc3[nH]c(-c4n[nH]c5ncc(-c6cncc(CN7CCCCC7)c6)cc45)nc23)s1] 377 |

TABLE 1-continued
| | |
|---|---|
| 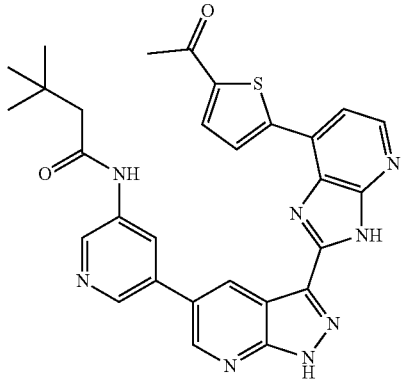 [SMILES: CC(=O)c1ccc(-c2ccnc3[nH]c(-c4n[nH]c5ncc(-c6cncc(NC(=O)CC(C)(C)C)c6)cc45)nc23)s1] | 378 |
| 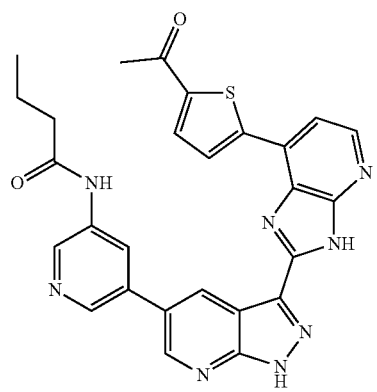 [SMILES: CCCC(=O)Nc1cncc(-c2cnc3[nH]nc(-c4nc5c(-c6ccc(C(C)=O)s6)ccnc5[nH]4)c3c2)c1] | 379 |
| 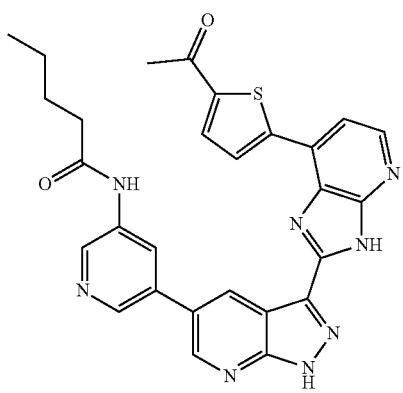 [SMILES: CCCCC(=O)Nc1cncc(-c2cnc3[nH]nc(-c4nc5c(-c6ccc(C(C)=O)s6)ccnc5[nH]4)c3c2)c1] | 380 |
| 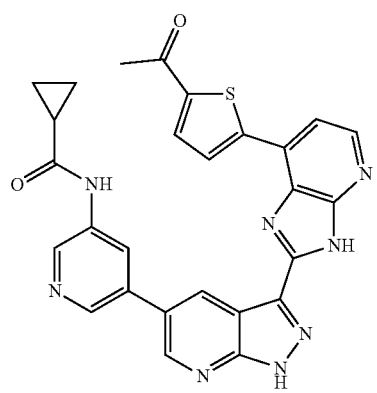 [SMILES: CC(=O)c1ccc(-c2ccnc3[nH]c(-c4n[nH]c5ncc(-c6cncc(NC(=O)C7CC7)c6)cc45)nc23)s1] | 381 |
| 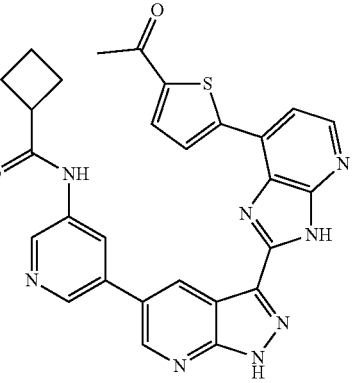 | 382 |
| 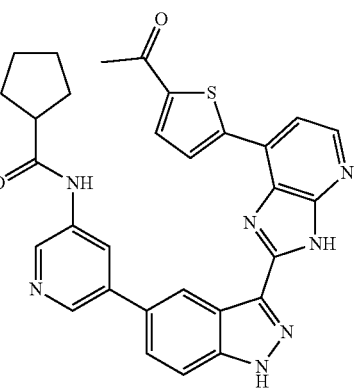 | 383 |
| 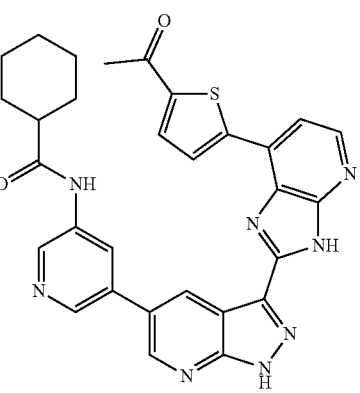 | 384 |
| 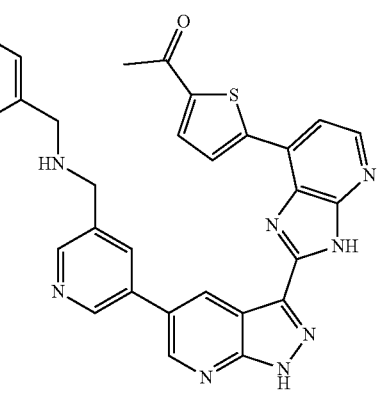 | 385 |

TABLE 1-continued
| | |
|---|---|
| 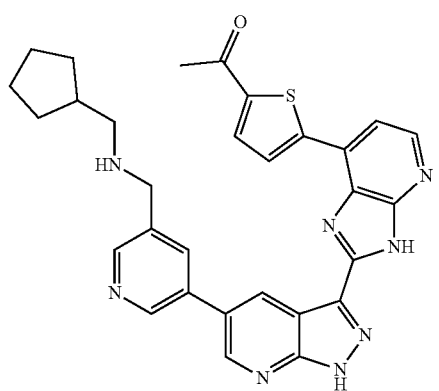 [SMILES: CC(=O)c1ccc(-c2ccnc3[nH]c(-c4n[nH]c5ncc(-c6cncc(CNCC7CCCC7)c6)cc45)nc23)s1] 386 | 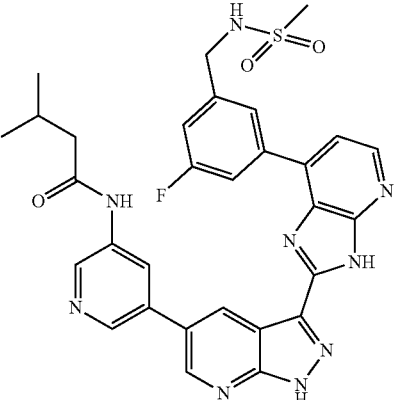 390 |
| 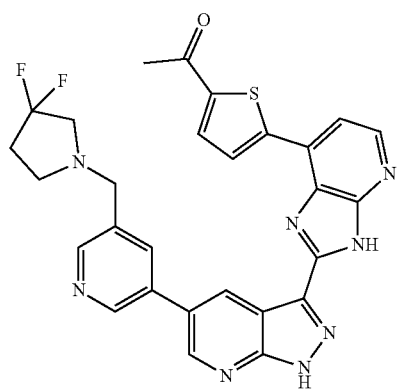 [SMILES: CC(=O)c1ccc(-c2ccnc3[nH]c(-c4n[nH]c5ncc(-c6cncc(CN7CCC(F)(F)C7)c6)cc45)nc23)s1] 387 | 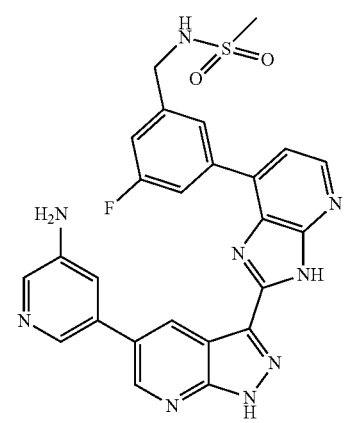 391 |
| 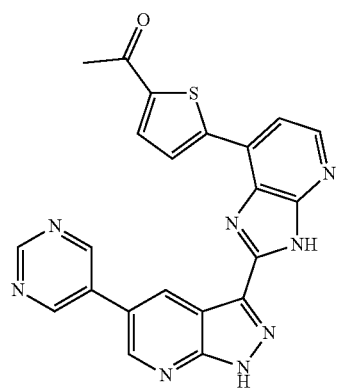 [SMILES: CC(=O)c1ccc(-c2ccnc3[nH]c(-c4n[nH]c5ncc(-c6cncnc6)cc45)nc23)s1] 388 | 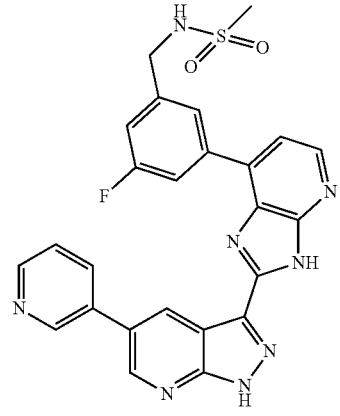 392 |
| 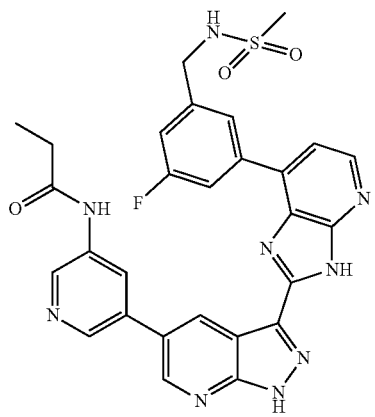 [SMILES: CCC(=O)Nc1cncc(-c2cnc3[nH]nc(-c4nc5c(-c6cc(F)cc(CNS(C)(=O)=O)c6)ccnc5[nH]4)c3c2)c1] 389 | 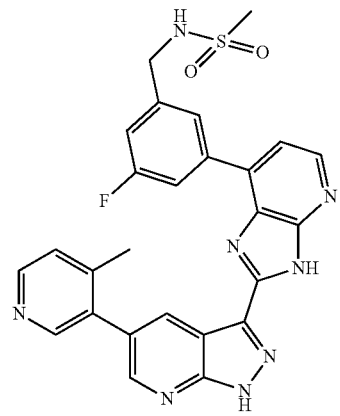 [SMILES: Cc1ccncc1-c1cnc2[nH]nc(-c3nc4c(-c5cc(F)cc(CNS(C)(=O)=O)c5)ccnc4[nH]3)c2c1] 393 |

TABLE 1-continued
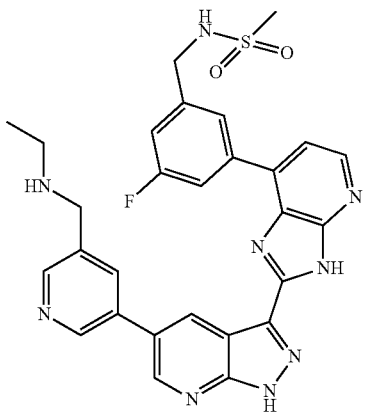 [SMILES: CCNCc1cncc(-c2cnc3[nH]nc(-c4nc5c(-c6cc(F)cc(CNS(C)(=O)=O)c6)ccnc5[nH]4)c3c2)c1]
394
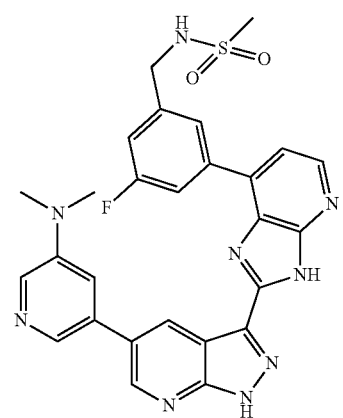 [SMILES: CN(C)c1cncc(-c2cnc3[nH]nc(-c4nc5c(-c6cc(F)cc(CNS(C)(=O)=O)c6)ccnc5[nH]4)c3c2)c1]
395
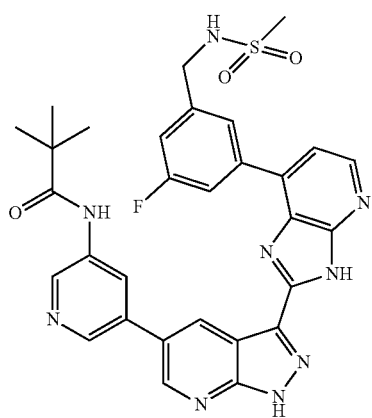 [SMILES: CC(C)(C)C(=O)Nc1cncc(-c2cnc3[nH]nc(-c4nc5c(-c6cc(F)cc(CNS(C)(=O)=O)c6)ccnc5[nH]4)c3c2)c1]
396
TABLE 1-continued
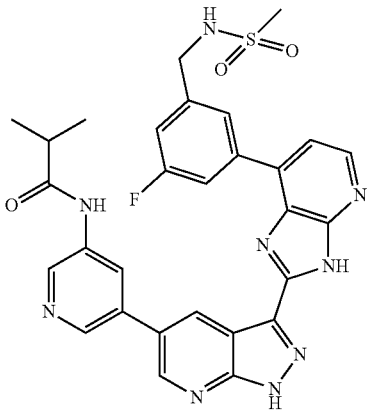 [SMILES: CC(C)C(=O)Nc1cncc(-c2cnc3[nH]nc(-c4nc5c(-c6cc(F)cc(CNS(C)(=O)=O)c6)ccnc5[nH]4)c3c2)c1]
397
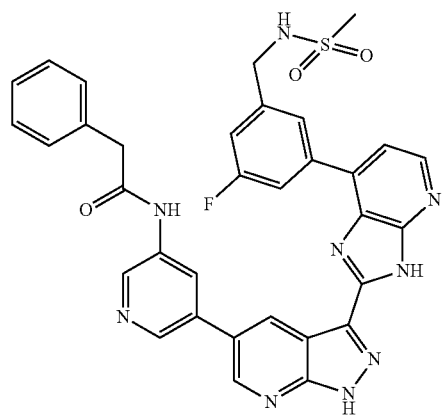 [SMILES: CS(=O)(=O)NCc1cc(F)cc(-c2ccnc3[nH]c(-c4n[nH]c5ncc(-c6cncc(NC(=O)Cc7ccccc7)c6)cc45)nc23)c1]
398
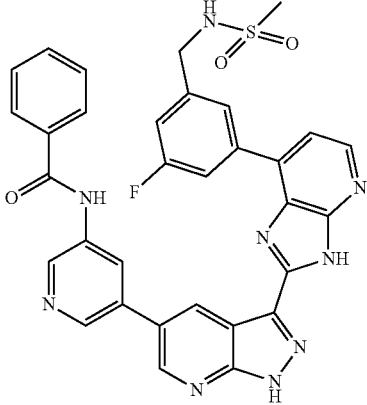 [SMILES: CS(=O)(=O)NCc1cc(F)cc(-c2ccnc3[nH]c(-c4n[nH]c5ncc(-c6cncc(NC(=O)c7ccccc7)c6)cc45)nc23)c1]
399
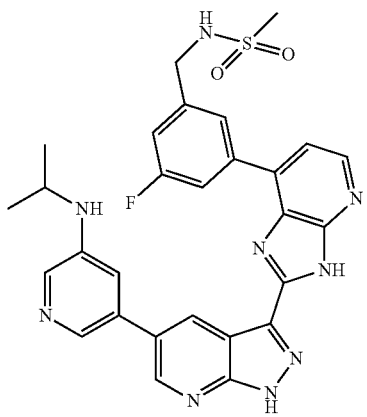 [SMILES: CC(C)Nc1cncc(-c2cnc3[nH]nc(-c4nc5c(-c6cc(F)cc(CNS(C)(=O)=O)c6)ccnc5[nH]4)c3c2)c1]
400

TABLE 1-continued
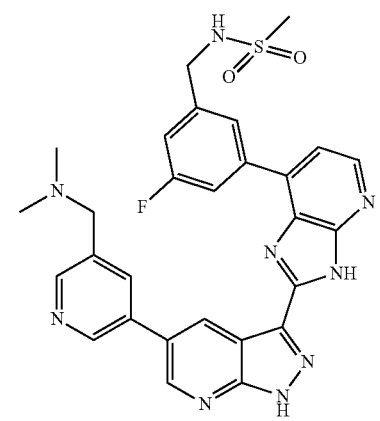 [SMILES: CN(C)Cc1cncc(-c2cnc3[nH]nc(-c4nc5c(-c6cc(F)cc(CNS(C)(=O)=O)c6)ccnc5[nH]4)c3c2)c1] 401
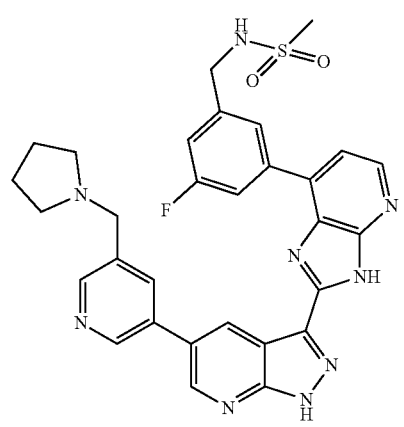 [SMILES: CS(=O)(=O)NCc1cc(F)cc(-c2ccnc3[nH]c(-c4n[nH]c5ncc(-c6cncc(CN7CCCC7)c6)cc45)nc23)c1] 402
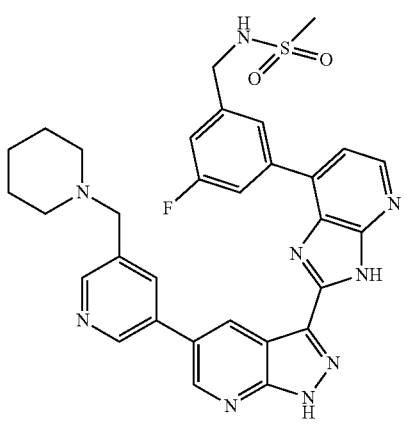 [SMILES: CS(=O)(=O)NCc1cc(F)cc(-c2ccnc3[nH]c(-c4n[nH]c5ncc(-c6cncc(CN7CCCCC7)c6)cc45)nc23)c1] 403
TABLE 1-continued
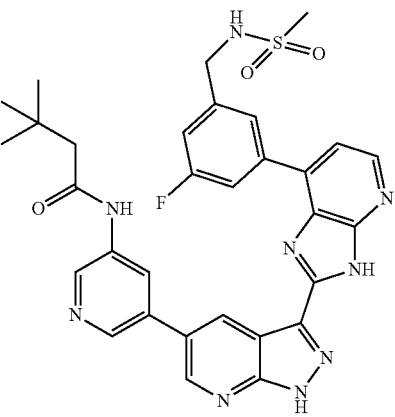 [SMILES: CC(C)(C)CC(=O)Nc1cncc(-c2cnc3[nH]nc(-c4nc5c(-c6cc(F)cc(CNS(C)(=O)=O)c6)ccnc5[nH]4)c3c2)c1] 404
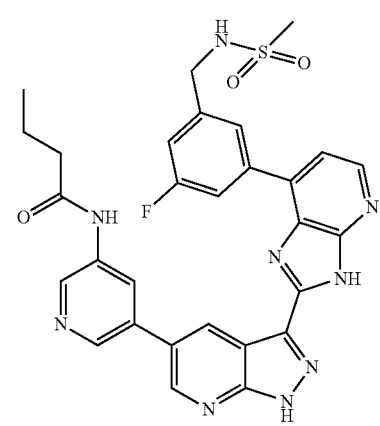 [SMILES: CCCC(=O)Nc1cncc(-c2cnc3[nH]nc(-c4nc5c(-c6cc(F)cc(CNS(C)(=O)=O)c6)ccnc5[nH]4)c3c2)c1] 405
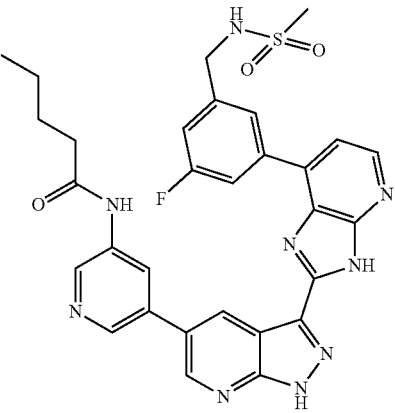 [SMILES: CCCCC(=O)Nc1cncc(-c2cnc3[nH]nc(-c4nc5c(-c6cc(F)cc(CNS(C)(=O)=O)c6)ccnc5[nH]4)c3c2)c1] 406
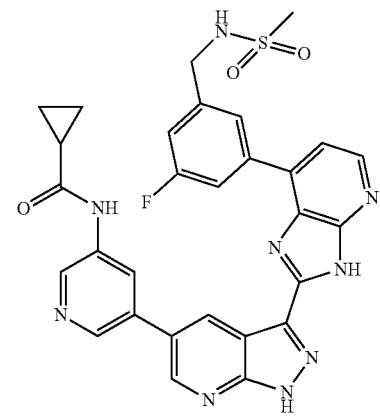 [SMILES: CS(=O)(=O)NCc1cc(F)cc(-c2ccnc3[nH]c(-c4n[nH]c5ncc(-c6cncc(NC(=O)C7CC7)c6)cc45)nc23)c1] 407

TABLE 1-continued
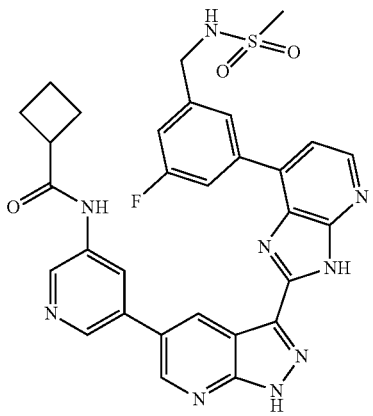 [SMILES: CS(=O)(=O)NCc1cc(F)cc(-c2ccnc3[nH]c(-c4n[nH]c5ncc(-c6cncc(NC(=O)C7CCC7)c6)cc45)nc23)c1]
408
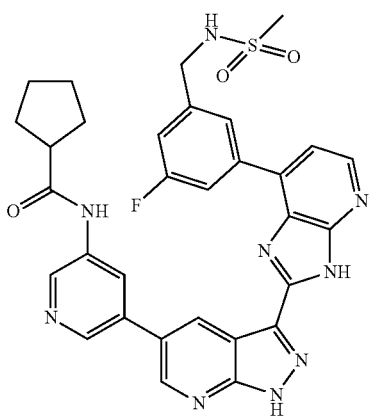 [SMILES: CS(=O)(=O)NCc1cc(F)cc(-c2ccnc3[nH]c(-c4n[nH]c5ncc(-c6cncc(NC(=O)C7CCCC7)c6)cc45)nc23)c1]
409
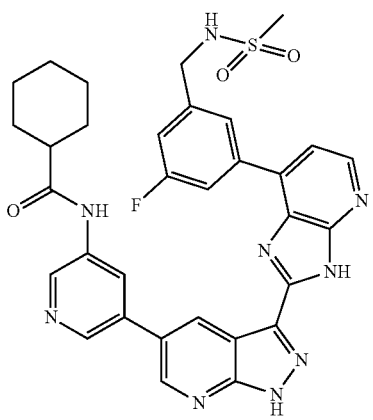 [SMILES: CS(=O)(=O)NCc1cc(F)cc(-c2ccnc3[nH]c(-c4n[nH]c5ncc(-c6cncc(NC(=O)C7CCCCC7)c6)cc45)nc23)c1]
410
TABLE 1-continued
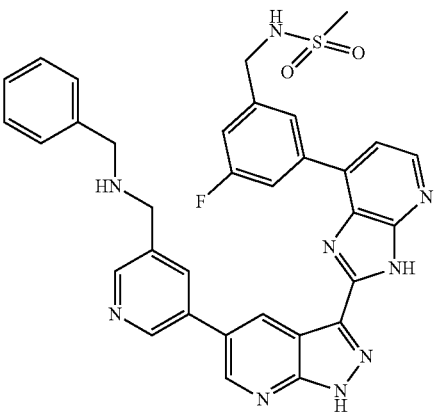 [SMILES: CS(=O)(=O)NCc1cc(F)cc(-c2ccnc3[nH]c(-c4n[nH]c5ncc(-c6cncc(CNCc7ccccc7)c6)cc45)nc23)c1]
411
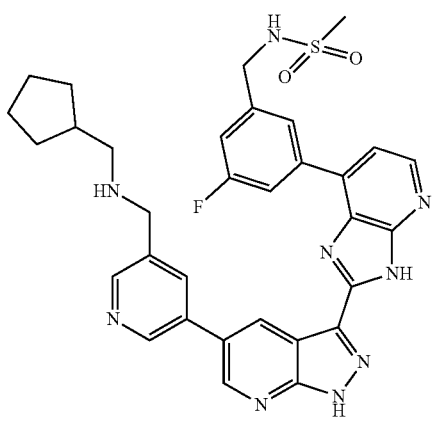 [SMILES: CS(=O)(=O)NCc1cc(F)cc(-c2ccnc3[nH]c(-c4n[nH]c5ncc(-c6cncc(CNCC7CCCC7)c6)cc45)nc23)c1]
412
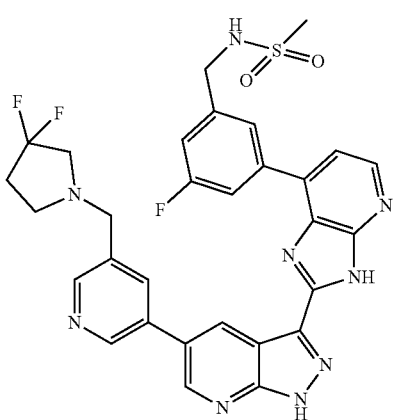 [SMILES: CS(=O)(=O)NCc1cc(F)cc(-c2ccnc3[nH]c(-c4n[nH]c5ncc(-c6cncc(CN7CCC(F)(F)C7)c6)cc45)nc23)c1]
413
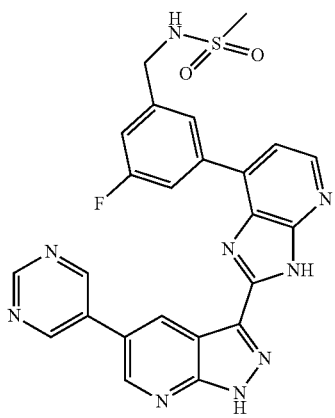
414

TABLE 1-continued
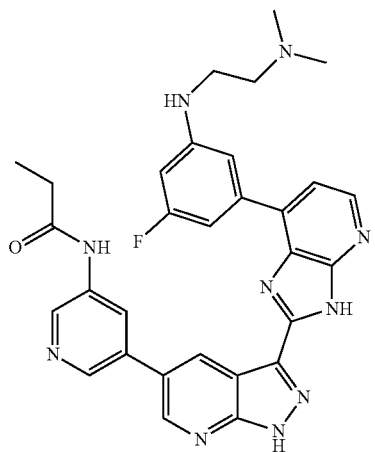 [SMILES: CCC(=O)Nc1cncc(-c2cnc3[nH]nc(-c4nc5c(-c6cc(F)cc(NCCN(C)C)c6)ccnc5[nH]4)c3c2)c1]
415
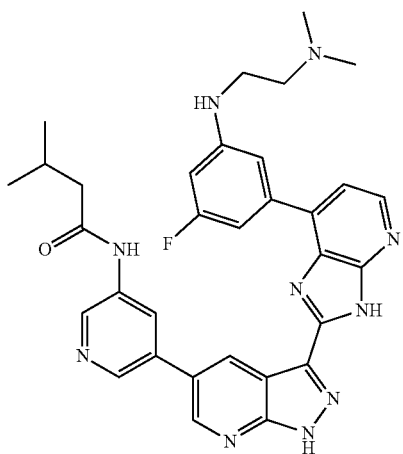
416
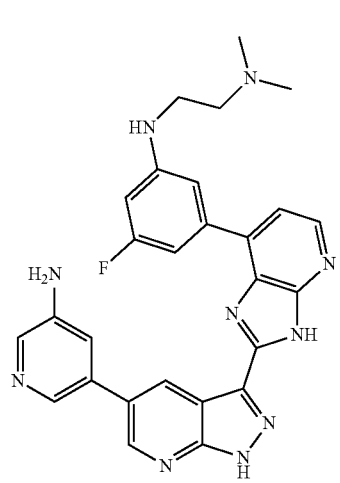 [SMILES: CN(C)CCNc1cc(F)cc(-c2ccnc3[nH]c(-c4n[nH]c5ncc(-c6cncc(N)c6)cc45)nc23)c1]
417
TABLE 1-continued
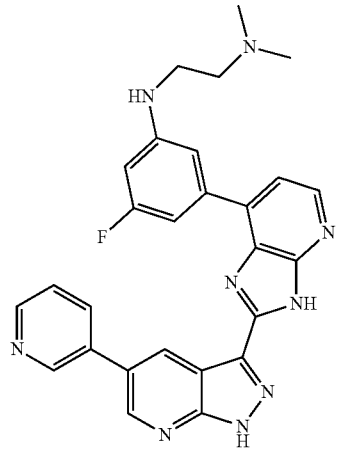 [SMILES: CN(C)CCNc1cc(F)cc(-c2ccnc3[nH]c(-c4n[nH]c5ncc(-c6cccnc6)cc45)nc23)c1]
418
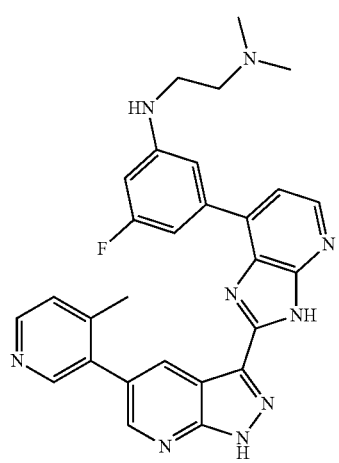 [SMILES: Cc1ccncc1-c1cnc2[nH]nc(-c3nc4c(-c5cc(F)cc(NCCN(C)C)c5)ccnc4[nH]3)c2c1]
419
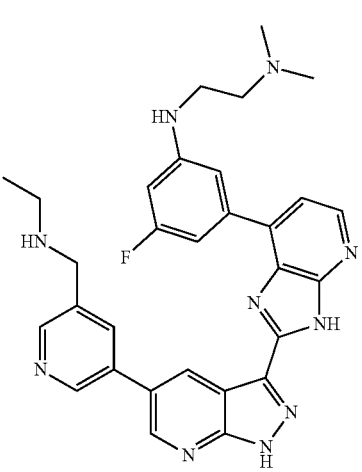 [SMILES: CCNCc1cncc(-c2cnc3[nH]nc(-c4nc5c(-c6cc(F)cc(NCCN(C)C)c6)ccnc5[nH]4)c3c2)c1]
420

TABLE 1-continued
421
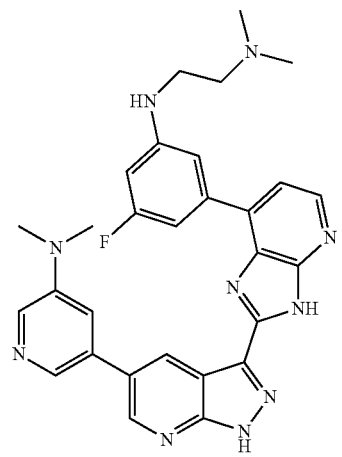 [SMILES: CN(C)CCNc1cc(F)cc(-c2ccnc3[nH]c(-c4n[nH]c5ncc(-c6cncc(N(C)C)c6)cc45)nc23)c1]
422
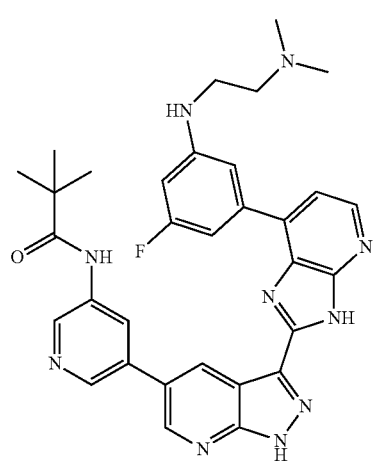 [SMILES: CN(C)CCNc1cc(F)cc(-c2ccnc3[nH]c(-c4n[nH]c5ncc(-c6cncc(NC(=O)C(C)(C)C)c6)cc45)nc23)c1]
423
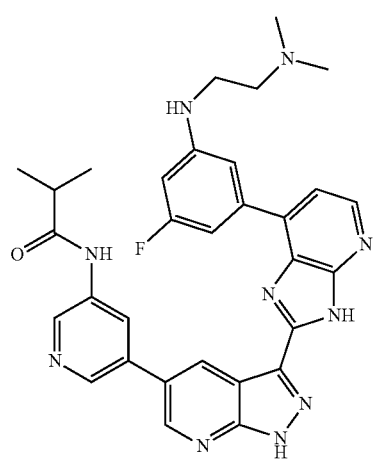 [SMILES: CC(C)C(=O)Nc1cncc(-c2cnc3[nH]nc(-c4nc5c(-c6cc(F)cc(NCCN(C)C)c6)ccnc5[nH]4)c3c2)c1]
TABLE 1-continued
424
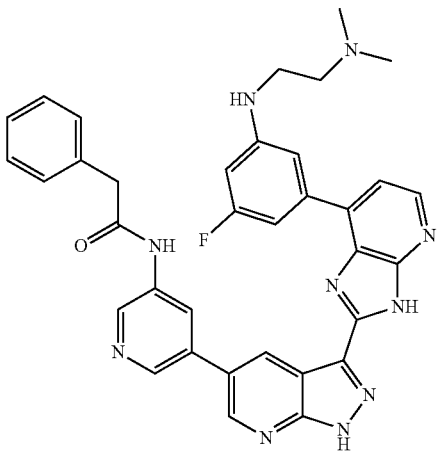 [SMILES: CN(C)CCNc1cc(F)cc(-c2ccnc3[nH]c(-c4n[nH]c5ncc(-c6cncc(NC(=O)Cc7ccccc7)c6)cc45)nc23)c1]
425
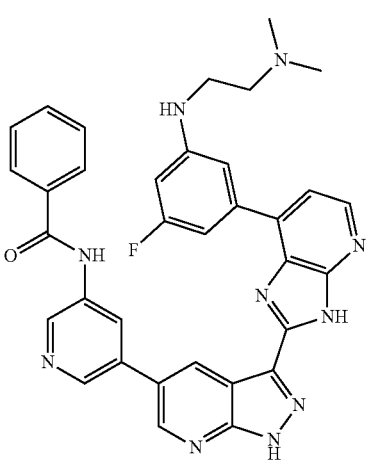 [SMILES: CN(C)CCNc1cc(F)cc(-c2ccnc3[nH]c(-c4n[nH]c5ncc(-c6cncc(NC(=O)c7ccccc7)c6)cc45)nc23)c1]
426
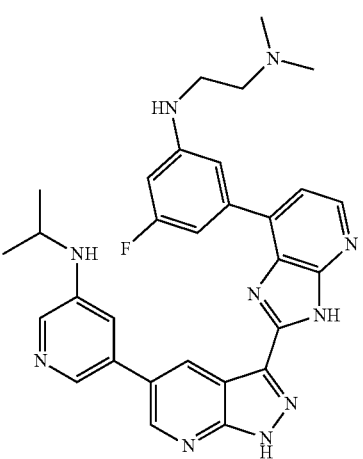 [SMILES: CC(C)Nc1cncc(-c2cnc3[nH]nc(-c4nc5c(-c6cc(F)cc(NCCN(C)C)c6)ccnc5[nH]4)c3c2)c1]

TABLE 1-continued
427
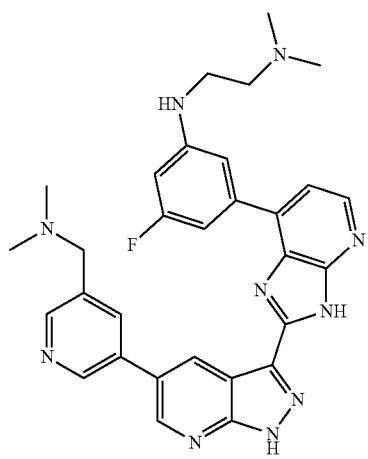 [SMILES: CN(C)CCNc1cc(F)cc(-c2ccnc3[nH]c(-c4n[nH]c5ncc(-c6cncc(CN(C)C)c6)cc45)nc23)c1]
428
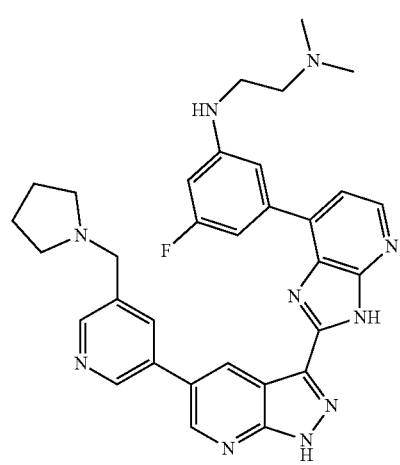 [SMILES: CN(C)CCNc1cc(F)cc(-c2ccnc3[nH]c(-c4n[nH]c5ncc(-c6cncc(CN7CCCC7)c6)cc45)nc23)c1]
429
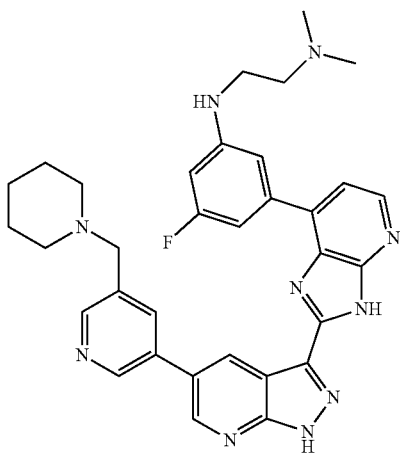 [SMILES: CN(C)CCNc1cc(F)cc(-c2ccnc3[nH]c(-c4n[nH]c5ncc(-c6cncc(CN7CCCCC7)c6)cc45)nc23)c1]
TABLE 1-continued
430
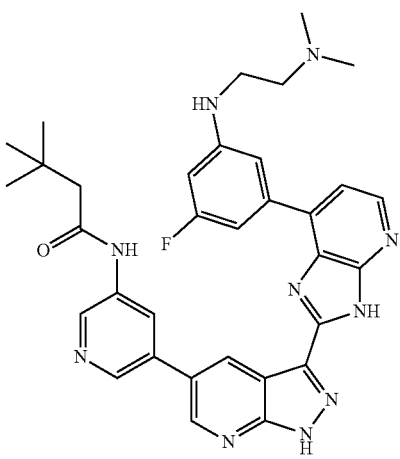 [SMILES: CN(C)CCNc1cc(F)cc(-c2ccnc3[nH]c(-c4n[nH]c5ncc(-c6cncc(NC(=O)CC(C)(C)C)c6)cc45)nc23)c1]
431
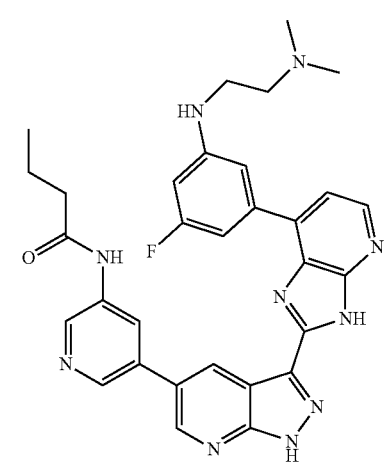 [SMILES: CCCC(=O)Nc1cncc(-c2cnc3[nH]nc(-c4nc5c(-c6cc(F)cc(NCCN(C)C)c6)ccnc5[nH]4)c3c2)c1]
432
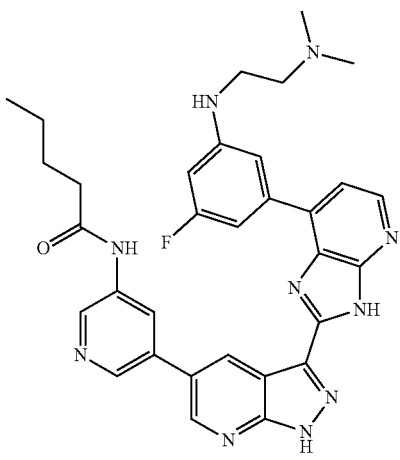 [SMILES: CCCCC(=O)Nc1cncc(-c2cnc3[nH]nc(-c4nc5c(-c6cc(F)cc(NCCN(C)C)c6)ccnc5[nH]4)c3c2)c1]

TABLE 1-continued
| | |
|---|---|
| 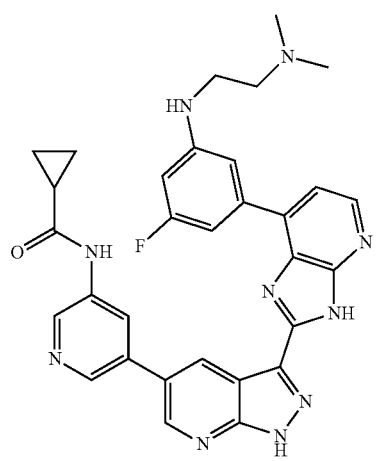 [SMILES: CN(C)CCNc1cc(F)cc(-c2ccnc3[nH]c(-c4n[nH]c5ncc(-c6cncc(NC(=O)C7CC7)c6)cc45)nc23)c1] | 433 |
| 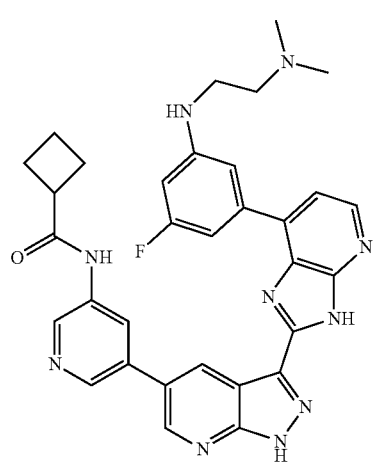 [SMILES: CN(C)CCNc1cc(F)cc(-c2ccnc3[nH]c(-c4n[nH]c5ncc(-c6cncc(NC(=O)C7CCC7)c6)cc45)nc23)c1] | 434 |
| 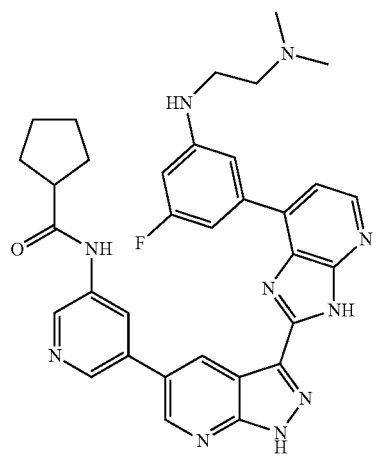 [SMILES: CN(C)CCNc1cc(F)cc(-c2ccnc3[nH]c(-c4n[nH]c5ncc(-c6cncc(NC(=O)C7CCCC7)c6)cc45)nc23)c1] | 435 |
TABLE 1-continued
| | |
|---|---|
| 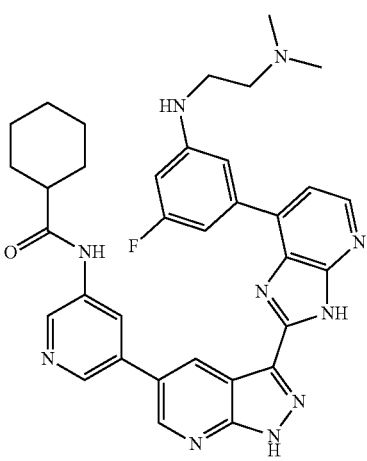 [SMILES: CN(C)CCNc1cc(F)cc(-c2ccnc3[nH]c(-c4n[nH]c5ncc(-c6cncc(NC(=O)C7CCCCC7)c6)cc45)nc23)c1] | 436 |
| 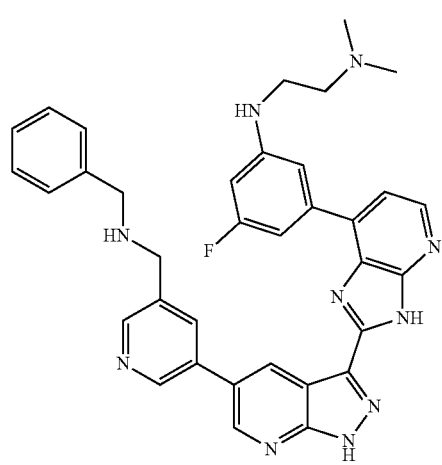 [SMILES: CN(C)CCNc1cc(F)cc(-c2ccnc3[nH]c(-c4n[nH]c5ncc(-c6cncc(CNCc7ccccc7)c6)cc45)nc23)c1] | 437 |
| 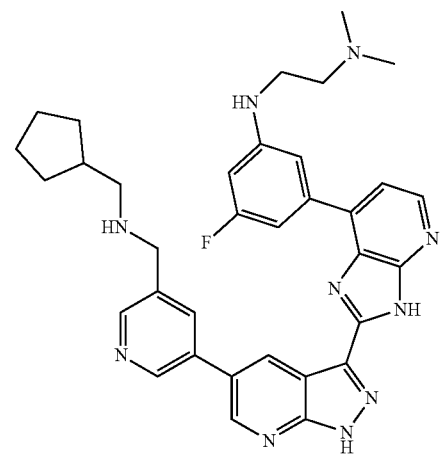 [SMILES: CN(C)CCNc1cc(F)cc(-c2ccnc3[nH]c(-c4n[nH]c5ncc(-c6cncc(CNCC7CCCC7)c6)cc45)nc23)c1] | 438 |

TABLE 1-continued
| | |
|---|---|
| 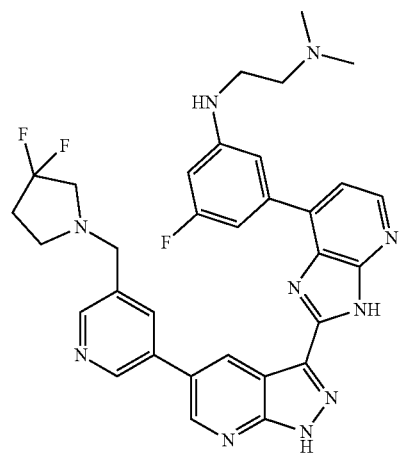 | 439 |
| 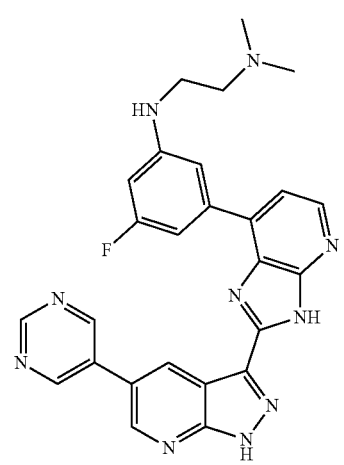 [SMILES: CN(C)CCNc1cc(F)cc(-c2ccnc3[nH]c(-c4n[nH]c5ncc(-c6cncnc6)cc45)nc23)c1] | 440 |
| 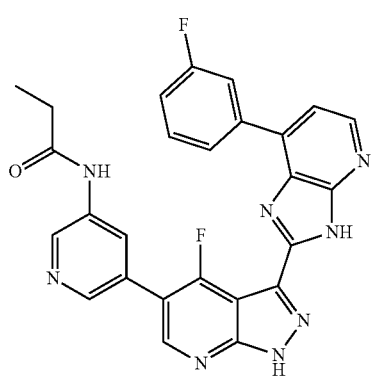 [SMILES: CCC(=O)Nc1cncc(-c2cnc3[nH]nc(-c4nc5c(-c6cccc(F)c6)ccnc5[nH]4)c3c2F)c1] | 441 |
| 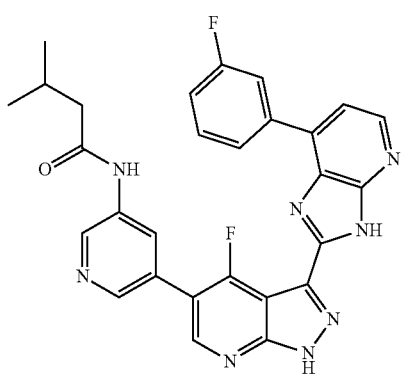 [SMILES: CC(C)CC(=O)Nc1cncc(-c2cnc3[nH]nc(-c4nc5c(-c6cccc(F)c6)ccnc5[nH]4)c3c2F)c1] | 442 |
| 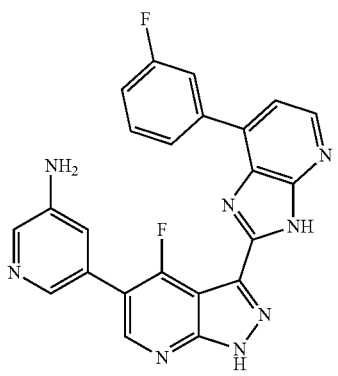 [SMILES: Nc1cncc(-c2cnc3[nH]nc(-c4nc5c(-c6cccc(F)c6)ccnc5[nH]4)c3c2F)c1] | 443 |
| 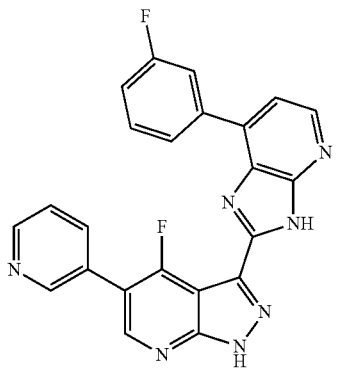 [SMILES: Fc1cccc(-c2ccnc3[nH]c(-c4n[nH]c5ncc(-c6cccnc6)c(F)c45)nc23)c1] | 444 |
| 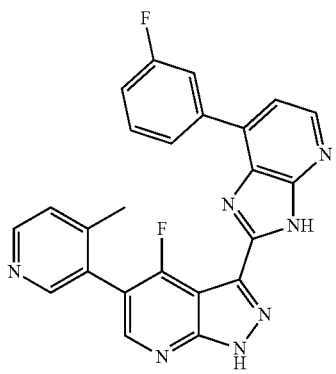 [SMILES: Cc1ccncc1-c1cnc2[nH]nc(-c3nc4c(-c5cccc(F)c5)ccnc4[nH]3)c2c1F] | 445 |
| 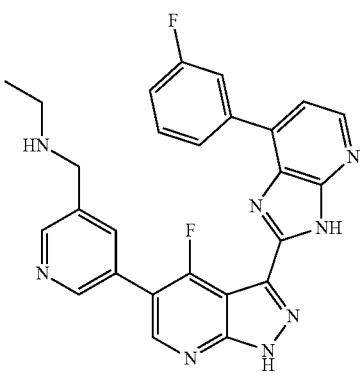 [SMILES: CCNCc1cncc(-c2cnc3[nH]nc(-c4nc5c(-c6cccc(F)c6)ccnc5[nH]4)c3c2F)c1] | 446 |

TABLE 1-continued
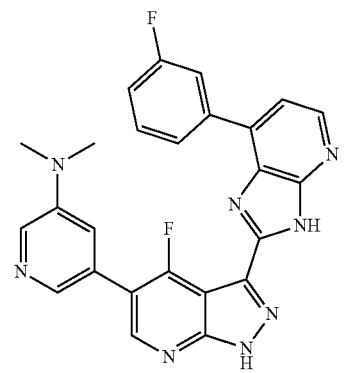 447
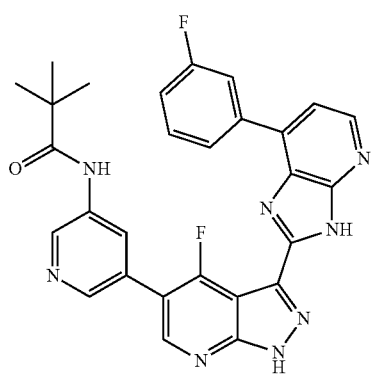 [SMILES: CC(C)(C)C(=O)Nc1cncc(-c2cnc3[nH]nc(-c4nc5c(-c6cccc(F)c6)ccnc5[nH]4)c3c2F)c1] 448
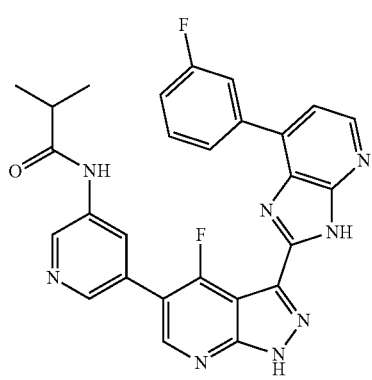 [SMILES: CC(C)C(=O)Nc1cncc(-c2cnc3[nH]nc(-c4nc5c(-c6cccc(F)c6)ccnc5[nH]4)c3c2F)c1] 449
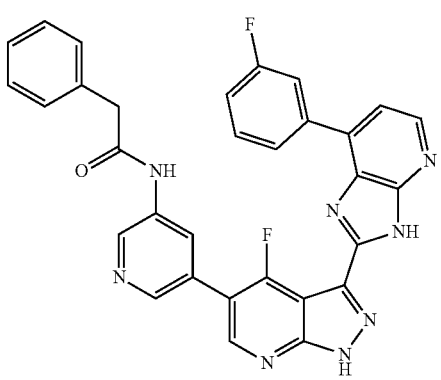 [SMILES: O=C(Cc1ccccc1)Nc1cncc(-c2cnc3[nH]nc(-c4nc5c(-c6cccc(F)c6)ccnc5[nH]4)c3c2F)c1] 450
TABLE 1-continued
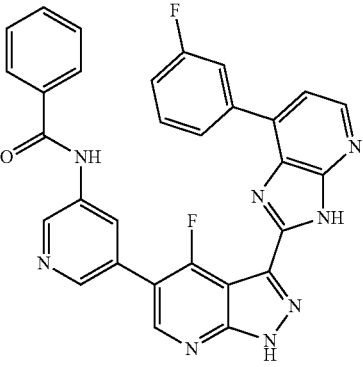 [SMILES: O=C(Nc1cncc(-c2cnc3[nH]nc(-c4nc5c(-c6cccc(F)c6)ccnc5[nH]4)c3c2F)c1)c1ccccc1] 451
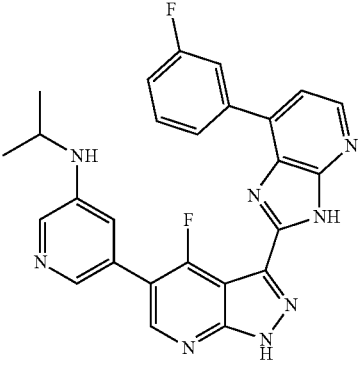 [SMILES: CC(C)Nc1cncc(-c2cnc3[nH]nc(-c4nc5c(-c6cccc(F)c6)ccnc5[nH]4)c3c2F)c1] 452
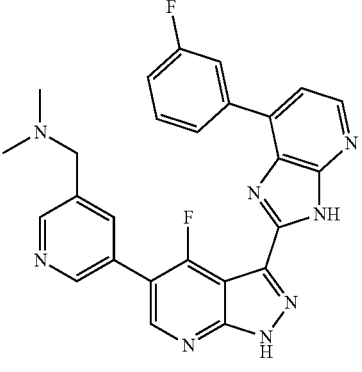 [SMILES: CN(C)Cc1cncc(-c2cnc3[nH]nc(-c4nc5c(-c6cccc(F)c6)ccnc5[nH]4)c3c2F)c1] 453
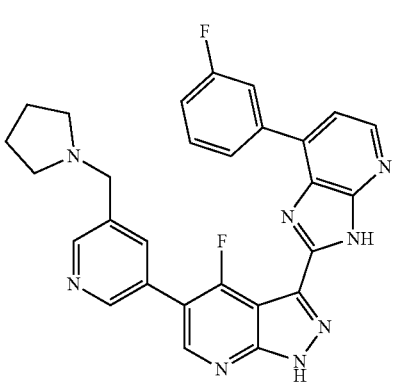 [SMILES: Fc1cccc(-c2ccnc3[nH]c(-c4n[nH]c5ncc(-c6cncc(CN7CCCC7)c6)c(F)c45)nc23)c1] 454

TABLE 1-continued
 455
 456
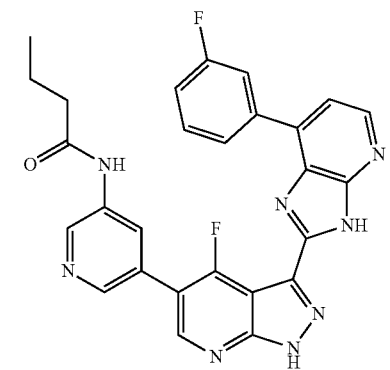 [SMILES: CCCC(=O)Nc1cncc(-c2cnc3[nH]nc(-c4nc5c(-c6cccc(F)c6)ccnc5[nH]4)c3c2F)c1] 457
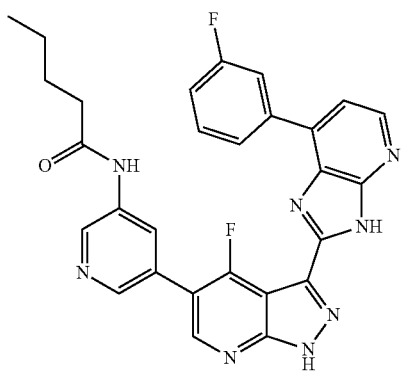 [SMILES: CCCCC(=O)Nc1cncc(-c2cnc3[nH]nc(-c4nc5c(-c6cccc(F)c6)ccnc5[nH]4)c3c2F)c1] 458
TABLE 1-continued
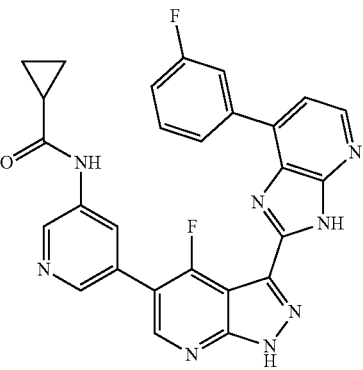 [SMILES: O=C(Nc1cncc(-c2cnc3[nH]nc(-c4nc5c(-c6cccc(F)c6)ccnc5[nH]4)c3c2F)c1)C1CC1] 459
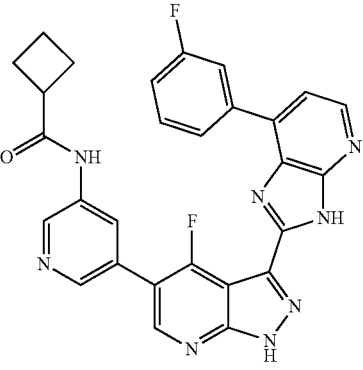 [SMILES: O=C(Nc1cncc(-c2cnc3[nH]nc(-c4nc5c(-c6cccc(F)c6)ccnc5[nH]4)c3c2F)c1)C1CCC1] 460
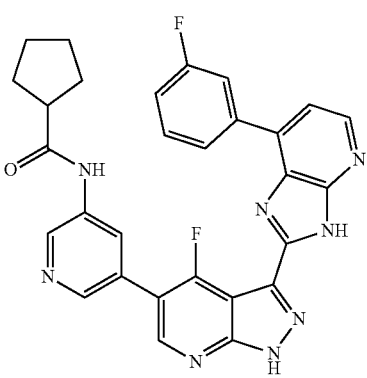 [SMILES: O=C(Nc1cncc(-c2cnc3[nH]nc(-c4nc5c(-c6cccc(F)c6)ccnc5[nH]4)c3c2F)c1)C1CCCC1] 461
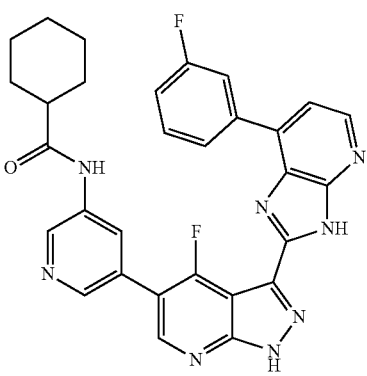 [SMILES: O=C(Nc1cncc(-c2cnc3[nH]nc(-c4nc5c(-c6cccc(F)c6)ccnc5[nH]4)c3c2F)c1)C1CCCCC1] 462

TABLE 1-continued
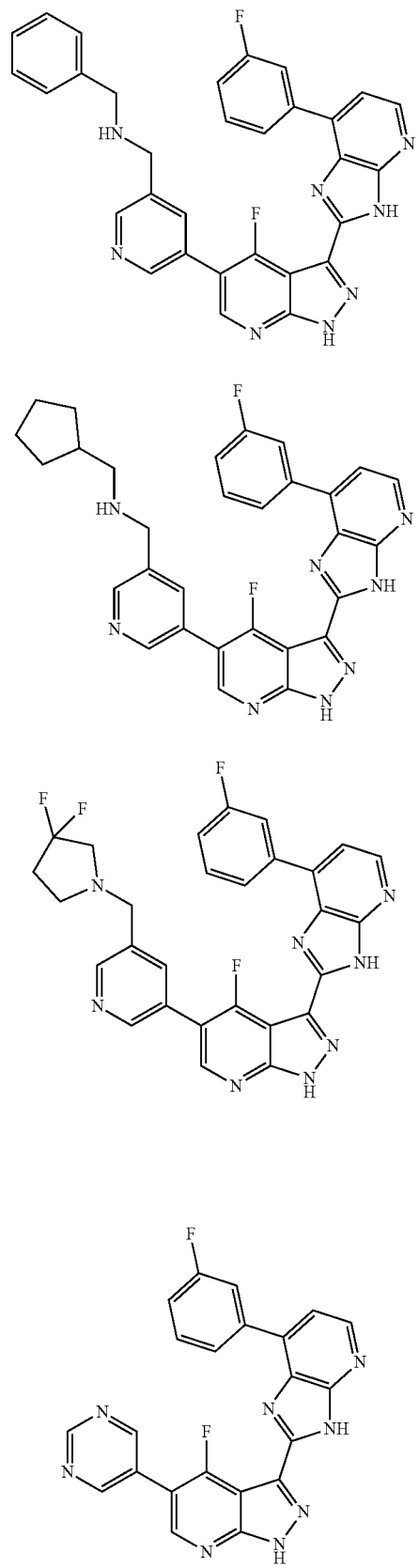
463
464
465
466
TABLE 1-continued
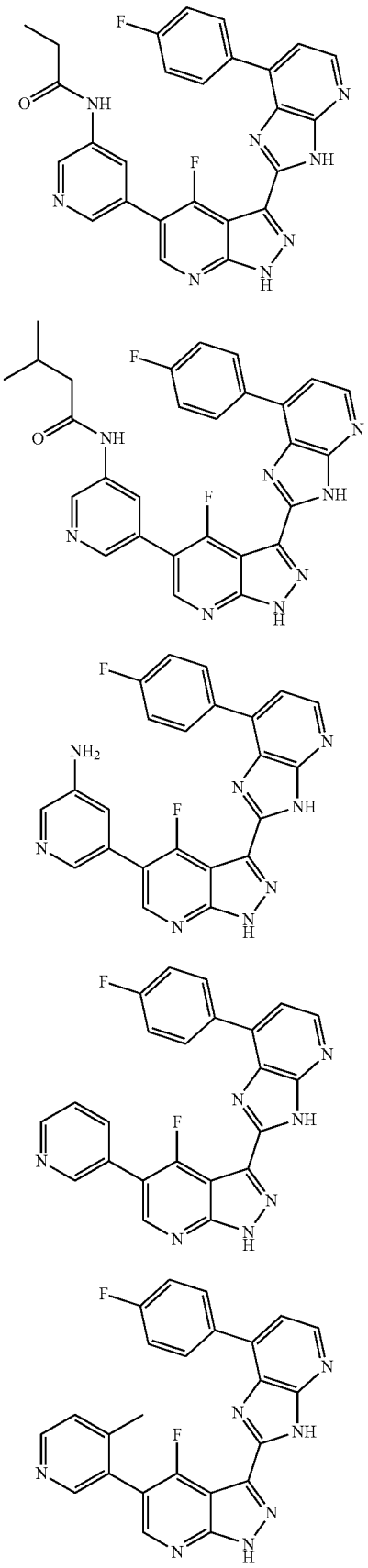
467
468
469
470
471

TABLE 1-continued
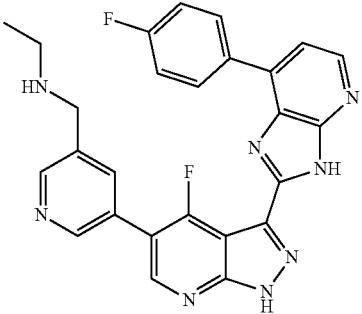 [SMILES: CCNCc1cncc(-c2cnc3[nH]nc(-c4nc5c(-c6ccc(F)cc6)ccnc5[nH]4)c3c2F)c1]
472
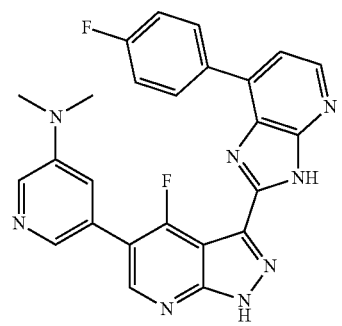 [SMILES: CN(C)c1cncc(-c2cnc3[nH]nc(-c4nc5c(-c6ccc(F)cc6)ccnc5[nH]4)c3c2F)c1]
473
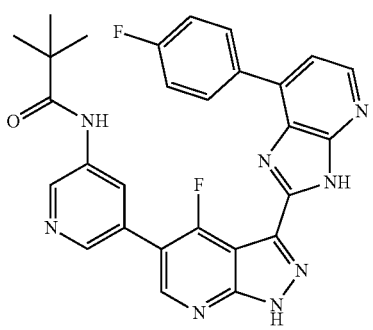 [SMILES: CC(C)(C)C(=O)Nc1cncc(-c2cnc3[nH]nc(-c4nc5c(-c6ccc(F)cc6)ccnc5[nH]4)c3c2F)c1]
474
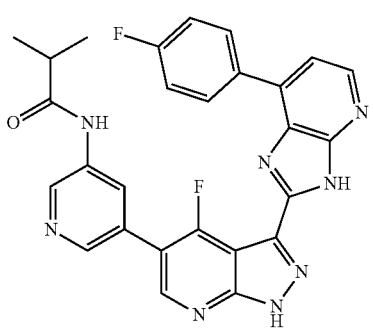 [SMILES: CC(C)C(=O)Nc1cncc(-c2cnc3[nH]nc(-c4nc5c(-c6ccc(F)cc6)ccnc5[nH]4)c3c2F)c1]
475
TABLE 1-continued
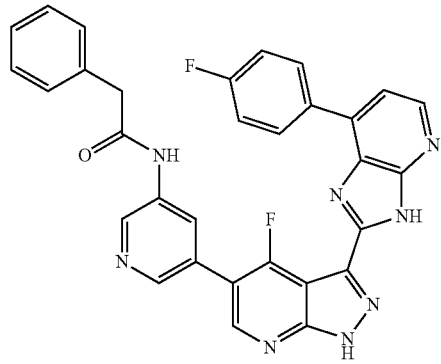 [SMILES: O=C(Cc1ccccc1)Nc1cncc(-c2cnc3[nH]nc(-c4nc5c(-c6ccc(F)cc6)ccnc5[nH]4)c3c2F)c1]
476
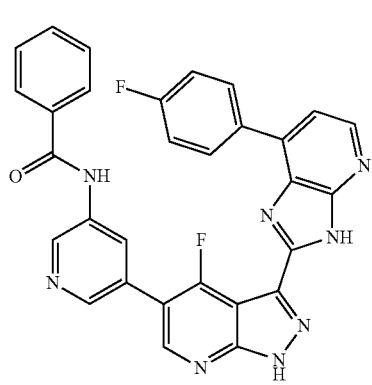 [SMILES: O=C(Nc1cncc(-c2cnc3[nH]nc(-c4nc5c(-c6ccc(F)cc6)ccnc5[nH]4)c3c2F)c1)c1ccccc1]
477
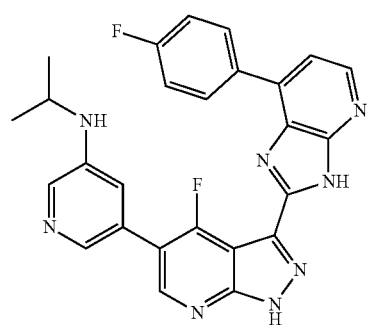 [SMILES: CC(C)Nc1cncc(-c2cnc3[nH]nc(-c4nc5c(-c6ccc(F)cc6)ccnc5[nH]4)c3c2F)c1]
478
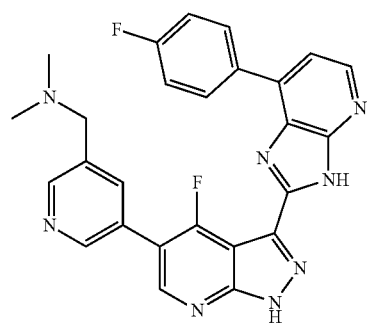 [SMILES: CN(C)Cc1cncc(-c2cnc3[nH]nc(-c4nc5c(-c6ccc(F)cc6)ccnc5[nH]4)c3c2F)c1]
479

TABLE 1-continued
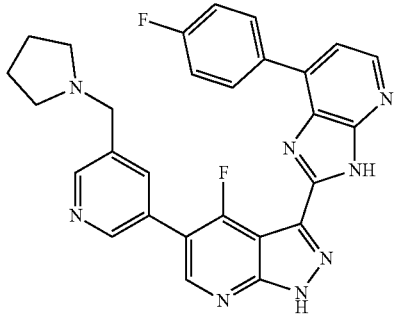 [SMILES: Fc1ccc(-c2ccnc3[nH]c(-c4n[nH]c5ncc(-c6cncc(CN7CCCC7)c6)c(F)c45)nc23)cc1] 480
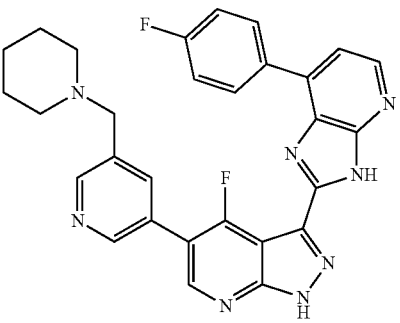 [SMILES: Fc1ccc(-c2ccnc3[nH]c(-c4n[nH]c5ncc(-c6cncc(CN7CCCCC7)c6)c(F)c45)nc23)cc1] 481
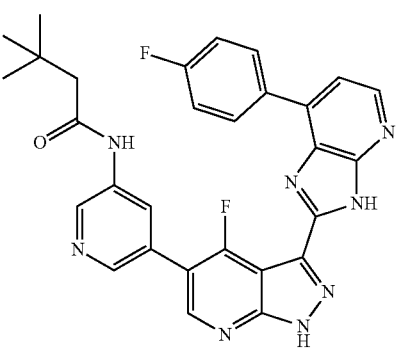 [SMILES: CC(C)(C)CC(=O)Nc1cncc(-c2cnc3[nH]nc(-c4nc5c(-c6ccc(F)cc6)ccnc5[nH]4)c3c2F)c1] 482
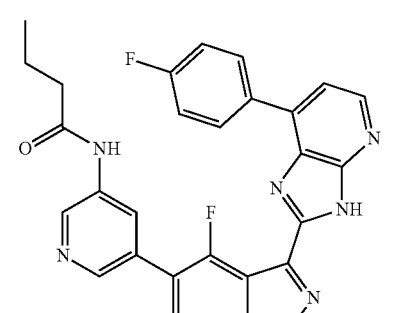 483
TABLE 1-continued
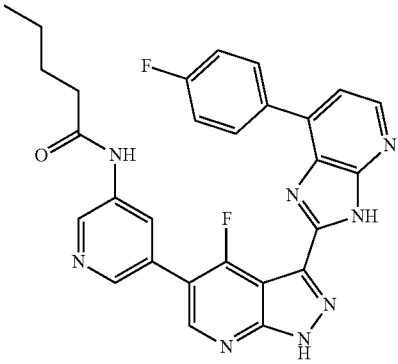 [SMILES: CCCCC(=O)Nc1cncc(-c2cnc3[nH]nc(-c4nc5c(-c6ccc(F)cc6)ccnc5[nH]4)c3c2F)c1] 484
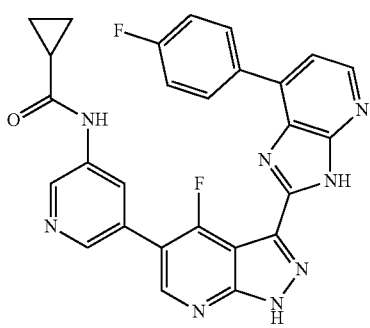 [SMILES: O=C(Nc1cncc(-c2cnc3[nH]nc(-c4nc5c(-c6ccc(F)cc6)ccnc5[nH]4)c3c2F)c1)C1CC1] 485
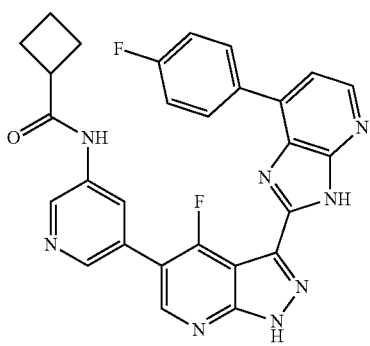 [SMILES: O=C(Nc1cncc(-c2cnc3[nH]nc(-c4nc5c(-c6ccc(F)cc6)ccnc5[nH]4)c3c2F)c1)C1CCC1] 486
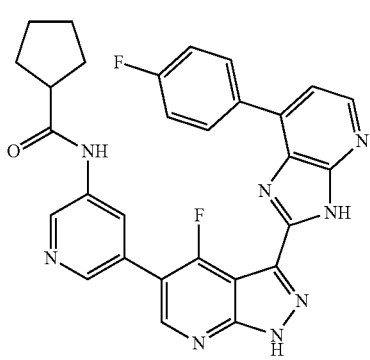 [SMILES: O=C(Nc1cncc(-c2cnc3[nH]nc(-c4nc5c(-c6ccc(F)cc6)ccnc5[nH]4)c3c2F)c1)C1CCCC1] 487

TABLE 1-continued
488 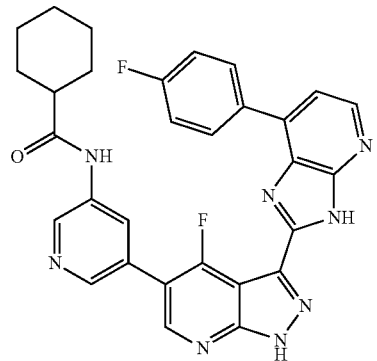 [SMILES: O=C(Nc1cncc(-c2cnc3[nH]nc(-c4nc5c(-c6ccc(F)cc6)ccnc5[nH]4)c3c2F)c1)C1CCCCC1]
489 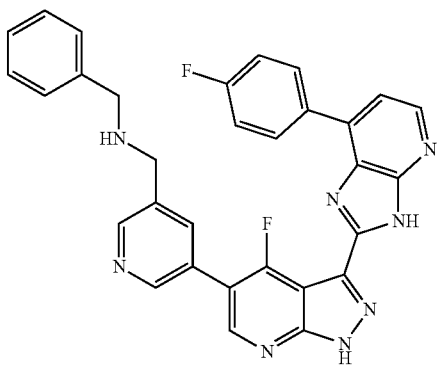 [SMILES: Fc1ccc(-c2ccnc3[nH]c(-c4n[nH]c5ncc(-c6cncc(CNCc7ccccc7)c6)c(F)c45)nc23)cc1]
490 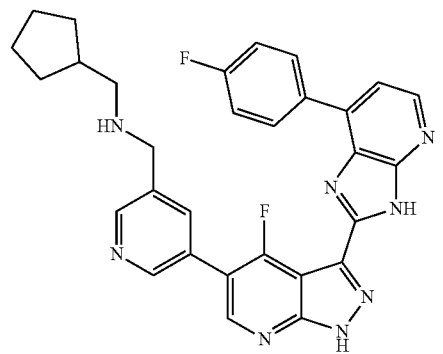 [SMILES: Fc1ccc(-c2ccnc3[nH]c(-c4n[nH]c5ncc(-c6cncc(CNCC7CCCC7)c6)c(F)c45)nc23)cc1]
491 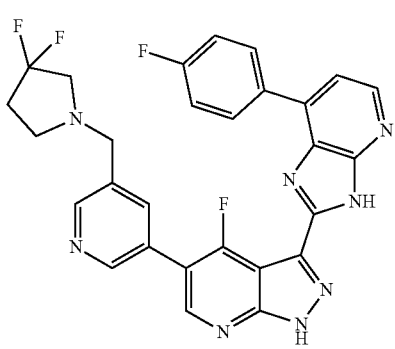 [SMILES: Fc1ccc(-c2ccnc3[nH]c(-c4n[nH]c5ncc(-c6cncc(CN7CCC(F)(F)C7)c6)c(F)c45)nc23)cc1]
492 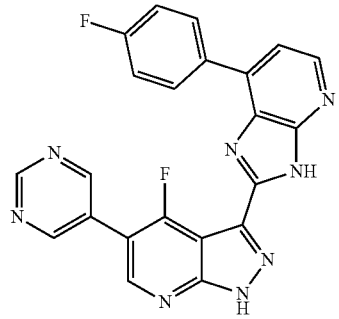 [SMILES: Fc1ccc(-c2ccnc3[nH]c(-c4n[nH]c5ncc(-c6cncnc6)c(F)c45)nc23)cc1]
493 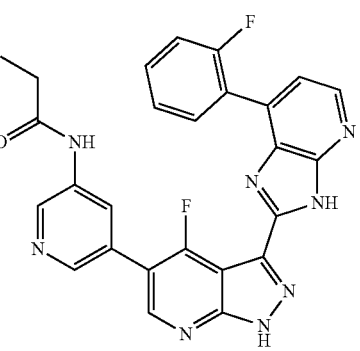
494 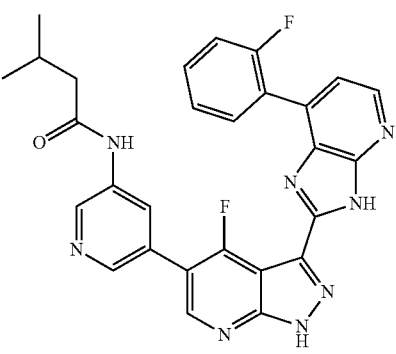 [SMILES: CC(C)CC(=O)Nc1cncc(-c2cnc3[nH]nc(-c4nc5c(-c6ccccc6F)ccnc5[nH]4)c3c2F)c1]
495 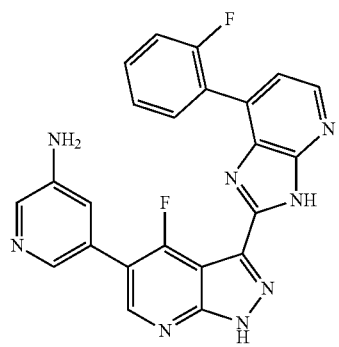 [SMILES: Nc1cncc(-c2cnc3[nH]nc(-c4nc5c(-c6ccccc6F)ccnc5[nH]4)c3c2F)c1]

TABLE 1-continued
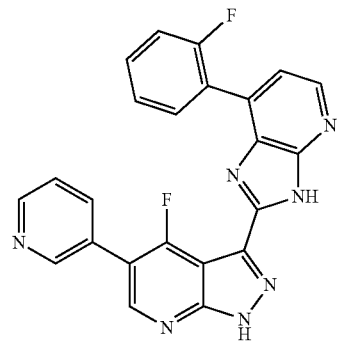 [SMILES: Fc1ccccc1-c1ccnc2[nH]c(-c3n[nH]c4ncc(-c5cccnc5)c(F)c34)nc12] 496
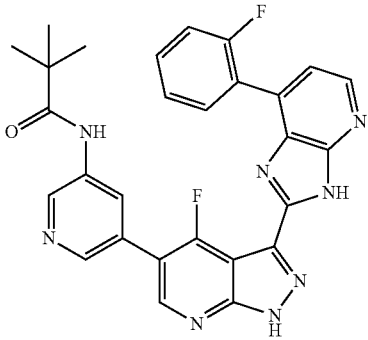 500
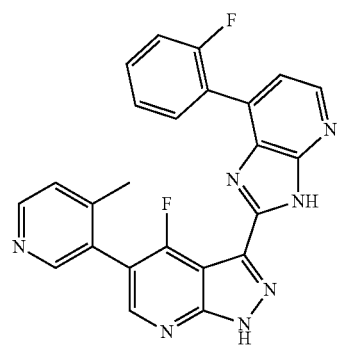 [SMILES: Cc1ccncc1-c1cnc2[nH]nc(-c3nc4c(-c5ccccc5F)ccnc4[nH]3)c2c1F] 497
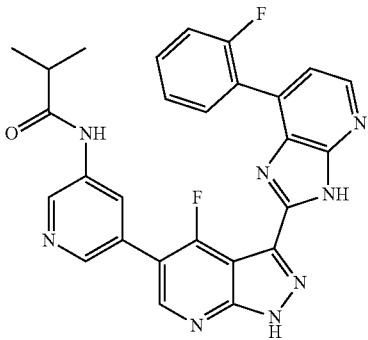 501
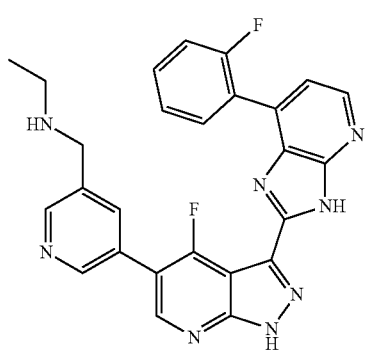 [SMILES: CCNCc1cncc(-c2cnc3[nH]nc(-c4nc5c(-c6ccccc6F)ccnc5[nH]4)c3c2F)c1] 498
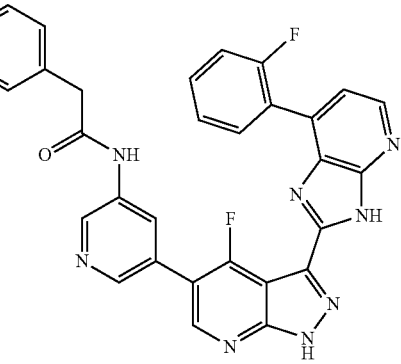 502
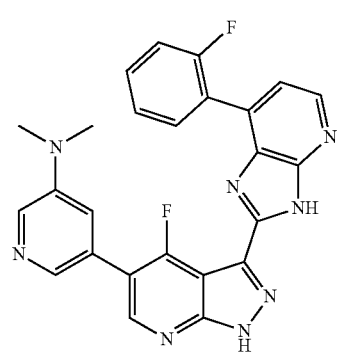 [SMILES: CN(C)c1cncc(-c2cnc3[nH]nc(-c4nc5c(-c6ccccc6F)ccnc5[nH]4)c3c2F)c1] 499
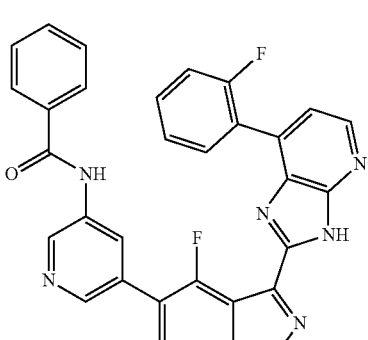 503

TABLE 1-continued
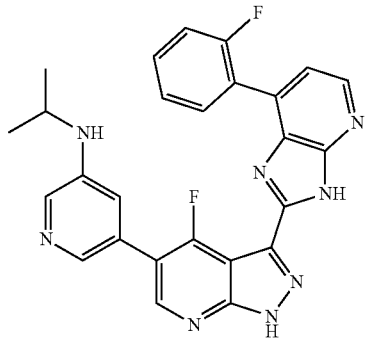 [SMILES: CC(C)Nc1cncc(-c2cnc3[nH]nc(-c4nc5c(-c6ccccc6F)ccnc5[nH]4)c3c2F)c1] 504
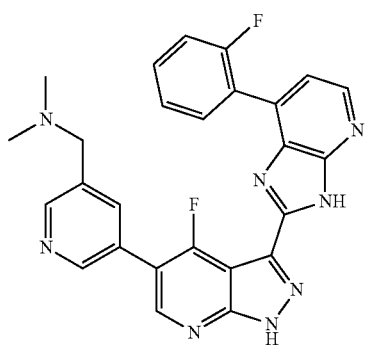 [SMILES: CN(C)Cc1cncc(-c2cnc3[nH]nc(-c4nc5c(-c6ccccc6F)ccnc5[nH]4)c3c2F)c1] 505
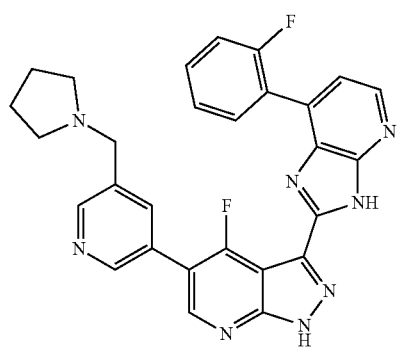 [SMILES: Fc1ccccc1-c1ccnc2[nH]c(-c3n[nH]c4ncc(-c5cncc(CN6CCCC6)c5)c(F)c34)nc12] 506
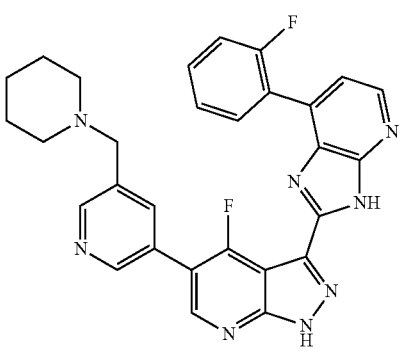 [SMILES: Fc1ccccc1-c1ccnc2[nH]c(-c3n[nH]c4ncc(-c5cncc(CN6CCCCC6)c5)c(F)c34)nc12] 507
TABLE 1-continued
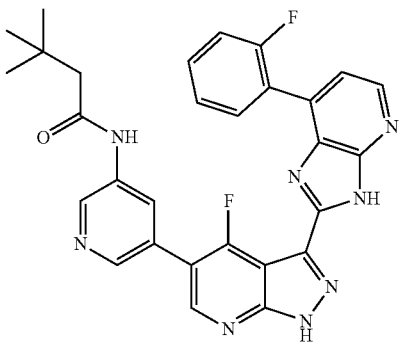 [SMILES: CC(C)(C)CC(=O)Nc1cncc(-c2cnc3[nH]nc(-c4nc5c(-c6ccccc6F)ccnc5[nH]4)c3c2F)c1] 508
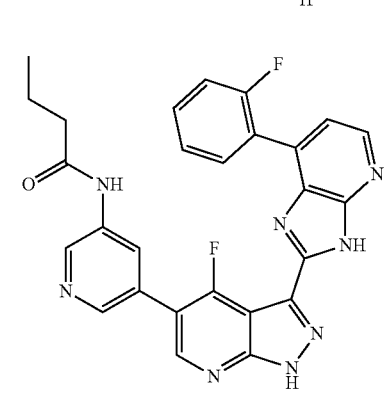 509
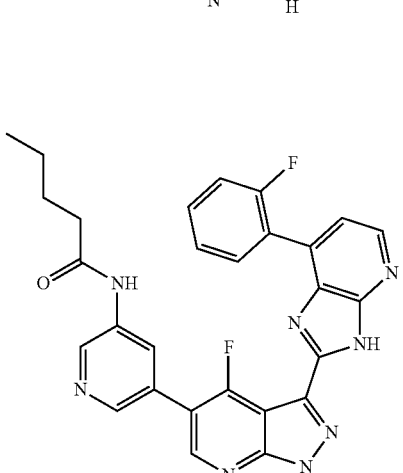 510
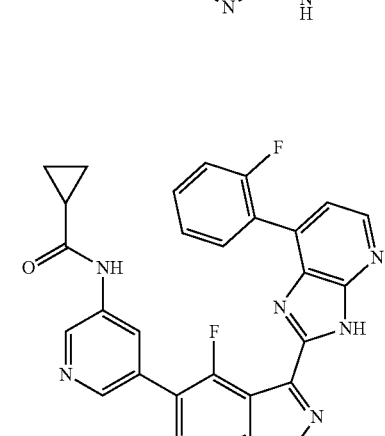 511

TABLE 1-continued
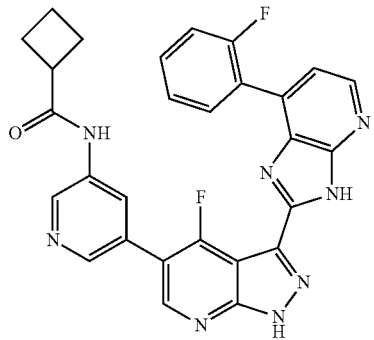 [SMILES: O=C(Nc1cncc(-c2cnc3[nH]nc(-c4nc5c(-c6ccccc6F)ccnc5[nH]4)c3c2F)c1)C1CCC1] 512
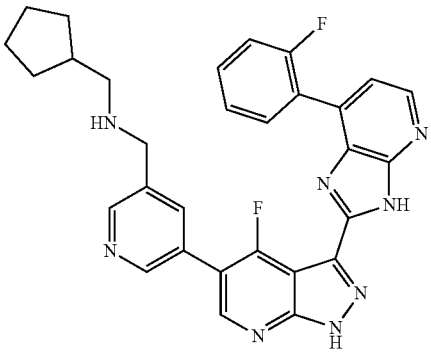
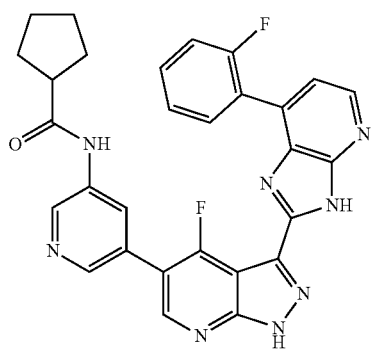 [SMILES: O=C(Nc1cncc(-c2cnc3[nH]nc(-c4nc5c(-c6ccccc6F)ccnc5[nH]4)c3c2F)c1)C1CCCC1] 513
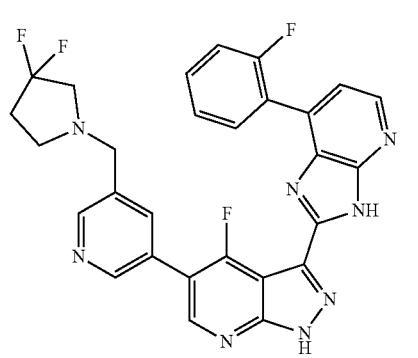 517
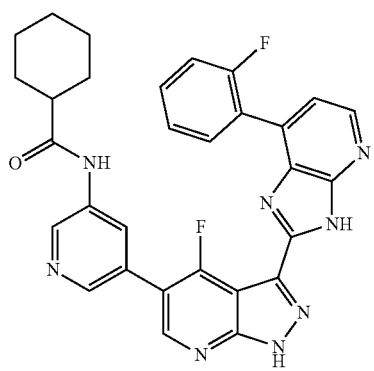 [SMILES: O=C(Nc1cncc(-c2cnc3[nH]nc(-c4nc5c(-c6ccccc6F)ccnc5[nH]4)c3c2F)c1)C1CCCCC1] 514
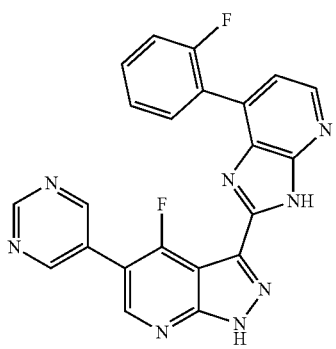 518
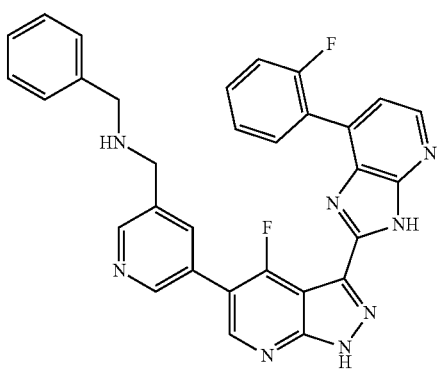 [SMILES: Fc1ccccc1-c1ccnc2[nH]c(-c3n[nH]c4ncc(-c5cncc(CNCc6ccccc6)c5)c(F)c34)nc12] 515
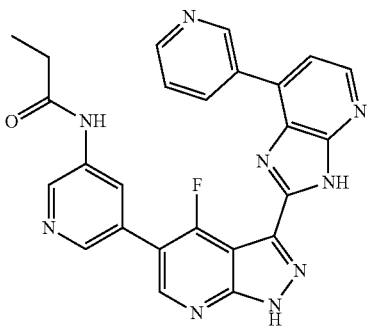 [SMILES: CCC(=O)Nc1cncc(-c2cnc3[nH]nc(-c4nc5c(-c6cccnc6)ccnc5[nH]4)c3c2F)c1] 519

TABLE 1-continued
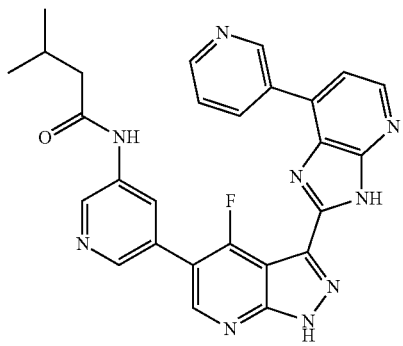 [SMILES: CC(C)CC(=O)Nc1cncc(-c2cnc3[nH]nc(-c4nc5c(-c6cccnc6)ccnc5[nH]4)c3c2F)c1]
520
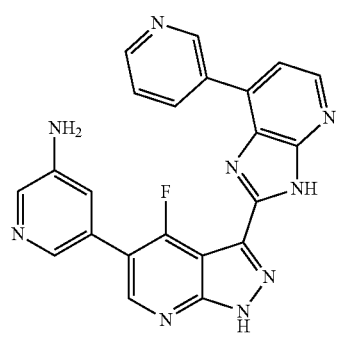 [SMILES: Nc1cncc(-c2cnc3[nH]nc(-c4nc5c(-c6cccnc6)ccnc5[nH]4)c3c2F)c1]
521
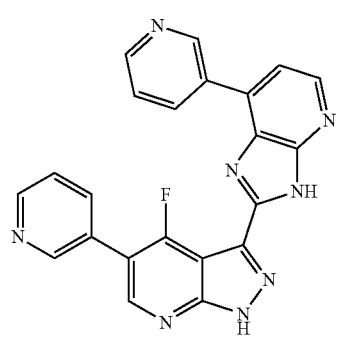 [SMILES: Fc1c(-c2cccnc2)cnc2[nH]nc(-c3nc4c(-c5cccnc5)ccnc4[nH]3)c12]
522
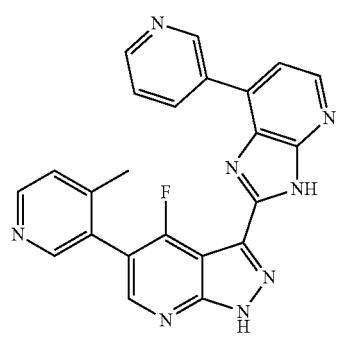 [SMILES: Cc1ccncc1-c1cnc2[nH]nc(-c3nc4c(-c5cccnc5)ccnc4[nH]3)c2c1F]
523
TABLE 1-continued
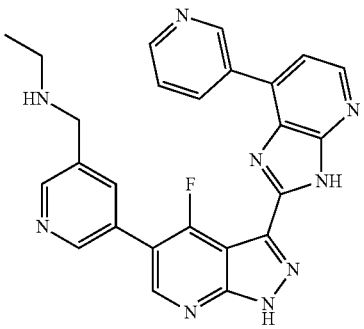 [SMILES: CCNCc1cncc(-c2cnc3[nH]nc(-c4nc5c(-c6cccnc6)ccnc5[nH]4)c3c2F)c1]
524
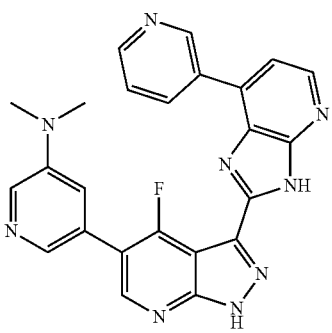 [SMILES: CN(C)c1cncc(-c2cnc3[nH]nc(-c4nc5c(-c6cccnc6)ccnc5[nH]4)c3c2F)c1]
525
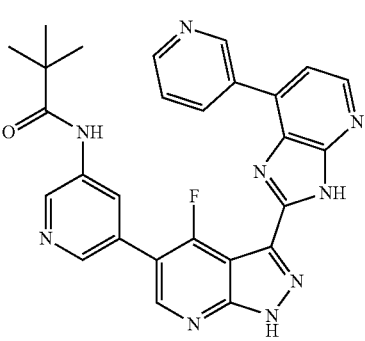 [SMILES: CC(C)(C)C(=O)Nc1cncc(-c2cnc3[nH]nc(-c4nc5c(-c6cccnc6)ccnc5[nH]4)c3c2F)c1]
526
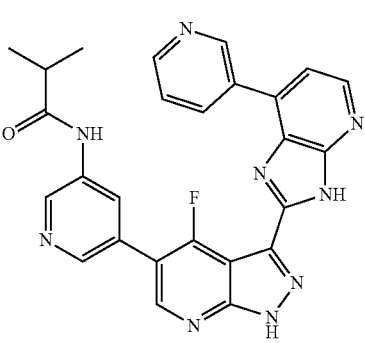 [SMILES: CC(C)C(=O)Nc1cncc(-c2cnc3[nH]nc(-c4nc5c(-c6cccnc6)ccnc5[nH]4)c3c2F)c1]
527

TABLE 1-continued
528 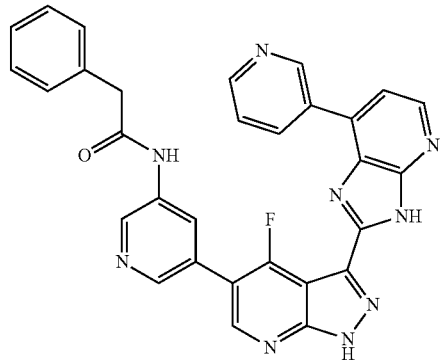 [SMILES: O=C(Cc1ccccc1)Nc1cncc(-c2cnc3[nH]nc(-c4nc5c(-c6cccnc6)ccnc5[nH]4)c3c2F)c1]
529 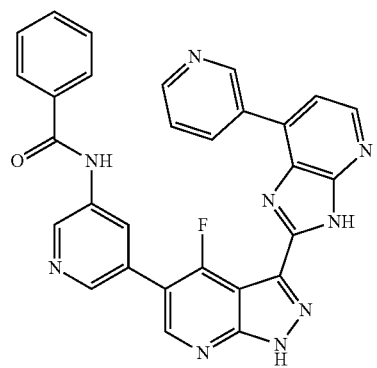 [SMILES: O=C(Nc1cncc(-c2cnc3[nH]nc(-c4nc5c(-c6cccnc6)ccnc5[nH]4)c3c2F)c1)c1ccccc1]
530 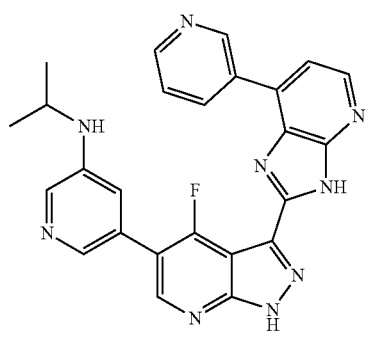 [SMILES: CC(C)Nc1cncc(-c2cnc3[nH]nc(-c4nc5c(-c6cccnc6)ccnc5[nH]4)c3c2F)c1]
531 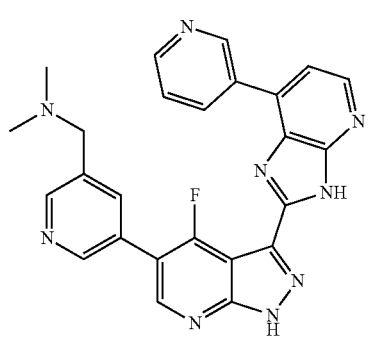 [SMILES: CN(C)Cc1cncc(-c2cnc3[nH]nc(-c4nc5c(-c6cccnc6)ccnc5[nH]4)c3c2F)c1]
TABLE 1-continued
532 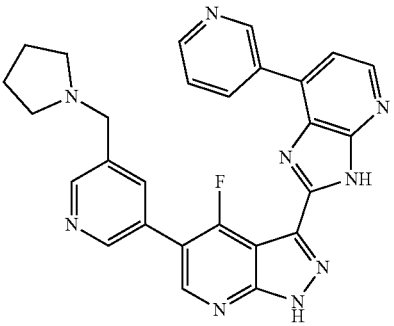 [SMILES: Fc1c(-c2cncc(CN3CCCC3)c2)cnc2[nH]nc(-c3nc4c(-c5cccnc5)ccnc4[nH]3)c12]
533 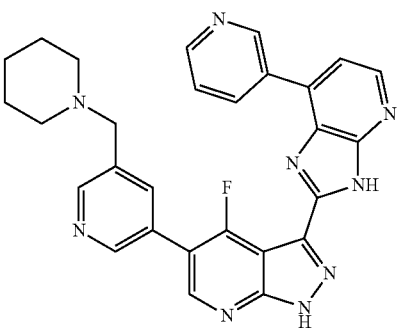 [SMILES: Fc1c(-c2cncc(CN3CCCCC3)c2)cnc2[nH]nc(-c3nc4c(-c5cccnc5)ccnc4[nH]3)c12]
534 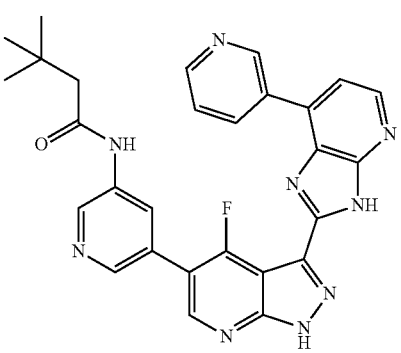 [SMILES: CC(C)(C)CC(=O)Nc1cncc(-c2cnc3[nH]nc(-c4nc5c(-c6cccnc6)ccnc5[nH]4)c3c2F)c1]
535 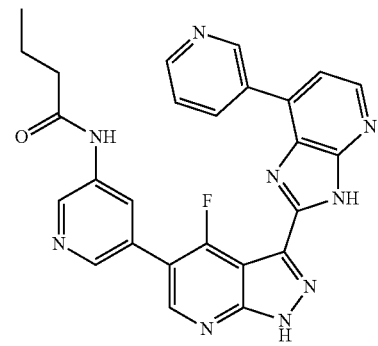 [SMILES: CCCC(=O)Nc1cncc(-c2cnc3[nH]nc(-c4nc5c(-c6cccnc6)ccnc5[nH]4)c3c2F)c1]

TABLE 1-continued
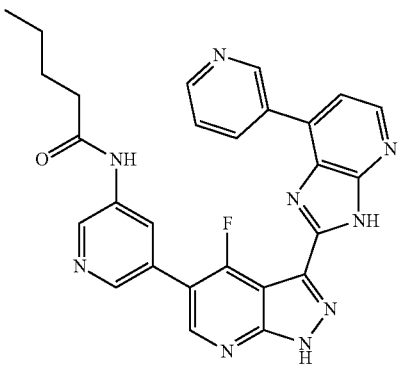 [SMILES: CCCCC(=O)Nc1cncc(-c2cnc3[nH]nc(-c4nc5c(-c6cccnc6)ccnc5[nH]4)c3c2F)c1] 536
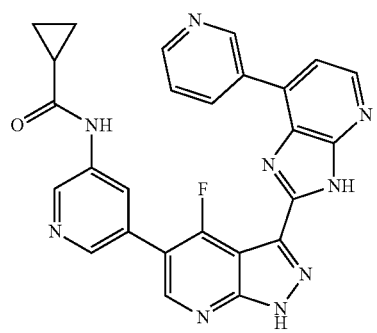 [SMILES: O=C(Nc1cncc(-c2cnc3[nH]nc(-c4nc5c(-c6cccnc6)ccnc5[nH]4)c3c2F)c1)C1CC1] 537
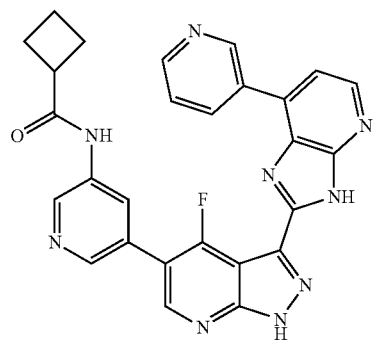 [SMILES: O=C(Nc1cncc(-c2cnc3[nH]nc(-c4nc5c(-c6cccnc6)ccnc5[nH]4)c3c2F)c1)C1CCC1] 538
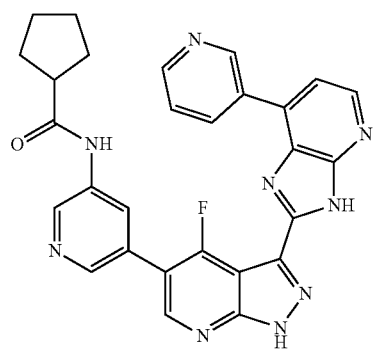 [SMILES: O=C(Nc1cncc(-c2cnc3[nH]nc(-c4nc5c(-c6cccnc6)ccnc5[nH]4)c3c2F)c1)C1CCCC1] 539
TABLE 1-continued
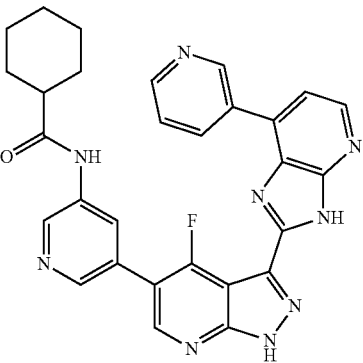 [SMILES: O=C(Nc1cncc(-c2cnc3[nH]nc(-c4nc5c(-c6cccnc6)ccnc5[nH]4)c3c2F)c1)C1CCCCC1] 540
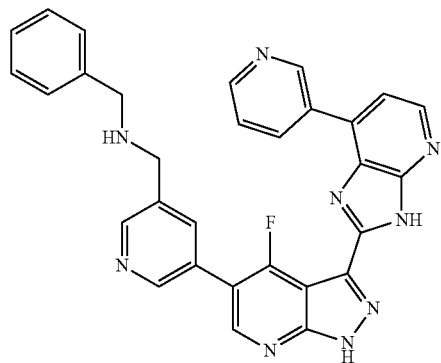 [SMILES: Fc1c(-c2cncc(CNCc3ccccc3)c2)cnc2[nH]nc(-c3nc4c(-c5cccnc5)ccnc4[nH]3)c12] 541
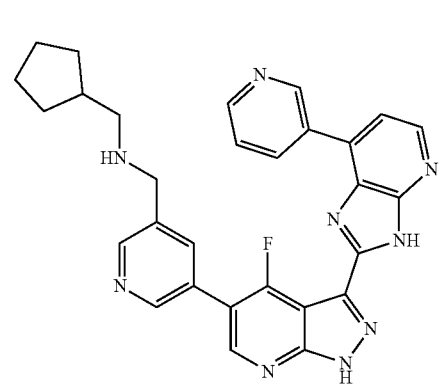 542
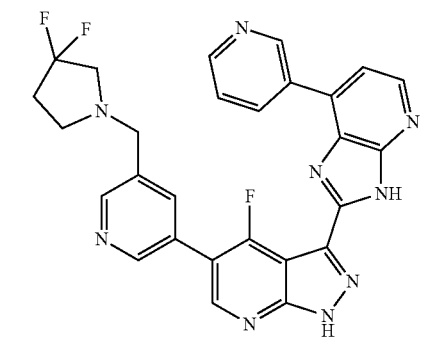 [SMILES: Fc1c(-c2cncc(CN3CCC(F)(F)C3)c2)cnc2[nH]nc(-c3nc4c(-c5cccnc5)ccnc4[nH]3)c12] 543

TABLE 1-continued
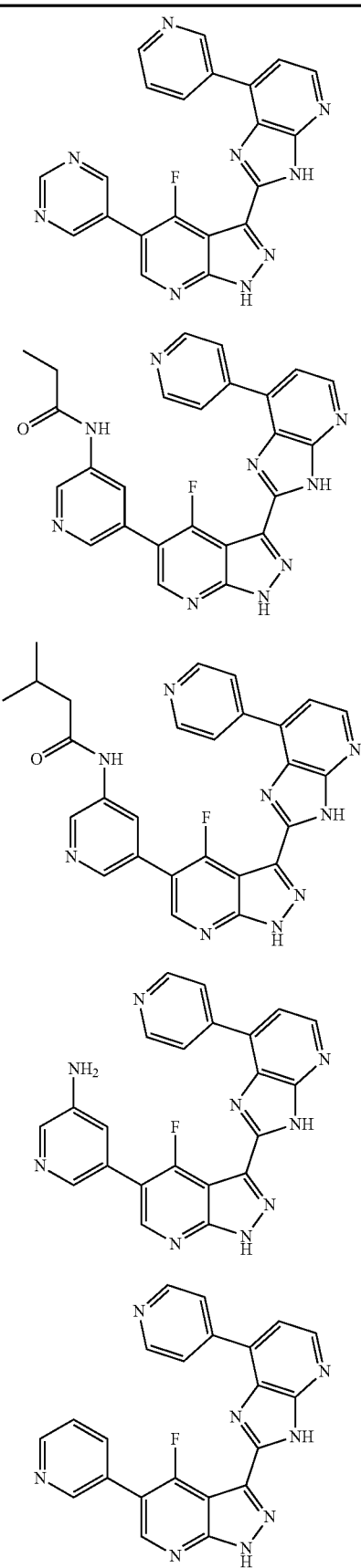
TABLE 1-continued
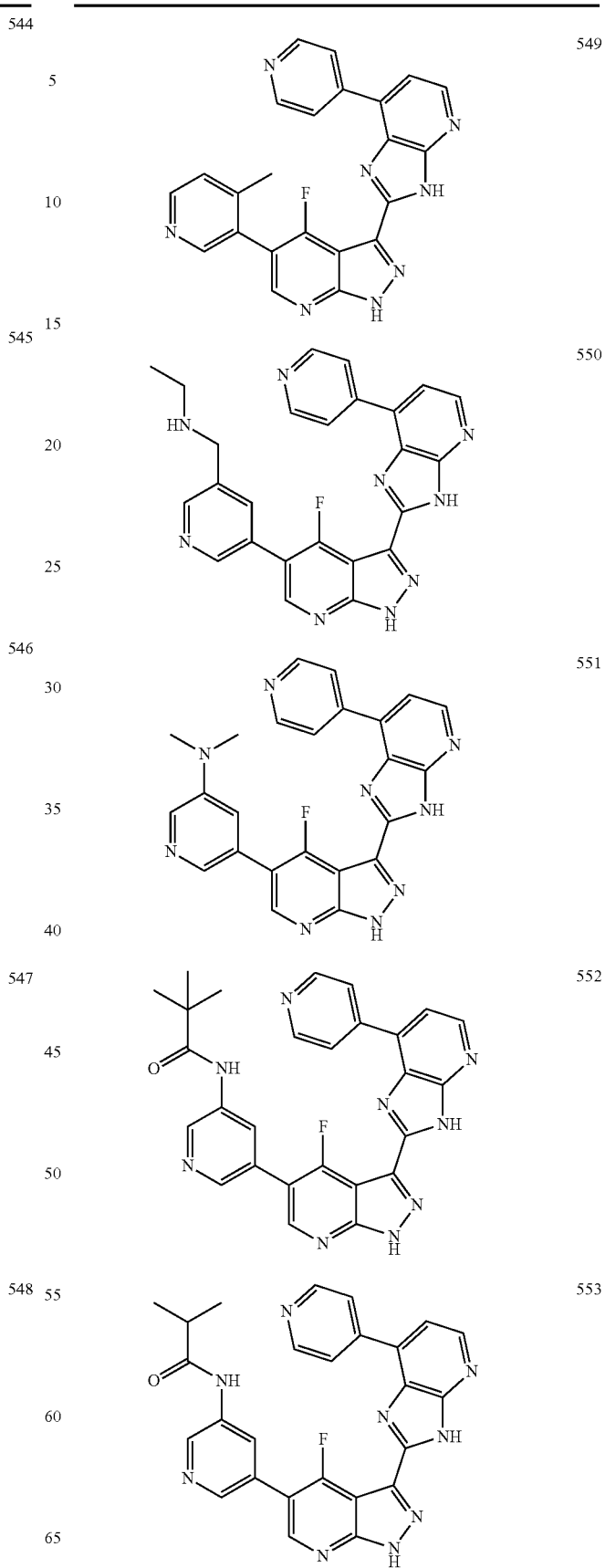

TABLE 1-continued
554 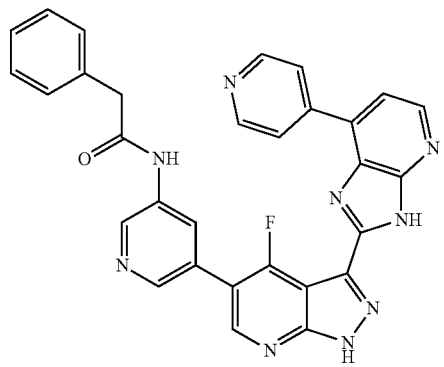 [SMILES: O=C(Cc1ccccc1)Nc1cncc(-c2cnc3[nH]nc(-c4nc5c(-c6ccncc6)ccnc5[nH]4)c3c2F)c1]
555 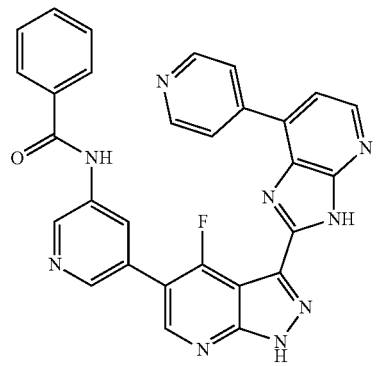 [SMILES: O=C(Nc1cncc(-c2cnc3[nH]nc(-c4nc5c(-c6ccncc6)ccnc5[nH]4)c3c2F)c1)c1ccccc1]
556 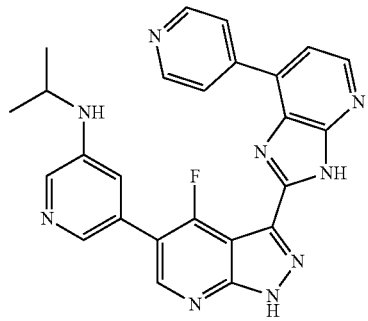 [SMILES: CC(C)Nc1cncc(-c2cnc3[nH]nc(-c4nc5c(-c6ccncc6)ccnc5[nH]4)c3c2F)c1]
557 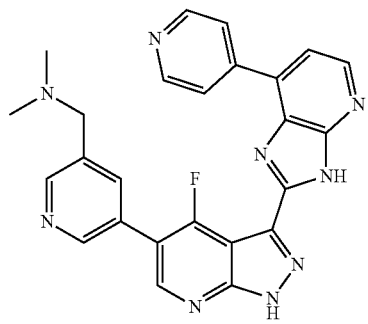 [SMILES: CN(C)Cc1cncc(-c2cnc3[nH]nc(-c4nc5c(-c6ccncc6)ccnc5[nH]4)c3c2F)c1]
TABLE 1-continued
558 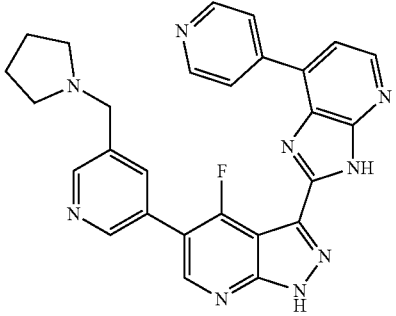 [SMILES: Fc1c(-c2cncc(CN3CCCC3)c2)cnc2[nH]nc(-c3nc4c(-c5ccncc5)ccnc4[nH]3)c12]
559 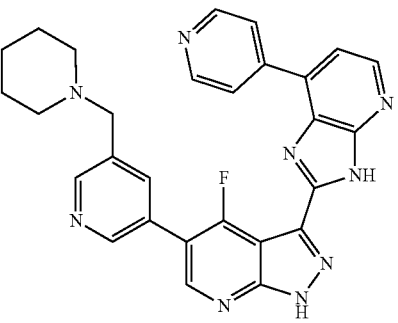 [SMILES: Fc1c(-c2cncc(CN3CCCCC3)c2)cnc2[nH]nc(-c3nc4c(-c5ccncc5)ccnc4[nH]3)c12]
560 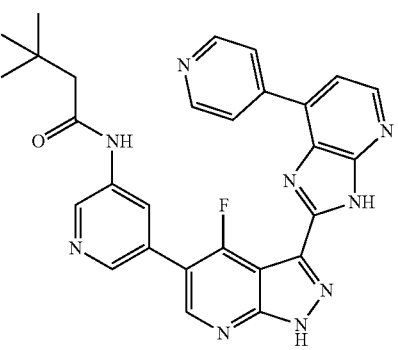 [SMILES: CC(C)(C)CC(=O)Nc1cncc(-c2cnc3[nH]nc(-c4nc5c(-c6ccncc6)ccnc5[nH]4)c3c2F)c1]
561 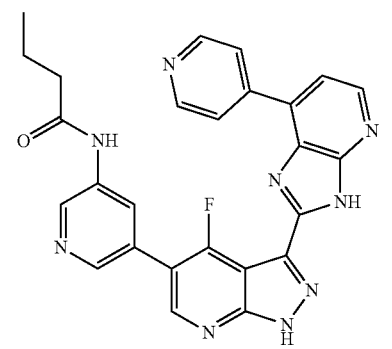 [SMILES: CCCC(=O)Nc1cncc(-c2cnc3[nH]nc(-c4nc5c(-c6ccncc6)ccnc5[nH]4)c3c2F)c1]

TABLE 1-continued
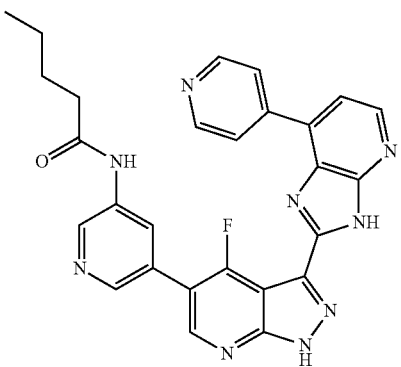 [SMILES: CCCCC(=O)Nc1cncc(-c2cnc3[nH]nc(-c4nc5c(-c6ccncc6)ccnc5[nH]4)c3c2F)c1]
562
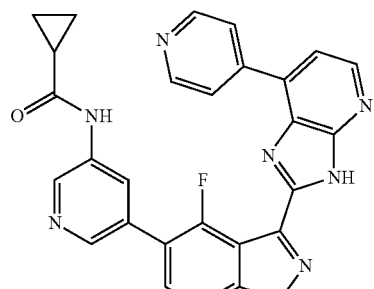
563
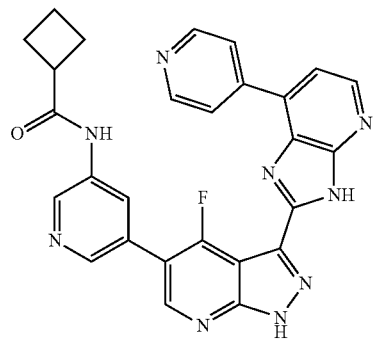 [SMILES: O=C(Nc1cncc(-c2cnc3[nH]nc(-c4nc5c(-c6ccncc6)ccnc5[nH]4)c3c2F)c1)C1CCC1]
564
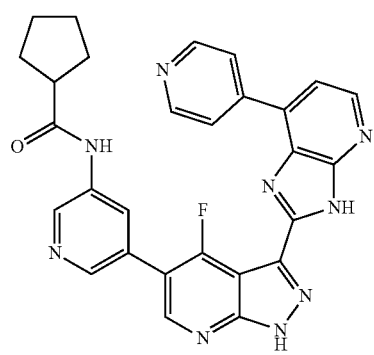 [SMILES: O=C(Nc1cncc(-c2cnc3[nH]nc(-c4nc5c(-c6ccncc6)ccnc5[nH]4)c3c2F)c1)C1CCCC1]
565
TABLE 1-continued
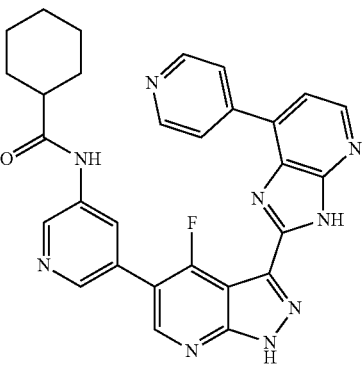 [SMILES: O=C(Nc1cncc(-c2cnc3[nH]nc(-c4nc5c(-c6ccncc6)ccnc5[nH]4)c3c2F)c1)C1CCCCC1]
566
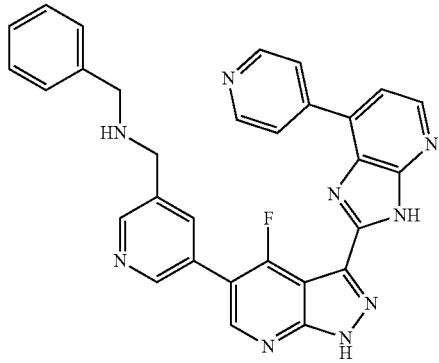 [SMILES: Fc1c(-c2cncc(CNCc3ccccc3)c2)cnc2[nH]nc(-c3nc4c(-c5ccncc5)ccnc4[nH]3)c12]
567
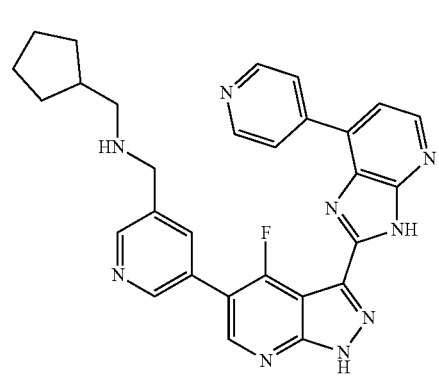 [SMILES: Fc1c(-c2cncc(CNCC3CCCC3)c2)cnc2[nH]nc(-c3nc4c(-c5ccncc5)ccnc4[nH]3)c12]
568
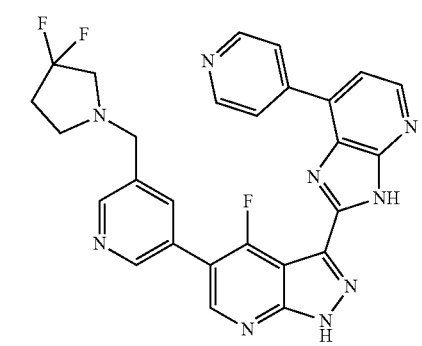
569

TABLE 1-continued
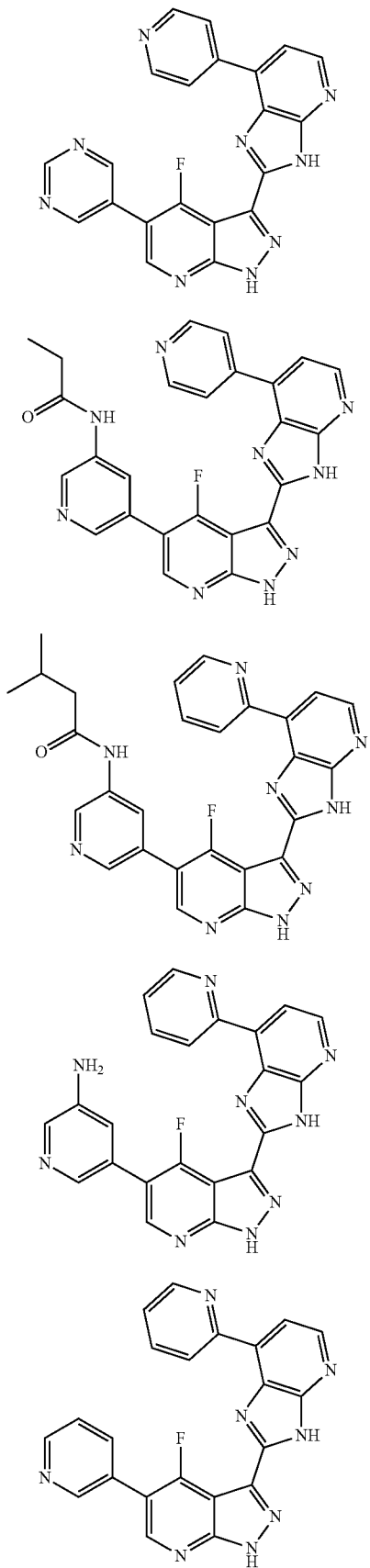
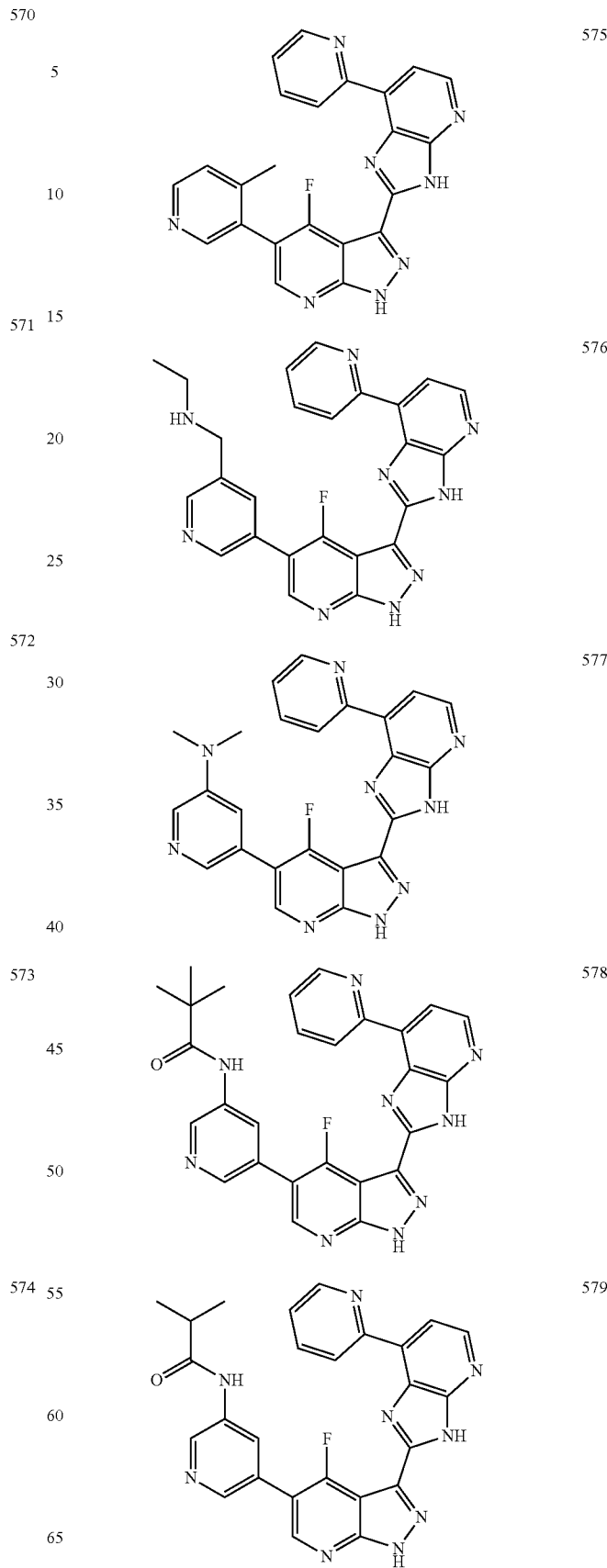

TABLE 1-continued
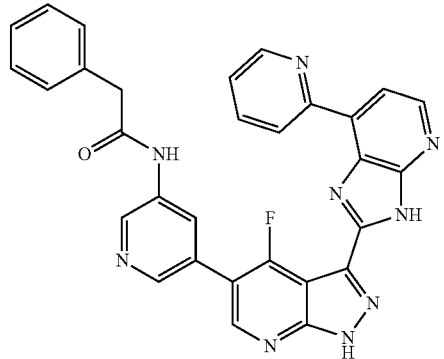 [SMILES: O=C(Cc1ccccc1)Nc1cncc(-c2cnc3[nH]nc(-c4nc5c(-c6ccccn6)ccnc5[nH]4)c3c2F)c1]
580
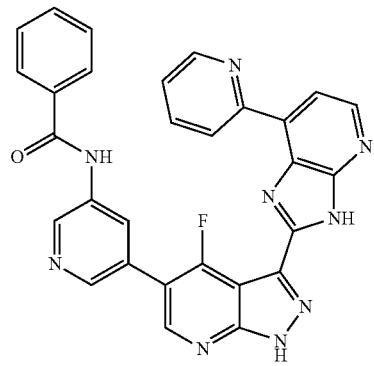 [SMILES: O=C(Nc1cncc(-c2cnc3[nH]nc(-c4nc5c(-c6ccccn6)ccnc5[nH]4)c3c2F)c1)c1ccccc1]
581
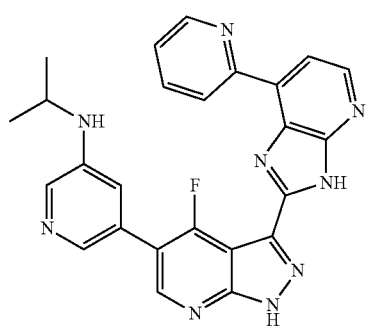 [SMILES: CC(C)Nc1cncc(-c2cnc3[nH]nc(-c4nc5c(-c6ccccn6)ccnc5[nH]4)c3c2F)c1]
582
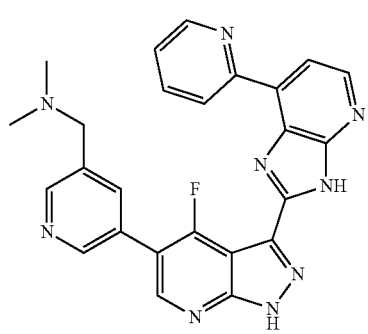 [SMILES: CN(C)Cc1cncc(-c2cnc3[nH]nc(-c4nc5c(-c6ccccn6)ccnc5[nH]4)c3c2F)c1]
583
TABLE 1-continued
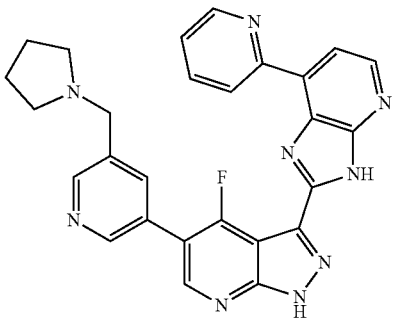 [SMILES: Fc1c(-c2cncc(CN3CCCC3)c2)cnc2[nH]nc(-c3nc4c(-c5ccccn5)ccnc4[nH]3)c12]
584
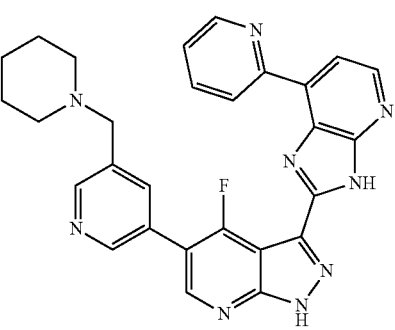 [SMILES: Fc1c(-c2cncc(CN3CCCCC3)c2)cnc2[nH]nc(-c3nc4c(-c5ccccn5)ccnc4[nH]3)c12]
585
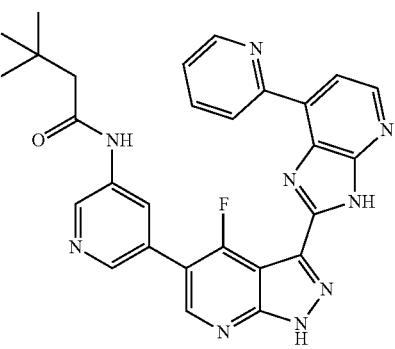 [SMILES: CC(C)(C)CC(=O)Nc1cncc(-c2cnc3[nH]nc(-c4nc5c(-c6ccccn6)ccnc5[nH]4)c3c2F)c1]
586
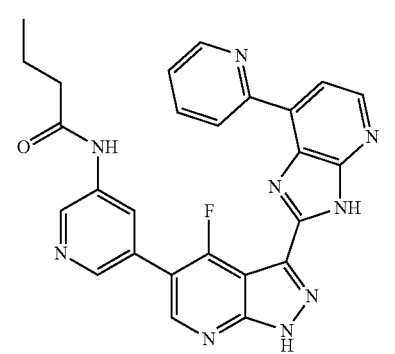 [SMILES: CCCC(=O)Nc1cncc(-c2cnc3[nH]nc(-c4nc5c(-c6ccccn6)ccnc5[nH]4)c3c2F)c1]
587

TABLE 1-continued
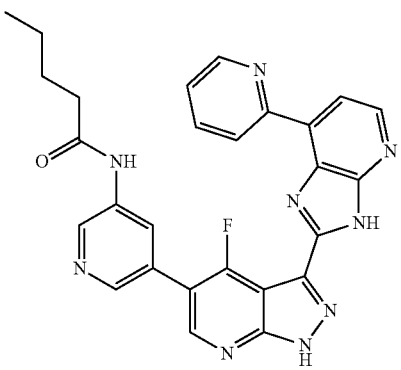 [SMILES: CCCCC(=O)Nc1cncc(-c2cnc3[nH]nc(-c4nc5c(-c6ccccn6)ccnc5[nH]4)c3c2F)c1] 588
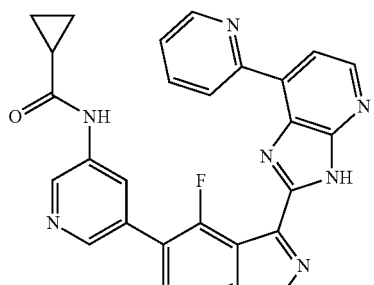 589
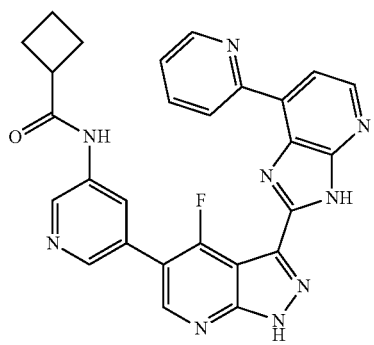 [SMILES: O=C(Nc1cncc(-c2cnc3[nH]nc(-c4nc5c(-c6ccccn6)ccnc5[nH]4)c3c2F)c1)C1CCC1] 590
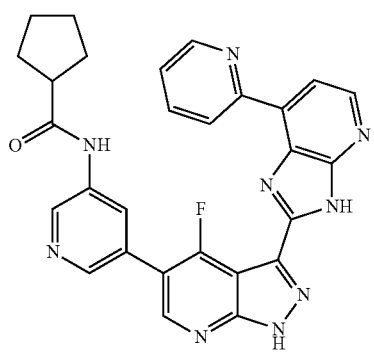 [SMILES: O=C(Nc1cncc(-c2cnc3[nH]nc(-c4nc5c(-c6ccccn6)ccnc5[nH]4)c3c2F)c1)C1CCCC1] 591
TABLE 1-continued
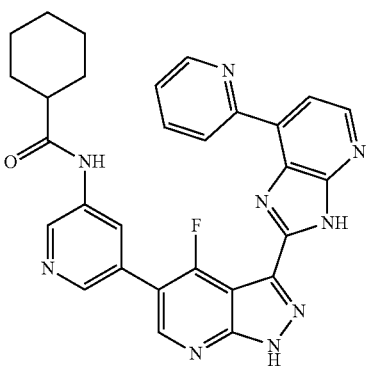 [SMILES: O=C(Nc1cncc(-c2cnc3[nH]nc(-c4nc5c(-c6ccccn6)ccnc5[nH]4)c3c2F)c1)C1CCCCC1] 592
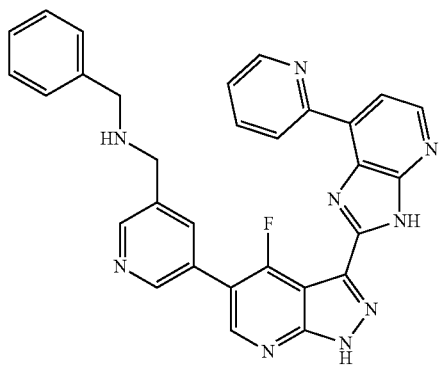 [SMILES: Fc1c(-c2cncc(CNCc3ccccc3)c2)cnc2[nH]nc(-c3nc4c(-c5ccccn5)ccnc4[nH]3)c12] 593
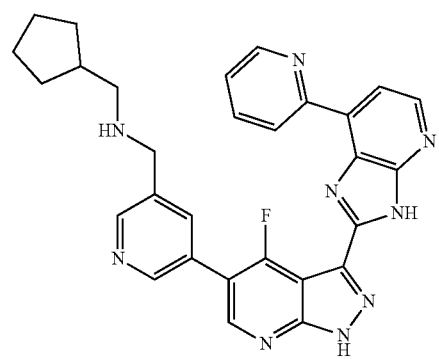 [SMILES: Fc1c(-c2cncc(CNCC3CCCC3)c2)cnc2[nH]nc(-c3nc4c(-c5ccccn5)ccnc4[nH]3)c12] 594
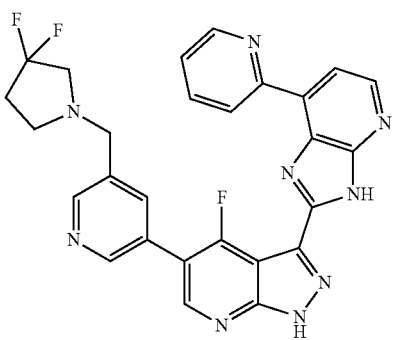 [SMILES: Fc1c(-c2cncc(CN3CCC(F)(F)C3)c2)cnc2[nH]nc(-c3nc4c(-c5ccccn5)ccnc4[nH]3)c12] 595

TABLE 1-continued
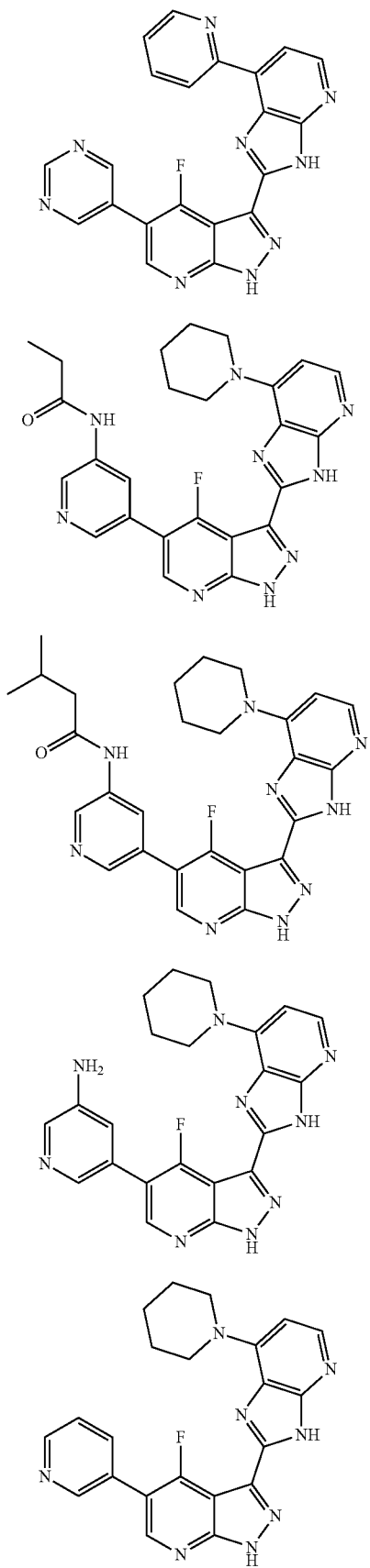
596
597
598
599
600
TABLE 1-continued
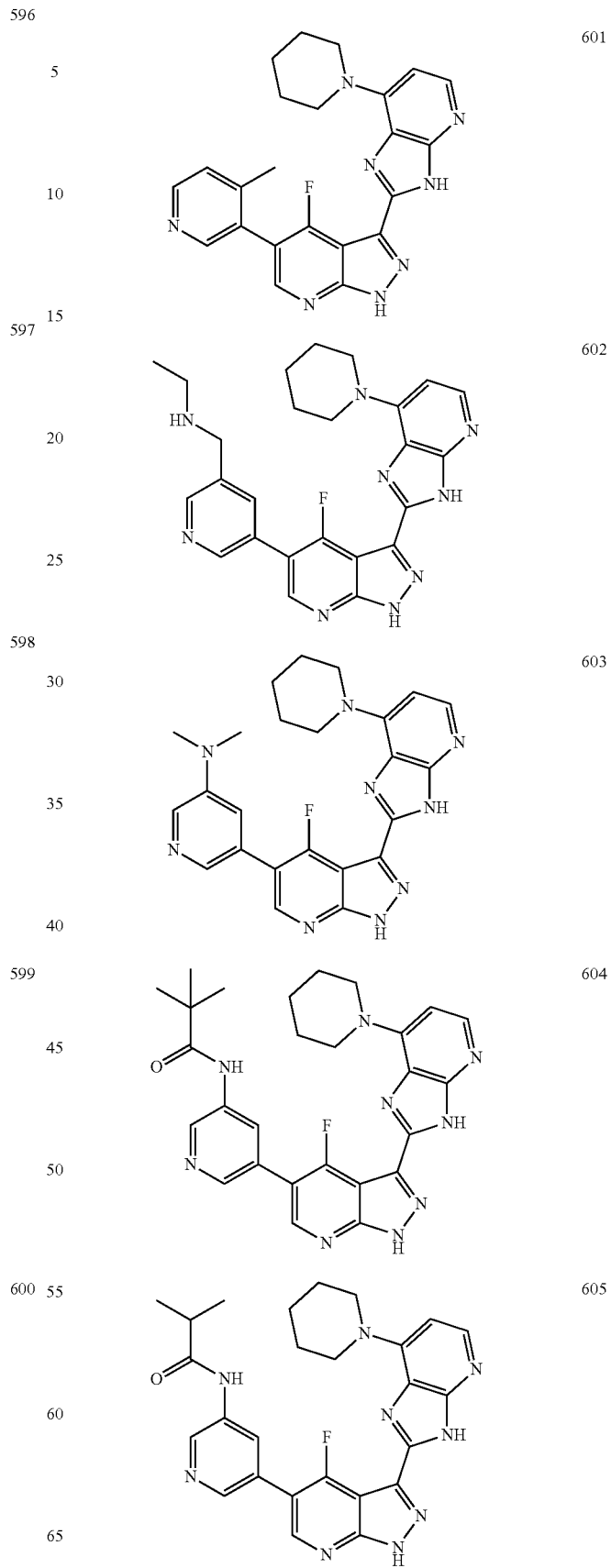
601
602
603
604
605

TABLE 1-continued
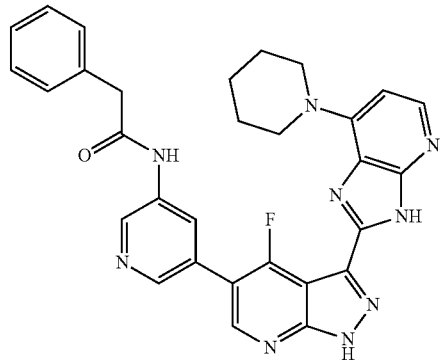 [SMILES: O=C(Cc1ccccc1)Nc1cncc(-c2cnc3[nH]nc(-c4nc5c(N6CCCCC6)ccnc5[nH]4)c3c2F)c1]
606
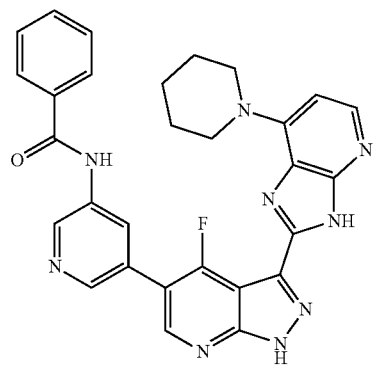 [SMILES: O=C(Nc1cncc(-c2cnc3[nH]nc(-c4nc5c(N6CCCCC6)ccnc5[nH]4)c3c2F)c1)c1ccccc1]
607
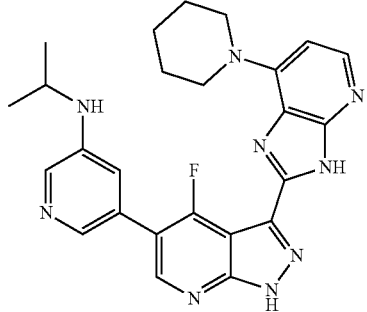 [SMILES: CC(C)Nc1cncc(-c2cnc3[nH]nc(-c4nc5c(N6CCCCC6)ccnc5[nH]4)c3c2F)c1]
608
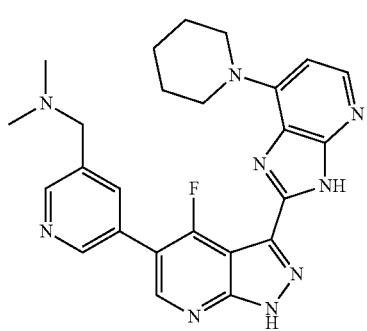 [SMILES: CN(C)Cc1cncc(-c2cnc3[nH]nc(-c4nc5c(N6CCCCC6)ccnc5[nH]4)c3c2F)c1]
609
TABLE 1-continued
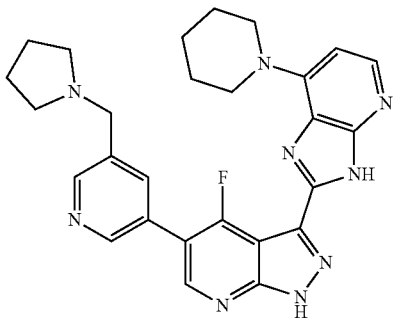 [SMILES: Fc1c(-c2cncc(CN3CCCC3)c2)cnc2[nH]nc(-c3nc4c(N5CCCCC5)ccnc4[nH]3)c12]
610
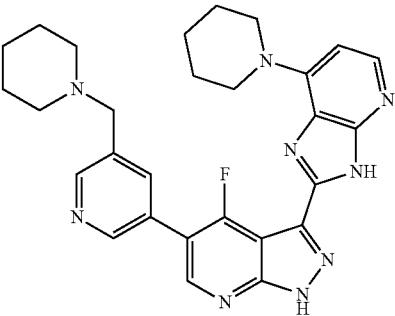 [SMILES: Fc1c(-c2cncc(CN3CCCCC3)c2)cnc2[nH]nc(-c3nc4c(N5CCCCC5)ccnc4[nH]3)c12]
611
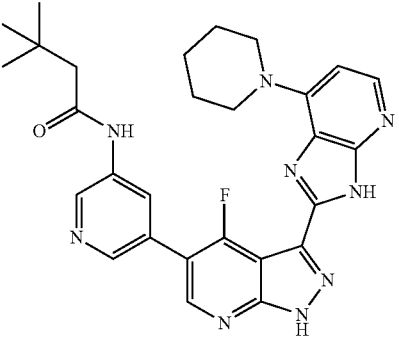 [SMILES: CC(C)(C)CC(=O)Nc1cncc(-c2cnc3[nH]nc(-c4nc5c(N6CCCCC6)ccnc5[nH]4)c3c2F)c1]
612
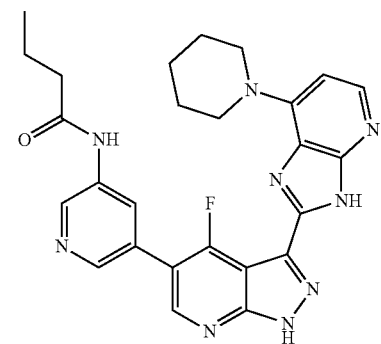 [SMILES: CCCC(=O)Nc1cncc(-c2cnc3[nH]nc(-c4nc5c(N6CCCCC6)ccnc5[nH]4)c3c2F)c1]
613

TABLE 1-continued
614 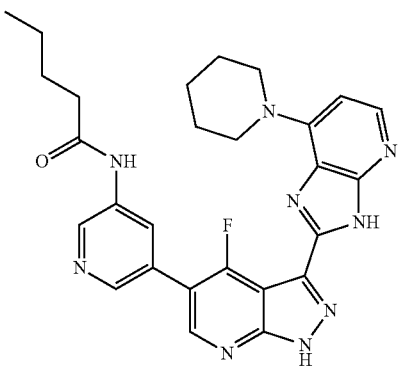 [SMILES: CCCCC(=O)Nc1cncc(-c2cnc3[nH]nc(-c4nc5c(N6CCCCC6)ccnc5[nH]4)c3c2F)c1]
615 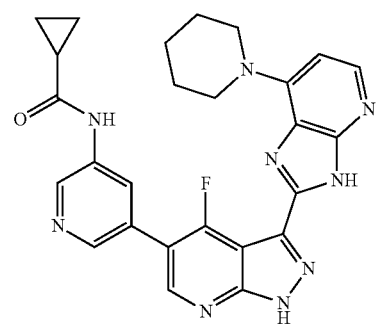 [SMILES: O=C(Nc1cncc(-c2cnc3[nH]nc(-c4nc5c(N6CCCCC6)ccnc5[nH]4)c3c2F)c1)C1CC1]
616 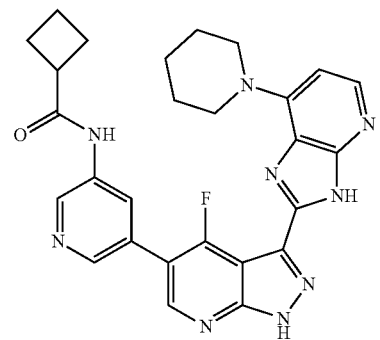 [SMILES: O=C(Nc1cncc(-c2cnc3[nH]nc(-c4nc5c(N6CCCCC6)ccnc5[nH]4)c3c2F)c1)C1CCC1]
617 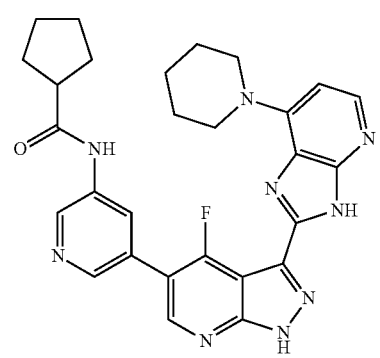 [SMILES: O=C(Nc1cncc(-c2cnc3[nH]nc(-c4nc5c(N6CCCCC6)ccnc5[nH]4)c3c2F)c1)C1CCCC1]
TABLE 1-continued
618 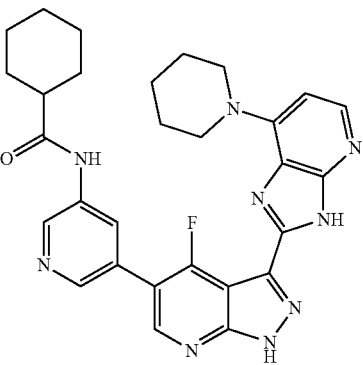 [SMILES: O=C(Nc1cncc(-c2cnc3[nH]nc(-c4nc5c(N6CCCCC6)ccnc5[nH]4)c3c2F)c1)C1CCCCC1]
619 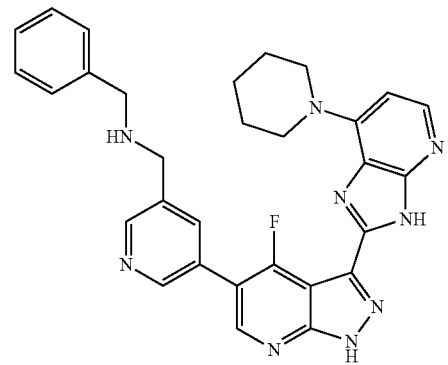 [SMILES: Fc1c(-c2cncc(CNCc3ccccc3)c2)cnc2[nH]nc(-c3nc4c(N5CCCCC5)ccnc4[nH]3)c12]
620 
621 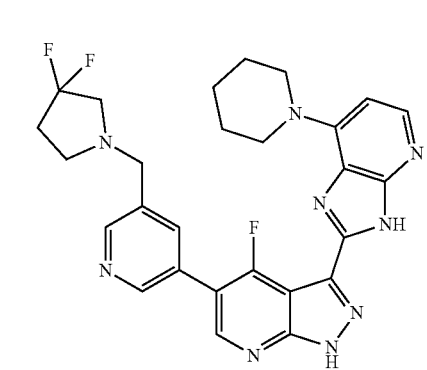 [SMILES: Fc1c(-c2cncc(CN3CCC(F)(F)C3)c2)cnc2[nH]nc(-c3nc4c(N5CCCCC5)ccnc4[nH]3)c12]

TABLE 1-continued
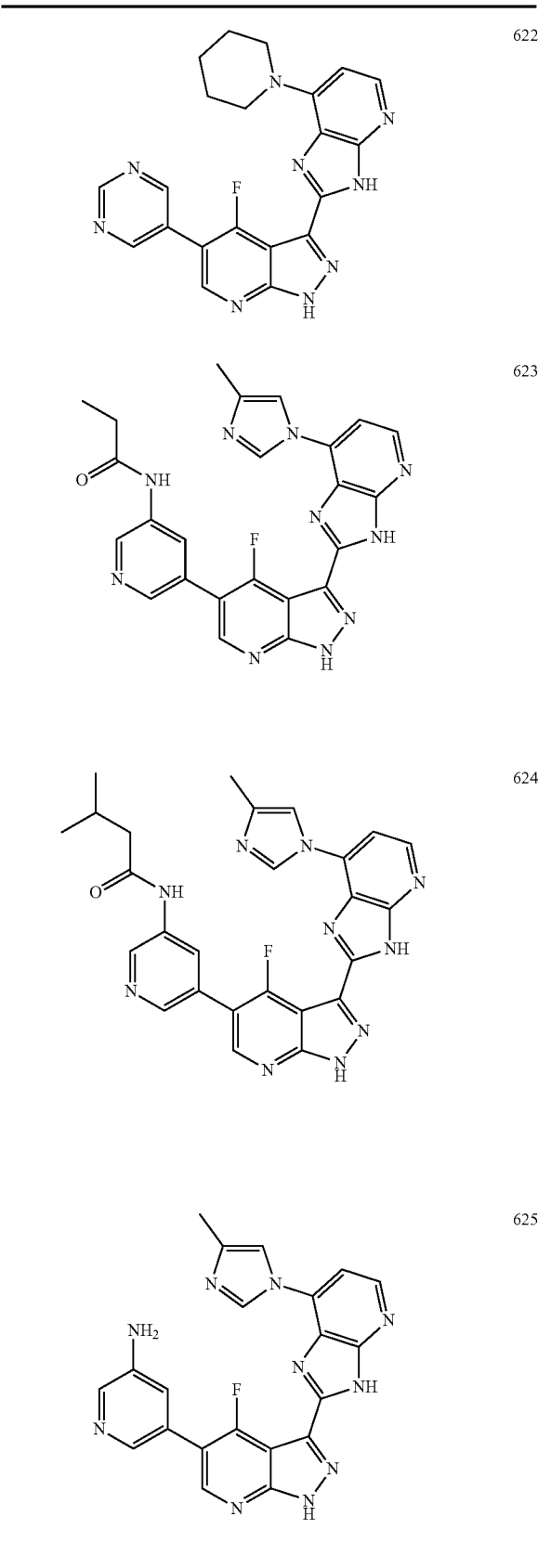
622
623
624
625
TABLE 1-continued
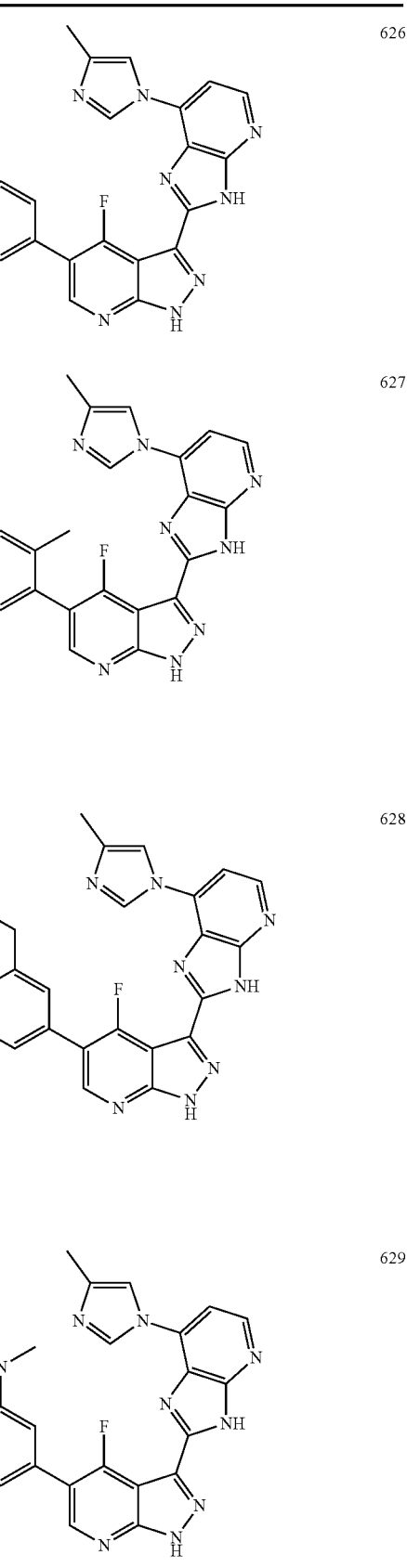
626
627
628
629

TABLE 1-continued
630
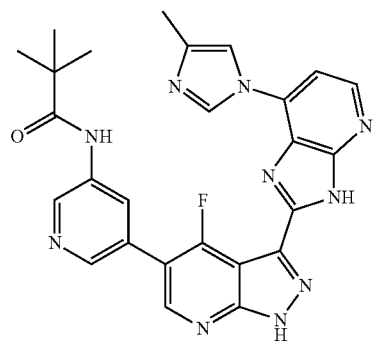 [SMILES: Cc1cn(-c2ccnc3[nH]c(-c4n[nH]c5ncc(-c6cncc(NC(=O)C(C)(C)C)c6)c(F)c45)nc23)cn1]
631
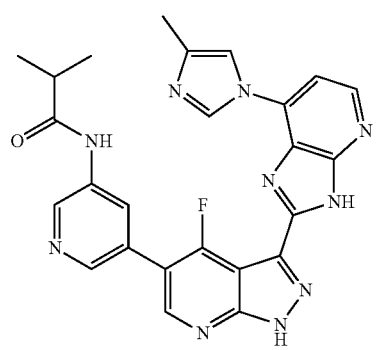 [SMILES: Cc1cn(-c2ccnc3[nH]c(-c4n[nH]c5ncc(-c6cncc(NC(=O)C(C)C)c6)c(F)c45)nc23)cn1]
632
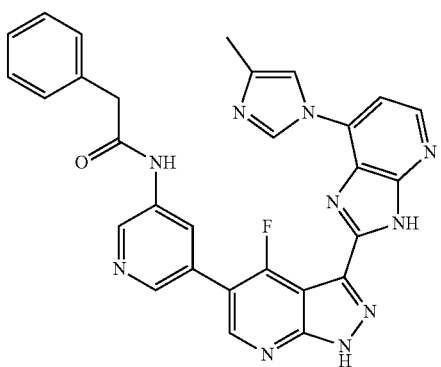 [SMILES: Cc1cn(-c2ccnc3[nH]c(-c4n[nH]c5ncc(-c6cncc(NC(=O)Cc7ccccc7)c6)c(F)c45)nc23)cn1]
633
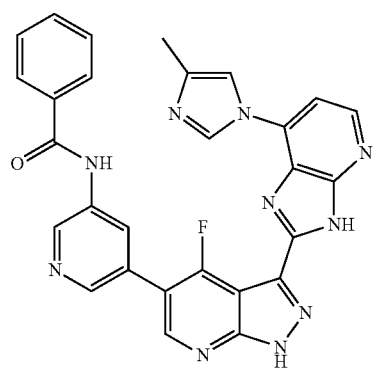 [SMILES: Cc1cn(-c2ccnc3[nH]c(-c4n[nH]c5ncc(-c6cncc(NC(=O)c7ccccc7)c6)c(F)c45)nc23)cn1]
TABLE 1-continued
634
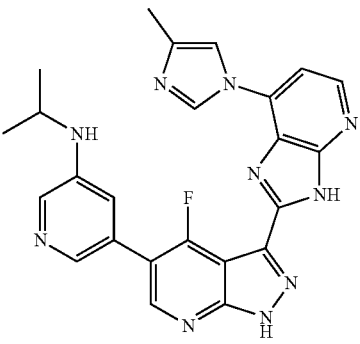 [SMILES: Cc1cn(-c2ccnc3[nH]c(-c4n[nH]c5ncc(-c6cncc(NC(C)C)c6)c(F)c45)nc23)cn1]
635
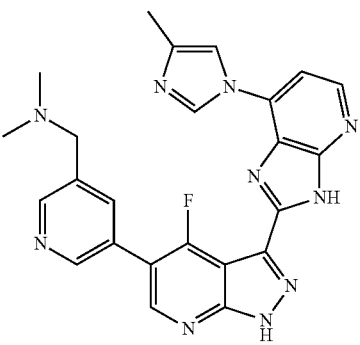 [SMILES: Cc1cn(-c2ccnc3[nH]c(-c4n[nH]c5ncc(-c6cncc(CN(C)C)c6)c(F)c45)nc23)cn1]
636
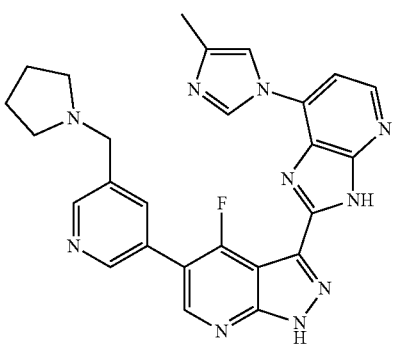 [SMILES: Cc1cn(-c2ccnc3[nH]c(-c4n[nH]c5ncc(-c6cncc(CN7CCCC7)c6)c(F)c45)nc23)cn1]
637
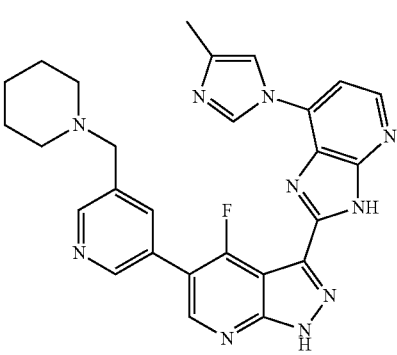 [SMILES: Cc1cn(-c2ccnc3[nH]c(-c4n[nH]c5ncc(-c6cncc(CN7CCCCC7)c6)c(F)c45)nc23)cn1]

TABLE 1-continued
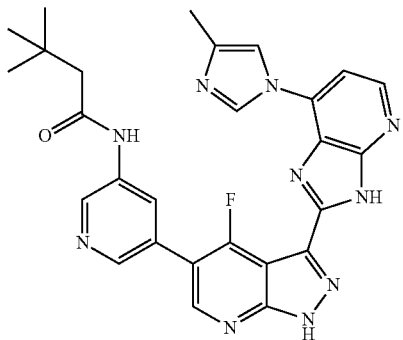 [SMILES: Cc1cn(-c2ccnc3[nH]c(-c4n[nH]c5ncc(-c6cncc(NC(=O)CC(C)(C)C)c6)c(F)c45)nc23)cn1]
638
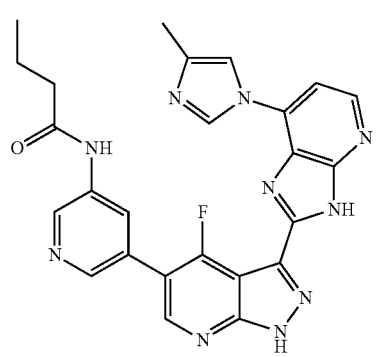 [SMILES: CCCC(=O)Nc1cncc(-c2cnc3[nH]nc(-c4nc5c(-n6cnc(C)c6)ccnc5[nH]4)c3c2F)c1]
639
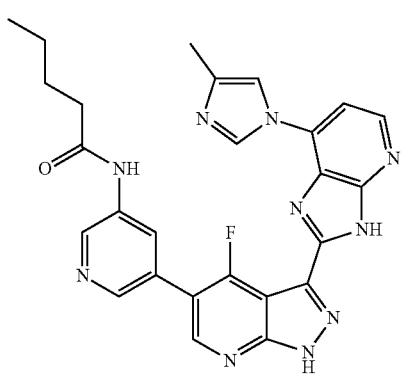 [SMILES: CCCCC(=O)Nc1cncc(-c2cnc3[nH]nc(-c4nc5c(-n6cnc(C)c6)ccnc5[nH]4)c3c2F)c1]
640
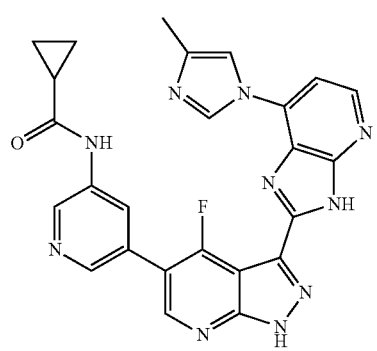 [SMILES: Cc1cn(-c2ccnc3[nH]c(-c4n[nH]c5ncc(-c6cncc(NC(=O)C7CC7)c6)c(F)c45)nc23)cn1]
641
TABLE 1-continued
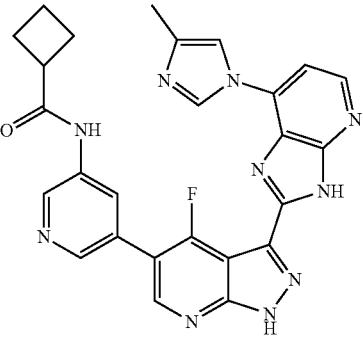 [SMILES: Cc1cn(-c2ccnc3[nH]c(-c4n[nH]c5ncc(-c6cncc(NC(=O)C7CCC7)c6)c(F)c45)nc23)cn1]
642
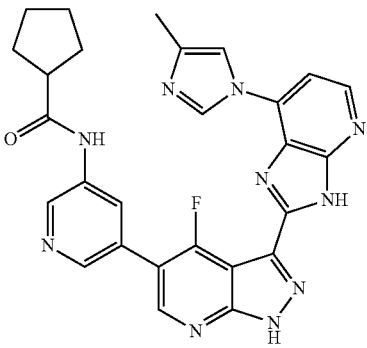 [SMILES: Cc1cn(-c2ccnc3[nH]c(-c4n[nH]c5ncc(-c6cncc(NC(=O)C7CCCC7)c6)c(F)c45)nc23)cn1]
643
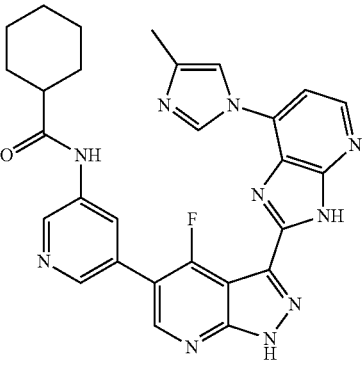 [SMILES: Cc1cn(-c2ccnc3[nH]c(-c4n[nH]c5ncc(-c6cncc(NC(=O)C7CCCCC7)c6)c(F)c45)nc23)cn1]
644
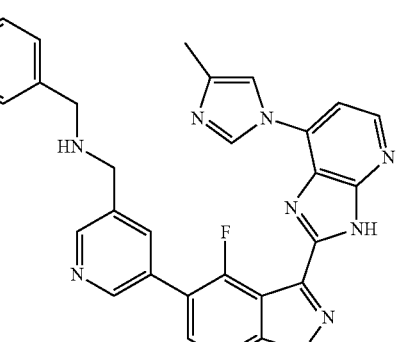
645

TABLE 1-continued
| | |
|---|---|
| 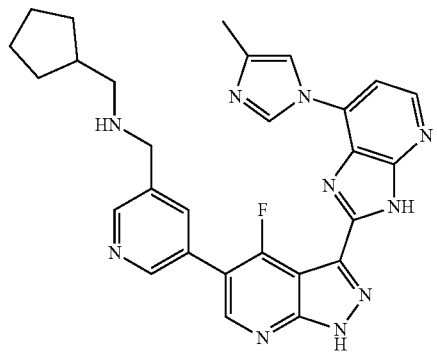 [SMILES: Cc1cn(-c2ccnc3[nH]c(-c4n[nH]c5ncc(-c6cncc(CNCC7CCCC7)c6)c(F)c45)nc23)cn1] | 646 |
| 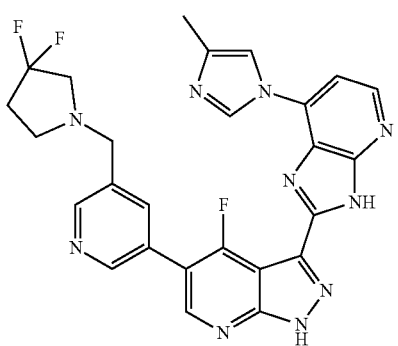 [SMILES: Cc1cn(-c2ccnc3[nH]c(-c4n[nH]c5ncc(-c6cncc(CN7CCC(F)(F)C7)c6)c(F)c45)nc23)cn1] | 647 |
| 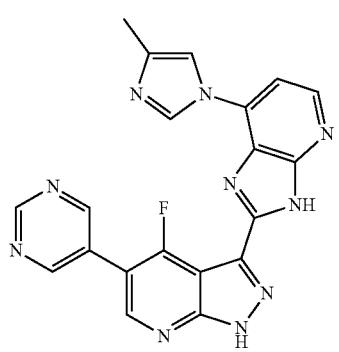 [SMILES: Cc1cn(-c2ccnc3[nH]c(-c4n[nH]c5ncc(-c6cncnc6)c(F)c45)nc23)cn1] | 648 |
| 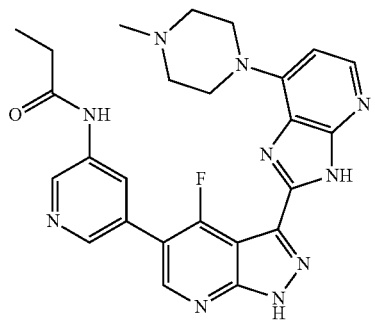 [SMILES: CCC(=O)Nc1cncc(-c2cnc3[nH]nc(-c4nc5c(N6CCN(C)CC6)ccnc5[nH]4)c3c2F)c1] | 649 |
TABLE 1-continued
| | |
|---|---|
| 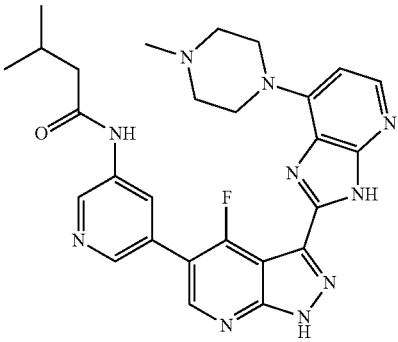 [SMILES: CC(C)CC(=O)Nc1cncc(-c2cnc3[nH]nc(-c4nc5c(N6CCN(C)CC6)ccnc5[nH]4)c3c2F)c1] | 650 |
| 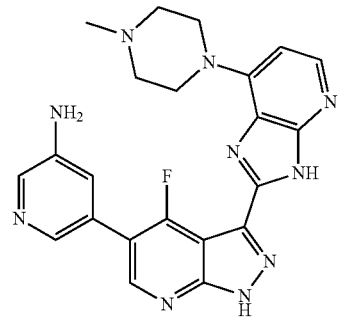 [SMILES: CN1CCN(c2ccnc3[nH]c(-c4n[nH]c5ncc(-c6cncc(N)c6)c(F)c45)nc23)CC1] | 651 |
| 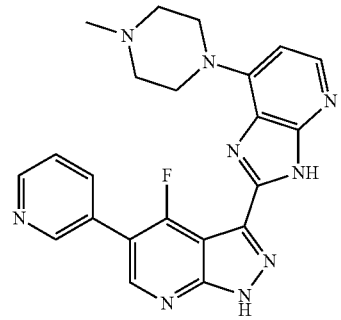 | 652 |
| 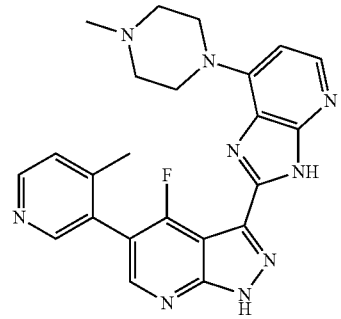 [SMILES: Cc1ccncc1-c1cnc2[nH]nc(-c3nc4c(N5CCN(C)CC5)ccnc4[nH]3)c2c1F] | 653 |
| 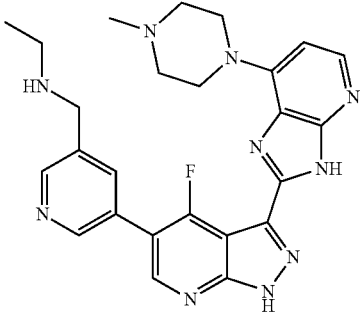 [SMILES: CCNCc1cncc(-c2cnc3[nH]nc(-c4nc5c(N6CCN(C)CC6)ccnc5[nH]4)c3c2F)c1] | 654 |

TABLE 1-continued
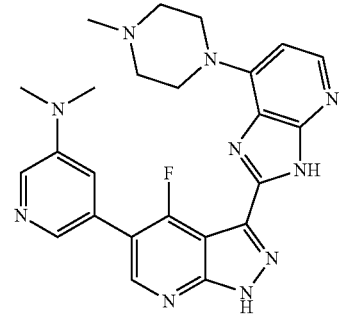 [SMILES: CN1CCN(c2ccnc3[nH]c(-c4n[nH]c5ncc(-c6cncc(N(C)C)c6)c(F)c45)nc23)CC1]
655
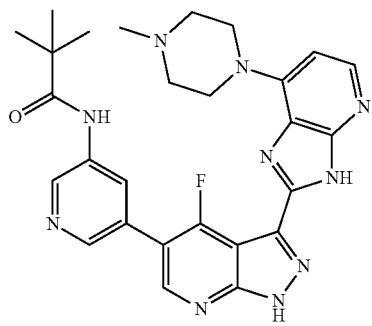
656
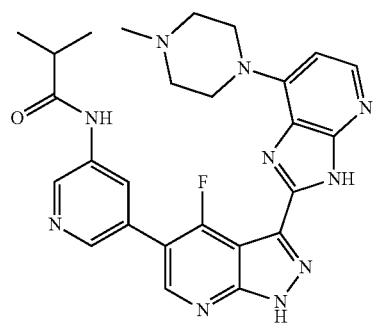 [SMILES: CC(C)C(=O)Nc1cncc(-c2cnc3[nH]nc(-c4nc5c(N6CCN(C)CC6)ccnc5[nH]4)c3c2F)c1]
657
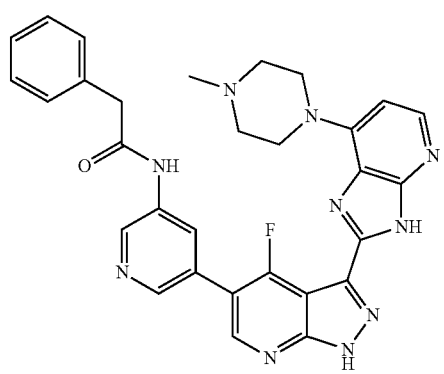 [SMILES: CN1CCN(c2ccnc3[nH]c(-c4n[nH]c5ncc(-c6cncc(NC(=O)Cc7ccccc7)c6)c(F)c45)nc23)CC1]
658
TABLE 1-continued
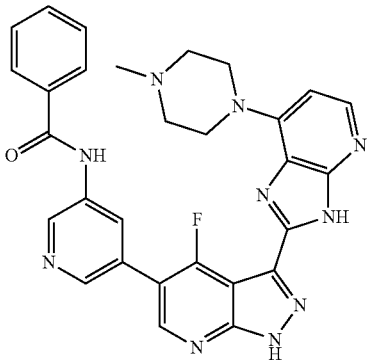 [SMILES: CN1CCN(c2ccnc3[nH]c(-c4n[nH]c5ncc(-c6cncc(NC(=O)c7ccccc7)c6)c(F)c45)nc23)CC1]
659
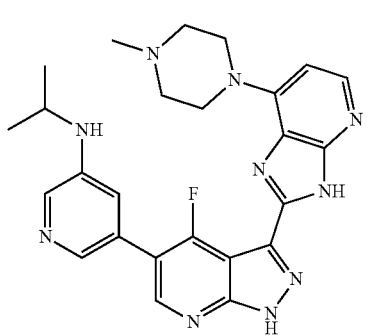 [SMILES: CC(C)Nc1cncc(-c2cnc3[nH]nc(-c4nc5c(N6CCN(C)CC6)ccnc5[nH]4)c3c2F)c1]
660
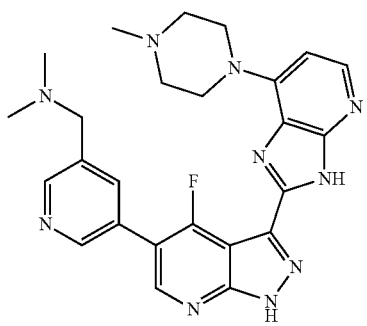 [SMILES: CN(C)Cc1cncc(-c2cnc3[nH]nc(-c4nc5c(N6CCN(C)CC6)ccnc5[nH]4)c3c2F)c1]
661
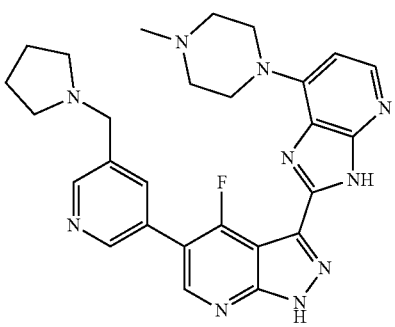 [SMILES: CN1CCN(c2ccnc3[nH]c(-c4n[nH]c5ncc(-c6cncc(CN7CCCC7)c6)c(F)c45)nc23)CC1]
662

TABLE 1-continued
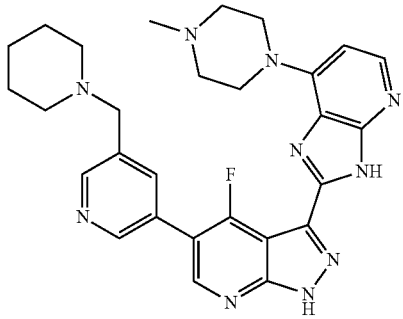 [SMILES: CN1CCN(c2ccnc3[nH]c(-c4n[nH]c5ncc(-c6cncc(CN7CCCCC7)c6)c(F)c45)nc23)CC1]
663
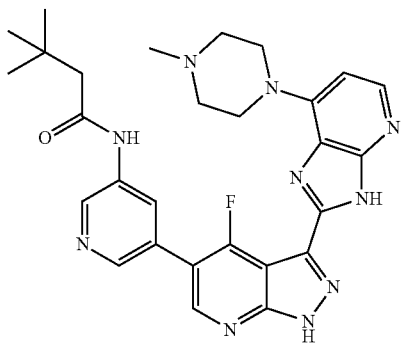 [SMILES: CN1CCN(c2ccnc3[nH]c(-c4n[nH]c5ncc(-c6cncc(NC(=O)CC(C)(C)C)c6)c(F)c45)nc23)CC1]
664
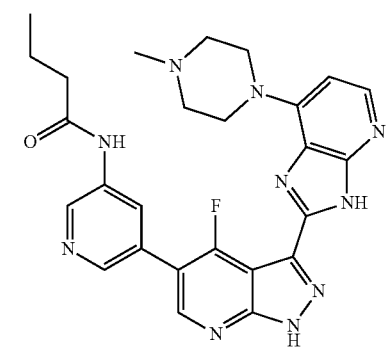 [SMILES: CCCC(=O)Nc1cncc(-c2cnc3[nH]nc(-c4nc5c(N6CCN(C)CC6)ccnc5[nH]4)c3c2F)c1]
665
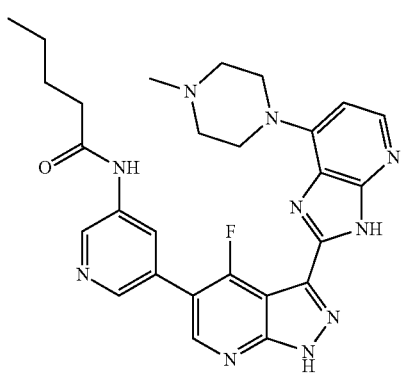 [SMILES: CCCCC(=O)Nc1cncc(-c2cnc3[nH]nc(-c4nc5c(N6CCN(C)CC6)ccnc5[nH]4)c3c2F)c1]
666
TABLE 1-continued
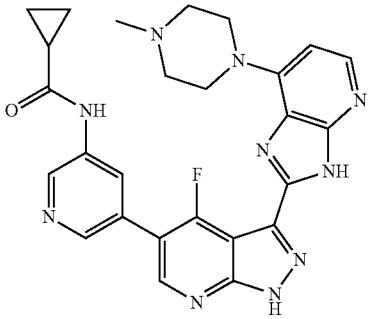 [SMILES: CN1CCN(c2ccnc3[nH]c(-c4n[nH]c5ncc(-c6cncc(NC(=O)C7CC7)c6)c(F)c45)nc23)CC1]
667
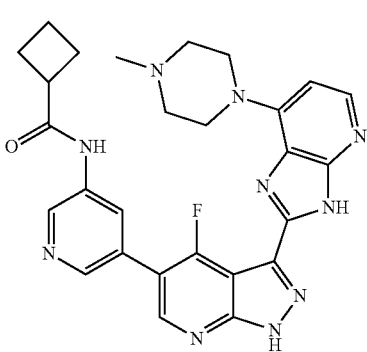 [SMILES: CN1CCN(c2ccnc3[nH]c(-c4n[nH]c5ncc(-c6cncc(NC(=O)C7CCC7)c6)c(F)c45)nc23)CC1]
668
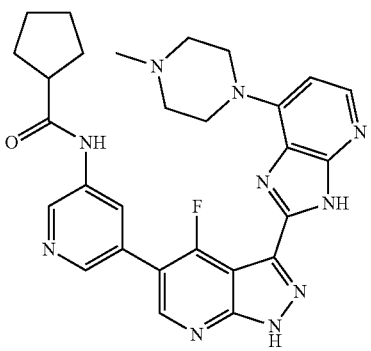 [SMILES: CN1CCN(c2ccnc3[nH]c(-c4n[nH]c5ncc(-c6cncc(NC(=O)C7CCCC7)c6)c(F)c45)nc23)CC1]
669
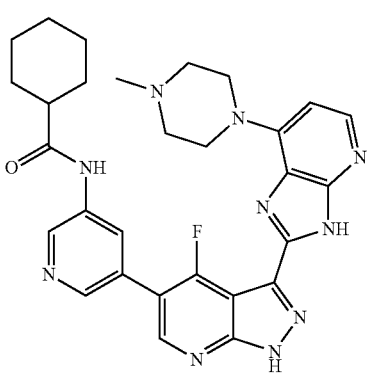 [SMILES: CN1CCN(c2ccnc3[nH]c(-c4n[nH]c5ncc(-c6cncc(NC(=O)C7CCCCC7)c6)c(F)c45)nc23)CC1]
670

TABLE 1-continued
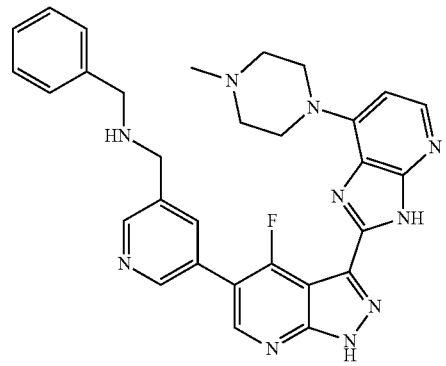 [SMILES: CN1CCN(c2ccnc3[nH]c(-c4n[nH]c5ncc(-c6cncc(CNCc7ccccc7)c6)c(F)c45)nc23)CC1] 671
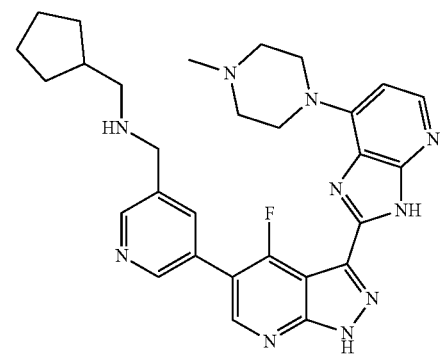 [SMILES: CN1CCN(c2ccnc3[nH]c(-c4n[nH]c5ncc(-c6cncc(CNCC7CCCC7)c6)c(F)c45)nc23)CC1] 672
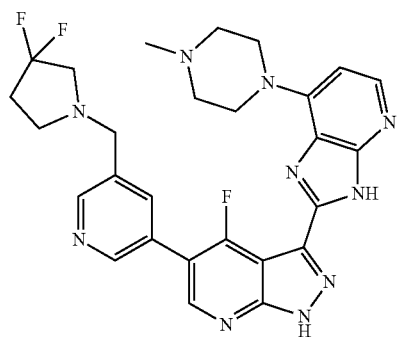 [SMILES: CN1CCN(c2ccnc3[nH]c(-c4n[nH]c5ncc(-c6cncc(CN7CCC(F)(F)C7)c6)c(F)c45)nc23)CC1] 673
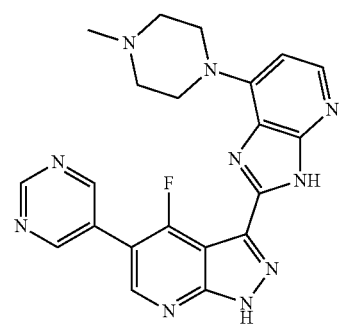 [SMILES: CN1CCN(c2ccnc3[nH]c(-c4n[nH]c5ncc(-c6cncnc6)c(F)c45)nc23)CC1] 674
TABLE 1-continued
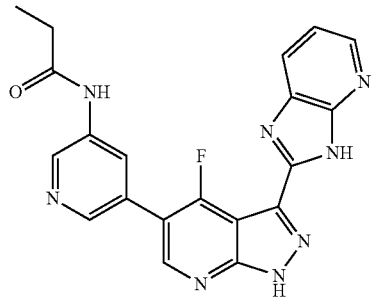 [SMILES: CCC(=O)Nc1cncc(-c2cnc3[nH]nc(-c4nc5cccnc5[nH]4)c3c2F)c1] 675
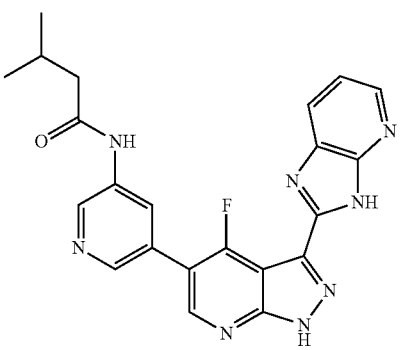 [SMILES: CC(C)CC(=O)Nc1cncc(-c2cnc3[nH]nc(-c4nc5cccnc5[nH]4)c3c2F)c1] 676
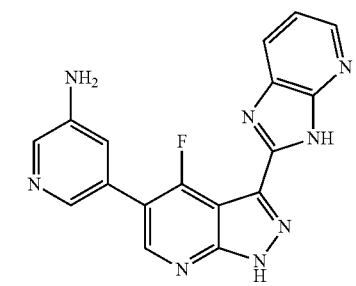 [SMILES: Nc1cncc(-c2cnc3[nH]nc(-c4nc5cccnc5[nH]4)c3c2F)c1] 677
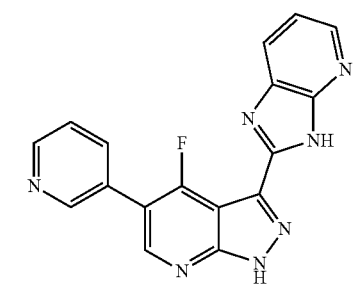 [SMILES: Fc1c(-c2cccnc2)cnc2[nH]nc(-c3nc4cccnc4[nH]3)c12] 678
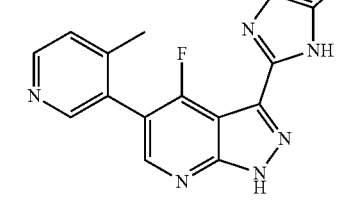 679

TABLE 1-continued
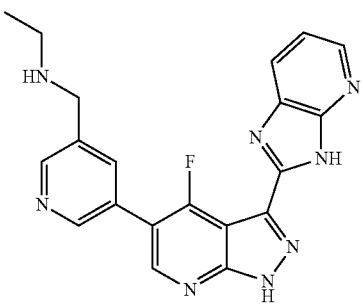 [SMILES: CCNCc1cncc(-c2cnc3[nH]nc(-c4nc5cccnc5[nH]4)c3c2F)c1]
680
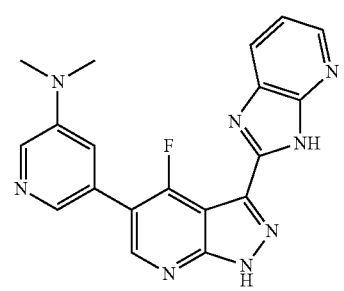 [SMILES: CN(C)c1cncc(-c2cnc3[nH]nc(-c4nc5cccnc5[nH]4)c3c2F)c1]
681
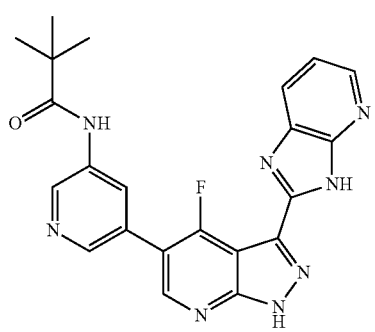 [SMILES: CC(C)(C)C(=O)Nc1cncc(-c2cnc3[nH]nc(-c4nc5cccnc5[nH]4)c3c2F)c1]
682
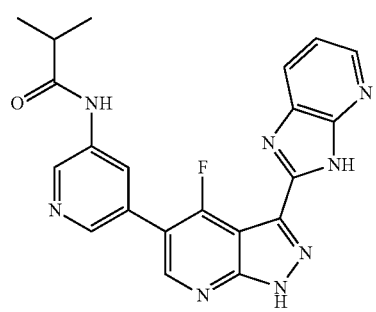 [SMILES: CC(C)C(=O)Nc1cncc(-c2cnc3[nH]nc(-c4nc5cccnc5[nH]4)c3c2F)c1]
683
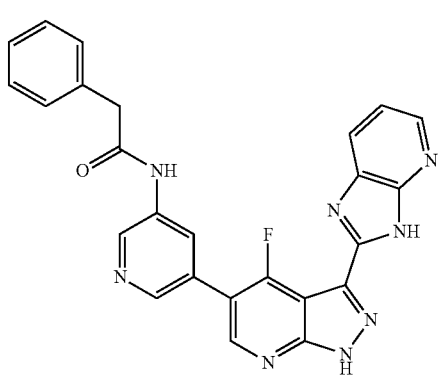 [SMILES: O=C(Cc1ccccc1)Nc1cncc(-c2cnc3[nH]nc(-c4nc5cccnc5[nH]4)c3c2F)c1]
684
TABLE 1-continued
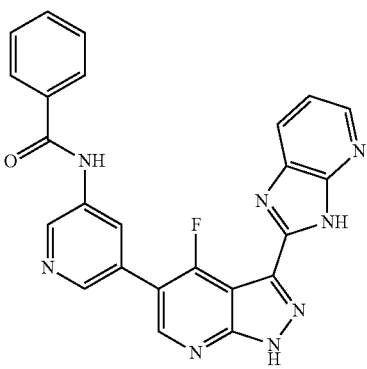 [SMILES: O=C(Nc1cncc(-c2cnc3[nH]nc(-c4nc5cccnc5[nH]4)c3c2F)c1)c1ccccc1]
685
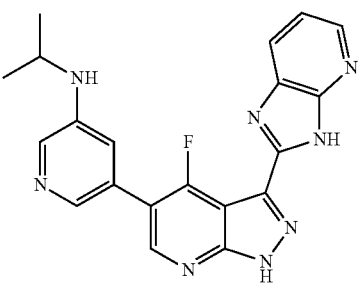 [SMILES: CC(C)Nc1cncc(-c2cnc3[nH]nc(-c4nc5cccnc5[nH]4)c3c2F)c1]
686
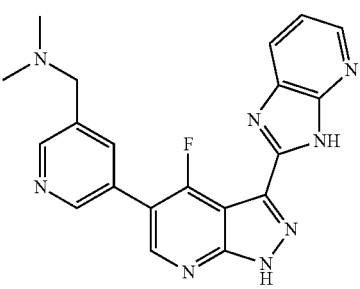 [SMILES: CN(C)Cc1cncc(-c2cnc3[nH]nc(-c4nc5cccnc5[nH]4)c3c2F)c1]
687
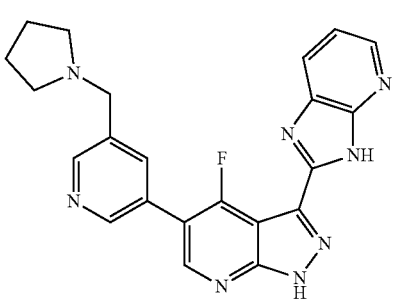 [SMILES: Fc1c(-c2cncc(CN3CCCC3)c2)cnc2[nH]nc(-c3nc4cccnc4[nH]3)c12]
688
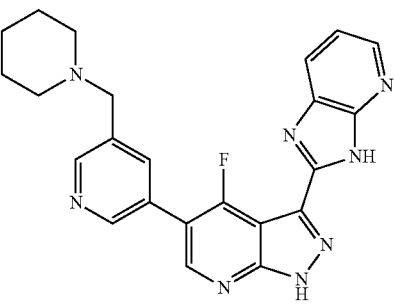 [SMILES: Fc1c(-c2cncc(CN3CCCCC3)c2)cnc2[nH]nc(-c3nc4cccnc4[nH]3)c12]
689

US 10,526,347 B2
213
TABLE 1-continued
214
TABLE 1-continued
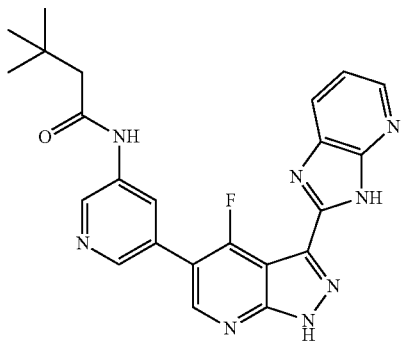 [SMILES: CC(C)(C)CC(=O)Nc1cncc(-c2cnc3[nH]nc(-c4nc5cccnc5[nH]4)c3c2F)c1]
690
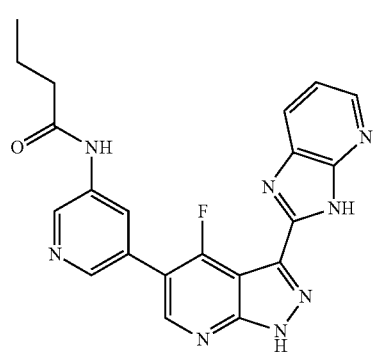 [SMILES: CCCC(=O)Nc1cncc(-c2cnc3[nH]nc(-c4nc5cccnc5[nH]4)c3c2F)c1]
691
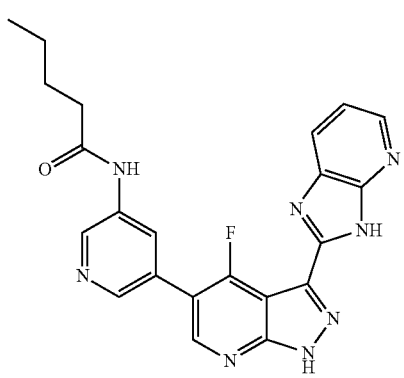 [SMILES: CCCCC(=O)Nc1cncc(-c2cnc3[nH]nc(-c4nc5cccnc5[nH]4)c3c2F)c1]
692
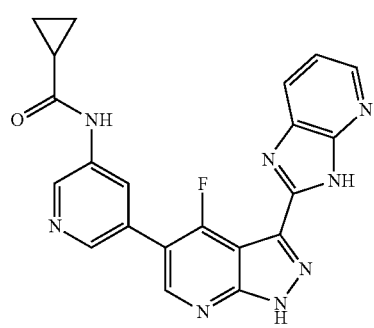 [SMILES: O=C(Nc1cncc(-c2cnc3[nH]nc(-c4nc5cccnc5[nH]4)c3c2F)c1)C1CC1]
693
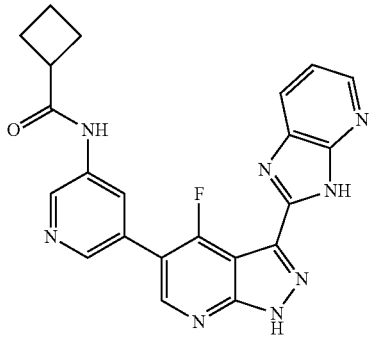 [SMILES: O=C(Nc1cncc(-c2cnc3[nH]nc(-c4nc5cccnc5[nH]4)c3c2F)c1)C1CCC1]
694
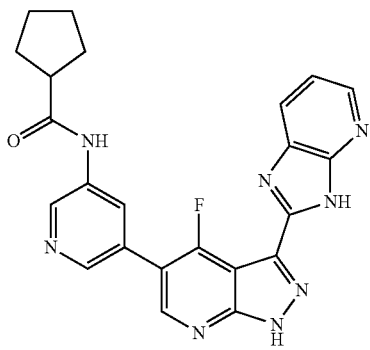 [SMILES: O=C(Nc1cncc(-c2cnc3[nH]nc(-c4nc5cccnc5[nH]4)c3c2F)c1)C1CCCC1]
695
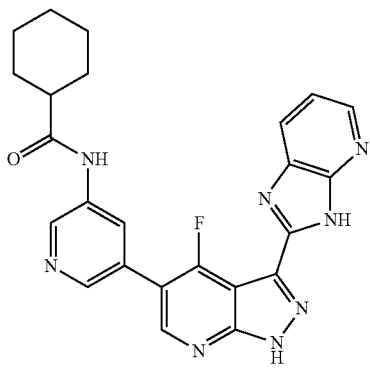 [SMILES: O=C(Nc1cncc(-c2cnc3[nH]nc(-c4nc5cccnc5[nH]4)c3c2F)c1)C1CCCCC1]
696
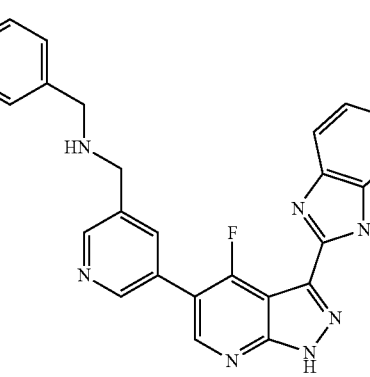
697

TABLE 1-continued
698 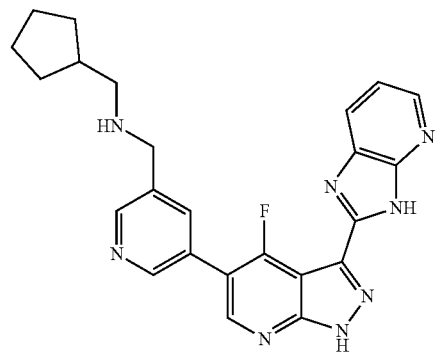 [SMILES: Fc1c(-c2cncc(CNCC3CCCC3)c2)cnc2[nH]nc(-c3nc4cccnc4[nH]3)c12]
699 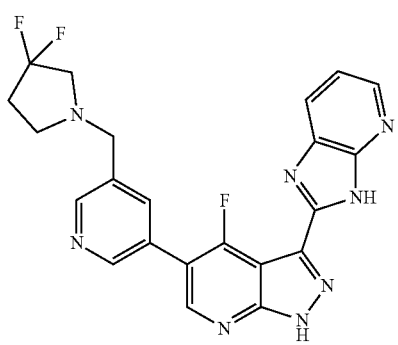 [SMILES: Fc1c(-c2cncc(CN3CCC(F)(F)C3)c2)cnc2[nH]nc(-c3nc4cccnc4[nH]3)c12]
700 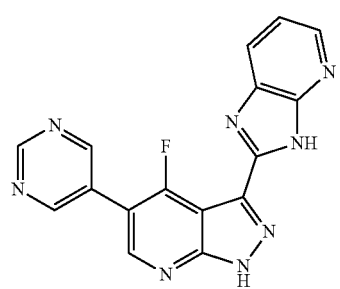 [SMILES: Fc1c(-c2cncnc2)cnc2[nH]nc(-c3nc4cccnc4[nH]3)c12]
701 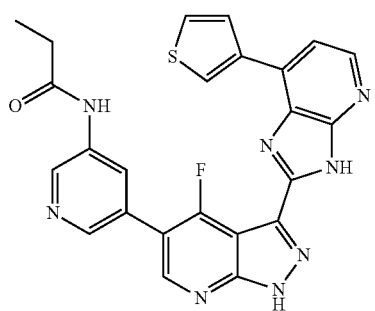 [SMILES: CCC(=O)Nc1cncc(-c2cnc3[nH]nc(-c4nc5c(-c6ccsc6)ccnc5[nH]4)c3c2F)c1]
702 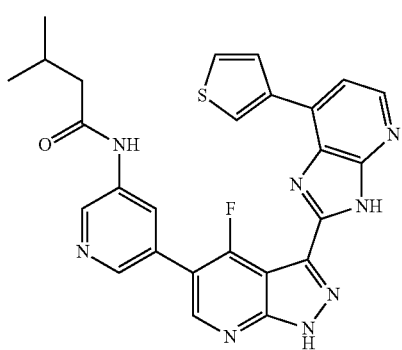
TABLE 1-continued
703 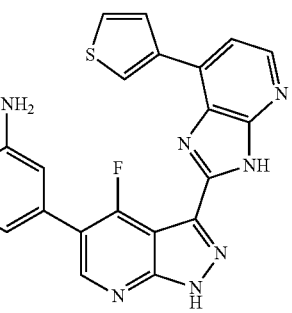
704 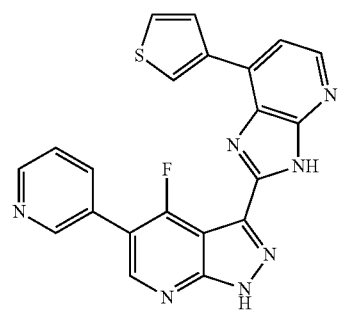 [SMILES: Fc1c(-c2cccnc2)cnc2[nH]nc(-c3nc4c(-c5ccsc5)ccnc4[nH]3)c12]
705 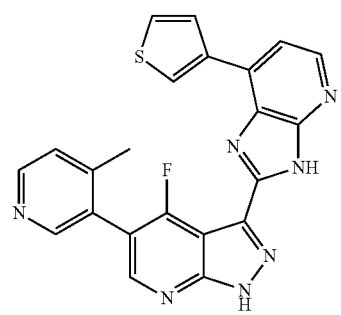
706 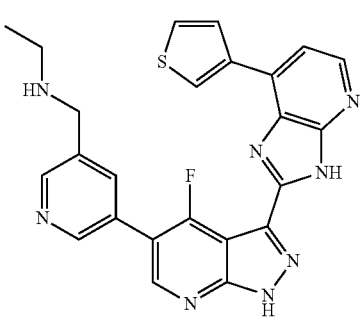 [SMILES: CCNCc1cncc(-c2cnc3[nH]nc(-c4nc5c(-c6ccsc6)ccnc5[nH]4)c3c2F)c1]
707 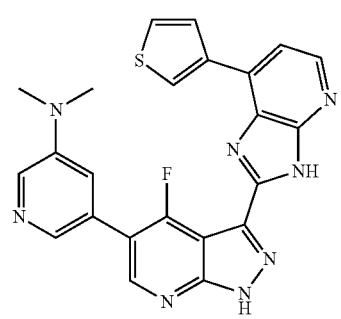

TABLE 1-continued
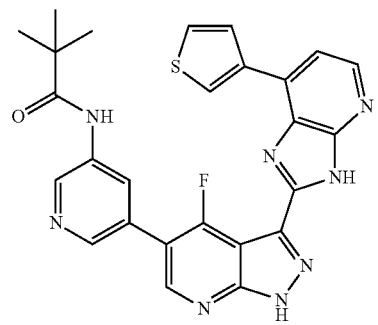 708
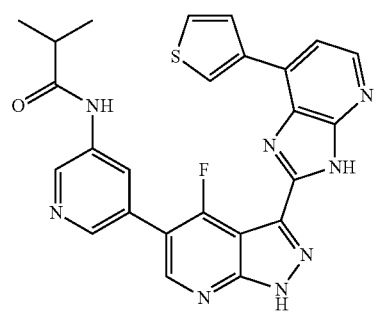 709
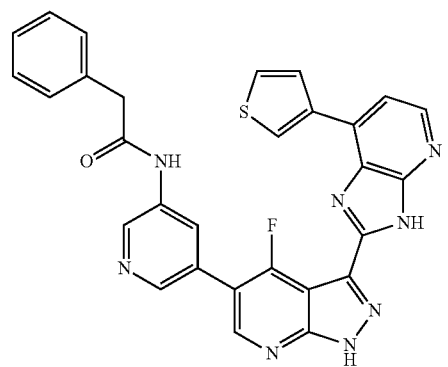 710
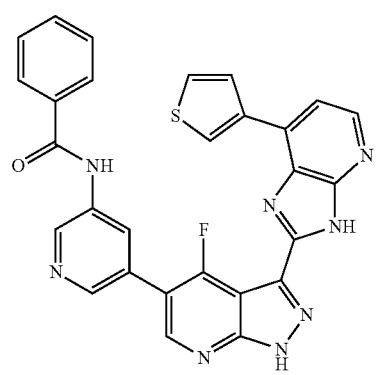 [SMILES: O=C(Nc1cncc(-c2cnc3[nH]nc(-c4nc5c(-c6ccsc6)ccnc5[nH]4)c3c2F)c1)c1ccccc1] 711
TABLE 1-continued
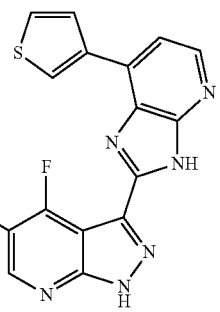 712
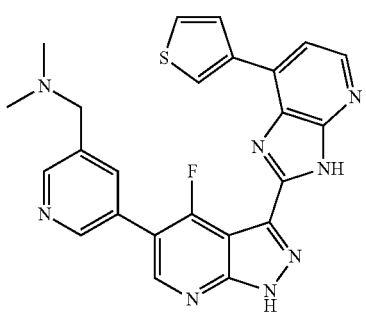 713
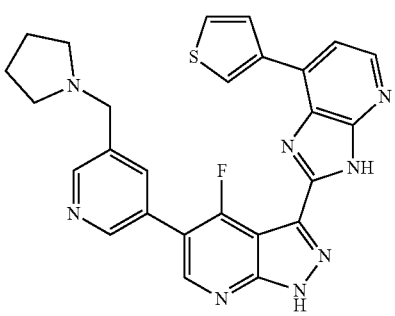 [SMILES: Fc1c(-c2cncc(CN3CCCC3)c2)cnc2[nH]nc(-c3nc4c(-c5ccsc5)ccnc4[nH]3)c12] 714
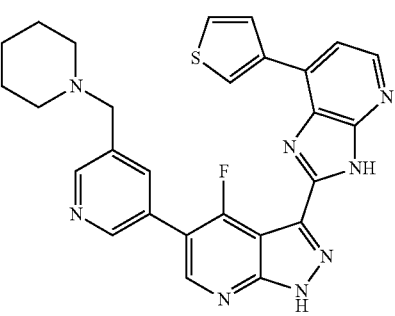 715
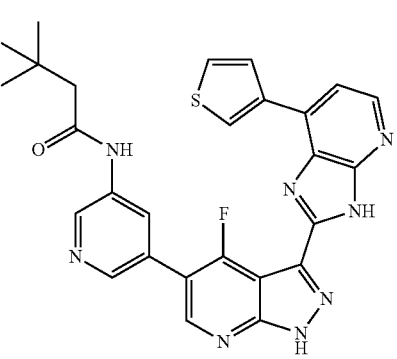 716

TABLE 1-continued
717 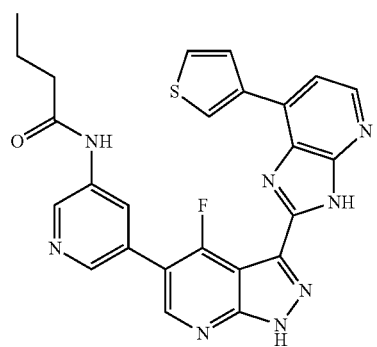 [SMILES: CCCC(=O)Nc1cncc(-c2cnc3[nH]nc(-c4nc5c(-c6ccsc6)ccnc5[nH]4)c3c2F)c1]
718 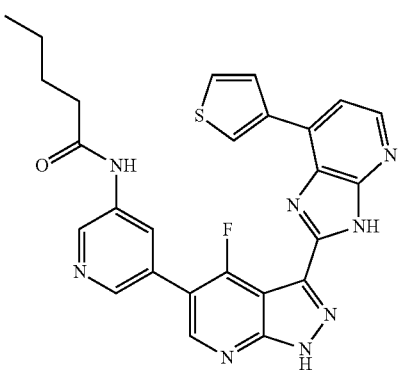
719 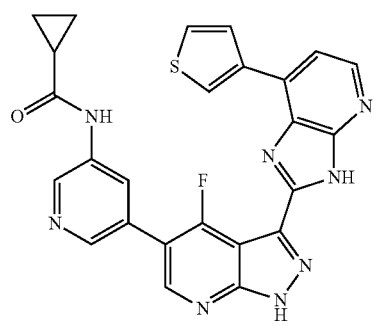 [SMILES: O=C(Nc1cncc(-c2cnc3[nH]nc(-c4nc5c(-c6ccsc6)ccnc5[nH]4)c3c2F)c1)C1CC1]
720 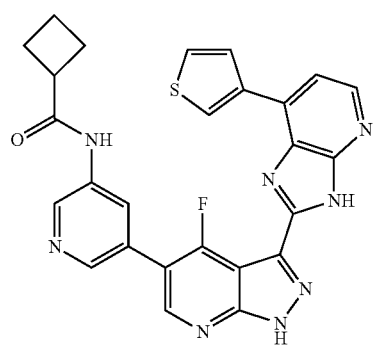 [SMILES: O=C(Nc1cncc(-c2cnc3[nH]nc(-c4nc5c(-c6ccsc6)ccnc5[nH]4)c3c2F)c1)C1CCC1]
TABLE 1-continued
721 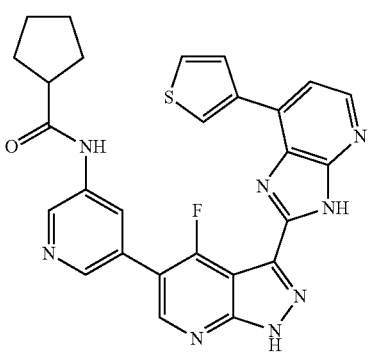 [SMILES: O=C(Nc1cncc(-c2cnc3[nH]nc(-c4nc5c(-c6ccsc6)ccnc5[nH]4)c3c2F)c1)C1CCCC1]
722 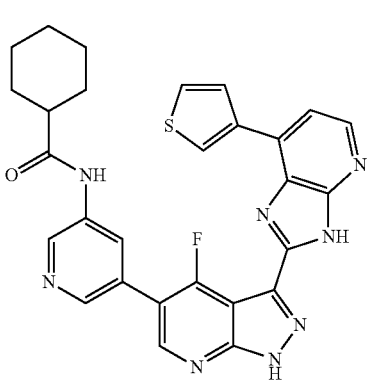 [SMILES: O=C(Nc1cncc(-c2cnc3[nH]nc(-c4nc5c(-c6ccsc6)ccnc5[nH]4)c3c2F)c1)C1CCCCC1]
723 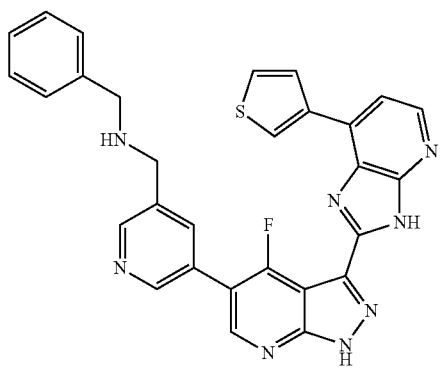
724 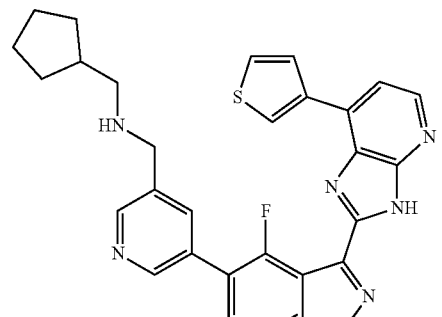

TABLE 1-continued
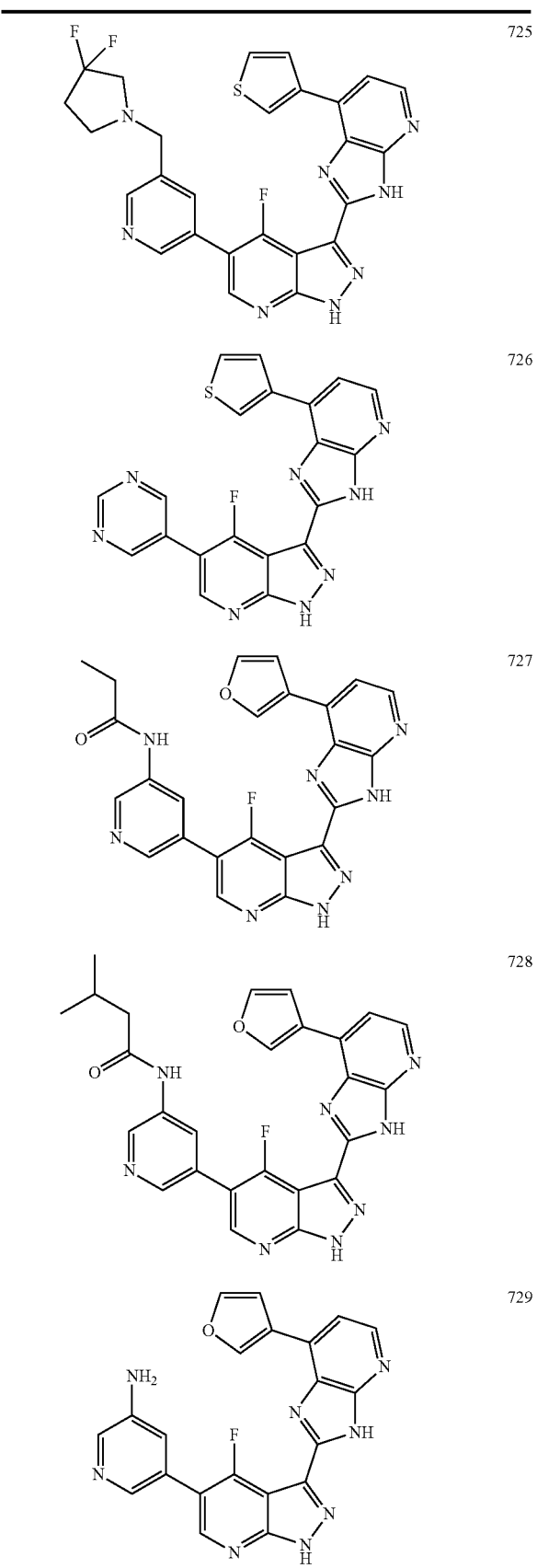
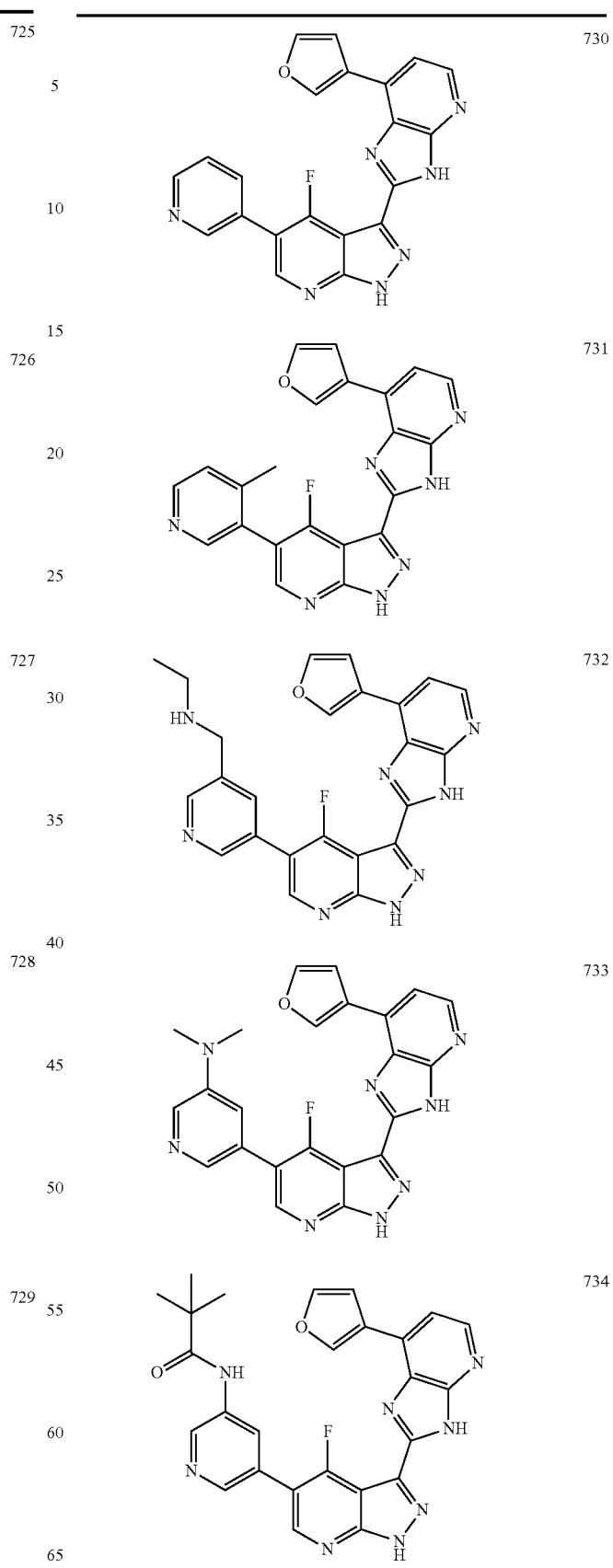

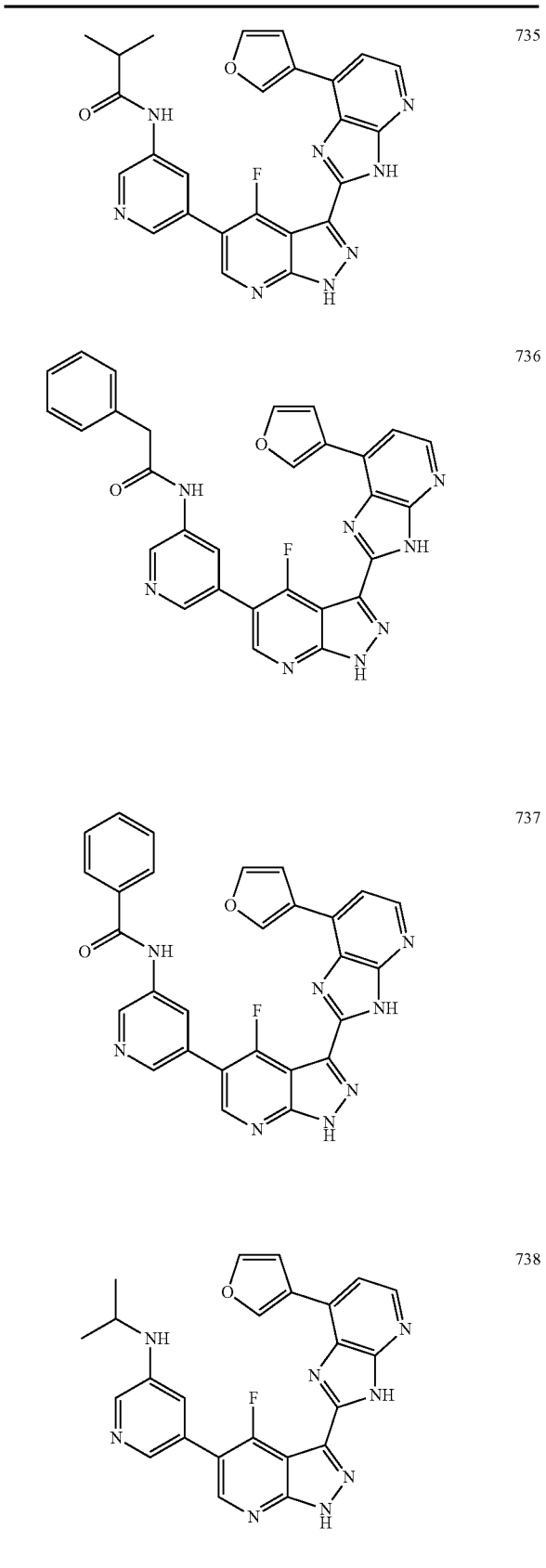

TABLE 1-continued
| | |
|---|---|
| 744 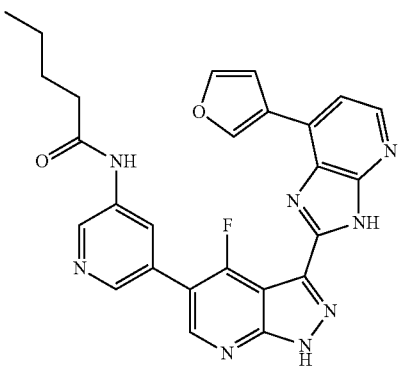 [SMILES: CCCCC(=O)Nc1cncc(-c2cnc3[nH]nc(-c4nc5c(-c6ccoc6)ccnc5[nH]4)c3c2F)c1] | 748 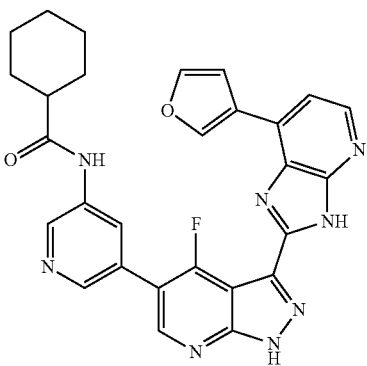 |
| 745 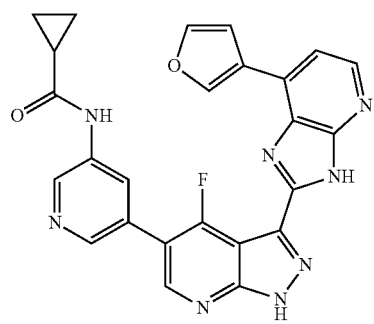 [SMILES: O=C(Nc1cncc(-c2cnc3[nH]nc(-c4nc5c(-c6ccoc6)ccnc5[nH]4)c3c2F)c1)C1CC1] | 749 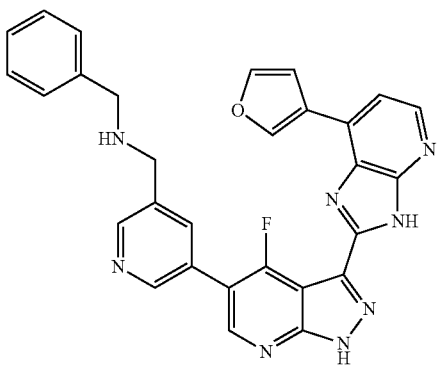 |
| 746 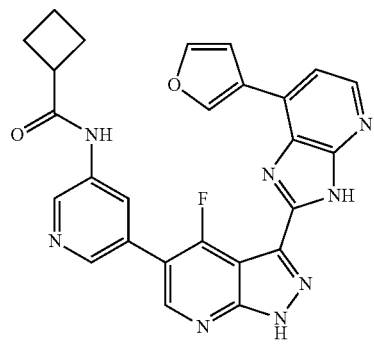 [SMILES: O=C(Nc1cncc(-c2cnc3[nH]nc(-c4nc5c(-c6ccoc6)ccnc5[nH]4)c3c2F)c1)C1CCC1] | 750 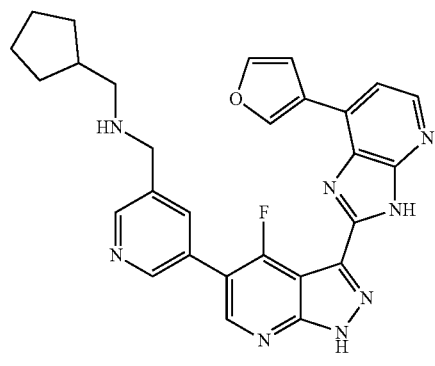 |
| 747 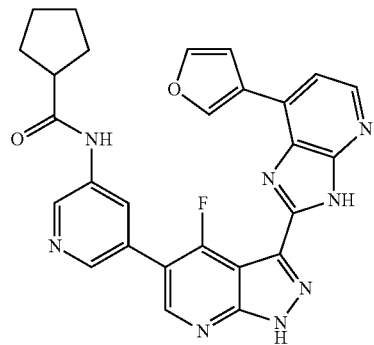 [SMILES: O=C(Nc1cncc(-c2cnc3[nH]nc(-c4nc5c(-c6ccoc6)ccnc5[nH]4)c3c2F)c1)C1CCCC1] | 751 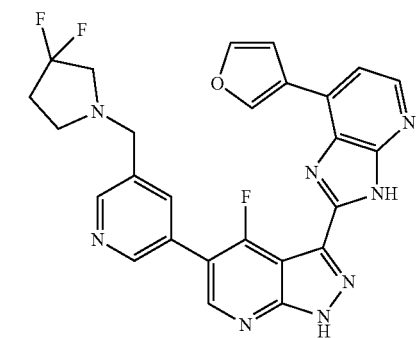 [SMILES: Fc1c(-c2cncc(CN3CCC(F)(F)C3)c2)cnc2[nH]nc(-c3nc4c(-c5ccoc5)ccnc4[nH]3)c12] |

TABLE 1-continued
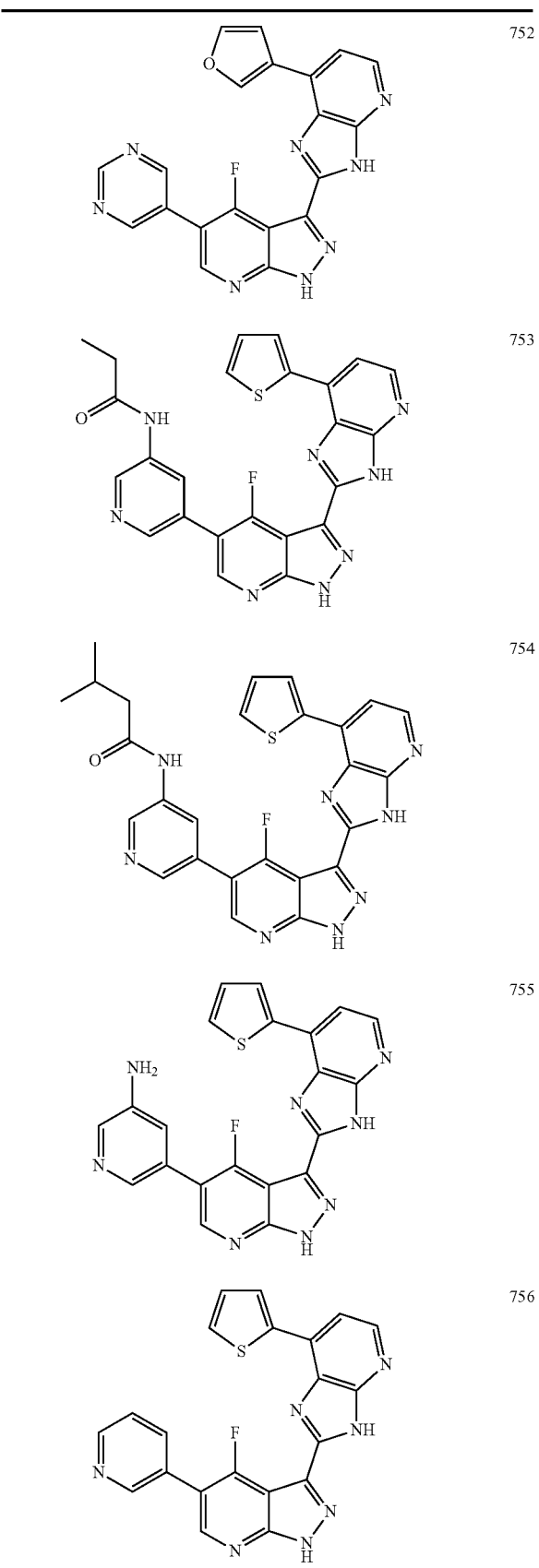
TABLE 1-continued
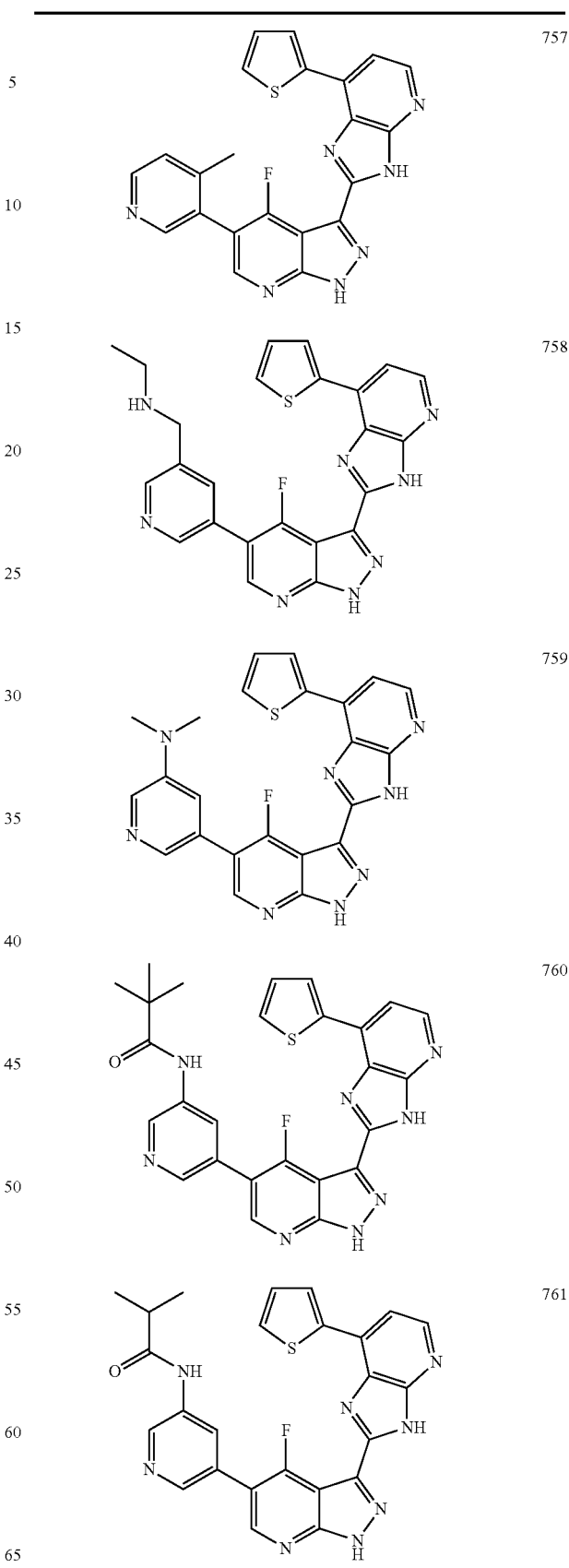

TABLE 1-continued
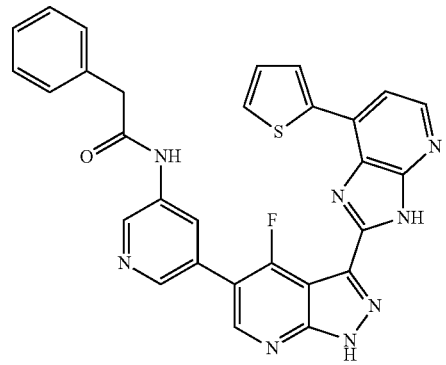 [SMILES: O=C(Cc1ccccc1)Nc1cncc(-c2cnc3[nH]nc(-c4nc5c(-c6cccs6)ccnc5[nH]4)c3c2F)c1] 762
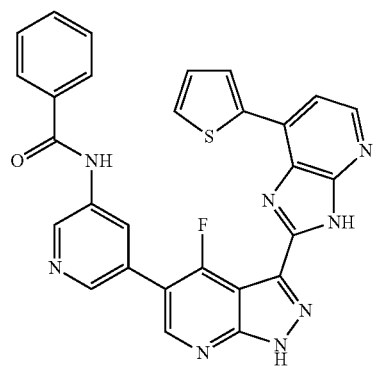 [SMILES: O=C(Nc1cncc(-c2cnc3[nH]nc(-c4nc5c(-c6cccs6)ccnc5[nH]4)c3c2F)c1)c1ccccc1] 763
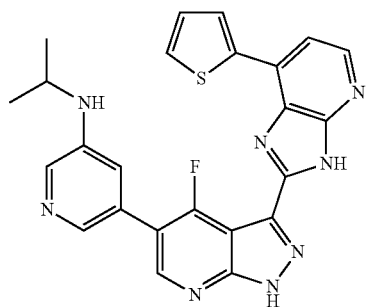 [SMILES: CC(C)Nc1cncc(-c2cnc3[nH]nc(-c4nc5c(-c6cccs6)ccnc5[nH]4)c3c2F)c1] 764
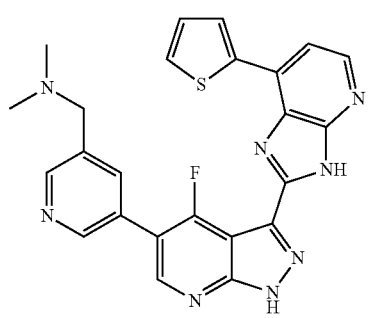 [SMILES: CN(C)Cc1cncc(-c2cnc3[nH]nc(-c4nc5c(-c6cccs6)ccnc5[nH]4)c3c2F)c1] 765
TABLE 1-continued
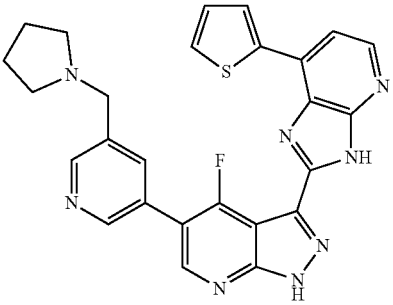 [SMILES: Fc1c(-c2cncc(CN3CCCC3)c2)cnc2[nH]nc(-c3nc4c(-c5cccs5)ccnc4[nH]3)c12] 766
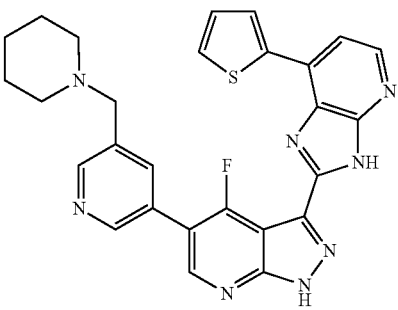 [SMILES: Fc1c(-c2cncc(CN3CCCCC3)c2)cnc2[nH]nc(-c3nc4c(-c5cccs5)ccnc4[nH]3)c12] 767
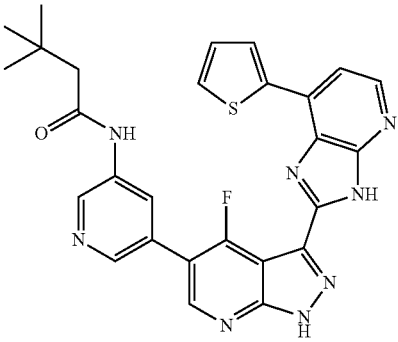 [SMILES: CC(C)(C)CC(=O)Nc1cncc(-c2cnc3[nH]nc(-c4nc5c(-c6cccs6)ccnc5[nH]4)c3c2F)c1] 768
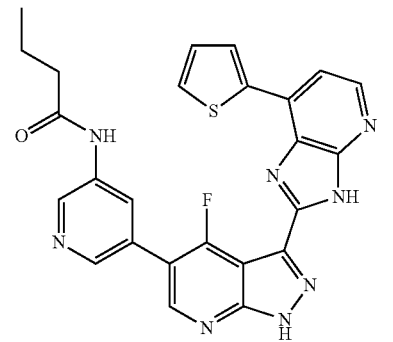 [SMILES: CCCC(=O)Nc1cncc(-c2cnc3[nH]nc(-c4nc5c(-c6cccs6)ccnc5[nH]4)c3c2F)c1] 769

TABLE 1-continued
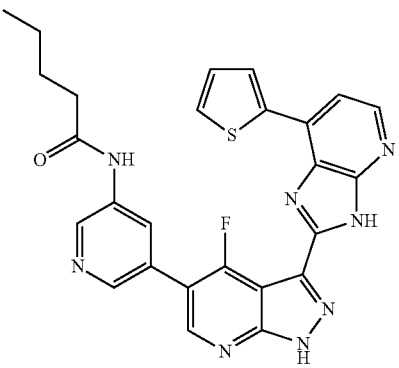 [SMILES: CCCCC(=O)Nc1cncc(-c2cnc3[nH]nc(-c4nc5c(-c6cccs6)ccnc5[nH]4)c3c2F)c1] 770
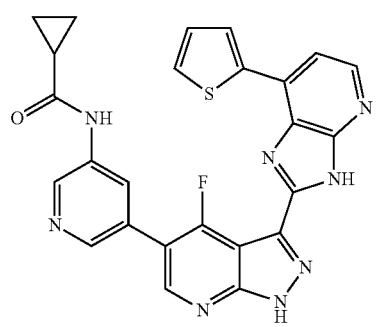 [SMILES: O=C(Nc1cncc(-c2cnc3[nH]nc(-c4nc5c(-c6cccs6)ccnc5[nH]4)c3c2F)c1)C1CC1] 771
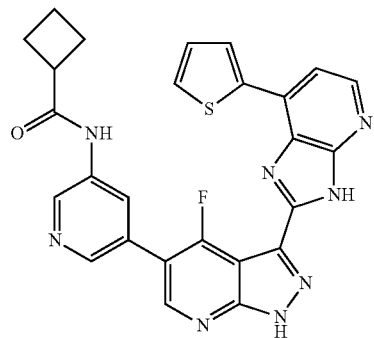 [SMILES: O=C(Nc1cncc(-c2cnc3[nH]nc(-c4nc5c(-c6cccs6)ccnc5[nH]4)c3c2F)c1)C1CCC1] 772
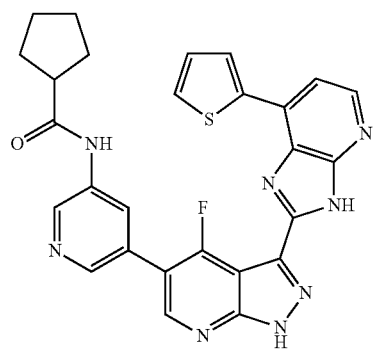 [SMILES: O=C(Nc1cncc(-c2cnc3[nH]nc(-c4nc5c(-c6cccs6)ccnc5[nH]4)c3c2F)c1)C1CCCC1] 773
TABLE 1-continued
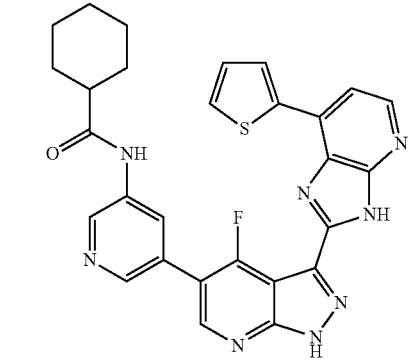 [SMILES: O=C(Nc1cncc(-c2cnc3[nH]nc(-c4nc5c(-c6cccs6)ccnc5[nH]4)c3c2F)c1)C1CCCCC1] 774
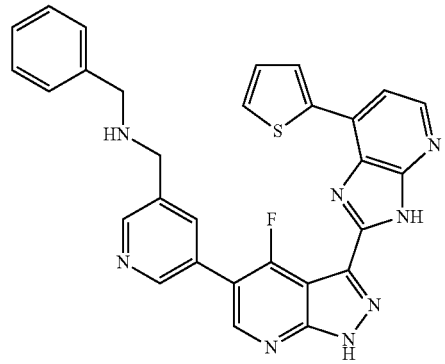 [SMILES: Fc1c(-c2cncc(CNCc3ccccc3)c2)cnc2[nH]nc(-c3nc4c(-c5cccs5)ccnc4[nH]3)c12] 775
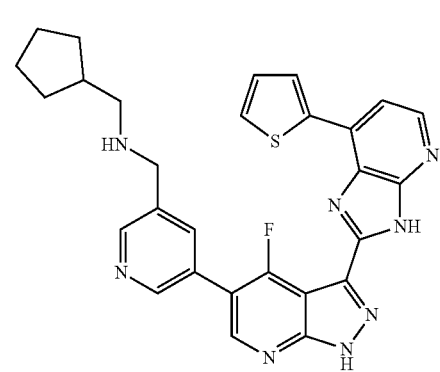 [SMILES: Fc1c(-c2cncc(CNCC3CCCC3)c2)cnc2[nH]nc(-c3nc4c(-c5cccs5)ccnc4[nH]3)c12] 776
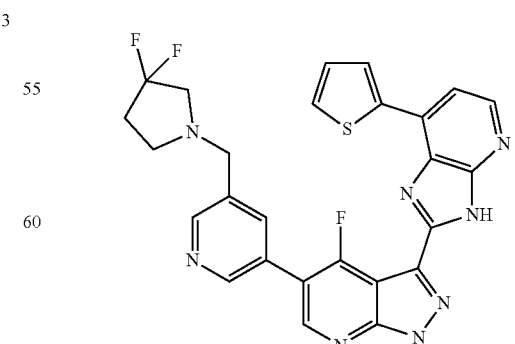 777

TABLE 1-continued
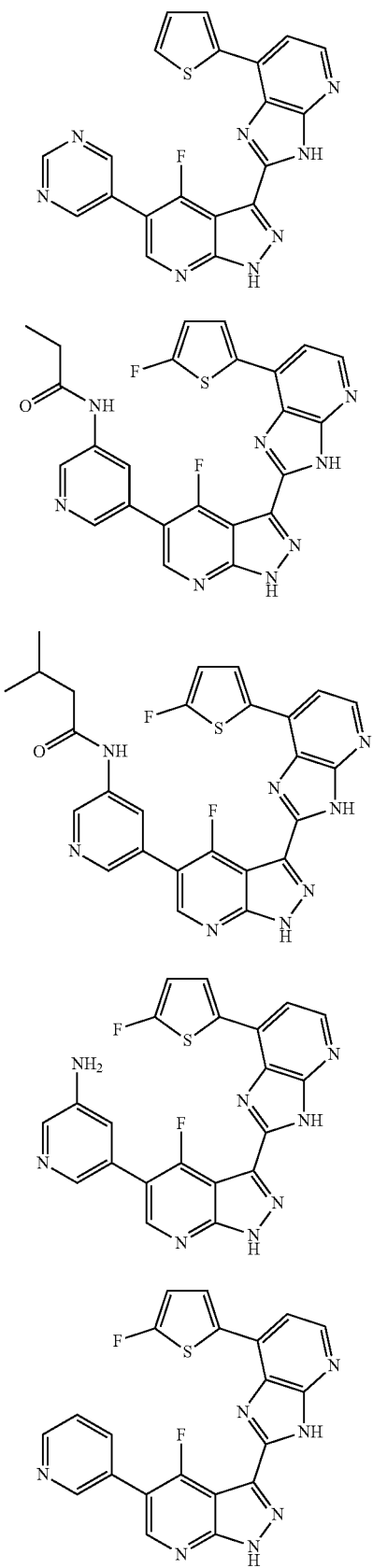
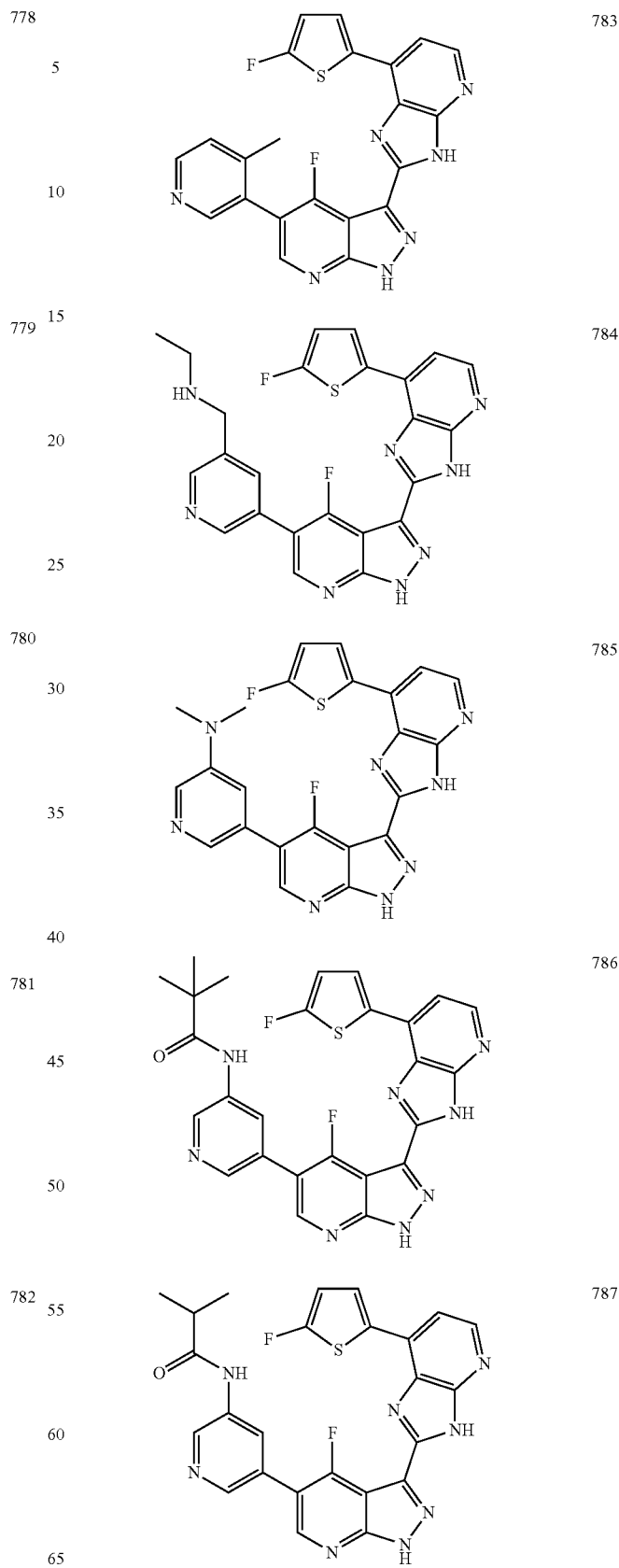

TABLE 1-continued
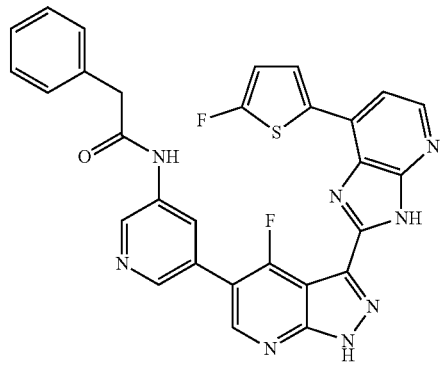
788
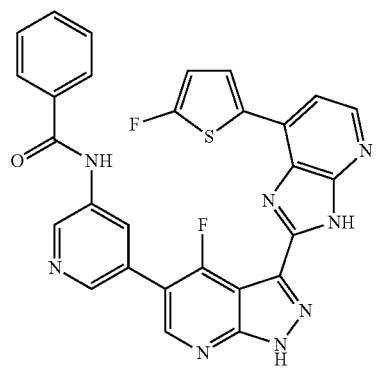 [SMILES: O=C(Nc1cncc(-c2cnc3[nH]nc(-c4nc5c(-c6ccc(F)s6)ccnc5[nH]4)c3c2F)c1)c1ccccc1]
789
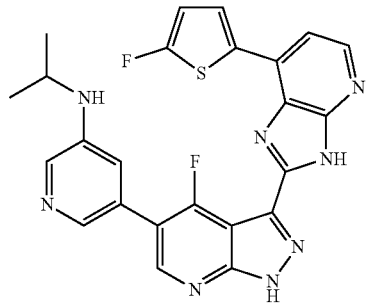
790
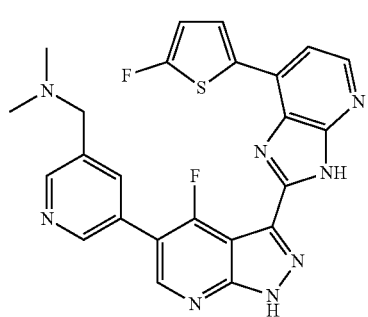
791
TABLE 1-continued
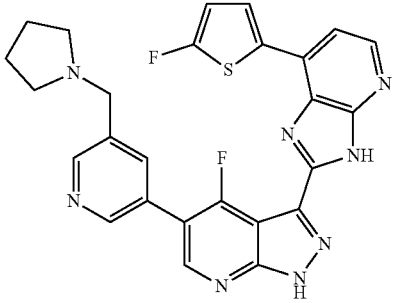 [SMILES: Fc1ccc(-c2ccnc3[nH]c(-c4n[nH]c5ncc(-c6cncc(CN7CCCC7)c6)c(F)c45)nc23)s1]
792
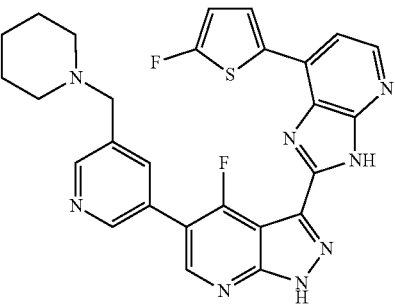 [SMILES: Fc1ccc(-c2ccnc3[nH]c(-c4n[nH]c5ncc(-c6cncc(CN7CCCCC7)c6)c(F)c45)nc23)s1]
793
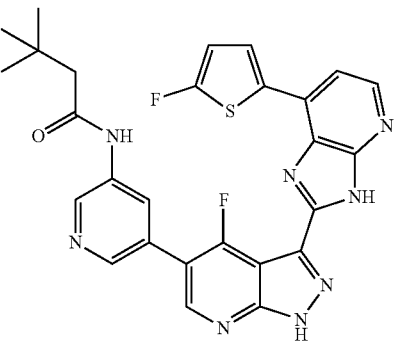 [SMILES: CC(C)(C)CC(=O)Nc1cncc(-c2cnc3[nH]nc(-c4nc5c(-c6ccc(F)s6)ccnc5[nH]4)c3c2F)c1]
794
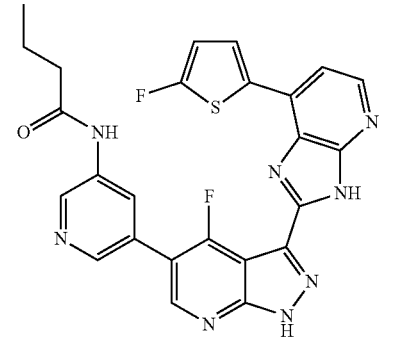 [SMILES: CCCC(=O)Nc1cncc(-c2cnc3[nH]nc(-c4nc5c(-c6ccc(F)s6)ccnc5[nH]4)c3c2F)c1]
795

TABLE 1-continued
| | |
|---|---|
| 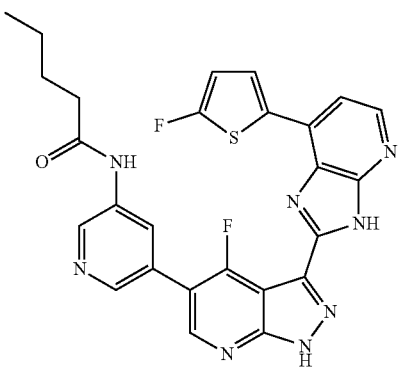 [SMILES: CCCCC(=O)Nc1cncc(-c2cnc3[nH]nc(-c4nc5c(-c6ccc(F)s6)ccnc5[nH]4)c3c2F)c1] | 796 |
| 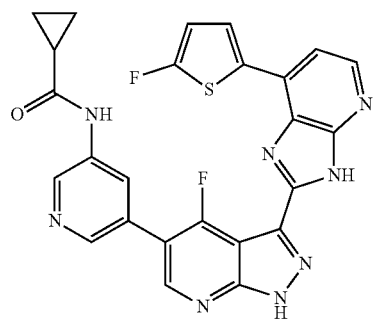 [SMILES: O=C(Nc1cncc(-c2cnc3[nH]nc(-c4nc5c(-c6ccc(F)s6)ccnc5[nH]4)c3c2F)c1)C1CC1] | 797 |
| 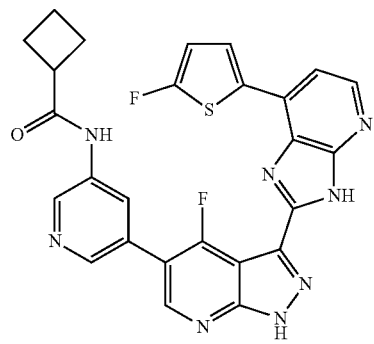 [SMILES: O=C(Nc1cncc(-c2cnc3[nH]nc(-c4nc5c(-c6ccc(F)s6)ccnc5[nH]4)c3c2F)c1)C1CCC1] | 798 |
| 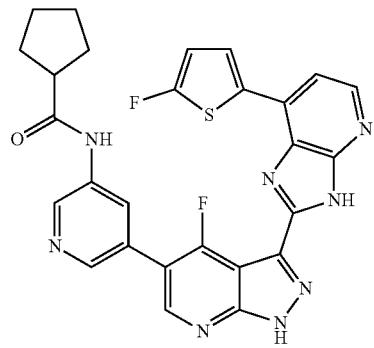 [SMILES: O=C(Nc1cncc(-c2cnc3[nH]nc(-c4nc5c(-c6ccc(F)s6)ccnc5[nH]4)c3c2F)c1)C1CCCC1] | 799 |
TABLE 1-continued
| | |
|---|---|
| 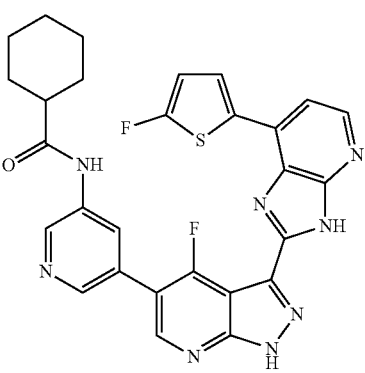 | 800 |
| 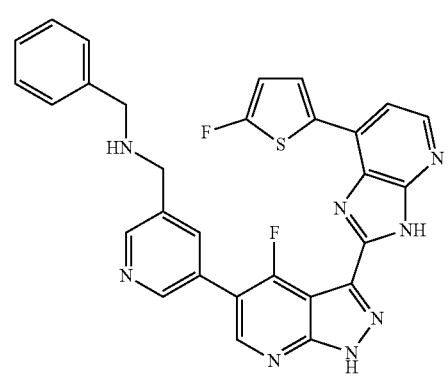 [SMILES: Fc1ccc(-c2ccnc3[nH]c(-c4n[nH]c5ncc(-c6cncc(CNCc7ccccc7)c6)c(F)c45)nc23)s1] | 801 |
|  | 802 |
| 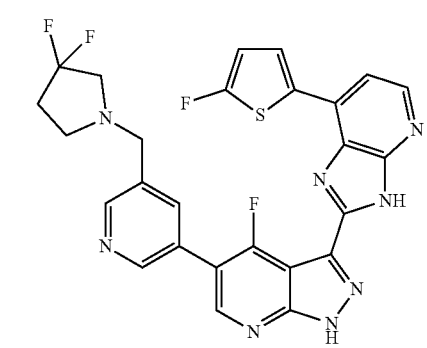 [SMILES: Fc1ccc(-c2ccnc3[nH]c(-c4n[nH]c5ncc(-c6cncc(CN7CCC(F)(F)C7)c6)c(F)c45)nc23)s1] | 803 |

TABLE 1-continued

TABLE 1-continued
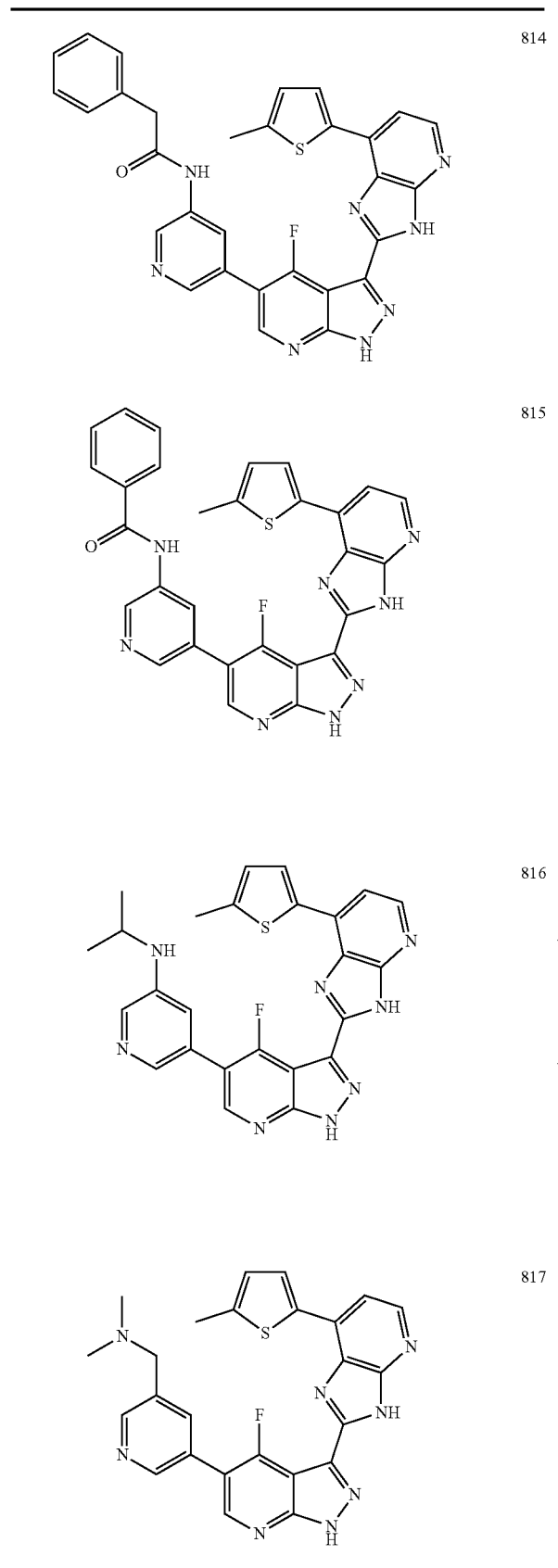
814
815
816
817
TABLE 1-continued
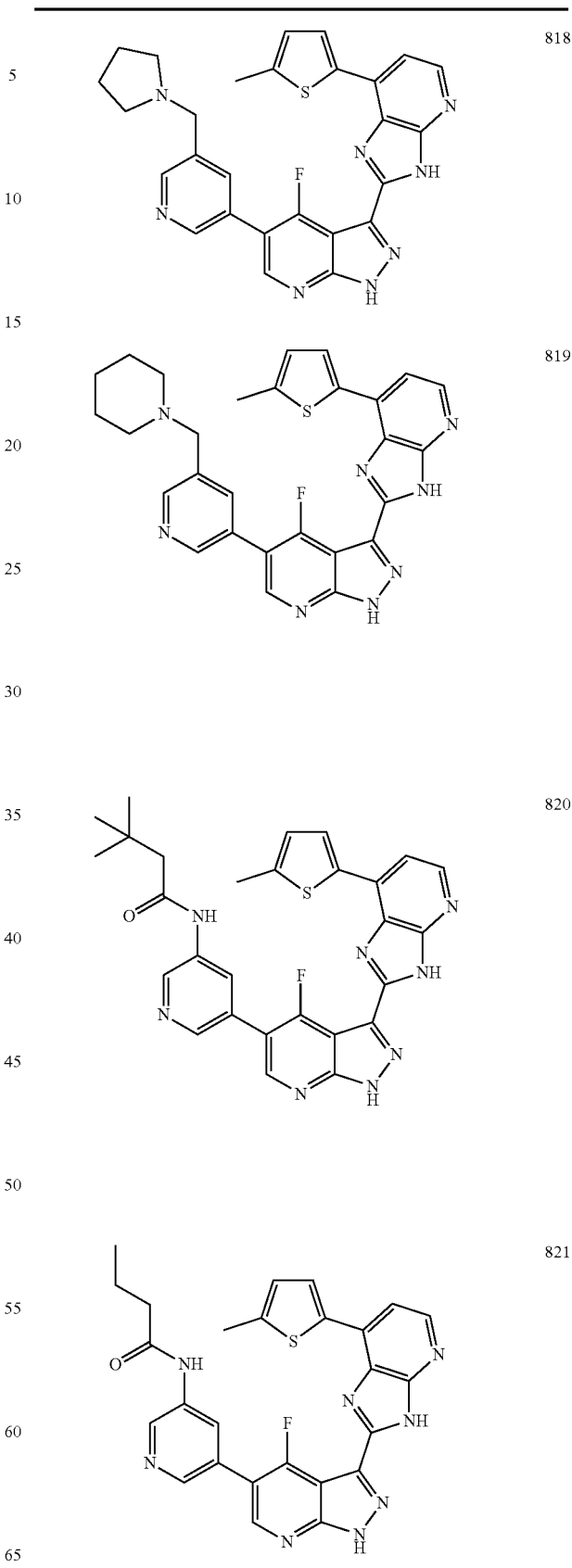
818
819
820
821

TABLE 1-continued
| | |
|---|---|
| 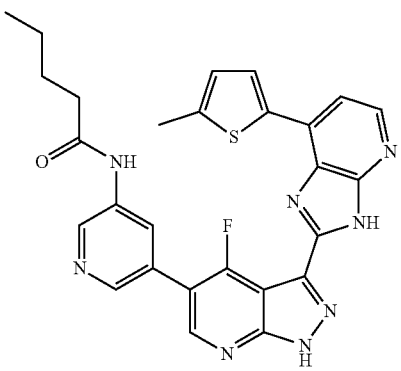 [SMILES: CCCCC(=O)Nc1cncc(-c2cnc3[nH]nc(-c4nc5c(-c6ccc(C)s6)ccnc5[nH]4)c3c2F)c1] | 822 |
| 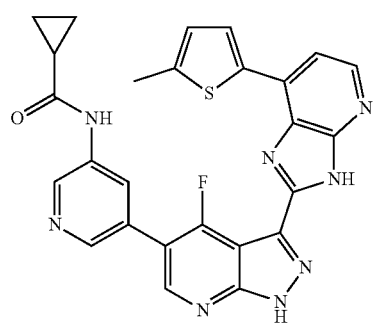 [SMILES: Cc1ccc(-c2ccnc3[nH]c(-c4n[nH]c5ncc(-c6cncc(NC(=O)C7CC7)c6)c(F)c45)nc23)s1] | 823 |
| 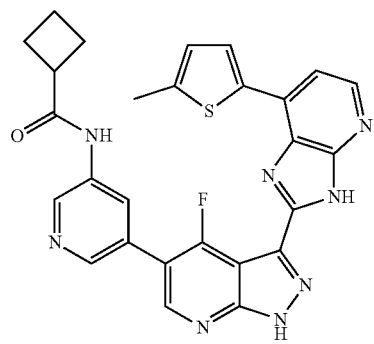 [SMILES: Cc1ccc(-c2ccnc3[nH]c(-c4n[nH]c5ncc(-c6cncc(NC(=O)C7CCC7)c6)c(F)c45)nc23)s1] | 824 |
| 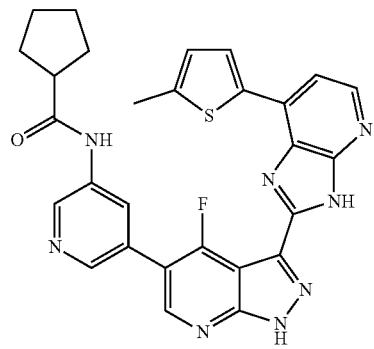 [SMILES: Cc1ccc(-c2ccnc3[nH]c(-c4n[nH]c5ncc(-c6cncc(NC(=O)C7CCCC7)c6)c(F)c45)nc23)s1] | 825 |
| 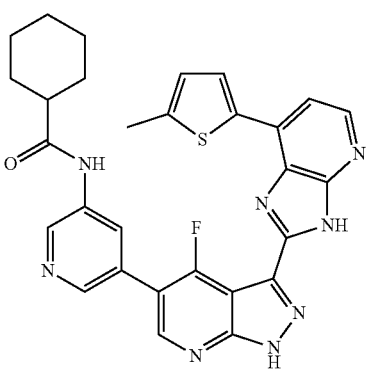 [SMILES: Cc1ccc(-c2ccnc3[nH]c(-c4n[nH]c5ncc(-c6cncc(NC(=O)C7CCCCC7)c6)c(F)c45)nc23)s1] | 826 |
| 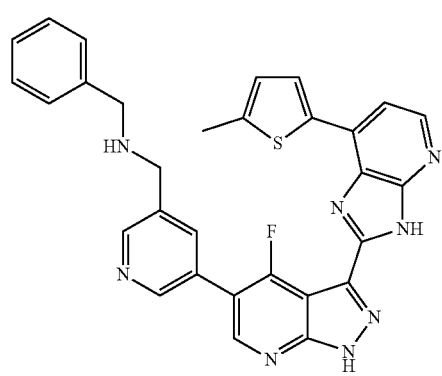 [SMILES: Cc1ccc(-c2ccnc3[nH]c(-c4n[nH]c5ncc(-c6cncc(CNCc7ccccc7)c6)c(F)c45)nc23)s1] | 827 |
| 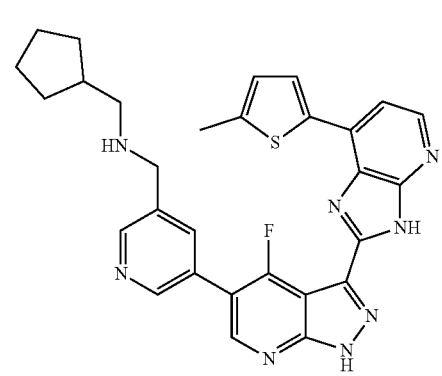 [SMILES: Cc1ccc(-c2ccnc3[nH]c(-c4n[nH]c5ncc(-c6cncc(CNCC7CCCC7)c6)c(F)c45)nc23)s1] | 828 |
| 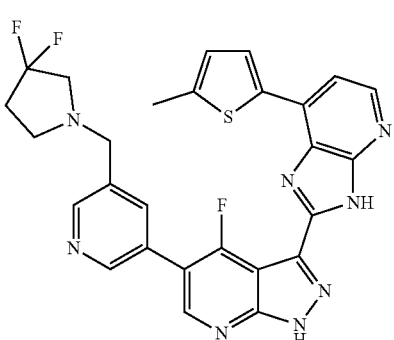 | 829 |

TABLE 1-continued
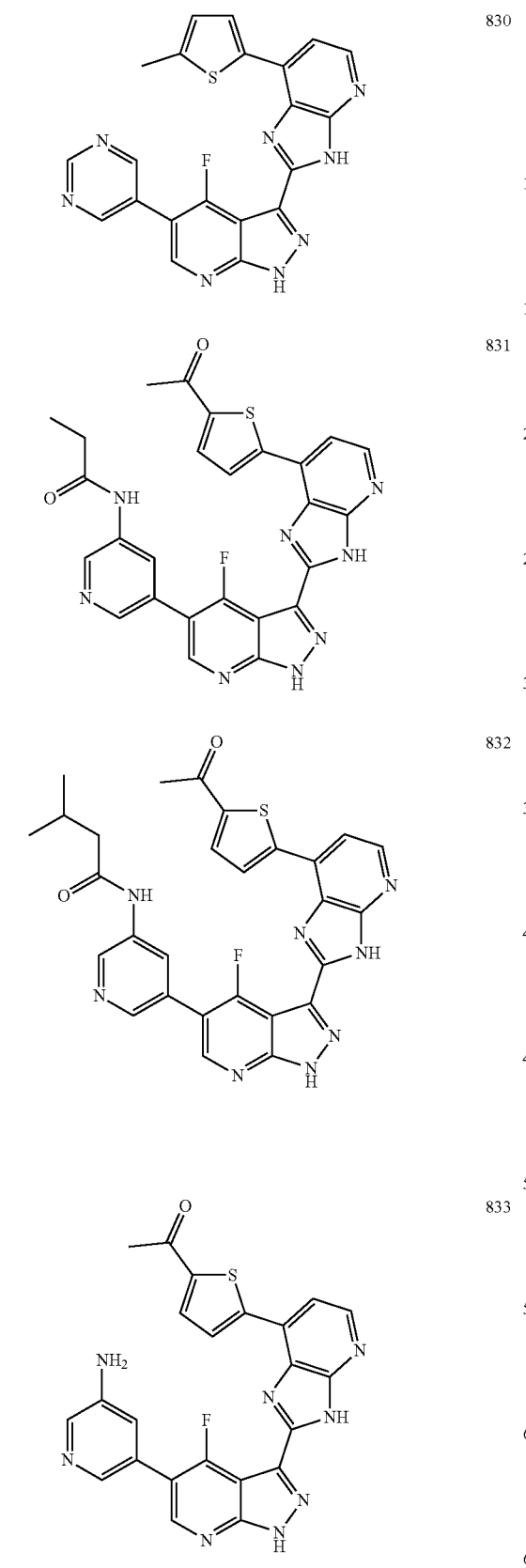
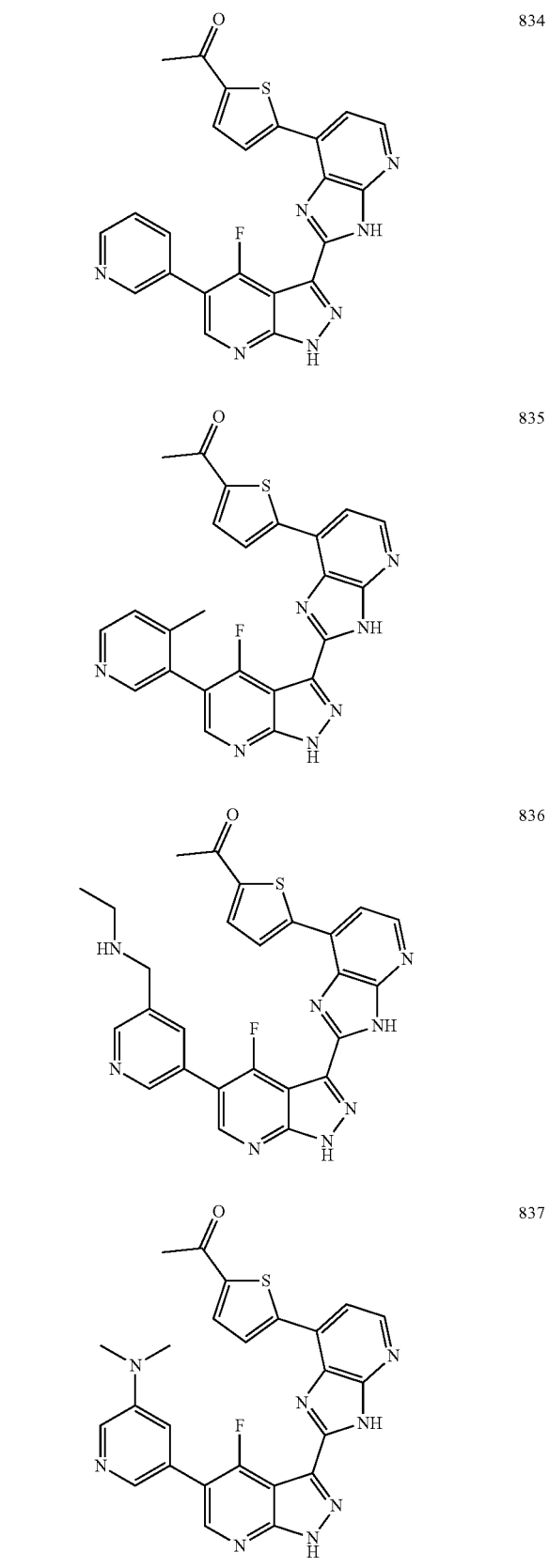

TABLE 1-continued
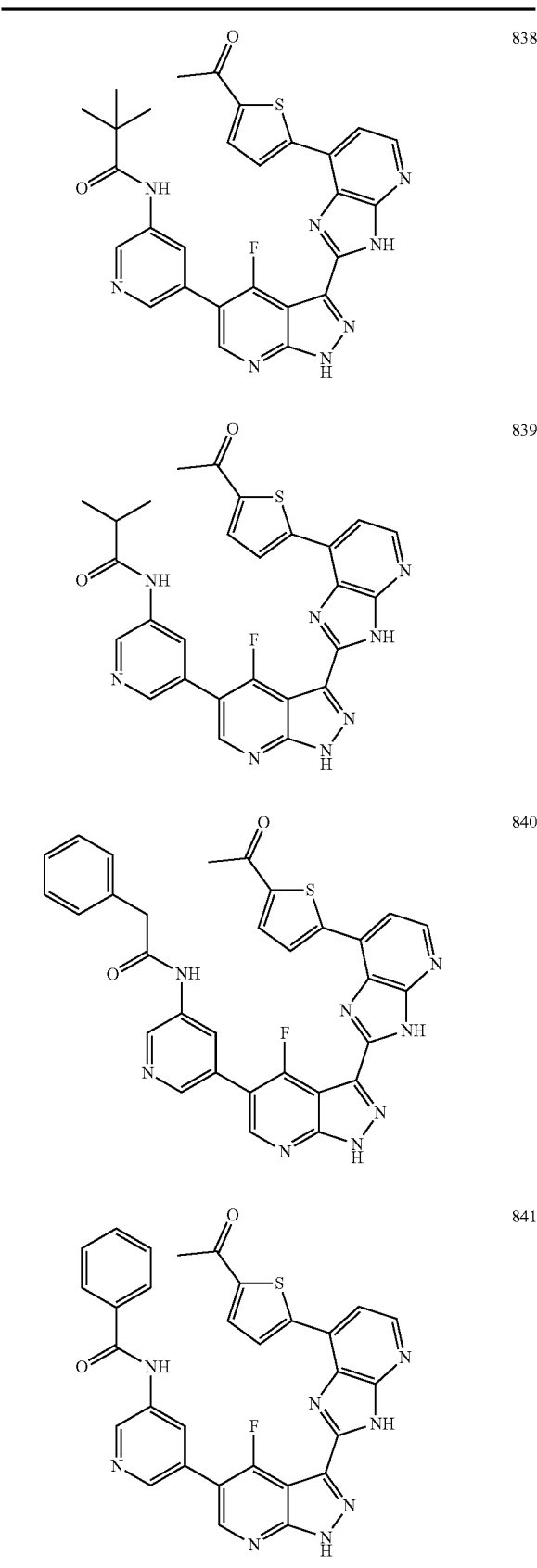
838
839
840
841
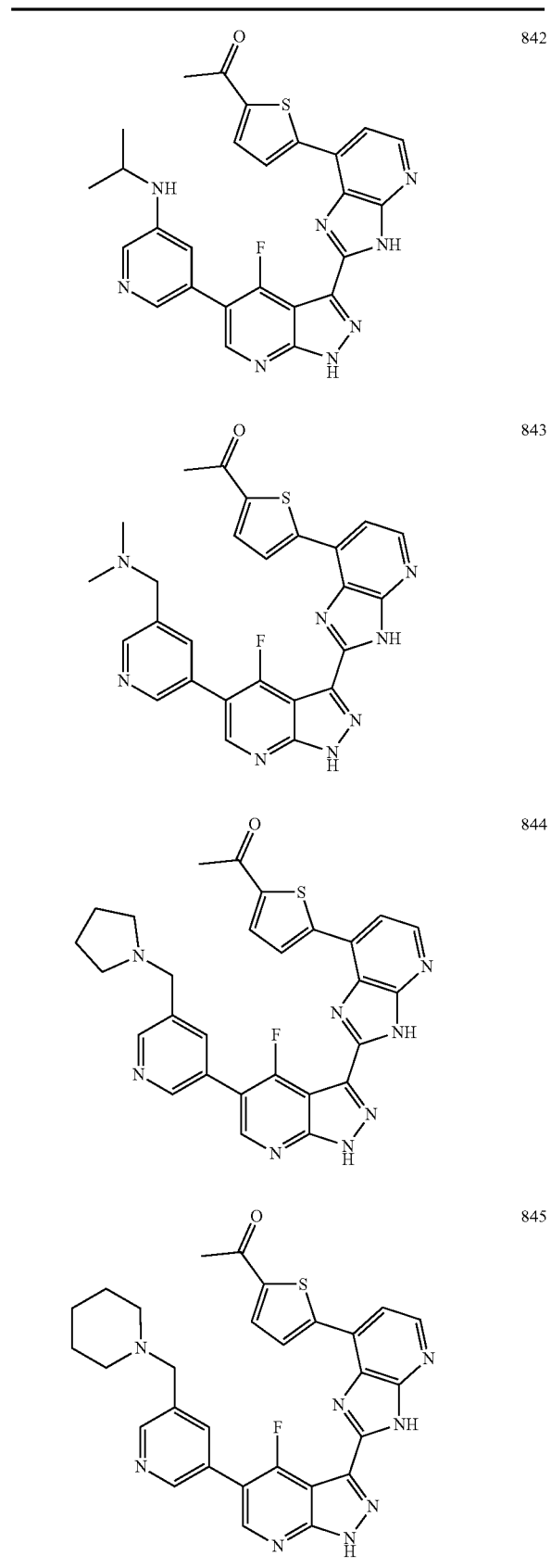
842
843
844
845

TABLE 1-continued
| | |
|---|---|
| 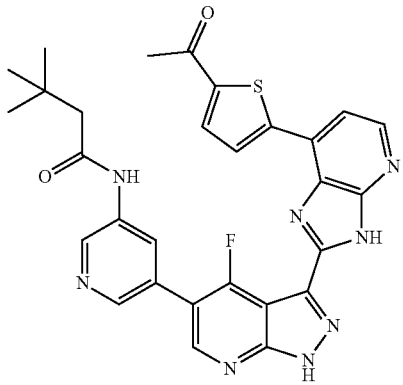 [SMILES: CC(=O)c1ccc(-c2ccnc3[nH]c(-c4n[nH]c5ncc(-c6cncc(NC(=O)CC(C)(C)C)c6)c(F)c45)nc23)s1] 846 | 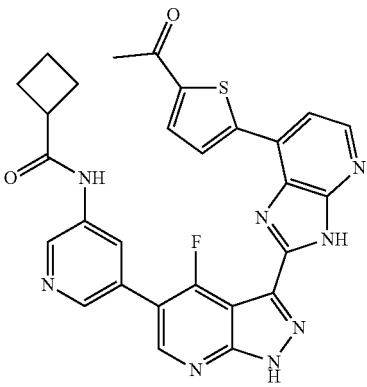 850 |
| 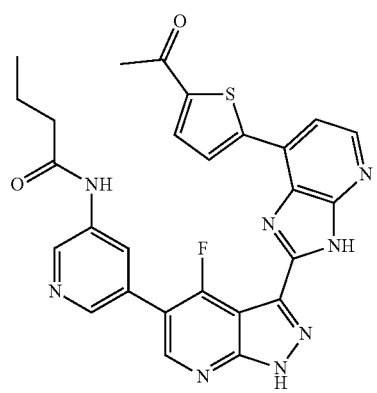 [SMILES: CCCC(=O)Nc1cncc(-c2cnc3[nH]nc(-c4nc5c(-c6ccc(C(C)=O)s6)ccnc5[nH]4)c3c2F)c1] 847 | 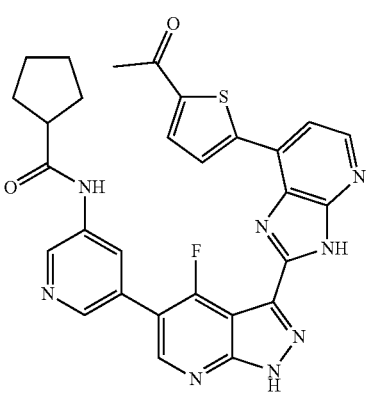 851 |
| 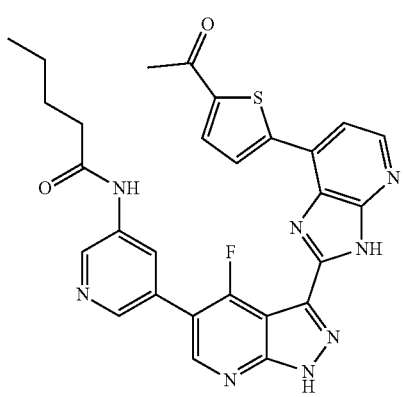 [SMILES: CCCCC(=O)Nc1cncc(-c2cnc3[nH]nc(-c4nc5c(-c6ccc(C(C)=O)s6)ccnc5[nH]4)c3c2F)c1] 848 | 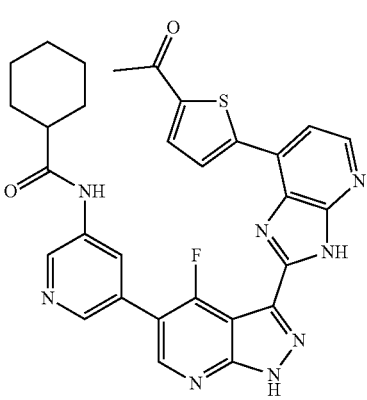 852 |
| 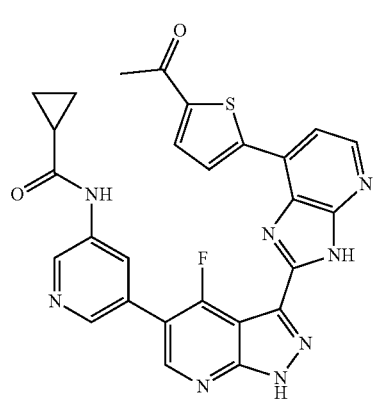 [SMILES: CC(=O)c1ccc(-c2ccnc3[nH]c(-c4n[nH]c5ncc(-c6cncc(NC(=O)C7CC7)c6)c(F)c45)nc23)s1] 849 | 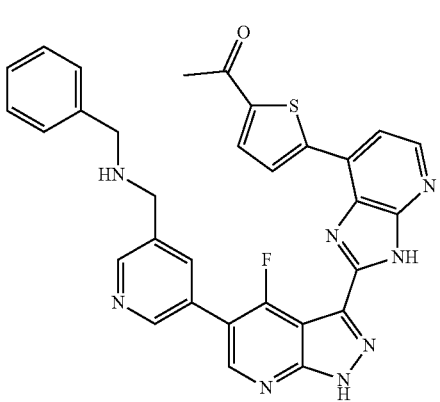 [SMILES: CC(=O)c1ccc(-c2ccnc3[nH]c(-c4n[nH]c5ncc(-c6cncc(CNCc7ccccc7)c6)c(F)c45)nc23)s1] 853 |

US 10,526,347 B2
TABLE 1-continued
| 854 | 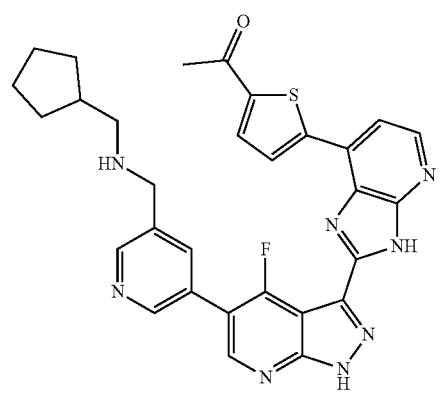 [SMILES: CC(=O)c1ccc(-c2ccnc3[nH]c(-c4n[nH]c5ncc(-c6cncc(CNCC7CCCC7)c6)c(F)c45)nc23)s1] |
| 855 | 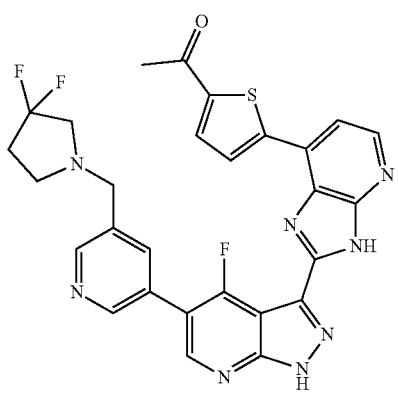 [SMILES: CC(=O)c1ccc(-c2ccnc3[nH]c(-c4n[nH]c5ncc(-c6cncc(CN7CCC(F)(F)C7)c6)c(F)c45)nc23)s1] |
| 856 | 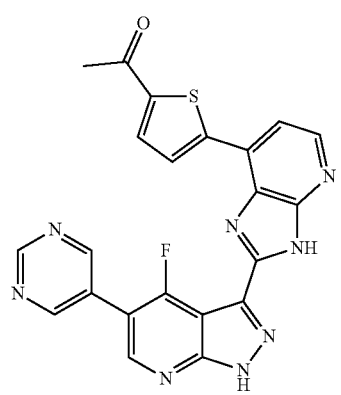 [SMILES: CC(=O)c1ccc(-c2ccnc3[nH]c(-c4n[nH]c5ncc(-c6cncnc6)c(F)c45)nc23)s1] |
| 857 | 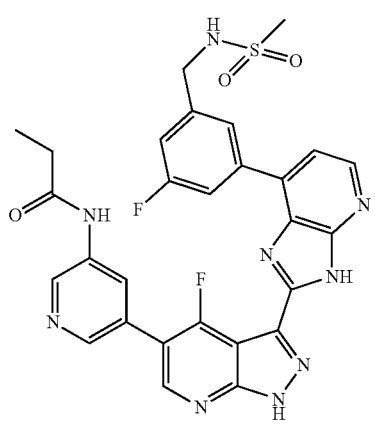 [SMILES: CCC(=O)Nc1cncc(-c2cnc3[nH]nc(-c4nc5c(-c6cc(F)cc(CNS(C)(=O)=O)c6)ccnc5[nH]4)c3c2F)c1] |
TABLE 1-continued
| 858 | 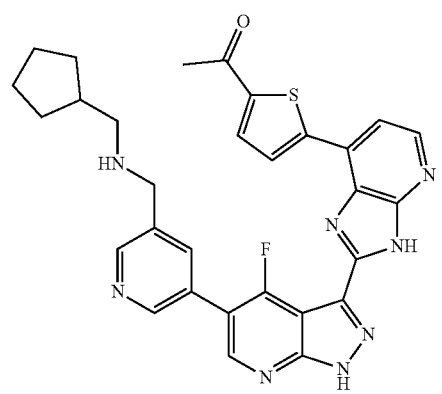 |
| 859 | 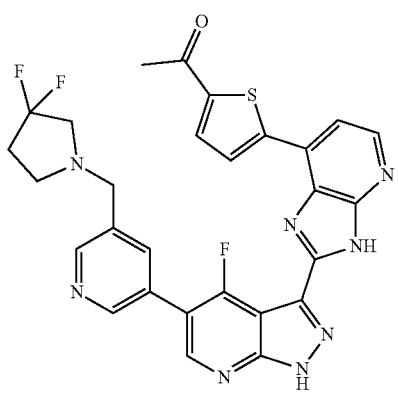 [SMILES: CC(=O)c1ccc(-c2ccnc3[nH]c(-c4n[nH]c5ncc(-c6cncc(CN7CCC(F)(F)C7)c6)c(F)c45)nc23)s1] |
| 860 | 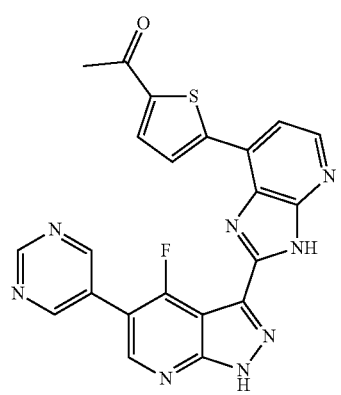 |
| 861 | 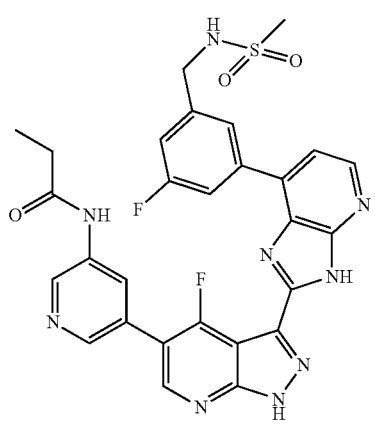 [SMILES: CCC(=O)Nc1cncc(-c2cnc3[nH]nc(-c4nc5c(-c6cc(F)cc(CNS(C)(=O)=O)c6)ccnc5[nH]4)c3c2F)c1] |

TABLE 1-continued
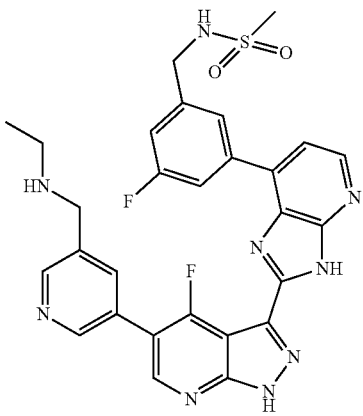 [SMILES: CCNCc1cncc(-c2cnc3[nH]nc(-c4nc5c(-c6cc(F)cc(CNS(C)(=O)=O)c6)ccnc5[nH]4)c3c2F)c1]
862
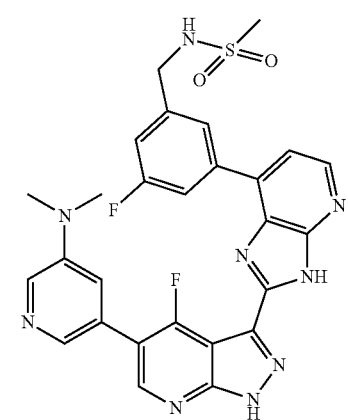 [SMILES: CN(C)c1cncc(-c2cnc3[nH]nc(-c4nc5c(-c6cc(F)cc(CNS(C)(=O)=O)c6)ccnc5[nH]4)c3c2F)c1]
863
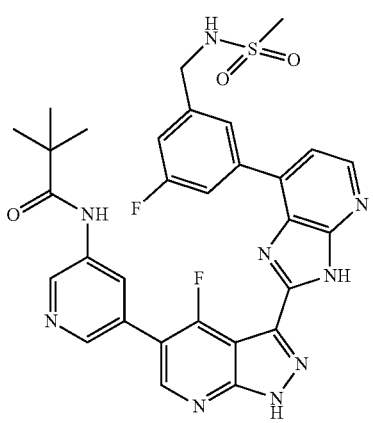 [SMILES: CC(C)(C)C(=O)Nc1cncc(-c2cnc3[nH]nc(-c4nc5c(-c6cc(F)cc(CNS(C)(=O)=O)c6)ccnc5[nH]4)c3c2F)c1]
864
TABLE 1-continued
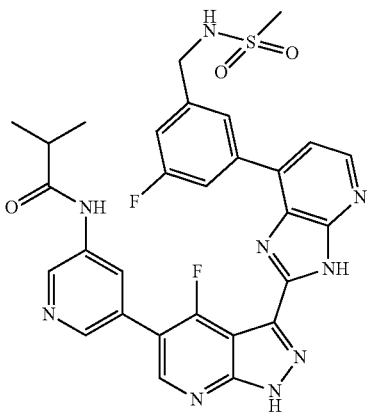 [SMILES: CC(C)C(=O)Nc1cncc(-c2cnc3[nH]nc(-c4nc5c(-c6cc(F)cc(CNS(C)(=O)=O)c6)ccnc5[nH]4)c3c2F)c1]
865
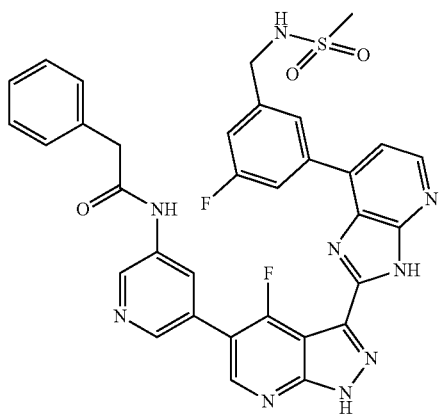 [SMILES: CS(=O)(=O)NCc1cc(F)cc(-c2ccnc3[nH]c(-c4n[nH]c5ncc(-c6cncc(NC(=O)Cc7ccccc7)c6)c(F)c45)nc23)c1]
866
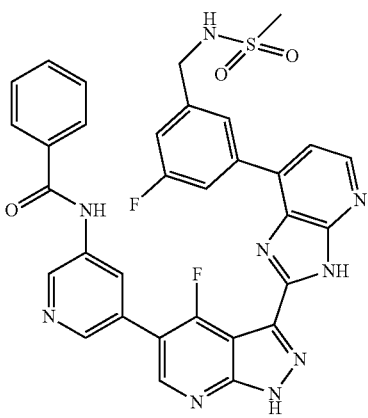 [SMILES: CS(=O)(=O)NCc1cc(F)cc(-c2ccnc3[nH]c(-c4n[nH]c5ncc(-c6cncc(NC(=O)c7ccccc7)c6)c(F)c45)nc23)c1]
867
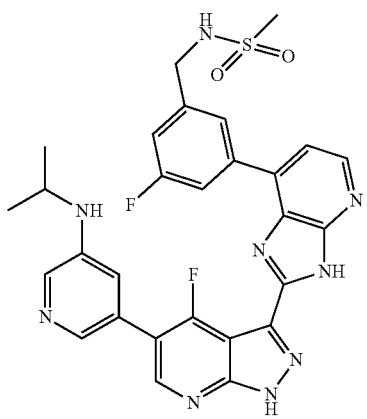 [SMILES: CC(C)Nc1cncc(-c2cnc3[nH]nc(-c4nc5c(-c6cc(F)cc(CNS(C)(=O)=O)c6)ccnc5[nH]4)c3c2F)c1]
868

TABLE 1-continued
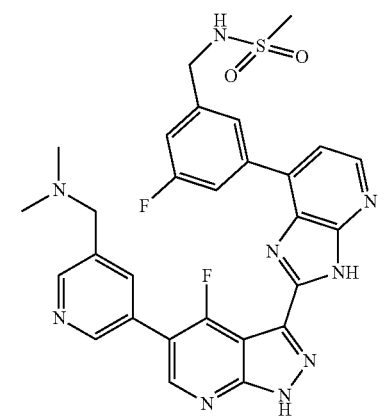 [SMILES: CN(C)Cc1cncc(-c2cnc3[nH]nc(-c4nc5c(-c6cc(F)cc(CNS(C)(=O)=O)c6)ccnc5[nH]4)c3c2F)c1]
869
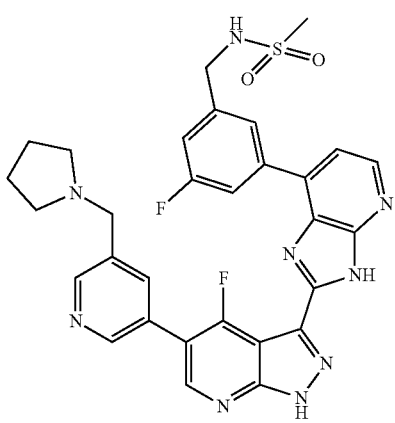 [SMILES: CS(=O)(=O)NCc1cc(F)cc(-c2ccnc3[nH]c(-c4n[nH]c5ncc(-c6cncc(CN7CCCC7)c6)c(F)c45)nc23)c1]
870
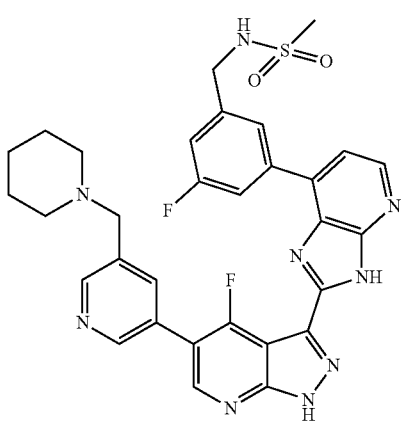 [SMILES: CS(=O)(=O)NCc1cc(F)cc(-c2ccnc3[nH]c(-c4n[nH]c5ncc(-c6cncc(CN7CCCCC7)c6)c(F)c45)nc23)c1]
871
TABLE 1-continued
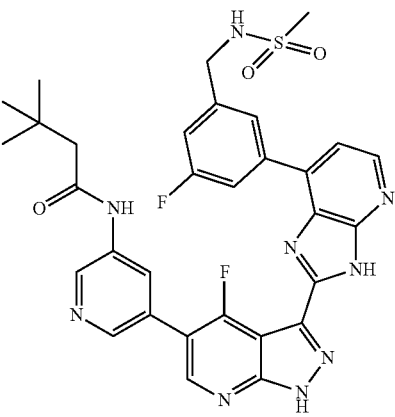 [SMILES: CC(C)(C)CC(=O)Nc1cncc(-c2cnc3[nH]nc(-c4nc5c(-c6cc(F)cc(CNS(C)(=O)=O)c6)ccnc5[nH]4)c3c2F)c1]
872
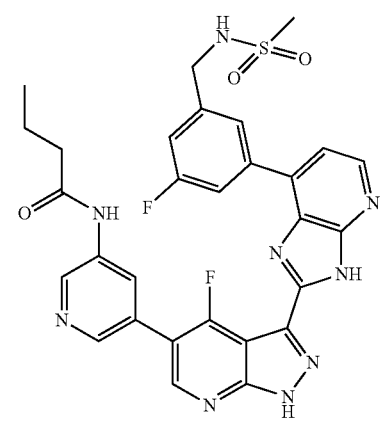 [SMILES: CCCC(=O)Nc1cncc(-c2cnc3[nH]nc(-c4nc5c(-c6cc(F)cc(CNS(C)(=O)=O)c6)ccnc5[nH]4)c3c2F)c1]
873
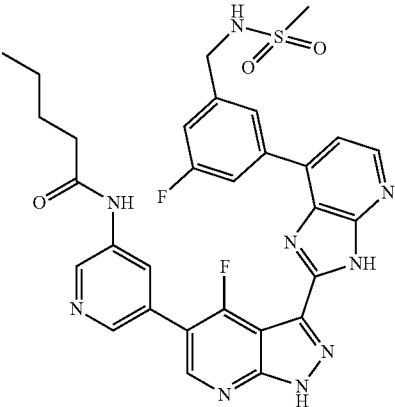 [SMILES: CCCCC(=O)Nc1cncc(-c2cnc3[nH]nc(-c4nc5c(-c6cc(F)cc(CNS(C)(=O)=O)c6)ccnc5[nH]4)c3c2F)c1]
874
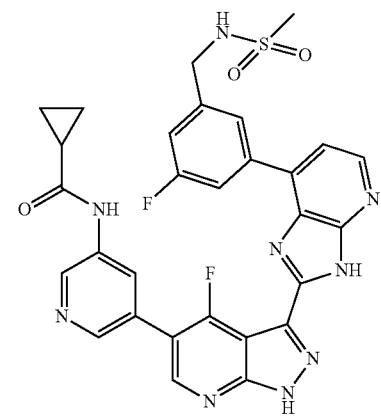 [SMILES: CS(=O)(=O)NCc1cc(F)cc(-c2ccnc3[nH]c(-c4n[nH]c5ncc(-c6cncc(NC(=O)C7CC7)c6)c(F)c45)nc23)c1]
875

TABLE 1-continued
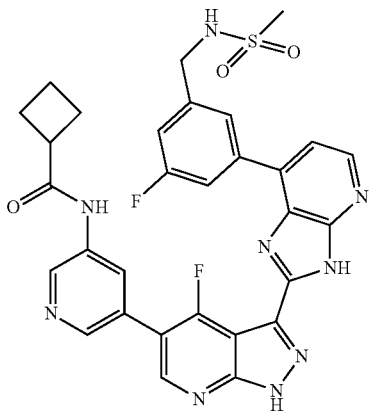 [SMILES: CS(=O)(=O)NCc1cc(F)cc(-c2ccnc3[nH]c(-c4n[nH]c5ncc(-c6cncc(NC(=O)C7CCC7)c6)c(F)c45)nc23)c1]
876
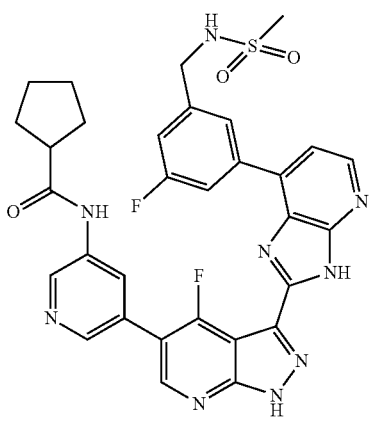 [SMILES: CS(=O)(=O)NCc1cc(F)cc(-c2ccnc3[nH]c(-c4n[nH]c5ncc(-c6cncc(NC(=O)C7CCCC7)c6)c(F)c45)nc23)c1]
877
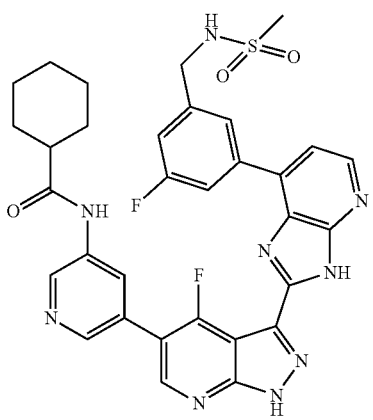 [SMILES: CS(=O)(=O)NCc1cc(F)cc(-c2ccnc3[nH]c(-c4n[nH]c5ncc(-c6cncc(NC(=O)C7CCCCC7)c6)c(F)c45)nc23)c1]
878
TABLE 1-continued
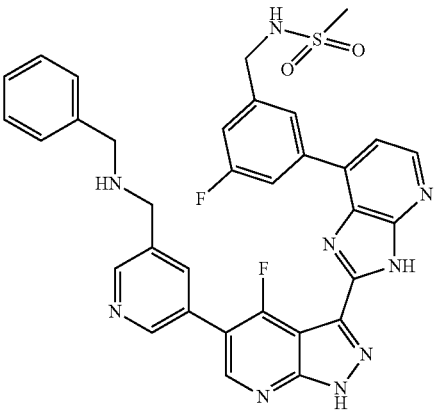 [SMILES: CS(=O)(=O)NCc1cc(F)cc(-c2ccnc3[nH]c(-c4n[nH]c5ncc(-c6cncc(CNCc7ccccc7)c6)c(F)c45)nc23)c1]
879
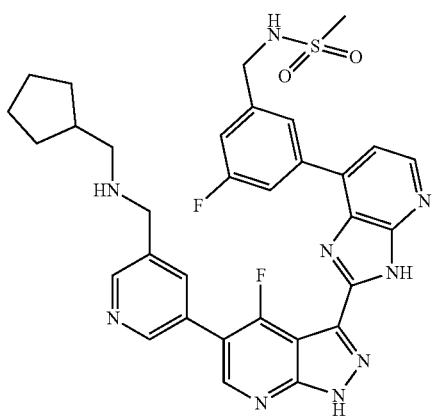 [SMILES: CS(=O)(=O)NCc1cc(F)cc(-c2ccnc3[nH]c(-c4n[nH]c5ncc(-c6cncc(CNCC7CCCC7)c6)c(F)c45)nc23)c1]
880
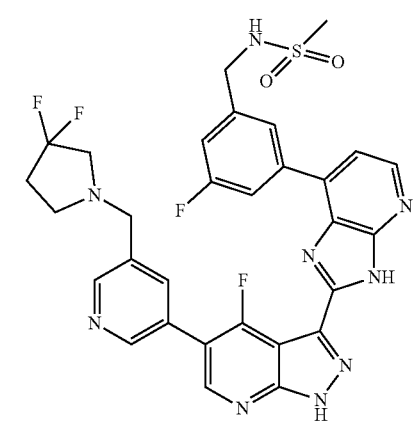 [SMILES: CS(=O)(=O)NCc1cc(F)cc(-c2ccnc3[nH]c(-c4n[nH]c5ncc(-c6cncc(CN7CCC(F)(F)C7)c6)c(F)c45)nc23)c1]
881
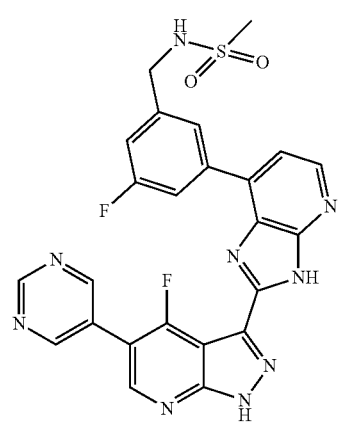 [SMILES: CS(=O)(=O)NCc1cc(F)cc(-c2ccnc3[nH]c(-c4n[nH]c5ncc(-c6cncnc6)c(F)c45)nc23)c1]
882

TABLE 1-continued
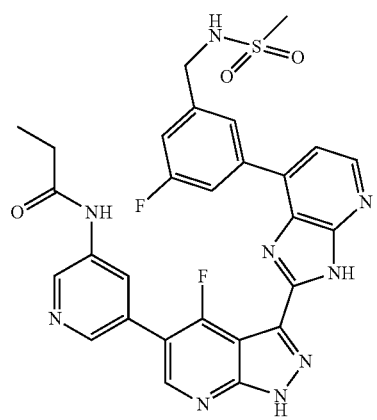 [SMILES: CCC(=O)Nc1cncc(-c2cnc3[nH]nc(-c4nc5c(-c6cc(F)cc(CNS(C)(=O)=O)c6)ccnc5[nH]4)c3c2F)c1]
883
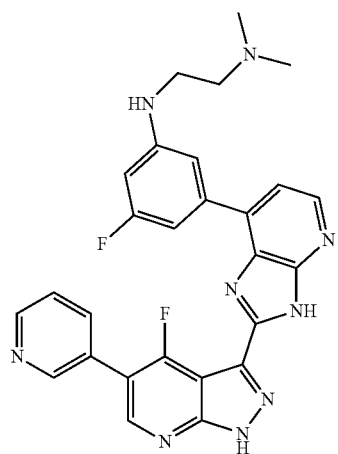
886
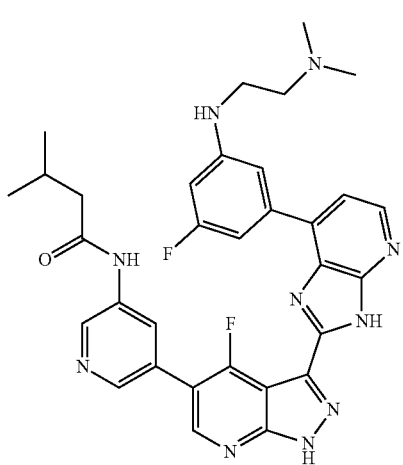 [SMILES: CC(C)CC(=O)Nc1cncc(-c2cnc3[nH]nc(-c4nc5c(-c6cc(F)cc(NCCN(C)C)c6)ccnc5[nH]4)c3c2F)c1]
884
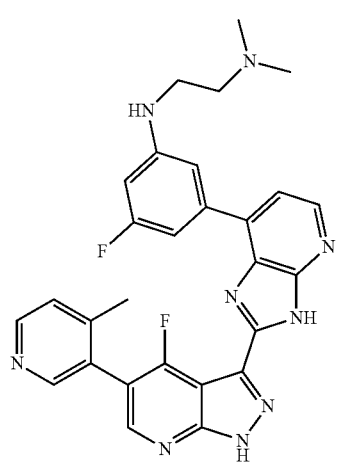
887
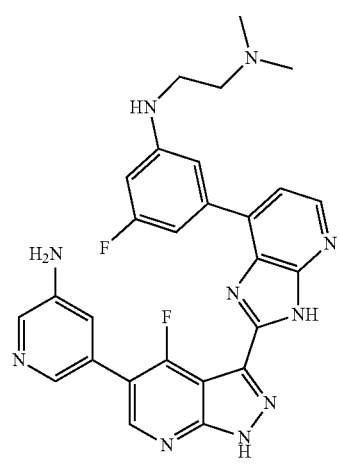 [SMILES: CN(C)CCNc1cc(F)cc(-c2ccnc3[nH]c(-c4n[nH]c5ncc(-c6cncc(N)c6)c(F)c45)nc23)c1]
885
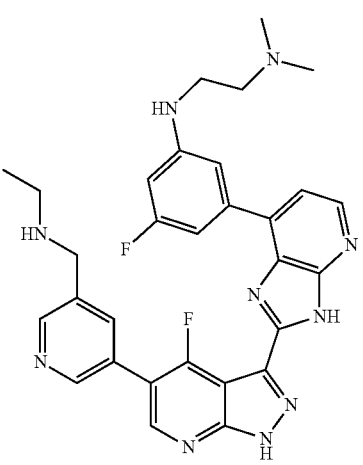 [SMILES: CCNCc1cncc(-c2cnc3[nH]nc(-c4nc5c(-c6cc(F)cc(NCCN(C)C)c6)ccnc5[nH]4)c3c2F)c1]
888

TABLE 1-continued
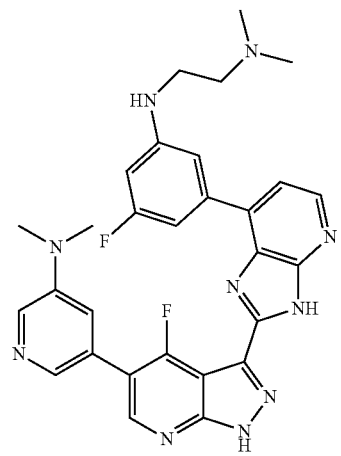 [SMILES: CN(C)CCNc1cc(F)cc(-c2ccnc3[nH]c(-c4n[nH]c5ncc(-c6cncc(N(C)C)c6)c(F)c45)nc23)c1]
889
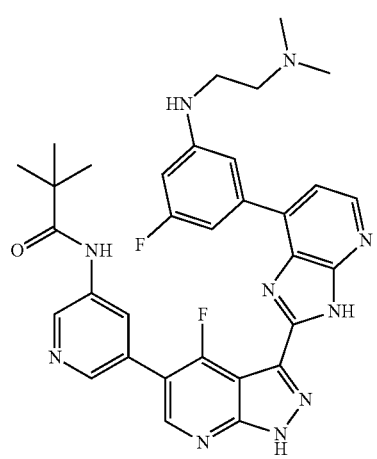 [SMILES: CN(C)CCNc1cc(F)cc(-c2ccnc3[nH]c(-c4n[nH]c5ncc(-c6cncc(NC(=O)C(C)(C)C)c6)c(F)c45)nc23)c1]
890
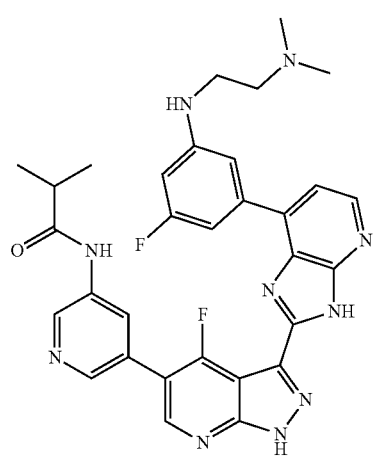 [SMILES: CC(C)C(=O)Nc1cncc(-c2cnc3[nH]nc(-c4nc5c(-c6cc(F)cc(NCCN(C)C)c6)ccnc5[nH]4)c3c2F)c1]
891
TABLE 1-continued
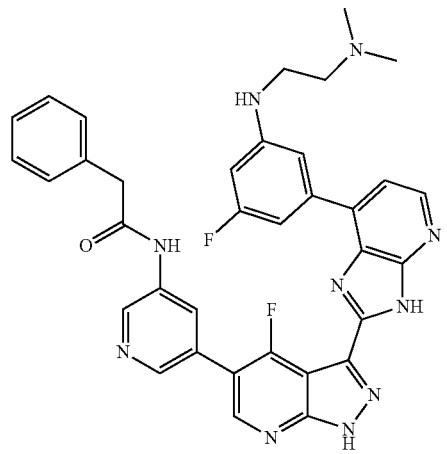 [SMILES: CN(C)CCNc1cc(F)cc(-c2ccnc3[nH]c(-c4n[nH]c5ncc(-c6cncc(NC(=O)Cc7ccccc7)c6)c(F)c45)nc23)c1]
892
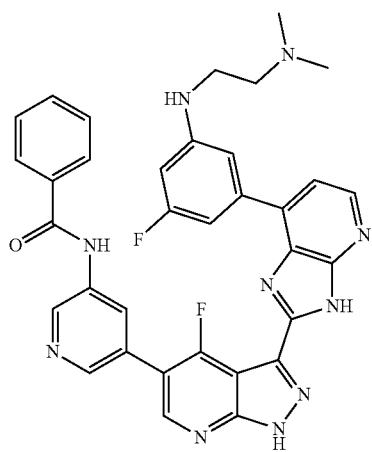 [SMILES: CN(C)CCNc1cc(F)cc(-c2ccnc3[nH]c(-c4n[nH]c5ncc(-c6cncc(NC(=O)c7ccccc7)c6)c(F)c45)nc23)c1]
893
894

TABLE 1-continued
895
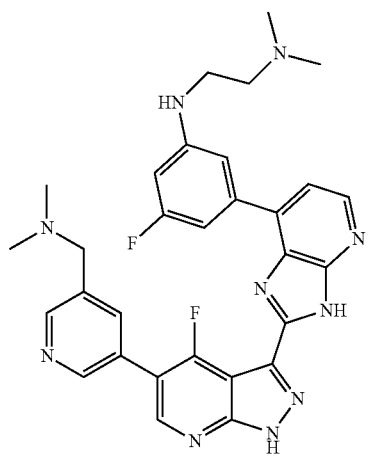 [SMILES: CN(C)CCNc1cc(F)cc(-c2ccnc3[nH]c(-c4n[nH]c5ncc(-c6cncc(CN(C)C)c6)c(F)c45)nc23)c1]
896
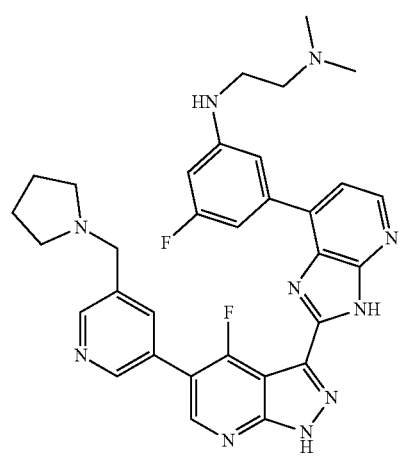 [SMILES: CN(C)CCNc1cc(F)cc(-c2ccnc3[nH]c(-c4n[nH]c5ncc(-c6cncc(CN7CCCC7)c6)c(F)c45)nc23)c1]
897
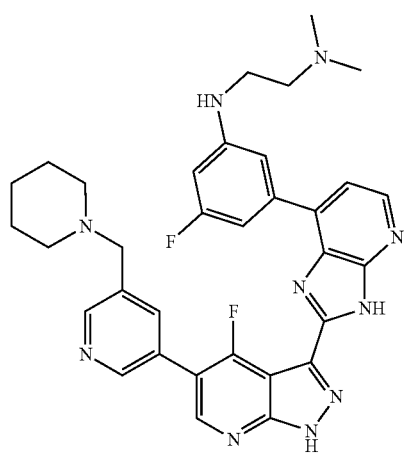 [SMILES: CN(C)CCNc1cc(F)cc(-c2ccnc3[nH]c(-c4n[nH]c5ncc(-c6cncc(CN7CCCCC7)c6)c(F)c45)nc23)c1]
TABLE 1-continued
898
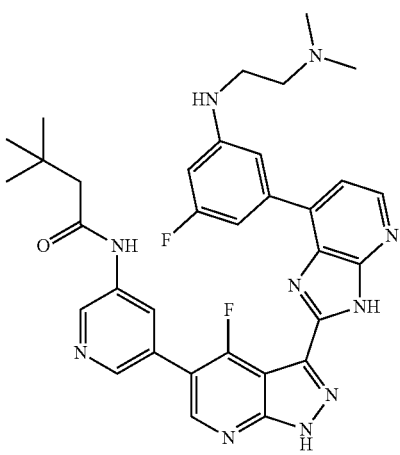 [SMILES: CN(C)CCNc1cc(F)cc(-c2ccnc3[nH]c(-c4n[nH]c5ncc(-c6cncc(NC(=O)CC(C)(C)C)c6)c(F)c45)nc23)c1]
899
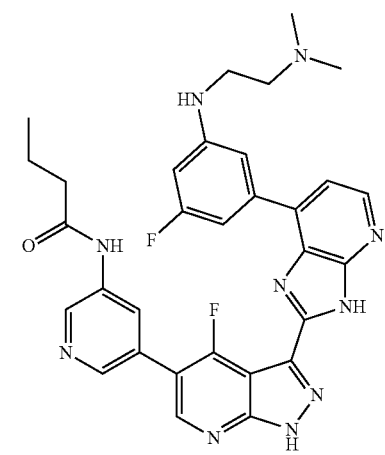 [SMILES: CCCC(=O)Nc1cncc(-c2cnc3[nH]nc(-c4nc5c(-c6cc(F)cc(NCCN(C)C)c6)ccnc5[nH]4)c3c2F)c1]
900
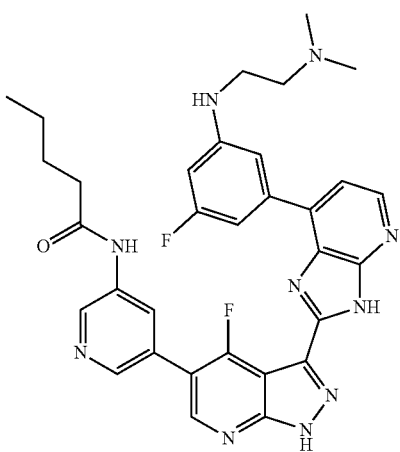 [SMILES: CCCCC(=O)Nc1cncc(-c2cnc3[nH]nc(-c4nc5c(-c6cc(F)cc(NCCN(C)C)c6)ccnc5[nH]4)c3c2F)c1]

TABLE 1-continued
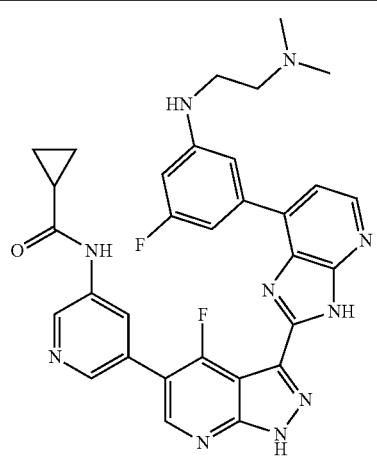
901
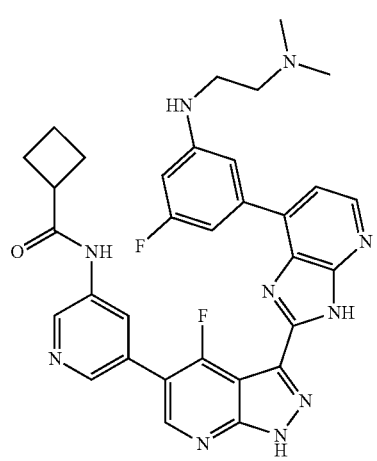 [SMILES: CN(C)CCNc1cc(F)cc(-c2ccnc3[nH]c(-c4n[nH]c5ncc(-c6cncc(NC(=O)C7CCC7)c6)c(F)c45)nc23)c1]
902
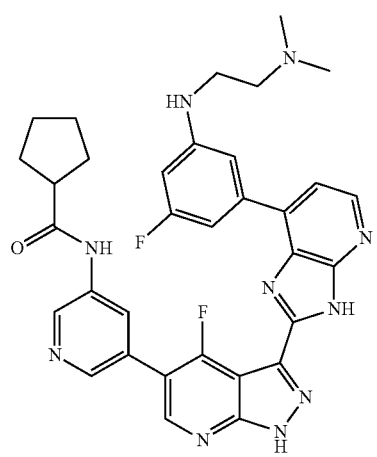 [SMILES: CN(C)CCNc1cc(F)cc(-c2ccnc3[nH]c(-c4n[nH]c5ncc(-c6cncc(NC(=O)C7CCCC7)c6)c(F)c45)nc23)c1]
903
TABLE 1-continued
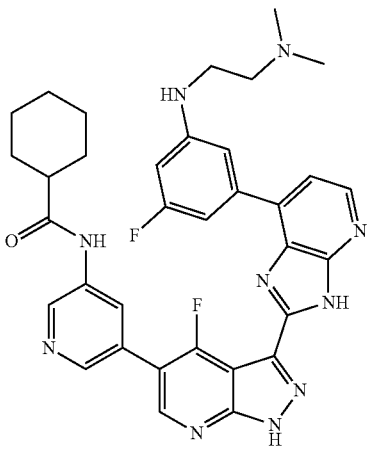 [SMILES: CN(C)CCNc1cc(F)cc(-c2ccnc3[nH]c(-c4n[nH]c5ncc(-c6cncc(NC(=O)C7CCCCC7)c6)c(F)c45)nc23)c1]
904
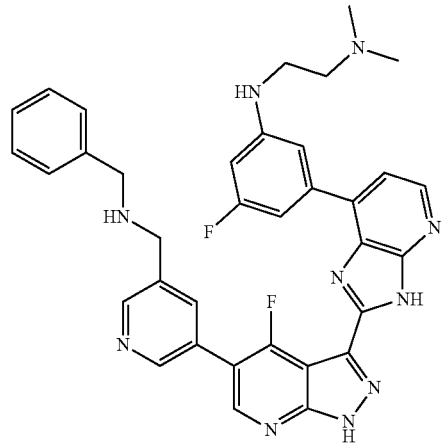 [SMILES: CN(C)CCNc1cc(F)cc(-c2ccnc3[nH]c(-c4n[nH]c5ncc(-c6cncc(CNCc7ccccc7)c6)c(F)c45)nc23)c1]
905
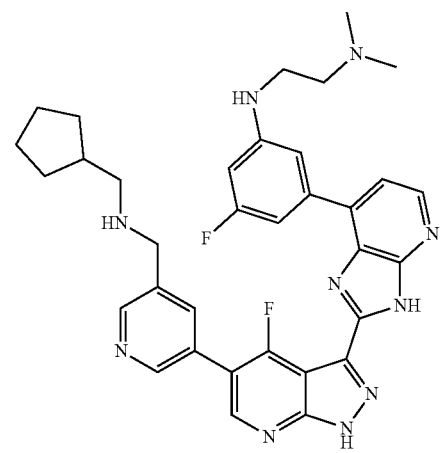 [SMILES: CN(C)CCNc1cc(F)cc(-c2ccnc3[nH]c(-c4n[nH]c5ncc(-c6cncc(CNCC7CCCC7)c6)c(F)c45)nc23)c1]
906

TABLE 1-continued
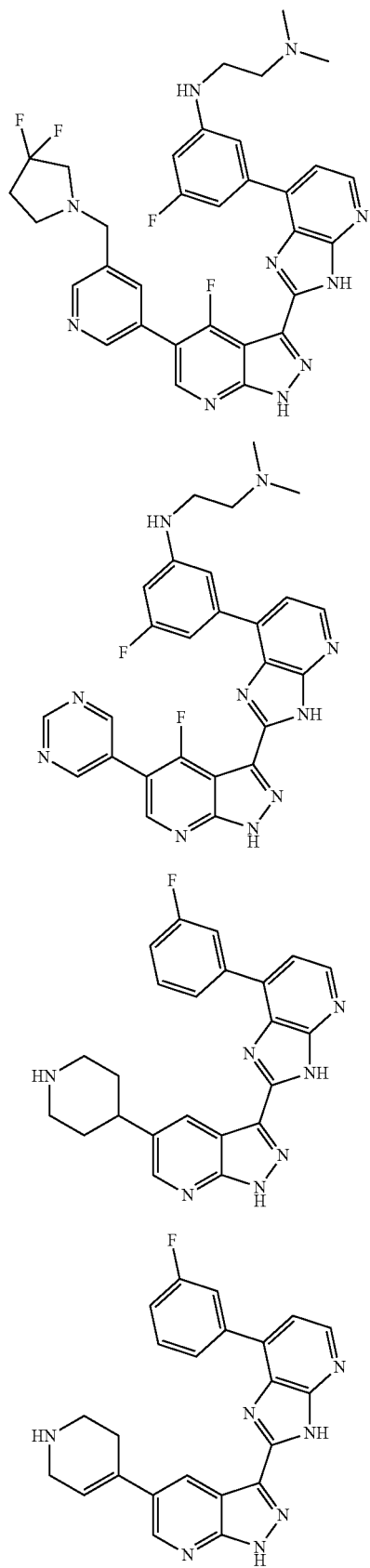
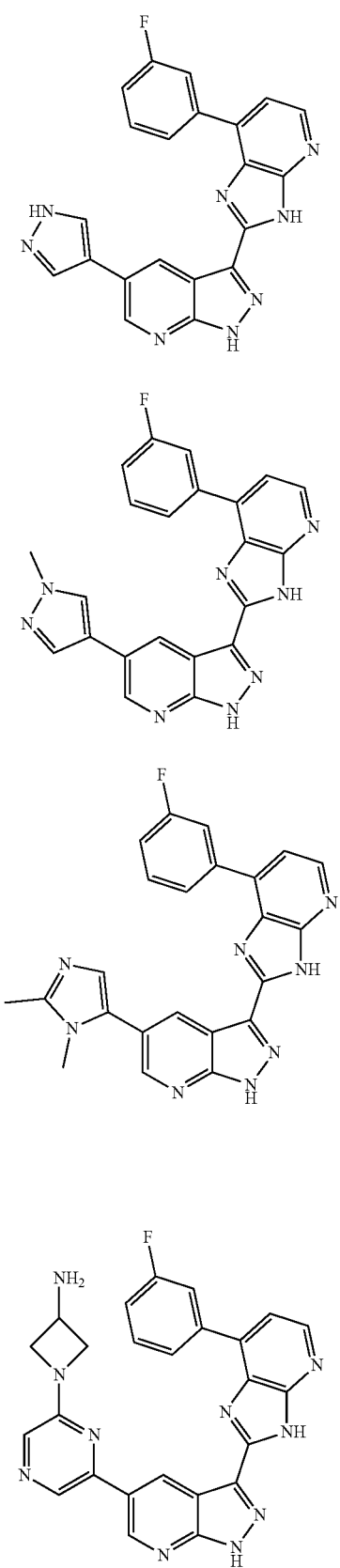

TABLE 1-continued
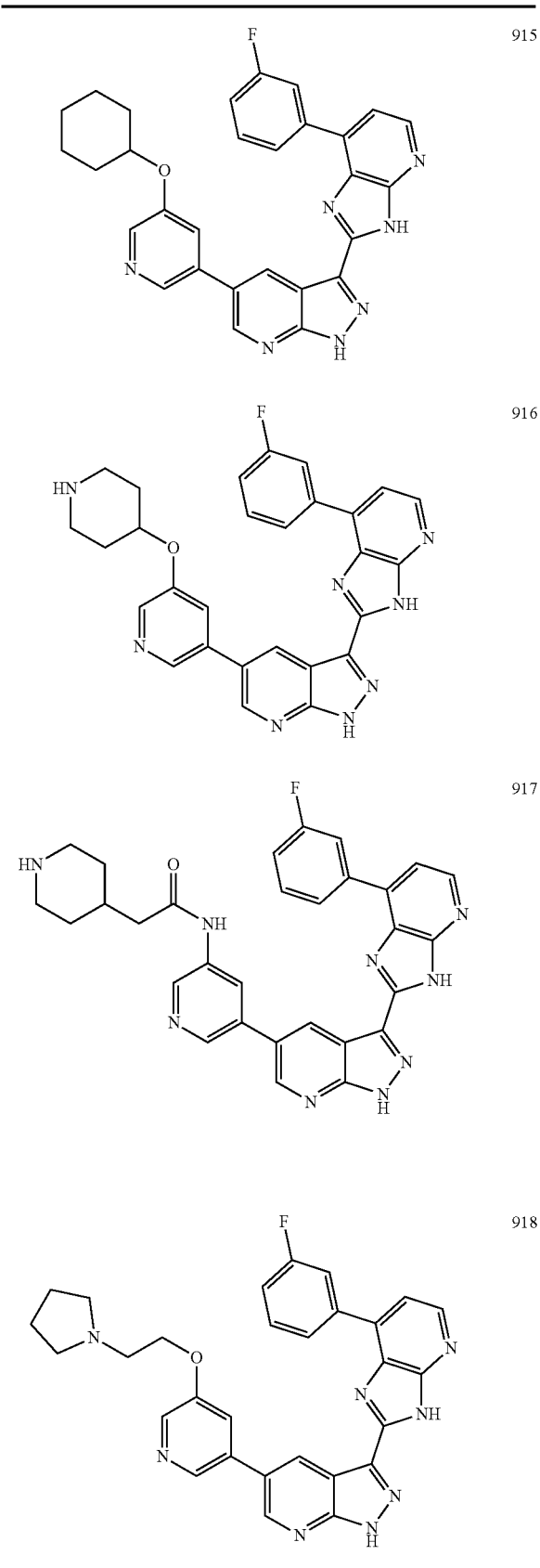
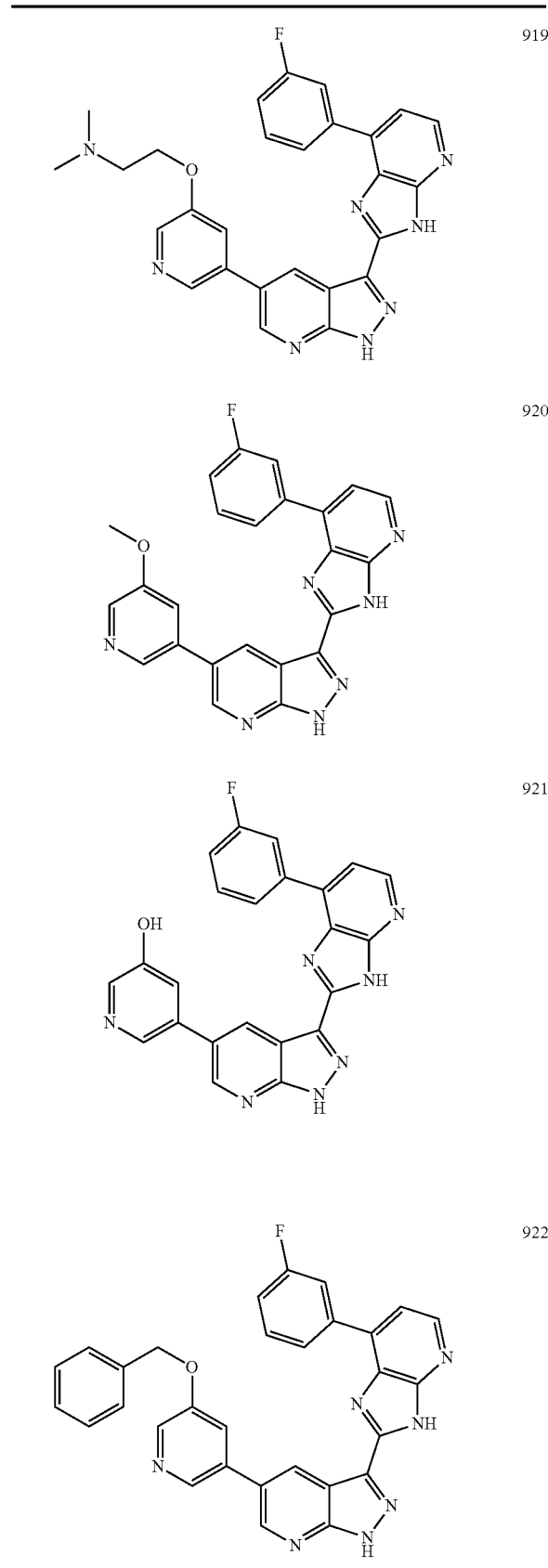

TABLE 1-continued
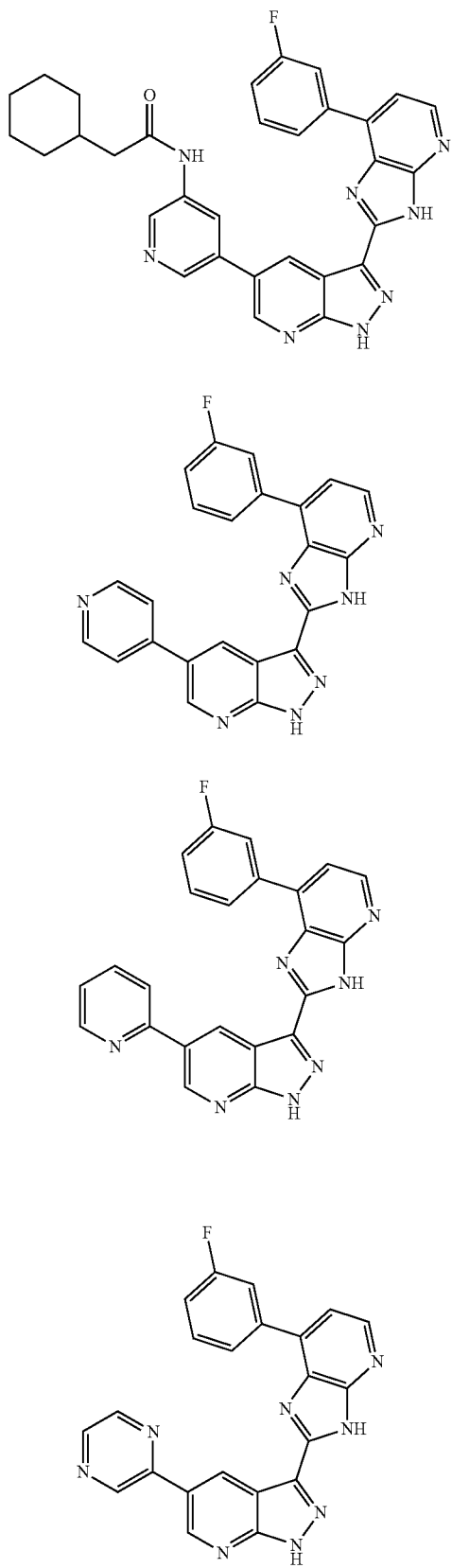
923
924
925
926
TABLE 1-continued
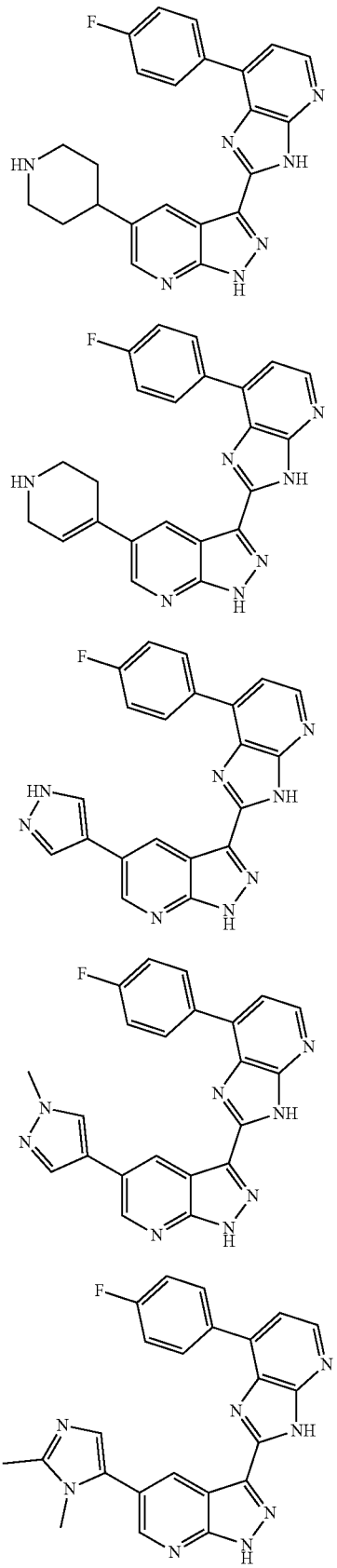
927
928
929
930
931

TABLE 1-continued
| | |
|---|---|
| 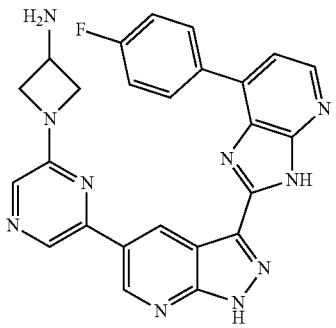 [SMILES: NC1CN(c2cncc(-c3cnc4[nH]nc(-c5nc6c(-c7ccc(F)cc7)ccnc6[nH]5)c4c3)n2)C1] 932 | 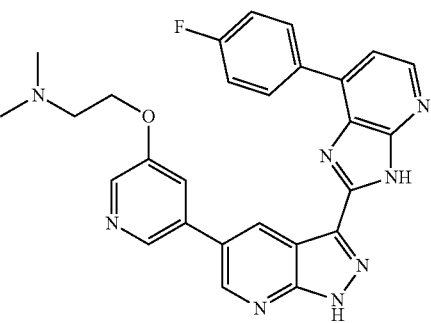 937 |
| 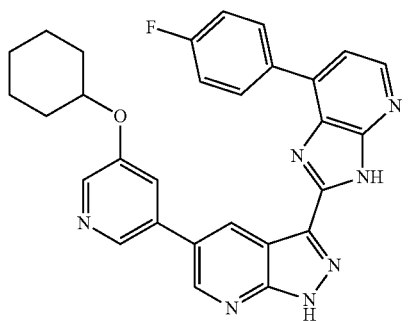 [SMILES: Fc1ccc(-c2ccnc3[nH]c(-c4n[nH]c5ncc(-c6cncc(OC7CCCCC7)c6)cc45)nc23)cc1] 933 | 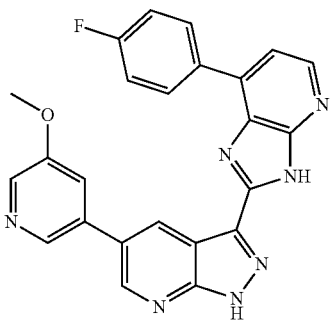 938 |
| 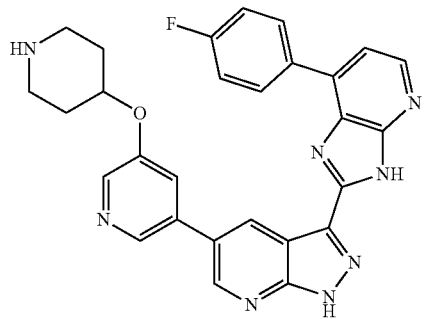 [SMILES: Fc1ccc(-c2ccnc3[nH]c(-c4n[nH]c5ncc(-c6cncc(OC7CCNCC7)c6)cc45)nc23)cc1] 934 | 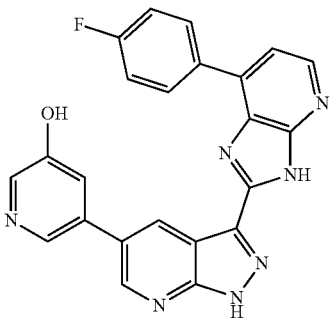 939 |
| 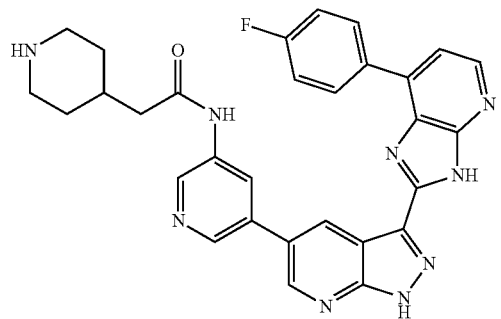 [SMILES: O=C(CC1CCNCC1)Nc1cncc(-c2cnc3[nH]nc(-c4nc5c(-c6ccc(F)cc6)ccnc5[nH]4)c3c2)c1] 935 | 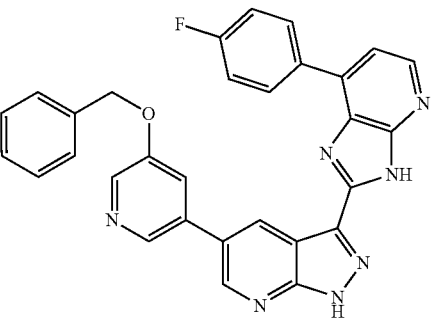 940 |
| 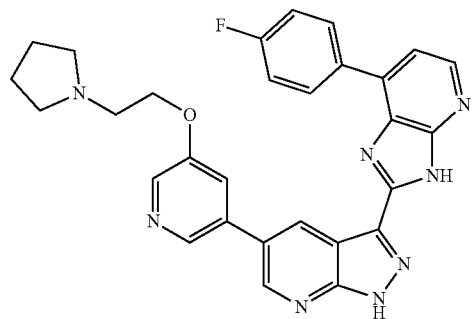 [SMILES: Fc1ccc(-c2ccnc3[nH]c(-c4n[nH]c5ncc(-c6cncc(OCCN7CCCC7)c6)cc45)nc23)cc1] 936 | 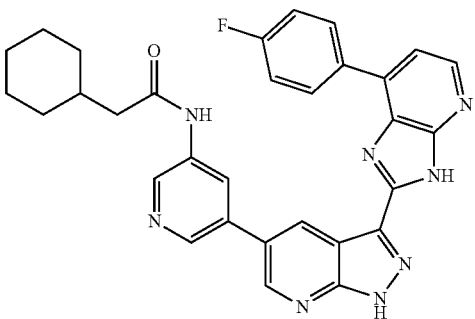 [SMILES: O=C(CC1CCCCC1)Nc1cncc(-c2cnc3[nH]nc(-c4nc5c(-c6ccc(F)cc6)ccnc5[nH]4)c3c2)c1] 941 |

TABLE 1-continued
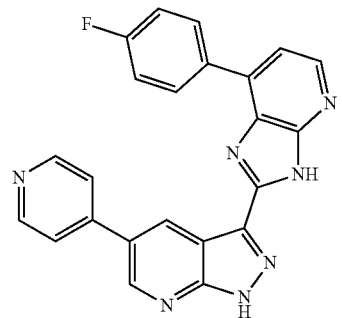 [SMILES: Fc1ccc(-c2ccnc3[nH]c(-c4n[nH]c5ncc(-c6ccncc6)cc45)nc23)cc1]
942
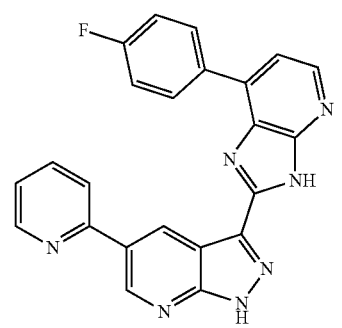 [SMILES: Fc1ccc(-c2ccnc3[nH]c(-c4n[nH]c5ncc(-c6ccccn6)cc45)nc23)cc1]
943
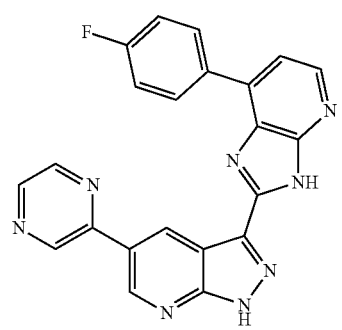 [SMILES: Fc1ccc(-c2ccnc3[nH]c(-c4n[nH]c5ncc(-c6cnccn6)cc45)nc23)cc1]
944
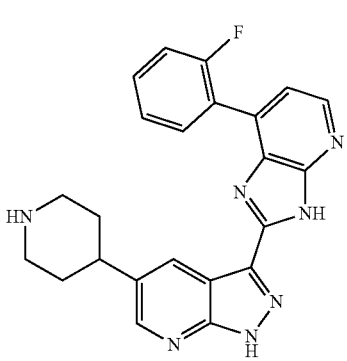 [SMILES: Fc1ccccc1-c1ccnc2[nH]c(-c3n[nH]c4ncc(C5CCNCC5)cc34)nc12]
945
TABLE 1-continued
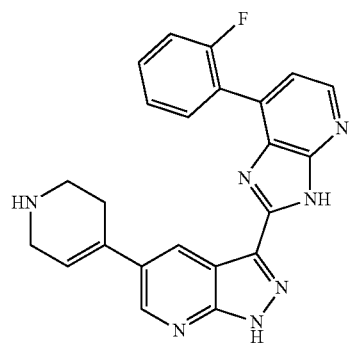 [SMILES: Fc1ccccc1-c1ccnc2[nH]c(-c3n[nH]c4ncc(C5=CCNCC5)cc34)nc12]
946
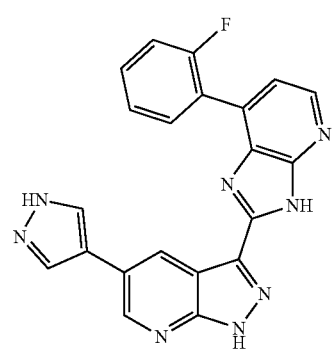 [SMILES: Fc1ccccc1-c1ccnc2[nH]c(-c3n[nH]c4ncc(-c5cn[nH]c5)cc34)nc12]
947
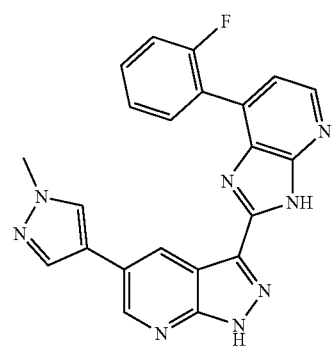 [SMILES: Cn1cc(-c2cnc3[nH]nc(-c4nc5c(-c6ccccc6F)ccnc5[nH]4)c3c2)cn1]
948
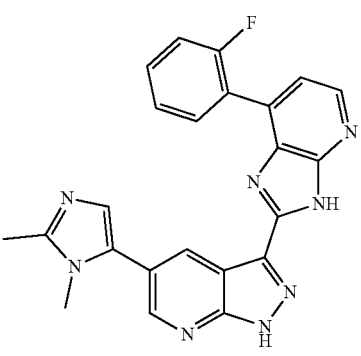 [SMILES: Cc1ncc(-c2cnc3[nH]nc(-c4nc5c(-c6ccccc6F)ccnc5[nH]4)c3c2)n1C]
949

TABLE 1-continued
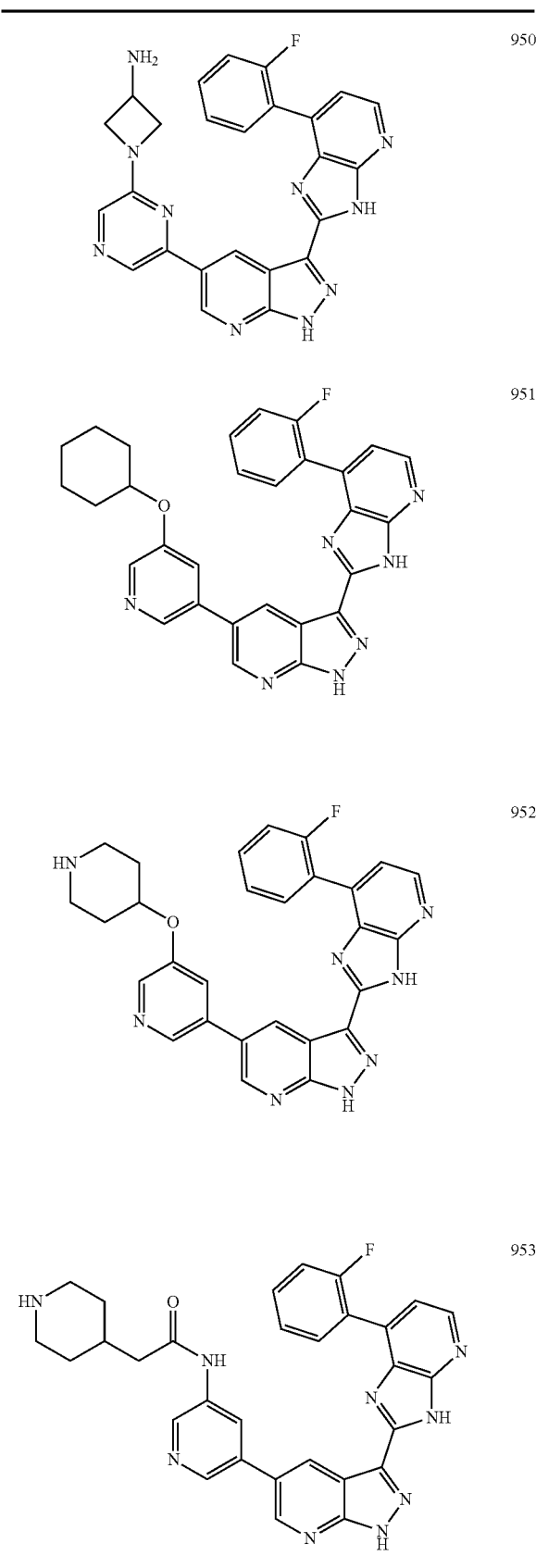
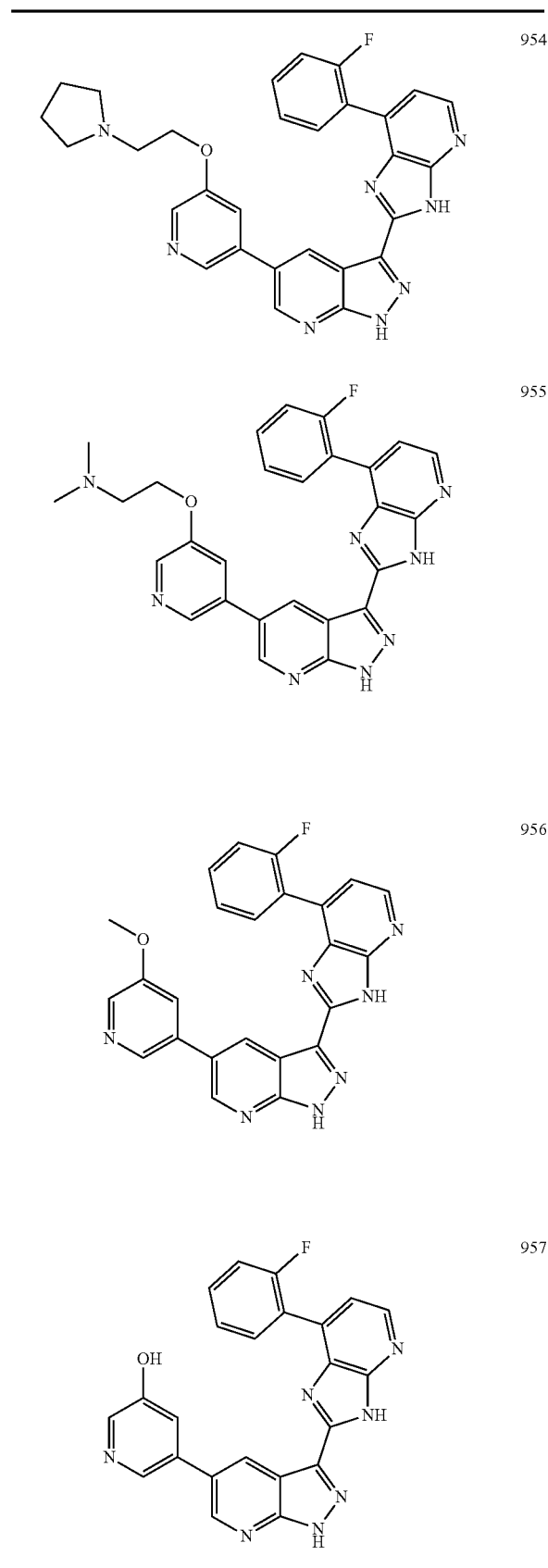

TABLE 1-continued
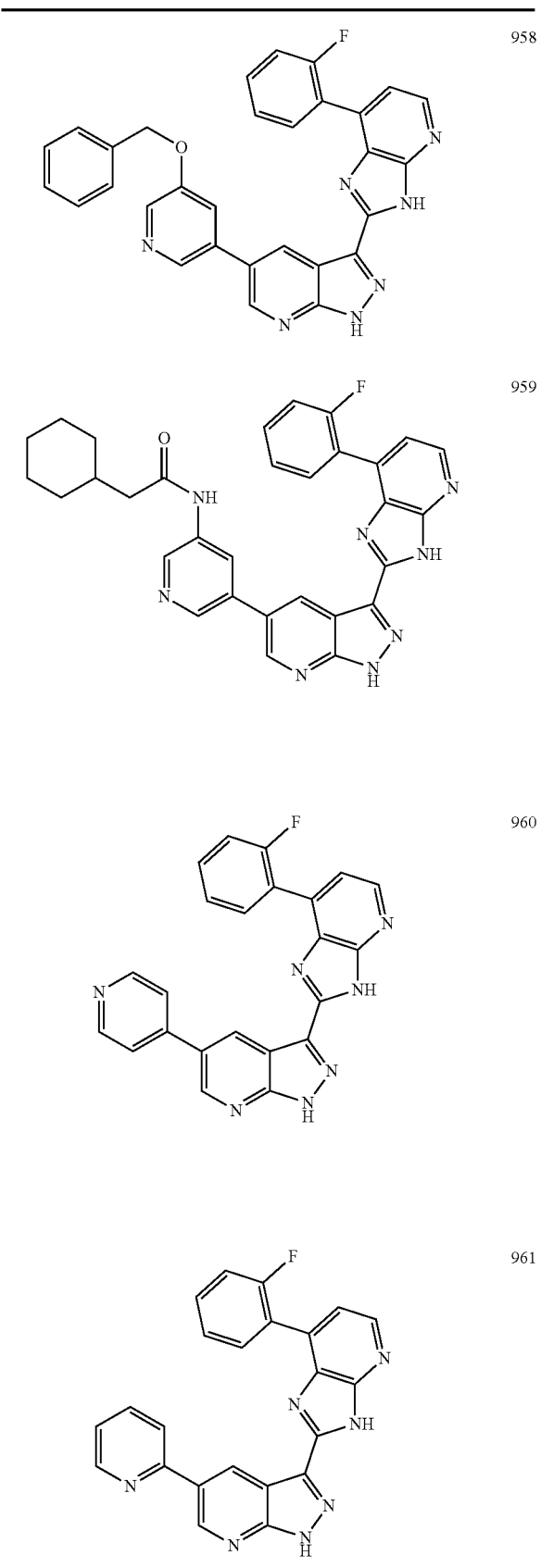
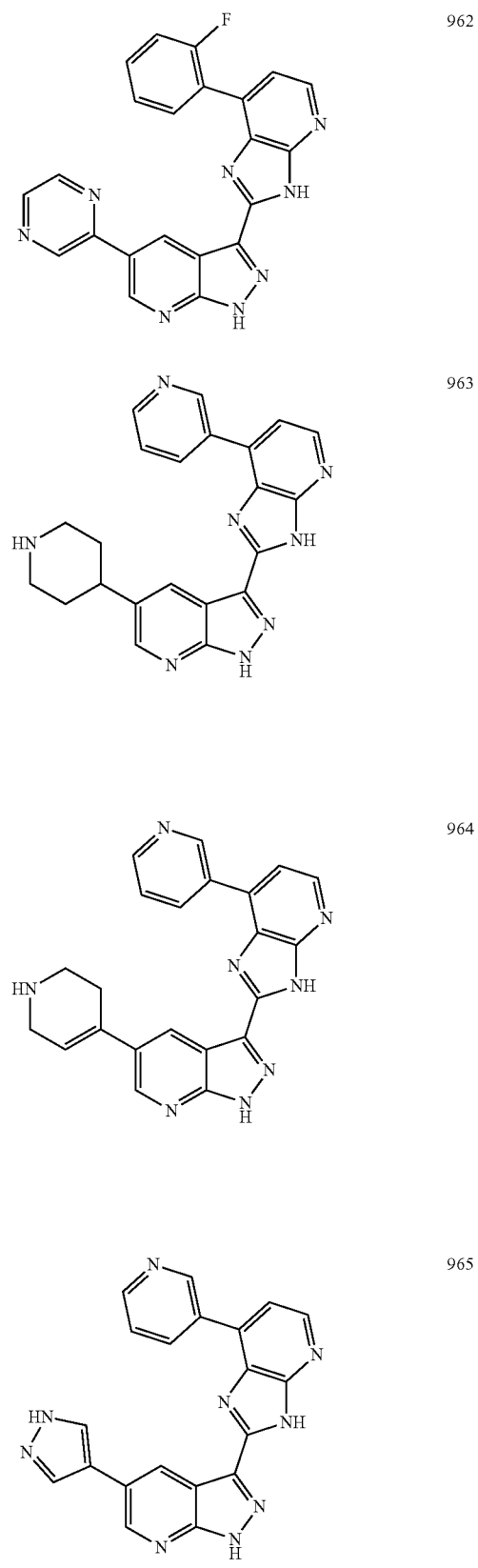

TABLE 1-continued
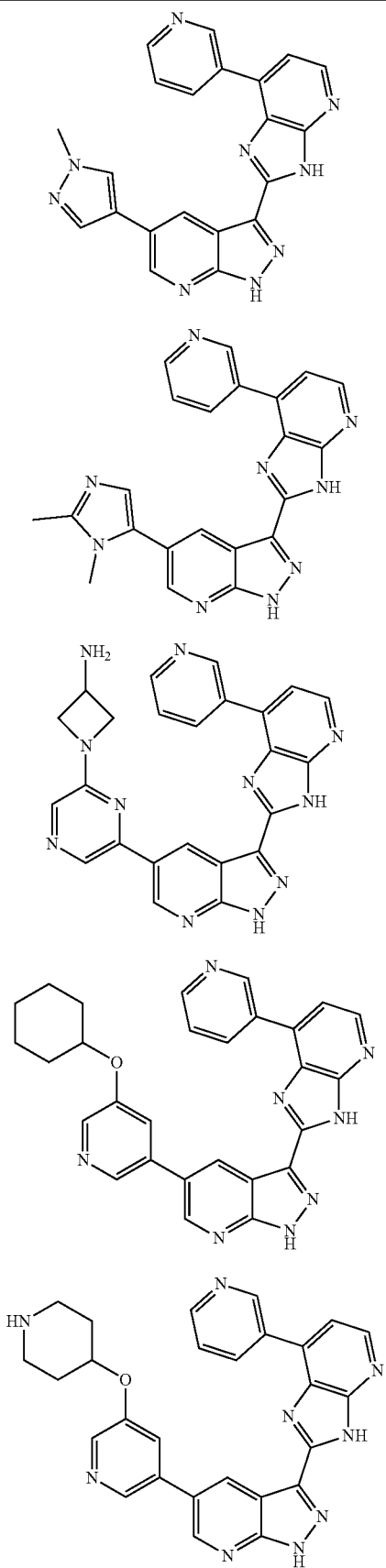
TABLE 1-continued
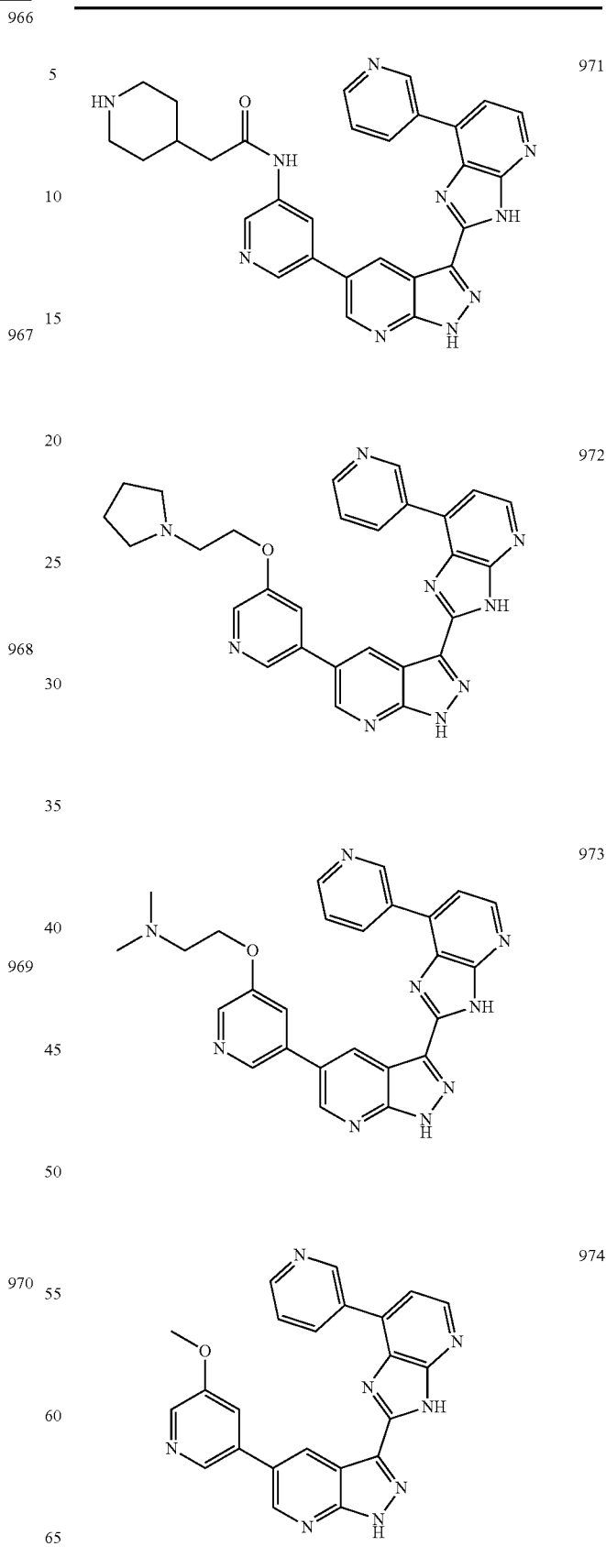

TABLE 1-continued
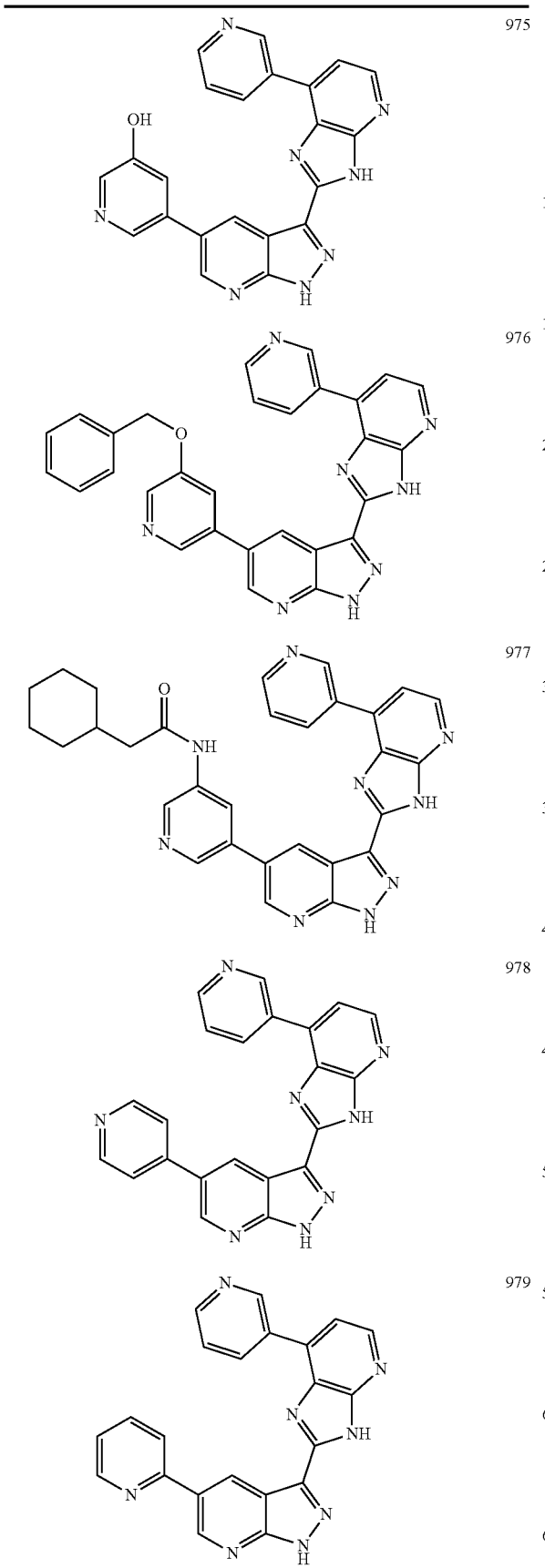
TABLE 1-continued
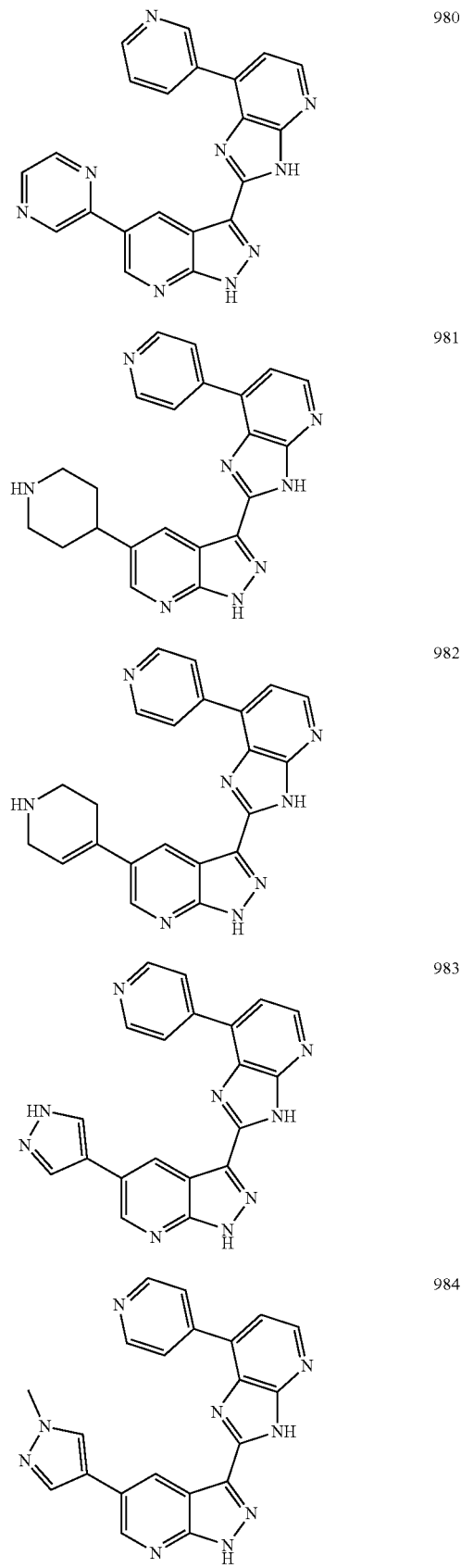

TABLE 1-continued
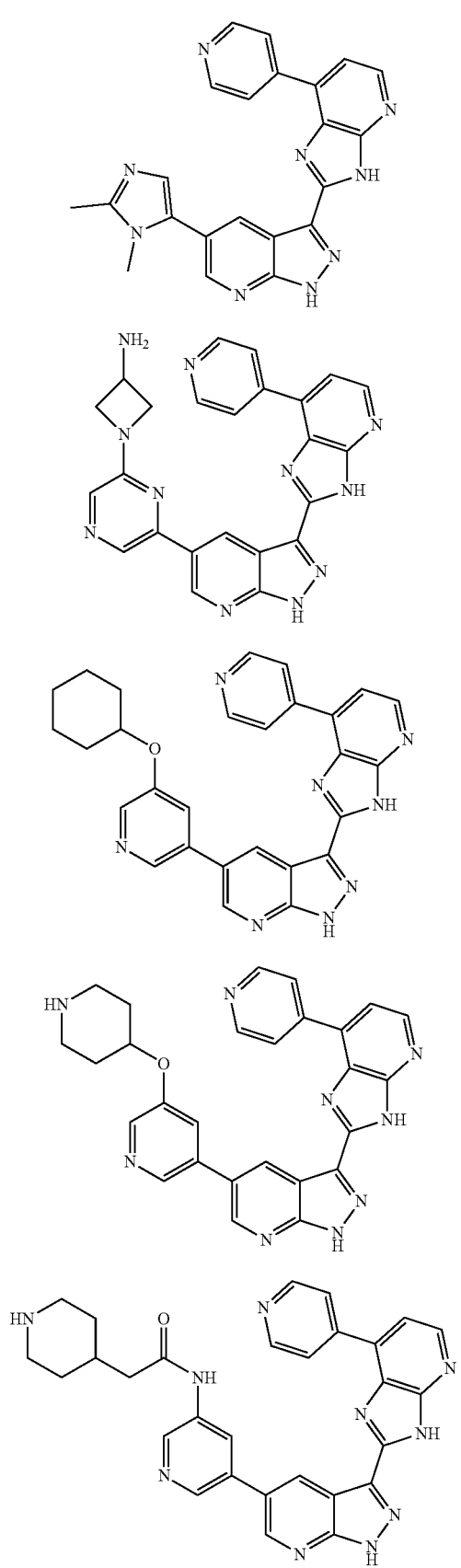
985
986
987
988
989
TABLE 1-continued
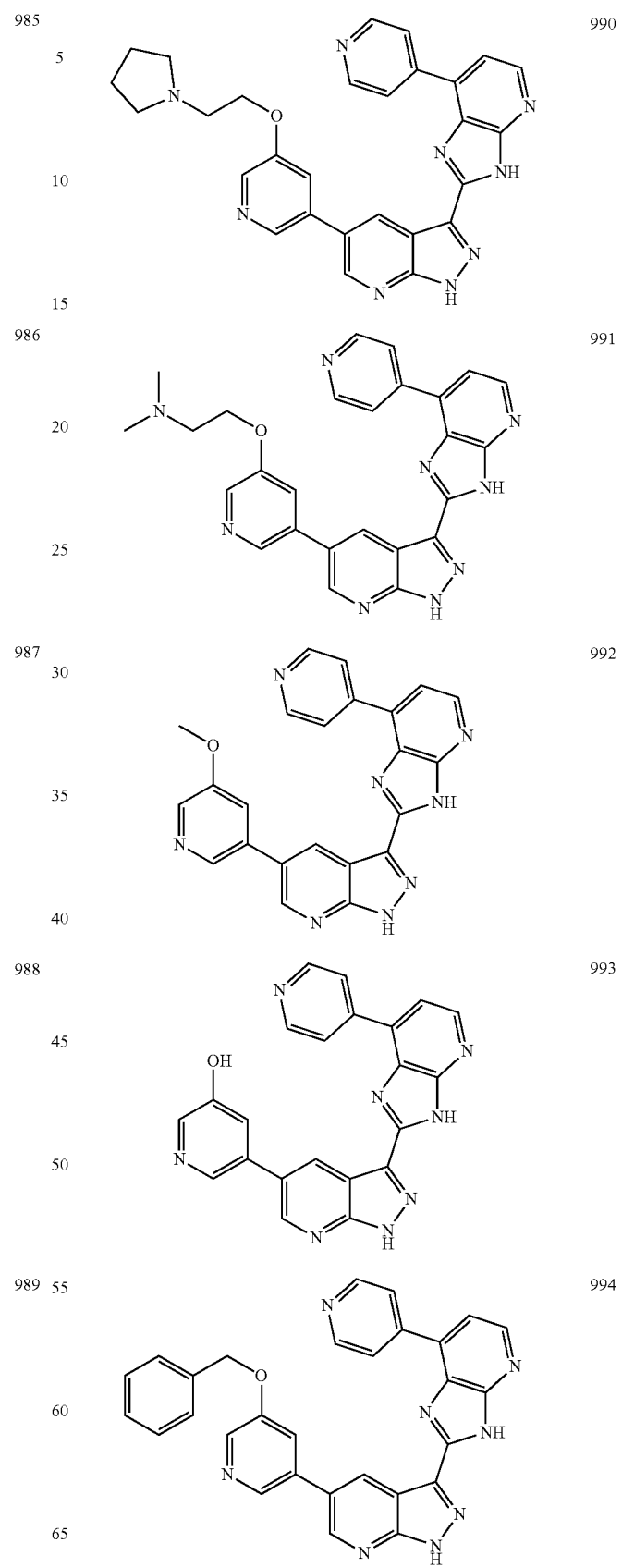
990
991
992
993
994

TABLE 1-continued
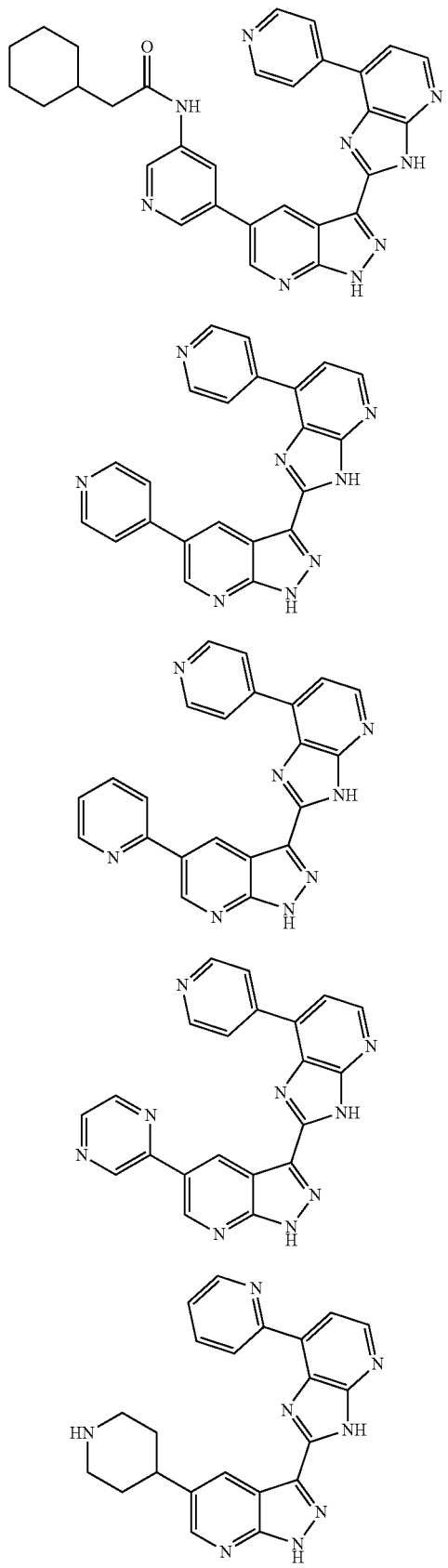
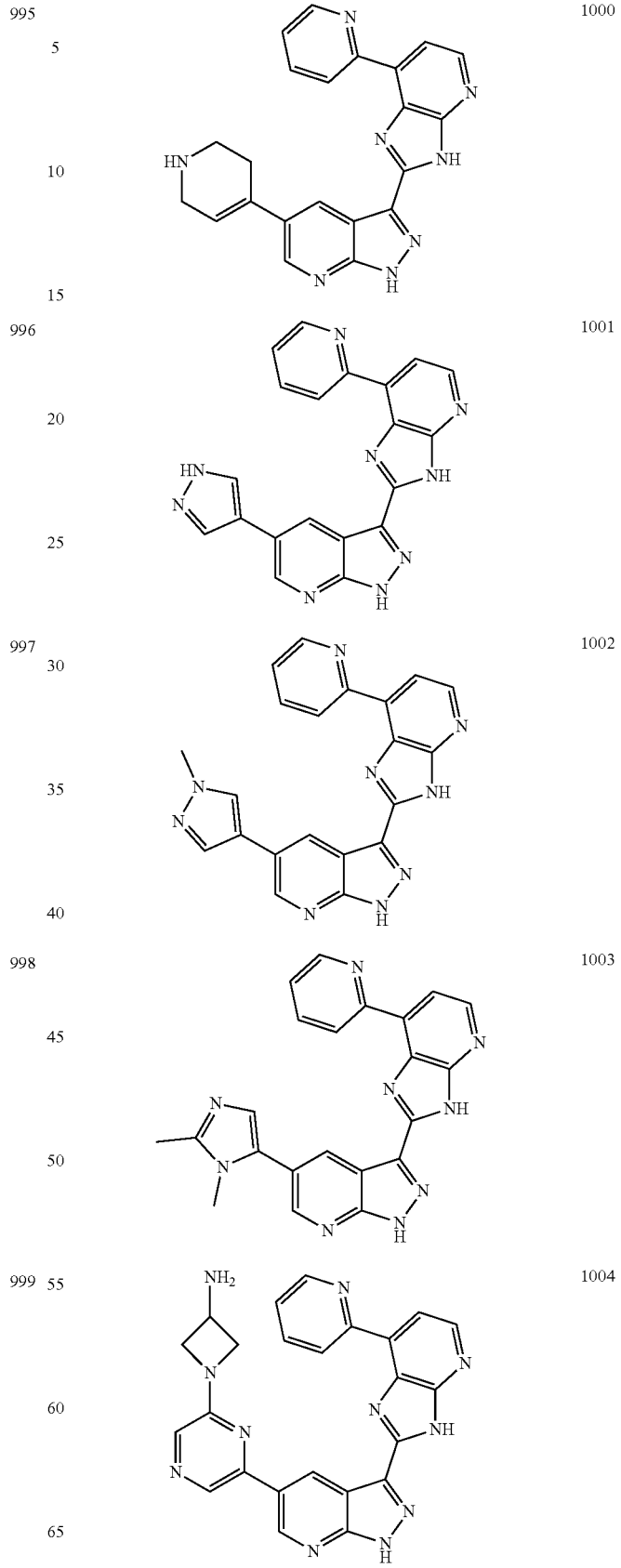

TABLE 1-continued
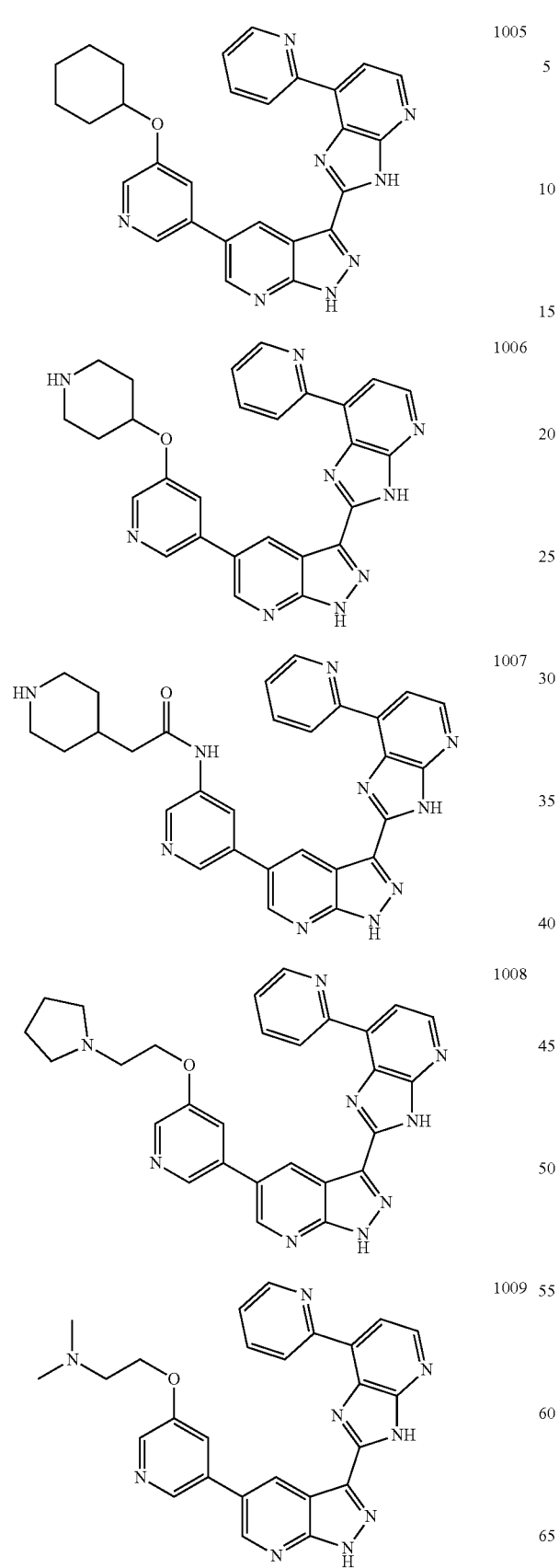
TABLE 1-continued
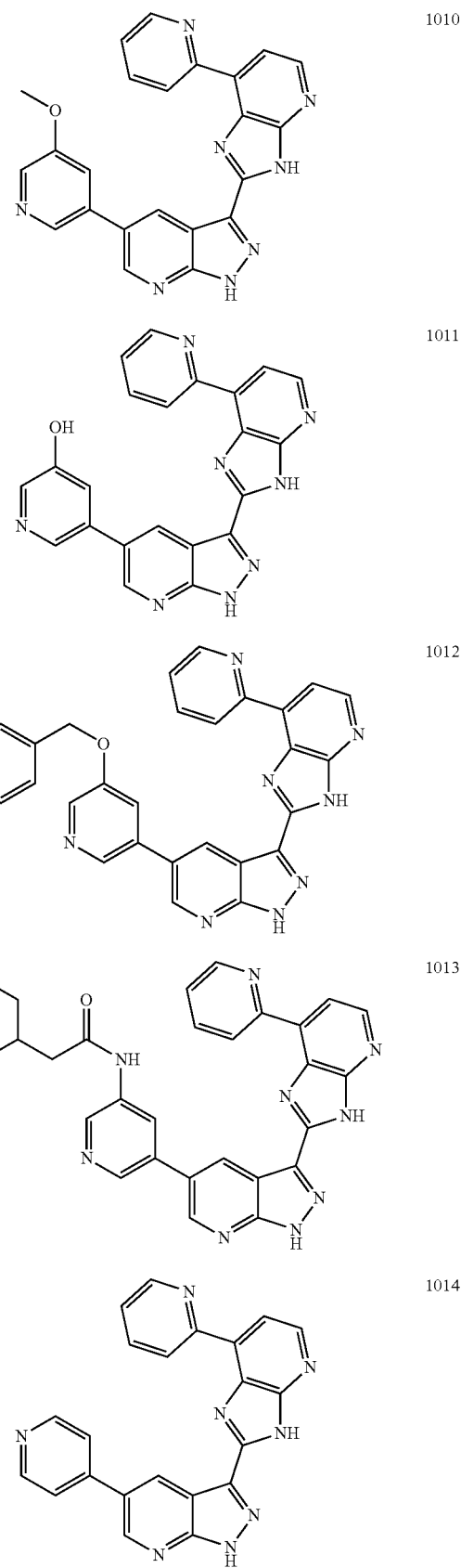

TABLE 1-continued
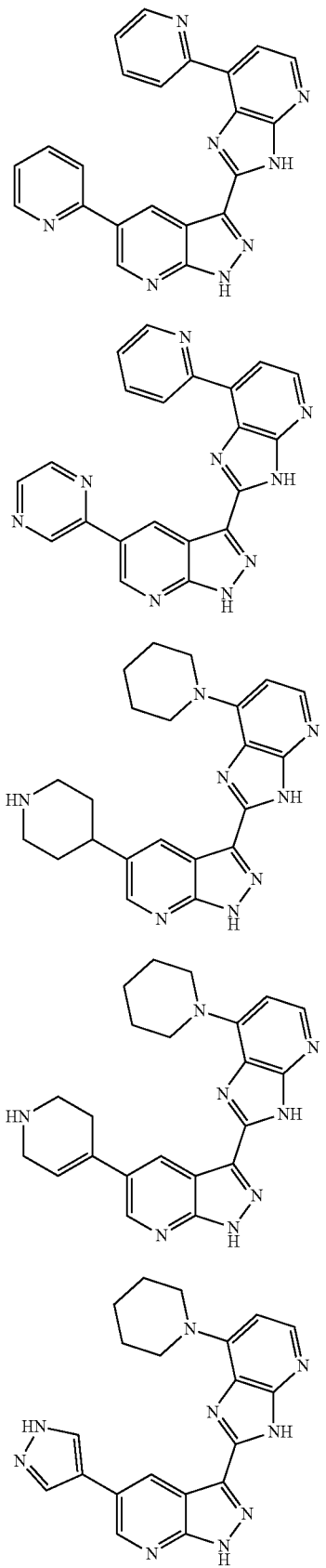
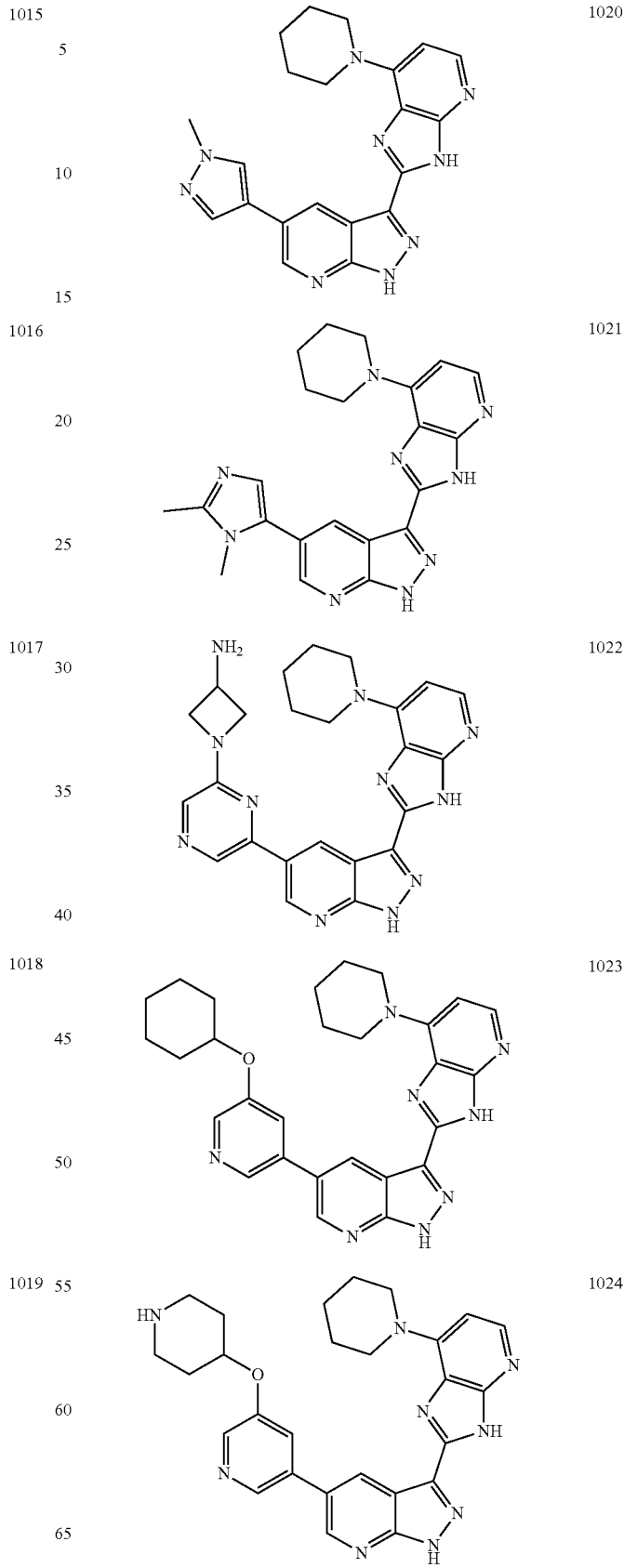

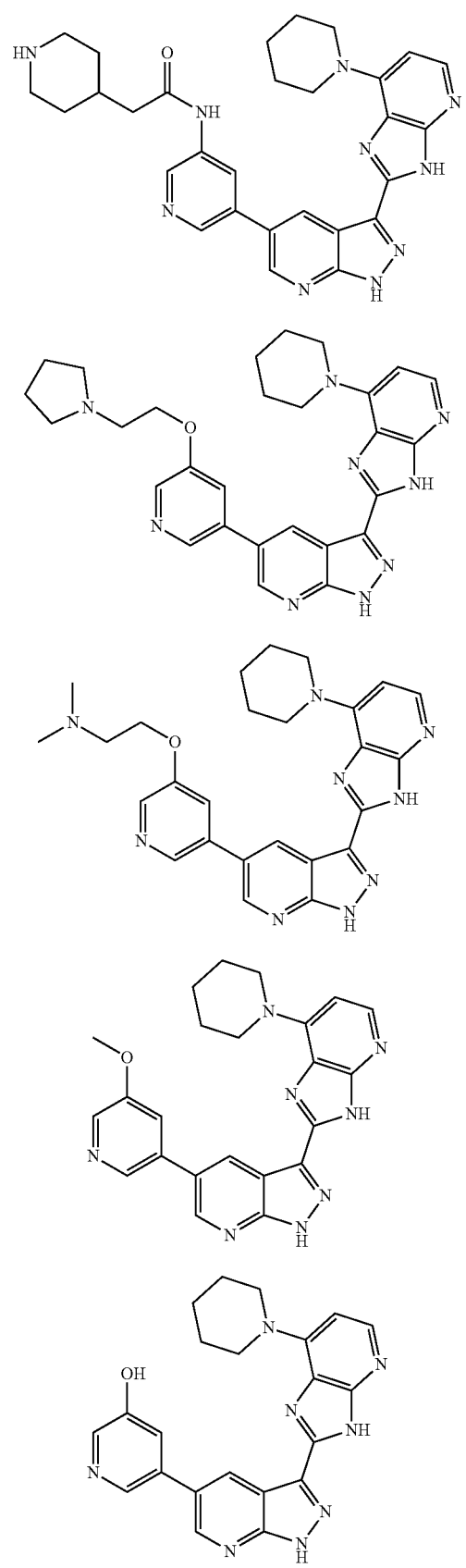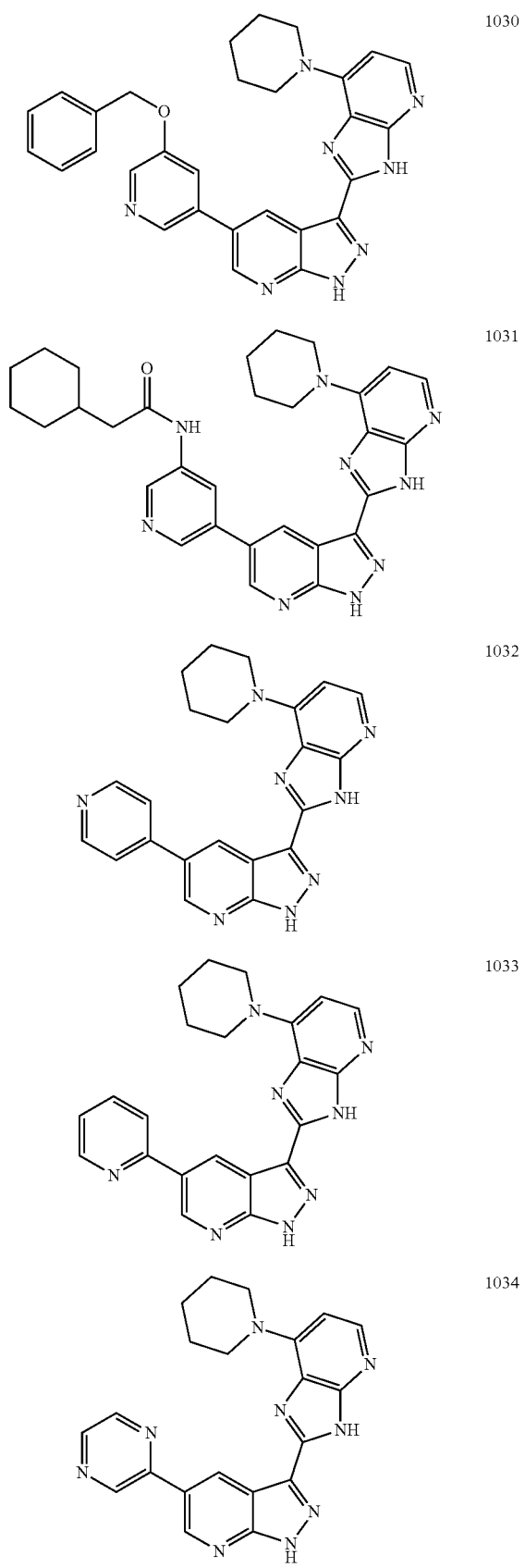

TABLE 1-continued
1035 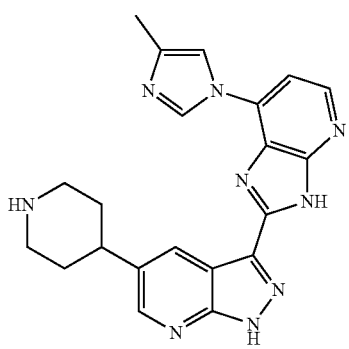 [SMILES: Cc1cn(-c2ccnc3[nH]c(-c4n[nH]c5ncc(C6CCNCC6)cc45)nc23)cn1]
1036 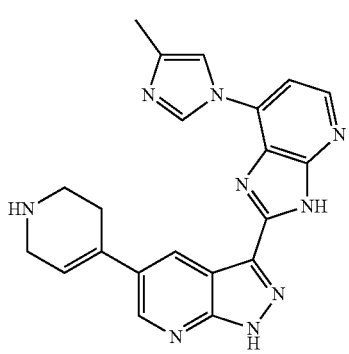 [SMILES: Cc1cn(-c2ccnc3[nH]c(-c4n[nH]c5ncc(C6=CCNCC6)cc45)nc23)cn1]
1037 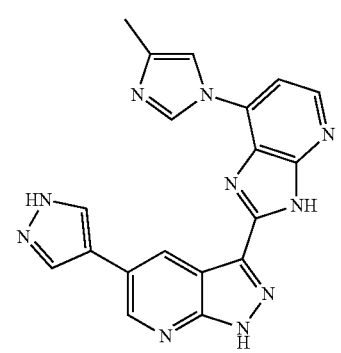 [SMILES: Cc1cn(-c2ccnc3[nH]c(-c4n[nH]c5ncc(-c6cn[nH]c6)cc45)nc23)cn1]
1038 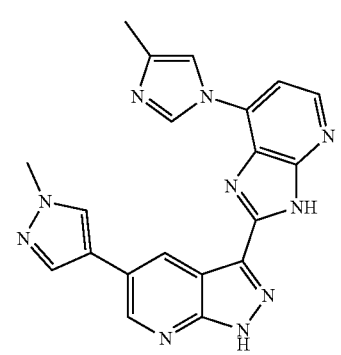 [SMILES: Cc1cn(-c2ccnc3[nH]c(-c4n[nH]c5ncc(-c6cnn(C)c6)cc45)nc23)cn1]
TABLE 1-continued
1039 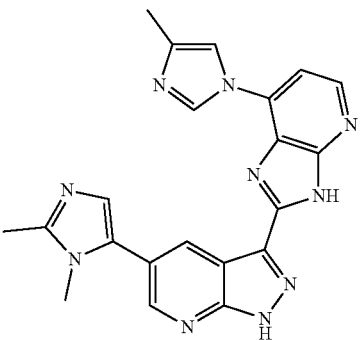 [SMILES: Cc1cn(-c2ccnc3[nH]c(-c4n[nH]c5ncc(-c6cnc(C)n6C)cc45)nc23)cn1]
1040 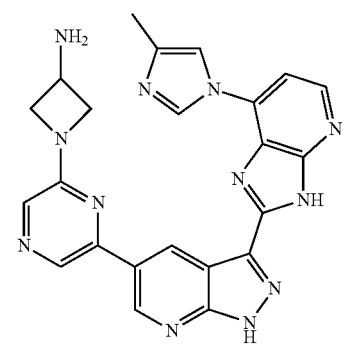 [SMILES: Cc1cn(-c2ccnc3[nH]c(-c4n[nH]c5ncc(-c6cncc(N7CC(N)C7)n6)cc45)nc23)cn1]
1041 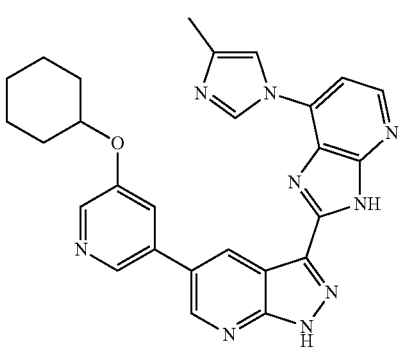 [SMILES: Cc1cn(-c2ccnc3[nH]c(-c4n[nH]c5ncc(-c6cncc(OC7CCCCC7)c6)cc45)nc23)cn1]
1042 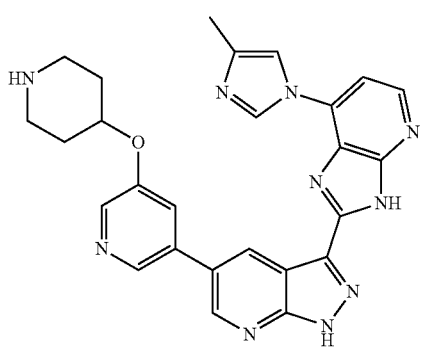 [SMILES: Cc1cn(-c2ccnc3[nH]c(-c4n[nH]c5ncc(-c6cncc(OC7CCNCC7)c6)cc45)nc23)cn1]

TABLE 1-continued
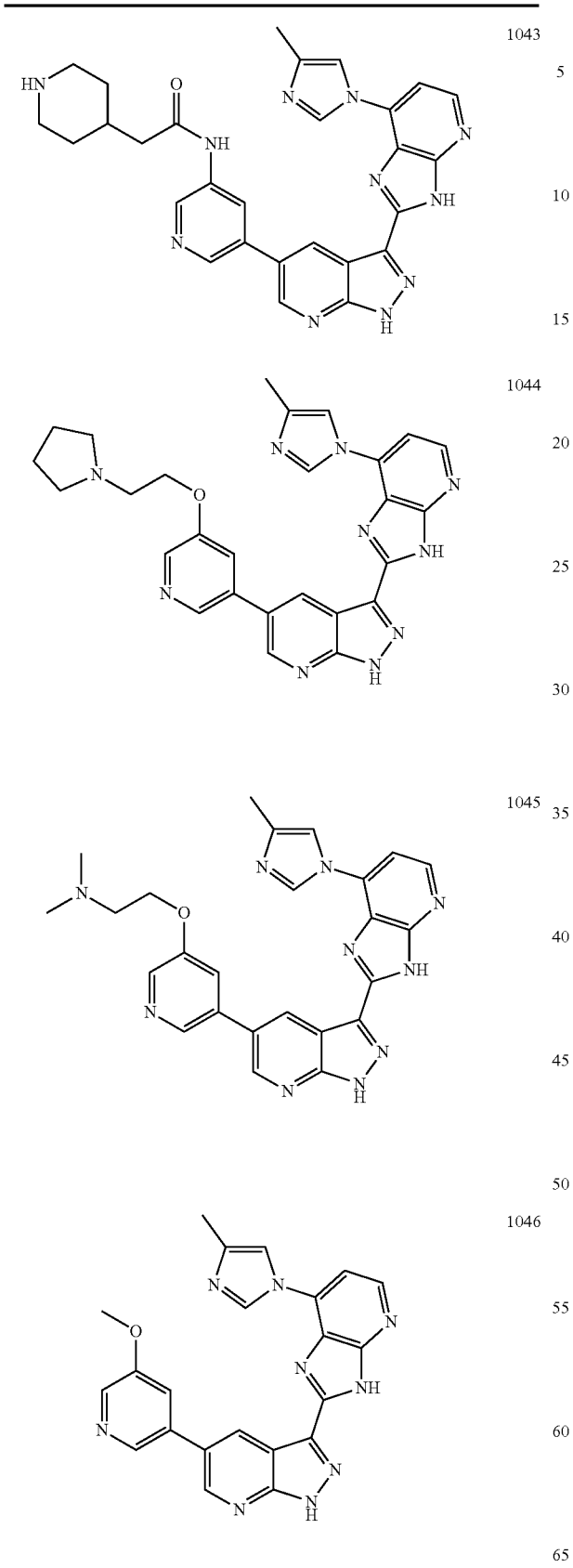
1043
1044
1045
1046
TABLE 1-continued
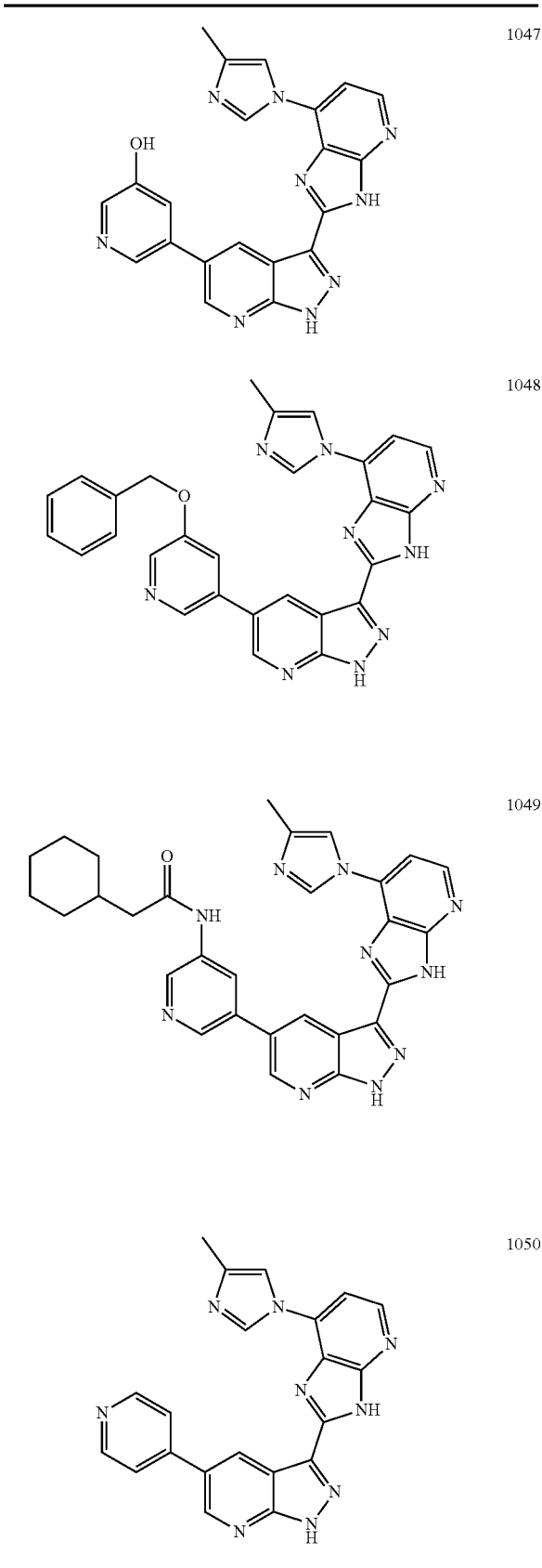
1047
1048
1049
1050

TABLE 1-continued
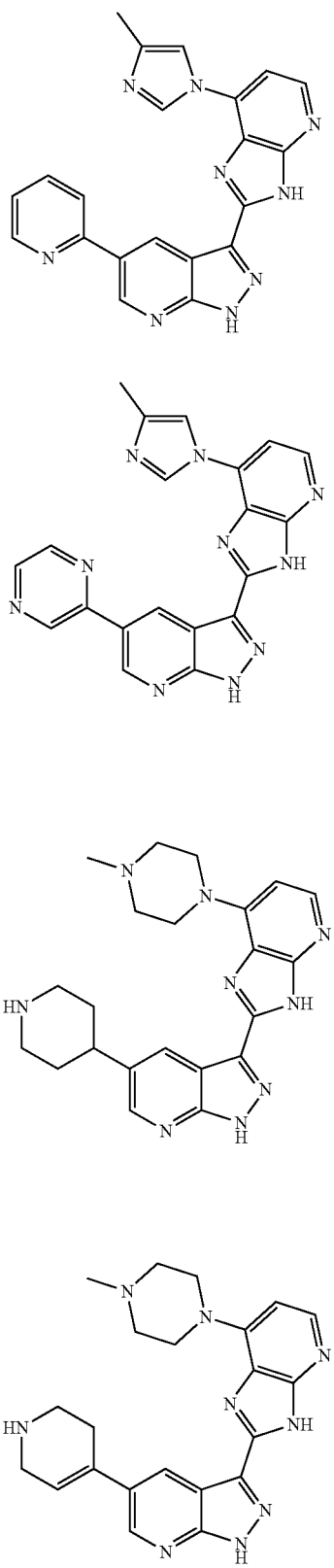
1051
1052
1053
1054
TABLE 1-continued
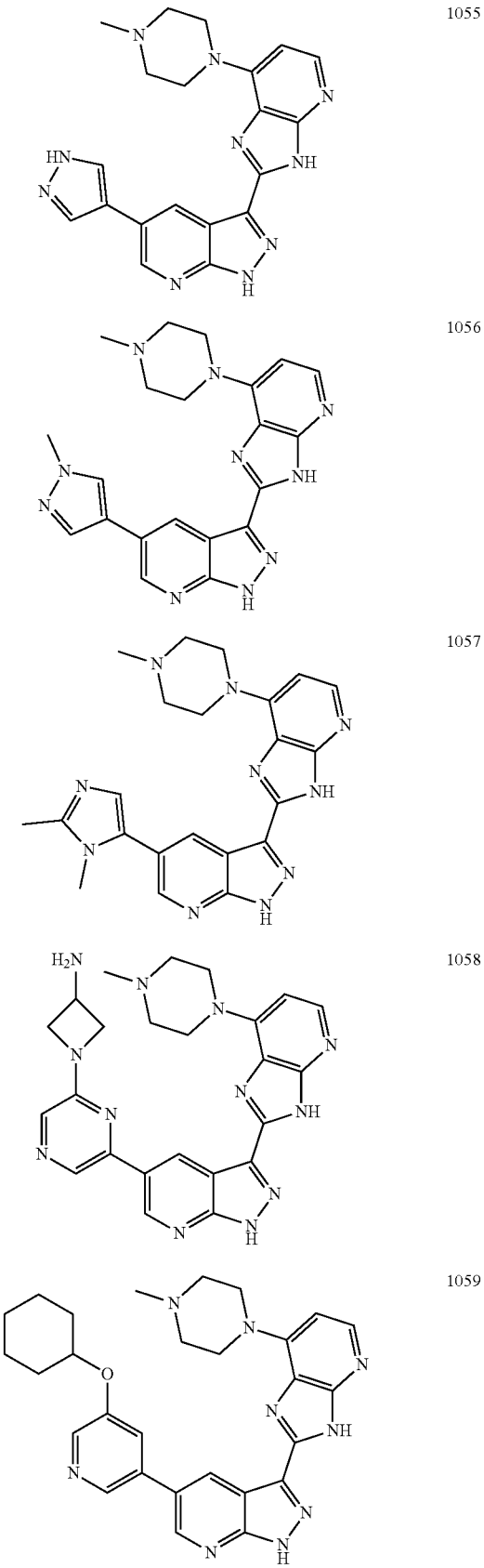
1055
1056
1057
1058
1059

TABLE 1-continued
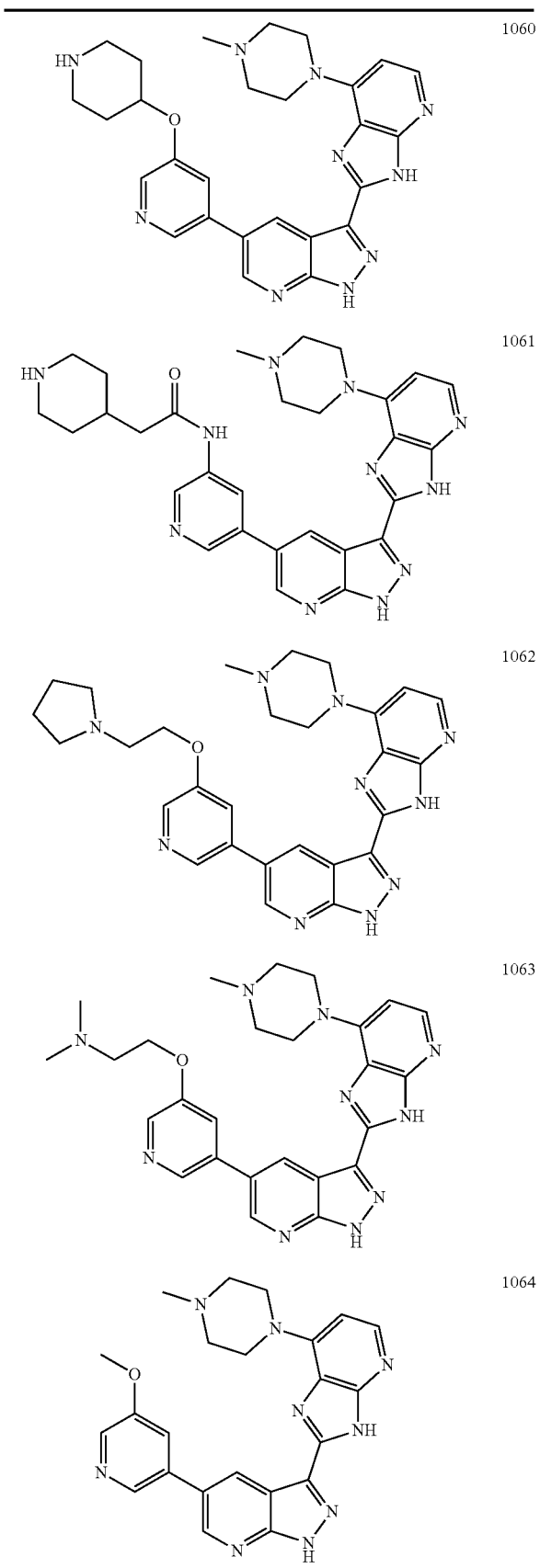
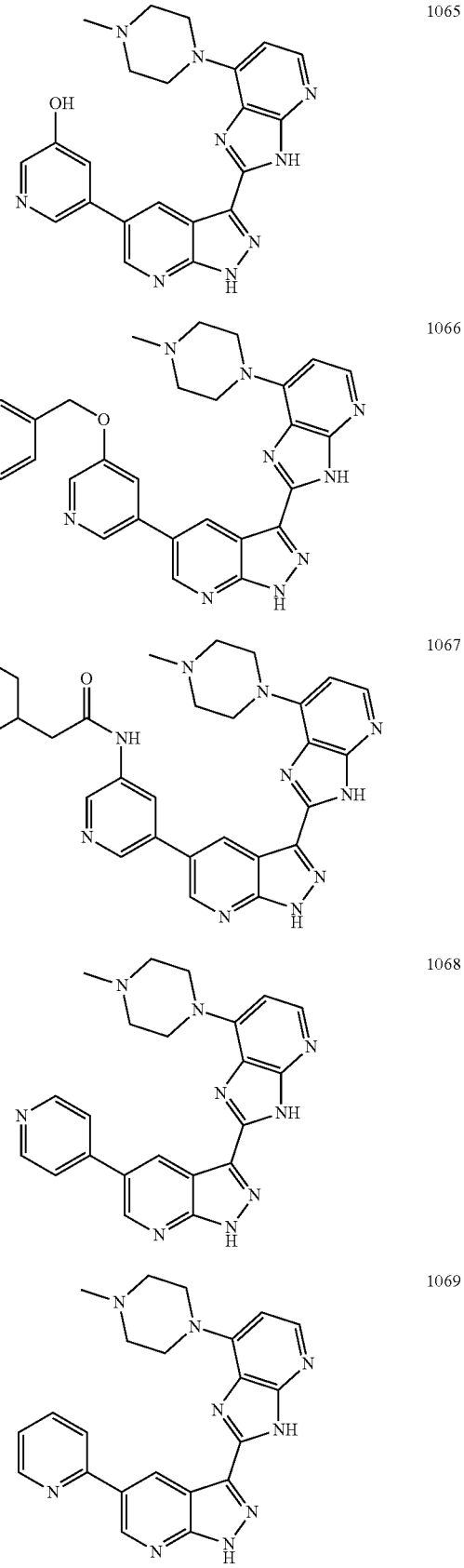

TABLE 1-continued
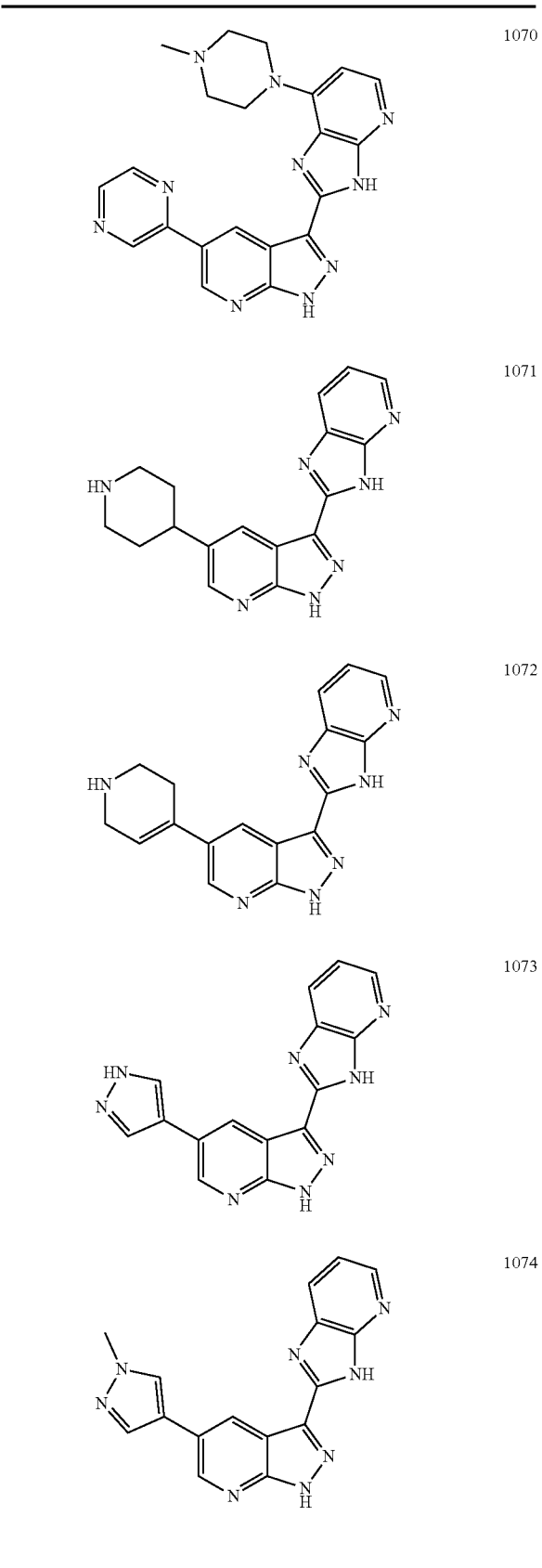
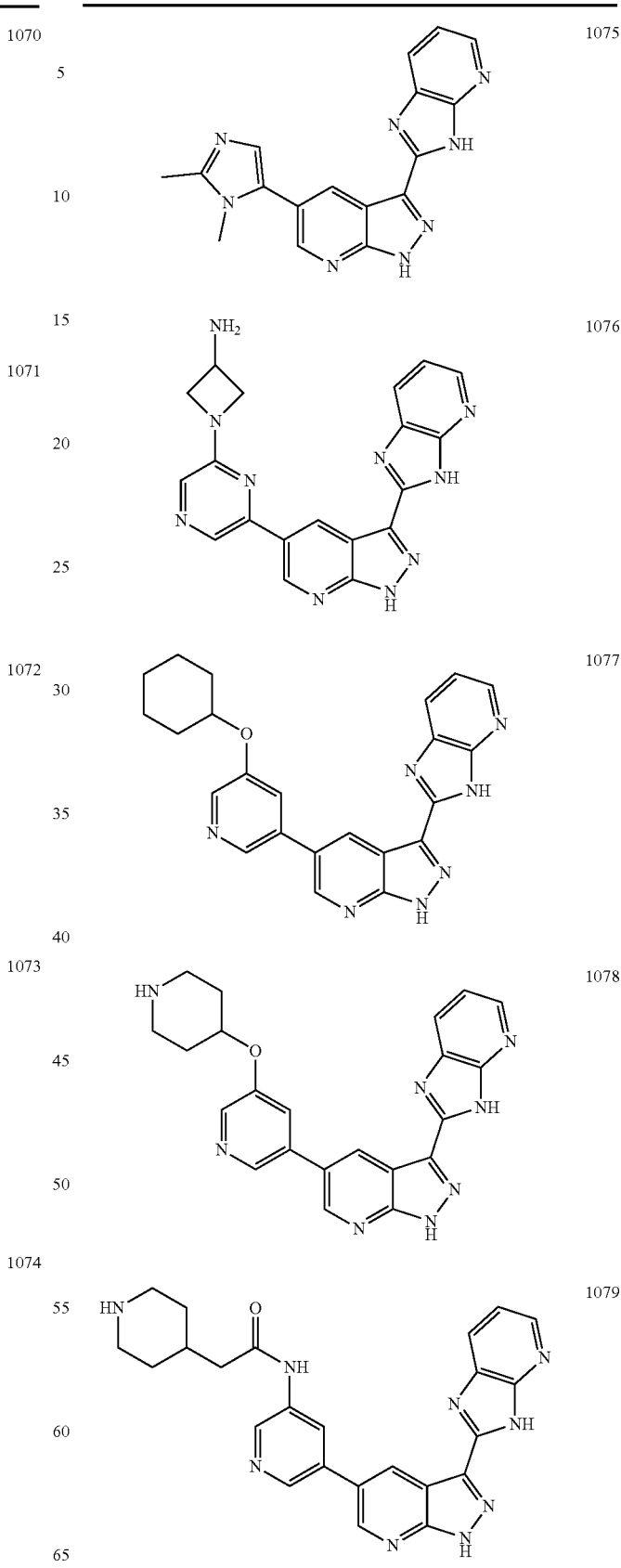

TABLE 1-continued
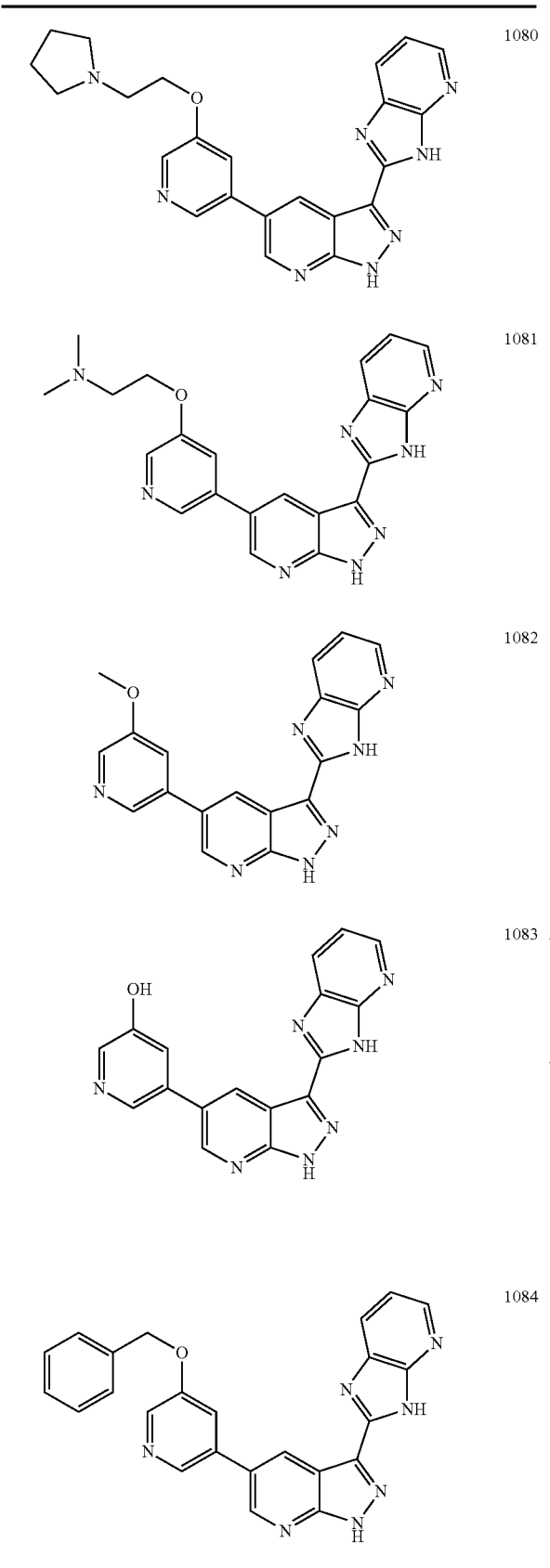
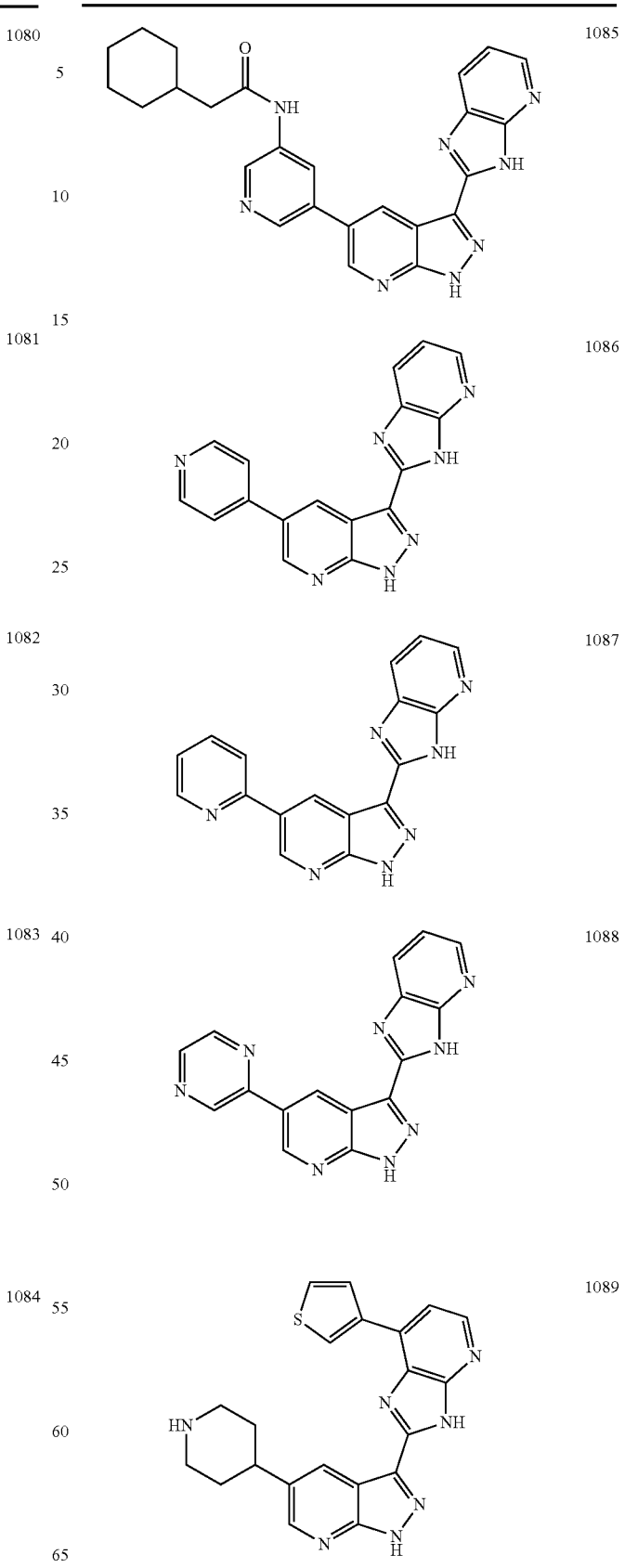

TABLE 1-continued
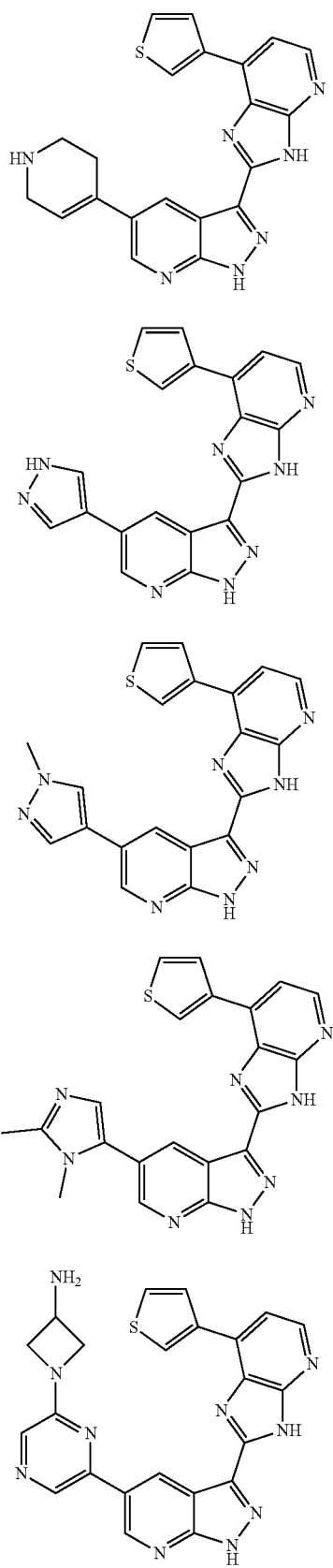
1090
1091
1092
1093
1094
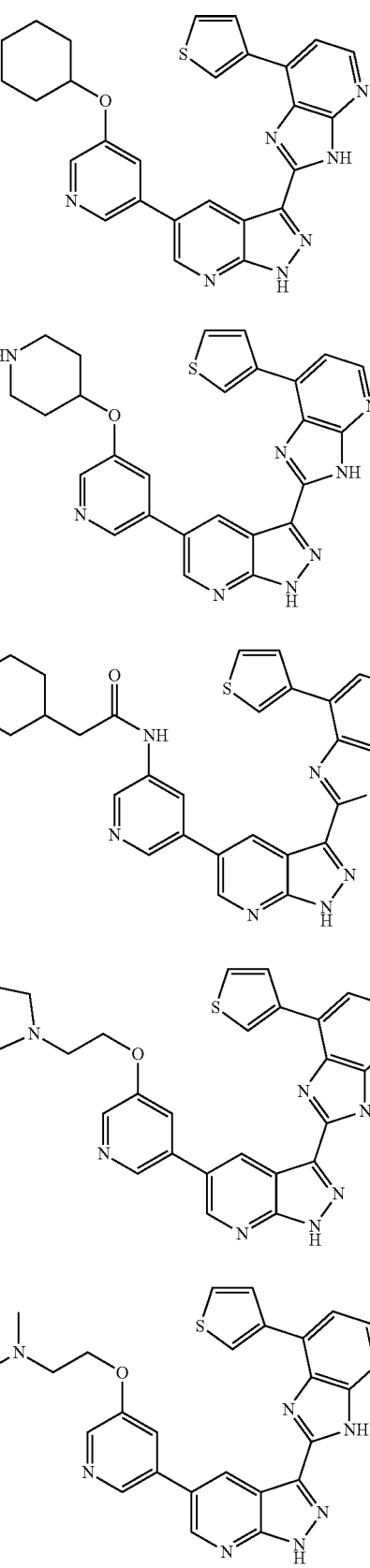
1095
1096
1097
1098
1099

TABLE 1-continued
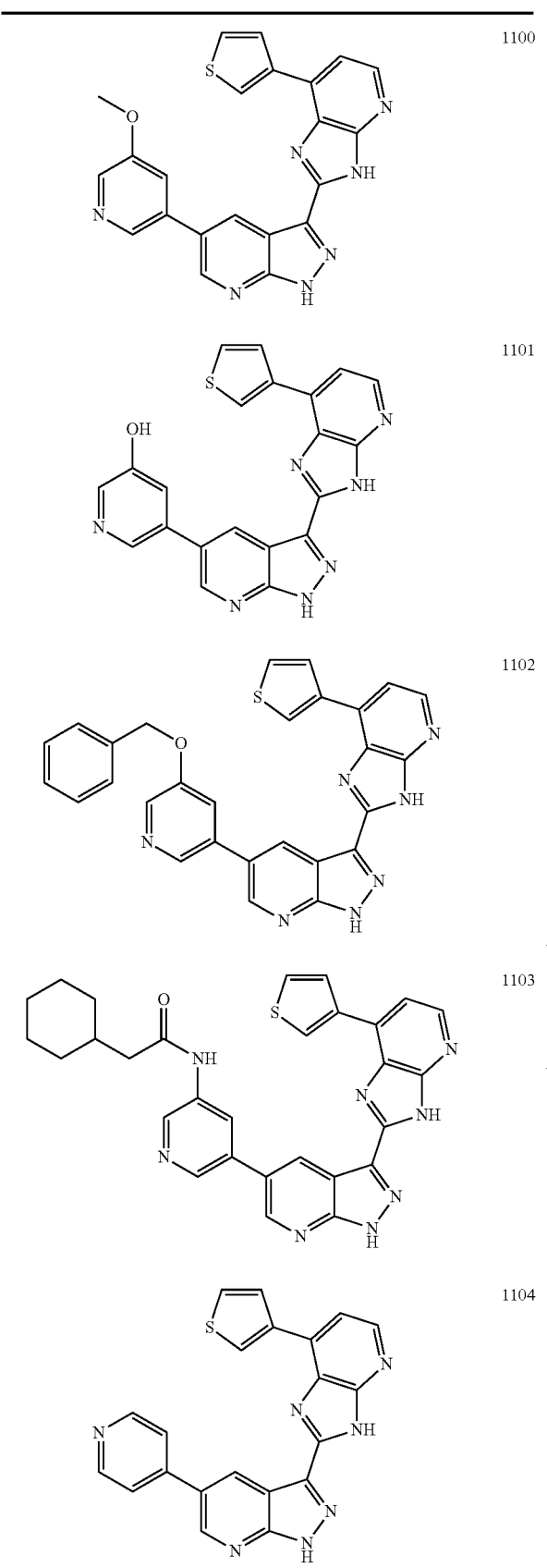
TABLE 1-continued
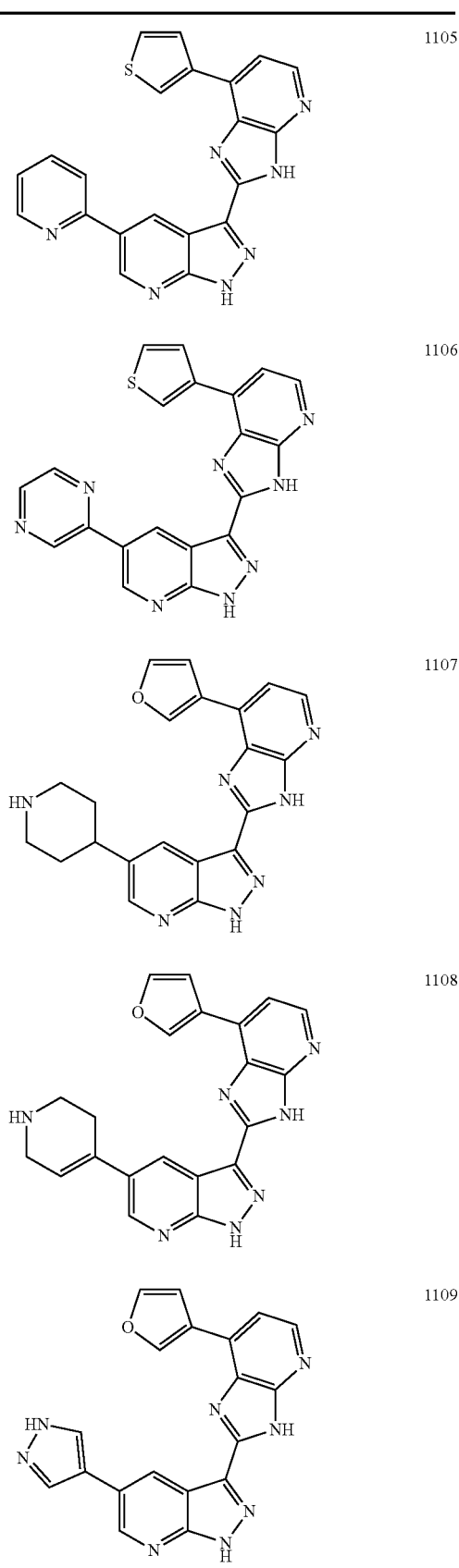

TABLE 1-continued
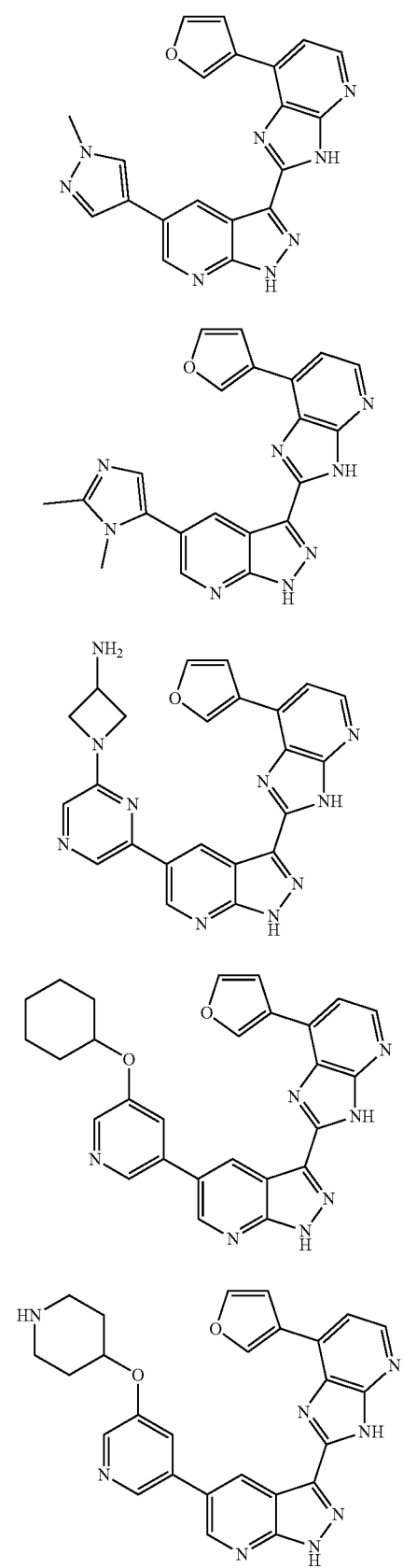
TABLE 1-continued
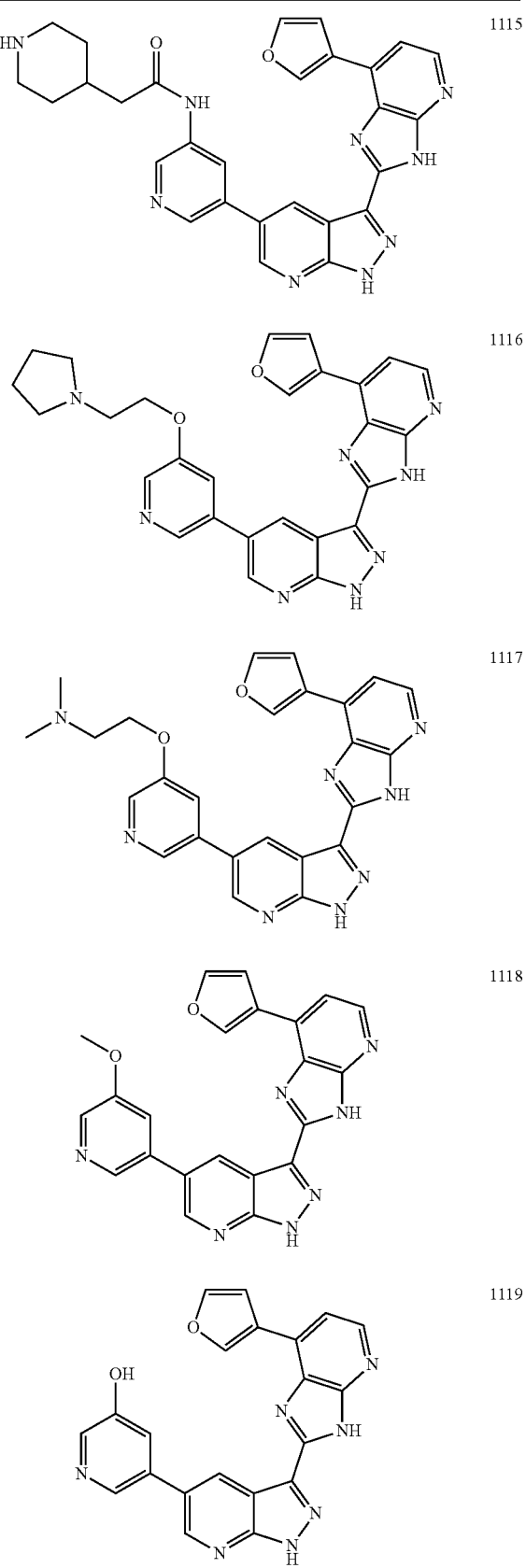

TABLE 1-continued
| | |
|---|---|
| 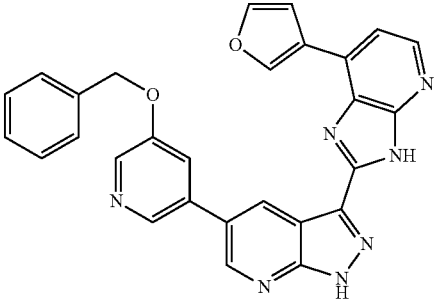 | 1120 |
| 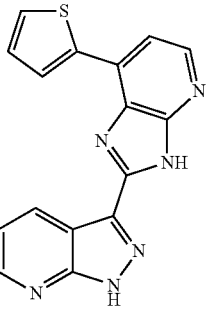 | 1121 |
| 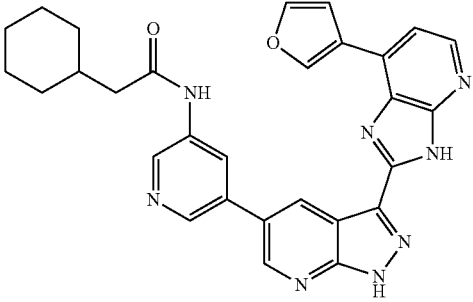 [SMILES: O=C(CC1CCCCC1)Nc1cncc(-c2cnc3[nH]nc(-c4nc5c(-c6ccsc6)ccnc5[nH]4)c3c2)c1] | 1122 |
| 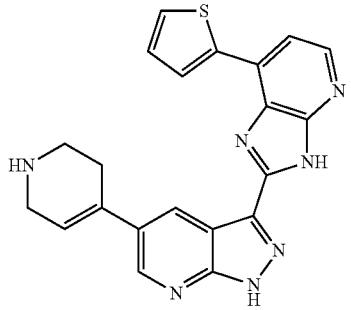 | 1123 |
| 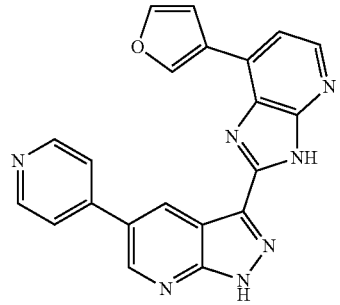 [SMILES: c1cc(-c2cnc3[nH]nc(-c4nc5c(-c6ccsc6)ccnc5[nH]4)c3c2)ccn1] | 1124 |ида
TABLE 1-continued
| | |
|---|---|
| 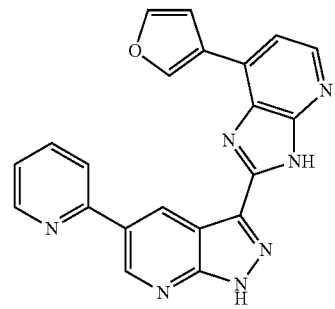 [SMILES: c1ccc(-c2cnc3[nH]nc(-c4nc5c(-c6ccoc6)ccnc5[nH]4)c3c2)nc1] | 1125 |
| 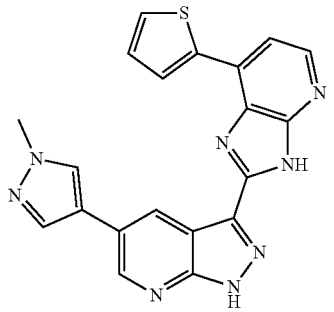 [SMILES: Cn1cc(-c2cnc3[nH]nc(-c4nc5c(-c6cccs6)ccnc5[nH]4)c3c2)cn1] | 1126 |
| 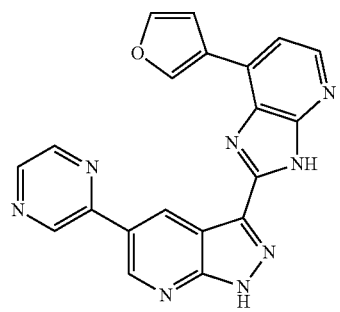 | 1127 |
| 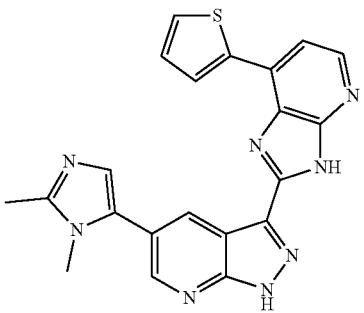 [SMILES: Cc1ncc(-c2cnc3[nH]nc(-c4nc5c(-c6cccs6)ccnc5[nH]4)c3c2)n1C] | 1128 |
| 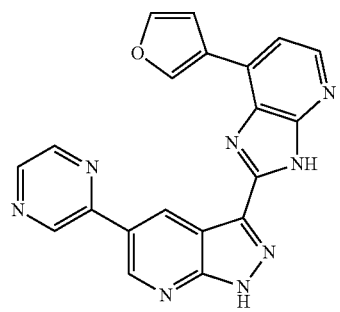 | 1129 |

TABLE 1-continued
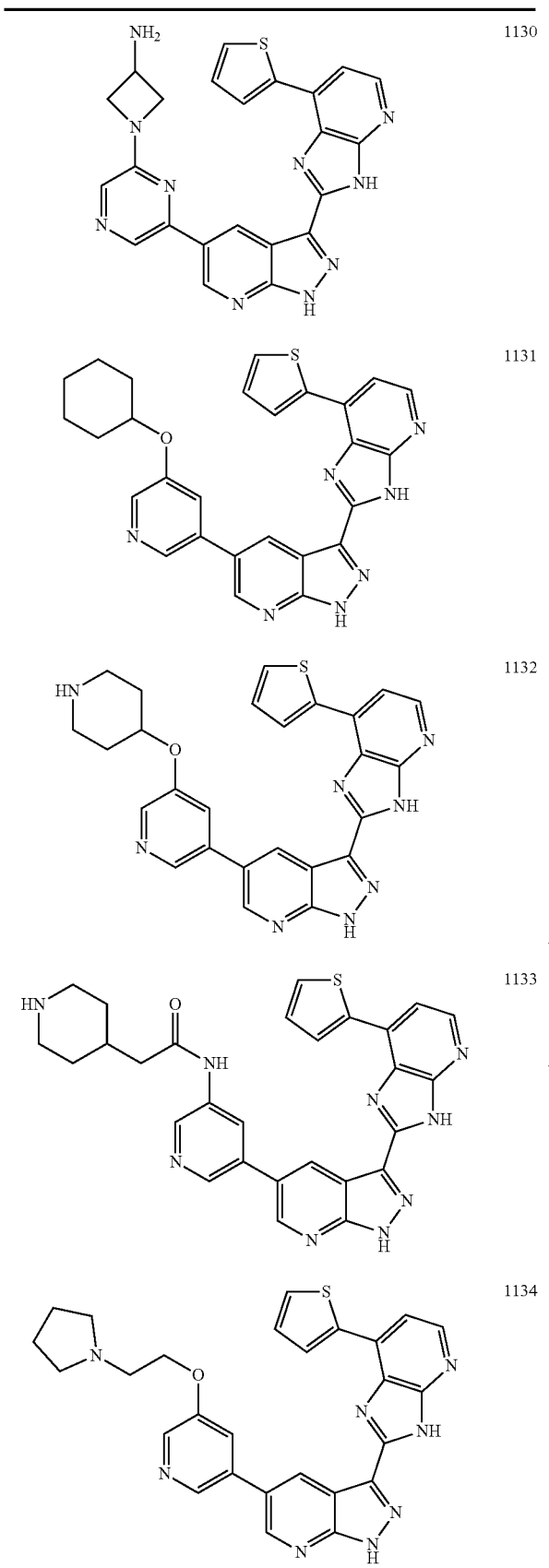
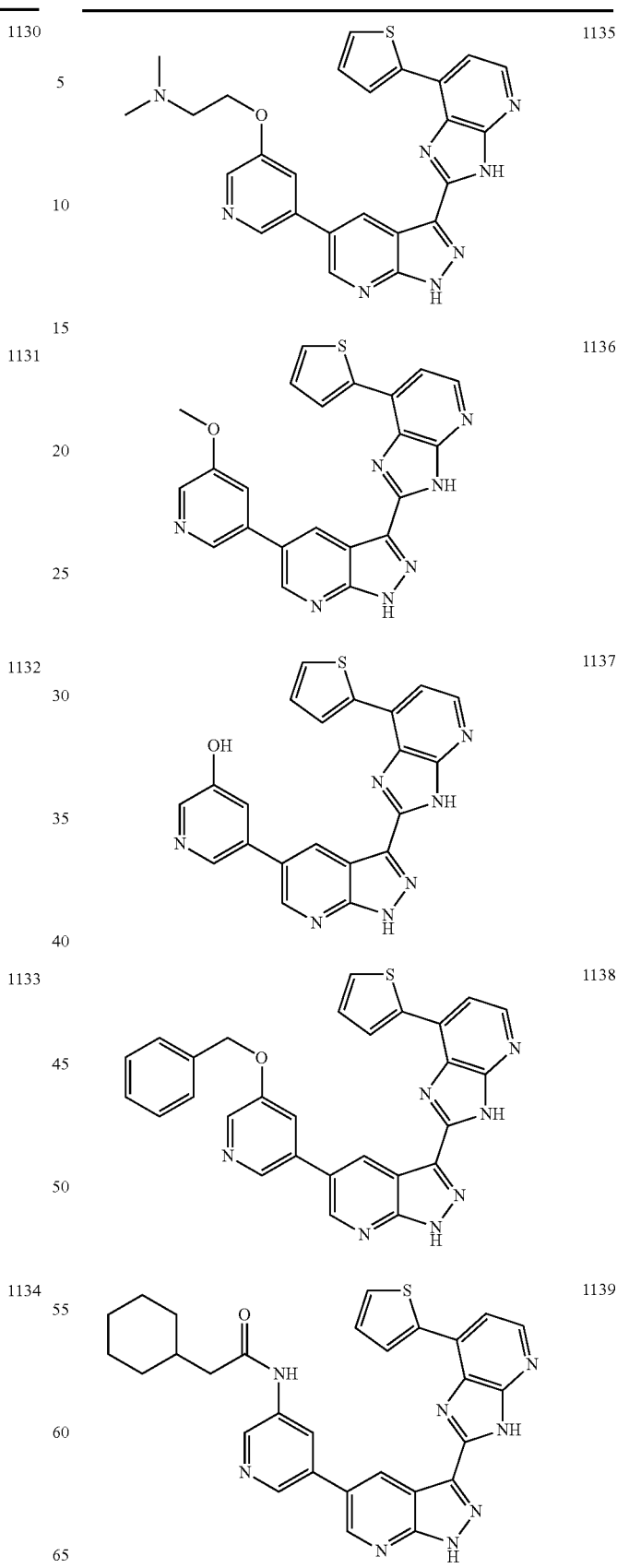

TABLE 1-continued
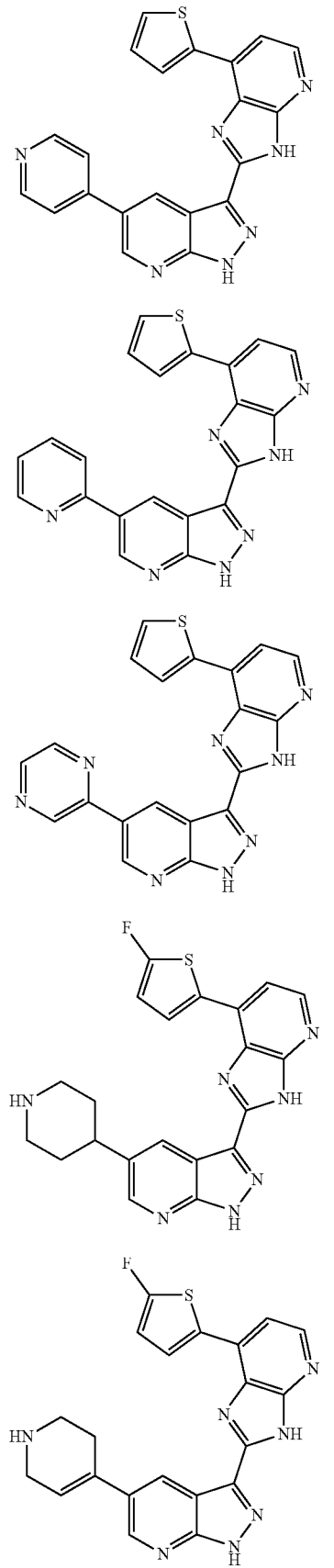
1140
1141
1142
1143
1144
TABLE 1-continued
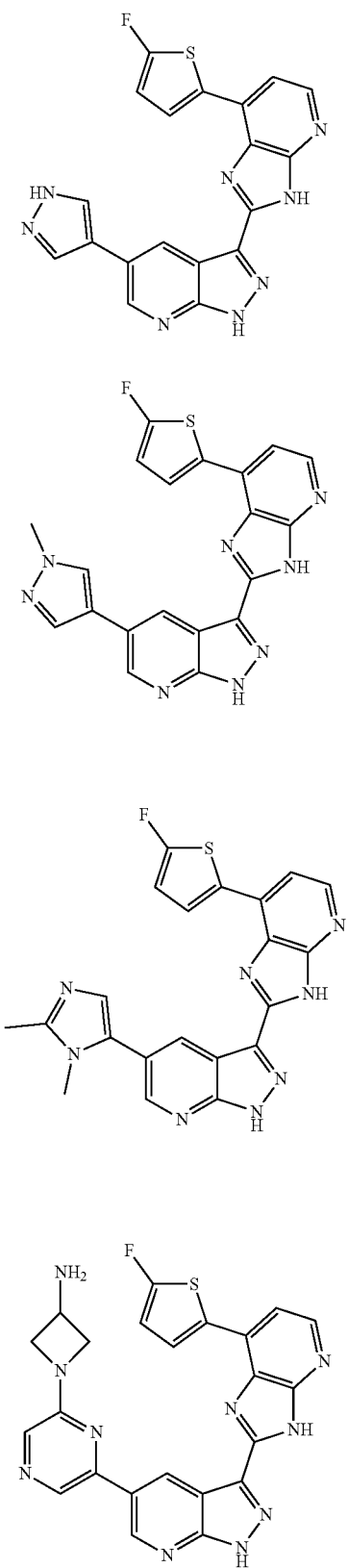
1145
1146
1147
1148

TABLE 1-continued
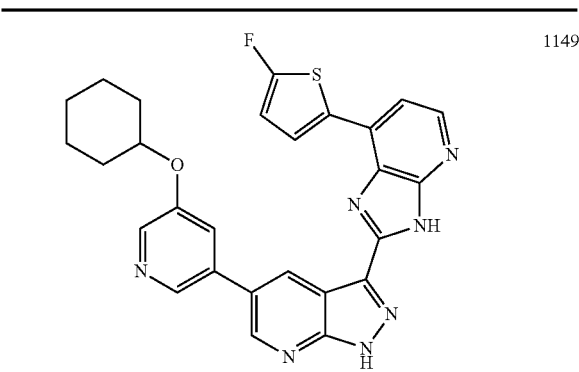
1149
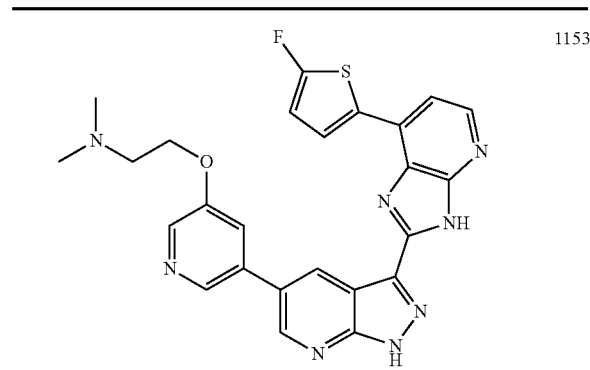
1153
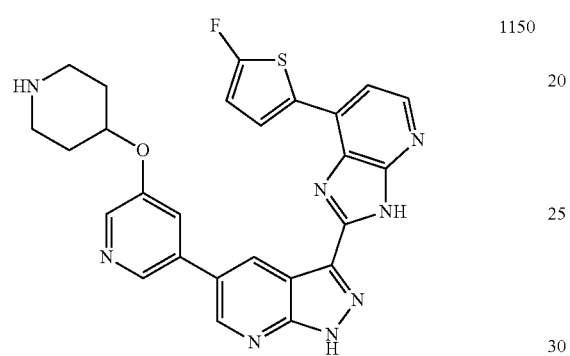
1150
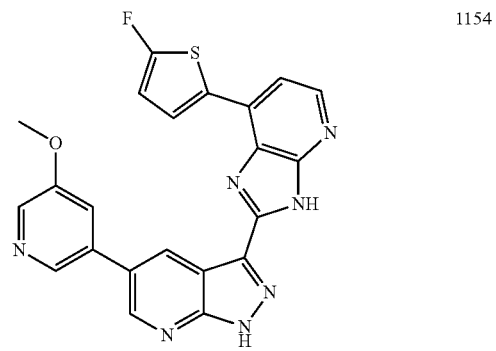
1154
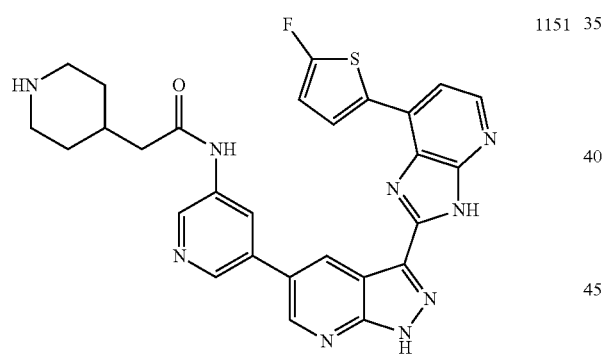
1151
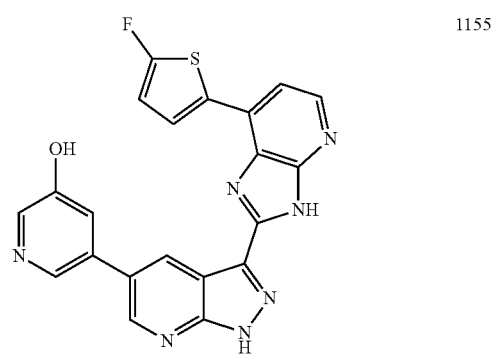
1155
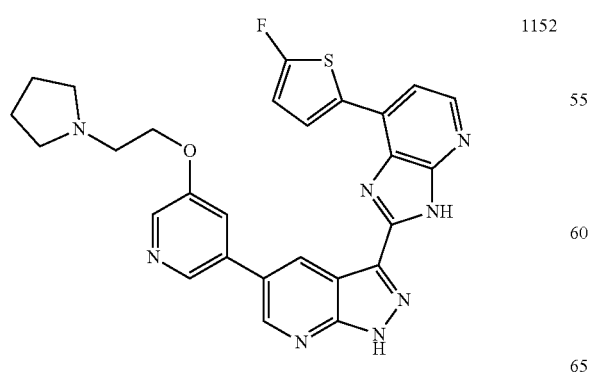
1152
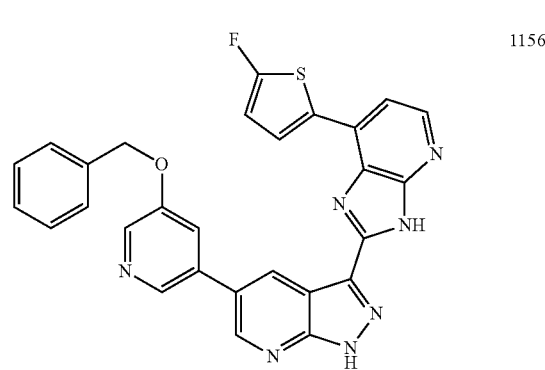
1156

TABLE 1-continued
| | |
|---|---|
| 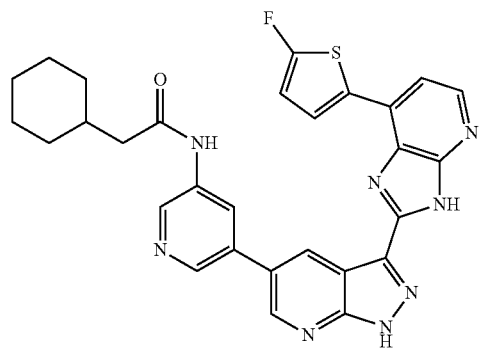 [SMILES: O=C(CC1CCCCC1)Nc1cncc(-c2cnc3[nH]nc(-c4nc5c(-c6ccc(F)s6)ccnc5[nH]4)c3c2)c1] | 1157 |
| 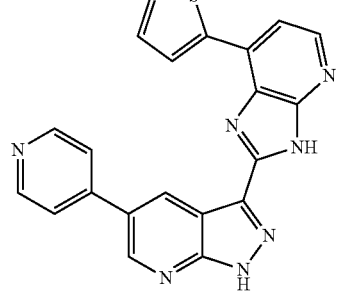 | 1158 |
| 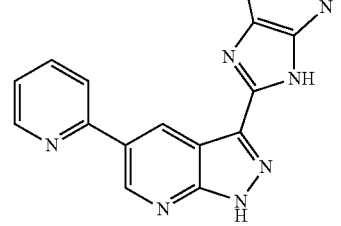 | 1159 |
| 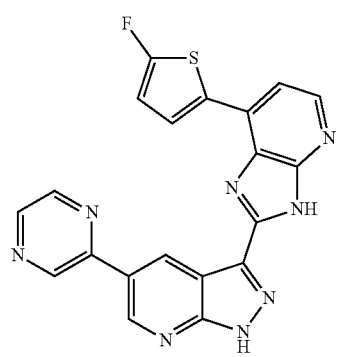 [SMILES: Fc1ccc(-c2ccnc3[nH]c(-c4n[nH]c5ncc(-c6cnccn6)cc45)nc23)s1] | 1160 |
TABLE 1-continued
| | |
|---|---|
| 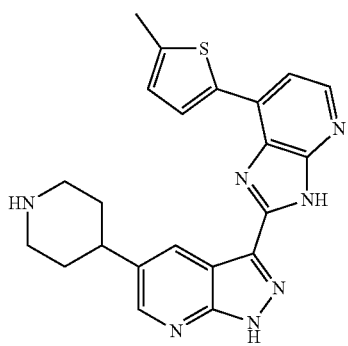 [SMILES: Cc1ccc(-c2ccnc3[nH]c(-c4n[nH]c5ncc(C6CCNCC6)cc45)nc23)s1] | 1161 |
| 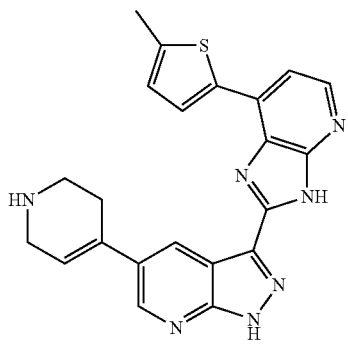 [SMILES: Cc1ccc(-c2ccnc3[nH]c(-c4n[nH]c5ncc(C6=CCNCC6)cc45)nc23)s1] | 1162 |
| 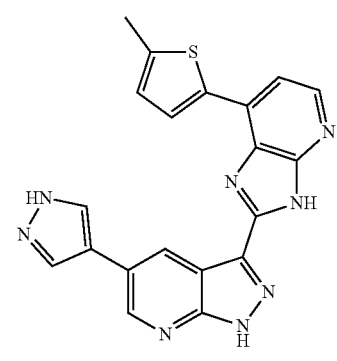 [SMILES: Cc1ccc(-c2ccnc3[nH]c(-c4n[nH]c5ncc(-c6cn[nH]c6)cc45)nc23)s1] | 1163 |
| 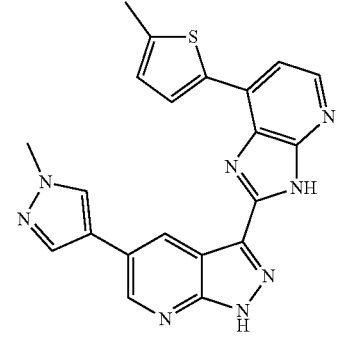 [SMILES: Cc1ccc(-c2ccnc3[nH]c(-c4n[nH]c5ncc(-c6cnn(C)c6)cc45)nc23)s1] | 1164 |

TABLE 1-continued
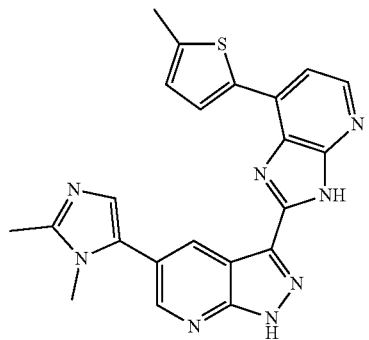 [SMILES: Cc1ccc(-c2ccnc3[nH]c(-c4n[nH]c5ncc(-c6cnc(C)n6C)cc45)nc23)s1]
1165
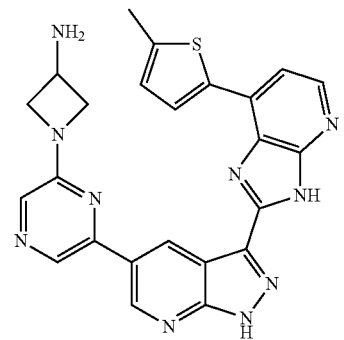 [SMILES: Cc1ccc(-c2ccnc3[nH]c(-c4n[nH]c5ncc(-c6cncc(N7CC(N)C7)n6)cc45)nc23)s1]
1166
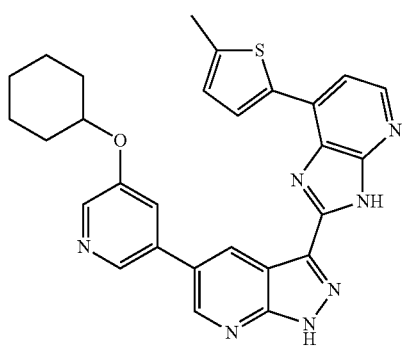 [SMILES: Cc1ccc(-c2ccnc3[nH]c(-c4n[nH]c5ncc(-c6cncc(OC7CCCCC7)c6)cc45)nc23)s1]
1167
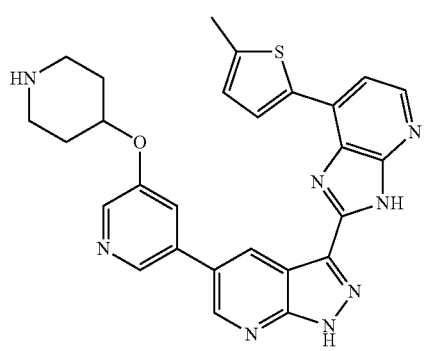 [SMILES: Cc1ccc(-c2ccnc3[nH]c(-c4n[nH]c5ncc(-c6cncc(OC7CCNCC7)c6)cc45)nc23)s1]
1168
TABLE 1-continued
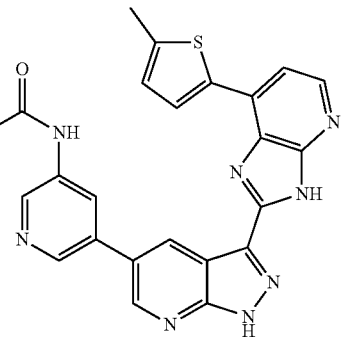
1169
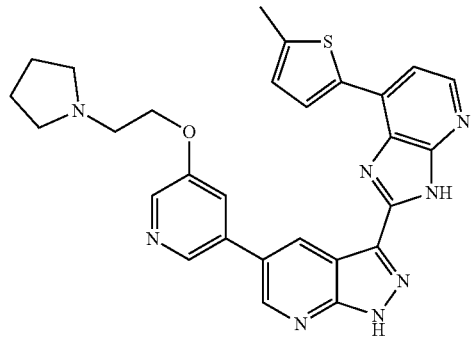 [SMILES: Cc1ccc(-c2ccnc3[nH]c(-c4n[nH]c5ncc(-c6cncc(OCCN7CCCC7)c6)cc45)nc23)s1]
1170
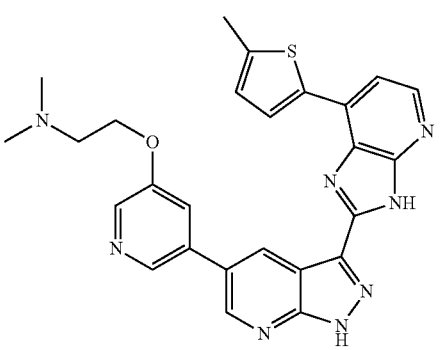 [SMILES: Cc1ccc(-c2ccnc3[nH]c(-c4n[nH]c5ncc(-c6cncc(OCCN(C)C)c6)cc45)nc23)s1]
1171
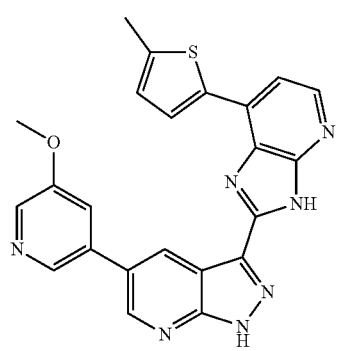 [SMILES: COc1cncc(-c2cnc3[nH]nc(-c4nc5c(-c6ccc(C)s6)ccnc5[nH]4)c3c2)c1]
1172

TABLE 1-continued
1173
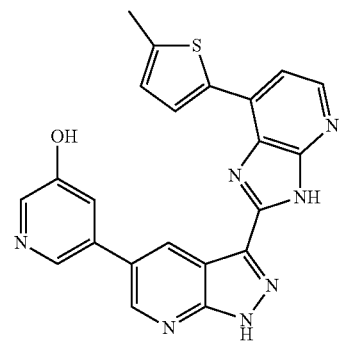 [SMILES: Cc1ccc(-c2ccnc3[nH]c(-c4n[nH]c5ncc(-c6cncc(O)c6)cc45)nc23)s1]
1174
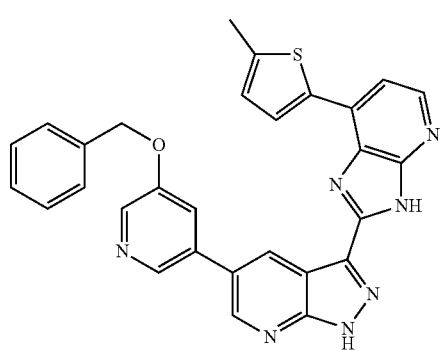 [SMILES: Cc1ccc(-c2ccnc3[nH]c(-c4n[nH]c5ncc(-c6cncc(OCc7ccccc7)c6)cc45)nc23)s1]
1175
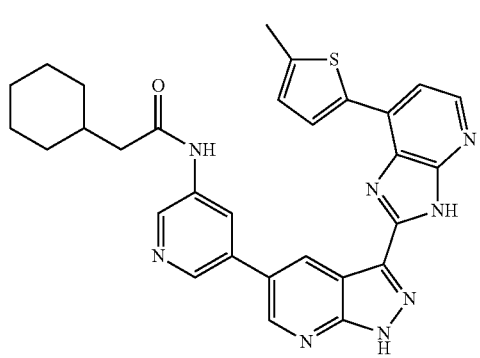 [SMILES: Cc1ccc(-c2ccnc3[nH]c(-c4n[nH]c5ncc(-c6cncc(NC(=O)CC7CCCCC7)c6)cc45)nc23)s1]
1176
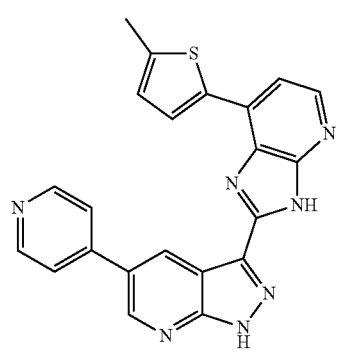 [SMILES: Cc1ccc(-c2ccnc3[nH]c(-c4n[nH]c5ncc(-c6ccncc6)cc45)nc23)s1]
TABLE 1-continued
1177
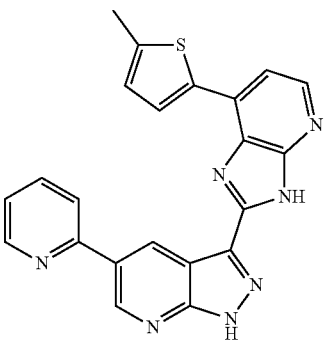 [SMILES: Cc1ccc(-c2ccnc3[nH]c(-c4n[nH]c5ncc(-c6ccccn6)cc45)nc23)s1]
1178
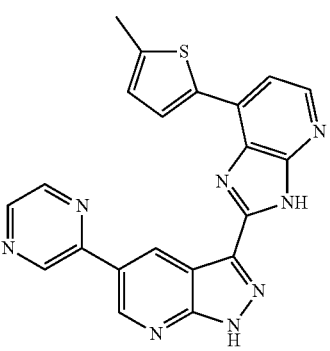 [SMILES: Cc1ccc(-c2ccnc3[nH]c(-c4n[nH]c5ncc(-c6cnccn6)cc45)nc23)s1]
1179
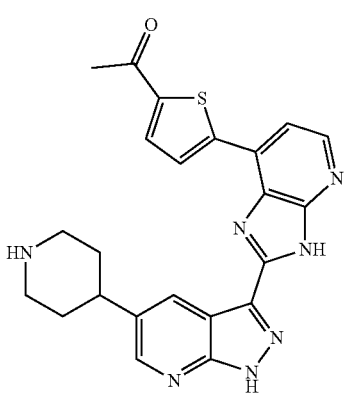 [SMILES: CC(=O)c1ccc(-c2ccnc3[nH]c(-c4n[nH]c5ncc(C6CCNCC6)cc45)nc23)s1]
1180
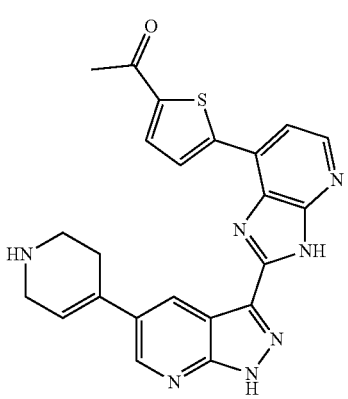 [SMILES: CC(=O)c1ccc(-c2ccnc3[nH]c(-c4n[nH]c5ncc(C6=CCNCC6)cc45)nc23)s1]

TABLE 1-continued
| | |
|---|---|
| 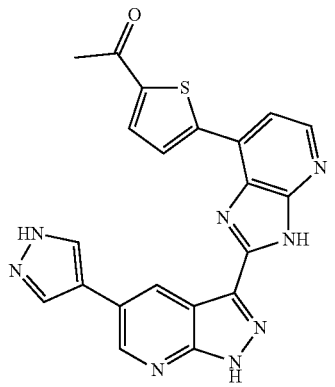 [SMILES: CC(=O)c1ccc(-c2ccnc3[nH]c(-c4n[nH]c5ncc(-c6cn[nH]c6)cc45)nc23)s1] 1181 | 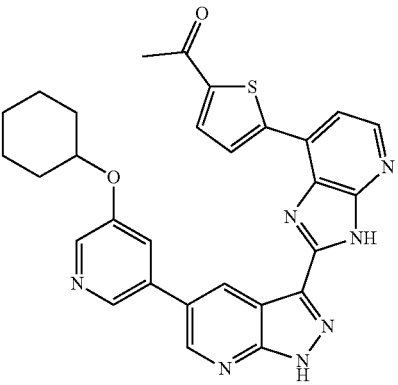 1185 |
| 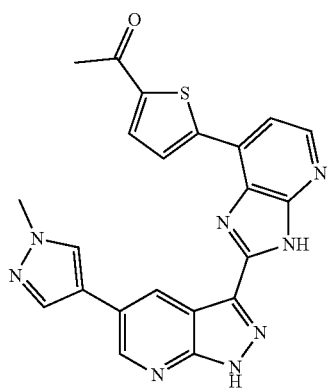 [SMILES: CC(=O)c1ccc(-c2ccnc3[nH]c(-c4n[nH]c5ncc(-c6cnn(C)c6)cc45)nc23)s1] 1182 | 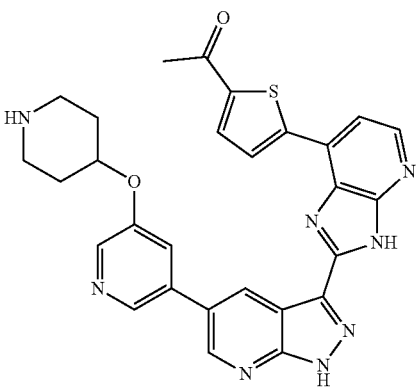 1186 |
| 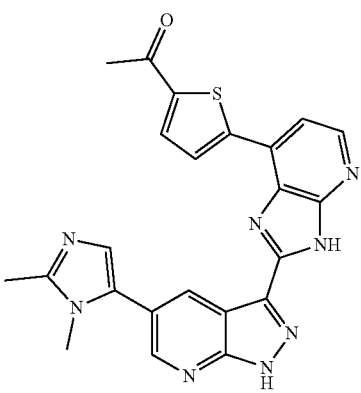 [SMILES: CC(=O)c1ccc(-c2ccnc3[nH]c(-c4n[nH]c5ncc(-c6cnc(C)n6C)cc45)nc23)s1] 1183 | 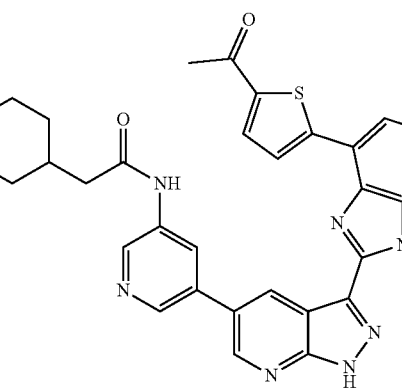 1187 |
| 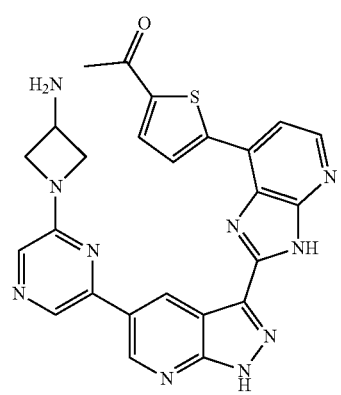 [SMILES: CC(=O)c1ccc(-c2ccnc3[nH]c(-c4n[nH]c5ncc(-c6cncc(N7CC(N)C7)n6)cc45)nc23)s1] 1184 | 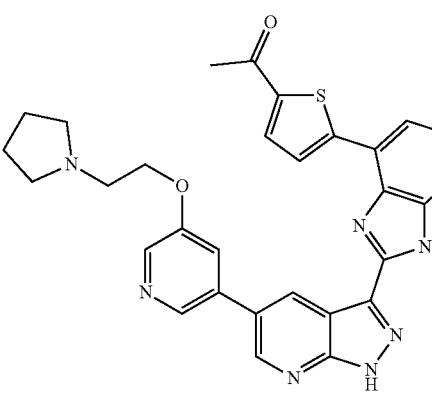 1188 |

TABLE 1-continued
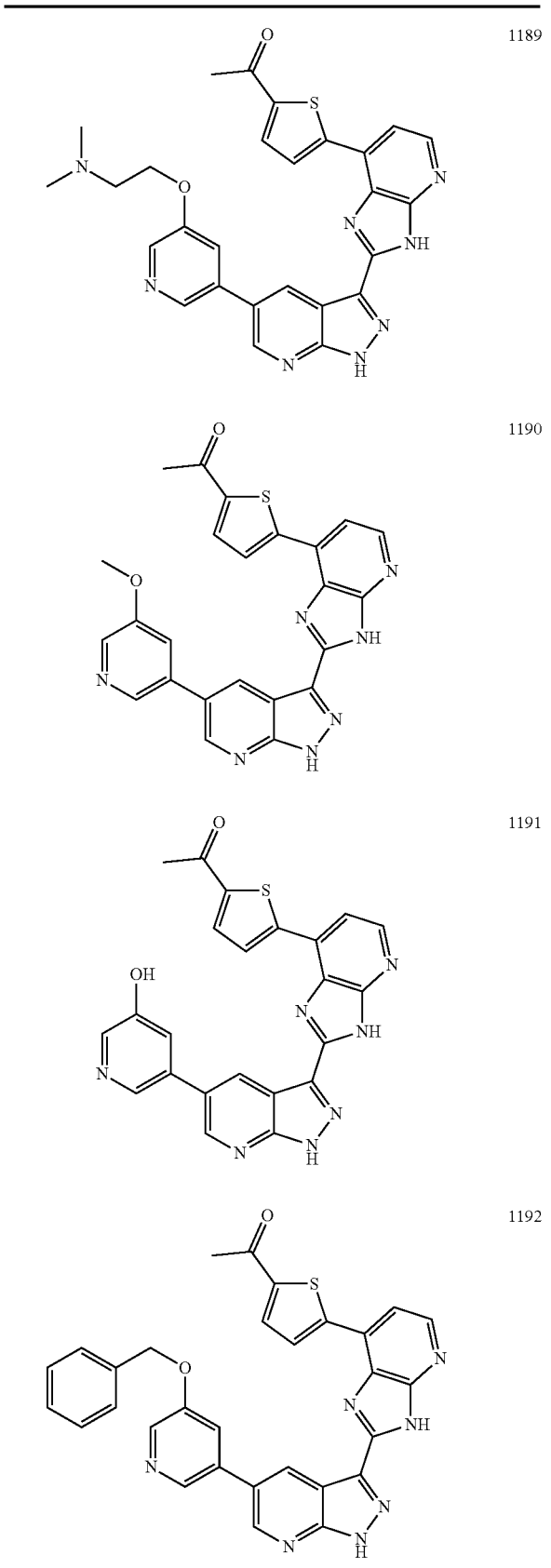
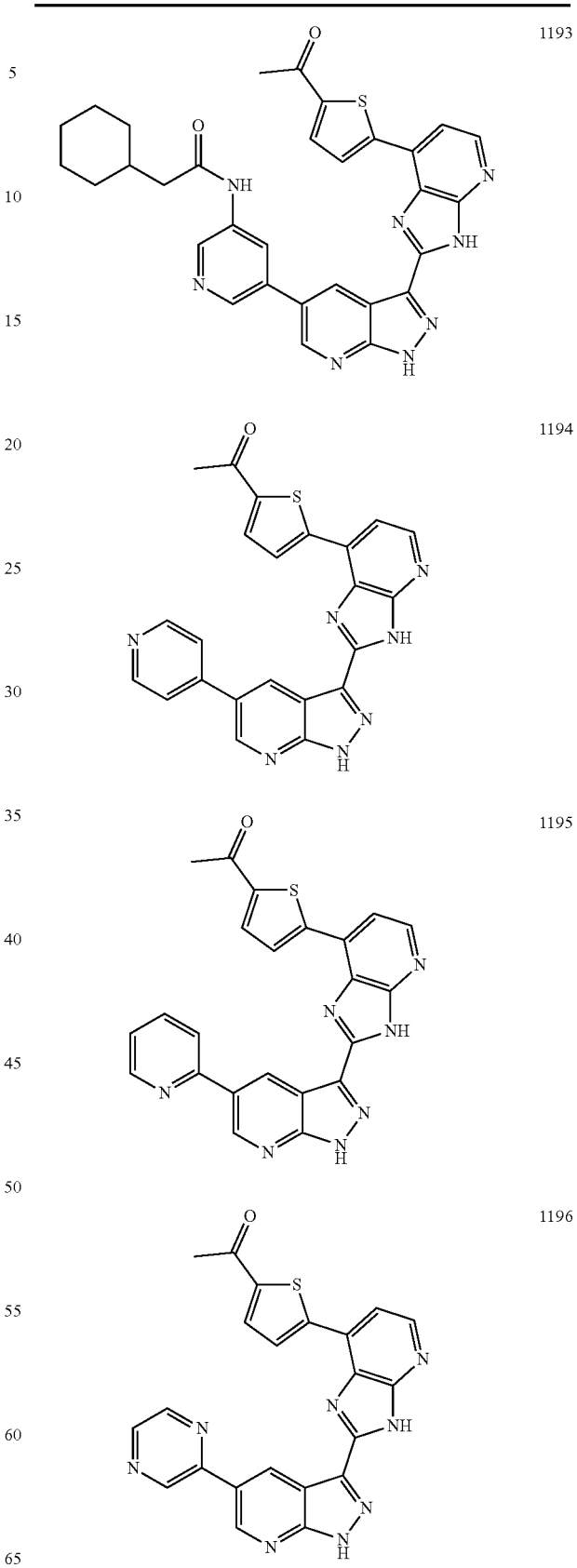

TABLE 1-continued
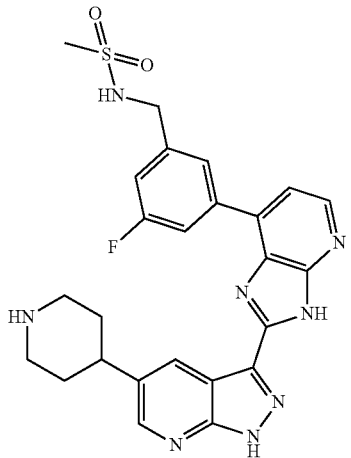 [SMILES: CS(=O)(=O)NCc1cc(F)cc(-c2ccnc3[nH]c(-c4n[nH]c5ncc(C6CCNCC6)cc45)nc23)c1]
1197
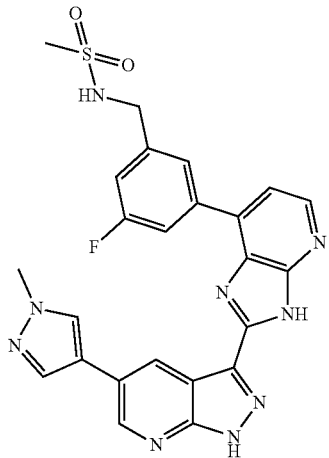
1200
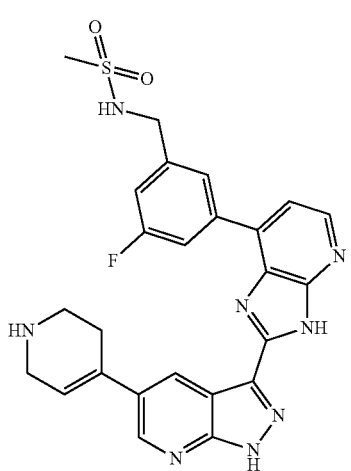 [SMILES: CS(=O)(=O)NCc1cc(F)cc(-c2ccnc3[nH]c(-c4n[nH]c5ncc(C6=CCNCC6)cc45)nc23)c1]
1198
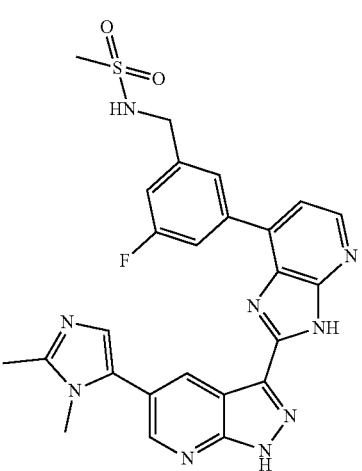
1201
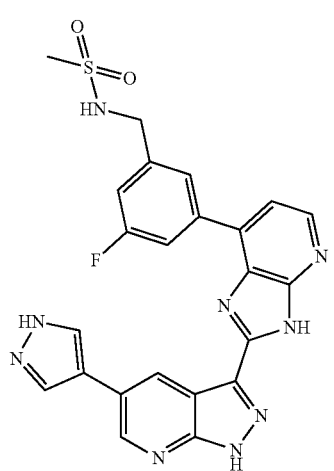 [SMILES: CS(=O)(=O)NCc1cc(F)cc(-c2ccnc3[nH]c(-c4n[nH]c5ncc(-c6cn[nH]c6)cc45)nc23)c1]
1199
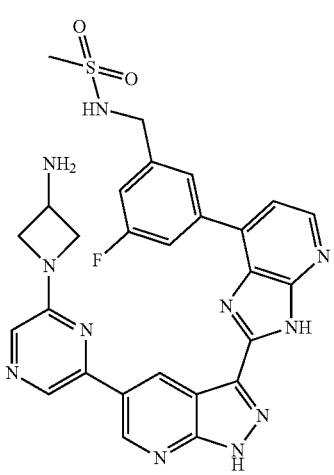 [SMILES: CS(=O)(=O)NCc1cc(F)cc(-c2ccnc3[nH]c(-c4n[nH]c5ncc(-c6cncc(N7CC(N)C7)n6)cc45)nc23)c1]
1202

333
TABLE 1-continued
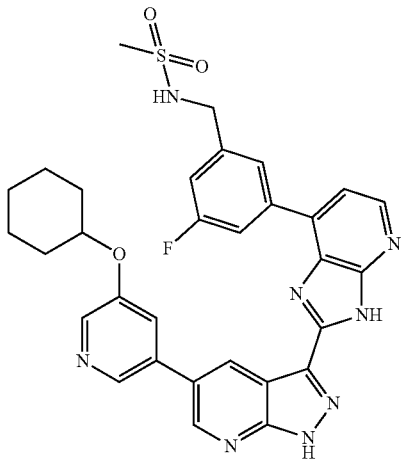 [SMILES: CS(=O)(=O)NCc1cc(F)cc(-c2ccnc3[nH]c(-c4n[nH]c5ncc(-c6cncc(OC7CCCCC7)c6)cc45)nc23)c1]
1203
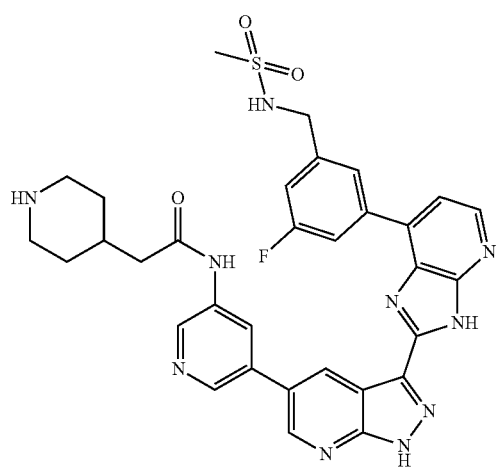 [SMILES: CS(=O)(=O)NCc1cc(F)cc(-c2ccnc3[nH]c(-c4n[nH]c5ncc(-c6cncc(NC(=O)CC7CCNCC7)c6)cc45)nc23)c1]
1204
1205
334
TABLE 1-continued
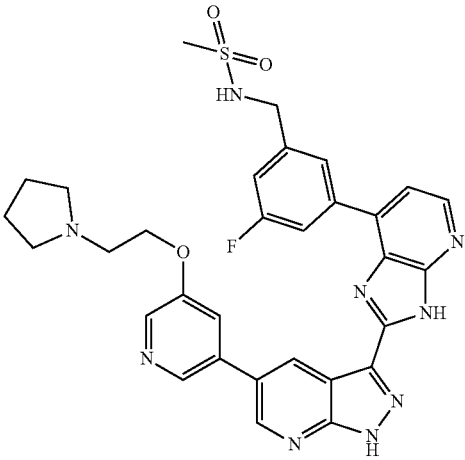 [SMILES: CS(=O)(=O)NCc1cc(F)cc(-c2ccnc3[nH]c(-c4n[nH]c5ncc(-c6cncc(OCCN7CCCC7)c6)cc45)nc23)c1]
1206
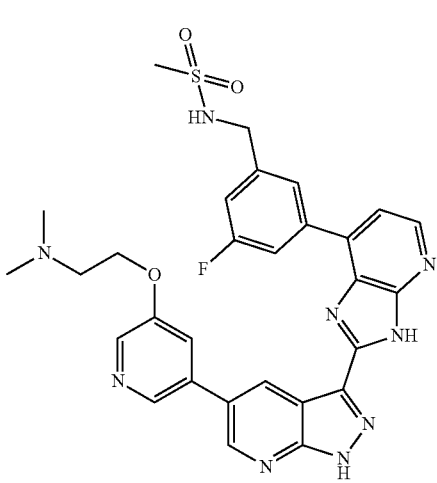 [SMILES: CN(C)CCOc1cncc(-c2cnc3[nH]nc(-c4nc5c(-c6cc(F)cc(CNS(C)(=O)=O)c6)ccnc5[nH]4)c3c2)c1]
1207
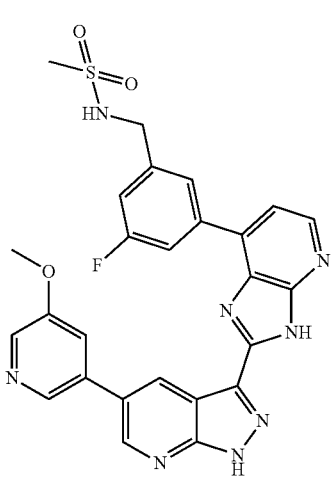 [SMILES: COc1cncc(-c2cnc3[nH]nc(-c4nc5c(-c6cc(F)cc(CNS(C)(=O)=O)c6)ccnc5[nH]4)c3c2)c1]
1208

TABLE 1-continued
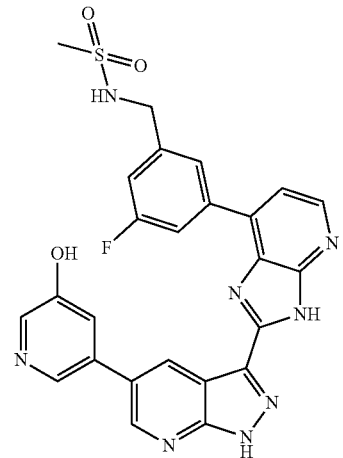 [SMILES: CS(=O)(=O)NCc1cc(F)cc(-c2ccnc3[nH]c(-c4n[nH]c5ncc(-c6cncc(O)c6)cc45)nc23)c1]
1209
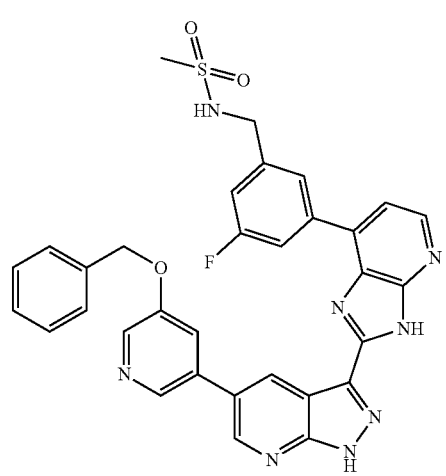 [SMILES: CS(=O)(=O)NCc1cc(F)cc(-c2ccnc3[nH]c(-c4n[nH]c5ncc(-c6cncc(OCc7ccccc7)c6)cc45)nc23)c1]
1210
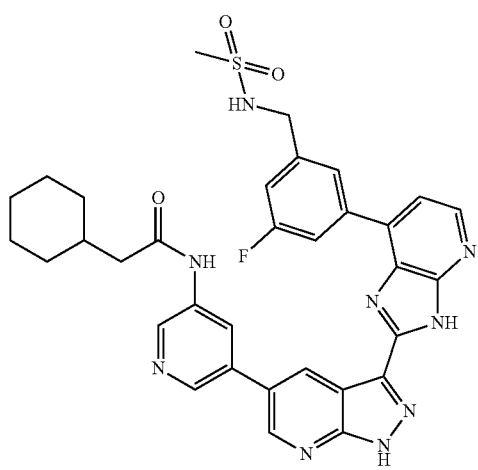 [SMILES: CS(=O)(=O)NCc1cc(F)cc(-c2ccnc3[nH]c(-c4n[nH]c5ncc(-c6cncc(NC(=O)CC7CCCCC7)c6)cc45)nc23)c1]
1211
TABLE 1-continued
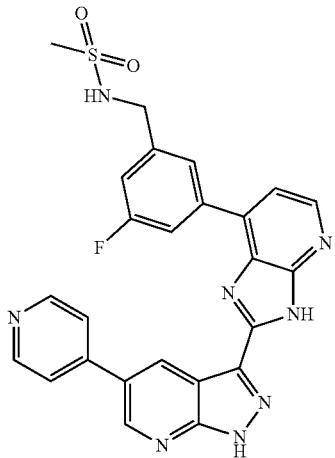 [SMILES: CS(=O)(=O)NCc1cc(F)cc(-c2ccnc3[nH]c(-c4n[nH]c5ncc(-c6ccncc6)cc45)nc23)c1]
1212
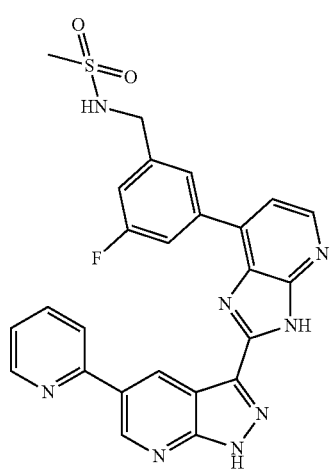 [SMILES: CS(=O)(=O)NCc1cc(F)cc(-c2ccnc3[nH]c(-c4n[nH]c5ncc(-c6ccccn6)cc45)nc23)c1]
1213
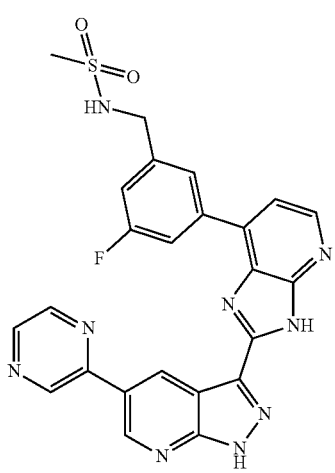 [SMILES: CS(=O)(=O)NCc1cc(F)cc(-c2ccnc3[nH]c(-c4n[nH]c5ncc(-c6cnccn6)cc45)nc23)c1]
1214

TABLE 1-continued
1215
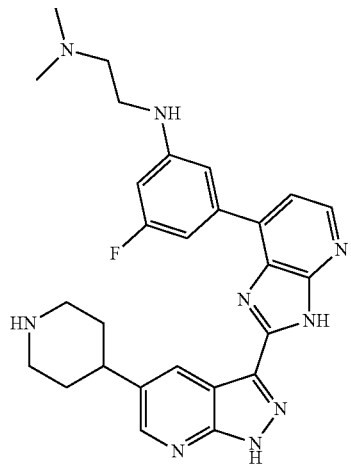 [SMILES: CN(C)CCNc1cc(F)cc(-c2ccnc3[nH]c(-c4n[nH]c5ncc(C6CCNCC6)cc45)nc23)c1]
1216
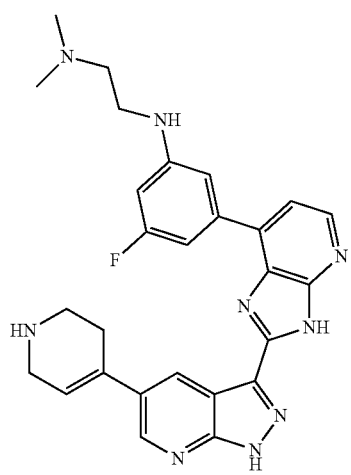 [SMILES: CN(C)CCNc1cc(F)cc(-c2ccnc3[nH]c(-c4n[nH]c5ncc(C6=CCNCC6)cc45)nc23)c1]
1217
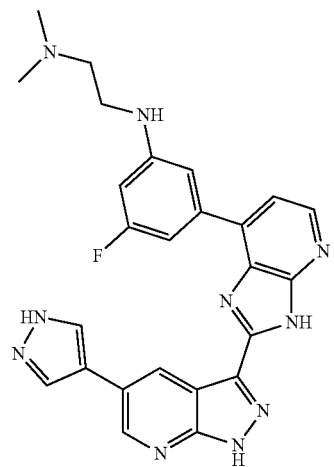 [SMILES: CN(C)CCNc1cc(F)cc(-c2ccnc3[nH]c(-c4n[nH]c5ncc(-c6cn[nH]c6)cc45)nc23)c1]
TABLE 1-continued
1218
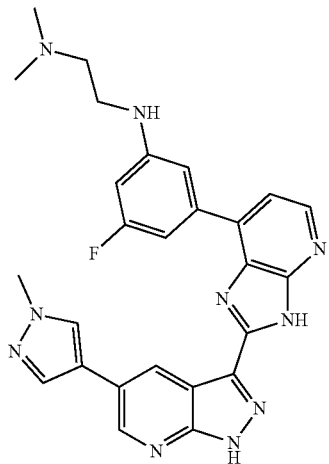 [SMILES: CN(C)CCNc1cc(F)cc(-c2ccnc3[nH]c(-c4n[nH]c5ncc(-c6cnn(C)c6)cc45)nc23)c1]
1219
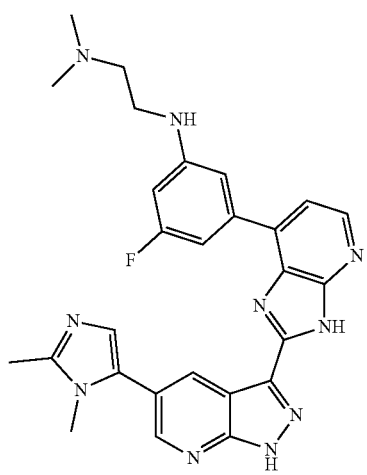
1220
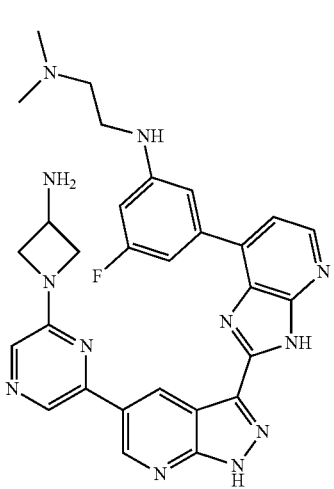 [SMILES: CN(C)CCNc1cc(F)cc(-c2ccnc3[nH]c(-c4n[nH]c5ncc(-c6cncc(N7CC(N)C7)n6)cc45)nc23)c1]

TABLE 1-continued
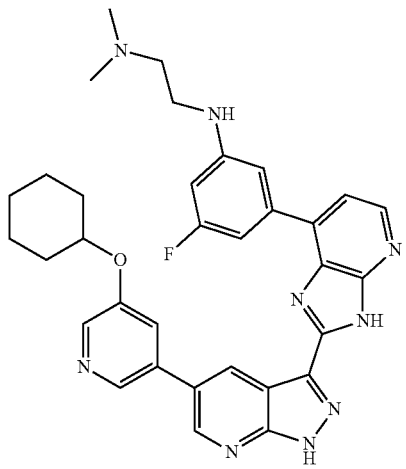
1221
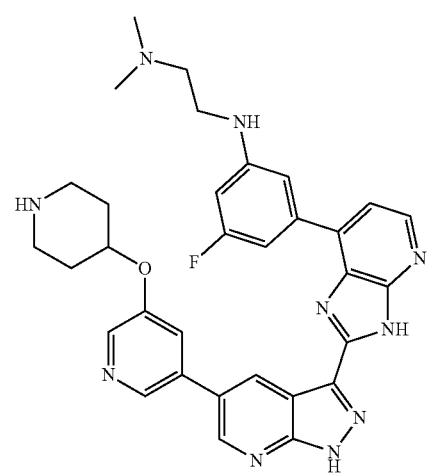
1222
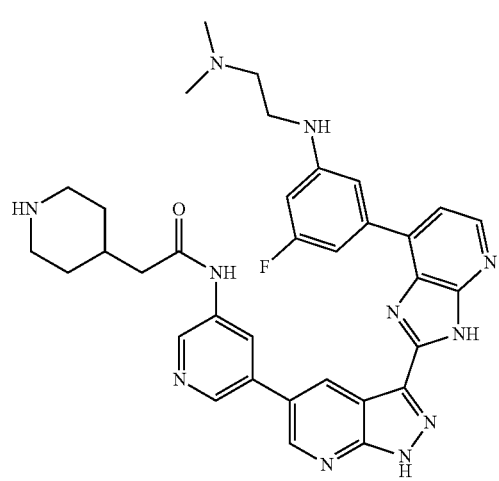 [SMILES: CN(C)CCNc1cc(F)cc(-c2ccnc3[nH]c(-c4n[nH]c5ncc(-c6cncc(NC(=O)CC7CCNCC7)c6)cc45)nc23)c1]
1223
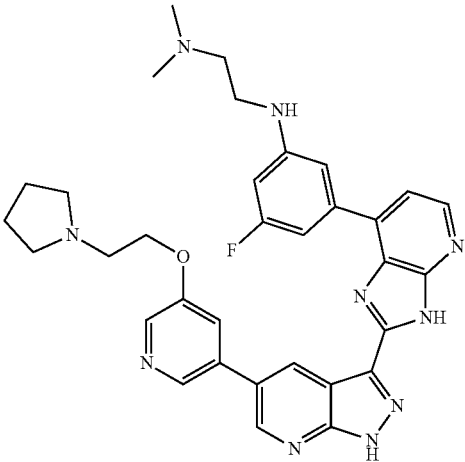 [SMILES: CN(C)CCNc1cc(F)cc(-c2ccnc3[nH]c(-c4n[nH]c5ncc(-c6cncc(OCCN7CCCC7)c6)cc45)nc23)c1]
1224
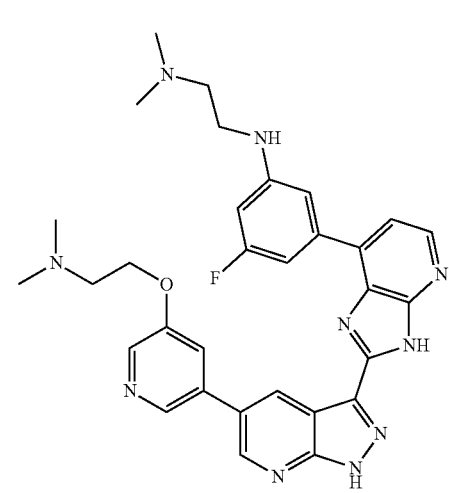 [SMILES: CN(C)CCNc1cc(F)cc(-c2ccnc3[nH]c(-c4n[nH]c5ncc(-c6cncc(OCCN(C)C)c6)cc45)nc23)c1]
1225
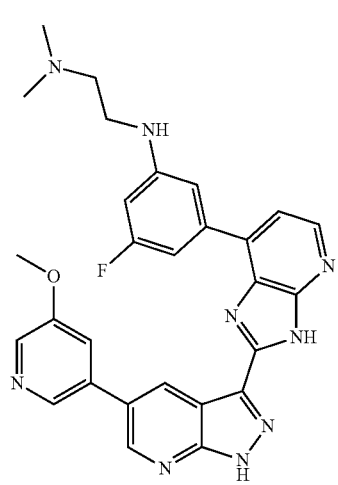 [SMILES: COc1cncc(-c2cnc3[nH]nc(-c4nc5c(-c6cc(F)cc(NCCN(C)C)c6)ccnc5[nH]4)c3c2)c1]
1226

TABLE 1-continued
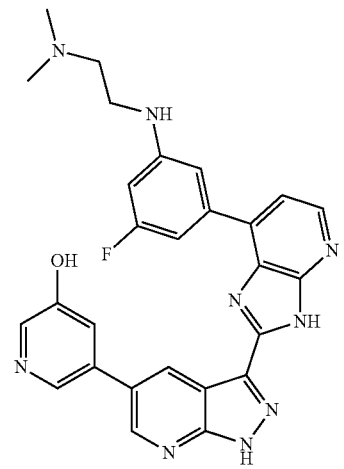 [SMILES: CN(C)CCNc1cc(F)cc(-c2ccnc3[nH]c(-c4n[nH]c5ncc(-c6cncc(O)c6)cc45)nc23)c1]
1227
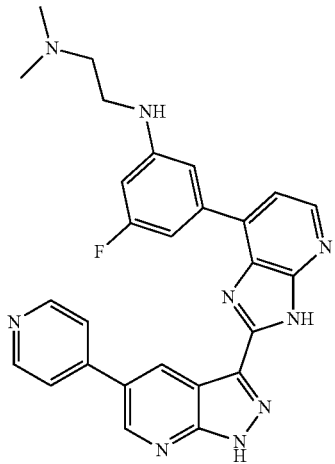
1230
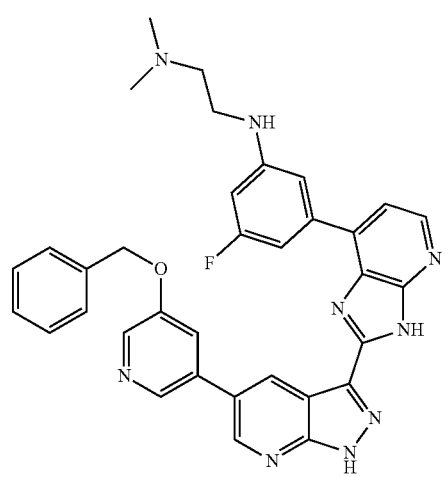 [SMILES: CN(C)CCNc1cc(F)cc(-c2ccnc3[nH]c(-c4n[nH]c5ncc(-c6cncc(OCc7ccccc7)c6)cc45)nc23)c1]
1228
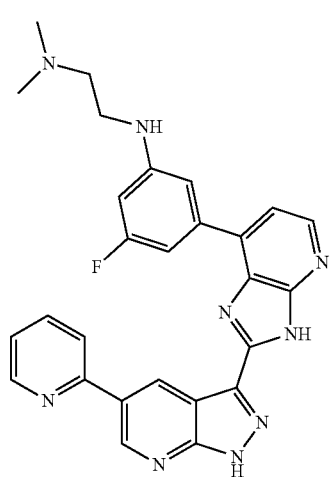
1231
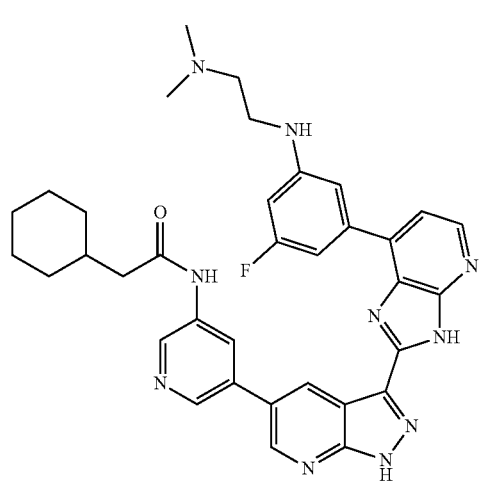 [SMILES: CN(C)CCNc1cc(F)cc(-c2ccnc3[nH]c(-c4n[nH]c5ncc(-c6cncc(NC(=O)CC7CCCCC7)c6)cc45)nc23)c1]
1229
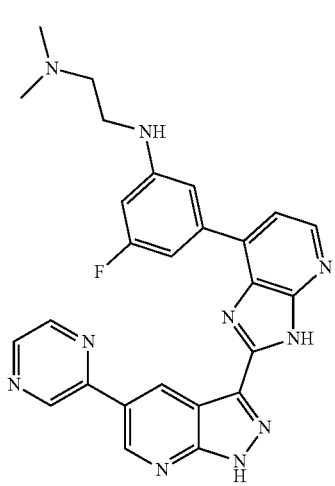 [SMILES: CN(C)CCNc1cc(F)cc(-c2ccnc3[nH]c(-c4n[nH]c5ncc(-c6cnccn6)cc45)nc23)c1]
1232

TABLE 1-continued
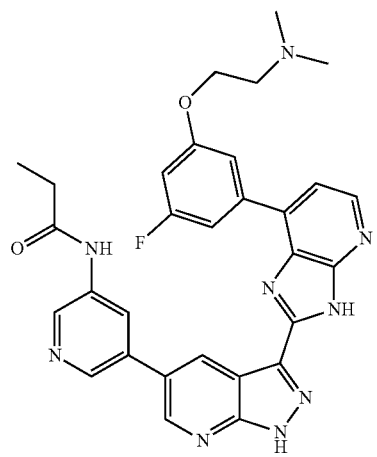 [SMILES: CCC(=O)Nc1cncc(-c2cnc3[nH]nc(-c4nc5c(-c6cc(F)cc(OCCN(C)C)c6)ccnc5[nH]4)c3c2)c1]
1233
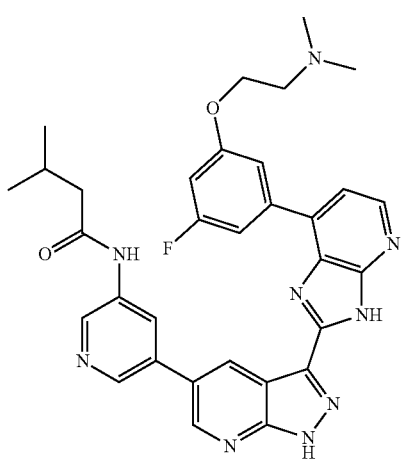 [SMILES: CC(C)CC(=O)Nc1cncc(-c2cnc3[nH]nc(-c4nc5c(-c6cc(F)cc(OCCN(C)C)c6)ccnc5[nH]4)c3c2)c1]
1234
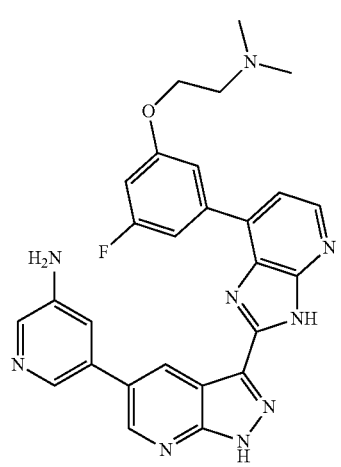 [SMILES: CN(C)CCOc1cc(F)cc(-c2ccnc3[nH]c(-c4n[nH]c5ncc(-c6cncc(N)c6)cc45)nc23)c1]
1235
TABLE 1-continued
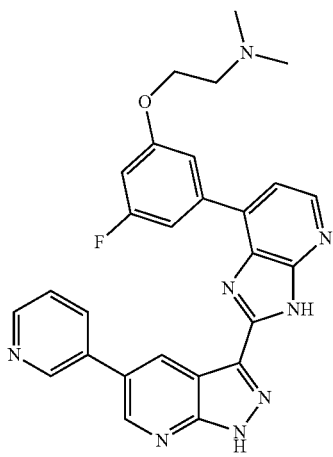 [SMILES: CN(C)CCOc1cc(F)cc(-c2ccnc3[nH]c(-c4n[nH]c5ncc(-c6cccnc6)cc45)nc23)c1]
1236
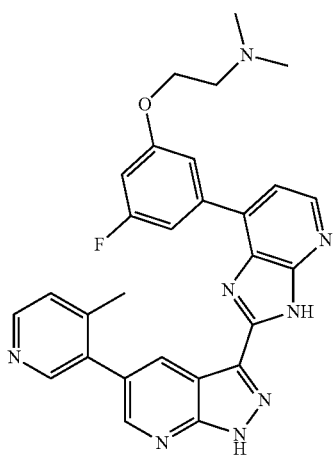 [SMILES: Cc1ccncc1-c1cnc2[nH]nc(-c3nc4c(-c5cc(F)cc(OCCN(C)C)c5)ccnc4[nH]3)c2c1]
1237
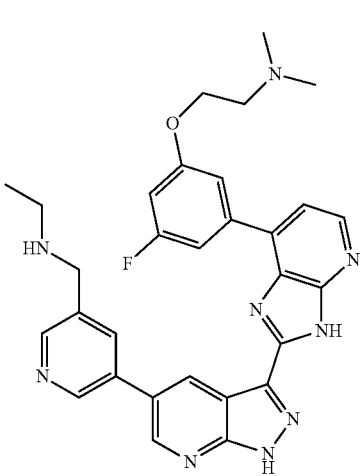 [SMILES: CCNCc1cncc(-c2cnc3[nH]nc(-c4nc5c(-c6cc(F)cc(OCCN(C)C)c6)ccnc5[nH]4)c3c2)c1]
1238

TABLE 1-continued
1239
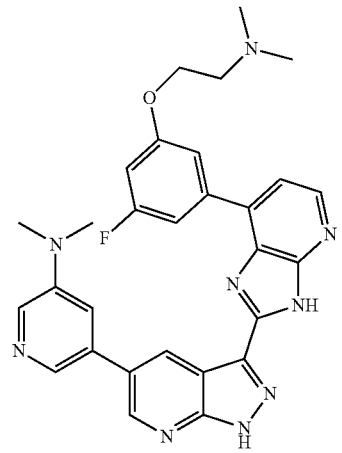 [SMILES: CN(C)CCOc1cc(F)cc(-c2ccnc3[nH]c(-c4n[nH]c5ncc(-c6cncc(N(C)C)c6)cc45)nc23)c1]
1240
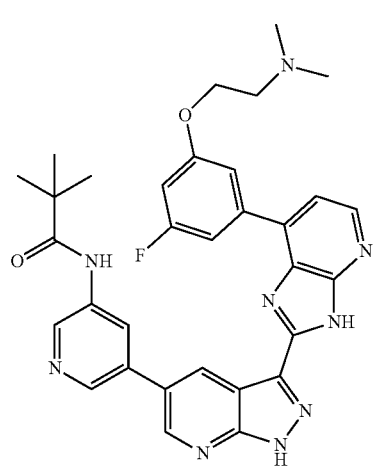 [SMILES: CN(C)CCOc1cc(F)cc(-c2ccnc3[nH]c(-c4n[nH]c5ncc(-c6cncc(NC(=O)C(C)(C)C)c6)cc45)nc23)c1]
1241
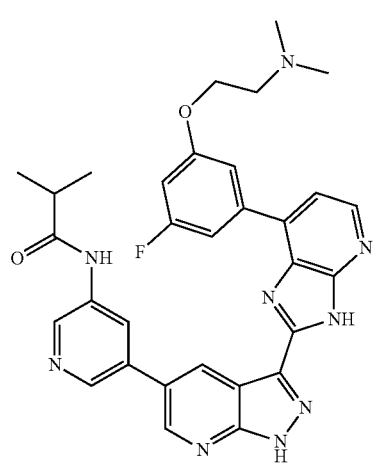 [SMILES: CC(C)C(=O)Nc1cncc(-c2cnc3[nH]nc(-c4nc5c(-c6cc(F)cc(OCCN(C)C)c6)ccnc5[nH]4)c3c2)c1]
TABLE 1-continued
1242
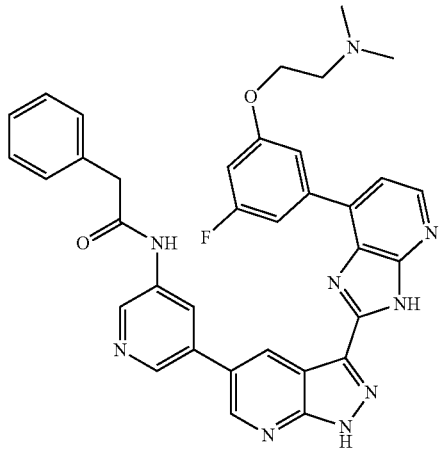 [SMILES: CN(C)CCOc1cc(F)cc(-c2ccnc3[nH]c(-c4n[nH]c5ncc(-c6cncc(NC(=O)Cc7ccccc7)c6)cc45)nc23)c1]
1243
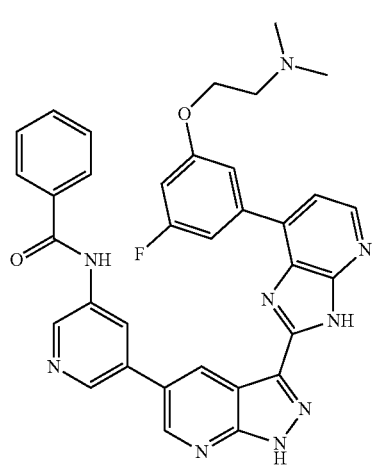 [SMILES: CN(C)CCOc1cc(F)cc(-c2ccnc3[nH]c(-c4n[nH]c5ncc(-c6cncc(NC(=O)c7ccccc7)c6)cc45)nc23)c1]
1244
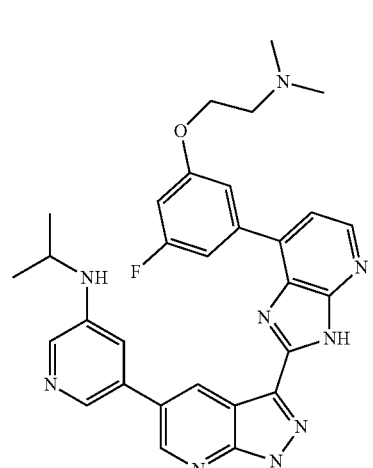

TABLE 1-continued
1245
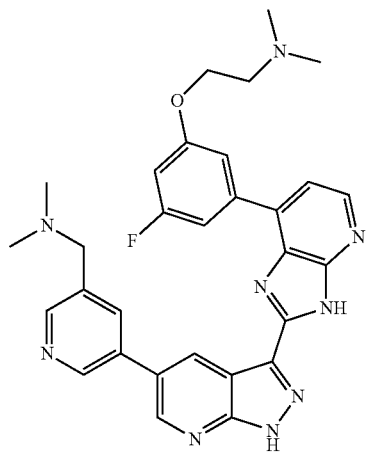 [SMILES: CN(C)CCOc1cc(F)cc(-c2ccnc3[nH]c(-c4n[nH]c5ncc(-c6cncc(CN(C)C)c6)cc45)nc23)c1]
1246
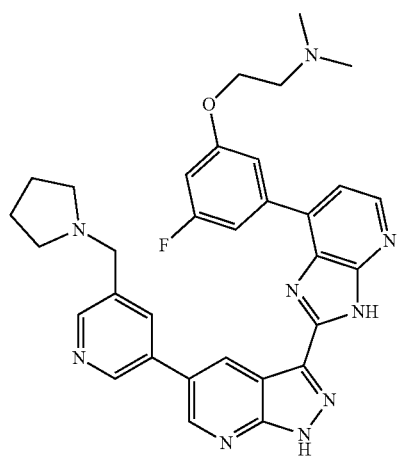 [SMILES: CN(C)CCOc1cc(F)cc(-c2ccnc3[nH]c(-c4n[nH]c5ncc(-c6cncc(CN7CCCC7)c6)cc45)nc23)c1]
1247
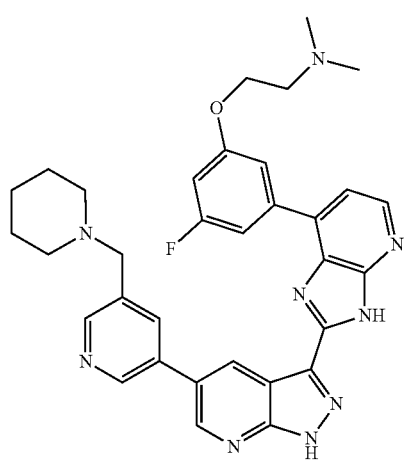 [SMILES: CN(C)CCOc1cc(F)cc(-c2ccnc3[nH]c(-c4n[nH]c5ncc(-c6cncc(CN7CCCCC7)c6)cc45)nc23)c1]
TABLE 1-continued
1248
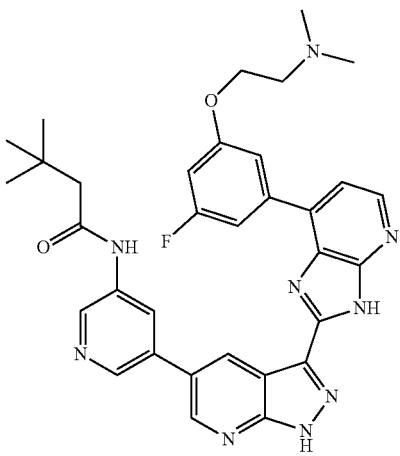 [SMILES: CN(C)CCOc1cc(F)cc(-c2ccnc3[nH]c(-c4n[nH]c5ncc(-c6cncc(NC(=O)CC(C)(C)C)c6)cc45)nc23)c1]
1249
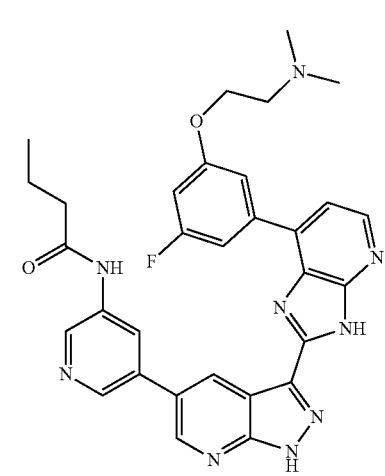 [SMILES: CCCC(=O)Nc1cncc(-c2cnc3[nH]nc(-c4nc5c(-c6cc(F)cc(OCCN(C)C)c6)ccnc5[nH]4)c3c2)c1]
1250
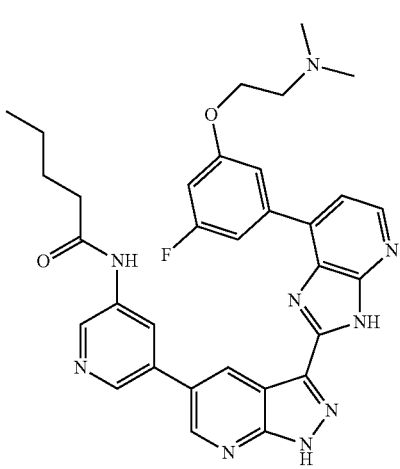 [SMILES: CCCCC(=O)Nc1cncc(-c2cnc3[nH]nc(-c4nc5c(-c6cc(F)cc(OCCN(C)C)c6)ccnc5[nH]4)c3c2)c1]

TABLE 1-continued
1251
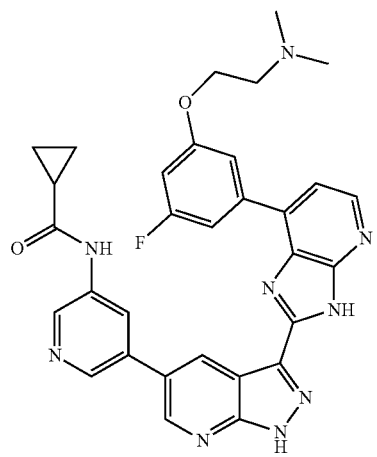 [SMILES: CN(C)CCOc1cc(F)cc(-c2ccnc3[nH]c(-c4n[nH]c5ncc(-c6cncc(NC(=O)C7CC7)c6)cc45)nc23)c1]
1252
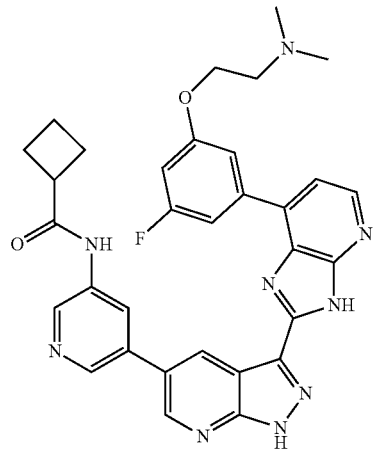 [SMILES: CN(C)CCOc1cc(F)cc(-c2ccnc3[nH]c(-c4n[nH]c5ncc(-c6cncc(NC(=O)C7CCC7)c6)cc45)nc23)c1]
1253
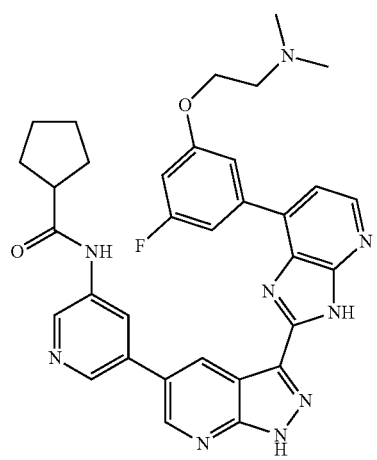 [SMILES: CN(C)CCOc1cc(F)cc(-c2ccnc3[nH]c(-c4n[nH]c5ncc(-c6cncc(NC(=O)C7CCCC7)c6)cc45)nc23)c1]
TABLE 1-continued
1254
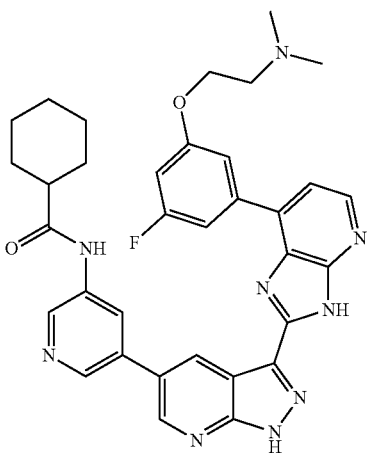 [SMILES: CN(C)CCOc1cc(F)cc(-c2ccnc3[nH]c(-c4n[nH]c5ncc(-c6cncc(NC(=O)C7CCCCC7)c6)cc45)nc23)c1]
1255
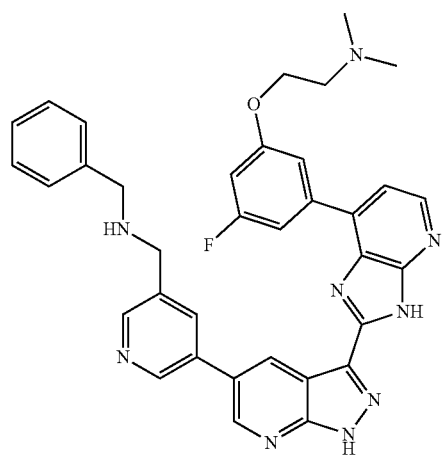 [SMILES: CN(C)CCOc1cc(F)cc(-c2ccnc3[nH]c(-c4n[nH]c5ncc(-c6cncc(CNCc7ccccc7)c6)cc45)nc23)c1]
1256
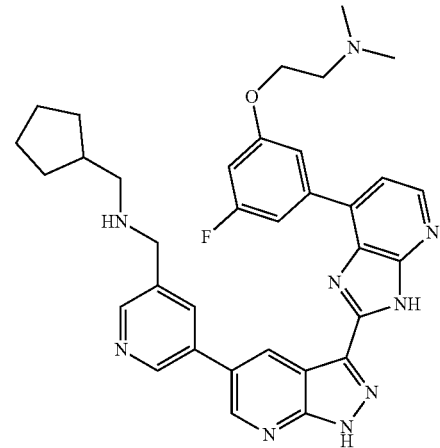 [SMILES: CN(C)CCOc1cc(F)cc(-c2ccnc3[nH]c(-c4n[nH]c5ncc(-c6cncc(CNCC7CCCC7)c6)cc45)nc23)c1]

TABLE 1-continued
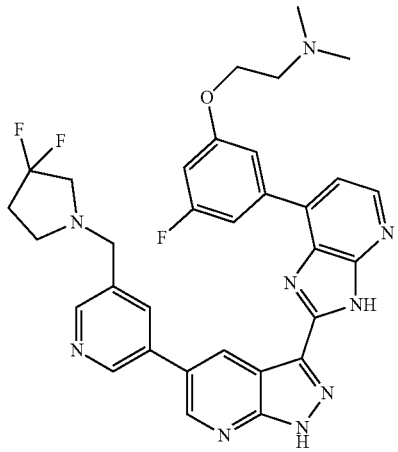 [SMILES: CN(C)CCOc1cc(F)cc(-c2ccnc3[nH]c(-c4n[nH]c5ncc(-c6cncc(CN7CCC(F)(F)C7)c6)cc45)nc23)c1]
1257
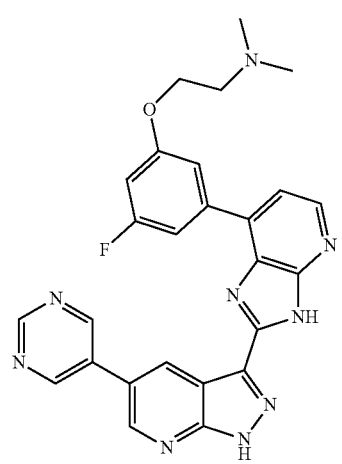 [SMILES: CN(C)CCOc1cc(F)cc(-c2ccnc3[nH]c(-c4n[nH]c5ncc(-c6cncnc6)cc45)nc23)c1]
1258
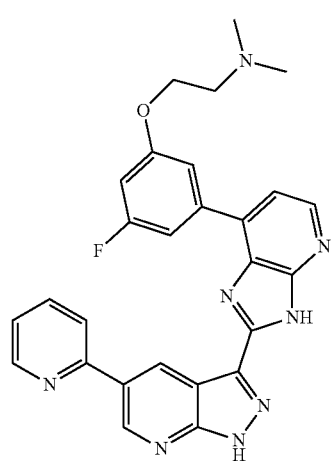 [SMILES: CN(C)CCOc1cc(F)cc(-c2ccnc3[nH]c(-c4n[nH]c5ncc(-c6ccccn6)cc45)nc23)c1]
1259
TABLE 1-continued
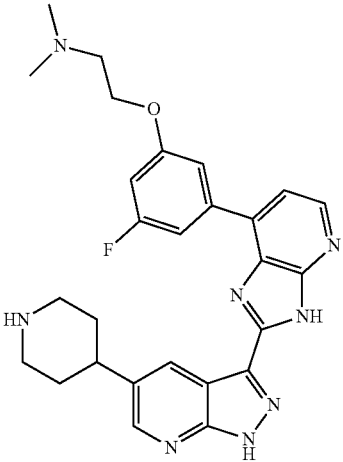 [SMILES: CN(C)CCOc1cc(F)cc(-c2ccnc3[nH]c(-c4n[nH]c5ncc(C6CCNCC6)cc45)nc23)c1]
1260
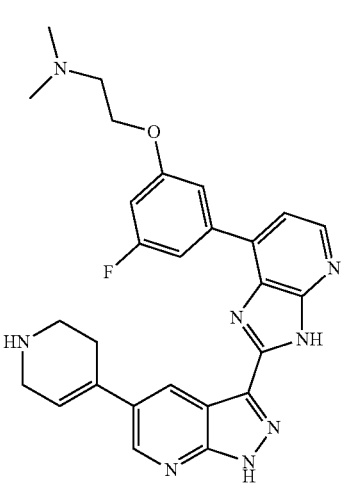 [SMILES: CN(C)CCOc1cc(F)cc(-c2ccnc3[nH]c(-c4n[nH]c5ncc(C6=CCNCC6)cc45)nc23)c1]
1261
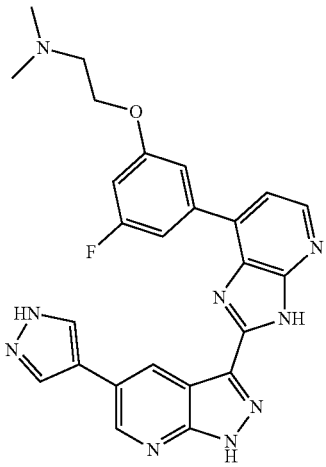 [SMILES: CN(C)CCOc1cc(F)cc(-c2ccnc3[nH]c(-c4n[nH]c5ncc(-c6cn[nH]c6)cc45)nc23)c1]
1262

TABLE 1-continued
1263
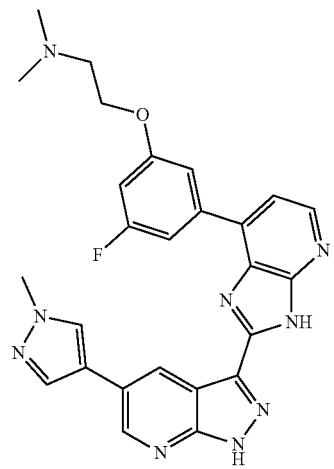 [SMILES: CN(C)CCOc1cc(F)cc(-c2ccnc3[nH]c(-c4n[nH]c5ncc(-c6cnn(C)c6)cc45)nc23)c1]
1264
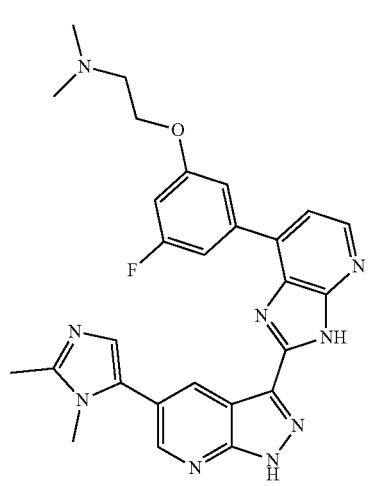 [SMILES: Cc1ncc(-c2cnc3[nH]nc(-c4nc5c(-c6cc(F)cc(OCCN(C)C)c6)ccnc5[nH]4)c3c2)n1C]
1265
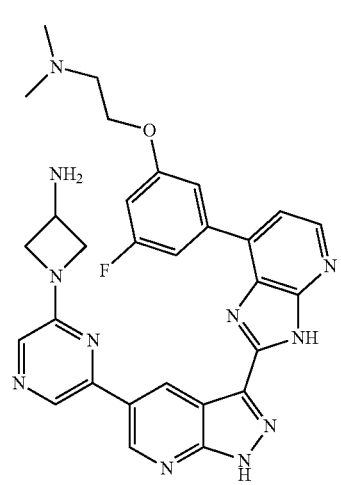 [SMILES: CN(C)CCOc1cc(F)cc(-c2ccnc3[nH]c(-c4n[nH]c5ncc(-c6cncc(N7CC(N)C7)n6)cc45)nc23)c1]
TABLE 1-continued
1266
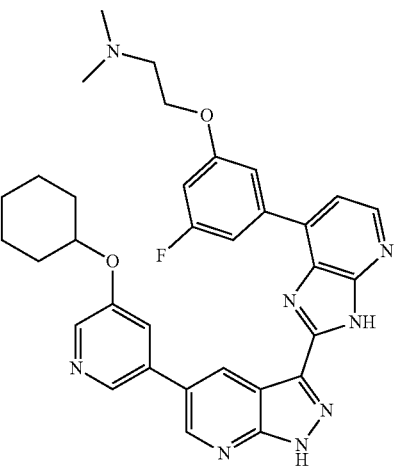 [SMILES: CN(C)CCOc1cc(F)cc(-c2ccnc3[nH]c(-c4n[nH]c5ncc(-c6cncc(OC7CCCCC7)c6)cc45)nc23)c1]
1267
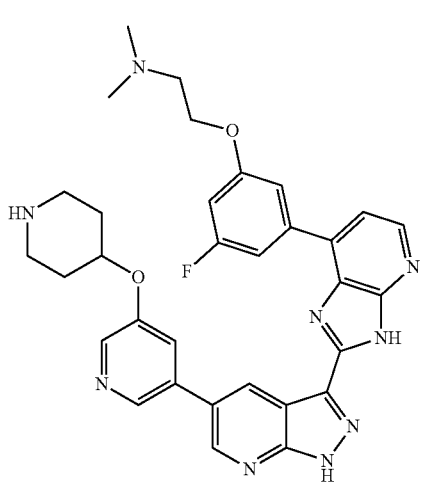 [SMILES: CN(C)CCOc1cc(F)cc(-c2ccnc3[nH]c(-c4n[nH]c5ncc(-c6cncc(OC7CCNCC7)c6)cc45)nc23)c1]
1268
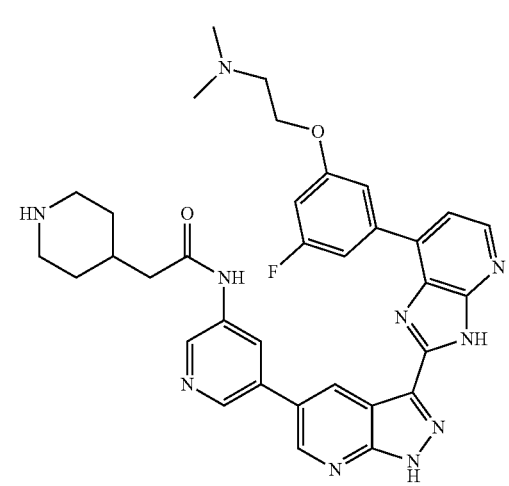 [SMILES: CN(C)CCOc1cc(F)cc(-c2ccnc3[nH]c(-c4n[nH]c5ncc(-c6cncc(NC(=O)CC7CCNCC7)c6)cc45)nc23)c1]

TABLE 1-continued
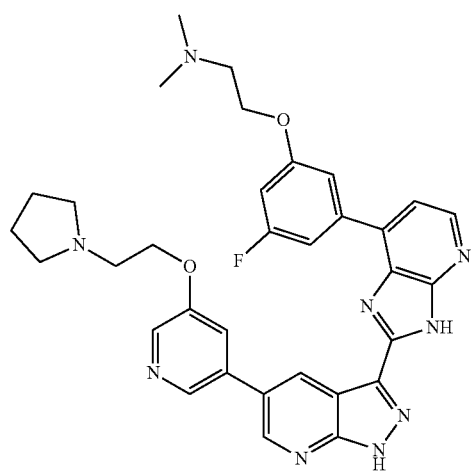 [SMILES: CN(C)CCOc1cc(F)cc(-c2ccnc3[nH]c(-c4n[nH]c5ncc(-c6cncc(OCCN7CCCC7)c6)cc45)nc23)c1]
1269
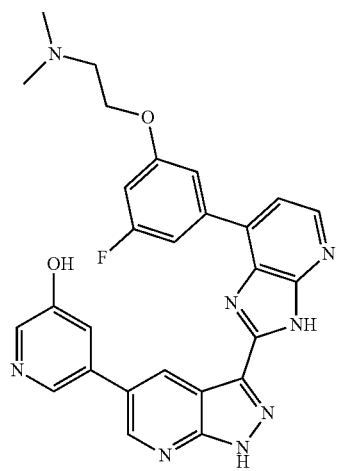
1272
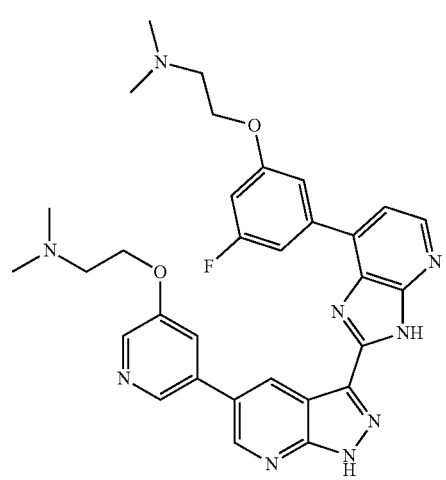 [SMILES: CN(C)CCOc1cncc(-c2cnc3[nH]nc(-c4nc5c(-c6cc(F)cc(OCCN(C)C)c6)ccnc5[nH]4)c3c2)c1]
1270
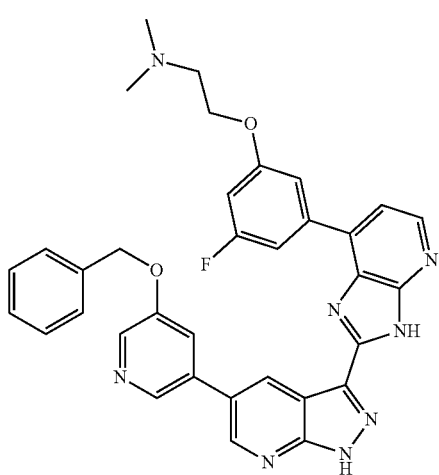
1273
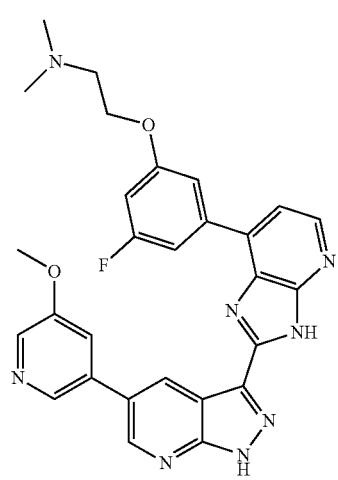 [SMILES: COc1cncc(-c2cnc3[nH]nc(-c4nc5c(-c6cc(F)cc(OCCN(C)C)c6)ccnc5[nH]4)c3c2)c1]
1271
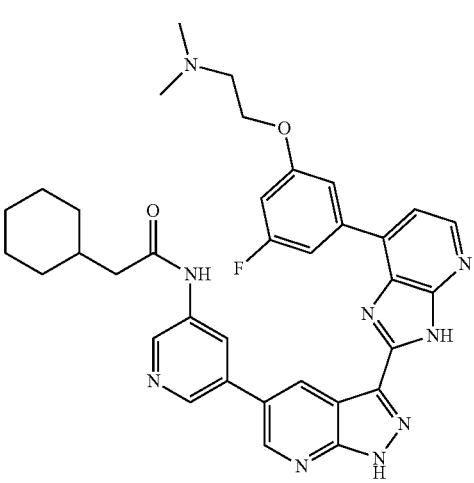 [SMILES: CN(C)CCOc1cc(F)cc(-c2ccnc3[nH]c(-c4n[nH]c5ncc(-c6cncc(NC(=O)CC7CCCCC7)c6)cc45)nc23)c1]
1274

TABLE 1-continued
1275
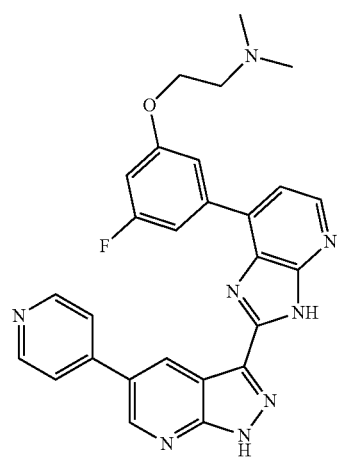 [SMILES: CN(C)CCOc1cc(F)cc(-c2ccnc3[nH]c(-c4n[nH]c5ncc(-c6ccncc6)cc45)nc23)c1]
1276
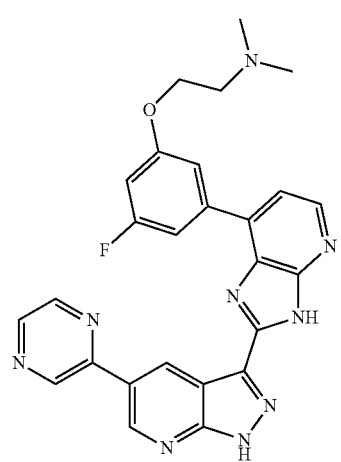 [SMILES: CN(C)CCOc1cc(F)cc(-c2ccnc3[nH]c(-c4n[nH]c5ncc(-c6cnccn6)cc45)nc23)c1]
1277
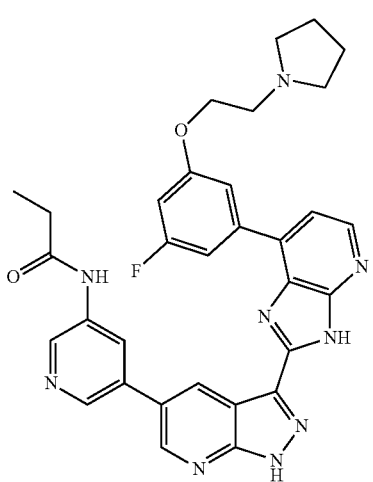 [SMILES: CCC(=O)Nc1cncc(-c2cnc3[nH]nc(-c4nc5c(-c6cc(F)cc(OCCN7CCCC7)c6)ccnc5[nH]4)c3c2)c1]
TABLE 1-continued
1278
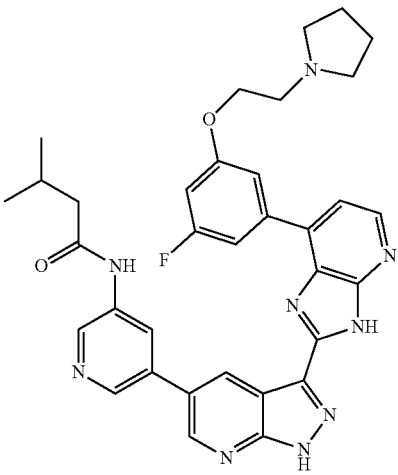 [SMILES: CC(C)CC(=O)Nc1cncc(-c2cnc3[nH]nc(-c4nc5c(-c6cc(F)cc(OCCN7CCCC7)c6)ccnc5[nH]4)c3c2)c1]
1279
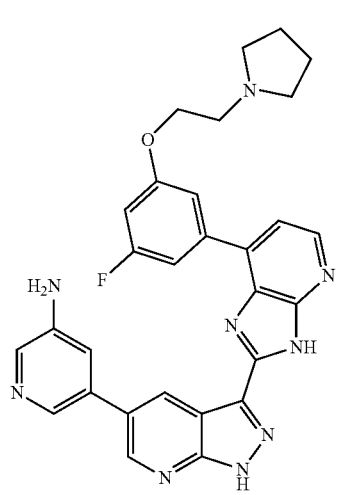 [SMILES: Nc1cncc(-c2cnc3[nH]nc(-c4nc5c(-c6cc(F)cc(OCCN7CCCC7)c6)ccnc5[nH]4)c3c2)c1]
1280
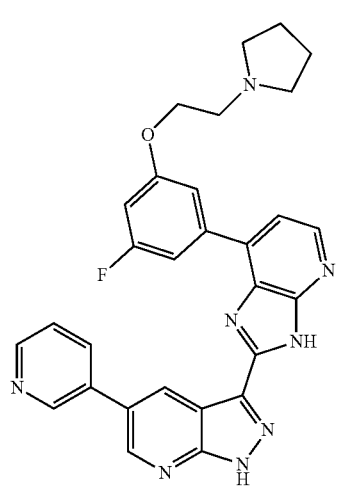 [SMILES: Fc1cc(OCCN2CCCC2)cc(-c2ccnc3[nH]c(-c4n[nH]c5ncc(-c6cccnc6)cc45)nc23)c1]

TABLE 1-continued
1281
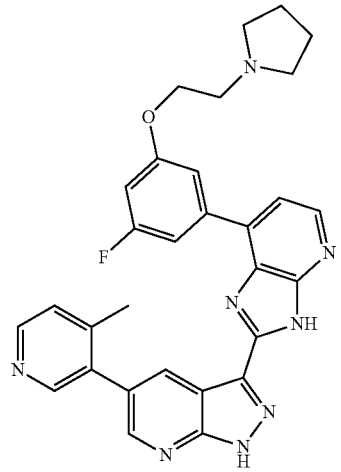 [SMILES: Cc1ccncc1-c1cnc2[nH]nc(-c3nc4c(-c5cc(F)cc(OCCN6CCCC6)c5)ccnc4[nH]3)c2c1]
1282
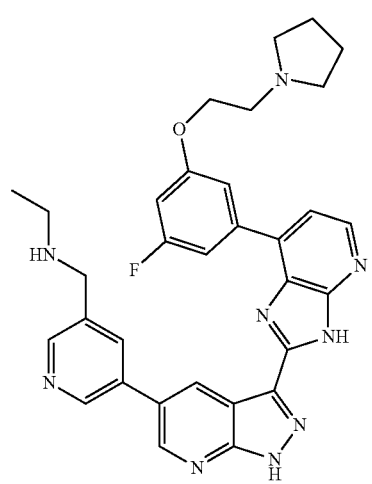 [SMILES: CCNCc1cncc(-c2cnc3[nH]nc(-c4nc5c(-c6cc(F)cc(OCCN7CCCC7)c6)ccnc5[nH]4)c3c2)c1]
1283
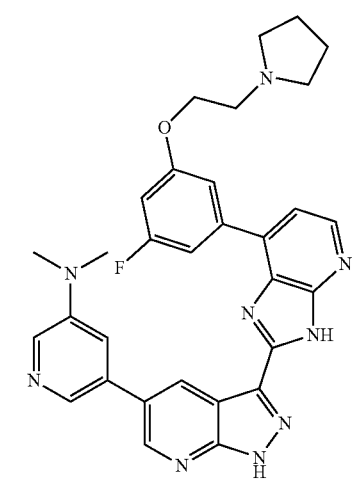 [SMILES: CN(C)c1cncc(-c2cnc3[nH]nc(-c4nc5c(-c6cc(F)cc(OCCN7CCCC7)c6)ccnc5[nH]4)c3c2)c1]
TABLE 1-continued
1284
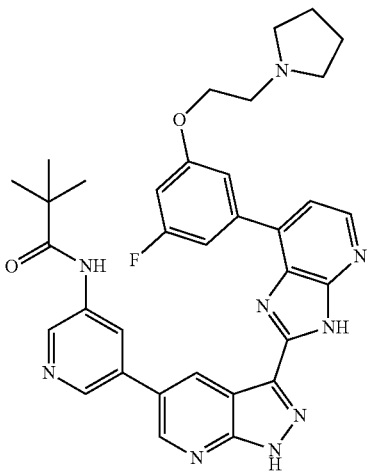 [SMILES: CC(C)(C)C(=O)Nc1cncc(-c2cnc3[nH]nc(-c4nc5c(-c6cc(F)cc(OCCN7CCCC7)c6)ccnc5[nH]4)c3c2)c1]
1285
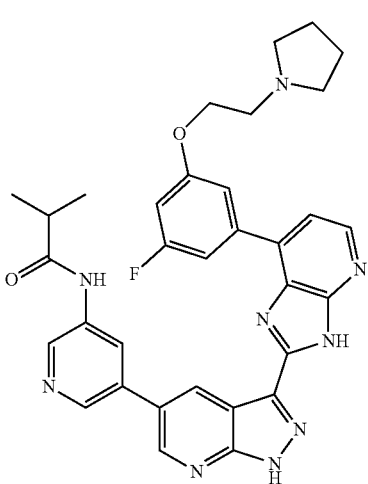 [SMILES: CC(C)C(=O)Nc1cncc(-c2cnc3[nH]nc(-c4nc5c(-c6cc(F)cc(OCCN7CCCC7)c6)ccnc5[nH]4)c3c2)c1]
1286
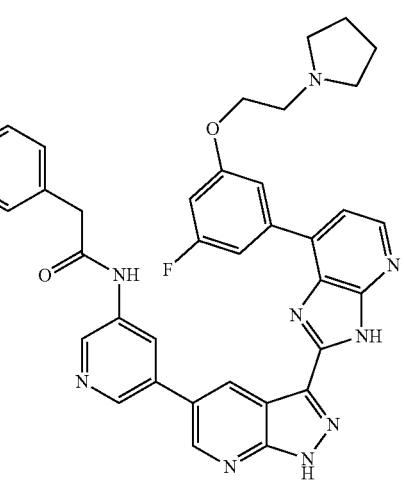

TABLE 1-continued
1287
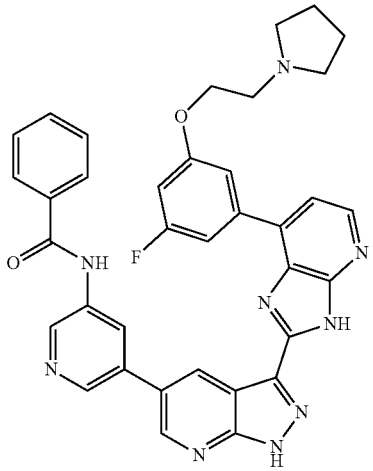 [SMILES: O=C(Nc1cncc(-c2cnc3[nH]nc(-c4nc5c(-c6cc(F)cc(OCCN7CCCC7)c6)ccnc5[nH]4)c3c2)c1)c1ccccc1]
1288
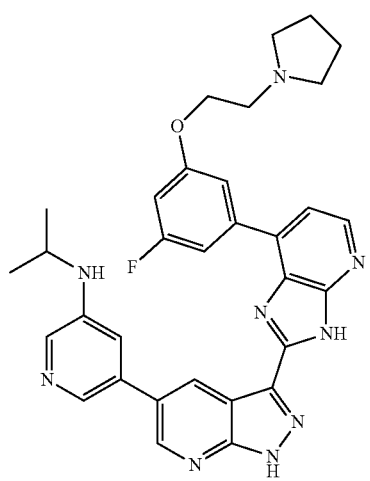 [SMILES: CC(C)Nc1cncc(-c2cnc3[nH]nc(-c4nc5c(-c6cc(F)cc(OCCN7CCCC7)c6)ccnc5[nH]4)c3c2)c1]
1289
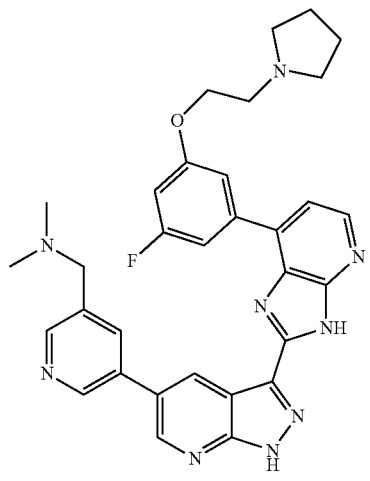 [SMILES: CN(C)Cc1cncc(-c2cnc3[nH]nc(-c4nc5c(-c6cc(F)cc(OCCN7CCCC7)c6)ccnc5[nH]4)c3c2)c1]
TABLE 1-continued
1290
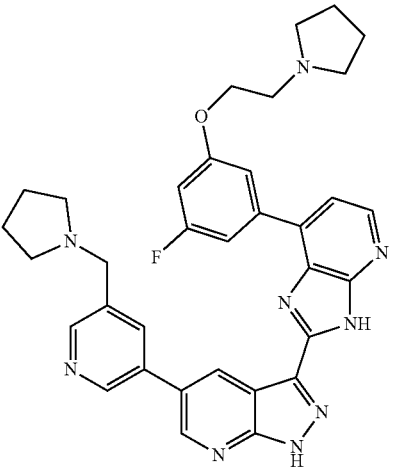 [SMILES: Fc1cc(OCCN2CCCC2)cc(-c2ccnc3[nH]c(-c4n[nH]c5ncc(-c6cncc(CN7CCCC7)c6)cc45)nc23)c1]
1291
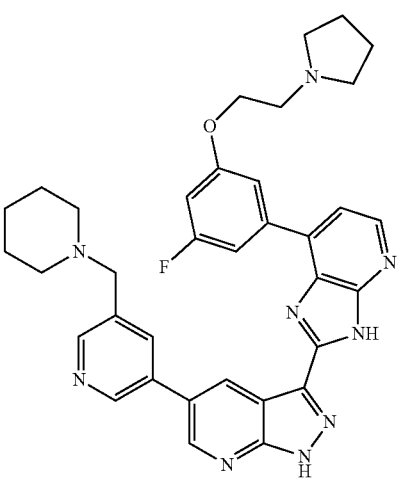 [SMILES: Fc1cc(OCCN2CCCC2)cc(-c2ccnc3[nH]c(-c4n[nH]c5ncc(-c6cncc(CN7CCCCC7)c6)cc45)nc23)c1]
1292
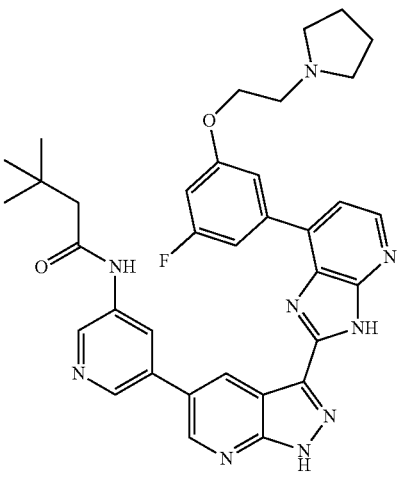 [SMILES: CC(C)(C)CC(=O)Nc1cncc(-c2cnc3[nH]nc(-c4nc5c(-c6cc(F)cc(OCCN7CCCC7)c6)ccnc5[nH]4)c3c2)c1]

TABLE 1-continued
1293
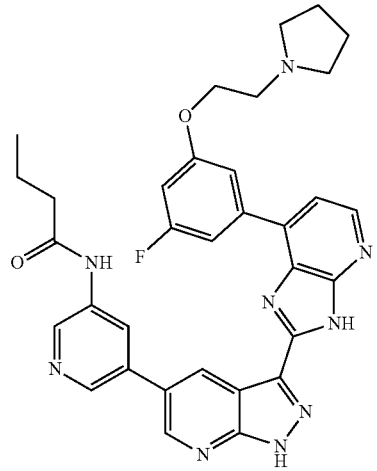 [SMILES: CCCC(=O)Nc1cncc(-c2cnc3[nH]nc(-c4nc5c(-c6cc(F)cc(OCCN7CCCC7)c6)ccnc5[nH]4)c3c2)c1]
1294
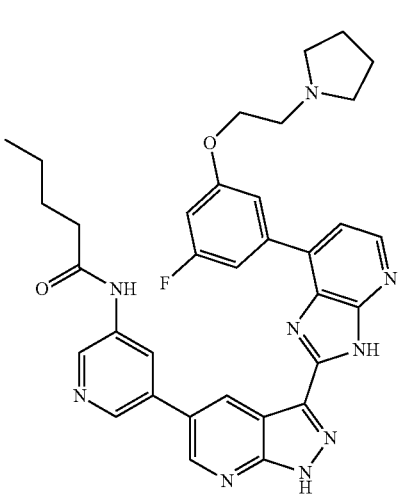 [SMILES: CCCCC(=O)Nc1cncc(-c2cnc3[nH]nc(-c4nc5c(-c6cc(F)cc(OCCN7CCCC7)c6)ccnc5[nH]4)c3c2)c1]
1295
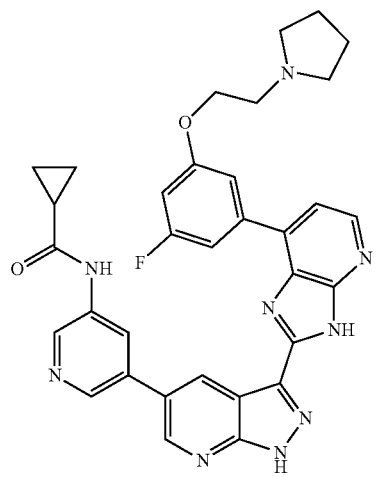 [SMILES: O=C(Nc1cncc(-c2cnc3[nH]nc(-c4nc5c(-c6cc(F)cc(OCCN7CCCC7)c6)ccnc5[nH]4)c3c2)c1)C1CC1]
TABLE 1-continued
1296
1297
1298

TABLE 1-continued
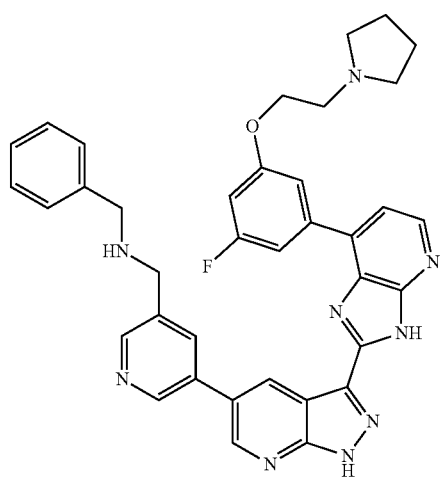 [SMILES: Fc1cc(OCCN2CCCC2)cc(-c2ccnc3[nH]c(-c4n[nH]c5ncc(-c6cncc(CNCc7ccccc7)c6)cc45)nc23)c1]
1299
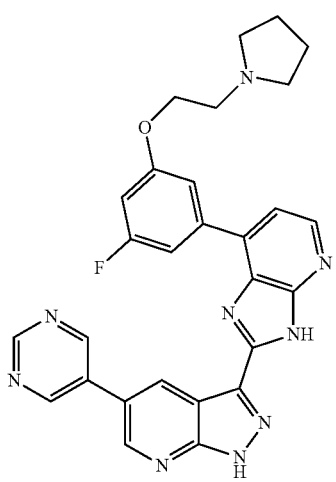 [SMILES: Fc1cc(OCCN2CCCC2)cc(-c2ccnc3[nH]c(-c4n[nH]c5ncc(-c6cncnc6)cc45)nc23)c1]
1302
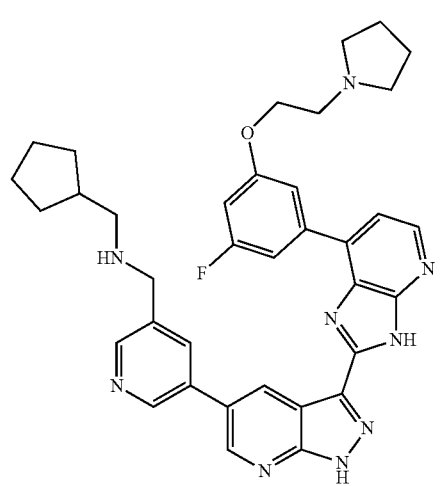 [SMILES: Fc1cc(OCCN2CCCC2)cc(-c2ccnc3[nH]c(-c4n[nH]c5ncc(-c6cncc(CNCC7CCCC7)c6)cc45)nc23)c1]
1300
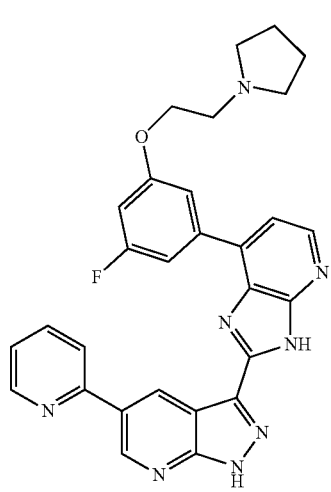
1303
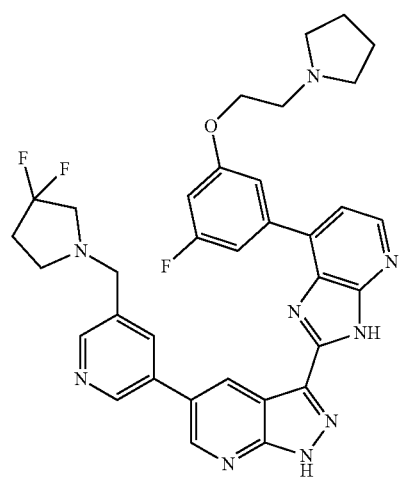 [SMILES: Fc1cc(OCCN2CCCC2)cc(-c2ccnc3[nH]c(-c4n[nH]c5ncc(-c6cncc(CN7CCC(F)(F)C7)c6)cc45)nc23)c1]
1301
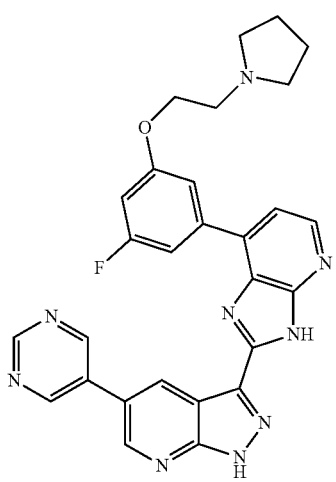 [SMILES: Fc1cc(OCCN2CCCC2)cc(-c2ccnc3[nH]c(-c4n[nH]c5ncc(-c6cncnc6)cc45)nc23)c1]
1304

TABLE 1-continued
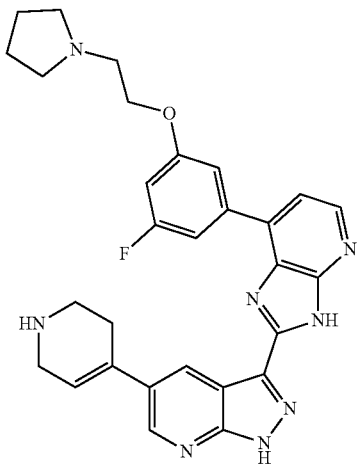 [SMILES: Fc1cc(OCCN2CCCC2)cc(-c2ccnc3[nH]c(-c4n[nH]c5ncc(C6=CCNCC6)cc45)nc23)c1]
1305
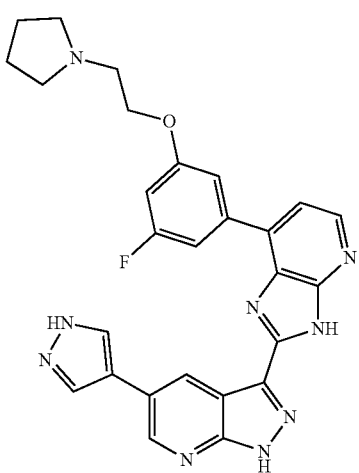 [SMILES: Fc1cc(OCCN2CCCC2)cc(-c2ccnc3[nH]c(-c4n[nH]c5ncc(-c6cn[nH]c6)cc45)nc23)c1]
1306
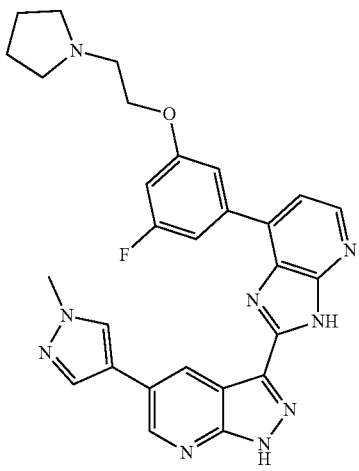 [SMILES: Cn1cc(-c2cnc3[nH]nc(-c4nc5c(-c6cc(F)cc(OCCN7CCCC7)c6)ccnc5[nH]4)c3c2)cn1]
1307
TABLE 1-continued
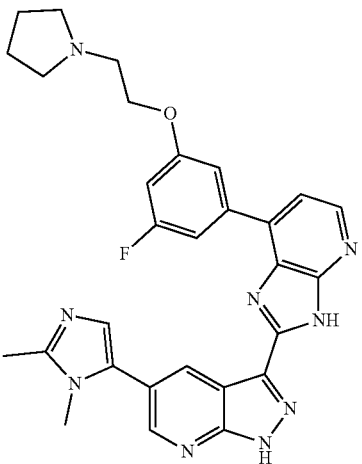 [SMILES: Cc1ncc(-c2cnc3[nH]nc(-c4nc5c(-c6cc(F)cc(OCCN7CCCC7)c6)ccnc5[nH]4)c3c2)n1C]
1308
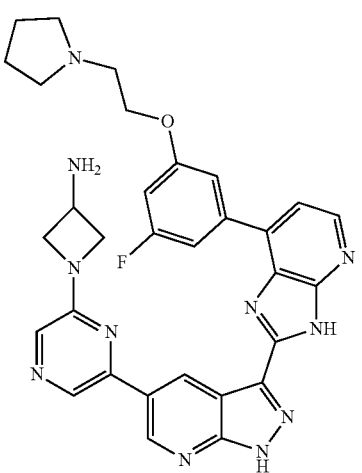 [SMILES: NC1CN(c2cncc(-c3cnc4[nH]nc(-c5nc6c(-c7cc(F)cc(OCCN8CCCC8)c7)ccnc6[nH]5)c4c3)n2)C1]
1309
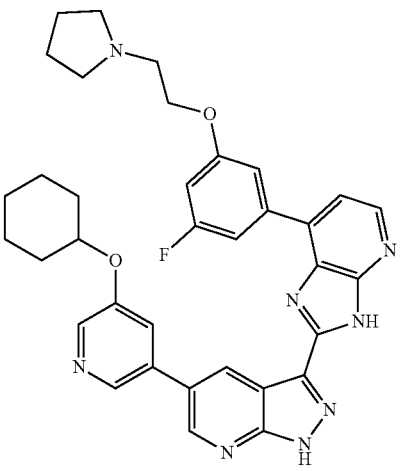 [SMILES: Fc1cc(OCCN2CCCC2)cc(-c2ccnc3[nH]c(-c4n[nH]c5ncc(-c6cncc(OC7CCCCC7)c6)cc45)nc23)c1]
1310

TABLE 1-continued
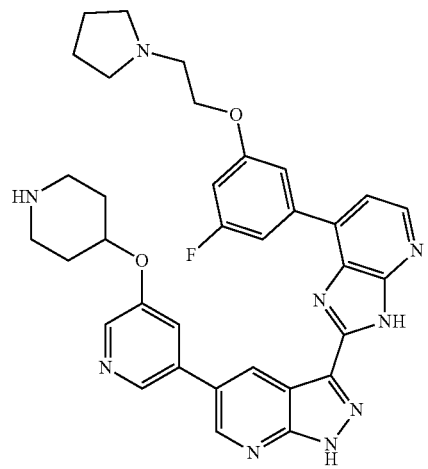 [SMILES: Fc1cc(OCCN2CCCC2)cc(-c2ccnc3[nH]c(-c4n[nH]c5ncc(-c6cncc(OC7CCNCC7)c6)cc45)nc23)c1]
1311
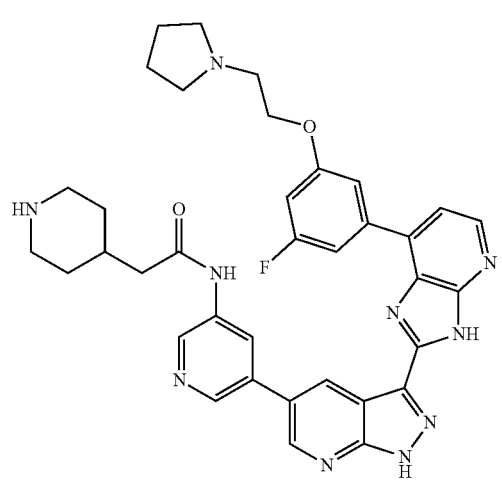 [SMILES: O=C(CC1CCNCC1)Nc1cncc(-c2cnc3[nH]nc(-c4nc5c(-c6cc(F)cc(OCCN7CCCC7)c6)ccnc5[nH]4)c3c2)c1]
1312
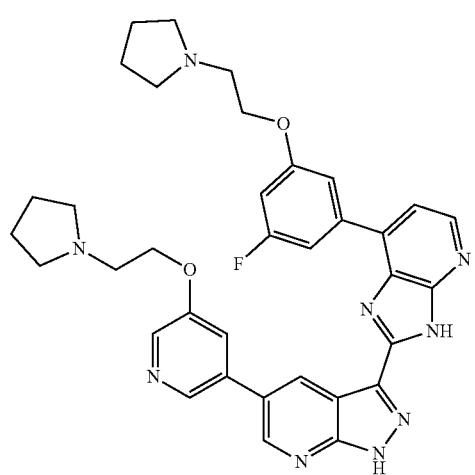 [SMILES: Fc1cc(OCCN2CCCC2)cc(-c2ccnc3[nH]c(-c4n[nH]c5ncc(-c6cncc(OCCN7CCCC7)c6)cc45)nc23)c1]
1313
TABLE 1-continued
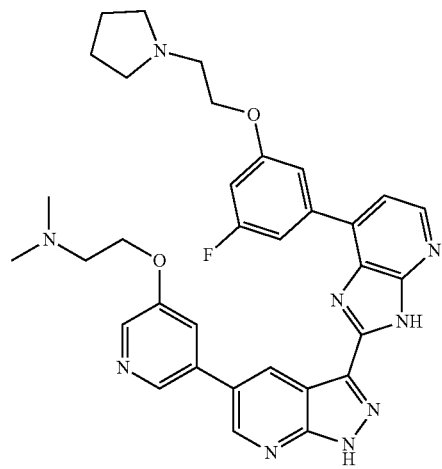 [SMILES: CN(C)CCOc1cncc(-c2cnc3[nH]nc(-c4nc5c(-c6cc(F)cc(OCCN7CCCC7)c6)ccnc5[nH]4)c3c2)c1]
1314
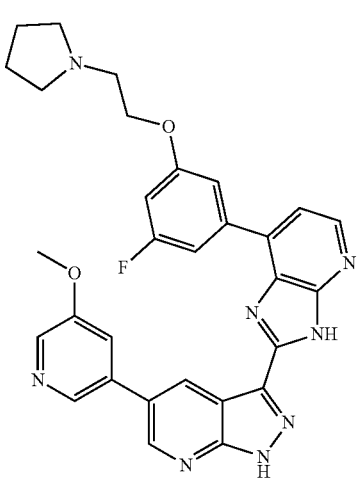 [SMILES: COc1cncc(-c2cnc3[nH]nc(-c4nc5c(-c6cc(F)cc(OCCN7CCCC7)c6)ccnc5[nH]4)c3c2)c1]
1315
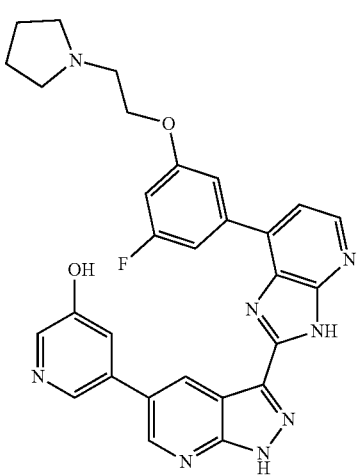 [SMILES: Oc1cncc(-c2cnc3[nH]nc(-c4nc5c(-c6cc(F)cc(OCCN7CCCC7)c6)ccnc5[nH]4)c3c2)c1]
1316

TABLE 1-continued
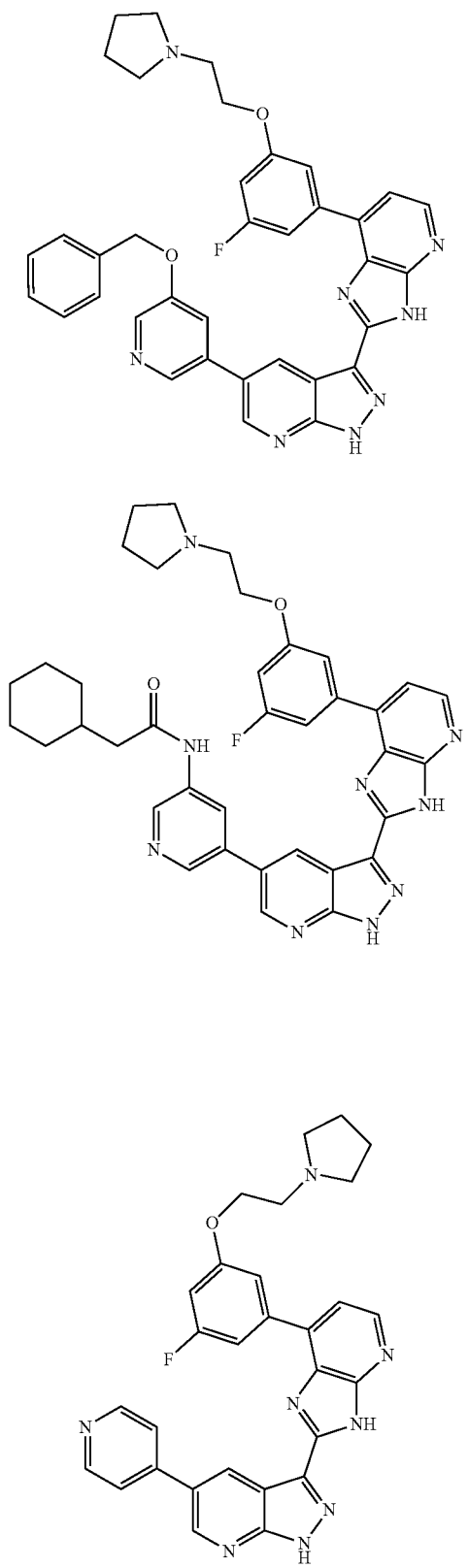
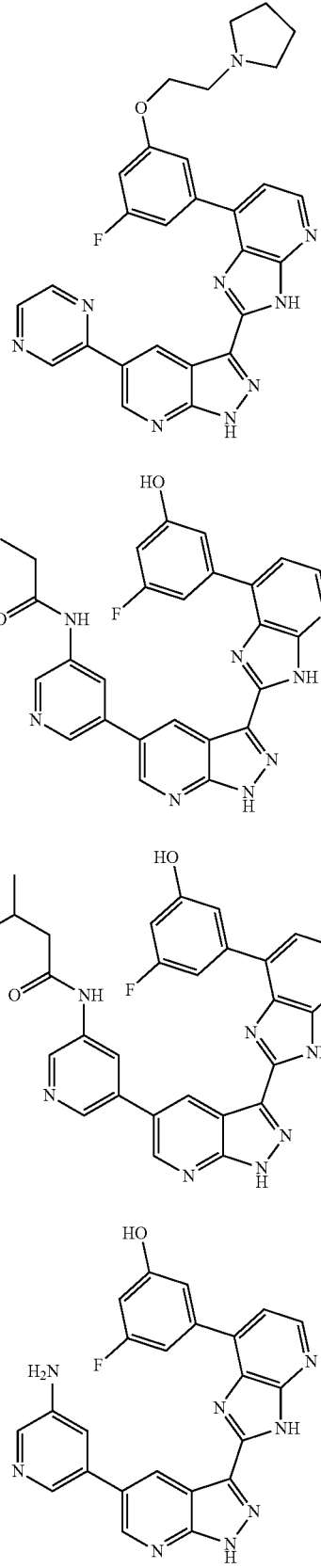

TABLE 1-continued
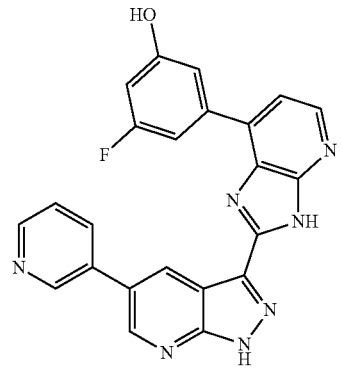 [SMILES: Oc1cc(F)cc(-c2ccnc3[nH]c(-c4n[nH]c5ncc(-c6cccnc6)cc45)nc23)c1] 1324
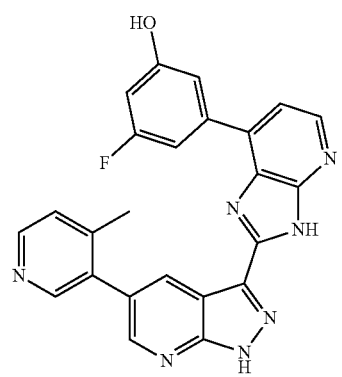 [SMILES: Cc1ccncc1-c1cnc2[nH]nc(-c3nc4c(-c5cc(O)cc(F)c5)ccnc4[nH]3)c2c1] 1325
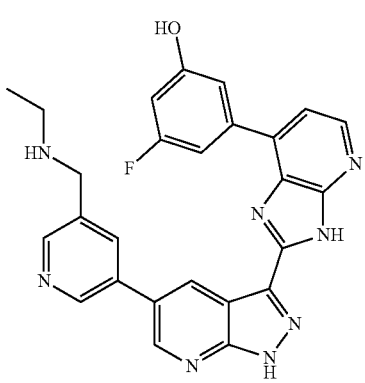 [SMILES: CCNCc1cncc(-c2cnc3[nH]nc(-c4nc5c(-c6cc(O)cc(F)c6)ccnc5[nH]4)c3c2)c1] 1326
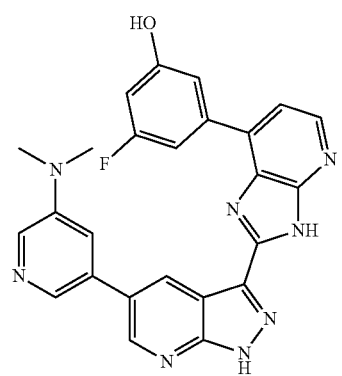 [SMILES: CN(C)c1cncc(-c2cnc3[nH]nc(-c4nc5c(-c6cc(O)cc(F)c6)ccnc5[nH]4)c3c2)c1] 1327
TABLE 1-continued
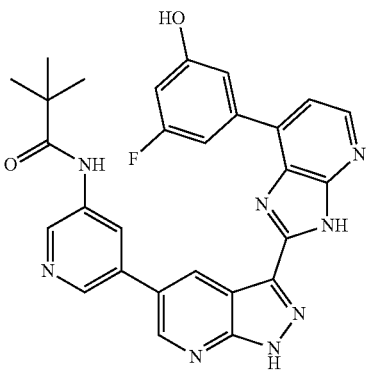 [SMILES: CC(C)(C)C(=O)Nc1cncc(-c2cnc3[nH]nc(-c4nc5c(-c6cc(O)cc(F)c6)ccnc5[nH]4)c3c2)c1] 1328
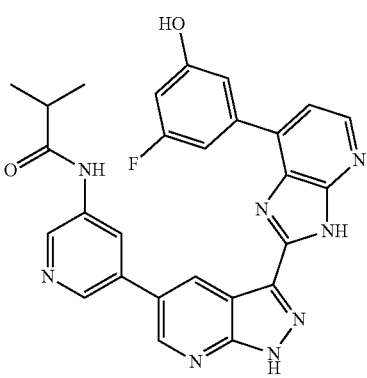 [SMILES: CC(C)C(=O)Nc1cncc(-c2cnc3[nH]nc(-c4nc5c(-c6cc(O)cc(F)c6)ccnc5[nH]4)c3c2)c1] 1329
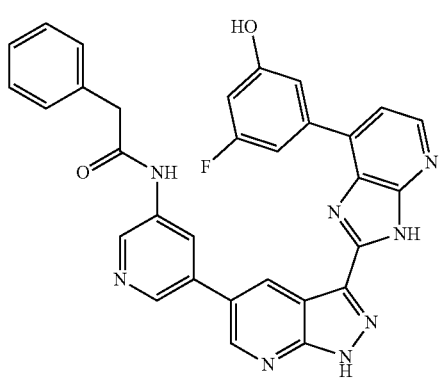 [SMILES: O=C(Cc1ccccc1)Nc1cncc(-c2cnc3[nH]nc(-c4nc5c(-c6cc(O)cc(F)c6)ccnc5[nH]4)c3c2)c1] 1330
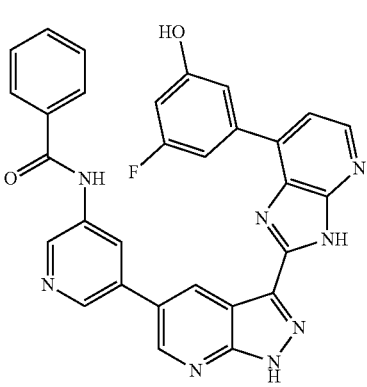 [SMILES: O=C(Nc1cncc(-c2cnc3[nH]nc(-c4nc5c(-c6cc(O)cc(F)c6)ccnc5[nH]4)c3c2)c1)c1ccccc1] 1331

TABLE 1-continued
| | |
|---|---|
| 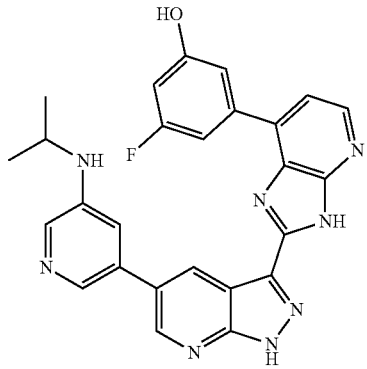 [SMILES: CC(C)Nc1cncc(-c2cnc3[nH]nc(-c4nc5c(-c6cc(O)cc(F)c6)ccnc5[nH]4)c3c2)c1] | 1332 |
| 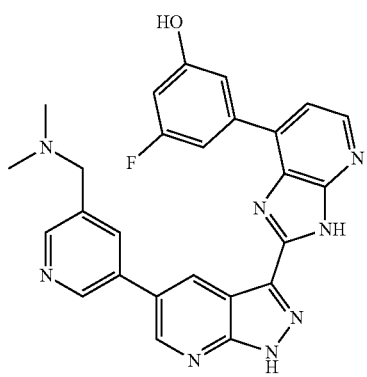 [SMILES: CN(C)Cc1cncc(-c2cnc3[nH]nc(-c4nc5c(-c6cc(O)cc(F)c6)ccnc5[nH]4)c3c2)c1] | 1333 |
| 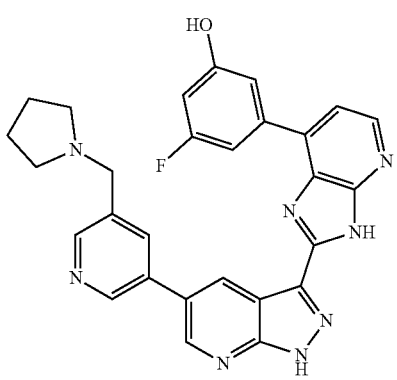 [SMILES: Oc1cc(F)cc(-c2ccnc3[nH]c(-c4n[nH]c5ncc(-c6cncc(CN7CCCC7)c6)cc45)nc23)c1] | 1334 |
| 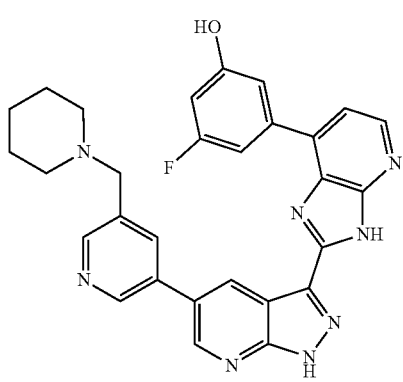 [SMILES: Oc1cc(F)cc(-c2ccnc3[nH]c(-c4n[nH]c5ncc(-c6cncc(CN7CCCCC7)c6)cc45)nc23)c1] | 1335 |
TABLE 1-continued
| | |
|---|---|
| 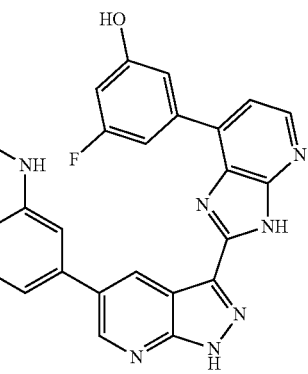 | 1336 |
| 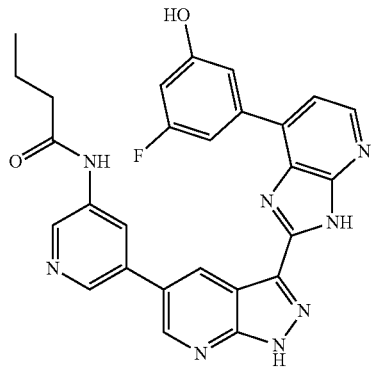 [SMILES: CCCC(=O)Nc1cncc(-c2cnc3[nH]nc(-c4nc5c(-c6cc(O)cc(F)c6)ccnc5[nH]4)c3c2)c1] | 1337 |
| 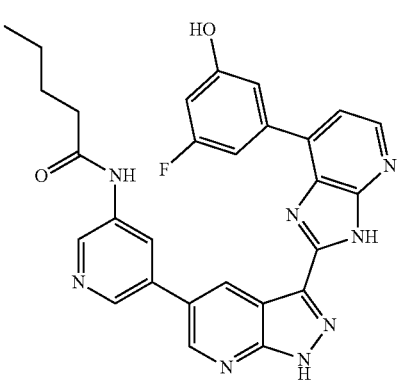 [SMILES: CCCCC(=O)Nc1cncc(-c2cnc3[nH]nc(-c4nc5c(-c6cc(O)cc(F)c6)ccnc5[nH]4)c3c2)c1] | 1338 |
| 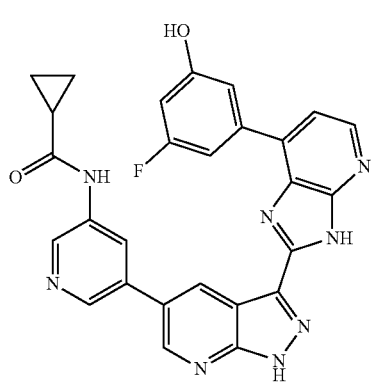 [SMILES: O=C(Nc1cncc(-c2cnc3[nH]nc(-c4nc5c(-c6cc(O)cc(F)c6)ccnc5[nH]4)c3c2)c1)C1CC1] | 1339 |

TABLE 1-continued
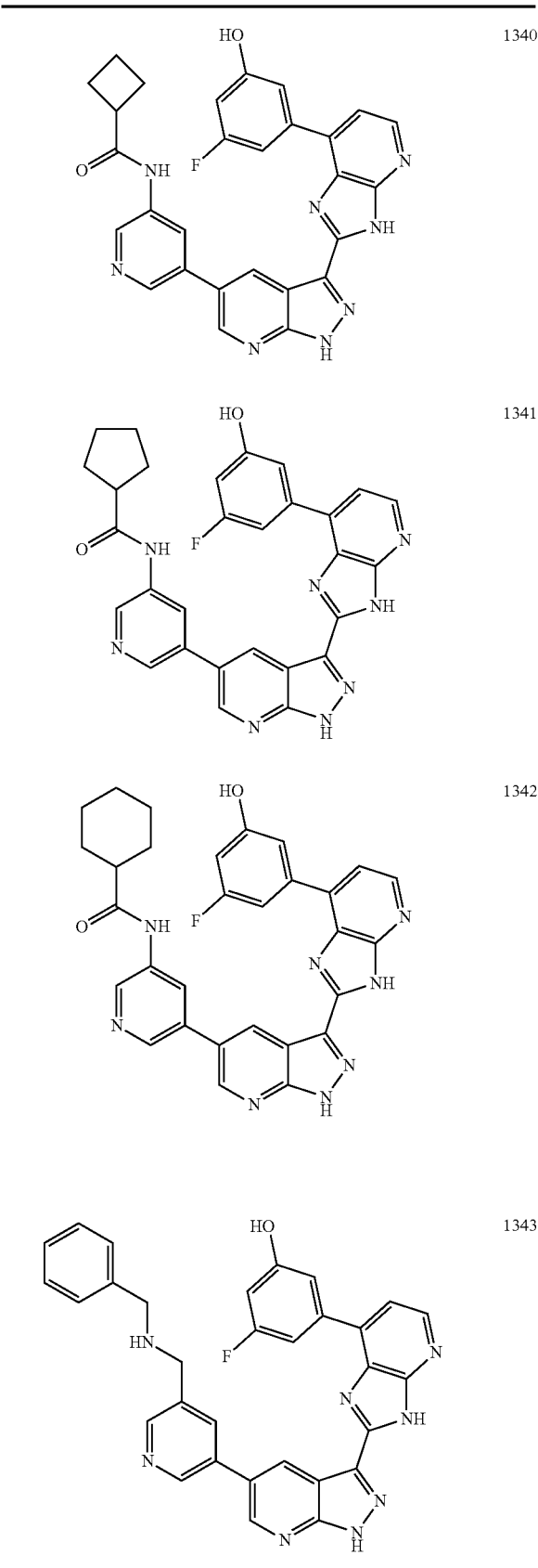
1340
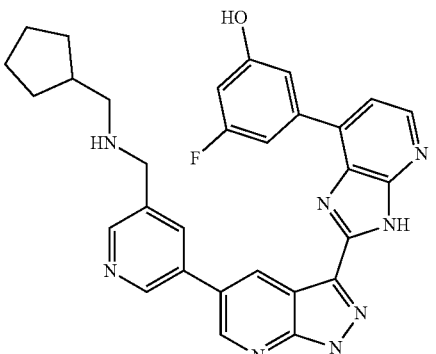
1344
1341
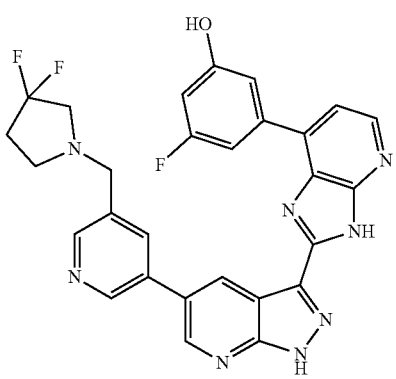 [SMILES: Oc1cc(F)cc(-c2ccnc3[nH]c(-c4n[nH]c5ncc(-c6cncc(CN7CCC(F)(F)C7)c6)cc45)nc23)c1]
1345
1342
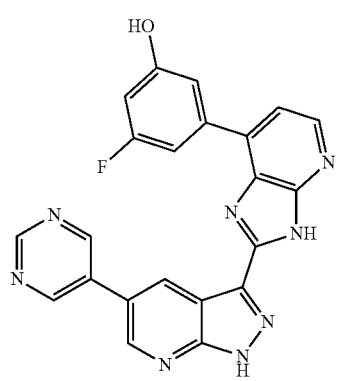 [SMILES: Oc1cc(F)cc(-c2ccnc3[nH]c(-c4n[nH]c5ncc(-c6cncnc6)cc45)nc23)c1]
1346
1343
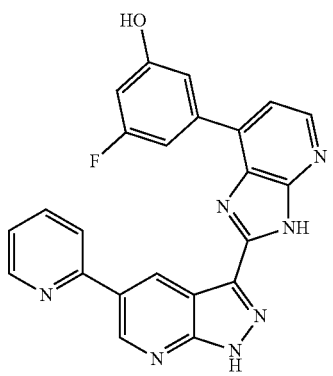
1347

TABLE 1-continued
| | |
|---|---|
| 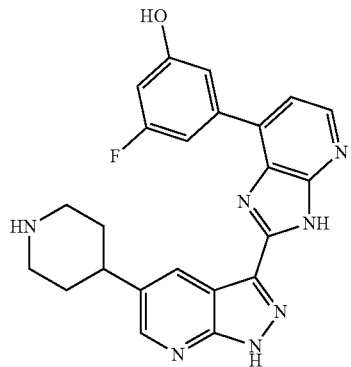 [SMILES: Oc1cc(F)cc(-c2ccnc3[nH]c(-c4n[nH]c5ncc(C6CCNCC6)cc45)nc23)c1] | 1348 |
| 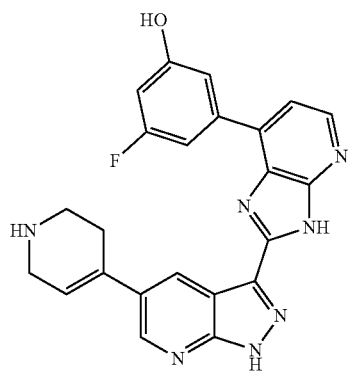 [SMILES: Oc1cc(F)cc(-c2ccnc3[nH]c(-c4n[nH]c5ncc(C6=CCNCC6)cc45)nc23)c1] | 1349 |
| 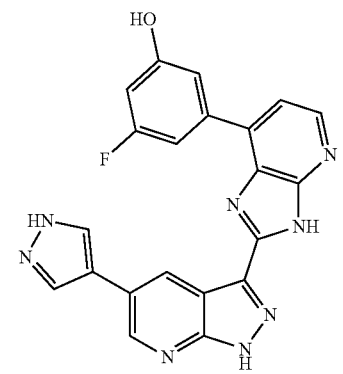 [SMILES: Oc1cc(F)cc(-c2ccnc3[nH]c(-c4n[nH]c5ncc(-c6cn[nH]c6)cc45)nc23)c1] | 1350 |
| 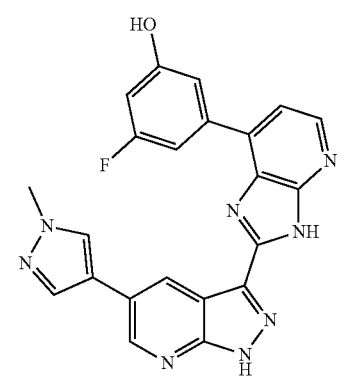 [SMILES: Cn1cc(-c2cnc3[nH]nc(-c4nc5c(-c6cc(O)cc(F)c6)ccnc5[nH]4)c3c2)cn1] | 1351 |
TABLE 1-continued
| | |
|---|---|
| 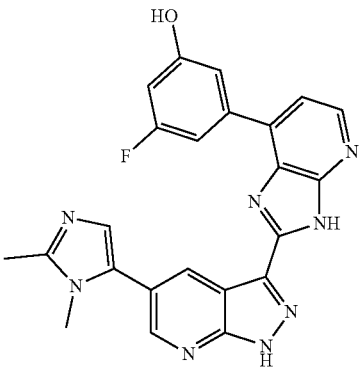 [SMILES: Cc1ncc(-c2cnc3[nH]nc(-c4nc5c(-c6cc(O)cc(F)c6)ccnc5[nH]4)c3c2)n1C] | 1352 |
| 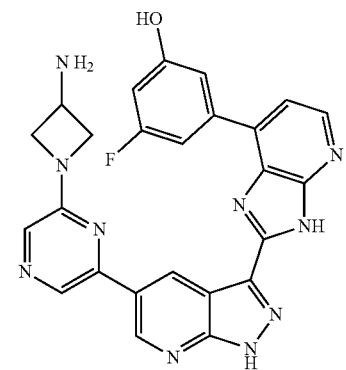 | 1353 |
| 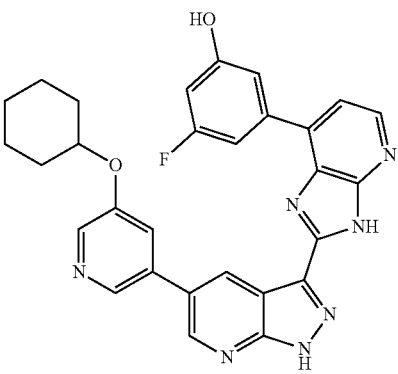 [SMILES: Oc1cc(F)cc(-c2ccnc3[nH]c(-c4n[nH]c5ncc(-c6cncc(OC7CCCCC7)c6)cc45)nc23)c1] | 1354 |
| 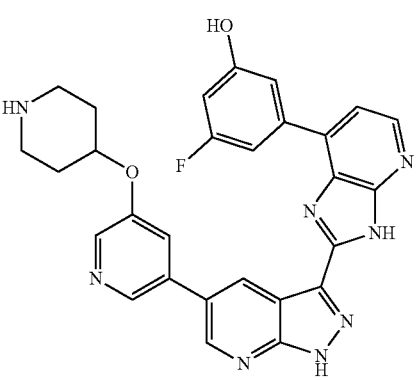 [SMILES: Oc1cc(F)cc(-c2ccnc3[nH]c(-c4n[nH]c5ncc(-c6cncc(OC7CCNCC7)c6)cc45)nc23)c1] | 1355 |

TABLE 1-continued
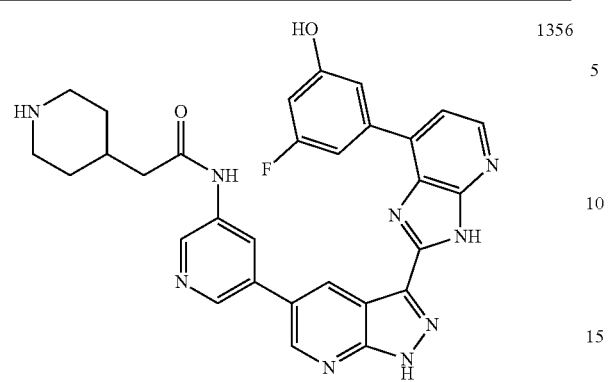 1356
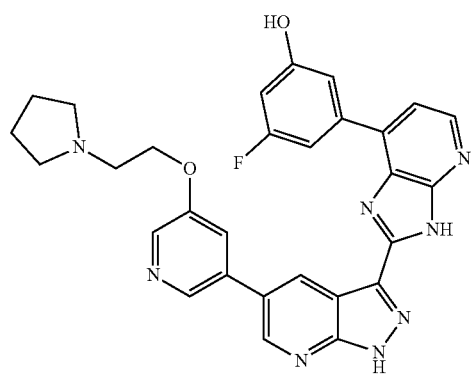 [SMILES: Oc1cc(F)cc(-c2ccnc3[nH]c(-c4n[nH]c5ncc(-c6cncc(OCCN7CCCC7)c6)cc45)nc23)c1] 1357
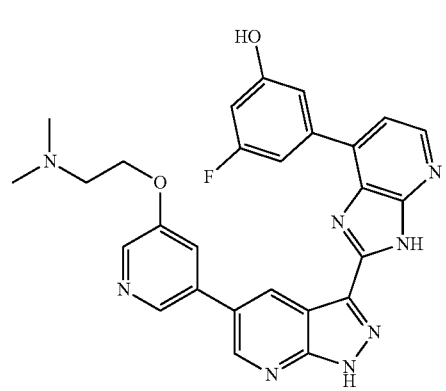 [SMILES: CN(C)CCOc1cncc(-c2cnc3[nH]nc(-c4nc5c(-c6cc(O)cc(F)c6)ccnc5[nH]4)c3c2)c1] 1358
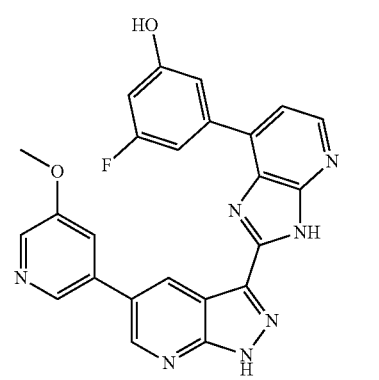 [SMILES: COc1cncc(-c2cnc3[nH]nc(-c4nc5c(-c6cc(O)cc(F)c6)ccnc5[nH]4)c3c2)c1] 1359
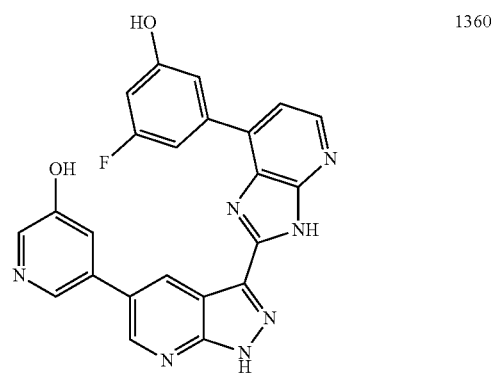 1360
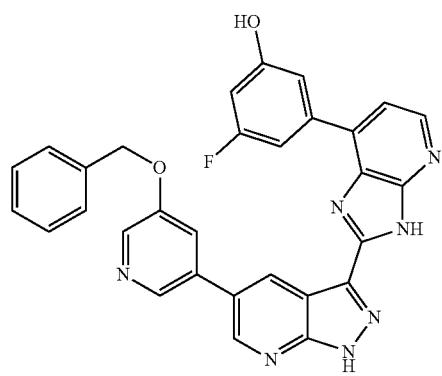 [SMILES: Oc1cc(F)cc(-c2ccnc3[nH]c(-c4n[nH]c5ncc(-c6cncc(OCc7ccccc7)c6)cc45)nc23)c1] 1361
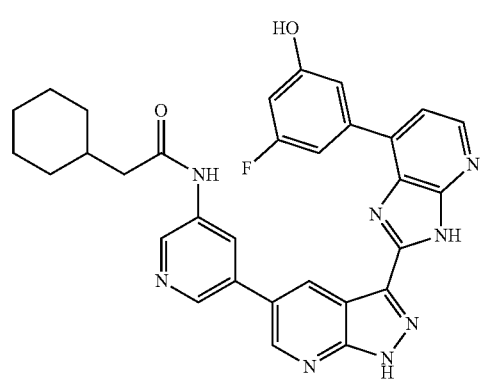 [SMILES: O=C(CC1CCCCC1)Nc1cncc(-c2cnc3[nH]nc(-c4nc5c(-c6cc(O)cc(F)c6)ccnc5[nH]4)c3c2)c1] 1362
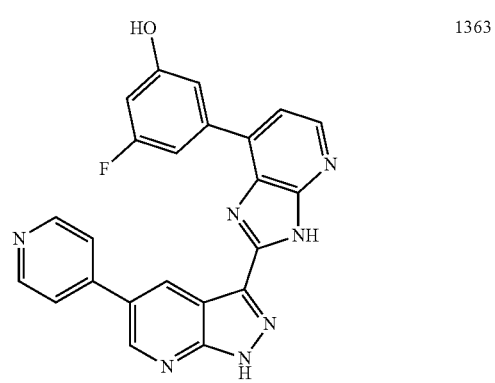 1363

TABLE 1-continued
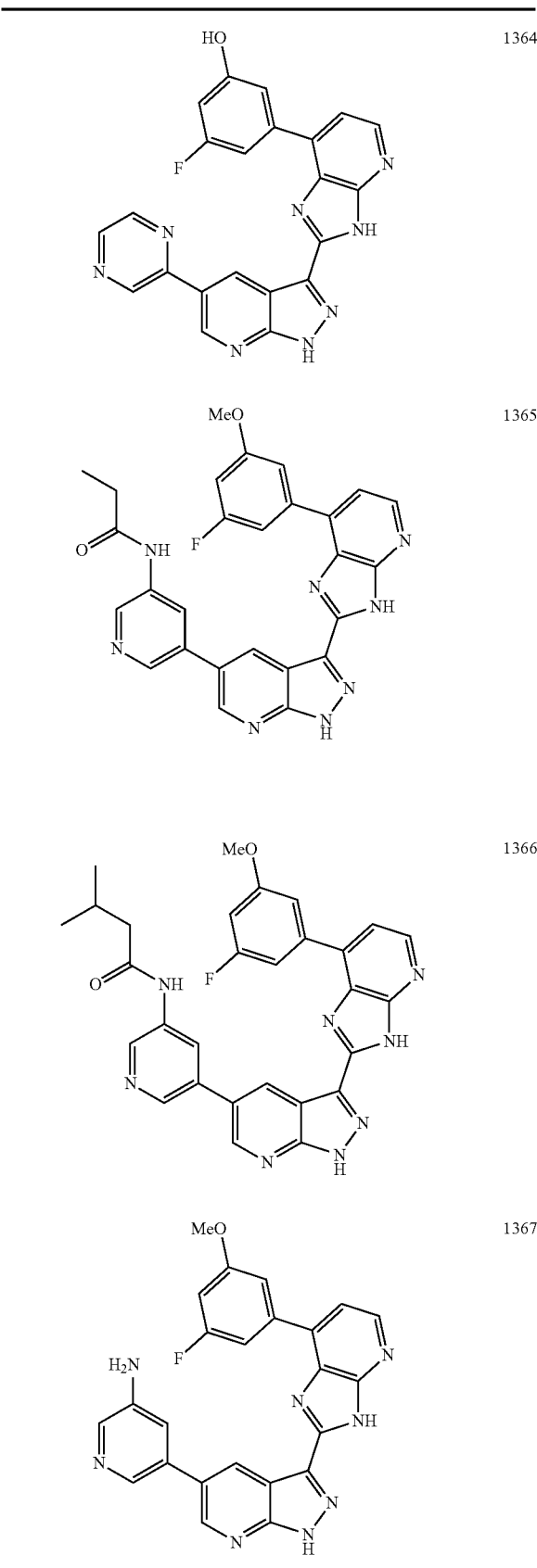
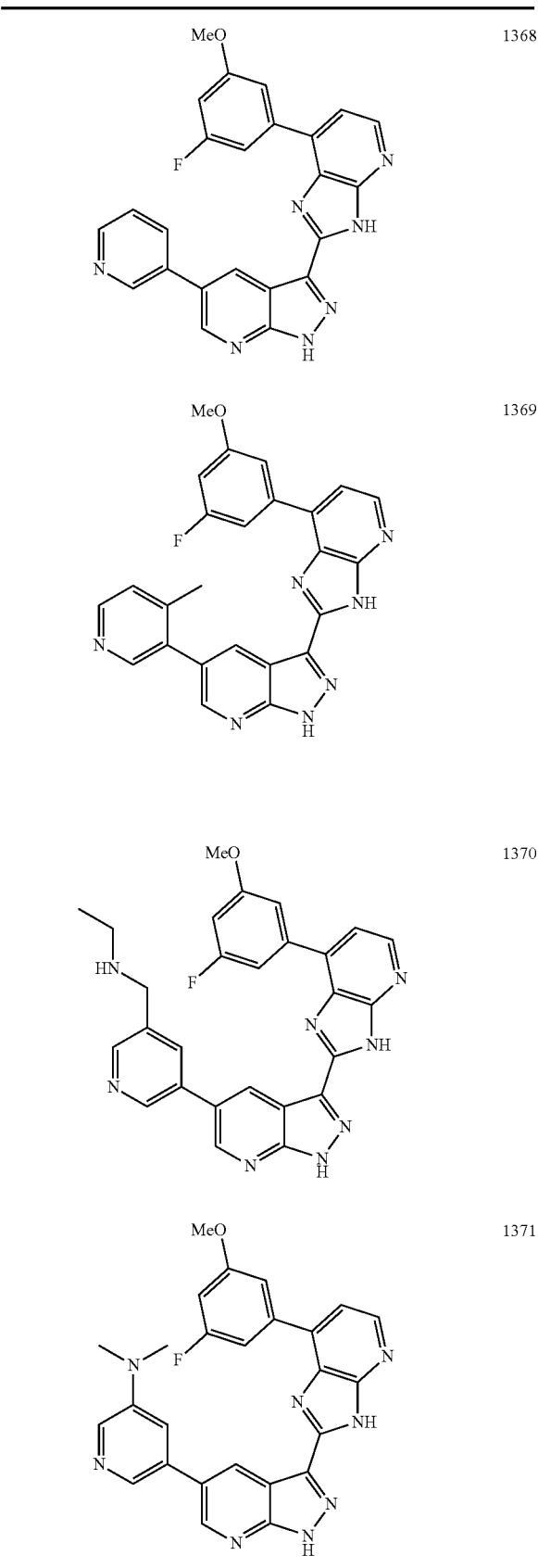

TABLE 1-continued
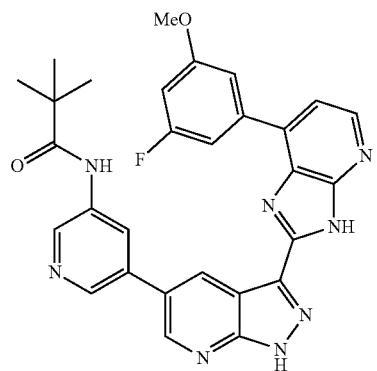 [SMILES: COc1cc(F)cc(-c2ccnc3[nH]c(-c4n[nH]c5ncc(-c6cncc(NC(=O)C(C)(C)C)c6)cc45)nc23)c1] 1372
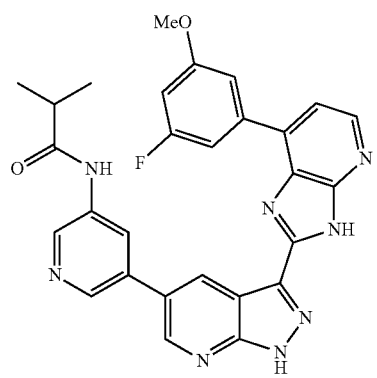 [SMILES: COc1cc(F)cc(-c2ccnc3[nH]c(-c4n[nH]c5ncc(-c6cncc(NC(=O)C(C)C)c6)cc45)nc23)c1] 1373
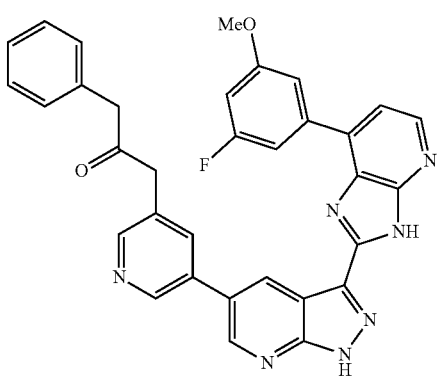 [SMILES: COc1cc(F)cc(-c2ccnc3[nH]c(-c4n[nH]c5ncc(-c6cncc(CC(=O)Cc7ccccc7)c6)cc45)nc23)c1] 1374
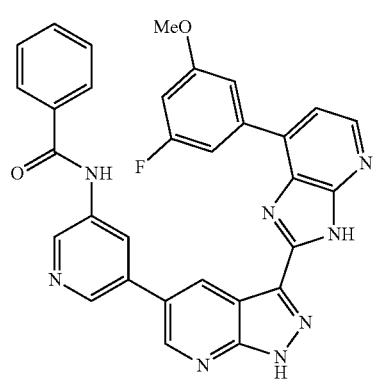 [SMILES: COc1cc(F)cc(-c2ccnc3[nH]c(-c4n[nH]c5ncc(-c6cncc(NC(=O)c7ccccc7)c6)cc45)nc23)c1] 1375
TABLE 1-continued
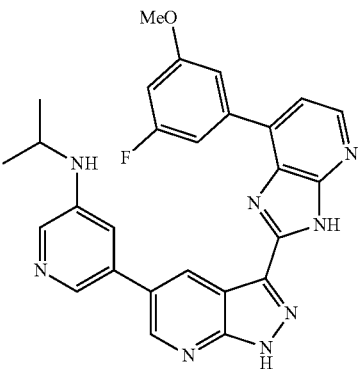 [SMILES: COc1cc(F)cc(-c2ccnc3[nH]c(-c4n[nH]c5ncc(-c6cncc(NC(C)C)c6)cc45)nc23)c1] 1376
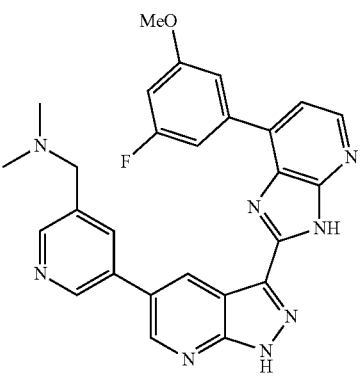 [SMILES: COc1cc(F)cc(-c2ccnc3[nH]c(-c4n[nH]c5ncc(-c6cncc(CN(C)C)c6)cc45)nc23)c1] 1377
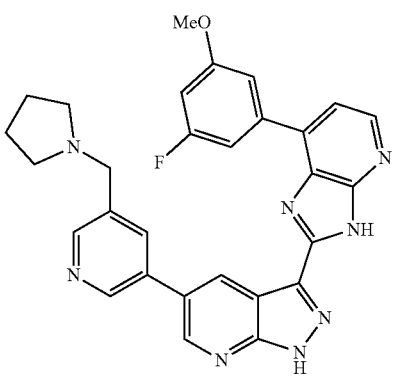 [SMILES: COc1cc(F)cc(-c2ccnc3[nH]c(-c4n[nH]c5ncc(-c6cncc(CN7CCCC7)c6)cc45)nc23)c1] 1378
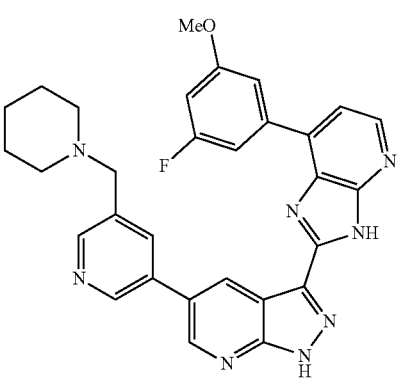 [SMILES: COc1cc(F)cc(-c2ccnc3[nH]c(-c4n[nH]c5ncc(-c6cncc(CN7CCCCC7)c6)cc45)nc23)c1] 1379

TABLE 1-continued
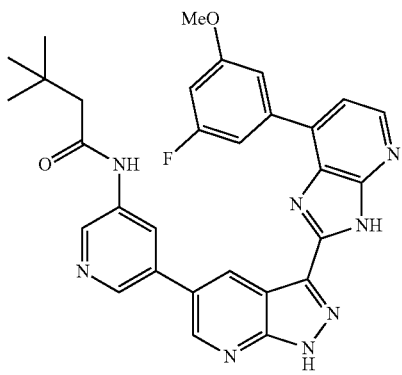 [SMILES: COc1cc(F)cc(-c2ccnc3[nH]c(-c4n[nH]c5ncc(-c6cncc(NC(=O)CC(C)(C)C)c6)cc45)nc23)c1] 1380
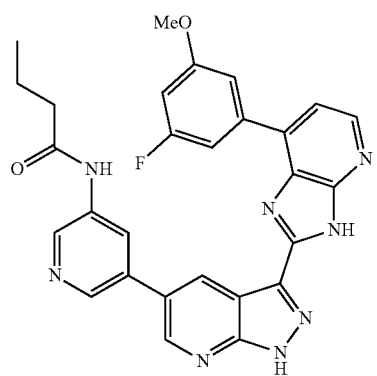 [SMILES: CCCC(=O)Nc1cncc(-c2cnc3[nH]nc(-c4nc5c(-c6cc(F)cc(OC)c6)ccnc5[nH]4)c3c2)c1] 1381
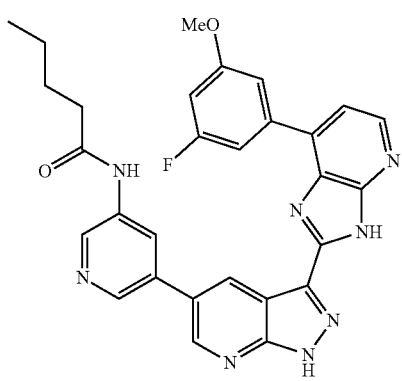 [SMILES: CCCCC(=O)Nc1cncc(-c2cnc3[nH]nc(-c4nc5c(-c6cc(F)cc(OC)c6)ccnc5[nH]4)c3c2)c1] 1382
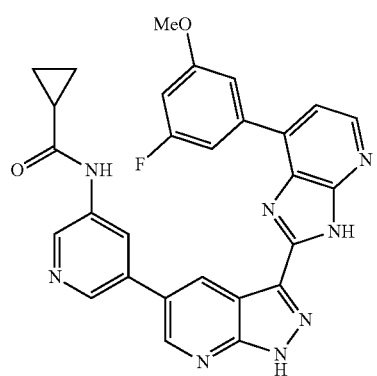 [SMILES: COc1cc(F)cc(-c2ccnc3[nH]c(-c4n[nH]c5ncc(-c6cncc(NC(=O)C7CC7)c6)cc45)nc23)c1] 1383
TABLE 1-continued
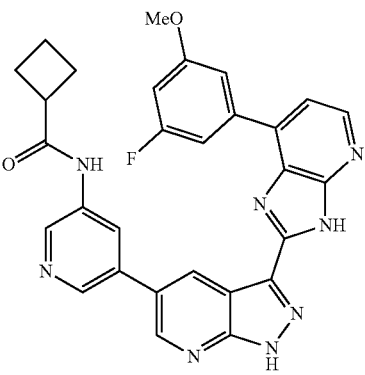 [SMILES: COc1cc(F)cc(-c2ccnc3[nH]c(-c4n[nH]c5ncc(-c6cncc(NC(=O)C7CCC7)c6)cc45)nc23)c1] 1384
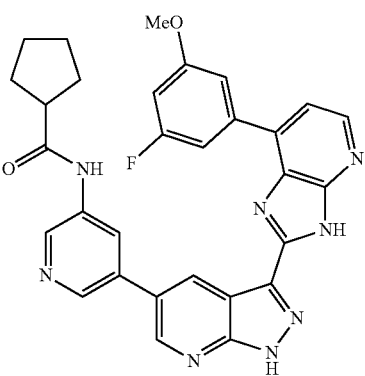 [SMILES: COc1cc(F)cc(-c2ccnc3[nH]c(-c4n[nH]c5ncc(-c6cncc(NC(=O)C7CCCC7)c6)cc45)nc23)c1] 1385
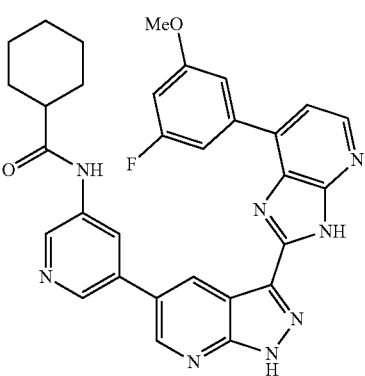 [SMILES: COc1cc(F)cc(-c2ccnc3[nH]c(-c4n[nH]c5ncc(-c6cncc(NC(=O)C7CCCCC7)c6)cc45)nc23)c1] 1386
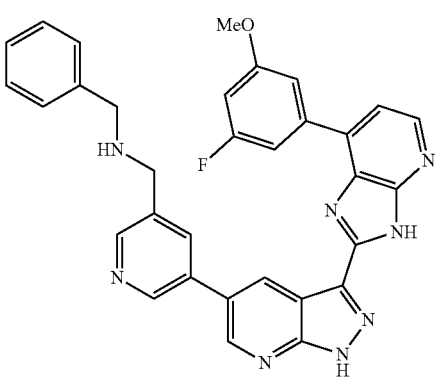 [SMILES: COc1cc(F)cc(-c2ccnc3[nH]c(-c4n[nH]c5ncc(-c6cncc(CNCc7ccccc7)c6)cc45)nc23)c1] 1387

TABLE 1-continued
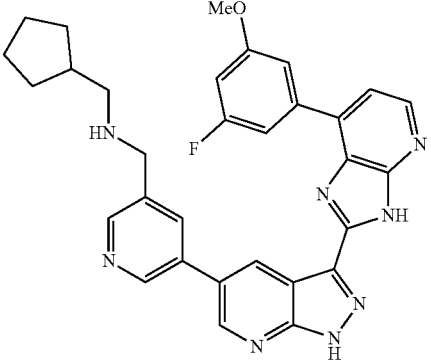 [SMILES: COc1cc(F)cc(-c2ccnc3[nH]c(-c4n[nH]c5ncc(-c6cncc(CNCC7CCCC7)c6)cc45)nc23)c1]

TABLE 1-continued
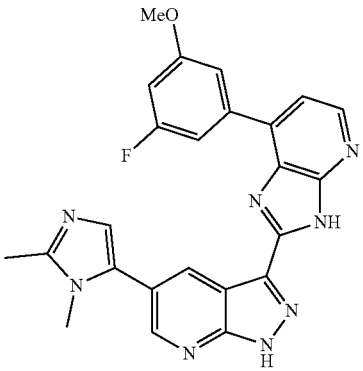 [SMILES: COc1cc(F)cc(-c2ccnc3[nH]c(-c4n[nH]c5ncc(-c6cnc(C)n6C)cc45)nc23)c1]
1396
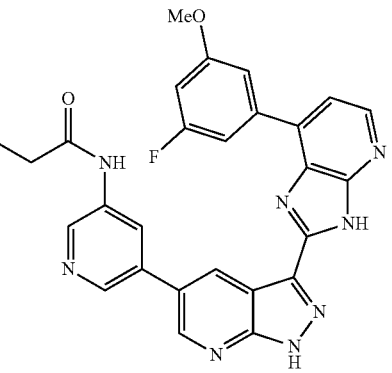
1400
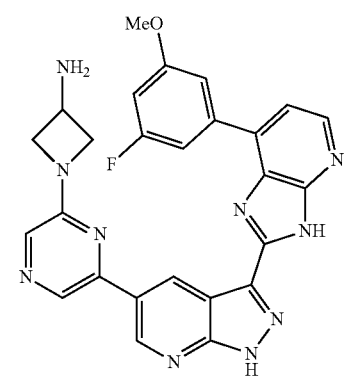 [SMILES: COc1cc(F)cc(-c2ccnc3[nH]c(-c4n[nH]c5ncc(-c6cncc(N7CC(N)C7)n6)cc45)nc23)c1]
1397
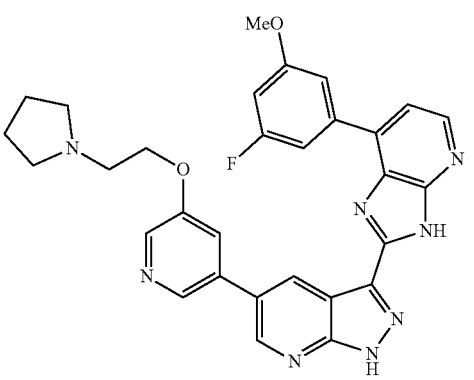
1401
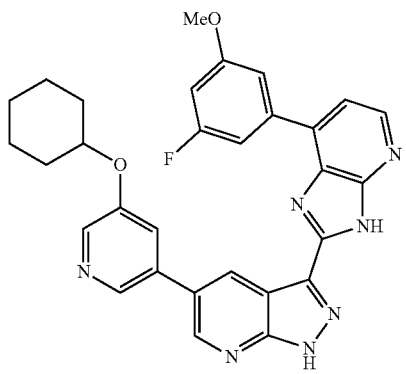 [SMILES: COc1cc(F)cc(-c2ccnc3[nH]c(-c4n[nH]c5ncc(-c6cncc(OC7CCCCC7)c6)cc45)nc23)c1]
1398
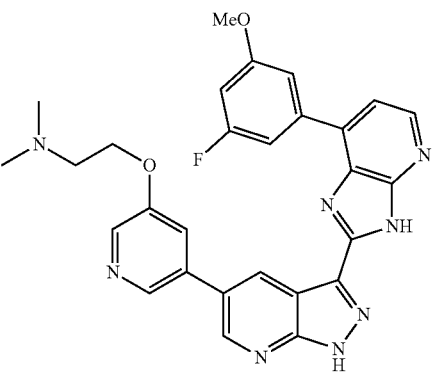
1402
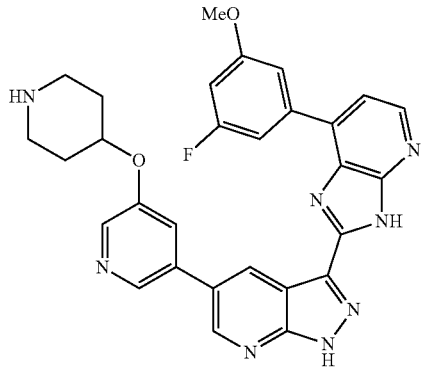 [SMILES: COc1cc(F)cc(-c2ccnc3[nH]c(-c4n[nH]c5ncc(-c6cncc(OC7CCNCC7)c6)cc45)nc23)c1]
1399
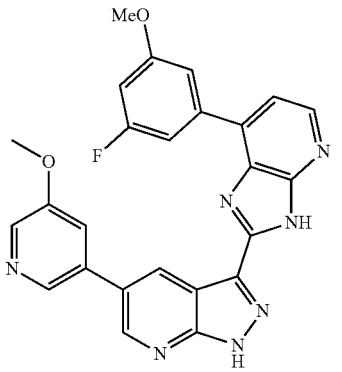 [SMILES: COc1cncc(-c2cnc3[nH]nc(-c4nc5c(-c6cc(F)cc(OC)c6)ccnc5[nH]4)c3c2)c1]
1403

TABLE 1-continued
| 1404 | 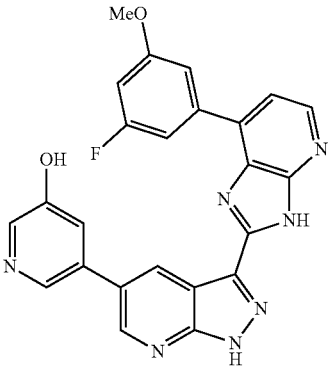 [SMILES: COc1cc(F)cc(-c2ccnc3[nH]c(-c4n[nH]c5ncc(-c6cncc(O)c6)cc45)nc23)c1] |
| 1405 | 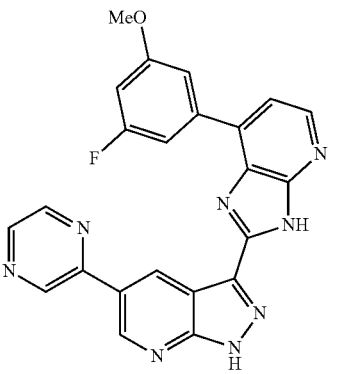 |
| 1406 | 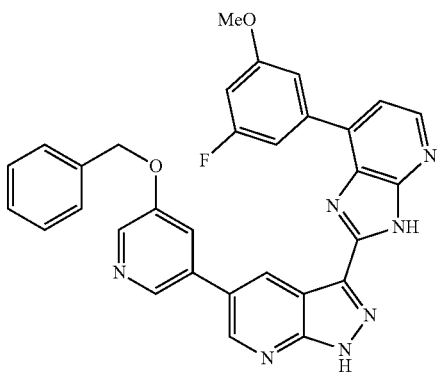 [SMILES: COc1cc(F)cc(-c2ccnc3[nH]c(-c4n[nH]c5ncc(-c6cncc(OCc7ccccc7)c6)cc45)nc23)c1] |
| 1407 | 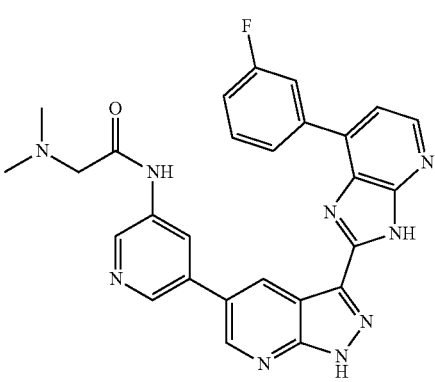 |
| 1408 | 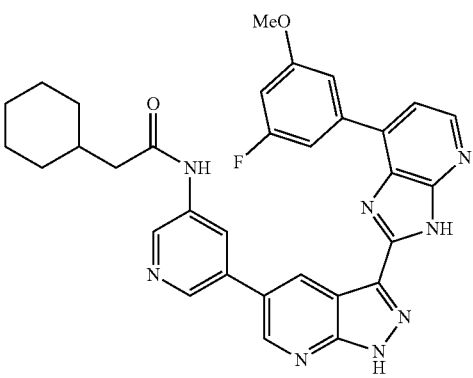 [SMILES: COc1cc(F)cc(-c2ccnc3[nH]c(-c4n[nH]c5ncc(-c6cncc(NC(=O)CC7CCCCC7)c6)cc45)nc23)c1] |
| 1409 | 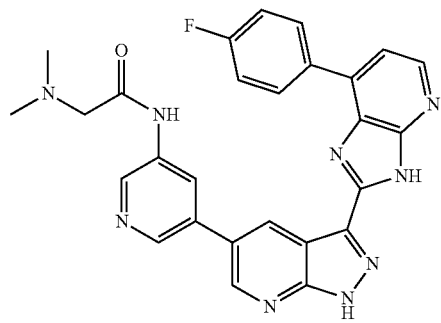 |
| 1410 | 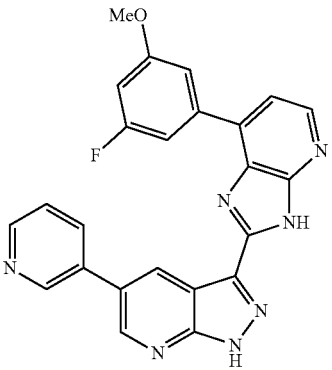 [SMILES: COc1cc(F)cc(-c2ccnc3[nH]c(-c4n[nH]c5ncc(-c6cccnc6)cc45)nc23)c1] |
| 1411 | 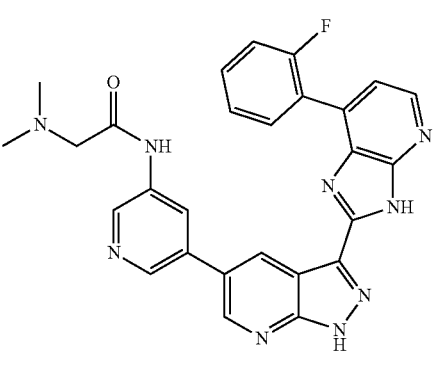 [SMILES: CN(C)CC(=O)Nc1cncc(-c2cnc3[nH]nc(-c4nc5c(-c6ccccc6F)ccnc5[nH]4)c3c2)c1] |

TABLE 1-continued
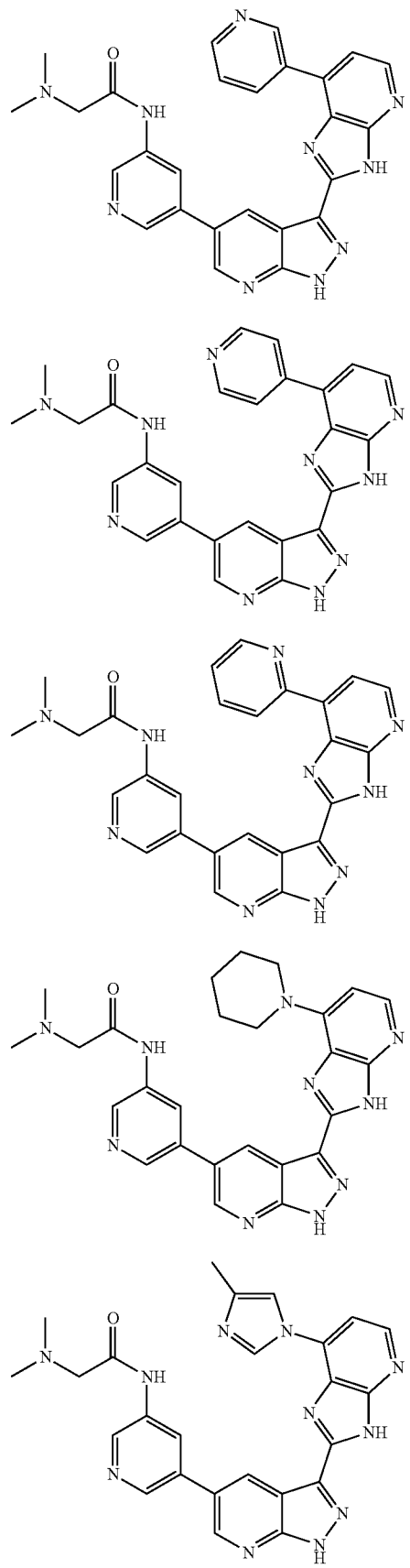
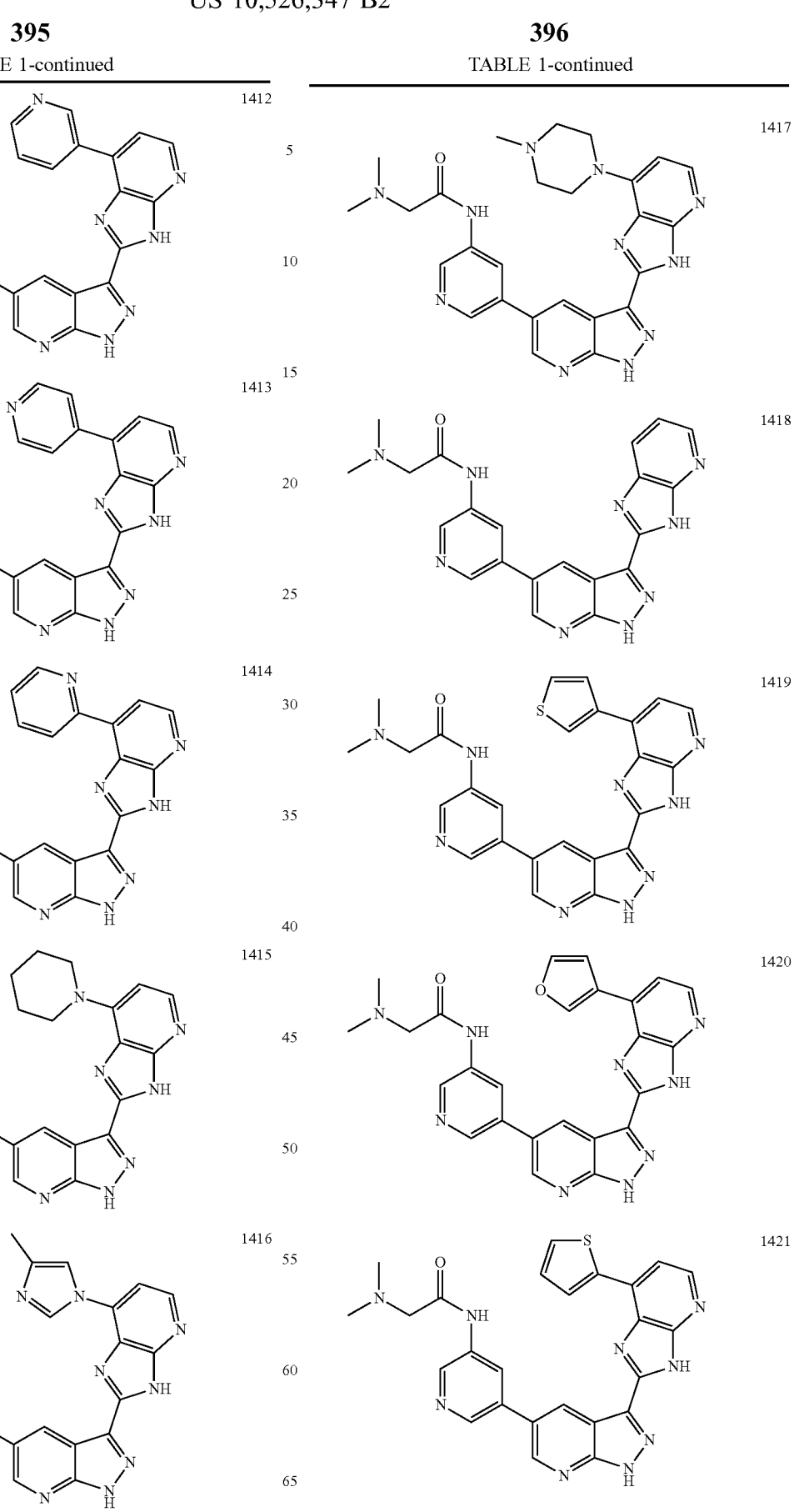

TABLE 1-continued
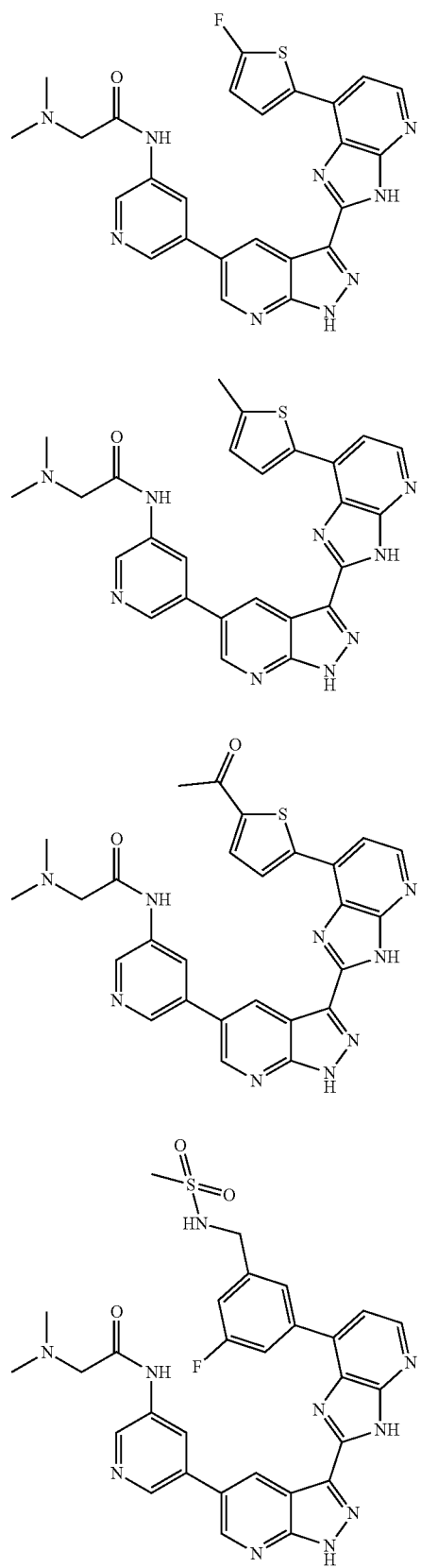
1422
1423
1424
1425
TABLE 1-continued
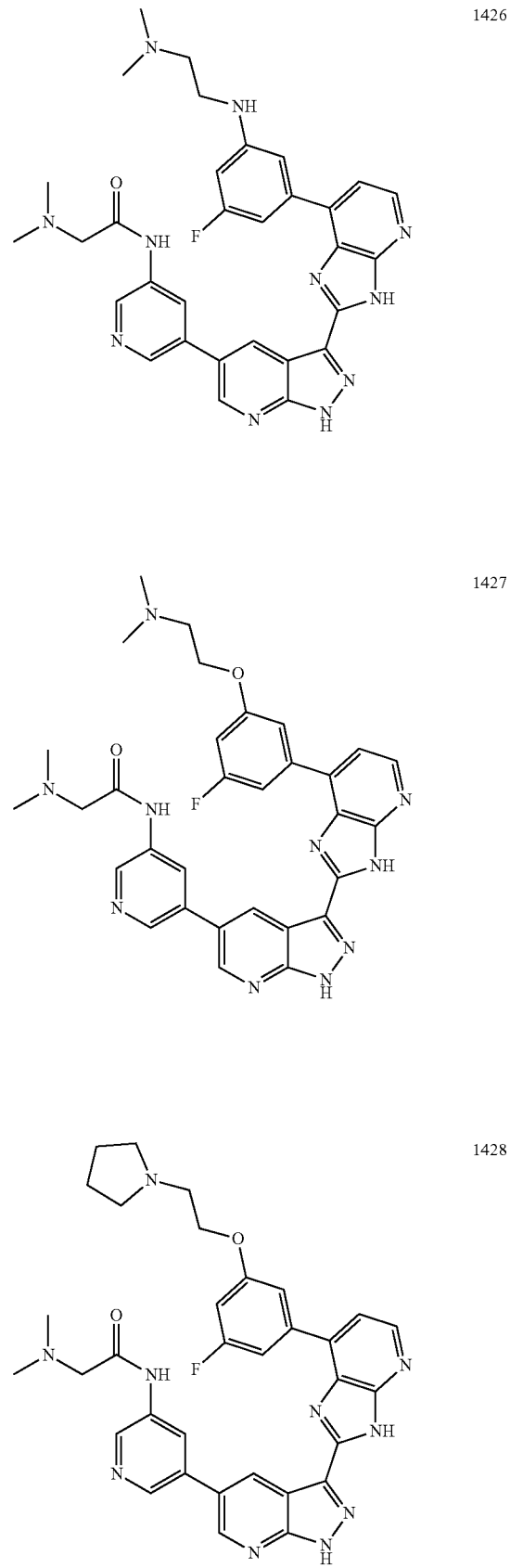
1426
1427
1428

TABLE 1-continued
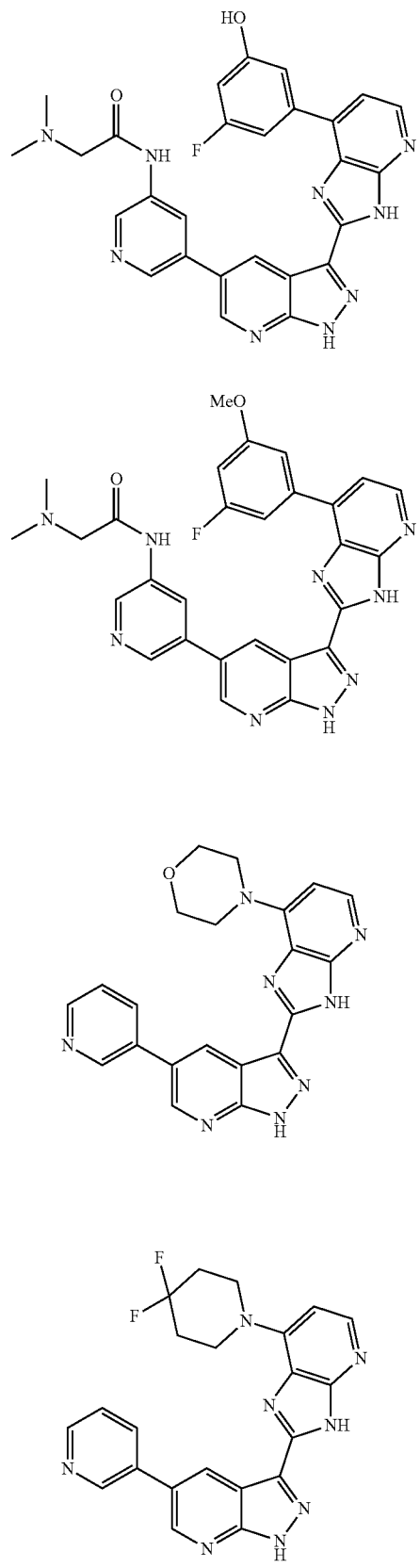
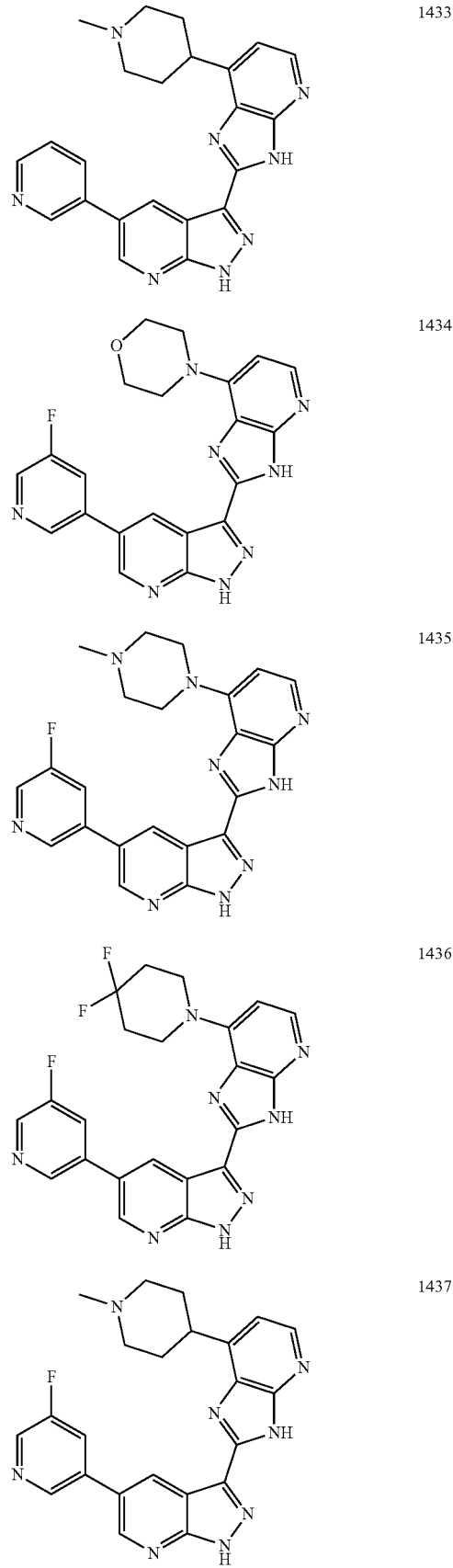

TABLE 1-continued
| | |
|---|---|
| 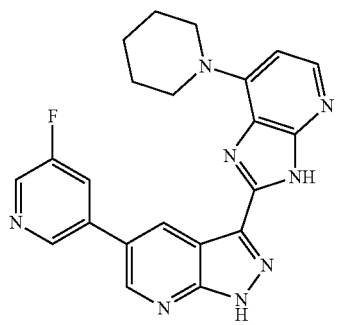 [SMILES: Fc1cncc(-c2cnc3[nH]nc(-c4nc5c(N6CCCCC6)ccnc5[nH]4)c3c2)c1] | 1438 |
| 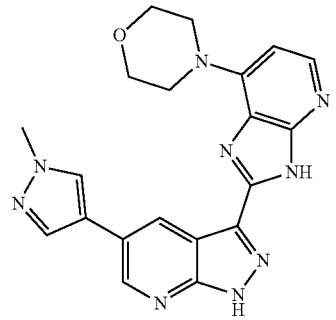 [SMILES: Cn1cc(-c2cnc3[nH]nc(-c4nc5c(N6CCOCC6)ccnc5[nH]4)c3c2)cn1] | 1439 |
| 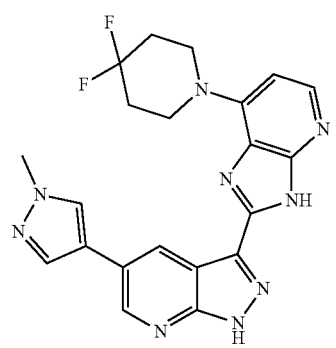 [SMILES: Cn1cc(-c2cnc3[nH]nc(-c4nc5c(N6CCC(F)(F)CC6)ccnc5[nH]4)c3c2)cn1] | 1440 |
| 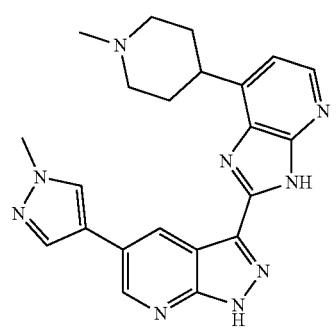 [SMILES: CN1CCC(c2ccnc3[nH]c(-c4n[nH]c5ncc(-c6cnn(C)c6)cc45)nc23)CC1] | 1441 |
TABLE 1-continued
| | |
|---|---|
| 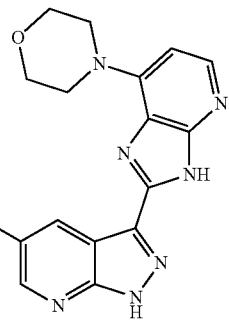 | 1442 |
| 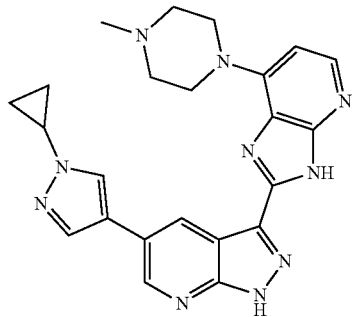 [SMILES: CN1CCN(c2ccnc3[nH]c(-c4n[nH]c5ncc(-c6cnn(C7CC7)c6)cc45)nc23)CC1] | 1443 |
| 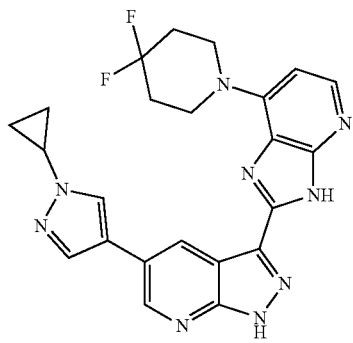 [SMILES: FC1(F)CCN(c2ccnc3[nH]c(-c4n[nH]c5ncc(-c6cnn(C7CC7)c6)cc45)nc23)CC1] | 1444 |
| 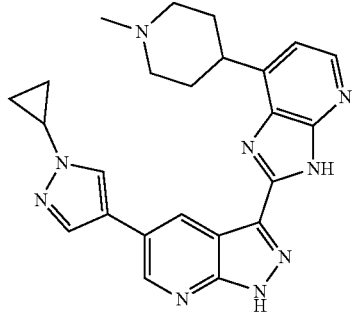 | 1445 |
| 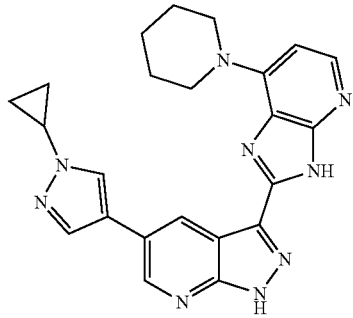 [SMILES: c1cc(N2CCCCC2)c2nc(-c3n[nH]c4ncc(-c5cnn(C6CC6)c5)cc34)[nH]c2n1] | 1446 |

Administration and Pharmaceutical Compositions

Some embodiments include pharmaceutical compositions comprising: (a) a therapeutically effective amount of a compound provided herein, or its corresponding enantiomer, diastereoisomer or tautomer, or pharmaceutically acceptable salt; and (b) a pharmaceutically acceptable carrier.

The compounds provided herein may also be useful in combination (administered together or sequentially) with other known agents.

Non-limiting examples of diseases which can be treated with a combination of a compound of Formula (I) and other known agents are colorectal cancer, ovarian cancer, retinitis pigmentosa, macular degeneration, diabetic retinopathy, idiopathic pulmonary fibrosis/pulmonary fibrosis, and osteoarthritis.

In some embodiments, colorectal cancer can be treated with a combination of a compound of Formula (I) and one or more of the following drugs: 5-Fluorouracil (5-FU), which can be administered with the vitamin-like drug leucovorin (also called folinic acid); capecitabine (XELODA®), irinotecan (CAMPOSTAR®), oxaliplatin (ELOXATIN®). Examples of combinations of these drugs which could be further combined with a compound of Formula (I) are FOLFOX (5-FU, leucovorin, and oxaliplatin), FOLFIRI (5-FU, leucovorin, and irinotecan), FOLFOXIRI (leucovorin, 5-FU, oxaliplatin, and irinotecan) and CapeOx (Capecitabine and oxaliplatin). For rectal cancer, chemo with 5-FU or capecitabine combined with radiation may be given before surgery (neoadjuvant treatment).

In some embodiments, ovarian cancer can be treated with a combination of a compound of Formula (I) and one or more of the following drugs: Topotecan, Liposomal doxorubicin (DOXIL®), Gemcitabine (GEMZAR®), Cyclophosphamide (CYTOXAN®), Vinorelbine (NAVELBINE®), Ifosfamide (IFEX®), Etoposide (VP-16), Altretamine (HEXALEN®), Capecitabine (XELODA®), Irinotecan (CPT-11, CAMPTOSAR®), Melphalan, Pemetrexed (ALIMTA®) and Albumin bound paclitaxel (nab-paclitaxel, ABRAXANE®). Examples of combinations of these drugs which could be further combined with a compound of Formula (I) are TIP (paclitaxel [Taxol], ifosfamide, and cisplatin), VeIP (vinblastine, ifosfamide, and cisplatin) and VIP (etoposide [VP-16], ifosfamide, and cisplatin).

In some embodiments, a compound of Formula (I) can be used to treat cancer in combination with any of the following methods: (a) Hormone therapy such as aromatase inhibitors, LHRH [luteinizing hormone-releasing hormone] analogs and inhibitors, and others; (b) Ablation or embolization procedures such as radiofrequency ablation (RFA), ethanol (alcohol) ablation, microwave thermotherapy and cryosurgery (cryotherapy); (c) Chemotherapy using alkylating agents such as cisplatin and carboplatin, oxaliplatin, mechlorethamine, cyclophosphamide, chlorambucil and ifosfamide; (d) Chemotherapy using anti-metabolites such as azathioprine and mercaptopurine; (e) Chemotherapy using plant alkaloids and terpenoids such as vinca alkaloids (i.e. Vincristine, Vinblastine, Vinorelbine and Vindesine) and taxanes; (f) Chemotherapy using podophyllotoxin, etoposide, teniposide and docetaxel; (g) Chemotherapy using topoisomerase inhibitors such as irinotecan, topotecan, amsacrine, etoposide, etoposide phosphate, and teniposide; (h) Chemotherapy using cytotoxic antibiotics such as actinomycin, anthracyclines, doxorubicin, daunorubicin, valrubicin, idarubicin, epirubicin, bleomycin, plicamycin and mitomycin; (i) Chemotherapy using tyrosine-kinase inhibitors such as Imatinib mesylate (GLEEVEC®, also known as STI-571), Gefitinib (Iressa, also known as ZD1839), Erlotinib (marketed as TARCEVA®), Bortezomib (VELCADE®), tamoxifen, tofacitinib, crizotinib, Bcl-2 inhibitors (e.g. obatoclax in clinical trials, ABT-263, and Gossypol), PARP inhibitors (e.g. Iniparib, Olaparib in clinical trials), PI3K inhibitors (eg. perifosine in a phase III trial), VEGF Receptor 2 inhibitors (e.g. Apatinib), AN-152, (AEZS-108), Braf inhibitors (e.g. vemurafenib, dabrafenib and LGX818), MEK inhibitors (e.g. trametinib and MEK162), CDK inhibitors, (e.g. PD-0332991), salinomycin and Sorafenib; (j) Chemotherapy using monoclonal antibodies such as Rituximab (marketed as MABTHERA® or RITUXAN®), Trastuzumab (Herceptin also known as ErbB2), Cetuximab (marketed as ERBITUX®), and Bevacizumab (marketed as AVASTIN®); and (k) radiation therapy.

In some embodiments, diabetic retinopathy can be treated with a combination of a compound of Formula (I) and one or more of the following natural supplements: Bilberry, Butcher's broom, Ginkgo, Grape seed extract, and Pycnogenol (Pine bark).

In some embodiments, idiopathic pulmonary fibrosis/pulmonary fibrosis can be treated with a combination of a compound of Formula (I) and one or more of the following drugs: pirfenidone (pirfenidone was approved for use in 2011 in Europe under the brand name Esbriet®), prednisone, azathioprine, N-acetylcysteine, interferon-γ 1b, bosentan (bosentan is currently being studied in patients with IPF, [*The American Journal of Respiratory and Critical Care Medicine* (2011), 184(1), 92-9]), Nintedanib (BIBF 1120 and Vargatef), QAX576 [*British Journal of Pharmacology* (2011), 163(1), 141-172], and anti-inflammatory agents such as corticosteroids.

In some embodiments, a compound of Formula (I) can be used to treat idiopathic pulmonary fibrosis/pulmonary fibrosis in combination with any of the following methods: oxygen therapy, pulmonary rehabilitation and surgery.

In some embodiments, a compound of Formula (I) can be used to treat osteoarthritis in combination with any of the following methods: (a) Nonsteroidal anti-inflammatory drugs (NSAIDs) such as ibuprofen, naproxen, aspirin and acetaminophen; (b) physical therapy; (c) injections of corticosteroid medications; (d) injections of hyaluronic acid derivatives (e.g. Hyalgan, Synvisc); (e) narcotics, like codeine; (f) in combination with braces and/or shoe inserts or any device that can immobilize or support your joint to help you keep pressure off it (e.g., splints, braces, shoe inserts or other medical devices); (g) realigning bones (osteotomy); (h) joint replacement (arthroplasty); and (i) in combination with a chronic pain class.

In some embodiments, macular degeneration can be treated with a combination of a compound of Formula (I) and one or more of the following drugs: Bevacizumab (Avastin®), Ranibizumab (Lucentis®), Pegaptanib (Macugen), Aflibercept (Eylea®), verteporfin (Visudyne®) in combination with photodynamic therapy (PDT) or with any of the following methods: (a) in combination with laser to destroy abnormal blood vessels (photocoagulation); and (b) in combination with increased vitamin intake of antioxidant vitamins and zinc.

In some embodiments, retinitis pigmentosa can be treated with a combination of a compound of Formula (I) and one or more of the following drugs: UF-021 (Ocuseva™), vitamin A palmitate and pikachurin or with any of the following methods: (a) with the Argus® II retinal implant; and (b) with stem cell and/or gene therapy.

Administration of the compounds disclosed herein or the pharmaceutically acceptable salts thereof can be via any of the accepted modes of administration, including, but not limited to, orally, subcutaneously, intravenously, intranasally, topically, transdermally, intraperitoneally, intramuscularly, intrapulmonarilly, vaginally, rectally, ontologically, neuro-otologically, intraocularly, subconjuctivally, via anterior eye chamber injection, intravitreally, intraperitoneally, intrathecally, intracystically, intrapleurally, via wound irrigation, intrabuccally, intra-abdominally, intra-articularly, intra-aurally, intrabronchially, intracapsularly, intrameningeally, via inhalation, via endotracheal or endobronchial instillation, via direct instillation into pulmonary cavities, intraspinally, intrasynovially, intrathoracically, via thoracostomy irrigation, epidurally, intratympanically, intracisternally, intravascularly, intraventricularly, intraosseously, via irrigation of infected bone, or via application as part of any admixture with a prosthetic devices. In some embodiments, the administration method includes oral or parenteral administration.

Compounds provided herein intended for pharmaceutical use may be administered as crystalline or amorphous products. Pharmaceutically acceptable compositions may include solid, semi-solid, liquid, solutions, colloidal, liposomes, emulsions, suspensions, complexes, coacervates and aerosols. Dosage forms, such as, e.g., tablets, capsules, powders, liquids, suspensions, suppositories, aerosols, implants, controlled release or the like. They may be obtained, for example, as solid plugs, powders, or films by methods such as precipitation, crystallization, milling, grinding, supercritical fluid processing, coacervation, complex coacervation, encapsulation, emulsification, complexation, freeze drying, spray drying, or evaporative drying. Microwave or radio frequency drying may be used for this purpose. The compounds can also be administered in sustained or controlled release dosage forms, including depot injections, osmotic pumps, pills (tablets and or capsules), transdermal (including electrotransport) patches, implants and the like, for prolonged and/or timed, pulsed administration at a predetermined rate.

The compounds can be administered either alone or in combination with a conventional pharmaceutical carrier, excipient or the like. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a compound as described herein in the range of 0.005% to 100% with the balance made up from non-toxic carrier may be prepared. The contemplated compositions may contain 0.001%-100% of a compound provided herein, in one embodiment 0.1-95%, in another embodiment 75-85%, in a further embodiment 20-80%. Actual methods of preparing such dosage forms are known, or will be apparent, to those skilled in this art; for example, see Remington: *The Science and Practice of Pharmacy,* 22$^{nd}$ Edition (Pharmaceutical Press, London, UK. 2012).

In one embodiment, the compositions will take the form of a unit dosage form such as a pill or tablet and thus the composition may contain, along with a compound provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEG's, poloxamer 124 or triglycerides) is encapsulated in a capsule (gelatin or cellulose base capsule). Unit dosage forms in which one or more compounds provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

Liquid pharmaceutically administrable compositions can, for example, be prepared by dissolving, dispersing, etc. a compound provided herein and optional pharmaceutical adjuvants in a carrier (e.g., water, saline, aqueous dextrose, glycerol, glycols, ethanol or the like) to form a solution, colloid, liposome, emulsion, complexes, coacervate or suspension. If desired, the pharmaceutical composition can also contain minor amounts of nontoxic auxiliary substances such as wetting agents, emulsifying agents, co-solvents, solubilizing agents, pH buffering agents and the like (e.g., sodium acetate, sodium citrate, cyclodextrin derivatives, sorbitan monolaurate, triethanolamine acetate, triethanolamine oleate, and the like).

In some embodiments, the unit dosage of compounds of Formula (I) is about 0.25 mg/Kg to about 50 mg/Kg in humans.

In some embodiments, the unit dosage of compounds of Formula (I) is about 0.25 mg/Kg to about 20 mg/Kg in humans.

In some embodiments, the unit dosage of compounds of Formula (I) is about 0.50 mg/Kg to about 19 mg/Kg in humans.

In some embodiments, the unit dosage of compounds of Formula (I) is about 0.75 mg/Kg to about 18 mg/Kg in humans.

In some embodiments, the unit dosage of compounds of Formula (I) is about 1.0 mg/Kg to about 17 mg/Kg in humans.

In some embodiments, the unit dosage of compounds of Formula (I) is about 1.25 mg/Kg to about 16 mg/Kg in humans.

In some embodiments, the unit dosage of compounds of Formula (I) is about 1.50 mg/Kg to about 15 mg/Kg in humans.

In some embodiments, the unit dosage of compounds of Formula (I) is about 1.75 mg/Kg to about 14 mg/Kg in humans.

In some embodiments, the unit dosage of compounds of Formula (I) is about 2.0 mg/Kg to about 13 mg/Kg in humans.

In some embodiments, the unit dosage of compounds of Formula (I) is about 3.0 mg/Kg to about 12 mg/Kg in humans.

In some embodiments, the unit dosage of compounds of Formula (I) is about 4.0 mg/Kg to about 11 mg/Kg in humans.

In some embodiments, the unit dosage of compounds of Formula (I) is about 5.0 mg/Kg to about 10 mg/Kg in humans.

In some embodiments, the compositions are provided in unit dosage forms suitable for single administration.

In some embodiments, the compositions are provided in unit dosage forms suitable for twice a day administration.

In some embodiments, the compositions are provided in unit dosage forms suitable for three times a day administration.

Injectables can be prepared in conventional forms, either as liquid solutions, colloid, liposomes, complexes, coacervate or suspensions, as emulsions, or in solid forms suitable for reconstitution in liquid prior to injection. The percentage of a compound provided herein contained in such parenteral compositions is highly dependent on the specific nature thereof, as well as the activity of the compound and the needs of the patient. However, percentages of active ingredient of 0.01% to 10% in solution are employable, and could be higher if the composition is a solid or suspension, which could be subsequently diluted to the above percentages.

In some embodiments, the composition will comprise about 0.1-10% of the active agent in solution.

In some embodiments, the composition will comprise about 0.1-5% of the active agent in solution.

In some embodiments, the composition will comprise about 0.1-4% of the active agent in solution.

In some embodiments, the composition will comprise about 0.15-3% of the active agent in solution.

In some embodiments, the composition will comprise about 0.2-2% of the active agent in solution.

In some embodiments, the compositions are provided in dosage forms suitable for continuous dosage by intravenous infusion over a period of about 1-96 hours.

In some embodiments, the compositions are provided in dosage forms suitable for continuous dosage by intravenous infusion over a period of about 1-72 hours.

In some embodiments, the compositions are provided in dosage forms suitable for continuous dosage by intravenous infusion over a period of about 1-48 hours.

In some embodiments, the compositions are provided in dosage forms suitable for continuous dosage by intravenous infusion over a period of about 1-24 hours.

In some embodiments, the compositions are provided in dosage forms suitable for continuous dosage by intravenous infusion over a period of about 1-12 hours.

In some embodiments, the compositions are provided in dosage forms suitable for continuous dosage by intravenous infusion over a period of about 1-6 hours.

In some embodiments, these compositions can be administered by intravenous infusion to humans at doses of about 5 mg/m$^2$ to about 300 mg/m$^2$.

In some embodiments, these compositions can be administered by intravenous infusion to humans at doses of about 5 mg/m$^2$ to about 200 mg/m$^2$.

In some embodiments, these compositions can be administered by intravenous infusion to humans at doses of about 5 mg/m$^2$ to about 100 mg/m$^2$.

In some embodiments, these compositions can be administered by intravenous infusion to humans at doses of about 10 mg/m$^2$ to about 50 mg/m$^2$.

In some embodiments, these compositions can be administered by intravenous infusion to humans at doses of about 50 mg/m$^2$ to about 200 mg/m$^2$.

In some embodiments, these compositions can be administered by intravenous infusion to humans at doses of about 75 mg/m$^2$ to about 175 mg/m$^2$.

In some embodiments, these compositions can be administered by intravenous infusion to humans at doses of about 100 mg/m$^2$ to about 150 mg/m$^2$.

It is to be noted that concentrations and dosage values may also vary depending on the specific compound and the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In one embodiment, the compositions can be administered to the respiratory tract (including nasal and pulmonary) e.g., through a nebulizer, metered-dose inhalers, atomizer, mister, aerosol, dry powder inhaler, insufflator, liquid instillation or other suitable device or technique.

In some embodiments, aerosols intended for delivery to the nasal mucosa are provided for inhalation through the nose. For optimal delivery to the nasal cavities, inhaled particle sizes of about 5 to about 100 microns are useful, with particle sizes of about 10 to about 60 microns being preferred. For nasal delivery, a larger inhaled particle size may be desired to maximize impaction on the nasal mucosa and to minimize or prevent pulmonary deposition of the administered formulation. In some embodiments, aerosols intended for delivery to the lung are provided for inhalation through the nose or the mouth. For delivery to the lung, inhaled aerodynamic particle sizes of about less than 10 µm are useful (e.g., about 1 to about 10 microns). Inhaled particles may be defined as liquid droplets containing dissolved drug, liquid droplets containing suspended drug particles (in cases where the drug is insoluble in the suspending medium), dry particles of pure drug substance, drug substance incorporated with excipients, liposomes, emulsions, colloidal systems, coacervates, aggregates of drug nanoparticles, or dry particles of a diluent which contain embedded drug nanoparticles.

In some embodiments, compounds of Formula (I) disclosed herein intended for respiratory delivery (either systemic or local) can be administered as aqueous formulations, as non-aqueous solutions or suspensions, as suspensions or solutions in halogenated hydrocarbon propellants with or without alcohol, as a colloidal system, as emulsions, coacervates, or as dry powders. Aqueous formulations may be aerosolized by liquid nebulizers employing either hydraulic or ultrasonic atomization or by modified micropump systems (like the soft mist inhalers, the Aerodose® or the AERx® systems). Propellant-based systems may use suitable pressurized metered-dose inhalers (pMDIs). Dry powders may use dry powder inhaler devices (DPIs), which are capable of dispersing the drug substance effectively. A desired particle size and distribution may be obtained by choosing an appropriate device.

In some embodiments, the compositions of Formula (I) disclosed herein can be administered to the ear by various methods. For example, a round window catheter (e.g., U.S. Pat. Nos. 6,440,102 and 6,648,873) can be used.

Alternatively, formulations can be incorporated into a wick for use between the outer and middle ear (e.g., U.S. Pat. No. 6,120,484) or absorbed to collagen sponge or other solid support (e.g., U.S. Pat. No. 4,164,559).

If desired, formulations of the invention can be incorporated into a gel formulation (e.g., U.S. Pat. Nos. 4,474,752 and 6,911,211).

In some embodiments, compounds of Formula (I) disclosed herein intended for delivery to the ear can be administered via an implanted pump and delivery system through a needle directly into the middle or inner ear (cochlea) or through a cochlear implant stylet electrode channel or alternative prepared drug delivery channel such as but not limited to a needle through temporal bone into the cochlea.

Other options include delivery via a pump through a thin film coated onto a multichannel electrode or electrode with a specially imbedded drug delivery channel (pathways) carved into the thin film for this purpose. In other embodiments the acidic or basic solid compound of Formula (I) can be delivered from the reservoir of an external or internal implanted pumping system.

Formulations of the invention also can be administered to the ear by intratympanic injection into the middle ear, inner ear, or cochlea (e.g., U.S. Pat. No. 6,377,849 and Ser. No. 11/337,815).

Intratympanic injection of therapeutic agents is the technique of injecting a therapeutic agent behind the tympanic membrane into the middle and/or inner ear. In one embodiment, the formulations described herein are administered directly onto the round window membrane via transtympanic injection. In another embodiment, the ion channel modulating agent auris-acceptable formulations described herein are administered onto the round window membrane via a non-transtympanic approach to the inner ear. In additional embodiments, the formulation described herein is administered onto the round window membrane via a surgical approach to the round window membrane comprising modification of the crista fenestrae cochleae.

In some embodiments, the compounds of Formula (I) are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG (like PEG ointments), and the like.

Suppositories for rectal administration of the drug (either as a solution, colloid, suspension or a complex) can be prepared by mixing a compound provided herein with a suitable non-irritating excipient that is solid at ordinary temperatures but liquid at the rectal temperature and will therefore melt or erode/dissolve in the rectum and release the compound. Such materials include cocoa butter, glycerinated gelatin, hydrogenated vegetable oils, poloxamers, mixtures of polyethylene glycols of various molecular weights and fatty acid esters of polyethylene glycol. In suppository forms of the compositions, a low-melting wax such as, but not limited to, a mixture of fatty acid glycerides, optionally in combination with cocoa butter, is first melted.

Solid compositions can be provided in various different types of dosage forms, depending on the physicochemical properties of the compound provided herein, the desired dissolution rate, cost considerations, and other criteria. In one of the embodiments, the solid composition is a single unit. This implies that one unit dose of the compound is comprised in a single, physically shaped solid form or article. In other words, the solid composition is coherent, which is in contrast to a multiple unit dosage form, in which the units are incoherent.

Examples of single units which may be used as dosage forms for the solid composition include tablets, such as compressed tablets, film-like units, foil-like units, wafers, lyophilized matrix units, and the like. In one embodiment, the solid composition is a highly porous lyophilized form. Such lyophilizates, sometimes also called wafers or lyophilized tablets, are particularly useful for their rapid disintegration, which also enables the rapid dissolution of the compound.

On the other hand, for some applications the solid composition may also be formed as a multiple unit dosage form as defined above. Examples of multiple units are powders, granules, microparticles, pellets, mini-tablets, beads, lyophilized powders, and the like. In one embodiment, the solid composition is a lyophilized powder. Such a dispersed lyophilized system comprises a multitude of powder particles, and due to the lyophilization process used in the formation of the powder, each particle has an irregular, porous microstructure through which the powder is capable of absorbing water very rapidly, resulting in quick dissolution. Effervescent compositions are also contemplated to aid the quick dispersion and absorption of the compound.

Another type of multiparticulate system which is also capable of achieving rapid drug dissolution is that of powders, granules, or pellets from water-soluble excipients which are coated with a compound provided herein so that the compound is located at the outer surface of the individual particles. In this type of system, the water-soluble low molecular weight excipient may be useful for preparing the cores of such coated particles, which can be subsequently coated with a coating composition comprising the compound and, for example, one or more additional excipients, such as a binder, a pore former, a saccharide, a sugar alcohol, a film-forming polymer, a plasticizer, or other excipients used in pharmaceutical coating compositions.

Also provided herein are kits. Typically, a kit includes one or more compounds or compositions as described herein. In certain embodiments, a kit can include one or more delivery systems, e.g., for delivering or administering a compound as provided herein, and directions for use of the kit (e.g., instructions for treating a patient). In another embodiment, the kit can include a compound or composition as described herein and a label that indicates that the contents are to be administered to a patient with cancer. In another embodiment, the kit can include a compound or composition as described herein and a label that indicates that the contents are to be administered to a patient with one or more of hepatocellular carcinoma, colon cancer, leukemia, lymphoma, sarcoma, ovarian cancer, diabetic retinopathy, pulmonary fibrosis, rheumatoid arthritis, sepsis, anklyosing spondylitis, psoriasis, scleroderma, mycotic and viral infections, bone and cartilage diseases, Alzheimer's disease, lung disease, bone/osteoporotic (wrist, spine, shoulder and hip) fractures, articular cartilage (chondral) defects, degenerative disc disease (or intervertebral disc degeneration), polyposis coli, bone density and vascular defects in the eye (Osteoporosis-pseudoglioma Syndrome, OPPG) and other eye diseases or syndromes associated with defects and/or damaged photoreceptors, familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman's syndrome, Prader-Willi syndrome, Beckwith-Wiedemann Syndrome, Norrie disease, and Rett syndrome.

Methods of Treatment

The compounds and compositions provided herein can be used as inhibitors and/or modulators of one or more components of the Wnt pathway, which may include one or more Wnt proteins, and thus can be used to treat a variety of disorders and diseases in which aberrant Wnt signaling is implicated, such as cancer and other diseases associated with abnormal angiogenesis, cellular proliferation, and cell cycling. Accordingly, the compounds and compositions provided herein can be used to treat cancer, to reduce or inhibit angiogenesis, to reduce or inhibit cellular proliferation, to correct a genetic disorder, and/or to treat a neurological condition/disorder/disease due to mutations or dysregulation of the Wnt pathway and/or of one or more of Wnt signaling components. Non-limiting examples of diseases which can be treated with the compounds and compositions provided herein include a variety of cancers, diabetic retinopathy, pulmonary fibrosis, rheumatoid arthritis, scleroderma, mycotic and viral infections, bone and cartilage diseases, neurological conditions/diseases such as Alzheimer's disease, amyotrophic lateral sclerosis (ALS), motor neuron disease, multiple sclerosis or autism, lung disease, bone/osteoporotic (wrist, spine, shoulder and hip) fractures, polyposis coli, bone density and vascular defects in the eye (Osteoporosis-pseudoglioma Syndrome, OPPG) and other eye diseases or syndromes associated with defects and/or damaged photoreceptors, familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman's syndrome, Prader-Willi syndrome, Beckwith-Wiedemann Syndrome, Norrie disease and Rett syndrome.

In some embodiments, non-limiting examples of eye diseases which can be treated with the compounds and compositions provided herein include age-related macular degeneration (AMD or ARMD), rod cone dystrophy, retinitis pigmentosa (RP), acute idiopathic blind spot enlargement (AIBSE), acute zonal occult outer retinopathy (AZOOR), acute macular neuroretinopathy (AMN), multiple evanescent white dot syndrome (MEWDS), multifocal choroiditis, opticneuropathy. Further causes of photoreceptor damage that can be treated with the compounds and compositions provided herein include retinal detachment, vascular disturbance, eye tumors or extreme light damage.

With respect to cancer, the Wnt pathway is known to be constitutively activated in a variety of cancers including, for example, colon cancer, hepatocellular carcinoma, lung cancer, ovarian cancer, prostate cancer, pancreatic cancer and leukemias such as CML, CLL and T-ALL. Accordingly, the compounds and compositions described herein may be used to treat these cancers in which the Wnt pathway is constitutively activated. In certain embodiments, the cancer is chosen from hepatocellular carcinoma, colon cancer, leukemia, lymphoma, sarcoma and ovarian cancer.

Other cancers can also be treated with the compounds and compositions described herein.

More particularly, cancers that may be treated by the compounds, compositions and methods described herein include, but are not limited to, the following:

1) Breast cancers, including, for example $ER^+$ breast cancer, $ER^-$ breast cancer, $her2^-$ breast cancer, $her2^+$ breast cancer, stromal tumors such as fibroadenomas, phyllodes tumors, and sarcomas, and epithelial tumors such as large duct papillomas; carcinomas of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma; and miscellaneous malignant neoplasms. Further examples of breast cancers can include luminal A, luminal B, basal A, basal B, and triple negative breast cancer, which is estrogen receptor negative ($ER^-$), progesterone receptor negative, and her2 negative ($her2^-$). In some embodiments, the breast cancer may have a high risk Oncotype score.

2) Cardiac cancers, including, for example sarcoma, e.g., angiosarcoma, fibrosarcoma, rhabdomyosarcoma, and liposarcoma; myxoma; rhabdomyoma; fibroma; lipoma and teratoma.

3) Lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma.

4) Gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma.

5) Genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma.

6) Liver cancers, including, for example, hepatoma, e.g., hepatocellular carcinoma; cholangiocarcinoma; hepatoblastoma; angiosarcoma; hepatocellular adenoma; and hemangioma.

7) Bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors.

8) Nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma.

9) Gynecological cancers, including, for example, cancers of the uterus, e.g., endometrial carcinoma; cancers of the cervix, e.g., cervical carcinoma, and pre tumor cervical dysplasia; cancers of the ovaries, e.g., ovarian carcinoma, including serous cystadenocarcinoma, mucinous cystadenocarcinoma, unclassified carcinoma, granulosa theca cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma.

10) Hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non-Hodgkin's lymphoma (malignant lymphoma) and Waldenström's macroglobulinemia.

11) Skin cancers and skin disorders, including, for example, malignant melanoma and metastatic melanoma, basal cell carcinoma, squamous cell carcinoma, Kaposi's sarcoma, moles dysplastic nevi, lipoma, angioma, dermatofibroma, keloids, and scleroderma.

12) Adrenal gland cancers, including, for example, neuroblastoma.

Cancers may be solid tumors that may or may not be metastatic. Cancers may also occur, as in leukemia, as a diffuse tissue. Thus, the term "tumor cell," as provided herein, includes a cell afflicted by any one of the above identified disorders.

A method of treating cancer using a compound or composition as described herein may be combined with existing methods of treating cancers, for example by chemotherapy, irradiation, or surgery (e.g., oophorectomy). In some embodiments, a compound or composition can be administered before, during, or after another anticancer agent or treatment.

The compounds and compositions described herein can be used as anti-angiogenesis agents and as agents for modulating and/or inhibiting the activity of protein kinases, thus providing treatments for cancer and other diseases associated with cellular proliferation mediated by protein kinases. For example, the compounds described herein can inhibit the activity of one or more kinases. Accordingly, provided herein is a method of treating cancer or preventing or reducing angiogenesis through kinase inhibition.

In addition, and including treatment of cancer, the compounds and compositions described herein can function as cell-cycle control agents for treating proliferative disorders in a patient. Disorders associated with excessive proliferation include, for example, cancers, scleroderma, immunological disorders involving undesired proliferation of leukocytes, and restenosis and other smooth muscle disorders. Furthermore, such compounds may be used to prevent de-differentiation of post-mitotic tissue and/or cells.

Diseases or disorders associated with uncontrolled or abnormal cellular proliferation include, but are not limited to, the following:

a variety of cancers, including, but not limited to, carcinoma, hematopoietic tumors of lymphoid lineage, hematopoietic tumors of myeloid lineage, tumors of mesenchymal origin, tumors of the central and peripheral nervous system and other tumors including melanoma, seminoma and Kaposi's sarcoma.

a disease process which features abnormal cellular proliferation, e.g., benign prostatic hyperplasia, familial adenomatosis polyposis, neurofibromatosis, atherosclerosis, arthritis, glomerulonephritis, restenosis following angioplasty or vascular surgery, inflammatory bowel disease, transplantation rejection, endotoxic shock, and fungal infections. Fibrotic disorders such as skin fibrosis; scleroderma; progressive systemic fibrosis; lung fibrosis; muscle fibrosis; kidney fibrosis; glomerulosclerosis; glomerulonephritis; hypertrophic scar formation; uterine fibrosis; renal fibrosis; cirrhosis of the liver, liver fibrosis; fatty liver disease (FLD); adhesions, such as those occurring in the abdomen, pelvis, spine or tendons; chronic obstructive pulmonary disease; fibrosis following myocardial infarction; pulmonary fibrosis; fibrosis and scarring associated with diffuse/interstitial lung disease; central nervous system fibrosis, such as fibrosis following stroke; fibrosis associated with neuro-degenerative disorders such as Alzheimer's Disease or multiple sclerosis; fibrosis associated with proliferative vitreoretinopathy (PVR); restenosis; endometriosis; ischemic disease and radiation fibrosis.

defective apoptosis-associated conditions, such as cancers (including but not limited to those types mentioned herein), viral infections (including but not limited to herpesvirus, poxvirus, Epstein-Barr virus, Sindbis virus and adenovirus), prevention of AIDS development in HIV-infected individuals, autoimmune diseases (including but not limited to systemic lupus erythematosus, rheumatoid arthritis, sepsis, ankylosing spondylitis, psoriasis, scleroderma, autoimmune mediated glomerulonephritis, inflammatory bowel disease and autoimmune diabetes mellitus), neuro-degenerative disorders (including but not limited to Alzheimer's disease, lung disease, amyotrophic lateral sclerosis, retinitis pigmentosa, Parkinson's disease, AIDS-related dementia, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis), tendinopathies such as tendinitis and tendinosis, aspirin-sensitive rhinosinusitis, cystic fibrosis, multiple sclerosis, kidney diseases and cancer pain.

genetic diseases due to mutations in Wnt signaling components, such as polyposis coli, bone density and vascular defects in the eye (Osteoporosis-pseudoglioma Syndrome, OPPG) and other eye diseases or syndromes associated with defects and/or damaged photoreceptors, familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman's syndrome, Prader-Willi syndrome, Beckwith-Wiedemann Syndrome, Norrie disease and Rett syndrome.

The compounds and compositions described herein can be used to treat neurological conditions, disorders and/or diseases caused by dysfunction in the Wnt signaling pathway. Non-limiting examples of neurological conditions/disorders/diseases which can be treated with the compounds and compositions provided herein include Alzheimer's disease, aphasia, apraxia, arachnoiditis, ataxia telangiectasia, attention deficit hyperactivity disorder, auditory processing disorder, autism, alcoholism, Bell's palsy, bipolar disorder, brachial plexus injury, Canavan disease, carpal tunnel syndrome, causalgia, central pain syndrome, central pontine myelinolysis, centronuclear myopathy, cephalic disorder, cerebral aneurysm, cerebral arteriosclerosis, cerebral atrophy, cerebral gigantism, cerebral palsy, cerebral vasculitis, cervical spinal stenosis, Charcot-Marie-Tooth disease, Chiari malformation, chronic fatigue syndrome, chronic inflammatory demyelinating polyneuropathy (CIDP), chronic pain, Coffin-Lowry syndrome, complex regional pain syndrome, compression neuropathy, congenital facial diplegia, corticobasal degeneration, cranial arteritis, craniosynostosis, Creutzfeldt-Jakob disease, cumulative trauma disorder, Cushing's syndrome, cytomegalic inclusion body disease (CIBD), Dandy-Walker syndrome, Dawson disease, de Morsier's syndrome, Dejerine-Klumpke palsy, Dejerine-Sottas disease, delayed sleep phase syndrome, dementia, dermatomyositis, developmental dyspraxia, diabetic neuropathy, diffuse sclerosis, Dravet syndrome, dysautonomia, dyscalculia, dysgraphia, dyslexia, dystonia, empty sella syndrome, encephalitis, encephalocele, encephalotrigeminal angiomatosis, encopresis, epilepsy, Erb's palsy, erythromelalgia, essential tremor, Fabry's disease, Fahr's syndrome, familial spastic paralysis, febrile seizure, Fisher syndrome, Friedreich's ataxia, fibromyalgia, Foville's syndrome, Gaucher's disease, Gerstmann's syndrome, giant cell arteritis, giant cell inclusion disease, globoid cell leukodystrophy, gray matter heterotopia, Guillain-Barré syndrome, HTLV-1 associated myelopathy, Hallervorden-Spatz disease, hemifacial spasm, hereditary spastic paraplegia, heredopathia atactica polyneuritiformis, herpes zoster oticus, herpes zoster, Hirayama syndrome, holoprosencephaly, Huntington's disease, hydranencephaly, hydrocephalus, hypercortisolism, hypoxia, immune-mediated encephalomyelitis, inclusion body myositis, incontinentia pigmenti, infantile phytanic acid storage disease, infantile Refsum disease, infantile spasms, inflammatory myopathy, intracranial cyst, intracranial hypertension, Joubert syndrome, Karak syndrome, Kearns-Sayre syndrome, Kennedy disease, Kinsbourne syndrome, Klippel Feil syndrome, Krabbe disease, Kugelberg-Welander disease, kuru, Lafora disease, Lambert-Eaton myasthenic syndrome, Landau-Kleffner syndrome, lateral medullary (Wallenberg) syndrome, Leigh's disease, Lennox-Gastaut syndrome, Lesch-Nyhan syndrome, leukodystrophy, Lewy body dementia, lissencephaly, locked-in syndrome, Lou Gehrig's disease, lumbar disc disease, lumbar spinal stenosis, Lyme disease, Machado-Joseph disease (Spinocerebellar ataxia type 3), macrencephaly, macropsia, megalencephaly, Melkersson-Rosenthal syndrome, Meniere's disease, meningitis, Menkes disease, metachromatic leukodystrophy, microcephaly, micropsia, Miller Fisher syndrome, misophonia, mitochondrial myopathy, Mobius syndrome, monomelic amyotrophy, motor neuron disease, motor skills disorder, Moyamoya disease, mucopolysaccharidoses, multi-infarct dementia, multifocal motor neuropathy, multiple sclerosis, multiple system atrophy, muscular dystrophy, myalgic encephalomyelitis, myasthenia gravis, myeloclastic diffuse sclerosis, myoclonic Encephalopathy of infants, myoclonus, myopathy, myotubular myopathy, myotonia congenital, narcolepsy, neurofibromatosis, neuroleptic malignant syndrome, lupus erythematosus, neuromyotonia, neuronal ceroid lipofuscinosis, Niemann-Pick disease, O'Sullivan-McLeod syndrome, occipital Neuralgia, occult Spinal Dysraphism Sequence, Ohtahara syndrome, olivopontocerebellar atrophy, opsoclonus myoclonus syndrome, optic neuritis, orthostatic hypotension, palinopsia, paresthesia, Parkinson's disease, paramyotonia Congenita, paraneoplastic diseases, paroxysmal attacks, Parry-Romberg syndrome, Pelizaeus-Merzbacher disease, periodic paralyses, peripheral neuropathy, photic sneeze reflex, phytanic acid storage disease, Pick's disease, polymicrogyria (PMG), polymyositis, porencephaly, post-polio syndrome, postherpetic neuralgia (PHN), postural hypotension, Prader-Willi syndrome, primary lateral sclerosis, prion diseases, progressive hemifacial atrophy, progressive multifocal leukoencephalopathy, progressive supranuclear palsy, pseudotumor cerebri, Ramsay Hunt syndrome type I, Ramsay Hunt syndrome type II, Ramsay Hunt syndrome type III, Rasmussen's encephalitis, reflex neurovascular dystrophy, Refsum disease, restless legs syndrome, retrovirus-associated myelopathy, Rett syndrome, Reye's syndrome, rhythmic movement disorder, Romberg syndrome, Saint Vitus dance, Sandhoff disease, schizophrenia, Schilder's disease, schizencephaly, sensory integration dysfunction, septo-optic dysplasia, Shy-Drager syndrome, Sjögren's syndrome, snatiation, Sotos syndrome, spasticity, spina bifida, spinal cord tumors, spinal muscular atrophy, spinocerebellar ataxia, Steele-Richardson-Olszewski syndrome, Stiff-person syndrome, stroke, Sturge-Weber syndrome, subacute sclerosing panencephalitis, subcortical arteriosclerotic encephalopathy, superficial siderosis, Sydenham's chorea, syncope, synesthesia, syringomyelia, tarsal tunnel syndrome, tardive dyskinesia, tardive dysphrenia, Tarlov cyst, Tay-Sachs disease, temporal arteritis, tetanus, tethered spinal cord syndrome, Thomsen disease, thoracic outlet syndrome, tic douloureux, Todd's paralysis, Tourette syndrome, toxic encephalopathy, transient ischemic attack, transmissible spongiform encephalopathies, transverse myelitis, tremor, trigeminal neuralgia, tropical spastic paraparesis, trypanosomiasis, tuberous sclerosis, ubisiosis, Von Hippel-Lindau disease (VHL), Viliuisk Encephalomyelitis (VE), Wallenberg's syndrome, Werdnig, Hoffman disease, west syndrome, Williams syndrome, Wilson's disease and Zellweger syndrome.

The compounds and compositions may also be useful in the inhibition of the development of invasive cancer, tumor angiogenesis and metastasis.

In some embodiments, the disclosure provides a method for treating a disease or disorder associated with aberrant cellular proliferation by administering to a patient in need of such treatment an effective amount of one or more of the compounds of Formula (I), in combination (simultaneously or sequentially) with at least one other agent.

In some embodiments, the disclosure provides a method of treating or ameliorating in a patient a disorder or disease selected from the group consisting of: cancer, pulmonary fibrosis, idiopathic pulmonary fibrosis (IPF), degenerative disc disease, bone/osteoporotic fractures, bone or cartilage disease, and osteoarthritis, the method comprising administering to the patient a therapeutically effective amount of a compound according to claim 1, or a pharmaceutically acceptable salt thereof.

In some embodiments, the pharmaceutical composition comprises a therapeutically effective amount of a compound of Formula (I), or a pharmaceutically acceptable salt thereof, and a pharmaceutically acceptable excipient.

In some embodiments, the method treats a disorder or disease in which aberrant Wnt signaling is implicated in a patient, the method comprises administering to the patient a therapeutically effective amount of a compound of Formula (I), or a pharmaceutically acceptable salt thereof.

In some embodiments, the disorder or disease is cancer.

In some embodiments, the disorder or disease is systemic inflammation.

In some embodiments, the disorder or disease is metastatic melanoma.

In some embodiments, the disorder or disease is fatty liver disease.

In some embodiments, the disorder or disease is liver fibrosis.

In some embodiments, the disorder or disease is tendonitis.

In some embodiments, the disorder or disease is damage to a tendon which would benefit from tendon regeneration.

In some embodiments, the disorder or disease is diabetes.

In some embodiments, the disorder or disease is degenerative disc disease.

In some embodiments, the disorder or disease is osteoarthritis.

In some embodiments, the disorder or disease is diabetic retinopathy.

In some embodiments, the disorder or disease is pulmonary fibrosis.

In some embodiments, the disorder or disease is idiopathic pulmonary fibrosis (IPF).

In some embodiments, the disorder or disease is degenerative disc disease.

In some embodiments, the disorder or disease is rheumatoid arthritis.

In some embodiments, the disorder or disease is scleroderma.

In some embodiments, the disorder or disease is a mycotic or viral infection.

In some embodiments, the disorder or disease is a bone or cartilage disease.

In some embodiments, the disorder or disease is Alzheimer's disease.

In some embodiments, the disorder or disease is osteoarthritis.

In some embodiments, the disorder or disease is lung disease

In some embodiments, the disorder or disease is a genetic disease caused by mutations in Wnt signaling components, wherein the genetic disease is selected from: polyposis coli, osteoporosis-pseudoglioma syndrome, familial exudative vitreoretinopathy, retinal angiogenesis, early coronary disease, tetra-amelia syndrome, Müllerian-duct regression and virilization, SERKAL syndrome, diabetes mellitus type 2, Fuhrmann syndrome, Al-Awadi/Raas-Rothschild/Schinzel phocomelia syndrome, odonto-onycho-dermal dysplasia, obesity, split-hand/foot malformation, caudal duplication syndrome, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease and Rett syndrome.

In some embodiments, the patient is a human.

In some embodiments, the cancer is chosen from: hepatocellular carcinoma, colon cancer, breast cancer, pancreatic cancer, chronic myeloid leukemia (CML), chronic myelomonocytic leukemia, chronic lymphocytic leukemia (CLL), acute myeloid leukemia, acute lymphocytic leukemia, Hodgkin lymphoma, lymphoma, sarcoma and ovarian cancer.

In some embodiments, the cancer is chosen from: lung cancer—non-small cell, lung cancer—small cell, multiple myeloma, nasopharyngeal cancer, neuroblastoma, osteosarcoma, penile cancer, pituitary tumors, prostate cancer, retinoblastoma, rhabdomyosarcoma, salivary gland cancer, skin cancer—basal and squamous cell, skin cancer—melanoma, small intestine cancer, stomach (gastric) cancers, testicular cancer, thymus cancer, thyroid cancer, uterine sarcoma, vaginal cancer, vulvar cancer, laryngeal or hypopharyngeal cancer, kidney cancer, Kaposi sarcoma, gestational trophoblastic disease, gastrointestinal stromal tumor, gastrointestinal carcinoid tumor, gallbladder cancer, eye cancer (melanoma and lymphoma), Ewing tumor, esophagus cancer, endometrial cancer, colorectal cancer, cervical cancer, brain or spinal cord tumor, bone metastasis, bone cancer, bladder cancer, bile duct cancer, anal cancer and adrenal cortical cancer.

In some embodiments, the cancer is hepatocellular carcinoma.

In some embodiments, the cancer is colon cancer.

In some embodiments, the cancer is colorectal cancer.

In some embodiments, the cancer is breast cancer.

In some embodiments, the cancer is pancreatic cancer.

In some embodiments, the cancer is chronic myeloid leukemia (CML).

In some embodiments, the cancer is chronic myelomonocytic leukemia.

In some embodiments, the cancer is chronic lymphocytic leukemia (CLL).

In some embodiments, the cancer is acute myeloid leukemia.

In some embodiments, the cancer is acute lymphocytic leukemia.

In some embodiments, the cancer is Hodgkin lymphoma.

In some embodiments, the cancer is lymphoma.

In some embodiments, the cancer is sarcoma.

In some embodiments, the cancer is ovarian cancer.

In some embodiments, the cancer is lung cancer—non-small cell.

In some embodiments, the cancer is lung cancer—small cell.

In some embodiments, the cancer is multiple myeloma.

In some embodiments, the cancer is nasopharyngeal cancer.

In some embodiments, the cancer is neuroblastoma.

In some embodiments, the cancer is osteosarcoma.

In some embodiments, the cancer is penile cancer.

In some embodiments, the cancer is pituitary tumors.

In some embodiments, the cancer is prostate cancer.

In some embodiments, the cancer is retinoblastoma.

In some embodiments, the cancer is rhabdomyosarcoma.

In some embodiments, the cancer is salivary gland cancer.

In some embodiments, the cancer is skin cancer—basal and squamous cell.

In some embodiments, the cancer is skin cancer—melanoma.

In some embodiments, the cancer is small intestine cancer.

In some embodiments, the cancer is stomach (gastric) cancers.

In some embodiments, the cancer is testicular cancer.

In some embodiments, the cancer is thymus cancer.

In some embodiments, the cancer is thyroid cancer.

In some embodiments, the cancer is uterine sarcoma.

In some embodiments, the cancer is vaginal cancer.

In some embodiments, the cancer is vulvar cancer.

In some embodiments, the cancer is Wilms tumor.

In some embodiments, the cancer is laryngeal or hypopharyngeal cancer.

In some embodiments, the cancer is kidney cancer.

In some embodiments, the cancer is Kaposi sarcoma.

In some embodiments, the cancer is gestational trophoblastic disease.

In some embodiments, the cancer is gastrointestinal stromal tumor.

In some embodiments, the cancer is gastrointestinal carcinoid tumor.

In some embodiments, the cancer is gallbladder cancer.

In some embodiments, the cancer is eye cancer (melanoma and lymphoma).

In some embodiments, the cancer is Ewing tumor.

In some embodiments, the cancer is esophagus cancer.

In some embodiments, the cancer is endometrial cancer.

In some embodiments, the cancer is colorectal cancer.

In some embodiments, the cancer is cervical cancer.

In some embodiments, the cancer is brain or spinal cord tumor.

In some embodiments, the cancer is bone metastasis.

In some embodiments, the cancer is bone cancer.

In some embodiments, the cancer is bladder cancer.

In some embodiments, the cancer is bile duct cancer.

In some embodiments, the cancer is anal cancer.

In some embodiments, the cancer is adrenal cortical cancer.

In some embodiments, the disorder or disease is a neurological condition, disorder or disease, wherein the neurological condition/disorder/disease is selected from: Alzheimer's disease, frontotemporal dementias, dementia with lewy bodies, prion diseases, Parkinson's disease, Huntington's disease, progressive supranuclear palsy, corticobasal degeneration, multiple system atrophy, amyotrophic lateral sclerosis (ALS), inclusion body myositis, autism, degenerative myopathies, diabetic neuropathy, other metabolic neuropathies, endocrine neuropathies, orthostatic hypotension, multiple sclerosis and Charcot-Marie-Tooth disease.

In some embodiments, the compound of Formula (I) inhibits one or more proteins in the Wnt pathway.

In some embodiments, the compound of Formula (I) inhibits signaling induced by one or more Wnt proteins.

In some embodiments, the Wnt proteins are chosen from: WNT1, WNT2, WNT2B, WNT3, WNT3A, WNT4, WNT5A, WNT5B, WNT6, WNT7A, WNT7B, WNT8A, WNT8B, WNT9A, WNT9B, WNT10A, WNT10B, WNT11, and WNT16.

In some embodiments, the method inhibits one or more proteins in the Wnt pathway, the method comprises contacting a cell with an effective amount of a compound of Formula (I).

In some embodiments, the cell is a human cell.

In some embodiments, the human cell is a cancerous cell.

In some embodiments, the cancerous cell is a colon cancer cell.

In some embodiments, the contacting is in vitro.

In some embodiments, the compound of Formula (I) inhibits a kinase activity.

In some embodiments, the method treats a disease or disorder mediated by the Wnt pathway in a patient, the method comprises administering to the patient a therapeutically effective amount of a compound (or compounds) of Formula (I), or a pharmaceutically acceptable salt thereof.

In some embodiments, the compound of Formula (I) inhibits one or more Wnt proteins.

In some embodiments, the method treats a disease or disorder mediated by kinase activity in a patient, the method comprises administering to the patient a therapeutically effective amount of a compound (or compounds) of Formula (I), or a pharmaceutically acceptable salt thereof.

In some embodiments, the disease or disorder comprises tumor growth, cell proliferation, or angiogenesis.

In some embodiments, the method inhibits the activity of a protein kinase receptor, the method comprises contacting the receptor with an effective amount of a compound (or compounds) of Formula (I), or a pharmaceutically acceptable salt thereof.

In some embodiments, the method treats a disease or disorder associated with aberrant cellular proliferation in a patient; the method comprises administering to the patient a therapeutically effective amount of a compound (or compounds) of Formula (I), or a pharmaceutically acceptable salt thereof.

In some embodiments, the method prevents or reduces angiogenesis in a patient; the method comprises administering to the patient a therapeutically effective amount of a compound (or compounds) of Formula (I), or a pharmaceutically acceptable salt thereof.

In some embodiments, the method prevents or reduces abnormal cellular proliferation in a patient; the method comprises administering to the patient a therapeutically effective amount of a compound (or compounds) of Formula (I), or a pharmaceutically acceptable salt thereof.

In some embodiments, the method treats a disease or disorder associated with aberrant cellular proliferation in a patient, the method comprises administering to the patient a pharmaceutical composition comprising one or more of the compounds of claim 1 in combination with a pharmaceutically acceptable carrier and one or more other agents.

Moreover, the compounds and compositions, for example, as inhibitors of the cyclin-dependent kinases (CDKs), can modulate the level of cellular RNA and DNA synthesis and therefore are expected to be useful in the treatment of viral infections such as HIV, human papilloma virus, herpes virus, Epstein-Barr virus, adenovirus, Sindbis virus, pox virus and the like.

Compounds and compositions described herein can inhibit the kinase activity of, for example, CDK/cyclin complexes, such as those active in the $G_0$- or $G_{-1}$ stage of the cell cycle, e.g., CDK2, CDK4, and/or CDK6 complexes.

Evaluation of Biological Activity

The biological activity of the compounds described herein can be tested using any suitable assay known to those of skill in the art, see, e.g., WO 2001/053268 and WO 2005/009997. For example, the activity of a compound may be tested using one or more of the test methods outlined below.

In one example, tumor cells may be screened for Wnt independent growth. In such a method, tumor cells of interest are contacted with a compound (i.e. inhibitor) of interest, and the proliferation of the cells, e.g. by uptake of tritiated thymidine, is monitored. In some embodiments, tumor cells may be isolated from a candidate patient who has been screened for the presence of a cancer that is associated with a mutation in the Wnt signaling pathway. Candidate cancers include, without limitation, those listed above.

In another example, one may utilize in vitro assays for Wnt biological activity, e.g. stabilization of β-catenin and promoting growth of stem cells. Assays for biological activity of Wnt include stabilization of β-catenin, which can be measured, for example, by serial dilutions of a candidate inhibitor composition. An exemplary assay for Wnt biological activity contacts a candidate inhibitor with cells containing constitutively active Wnt/β-catenin signaling. The cells are cultured for a period of time sufficient to stabilize β-catenin, usually at least about 1 hour, and lysed. The cell lysate is resolved by SDS PAGE, then transferred to nitrocellulose and probed with antibodies specific for β-catenin.

In a further example, the activity of a candidate compound can be measured in a Xenopus secondary axis bioassay (Leyns, L. et al. *Cell* (1997), 88(6), 747-756).

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples.

EXAMPLES

Compound Preparation

The starting materials used in preparing the compounds of the invention are known, made by known methods, or are commercially available. It will be apparent to the skilled artisan that methods for preparing precursors and functionality related to the compounds claimed herein are generally described in the literature. The skilled artisan given the literature and this disclosure is well equipped to prepare any of the compounds.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification and saponification and the like. These manipulations are discussed in standard texts such as *March's Advanced Organic Chemistry: Reactions, Mechanisms, and Structure* 7$^{th}$ Ed., John Wiley & Sons (2013), Carey and Sundberg, *Advanced Organic Chemistry* 5$^{th}$ Ed., Springer (2007), *Comprehensive Organic Transformations: A Guide to Functional Group Transformations*, 2$^{nd}$ Ed., John Wiley & Sons (1999) (incorporated herein by reference in its entirety) and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts *Protective Groups in Organic Synthesis*, 4th Ed., John Wiley & Sons (2007), incorporated herein by reference in its entirety.

Trademarks used herein are examples only and reflect illustrative materials used at the time of the invention. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the invention.

($^1$H) nuclear magnetic resonance spectra (NMR) were measured in the indicated solvents on a Bruker NMR spectrometer (Avance™ DRX300, 300 MHz for $^1$H or Avance™ DRX500, 500 MHz for $^1$H) or Varian NMR spectrometer (Mercury 400BB, 400 MHz for $^1$H). Peak positions are expressed in parts per million (ppm) downfield from tetramethylsilane. The peak multiplicities are denoted as follows, s, singlet; d, doublet; t, triplet; q, quartet; ABq, AB quartet; quin, quintet; sex, sextet; sep, septet; non, nonet; dd, doublet of doublets; ddd, doublet of doublets of doublets; d/ABq, doublet of AB quartet; dt, doublet of triplets; td, triplet of doublets; dq, doublet of quartets; m, multiplet.

The following abbreviations have the indicated meanings:
BH$_3$-Me$_2$S=borane dimethyl sulfide complex
(Boc)$_2$O=di-tert-butyl dicarbonate
brine=saturated aqueous sodium chloride
CDCl$_3$=deuterated chloroform
CD$_3$OD=deuterated methanol
DCAD=di-(4-chlorobenzyl)azodicarboxylate
DCE=dichloroethane
DCM=dichloromethane
DEAD=diethyl azodicarboxylate
DHP=dihydropyran
DMAP=4-dimethylaminopyridine
DMF=N,N-dimethylformamide
DMSO-d$_6$=deuterated dimethylsulfoxide
ESIMS=electron spray mass spectrometry
EtOAc=ethyl acetate
EtOH=ethanol
HCl=hydrochloric acid
HOAc=acetic acid
K$_2$CO$_3$=potassium carbonate
KOAc=potassium acetate
LDA=lithium diisopropylamide
LC/MS=liquid chromatography-mass spectrometry
MeOH=methanol
MgSO$_4$=magnesium sulfate
MsCl=methanesulfonyl chloride or mesyl chloride
MW=microwave
NaBH$_4$=sodium borohydride
NaBH(OAc)$_3$=sodium triacetoxyborohydride
NaCNBH$_3$=sodium cyanoborohydride
NaHCO$_3$=sodium bicarbonate
NaOH=sodium hydroxide
Na$_2$S$_2$O$_5$=sodium metabisulfite or sodium pyrosulfite
NH$_4$OH=ammonium hydroxide
NMR=nuclear magnetic resonance
ON=overnight
Pd/C=palladium(0) on carbon
Pd(dppf)Cl$_2$=1,1'-bis(diphenylphosphino)ferrocene]palladium(II) chloride
Pd(PPh$_3$)$_4$=tetrakis(triphenylphosphine)palladium(0)
Pd(PPh$_3$)$_2$Cl$_2$=bis(triphenylphosphine)palladium(II) dichloride
PE=petroleum ether
Pin$_2$B$_2$=bis(pinacolato)diboron
PPh$_3$=triphenylphosphine
PPTS=pyridinium p-toluenesulfonate
r.t.=room temperature
SEM-Cl=2-(trimethylsilyl)ethoxymethyl chloride
TEA=triethylamine
TFA=trifluoroacetic acid
THF=tetrahydrofuran
THP=tetrahydropyran
TLC=thin layer chromatography
p-TsOH=p-toluenesulfonic acid The following example schemes are provided for the guidance of the reader, and collectively represent an example method for making the compounds provided herein. Furthermore, other methods for preparing compounds of the invention will be readily apparent to the person of ordinary skill in the art in light of the following reaction schemes and examples. The skilled artisan is thoroughly equipped to prepare these compounds by those methods given the literature and this disclosure. The compound numberings used in the synthetic schemes depicted below are meant for those specific schemes only, and should not be construed as or confused with same numberings in other sections of the application. Unless otherwise indicated, all variables are as defined above.

General Procedure

Compounds of Formula (I) of the present invention can be prepared as depicted in Scheme 1.

Scheme 1 describes the method for preparation of 1H-pyrazolo[3,4-b]pyridine derivatives (VIII) by reacting 5-bromo-1-(tetrahydro-2H-pyran-2-yl)-1H-pyrazolo[3,4-b]pyridine-3-carbaldehyde (II) with bis(pinacolato)diboron to form the borate ester (III). Suzuki coupling with various halides (IV) yields 1H-pyrazolo[3,4-b]pyridine derivatives (V). Aldehyde (V) is reacted with various 1,2-diamines (VI) to produce (VII). Final deprotection of the pyrazole nitrogen yields the desired 1H-pyrazolo[3,4-b]pyridine derivatives (VIII).

Illustrative Compound Examples

Synthesis of intermediate 5-bromo-1-(tetrahydro-2H-pyran-2-yl)-1H-pyrazolo[3,4-b]pyridine-3-carbaldehyde (XIX) is depicted below in Scheme 2.

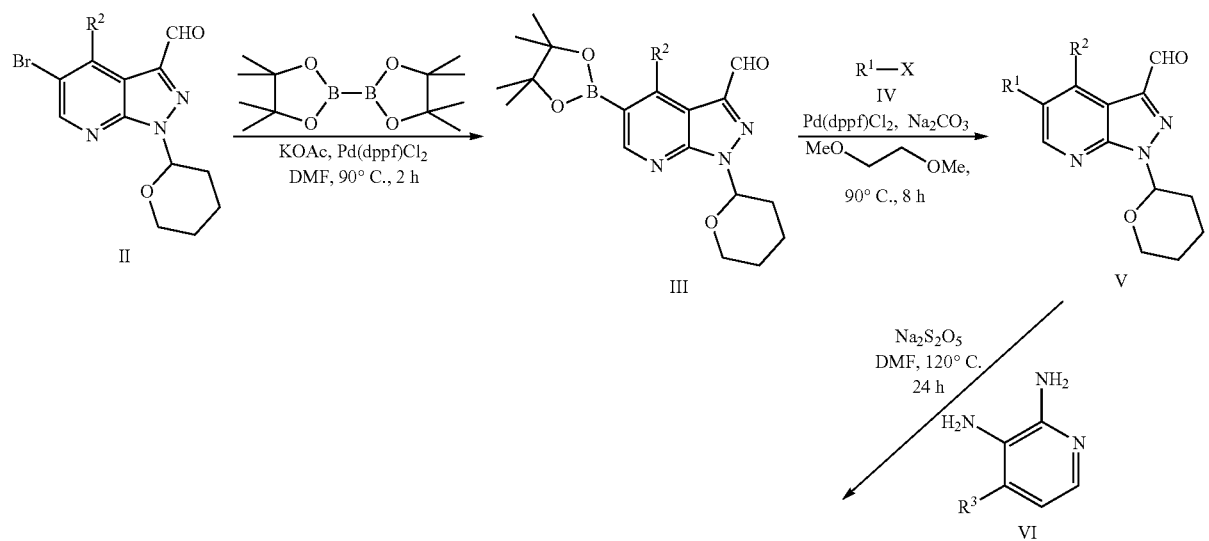

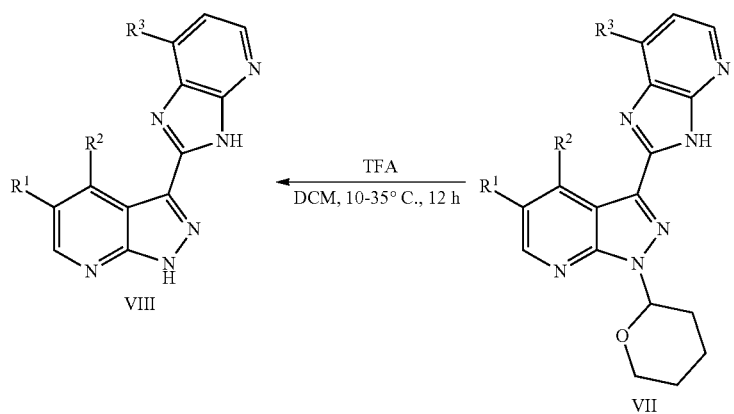

Scheme 2

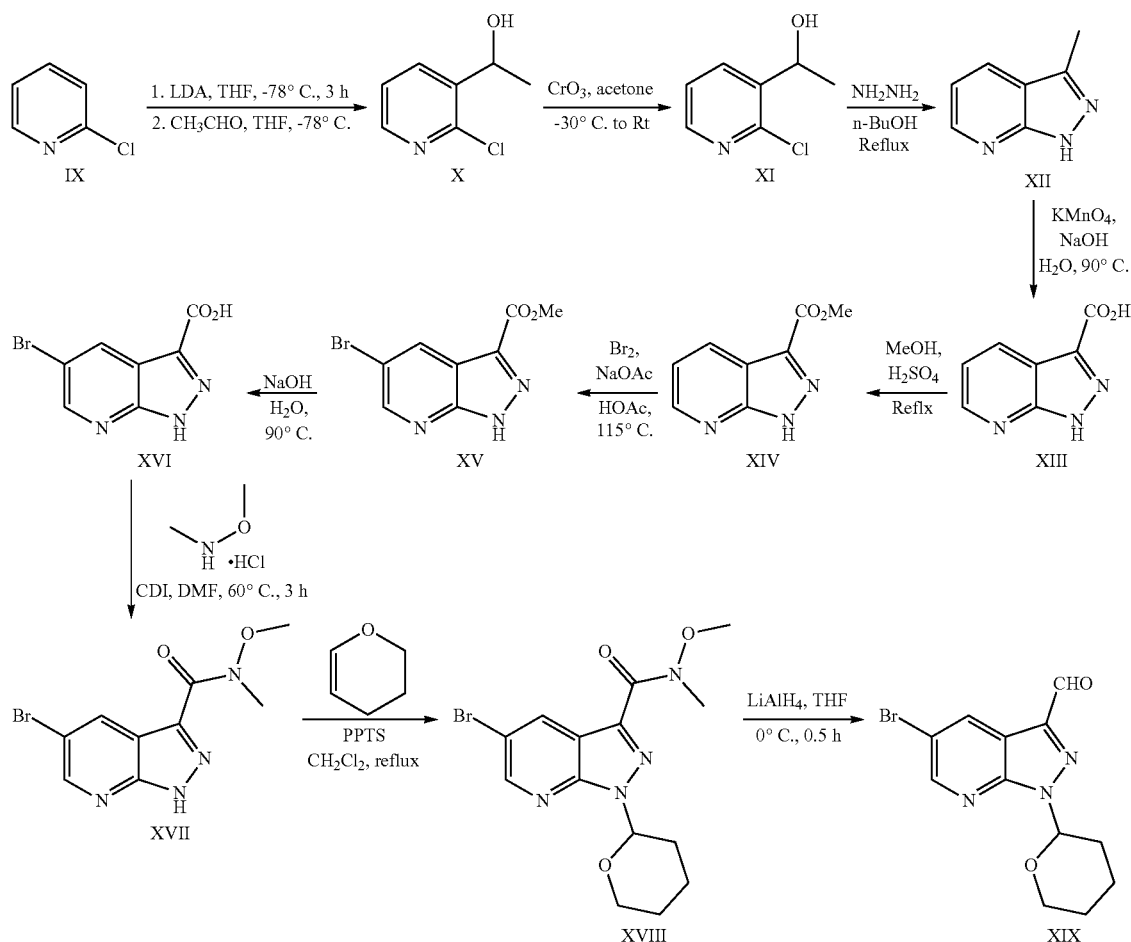

Step 1

A solution of 2-chloropyridine (IX) (9.39 mL, 0.1 mol) in anhydrous THF (50 mL) was added slowly to a solution of LDA (2.0 M solution in THF/hexane/ethylbenzene, 50 mL, 0.1 mol) in THF (200 mL) stirred at −78° C. under nitrogen. The stirring was continued at −78° C. for an additional 3 h before adding acetaldehyde (6.17 mL, 0.110 mol). The solution was stirred at −78° C. for another 2 h before allowing the temperature to rise to −40° C. A solution of water (4 mL) in THF (40 mL) was added slowly to the solution. When the temperature reached −10° C., additional water (200 mL) was added to the solution. The solution was extracted with ethyl ether (3×100 mL). The combined organic phase was dried over MgSO$_4$, filtered and evaporated under reduced pressure to get a brown viscous residue. The crude product was purified on a flash silica gel column (1:1 DCM:hexane→100% DCM) to produce 1-(2-chloropyridin-3-yl)ethanol (X) as a brown viscous oil (6 g, 38.1 mmol, 38% yield). $^1$H NMR (CDCl$_3$) δ ppm 1.52 (d, J=6.41 Hz, 3H), 2.51 (brs, 1H), 5.24 (m, 1H), 7.28 (m, 1H), 7.97 (dd, J=7.72 Hz, J=1.70 Hz, 1H), 8.27 (dd, J=7.72 Hz, J=1.79 Hz, 1H).

Step 2

To a solution of 1-(2-chloropyridin-3-yl)ethanol (X) in dry acetone at −30° C. under nitrogen was added in portions chromium (VI) oxide (1.80 g, 18 mmol). The solution was further stirred 15 min at −30° C. and allowed to warm to room temperature. The solution was stirred for 3 h at room temperature before adding isopropanol (10 mL). The solution was made alkaline by slowly adding a saturated aqueous NaHCO$_3$ solution. The solution was filtered through a bed of Celite. The solids were washed by DCM. The organic phase of the filtrate was separated and the aqueous phase extracted with DCM (2×50 mL). The combined organic layers were dried over MgSO$_4$, filtered and concentrated under reduced pressure to yield 1-(2-chloropyridin-3-yl)ethanone (XI) as a brown liquid (0.72 g, 4.63 mmol, 77% yield). $^1$H NMR (CDCl$_3$) δ ppm 2.71 (s, 3H), 7.35 (dd, J=7.63 Hz, J=4.80 Hz, 1H), 7.91 (dd, J=7.54 Hz, J=1.88 Hz, 1H), 8.55 (dd, J=4.71 Hz, J=1.88 Hz, 1H).

Step 3

To a solution of 1-(2-chloropyridin-3-yl)ethanone (XI) (0.311 g, 2 mmol) in n-butanol (10 mL) was added hydrazine hydrate (1.45 mL, 30 mmol). The reaction was refluxed overnight. The solution was cooled and the solvent was evaporated under vacuum. The residue was dissolved in DCM and washed successively by water and brine. The organic layers were dried over MgSO$_4$, filtered and concentrated under reduced pressure to give 3-methyl-1H-pyrazolo [3,4-b]pyridine (XII) as a white solid (192 mg, 1.44 mmol, 72% yield). $^1$H NMR (CDCl$_3$) δ ppm 2.64 (s, 3H), 7.14 (dd, J=8.01 Hz, J=4.62 Hz, 1H), 8.14 (dd, J=7.54 Hz, J=1.88 Hz, 1H), 8.59 (dd, J=4.52 Hz, J=1.32 Hz, 1H), 11.68 (brs, 1H).

Step 4

To a solution of NaOH (0.88 g, 22 mmol) in water (20 mL) was added 3-methyl-1H-pyrazolo[3,4-b]pyridine (XII) (0.4 g, 3 mmol). The suspension was heated at 80° C. until a clear solution was obtained. A solution of KMnO₄ (1.73 g, 11 mmol) in water (180 mL) was added slowly over 2 h while heating the solution at 80° C. The solution was heated at 90° C. for an additional 2 h until the complete disappearance of starting material was observed by TLC. The solution was cooled to 70° C. and filtered through a pad of Celite. The solids were washed by boiling water. The combined filtrate was cooled to 0° C., acidified with conc. H₂SO₄ to pH=2 and extracted with n-butanol (2×10 mL). The n-butanol layer was concentrated under reduced pressure to get a white residue which was dissolved in DCM by adding minimum amount of MeOH and then filtered. The filtrate was concentrated to give 1H-pyrazolo[3,4-b]pyridine-3-carboxylic acid (XIII) as a white solid (390 mg, 2.39 mmol, 81% yield). $^1$H NMR (CDCl₃) δ ppm 7.37 (dd, J=8.10 Hz, J=4.52 Hz, 1H), 8.47 (dd, J=7.54 Hz, J=1.88 Hz, 1H), 8.62 (dd, J=4.52 Hz, J=1.32 Hz, 1H), 14.37 (brs, 1H).

Step 5

To a solution of 1H-pyrazole[3,4-b]pyridine-3-carboxylic acid (XIII) (0.39 g, 2.4 mmol) in dry MeOH (10 mL) was added concentrated H₂SO₄ (4 drops) and refluxed for 6 h under nitrogen. The solution was cooled and the solvent was evaporated under vacuum. The residue was partitioned between DCM and saturated aqueous NaHCO₃ solution. The organic layer was separated, dried over MgSO₄, filtered and concentrated under reduced pressure. The crude product was purified on a flash silica gel column (100% DCM→3:97 MeOH:DCM) to produce methyl 1H-pyrazolo[3,4-b]pyridine-3-carboxylate (XIV) as a white solid (382 mg, 2.16 mmol, 90% yield). $^1$H NMR (CDCl₃) δ ppm 4.08 (s, 3H), 7.38 (m, 1H), 8.63 (dd, J=8.10 Hz, J=1.51 Hz, 1H), 8.72 (dd, J=4.62 Hz, J=1.41 Hz, 1H); ESIMS found for C₈H₇N₃O₂ m/z 178.2 (M+H).

Step 6

A mixture of methyl 1H-pyrazolo[3,4-b]pyridine-3-carboxylate (XIV) (0.177 g, 1 mmol), sodium acetate (0.492 g, 6 mmol) and bromine (0.308 mL, 6 mmol) in glacial acetic acid (5 mL) was heated overnight at 120° C. in a sealed tube. The solution was cooled and poured into water. The solids formed were filtered, washed with water and dried at room temperature under vacuum. The crude product was purified on a flash silica gel column (100% DCM→2:98 MeOH:DCM) to produce methyl 5-bromo-1H-pyrazolo[3,4-b]pyridine-3-carboxylate (XV) as a white solid (78 mg, 0.31 mmol, 30% yield). $^1$H NMR (CDCl₃) δ ppm 3.95 (s, 3H), 8.62 (d, J=3.01 Hz, 1H), 8.73 (d, J=3.01 Hz, 1H); ESIMS found for C₈H₆BrN₃O₂ m/z 256.3 (M+H).

Step 7

A suspension of methyl 5-bromo-1H-pyrazolo[3,4-b]pyridine-3-carboxylate (XV) (70 mg, 0.27 mmol) in aqueous 1N NaOH solution (20 mL) was heated at 90° C. for 3 h until the solution became clear. The solution was then cooled to 0° C. and acidified with a 10% HCl solution. The solids formed were filtered, washed with cold water and dried at room temperature under vacuum to give 5-bromo-1H-pyrazolo[3,4-b]pyridine-3-carboxylic acid (XVI) as a white solid (60 mg, 0.25 mmol, 92% yield). $^1$H NMR (CDCl₃) δ ppm 8.58 (d, J=3.01 Hz, 1H), 8.66 (d, J=3.01 Hz, 1H); ESIMS found for C₇H₄BrN₃O₂ m/z 242.1 (M+H).

Step 8

To a solution of 5-bromo-1H-pyrazole[3,4-b]pyridine-3-carboxylic acid (XVI) (0.242 g, 1 mmol) in dry DMF (5 mL) was added CDI (0.178 g, 1.1 mmol) and heated for 3 h at 65° C. under nitrogen. The solution was cooled to room temperature and N,O-dimethyl hydroxylamine hydrochloride (0.107 g, 1.1 mmol) was added to the solution. The solution was again heated for 3 h at 65° C. under nitrogen. The solution was cooled and the solvent was evaporated under reduced pressure. The residue was dissolved in DCM, washed successively with a 10% HCl solution, a saturated aqueous NaHCO₃ solution and brine. The organic phase was dried over MgSO₄, filtered and concentrated under reduced pressure to produce 5-bromo-N-methoxy-N-methyl-1H-pyrazolo[3,4-b]pyridine-3-carboxamide (XVII) as a white solid (260 mg, 0.91 mmol, 92% yield). $^1$H NMR (CDCl₃) δ ppm 3.55 (s, 3H), 3.78 (s, 3H), 8.59 (d, J=3.01 Hz, 1H), 8.67 (d, J=3.01 Hz, 1H); ESIMS found for C₉H₉BrN₄O₂ m/z 285.4 (M+H).

Step 9

To a solution of 5-bromo-N-methoxy-N-methyl-1H-pyrazolo[3,4-b]pyridine-3-carboxamide (XVII) (0.250 g, 0.88 mmol) in dry DCM (10 mL) was added 3,4-dihydro-2H-pyran (0.179 mL, 1.98 mmol) and PPTS (22 mg, 0.08 mmol) and refluxed 5 h under nitrogen. Another equivalent of 3,4-dihydro-2H-pyran (0.179 mL, 1.98 mmol) and PPTS (22 mg, 0.08 mmol) was added and the solution was further heated at refluxed overnight under nitrogen. The solution was cooled, diluted with DCM, washed subsequently with a saturated aqueous NaHCO₃ solution and brine. The organic layer was dried over MgSO₄, filtered and concentrated under reduced pressure to give 5-bromo-N-methoxy-N-methyl-1-(tetrahydro-2H-pyran-2-yl)-1H-pyrazolo[3,4-b]pyridine-3-carboxamide (XVIII) as a viscous liquid (302 mg, 0.82 mmol, 93% yield). $^1$H NMR (CDCl₃) δ ppm 1.51-1.62 (m, 2H), 1.91-2.13 (m, 2H), 2.33-2.44 (m, 2H), 3.40 (s, 3H), 3.66 (m, 1H), 3.75 (s, 3H), 3.87-3.98 (m, 1H), 6.07 (dd, J=10.07 Hz, J=2.52 Hz, 1H), 8.57 (d, J=3.01 Hz, 1H), 8.73 (d, J=3.01 Hz, 1H); ESIMS found for C₁₄H₁₇BrN₄O₃ m/z 369.4 (M+H).

Step 10

To a solution of 5-bromo-N-methoxy-N-methyl-1-(tetrahydro-2H-pyran-2-yl)-1H-pyrazolo[3,4-b]pyridine-3-carboxamide (XVIII) (0.290 g, 0.78) in dry THF (5 mL) stirred at 0° C. under nitrogen was added lithium aluminum hydride (36 mg, 0.94 mmol). The solution was further stirred at 0° C. for 30 min. The reaction was quenched with a 0.4 N NaHSO₄ solution (10 mL). The solution was extracted with DCM (3×15 mL). The combined organic layer was washed subsequently with water and brine. The organic layer was dried over MgSO₄, filtered and concentrated under reduced pressure to produce 1-(tetrahydro-2H-pyran-2-yl)-5-(4,4,5,5-tetramethyl-1,3,2-dioxaborolan-2-yl)-1H-pyrazolo[3,4-b]pyridine-3-carbaldehyde (XIX) as a viscous liquid (218 mg, 0.70 mmol, 91% yield). $^1$H NMR (CDCl₃) δ ppm 1.52-1.74 (m, 2H), 1.95-2.18 (m, 2H), 2.37-2.49 (m, 2H) 3.87-3.98 (m, 1H), 3.99 (m, 1H), 6.18 (dd, J=10.20 Hz, J=2.39 Hz, 1H), 8.73 (d, J=3.01 Hz, 1H), 8.85 (d, J=3.01 Hz, 1H), 10.16 (s, 1H); ESIMS found for C₁₂H₁₂BrN₃O₂ m/z 310.4 (M+H).

Preparation of intermediate N-(5-bromopyridin-3-yl) pivalamide (XXII) is depicted below in Scheme 3.

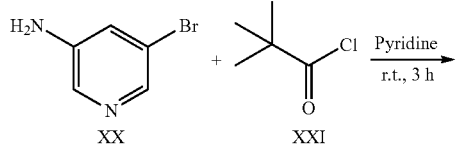

Scheme 3

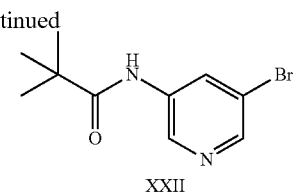

XXII

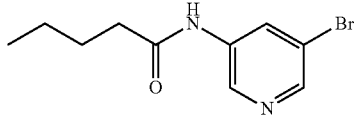

XXVI

Step 1

To a solution of 3-amino-5-bromo pyridine (XX) (1.0 g, 5.78 mmol) in dry pyridine (10 mL) was added pivaloyl chloride (XXI) (769 mg, 6.38 mmol). The reaction mixture was stirred at room temperature for 3 h. The reaction was poured into an ice water/saturated aqueous NaHCO$_3$ mixture and stirred for 30 min. The precipitate was filtered, washed with cold water and dried at room temperature to yield N-(5-bromopyridin-3-yl)pivalamide (XXII) as an off-white solid (1.082 g, 4.22 mmol, 73.1% yield). $^1$H NMR (DMSO-d$_6$, 500 MHz) δ ppm 1.23 (s, 9H), 8.37 (d, J=2 Hz, 1H), 8.39 (t, J=2 Hz, 1H), 8.80 (d, J=2 Hz, 1H), 9.58 (brs, 1H); ESIMS found C$_{10}$H$_{13}$BrN$_2$O m/z 258.9 (Br$^{81}$M+H).

The following intermediates were prepared in accordance with the procedure described in the above Scheme 3.

N-(5-Bromopyridin-3-yl)pentanamide (XXVI): Yellow solid (2.0 g, 7.78 mmol, 85.3% yield). $^1$H NMR (CD$_3$OD, 400 MHz) δ ppm 0.98 (t, J=7.4 Hz, 3H), 1.43 (sxt, J=7.4 Hz, 2H), 1.70 (quin, J=7.4 Hz, 2H), 2.43 (t, J=7.6 Hz, 2H), 8.35 (s, 1H), 8.45 (d, J=2 Hz, 1H), 8.64 (d, J=2 Hz, 1H); ESIMS found C$_{10}$H$_{13}$BrN$_2$O m/z 256.9 (Br$^{79}$M+H).

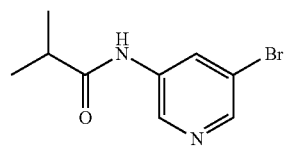

XXIII

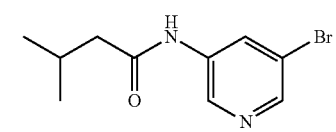

XXVII

N-(5-Bromopyridin-3-yl)isobutyramide (XXIII): Off-white solid, (71% yield). $^1$H NMR (CDCl$_3$) δ ppm 8.55-8.35 (m, 3H), 7.32 (s, 1H), 2.59-2.48 (m, 1H), 1.28-1.27 (d, 6H); ESIMS found C$_9$H$_{11}$BrN$_2$O m/z 242.9 (Br$^{79}$M+H).

N-(5-Bromopyridin-3-yl)-3-methylbutanamide (XXVII): Off white solid, (67% yield), $^1$H NMR (CDCl$_3$, 500 MHz) δ ppm 8.55-8.42 (m, 3H), 7.62 (s, 1H), 2.31-2.18 (m, 3H), 1.02-1.01 (d, J=6 Hz, 6H); ESIMS found C$_{10}$H$_{13}$BrN$_2$O m/z 258.9 (Br$^{81}$M+H).

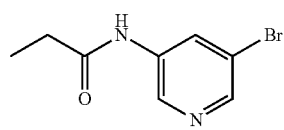

XXIV

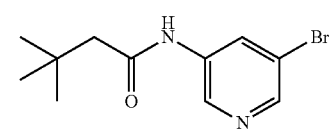

XXVIII

N-(5-Bromopyridin-3-yl)propionamide (XXIV): Off white solid (92% yield). $^1$H NMR (DMSO-d$_6$) δ ppm 1.09 (t, J=7.54 Hz, 3H), 2.36 (q, J=7.54 Hz, 2H), 8.36 (m, 2H), 8.65 (d, J=2.07 Hz, 1H), 10.26 (s, 1H); ESIMS found C$_8$H$_9$BrN$_2$O m/z 231.1 (Br$^{81}$M+H).

N-(5-Bromopyridin-3-yl)-3,3-dimethylbutanamide (XXVIII): Yellow solid (1.7 g, 6.27 mmol, 78.6% yield). $^1$H NMR (CD$_3$OD, 400 MHz) δ ppm 1.10 (s, 9H), 2.29 (s, 2H), 8.36 (d, J=1.6 Hz, 1H), 8.46 (d, J=2.0 Hz, 1H), 8.64 (d, J=2.0 Hz, 1H); ESIMS found C$_{11}$H$_{15}$BrN$_2$O m/z 273.1 ((Br$^{81}$M+H).

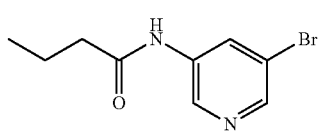

XXV

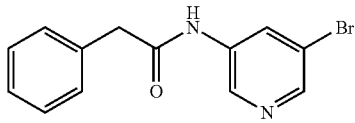

XXIX

N-(5-Bromopyridin-3-yl)butyramide (XXV): Yellow solid (2.1 g, 8.64 mmol, 88.8% yield). $^1$H NMR (CD$_3$OD, 400 MHz) δ ppm 1.02 (t, J=7.2 Hz, 3H), 1.74 (sxt, J=7.2 Hz, 2H), 2.40 (t, J=7.2 Hz, 2H), 8.35 (d, J=2 Hz, 1H), 8.46 (t, J=2 Hz, 1H), 8.63 (d, J=2 Hz, 1H); ESIMS found C$_9$H$_{11}$BrN$_2$O m/z 243.1 (Br$^{79}$M+H).

N-(5-Bromopyridin-3-yl)-2-phenylacetamide (XXIX): White solid (2.5 g, 8.59 mmol, 77.9% yield). $^1$H NMR (CDCl$_3$, 400 MHz) δ ppm 3.76 (s, 2H), 7.26-7.45 (m, 5H), 7.57 (brs, 1H), 8.33 (s, 1H), 8.37 (s, 2H); ESIMS found C$_{13}$H$_{11}$BrN$_2$O m/z 292.8 (Br$^{81}$M+H).

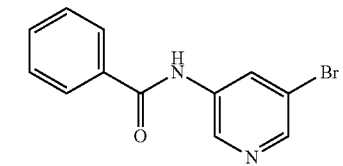

XXX

N-(5-Bromopyridin-3-yl)benzamide (XXX): White solid (2.7 g, 9.74 mmol, 60% yield). $^1$H NMR (CDCl$_3$, 400 MHz) δ ppm 7.40-7.52 (m, 2H), 7.52-7.62 (m, 1H), 7.86 (d, J=7.2 Hz, 2H), 8.39 (d, J=1.6 Hz, 1H), 8.46 (s, 1H), 8.55 (d, J=1.6 Hz, 1H), 8.57 (d, J=2.0 Hz, 1H); ESIMS found C$_{12}$H$_9$BrN$_2$O m/z 278.8 (Br$^{81}$M+H).

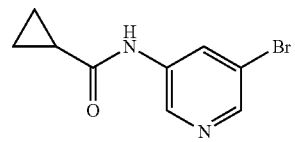

XXXI

N-(5-Bromopyridin-3-yl)cyclopropanecarboxamide (XXXI): Off-white solid, (83% yield), $^1$H NMR (CDCl$_3$, 500 MHz) δ ppm 8.46-8.39 (m, 3H), 7.54 (bs, 1H), 1.56-1.50 (m, 1H), 1.13-1.07 (m, 2H), 0.96-0.90 (m, 2H); ESIMS found for C$_9$H$_9$BrN$_2$O m/z 240.9 (Br$^{79}$M+H).

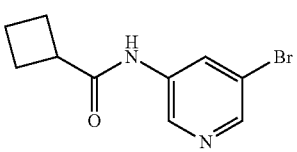

XXXII

N-(5-Bromopyridin-3-yl)cyclobutanecarboxamide (XXXII): Yellow solid (2.1 g, 6.27 mmol, 86.6% yield). $^1$H NMR (CD$_3$OD, 400 MHz) δ ppm 1.80-1.99 (m, 1H), 1.99-2.15 (m, 1H), 2.16-2.30 (m, 2H), 2.30-2.45 (m, 2H), 3.25-3.35 (m, 1H), 8.34 (d, J=2.0 Hz, 1H), 8.47 (s, 1H), 8.64 (d, J=2.0 Hz, 1H); ESIMS found C$_{10}$H$_{11}$BrN$_2$O m/z 257.1 (Br$^{81}$M+H).

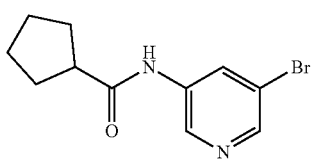

XXXIII

N-(5-Bromopyridin-3-yl)cyclopentanecarboxamide (XXXIII): Yellow solid (1.9 g, 7.06 mmol, 80.2% yield). $^1$H NMR (CD$_3$OD, 400 MHz) δ ppm 1.57-1.74 (m, 2H), 1.74-1.91 (m, 4H), 1.91-2.07 (m, 2H), 2.77-2.92 (m, 1H), 8.34 (d, J=1.6 Hz, 1H), 8.45 (s, 1H), 8.65 (d, J=2.0 Hz, 1H); ESIMS found C$_{11}$H$_{13}$BrN$_2$O m/z 271.1 (Br$^{81}$M+H).

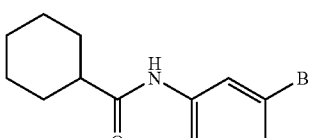

XXXIV

N-(5-Bromopyridin-3-yl)cyclohexanecarboxamide (XXXIV): Yellow solid (2.0 g, 7.06 mmol, 84.3% yield). $^1$H NMR (CD$_3$OD, 400 MHz) δ ppm 1.19-1.46 (m, 3H), 1.46-1.63 (m, 2H), 1.74 (d, J=11.6 Hz, 1H), 1.88 (t, J=14.0 Hz, 4H), 2.40 (tt, J=11.6 Hz, J=3.6 Hz, 1H), 8.34 (d, J=2.0 Hz, 1H), 8.44 (t, J=2.0 Hz, 1H), 8.64 (d, J=2.0 Hz, 1H); ESIMS found C$_{12}$H$_{15}$BrN$_2$O m/z 285.1 (Br$^{81}$M+H).

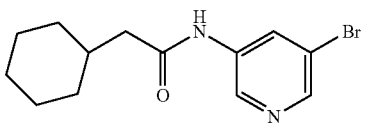

XXXV

N-(5-bromopyridin-3-yl)-2-cyclohexylacetamide (XXXV): Yellow solid (261 mg, 0.878 mmol, 84.4% yield). ESIMS found C$_{13}$H$_{17}$BrN$_2$O m/z 297.1 (Br$^{81}$M+H).

Preparation of intermediate 5-bromo-N,N-dimethylpyridin-3-amine (XXXVII) is depicted below in Scheme 4.

Scheme 4

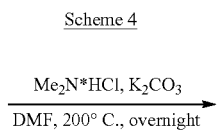

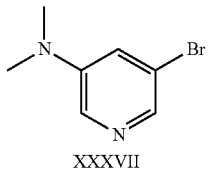

XXXVII

Step 1

To a solution of 3,5-dibromopyridine (XXXVI) (2.37 g, 10.0 mmol) in dry DMF (20.0 mL) was added K$_2$CO$_3$ (4.5 g, 33 mmol) and dimethylamino hydrochloride (1.79 g, 22 mmol). The mixture was heated overnight at 200° C. in a sealed tube. The solution was cooled to room temperature and excess DMF was removed under vacuum. The residue was partitioned between EtOAc and water. The organic phase was separated. The aqueous phase was washed with EtOAc and the combined organic phases were dried over MgSO$_4$, and concentrated to afford 5-bromo-N,N-dimethylpyridin-3-amine (XXXVII) as an off-white solid (1.78 g, 8.85 mmol, 88% yield). $^1$H NMR (DMSO-d$_6$, 500 MHz) δ ppm 2.94 (s, 6H), 7.25 (t, J=2 Hz, 1H), 7.91 (d, J=2 Hz, 1H), 8.07 (d, J=2 Hz, 1H); ESIMS found C$_7$H$_9$BrN$_2$ m/z 201.1 (M+H).

Preparation of intermediate 5-bromo-N-isopropylpyridin-3-amine (XXXVIII) is depicted below in Scheme 5.

Scheme 5

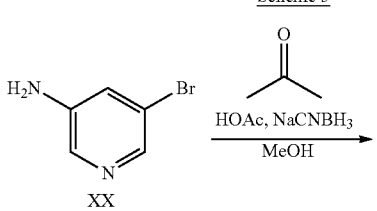

-continued

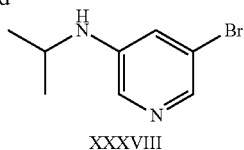

XXXVIII

Step 1

To a solution of 5-bromopyridin-3-amine (XX) (535 mg, 3.09 mmol) in MeOH (62 mL) was added acetone (296 μL, 4.02 mL). The pH was adjusted to 4 using HOAc and stirred for 30 min. NaCNBH$_3$ (272 mg, 4.33 mmol) was added and stirred at room temperature overnight. The MeOH was removed under vacuum and the residue was partitioned between EtOAc and saturated aqueous NaHCO$_3$. The organic layer was dried over MgSO$_4$ and evaporated under vacuum. The crude product was purified on a silica gel column (100% hexane→90:10 hexane:EtOAc) to produce 5-bromo-N-isopropylpyridin-3-amine (XXXVIII) as an oil which slowly solidified into an off-white solid (309 mg, 1.44 mmol, 47% yield). $^1$H NMR (DMSO-d$_6$, 500 MHz) δ ppm 1.12 (d, J=6.3 Hz, 6H), 3.55-3.59 (m, 1H), 6.03 (d, J=7.9 Hz, 1H), 7.05-7.06 (m, 1H), 7.75 (d, J=2 Hz, 1H), 7.90 (d, J=2 Hz, 1H); ESIMS found C$_8$H$_{11}$BrN$_2$ m/z 215.1 (M+H).

Preparation of intermediate 1-(5-bromopyridin-3-yl)-N,N-dimethylmethanamine (XL) is depicted below in Scheme 6.

Scheme 6

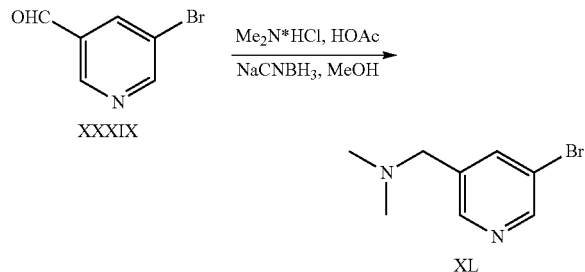

Step 1

Preparation of 1-(5-bromopyridin-3-yl)-N,N-dimethylmethanamine (XL) was performed following the procedure listed in Scheme 5, Step 1. Brown oil (1.20 g, 5.59 mmol, 45% yield). $^1$H NMR (DMSO-d$_6$, 500 MHz) δ ppm 2.15 (s, 6H), 3.43 (s, 2H), 7.94 (s, 1H), 8.47 (d, J=1.1 Hz, 1H), 8.59 (d, J=2.2 Hz, 1H); ESIMS found C$_8$H$_{11}$BrN$_2$ m/z 215 (M$^{Br79}$+H) and 217 (M$^{Br81}$+H).

Preparation of intermediate 3-bromo-5-((3,3-difluoropyrrolidin-1-yl)methyl)pyridine (XLI) is depicted below in Scheme 7.

Scheme 7

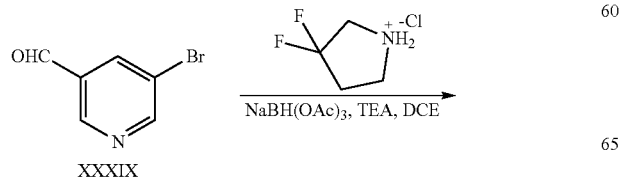

-continued

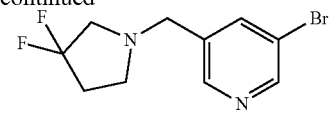

XLI

Step 1

To a mixture of 5-bromopyridine-3-carbaldehyde (XXXIX) (6.00 g, 32.26 mmol, 1.0 eq), 3,3-difluoropyrrolidine (5.56 g, 38.71 mmol, 1.20 eq) and TEA (5.39 mL, 38.71 mmol, 1.2 Eq) in DCE (200 mL) was stirred at room temperature for 30 min, then added sodium triacetoxyborohydride (10.25 g, 48.38 mmol, 1.50 eq) in one portion at room temperature under N$_2$. The mixture was stirred at room temperature for 6 hours. TLC showed the reaction was complete. The reaction was quenched with 1N NaOH (100 mL), extracted with DCE (100 mL×2). The combined organic layers were washed with brine (100 mL), dried and concentrated. The residue was purified by silica gel chromatography (column height: 50 mm, diameter: 50 mm, 300-400 mesh silica gel, DCM/MeOH=30/1→20/1) to give 3-bromo-5-((3,3-difluoropyrrolidin-1-yl)methyl) pyridine (XLI): Yellow oil (8.00 g, 28.9 mmol, 89.5% yield). $^1$H NMR (CDCl$_3$, 400 MHz) δ ppm 2.30 (spt, J=7.2 Hz. 2H), 2.75 (t, J=6.8 Hz, 2H), 2.91 (t, J=13.2 Hz, 2H), 7.85 (s, 1H), 8.45 (s, 1H), 8.59 (d, J=2 Hz, 1H); ESIMS found for C$_{10}$H$_{11}$BrF$_2$N$_2$ m/z 277.0 (M+H).

The following intermediates were prepared in accordance with the procedure described in the above Scheme 6 or Scheme 7.

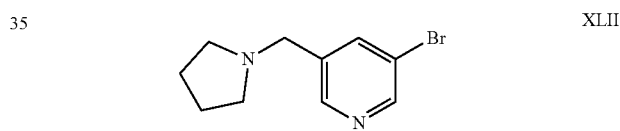

XLII

3-Bromo-5-(pyrrolidin-1-ylmethyl)pyridine (XLII): Golden liquid (1.35 g, 97% yield). $^1$H NMR (DMSO-d$_6$) 1.68-1.71 (m, 4H), 2.42-2.44 (m, 4H), 3.60 (s, 2H), 7.96 (s, 1H), 8.48 (d, J=2 Hz, 1H), 8.58 (d, J=3 Hz, 1H); ESIMS found for C$_{10}$H$_{13}$BrN$_2$ m/z 242.2 (M+H).

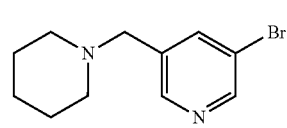

XLIII

3-Bromo-5-(piperidin-1-ylmethyl)pyridine (XLIII): Brown liquid (13.1 g, 94% yield). $^1$H NMR (DMSO-d$_6$) 1.36-1.39 (m, 2H), 1.46-1.51 (m, 4H), 2.31-2.32 (m, 4H), 3.46 (s, 2H), 7.94 (s, 1H), 8.47 (d, J=2 Hz, 1H), 8.58 (d, J=3 Hz, 1H); ESIMS found for C$_{11}$H$_{15}$BrN$_2$ m/z 257.0 (M+H).

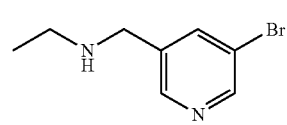

XLIV

N-((5-Bromopyridin-3-yl)methyl)ethanamine (XLIV): Golden liquid (1.29 g, 6.00 mmol, 60% yield). $^1$H NMR (CDCl$_3$, 400 MHz) δ ppm 1.14 (t, J=7.2 Hz, 3H), 2.67 (q, J=7.2 Hz, 2H), 3.79 (s, 2H), 7.85 (t, J=2 Hz, 1H), 8.46 (d, J=1.6 Hz, 1H), 8.56 (d, J=2.4 Hz, 1H); ESIMS found for $C_8H_{11}BrN_2$ m/z 215.1 (M+H).

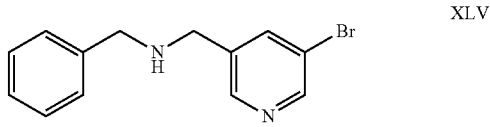 [SMILES: Brc1cncc(CNCc2ccccc2)c1]

XLV

N-Benzyl-1-(5-bromopyridin-3-yl)methanamine (XLV): Yellow oil (8.0 g, 28.9 mmol, 89.5% yield). $^1$H NMR (DMSO-d$_6$, 400 MHz) δ ppm 3.71 (s, 2H), 3.74 (s, 2H), 7.18-7.28 (m, 1H), 7.28-7.40 (m, 4H), 8.04 (s, 1H), 8.52 (s, 1H), 8.58 (s, 1H); ESIMS found for $C_{13}H_{13}BrN_2$ m/z 277.1 (M+H).

Preparation of intermediate tert-butyl (5-bromopyridin-3-yl)methyl (cyclopentylmethyl)carbamate (L) is depicted below in Scheme 8.

anhydrous THF (15 mL) was added DEAD (2.21 g, 12.75 mmol, 1.5 eq) dropwise at 0° C. under N$_2$. Then the reaction mixture was stirred at room temperature for 6 h. The mixture was washed with saturated NaHCO$_3$ solution (15 mL), water (15 mL) and brine (15 mL) subsequently. The organic layers were dried over MgSO$_4$, concentrated under reduced pressure, the resultant residue was purified by flash chromatography on silica gel (PE:EtOAc=4:1) to give 2-((5-bromopyridin-3-yl)methyl)isoindoline-1,3-dione (XLVII) (2.5 g, 7.88 mmol, 82.3% yield) as a white solid. ESIMS found for $C_{14}H_9BrN_2O_2$ m/z 317.1 (M+H).

Step 3

A solution of 2-((5-bromopyridin-3-yl)methyl)isoindoline-1,3-dione (XLVII) (1.9 g, 6.0 mmol, 1 eq) and hydrazine hydrate (2.0 g, 40 mmol, 6 eq) in EtOH (20 mL) was heated at 70° C. for 3 h. The mixture was filtered through a Celite® pad and the filtrate was concentrated in vacuo, the crude product was dissolved in 1N HCl solution (15 mL) and concentrated to dryness, then it was washed with acetone (10 mL×3), the precipitate was collected by filtration, dried in vacuo to give (5-bromopyridin-3-yl)methanamine (XLVIII) (1.3 g, 6.95 mmol, 97.7% yield) as a white solid. $^1$H NMR (D$_2$O, 500 MHz) δ ppm 4.34 (s, 2H), 8.56 (s, 1H), 8.75 (d, Scheme 8

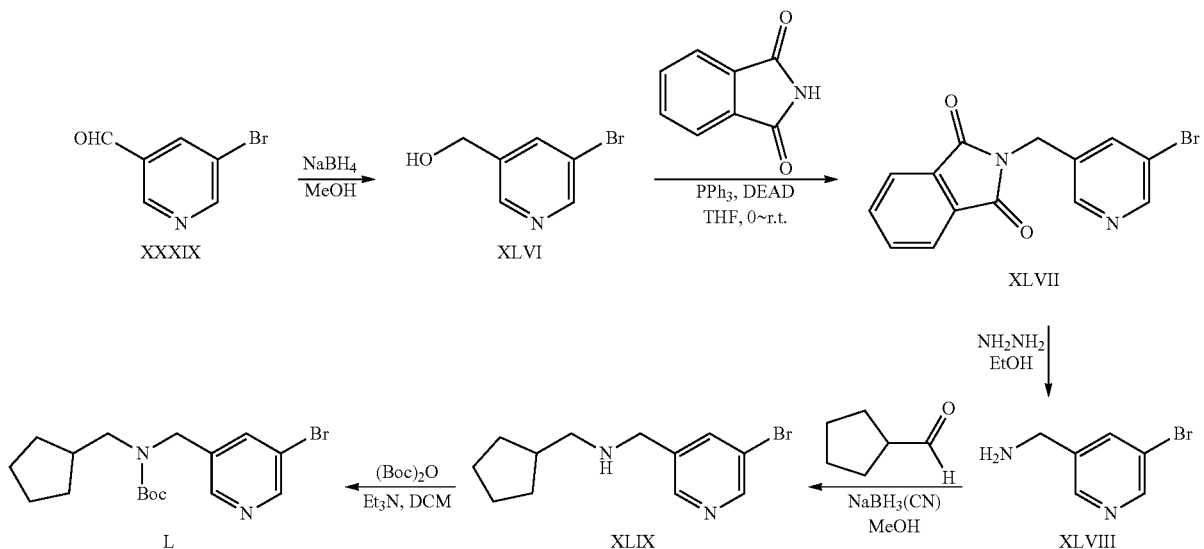

Step 1

To a solution of 5-bromonicotinaldehyde (XXXIX) (2.0 g, 10.8 mmol, 1 eq) in MeOH (20 mL) was added NaBH$_4$ (2.4 g, 64.9 mmol, 6 eq) and the reaction mixture was stirred at room temperature for 3 h. The mixture was concentrated in vacuo and the residue was diluted in water (15 mL), the aqueous phase was extracted with DCM (10 mL×3). The combined organic layers were dried over MgSO$_4$, filtered and concentrated in vacuo to afford (5-bromopyridin-3-yl)methanol (XLVI) (1.8 g, 9.57 mmol, 90.0% yield) as a colorless oil. $^1$H NMR (CDCl$_3$, 500 MHz) δ ppm 4.73 (s, 2H), 7.90 (s, 1H), 8.47 (s, 1H), 8.57 (s, 1H). ESIMS found for $C_6H_6BrNO$ m/z 188.0 (M+H).

Step 2

To a stirred solution of (5-bromopyridin-3-yl)methanol (XLVI) (1.60 g, 8.5 mmol, 1 eq), phthalimide (1.24 g, 8.5 mmol, 1 eq) and PPh$_3$ (3.33 g, 12.75 mmol, 1.5 eq) in J=1.2 Hz, 1H), 8.91 (d, J=1.6 Hz, 1H). ESIMS found for $C_6H_7BrN_2$ m/z 187.0 (M+H).

Step 4

A solution of (5-bromopyridin-3-yl)methanamine (XLVIII) (1.30 g, 5.8 mmol, 1.0 eq), cyclopentanecarbaldehyde (0.57 g, 5.8 mmol, 1.0 eq) and TEA (0.60 g, 5.8 mmol, 1.0 eq) in MeOH (15 mL) was stirred at room temperature for 2 h. Then NaBH$_3$CN (1.98 g, 34.6 mmol, 6.0 eq) was added and the mixture was stirred at the same temperature for another 3 h. The solvent was removed under reduced pressure and the residue was diluted in water (20 mL) and extracted with DCM (10 mL×3), combined organic layers were dried over MgSO$_4$ and concentrated in vacuo to give 1-(5-bromopyridin-3-yl)-N-(cyclopentylmethyl)methanamine (XLIX) (1.23 g, 4.57 mmol, 79.3% yield) as a yellow oil. $^1$H NMR (CDCl$_3$, 400 MHz) δ ppm 1.07-1.23 (m, 2H), 1.47-1.67 (m, 4H), 1.70-1.84 (m, 2H), 2.02 (spt, J=7.6 Hz, 1H), 2.53 (d, J=7.2 Hz, 2H), 3.80 (s, 2H), 7.86 (s, 1H), 8.47 (s, 1H), 8.56 (d, J=2.0 Hz, 1H); ESIMS found for C$_{12}$H$_{17}$BrN$_2$ m/z 269.1 (M+H).

Step 5

To a solution of 1-(5-bromopyridin-3-yl)-N-(cyclopentylmethyl) methanamine (XLIX) (1.00 g, 3.7 mmol, 1 eq) and TEA (0.93 g, 9.2 mmol, 2.5 eq) in DCM (20 mL) was added portionwise (Boc)$_2$O (0.85 g, 4.0 mmol, 1.1 eq) at 0° C., the reaction mixture was stirred at room temperature for 1 h. The mixture was washed with water (10 mL), brine (10 mL), the organic layer was separated, dried over MgSO$_4$ and concentrated in vacuo to give tert-butyl (5-bromopyridin-3-yl) methyl (cyclopentylmethyl) carbamate (L) (1.25 g, 3.38 mmol, 91.9% yield) as a white solid. ESIMS found for C$_{17}$H$_{25}$BrN$_2$O$_2$ m/z 369.1 (M+H).

Preparation of intermediate 3-bromo-5-(cyclohexyloxy)pyridine (LIII) is depicted below in Scheme 9.

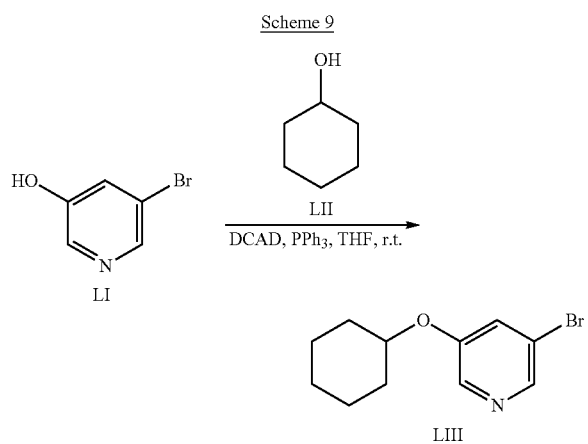

Step 1

To a solution of 5-bromopyridin-3-ol (LI) (523 mg, 3.01 mmol) in THF (30 mL) cooled to 0° C. were added triphenylphosphine (867 mg, 3.31 mmol) and cyclohexanol (LII) (331 mg, 3.31 mmol) followed by (E)-bis(4-chlorobenzyl) diazene-1,2-dicarboxylate (1.21 g, 3.31 mmol), added portionwise. The reaction mixture was then stirred at 25° C. overnight. The reaction was worked-up with a EtOAc—NaHCO$_3$ extraction and the solid filtered off. The solvent was removed and the residue was purified by Isco (20% EtOAc-Hexanes) to give 3-bromo-5-(cyclohexyloxy)pyridine (LIII) (209 mg, 0.82 mmol, 27.2% yield) as a yellow oil. $^1$H NMR (DMSO-d$_6$, 500 MHz) δ ppm 1.21-1.31 (m, 1H) 1.34-1.48 (m, 4H) 1.49-1.57 (m, 1H) 1.70 (br dd, J=9.74, 4.25 Hz, 2H) 1.88-1.96 (m, 2H) 2.50 (dt, J=3.70, 1.72 Hz, 5H) 4.46-4.54 (m, 1H) 7.72 (t, J=2.20 Hz, 1H) 8.24 (d, J=1.92 Hz, 1H) 8.27 (d, J=2.47 Hz, 1H).

The following intermediate was prepared in accordance with the procedure described in the above Scheme 9.

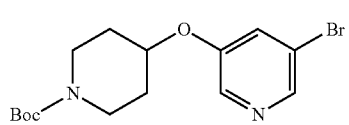

tert-Butyl 4-((5-bromopyridin-3-yl)oxy)piperidine-1-carboxylate (LIV): Yellow oil (244 mg, 0.683 mmol, 23.2% yield). ESIMS found for C$_{15}$H$_{21}$BrN$_2$O$_3$ m/z 358.3 (M+H).

Preparation of intermediate 3-(benzyloxy)-5-bromopyridine (LVI) is depicted below in Scheme 10.

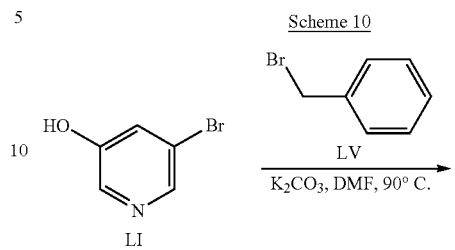

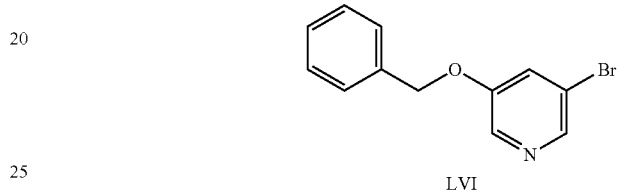

Step 1

To a solution of 5-bromopyridin-3-ol (LI) (174 mg, 1.0 mmol) in DMF (3 mL) was added potassium carbonate (415 mg, 3.0 mmol). The slurry was heated at 90° C. for 1 hour and then cooled to 25° C. The (bromomethyl)benzene (LV) (171 mg, 1.0 mmol) was added and the mixture was stirred at 25° C. overnight. The reaction was worked-up using a saturated sodium bicarbonate and ethyl acetate extraction. The product was purified by ISCO column eluted with 40-100% EtOAc-Hexanes. The 3-(benzyloxy)-5-bromopyridine (LVI) (105 mg, 0.398 mmol, 39.8% yield) was obtained as yellow oil. MS: 266.1. ESIMS found for C$_{12}$H$_{10}$BrNO m/z 266.1 (M+H).

The following intermediates were prepared in accordance with the procedure described in the above Scheme 10.

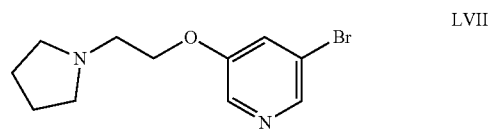 [SMILES: Brc1cncc(OCCN2CCCC2)c1]

3-Bomo-5-(2-(pyrrolidin-1-yl)ethoxy)pyridine (LVII): Yellow oil ((97 mg, 0.358 mmol, 15.56% yield). ESIMS found for C$_{11}$H$_{15}$BrN$_2$O m/z 272.2 (M+H).

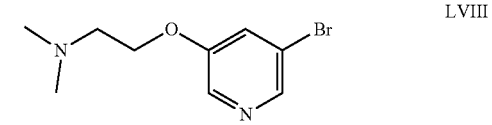

2-((5-bromopyridin-3-yl)oxy)-N,N-dimethylethan-1-amine (LVIII): Yellow oil (97 mg, 0.396 mmol, 28.9% yield). ESIMS found for C$_9$H$_{13}$BrN$_2$O m/z 245.1 (M+H).

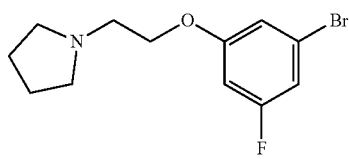

1-(2-(3-bromo-5-fluorophenoxy)ethyl)pyrrolidine (LIX): Yellow oil (370 mg, 1.284 mmol, 85.8% yield). ESIMS found for $C_{12}H_{15}BrFNO$ m/z 289.0 (M+H).

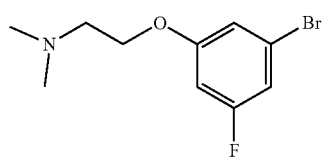

2-(3-bromo-5-fluorophenoxy)-N,N-dimethylethan-1-amine (LX): Yellow oil (364 mg, 1.389 mmol, 50.2% yield). ESIMS found for $C_{10}H_{13}BrFNO$ m/z 263.9 (M+H).

Preparation of intermediate tert-butyl 4-(2-((5-bromopyridin-3-yl)amino)-2-oxoethyl)piperidine-1-carboxylate (LXII) is depicted below in Scheme 11

Scheme 11

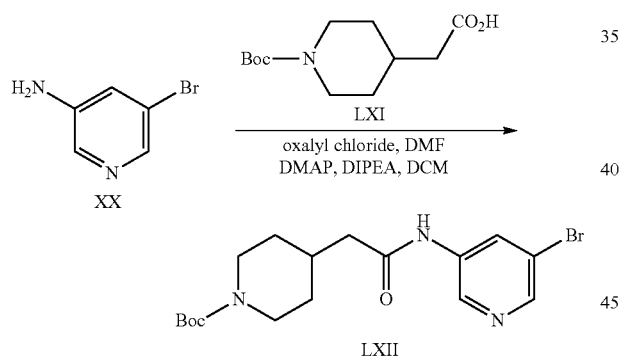

Step 1

To a solution of 2-(1-(tert-butoxycarbonyl)piperidin-4-yl)acetic acid (LXI) (3.4 g, 13.97 mmol) in DCM (10 mL) was added DMF (1 mL). The solution was cooled in ice-water to 0° C. Oxalyl chloride (1.835 mL, 20.96 mmol) was then added dropwise. The mixture was stirred for one hour at 25° C. The organic volatile was then removed under vacuum. The residue was dissolved in DCM (10 mL). DMAP (0.171 g, 1.397 mmol) and 5-bromopyridin-3-amine (XX) (2.418 g, 13.97 mmol) were added to the solution and cooled to 0° C. DIEA (4.88 ml, 27.9 mmol) was then added dropwise and the mixture was stirred for 2 hours at 25° C. The reaction was worked-up with DCM and saturated $NaHCO_3$. The product was purified by ISCO eluted with 0-100% EtOAc-Hexanes. The tert-butyl 4-(2-((5-bromopyridin-3-yl)amino)-2-oxoethyl)piperidine-1-carboxylate (LXII) (2.82 g, 7.08 mmol, 50.7% yield) was obtained as yellow oil. ESIMS found for $C_{17}H_{24}BrN_3O_3$ m/z 343.1 (M-56).

The following intermediate was prepared in accordance with the procedure described in the above Scheme 11.

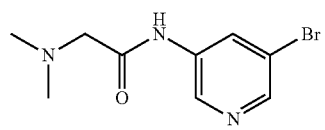

N-(5-Bromopyridin-3-yl)-2-(dimethylamino)acetamide (LXIII): Yellow oil (528 mg, 2.05 mmol, 19.0% yield). ESIMS found for $C_9H_{12}BrN_3O$ m/z 259.3 (M+H).

Preparation of tert-butyl (1-(6-chloropyrazin-2-yl)azetidin-3-yl)carbamate (LXVI) is depicted below in Scheme 12.

Scheme 12

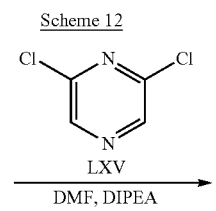

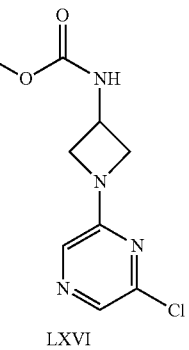

Step 1

To a solution of tert-butyl azetidin-3-ylcarbamate hydrochloride (LXIV) (2 g, 9.58 mmol) in dry DMF (19.2 mL) was added DIPEA (8.37 ml, 47.9 mmol). To this mixture was added 2,6-dichloropyrazine (LXV) (1.428 g, 9.58 mmol) and the reaction was stirred at 95° C. for 3 hours. The reaction was quenched with water (20 mL) and extracted with EtOAc. The organic layer was dried over anhydrous $Na_2SO_4$, filtered and concentrated. The residue was purified by silica gel column chromatography (40 g) (100% hexanes→hexanes:EtOAc 1:1) to yield tert-butyl (1-(6-chloropyrazin-2-yl)azetidin-3-yl)carbamate (LXVI) (2.2882 g, 8.04 mmol, 83.9% yield) as a white solid. ESIMS found for $C_{12}H_{17}ClN_4O_2$ m/z 285.1 (M+H).

Preparation of intermediate 4-(2-fluorophenyl)-3-nitropyridin-2-amine (LXX) is depicted below in Scheme 13.

Scheme 13

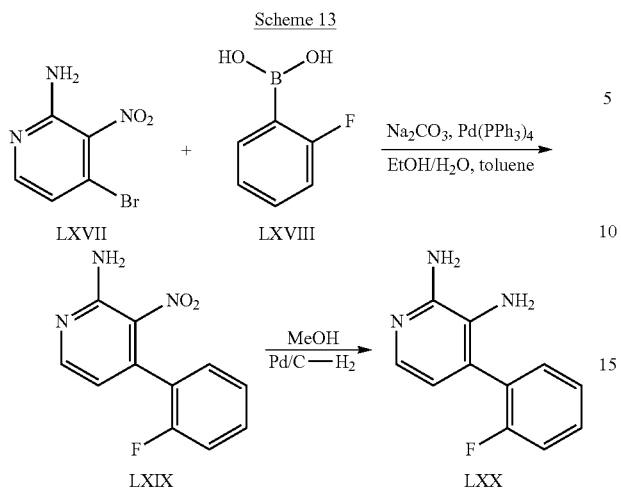

Step 1
A solution of 4-bromo-3-nitropyridin-2-amine (LXVII) (5.00 g, 22.9 mmol, 1.00 eq), (2-fluorophenyl)boronic acid (LXVIII) (3.82 g, 27.5 mmol, 1.20 eq), Pd(PPh$_3$)$_4$ (1.32 g, 1.14 mmol, 0.05 eq), and Na$_2$CO$_3$ (4.85 g, 45.8 mmol, 2 eq) in a mixture of toluene (25 mL), H$_2$O (9 mL) and EtOH (6 mL) was stirred at 75° C. for 15 h under nitrogen atmosphere. The reaction mixture was the washed with brine (50 mL) and dried over anhydrous Na$_2$SO$_4$, filtered and concentrated in vacuo. The resultant residue was purified by chromatography on silica gel (PE:EtOAc=3:1) to give 4-(2-fluorophenyl)-3-nitropyridin-2-amine (LXIX) (4.0 g, 17.15 mmol, 74.9%) as a yellow solid. $^1$H NMR (CDCl$_3$, 400 MHz) δ ppm 6.29 (brs, 2H), 6.68 (d, J=4.8 Hz, 1H), 7.14 (t, J=5.2 Hz, 1H), 7.23-7.50 (m, 3H), 8.32 (d, J=4.8 Hz, 1H); ESIMS found C$_{11}$H$_8$FN$_3$O$_2$ m/z 234.2 (M+H).

Step 2
A mixture of 4-(2-fluorophenyl)-3-nitropyridin-2-amine (LXIX) (2.8 g, 12.0 mmol, 1 eq) and Pd/C (0.2 g) in MeOH (200 mL) was stirred under 50 psi of H$_2$ at room temperature overnight. The reaction was monitored by TLC. The mixture was filtered and the filtrate was concentrated in vacuo to produce 4-(2-fluorophenyl)pyridine-2,3-diamine (LXX) (1.55 g, 7.63 mmol, 63.6% yield) as a black solid. $^1$H NMR (CDCl$_3$, 400 MHz) δ ppm 3.38 (brs, 2H), 4.40 (brs, 2H), 6.64 (d, J=4.8 Hz, 1H), 7.11-7.53 (m, 4H), 7.72 (d, J=4.8 Hz, 1H); ESIMS found C$_{11}$H$_{10}$FN$_3$ m/z 204.2 (M+H).

The following intermediates were prepared in accordance with the procedure described in the above Scheme 13.

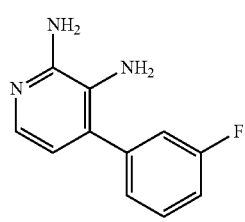

4-(3-Fluorophenyl)pyridine-2,3-diamine (LXXI): Grey solid, (1.55 g, 7.63 mmol, 86.0% yield). $^1$H NMR (CDCl$_3$, 400 MHz) δ ppm 3.50 (brs, 2H), 4.36 (brs, 2H), 6.63 (d, J=3.6 Hz, 1H), 7.3-7.37 (m, 3H), 7.47 (d, J=6 Hz, 1H), 7.72 (d, J=3.6 Hz, 1H); ESIMS found C$_{11}$H$_{10}$FN$_3$ m/z 204.2 (M+H).

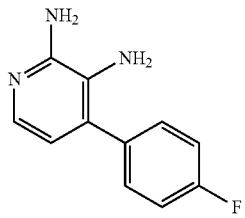

4-(4-Fluorophenyl)pyridine-2,3-diamine (LXXII): Grey solid, (1.55 g, 7.63 mmol, 60.0% yield). $^1$H NMR (CDCl$_3$, 400 MHz) δ ppm 3.46 (brs, 2H), 4.36 (brs, 2H), 6.62 (s, 1H), 7.19 (s, 2H), 7.43 (s, 2H), 7.70 (d, J=3.2 Hz, 1H); ESIMS found C$_{11}$H$_{10}$FN$_3$ m/z 204.1 (M+H).

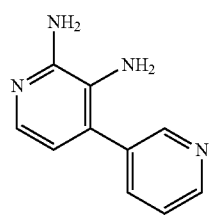

4-(4-Fluorophenyl)pyridine-2,3-diamine (LXXIII): Grey solid, (1.55 g, 7.63 mmol, 60.0% yield). $^1$H NMR (CDCl$_3$, 400 MHz) δ ppm 3.46 (brs, 2H), 4.36 (brs, 2H), 6.62 (s, 1H), 7.19 (s, 2H), 7.43 (s, 2H), 7.70 (d, J=3.2 Hz, 1H); ESIMS found C$_{11}$H$_{10}$FN$_3$ m/z 204.1 (M+H).

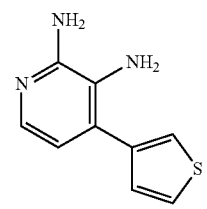

4-(Thiophen-3-yl)pyridine-2,3-diamine (LXXIV): Yellow solid, (1.9 g, 9.94 mmol, 84.9% yield). $^1$H NMR (CDCl$_3$, 400 MHz) δ ppm 3.80 (brs, 2H), 4.34 (brs, 2H), 6.77 (s, 1H), 7.18 (s, 1H), 7.27 (s, 2H), 7.44 (s, 1H), 7.68 (s, 1H); ESIMS found C$_9$H$_9$N$_3$S m/z 192.2 (M+H).

4-(Furan-3-yl)pyridine-2,3-diamine (LXXV): Black solid, (1.9 g, 10.84 mmol, 89.0% yield). $^1$H NMR (CDCl$_3$, 400 MHz) δ ppm 3.64 (brs, 2H), 4.32 (brs, 2H), 6.65 (s, 1H), 6.69 (d, J=4.8 Hz, 1H), 7.58 (s, 1H), 7.67 (d, J=4.8 Hz, 1H), 7.71 (s, 1H); ESIMS found C$_9$H$_9$N$_3$O m/z 176.3 (M+H).

LXXVI 4-(Thiophen-2-yl)pyridine-2,3-diamine (LXXVI): Yellow solid, (0.90 g, 4.71 mmol, 96.5% yield). $^1$H NMR (CDCl$_3$, 400 MHz) δ ppm 3.63 (brs, 2H), 4.35 (brs, 2H), 6.71 (s, 1H), 7.27 (s, 1H), 7.45 (s, 1H), 7.49 (s, 1H), 7.69 (s, 1H); ESIMS found C$_9$H$_9$N$_3$S m/z 192.1 (M+H).

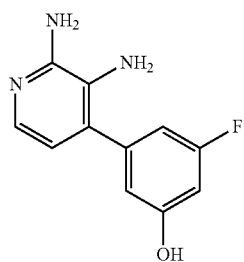

LXXVII 3-(2,3-Diaminopyridin-4-yl)-5-fluorophenol (LXXVII): White solid (303 mg, 1.38 mmol, 84.4% yield). ESIMS found for C$_{11}$H$_{10}$FN$_3$O m/z 220.1 (M+H).

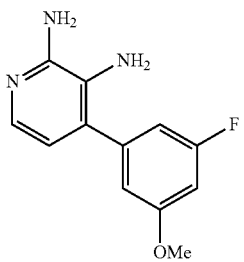

LXXVIII 4-(3-Fluoro-5-methoxyphenyl)pyridine-2,3-diamine (LXXVIII): White solid (404 mg, 1.73 mmol, 75.1% yield). ESIMS found for C$_{12}$H$_{12}$FN$_3$O m/z 234.1 (M+H).

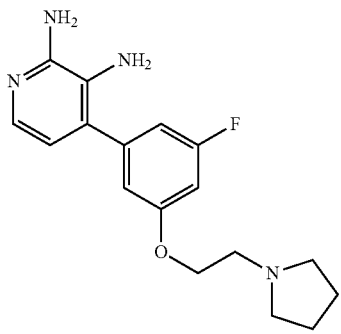

LXXIX 4-(3-Fluoro-5-(2-(pyrrolidin-1-yl)ethoxy)phenyl)pyridine-2,3-diamine (LXXIX): Black oil (368 mg, 1.163 mmol, 95.0% yield). ESIMS found for C$_{17}$H$_{21}$FN$_4$O m/z 317.1 (M+H).

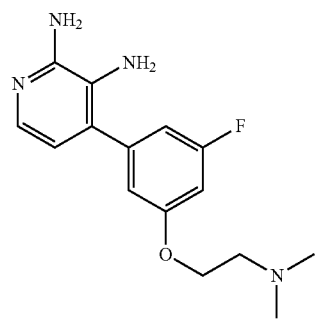

LXXX 4-(3-(2-(Dimethylamino)ethoxy)-5-fluorophenyl)pyridine-2,3-diamine (LXXX): Black oil (352 mg, 1.212 mmol, 83.6% yield). ESIMS found for C$_{15}$H$_{19}$FN$_4$O m/z 291.1 (M+H).

Preparation of intermediate 3-nitro-[4,4'-bipyridin]-2-amine (LXXXIV) is depicted below in Scheme 14.

Scheme 14

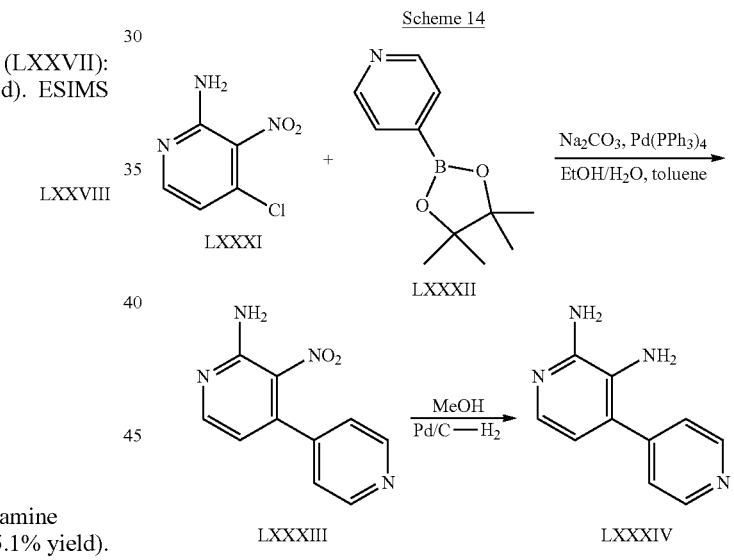

Step 1

To a solution of 4-chloro-3-nitropyridin-2-amine (LXXXI) (5.00 g, 28.9 mmol, 1.00 eq) and 4-(4,4,5,5-tetramethyl-1,3,2-dioxaborolan-2-yl)pyridine (LXXXII) (7.1 g, 34.6 mmol, 1.20 eq) in a mixture of toluene (30 mL), H$_2$O (18 mL) and EtOH (6 mL) was added Pd(PPh$_3$)$_4$ (1.0 g, 0.87 mmol, 0.03 eq) and Na$_2$CO$_3$ (6.1 g, 57.6 mmol, 2 eq). The mixture was stirred at 75° C. for 15 h under a nitrogen atmosphere. The reaction mixture was then poured into brine (100 mL) and extracted with EtOAc (30 mL×3), the combined organic layers were dried over anhydrous Na$_2$SO$_4$, filtered and concentrated in vacuo. The resultant residue was purified by chromatography on silica gel (PE:EtOAc=5: 1→1:1) to afford 3-nitro-[4,4'-bipyridin]-2-amine (LXXXIII) (1.80 g, 8.33 mmol, 28.8% yield) as a yellow solid. ESIMS found C$_{10}$H$_8$N$_4$O$_2$ m/z 217.1 (M+H).

Step 2

To a solution of 3-nitro-[4,4'-bipyridin]-2-amine (LXXXIII) (1.80 g, 8.33 mol, 1 eq) in MeOH (50 mL) was added Pd/C (0.5 g) under a nitrogen atmosphere. The mixture was stirred under 50 psi of H₂ for 6 h at room temperature. Then the mixture was filtered through a Celite pad and the filtrate was concentrated in vacuo to afford [4,4'-bipyridine]-2,3-diamine (LXXXIV) (1.4 g, 7.52 mmol, 90.4% yield) as a black solid. ESIMS found $C_{10}H_{10}N_4$ m/z 186.0 (M+H).

Preparation of intermediate 3-nitro-[4,4'-bipyridin]-2-amine (LXXXVII) is depicted below in Scheme 15.

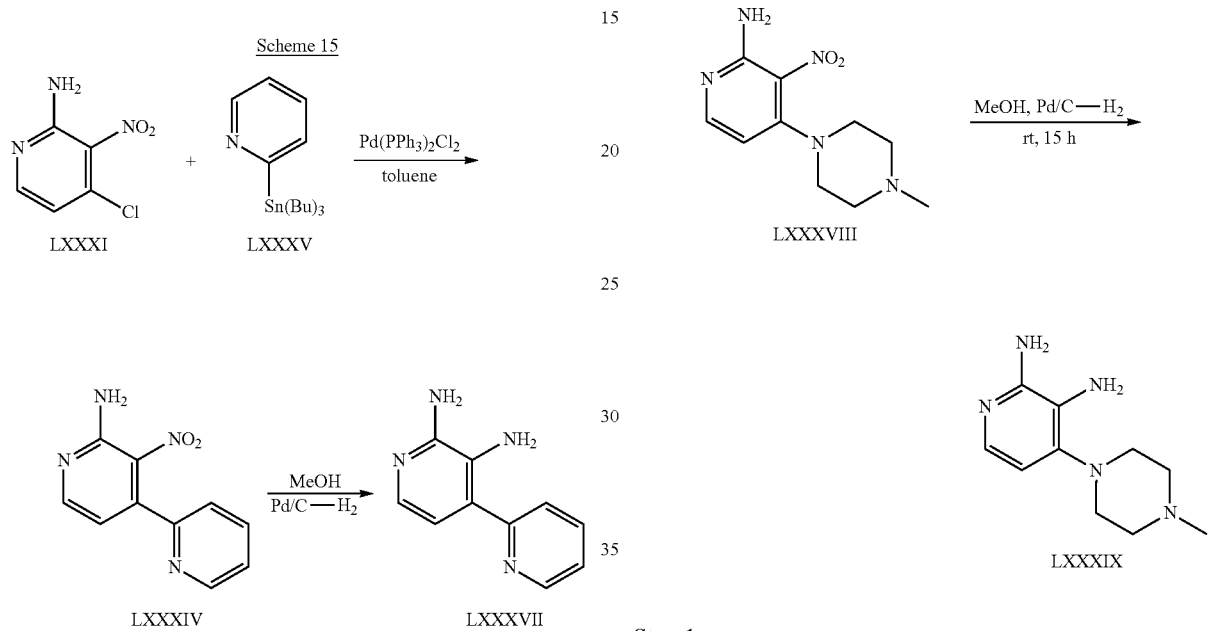

Step 1

A solution of 4-chloro-3-nitropyridin-2-amine (LXXXI) (5.00 g, 28.9 mmol, 1.00 eq), 2-(tributylstannyl)pyridine (LXXXV) (15.9 g, 43.4 mmol, 1.50 eq), and Pd(PPh₃)₂Cl₂ (1.05 g, 1.44 mmol, 0.05 eq) in a mixture of toluene (25 mL) and H₂O (9 mL) was stirred at 75° C. for 16 h under a nitrogen atmosphere. The reaction mixture was then poured into brine (80 mL) and extracted with EtOAc (30 mL×3). The combined organic layers were dried over anhydrous Na₂SO₄, filtered and concentrated in vacuo. The resultant residue was purified by chromatography on silica gel (PE:EtOAc=5:1→1:1) to afford 3'-nitro-[2,4'-bipyridin]-2'-amine (LXXXVI) (1.6 g, 7.40 mmol, 25.6% yield) as a yellow solid. ESIMS found $C_{10}H_8N_4O_2$ m/z 217.1 (M+H).

Step 2

To a solution of compound 3'-nitro-[2,4'-bipyridin]-2'-amine (LXXXVI) (1.6 g, 7.4 mmol, 1.0 eq) in MeOH (50 mL) was added Pd/C (0.5 g) under a nitrogen atmosphere. The mixture was stirred under 50 psi of H₂ for 6 h at room temperature. The mixture was then filtered and concentrated in vacuo to afford [2,4'-bipyridine]-2',3'-diamine (LXXXVII) (1.1 g, 5.91 mmol, 79.8%) as a black solid. ESIMS found $C_{10}H_{10}N_4$ m/z 186.1 (M+H).

Preparation of intermediate 4-(4-methylpiperazin-1-yl)pyridine-2,3-diamine (LXXXIX) is depicted below in Scheme 16.

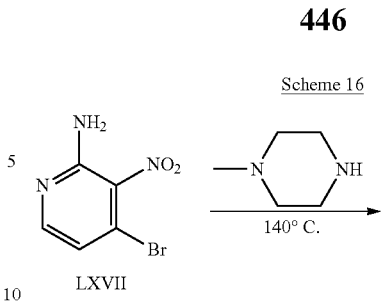

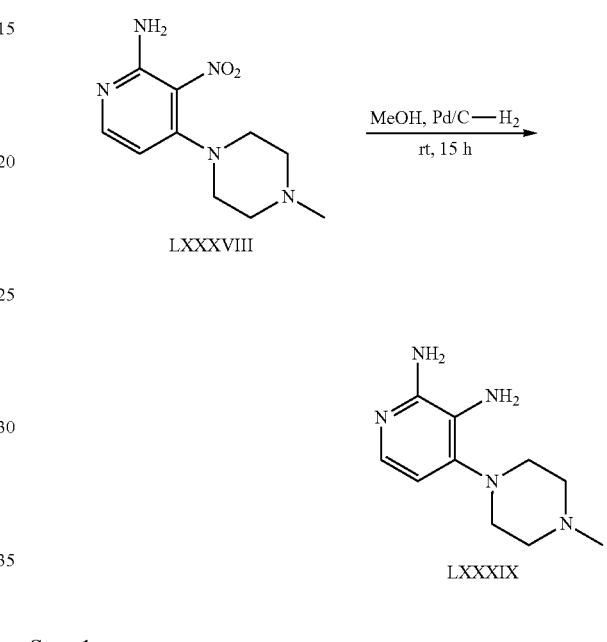

Step 1

A solution of 4-bromo-3-nitropyridin-2-amine (LXVII) (2.50 g, 11.47 mmol) in 1-methylpiperazine (4 mL, 34.5 mmol) was heated at 140° C. overnight. The reaction was poured into an EtOAc/H₂O mixture; the organic layer was separated, dried over MgSO₄ and concentrated under vacuum. The crude product was purified on a silica gel column (100% CHCl₃→3:97 MeOH(7N NH₃):CHCl₃) to give 4-(4-methylpiperazin-1-yl)-3-nitropyridin-2-amine (LXXXVIII) as a yellow solid (1.80 g, 7.59 mmol, 66.1% yield). ¹H NMR (CDCl₃, 400 MHz) δ ppm 2.36 (s, 3H), 2.54 (t, J=4.8 Hz, 4H), 3.25 (t, J=5 Hz, 4H), 6.18 (s, 2H), 6.22 (d, J=6 Hz, 1H), 7.85 (d, J=6 Hz, 1H); ESIMS found $C_{10}H_{15}N_5O_2$ m/z 238.0 (M+H).

Step 2

To a solution of 4-(4-methylpiperazin-1-yl)-3-nitropyridin-2-amine (LXXXVIII) (1.80 g, 7.59 mmol) in MeOH (52 mL) was added 10% Pd/C (0.5 g). The solution was purged with hydrogen and stirred at room temperature under hydrogen for 4 h. The suspension was filtered through Celite® and the concentrated under vacuum to produce 4-(4-methylpiperazin-1-yl)pyridine-2,3-diamine (LXXXIX) as black solid (1.4 g, 6.75 mmol, 89.0% yield). ¹H NMR (CDCl₃, 400 MHz): δ ppm 2.38 (s, 3H), 2.60 (brs, 4H), 2.99 (s, 4H), 3.49 (brs, 2H), 4.12 (brs, 2H), 6.52 (d, J=5.6 Hz, 1H), 7.64 (d, J=5.6 Hz, 1H); ESIMS found $C_{10}H_{17}N_5$ m/z 208.1 (M+H).

The following intermediate was prepared in accordance with the procedure described in the above Scheme 16.

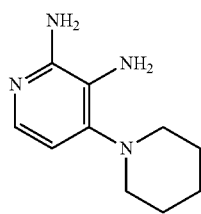

4-(Piperidin-1-yl)pyridine-2,3-diamine (XC): Black solid, (2.40 g, 12.48 mmol, 92.5% yield). $^1$H NMR (CDCl$_3$, 400 MHz): δ ppm 1.61 (brs, 2H), 1.73 (s, 4H), 2.88 (s, 4H), 3.48 (brs, 2H), 4.13 (brs, 2H), 6.50 (d, J=5.2 Hz, 1H), 7.63 (d, J=4.8 Hz, 1H); ESIMS found C$_{10}$H$_{16}$N$_4$ m/z 193.1 (M+H).

Preparation of intermediate 4-(2-fluorophenyl)-3-nitropyridin-2-amine (XCIII) is depicted below in Scheme 17.

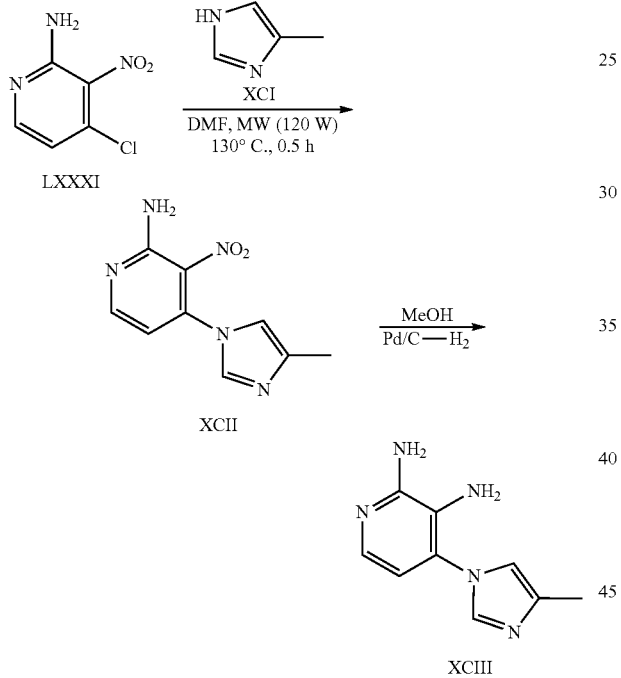

Step 1

4-Chloro-3-nitro-pyridin-2-amine (LXXXI) (3.00 g, 17.3 mmol, 1.0 eq) and 4-methyl-1H-imidazole (XCI) (2.84 g, 34.6 mmol, 2.0 eq) were taken up into a microwave tube in DMF (20 mL). The sealed tube was heated at 130° C. for 30 min under microwave. TLC showed the starting material was consumed, LC/MS showed the desired product was found. 10% NH$_4$Cl (60 mL) were added. The aqueous layer was extracted with DCM (2×100 mL). The combined organic layers were washed with brine (100 mL), dried over Na$_2$SO$_4$, concentrated in vacuum. The residue was purified by chromatography on silica gel (PE:THF=1:1) to give the product 4-(4-methylimidazol-1-yl)-3-nitro-pyridin-2-amine (XCII) (1.20 g, 5.47 mmol, 31.6% yield) as a yellow solid. $^1$H NMR (CDCl$_3$, 400 MHz) δ ppm 2.30 (d, J=0.75 Hz, 3H), 5.96-6.26 (m, 2H), 6.68 (d, J=5.02 Hz, 1H), 6.72-6.75 (m, 1H), 7.57 (d, J=1.0 Hz, 1H), 8.32 (d, J=5.14 Hz, 1H); ESIMS found C$_9$H$_9$N$_5$O$_2$ m/z 219.1 (M+H).

Step 2

To a solution of 4-(4-methylimidazol-1-yl)-3-nitro-pyridin-2-amine (XCII) (900.0 mg, 4.11 mmol, 1.0 eq) in MeOH (50 mL) was added Pd/C (100.0 mg, 4.11 mmol, 1.0 eq) at room temperature. The mixture was stirred at 20° C. under H$_2$ for 2 hr. TLC (DCM:MeOH=20:1) showed that starting the material was consumed completely. The mixture was filtered and concentrated to afford 4-(4-methyl-1H-imidazol-1-yl)pyridine-2,3-diamine (XCIII) (750.0 mg, 3.96 mmol, 96.4% yield) as a brown solid. $^1$H NMR (CDCl$_3$, 400 MHz) δ ppm 2.17 (s, 3H), 4.58 (brs, 2H), 5.85 (brs, 2H), 6.36 (d, J=5.4 Hz, 1H), 7.06 (s, 1H), 7.34 (s, 1H), 7.34 (s, 1H), 7.69 (d, J=0.88 Hz, 1H); ESIMS found C$_9$H$_{11}$N$_5$ m/z 190.1 (M+H).

Preparation of intermediate 4-(5-fluorothiophen-2-yl)pyridine-2,3-diamine (XCVI) is depicted below in Scheme 18.

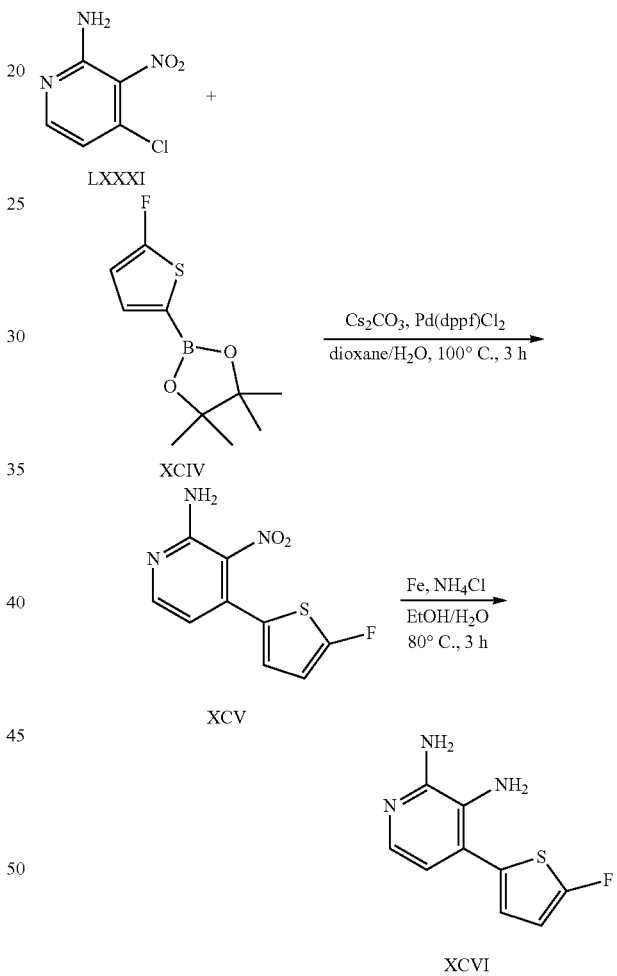

Step 1

A solution of 2-chloro-3-nitro-pyridin-4-amine (LXXXI) (1.5 g, 8.64 mmol), 2-(5-fluorothiophen-2-yl)-4,4,5,5-tetramethyl-1,3,2-dioxaborolane (XCIV) (2.96 g, 12.96 mmol), Pd(dppf)Cl$_2$ (632 mg, 0.86 mmol) and Cs$_2$CO$_3$ (5.63 g, 17.29 mmol) in dioxane (30 mL) and H$_2$O (5 mL) was de-gassed and then heated to 100° C. under N$^2$ for 3 h. TLC (PE:EtOAc=1:1) showed the starting material was consumed completely. The mixture was concentrated in vacuum to give a residue, which was purified by column chromatography to afford 4-(5-fluorothiophen-2-yl)-3-nitropyridin-2-amine (XCV) (800 mg, 3.34 mmol, 38.7% yield). ESIMS found C$_9$H$_6$FN$_3$O$_2$S m/z 240.1 (M+H).

Step 2

A solution of 4-(5-fluorothiophen-2-yl)-3-nitropyridin-2-amine (XCV) (700 mg, 2.93 mmol), Fe (817 mg, 14.63 mmol) and NH$_4$Cl (939 mg, 17.56 mmol) in EtOH (18 mL) and H$_2$O (6 mL) was heated to 80° C. for 2 h. TLC (PE:EtOAc=1:1) showed the starting material was consumed completely. The mixture was filtered, washed with HCl/EtOH, concentrated, basified to pH=7~8, extracted with EtOAc and H$_2$O, the organic layer was concentrated to give 4-(5-fluorothiophen-2-yl)pyridine-2,3-diamine (XCVI) (550 mg, 2.63 mmol, 89.7% yield). ESIMS found C$_9$H$_8$FN$_3$S m/z 210.0 (M+H).

The following intermediates were prepared in accordance with the procedure described in the above Scheme 18.

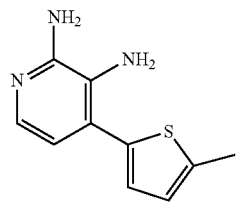

XCVII 4-(5-Methylthiophen-2-yl)pyridine-2,3-diamine (XCVII): Brown solid, (1.20 g, 5.85 mmol, 86.0% yield). $^1$H NMR (CD$_3$OD, 400 MHz) δ ppm 2.54 (s, 3H), 6.63 (d, J=4.8 Hz, 1H), 6.85 (s, 1H), 7.12 (s, 1H), 7.38 (d, J=5.2 Hz, 1H); ESIMS found C$_{10}$H$_{11}$N$_3$S m/z 206.2 (M+H).

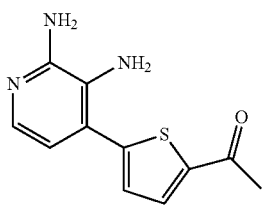

XCVIII 1-(5-(2,3-Diaminopyridin-4-yl)thiophen-2-yl)ethan-1-one (XCVIII): Brown solid, (500 mg, 2.14 mmol, 56.4% yield). $^1$H NMR (DMSO-d$_6$, 400 MHz) δ ppm 2.55 (s, 3H), 4.89 (brs, 2H), 5.80 (brs, 2H), 6.52 (d, J=5.2 Hz, 1H), 7.33 (d, J=5.2 Hz, 1H), 7.46 (d, J=4.0 Hz, 1H), 7.96 (d, J=4.0 Hz, 1H); ESIMS found C$_{11}$H$_{11}$N$_3$OS m/z 234 (M+H).

Preparation of intermediate 4-(3-((2-(dimethylamino)ethyl)amino)-5-fluorophenyl)pyridine-2,3-diamine (CIII) is depicted below in Scheme 19.

Scheme 19

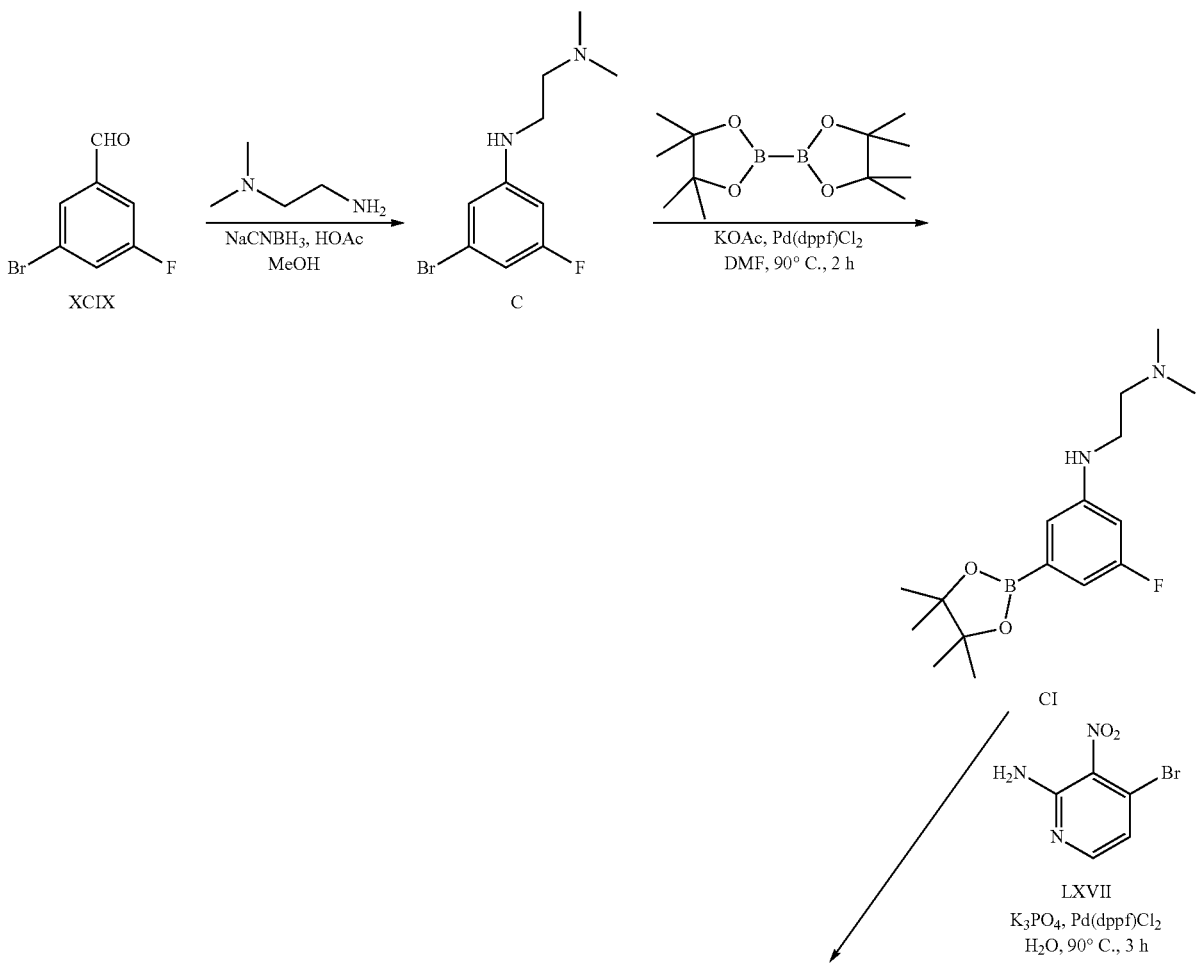

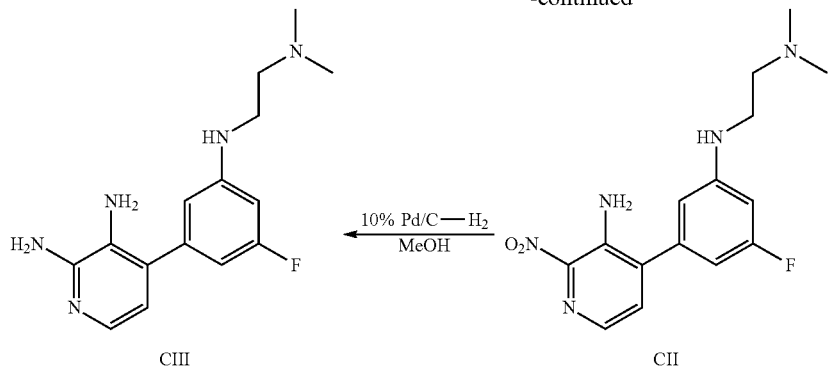

Step 1

A solution of 3-bromo-5-fluorobenzaldehyde (XCIX) (20.0 g, 98.2 mmol, 1.0 eq) in MeOH (1.8 L) was added $N^1,N^1$-dimethylethane-1,2-diamine (21.5 mL, 196.4 mmol, 2.0 eq). The pH was adjusted to 6 using HOAc and stirred for 1 h. $NaCNBH_3$ (8.6 g, 137.5 mmol, 1.4 eq) was added and stirred at room temperature overnight. The MeOH was removed under vacuum and the residue was partitioned between $CHCl_3$ and saturated aqueous $NaHCO_3$. The organic layer was dried over $MgSO_4$ and evaporated under vacuum. The crude product was purified on a silica gel column (100% $CHCl_3 \rightarrow$ 3:97 MeOH[7N $NH_3$]:$CHCl_3$) to produce $N^1$-(3-bromo-5-fluorophenyl)-$N^2,N^2$-dimethylethane-1,2-diamine (C) as a yellow oil (13.0 g, 49.9 mmol, 51% yield). $^1$H NMR (DMSO-$d_6$, 500 MHz) δ ppm 1.28 (s, 6H), 2.39 (t, J=4 Hz, 2H), 3.07 (q, J=6 Hz, 2H), 6.10 (t, J=5 Hz, 1H), 6.38 (td, J=12 Hz, J=2 Hz, 1H), 6.51 (td, J=8.6 Hz, J=2 Hz, 1H), 6.61 (t, J=2 Hz, 1H); ESIMS found $C_{10}H_{14}BrFN_2$ m/z 261.0 (M+H).

Step 2

A solution of $N^1$-(3-bromo-5-fluorophenyl)-$N^2,N^2$-dimethylethane-1,2-diamine (C) (13.0 g, 49.9 mmol, 1.0 eq), bis(pinacolato)diboron (12.6 g, 59.9 mmol, 1.2 eq), KOAc (12.1 g, 124.3 mmol, 2.5 eq) and dioxane (600 mL) was purged with argon. $Pd(dppf)Cl_2$ (2.0 g, 2.47 mmol, 0.05 eq) was added to the reaction and purged again with argon. The solution was heated at 90° C. for 2 h. Once TLC showed the disappearance of (C), the solution was cooled to room temperature and then concentrated under reduced pressure to produce crude $N^1$-(3-fluoro-5-(4,4,5,5-tetramethyl-1,3,2-dioxaborolan-2-yl)phenyl)-$N^2,N^2$-dimethylethane-1,2-diamine (CI) (7.4 g, 24.0 mmol, 48.2% yield).

Step 3

To a solution of $N^1$-(3-fluoro-5-(4,4,5,5-tetramethyl-1,3,2-dioxaborolan-2-yl)phenyl)-$N^2,N^2$-dimethylethane-1,2-diamine (CI) (5.0 g, 16.22 mmol, 1.2 eq) in water (25 mL) was added $K_2CO_3$ (448 mg, 3.24 mmol, 2.0 eq), 4-bromo-3-nitropyridin-2-amine (LXVII) (3.5 g, 16.22 mmol, 1.0 eq) and $Pd(dppf)Cl_2$ (1.0 g, 81.0 μmol, 0.05 eq). The solution was purged with argon and heated at 100° C. for 48 h. The solution was cooled to room temperature and then concentrated under reduced pressure. The residue was purified on a silica gel column (100% $CHCl_3 \rightarrow$ 2:98 MeOH[7N $NH_3$]:$CHCl_3$) to give $N^1$-(3-(3-amino-2-nitropyridin-4-yl)-5-fluorophenyl)-$N^2,N^2$-dimethylethane-1,2-diamine (CII) as a yellow amorphous solid (4.5 g, 14.1 mmol, 86.9% yield). ESIMS found for $C_{15}H_{18}FN_5O_2$ m/z 220.1 (M+H).

Step 4

To a solution of $N^1$-(3-(3-amino-2-nitropyridin-4-yl)-5-fluorophenyl)-$N^2,N^2$-dimethylethane-1,2-diamine (CII) (4.50 g, 10.43 mmol, 1.0 eq) in MeOH (15 mL) was added 10% Pd/C (540 mg, 15% by wt). The solution was purged with hydrogen and stirred for 48 h at room temperature under hydrogen (15 psi). The suspension was filtered through Celite® and concentrated under vacuum and purified by silica gel chromatography (MeOH:DCM=10:1) to produce 4-(3-((2-(dimethylamino)ethyl)amino)-5-fluorophenyl)pyridine-2,3-diamine (CIII) as a tan solid (750.0 mg, 2.59 mmol, 24.9% yield). $^1$H NMR (CD$_3$OD, 400 MHz) δ ppm 2.32 (s, 6H), 2.60 (t, J=6.8 Hz, 2H), 3.26 (t, J=6.8 Hz, 2H), 6.34-6.43 (m, 2H), 6.47 (d, J=5.6 Hz, 1H), 7.58 (s, 1H), 7.75 (s, 1H); ESIMS found $C_{15}H_{20}FN_5$ m/z 290.1 (M+H).

Preparation of intermediate N-(3-(2,3-diaminopyridin-4-yl)-5-fluorobenzyl)methanesulfonamide (CIX) is depicted below in Scheme 20.

Scheme 20

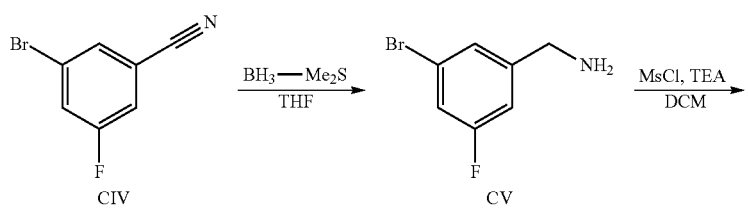

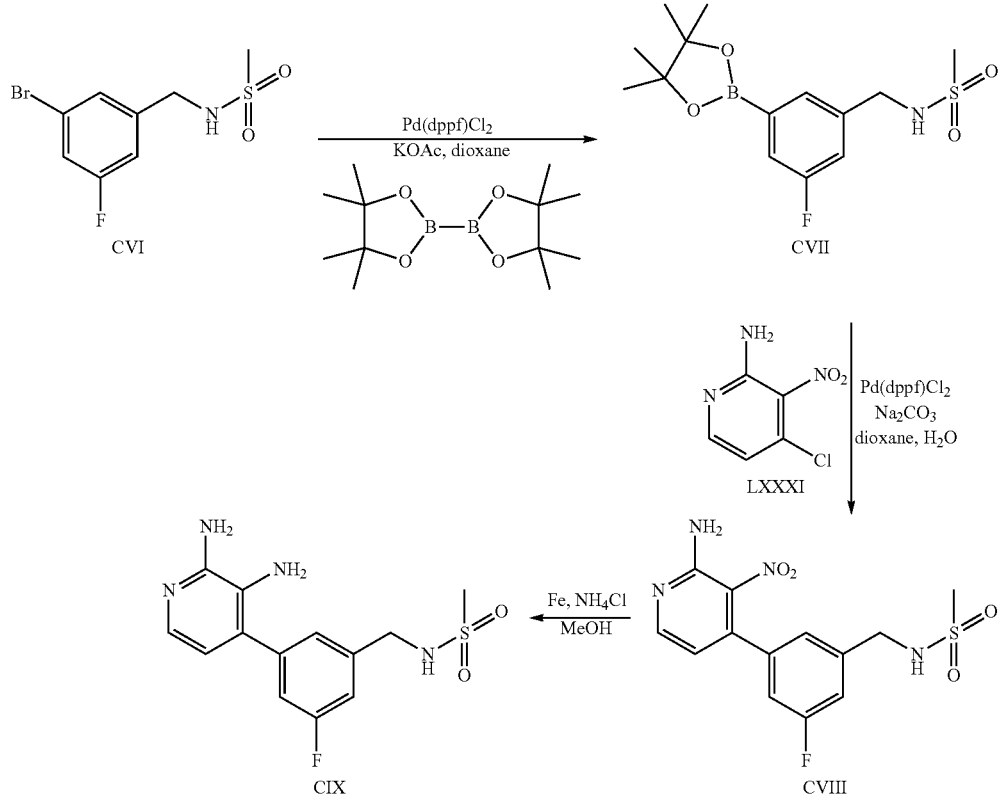

Step 1

A solution of 3-bromo-5-fluorobenzonitrile (CIV) (44.0 g, 220.0 mmol, 1.0 eq) was dissolved in THF (30 mL). $BH_3\text{-}Me_2S$ (33.43 g, 440.0 mmol, 2.0 eq) was added to the solution at 20° C. Then it was stirred at 80° C. for 2 h, HCl (6 N, 100 mL) was added to the mixture slowly at 20° C. The mixture was stirred at 80° C. for 1 h, then it was washed with EtOAc (300 ml). The water phase was basified with 50% aqueous NaOH and it was extracted with EtOAc (300 mL×3). The combined organic layers were dried over anhydrous $Na_2SO_4$ and concentrated in vacuo to produce (3-bromo-5-fluoro-phenyl)methanamine (CV) (24.0 g, 117.62 mmol, 53.5% yield). $^1$H NMR ($CDCl_3$, 300 MHz) 3.86 (s, 2H), 7.01 (d, J=8 Hz, 1H), 7.12 (d, J=8 Hz, 1H), 7.28 (s, 1H); ESIMS found $C_7H_7BrFN$ m/z 203.9 ($Br^{79}$M+H).

Step 2

A solution of (3-bromo-5-fluoro-phenyl)methanamine (CV) (23.0 g, 112.7 mmol, 1.0 eq) was dissolved in DCM (15 mL), TEA (34.22 g, 338.2 mmol, 3.0 eq) was added to the mixture. Then MsCl (13.44 g, 117.3 mmol, 1.04 eq) was added slowly to the solution at 0° C. It was stirred at 0-30° C. for 2 h. The reaction was washed with water and extracted with EtOAc. The combined organic layers were dried over anhydrous $Na_2SO_4$ and concentrated to give N-(3-bromo-5-fluorobenzyl)methanesulfonamide (CVI) (34.0 g, 102.44 mmol, 90.9% yield, 85% purity) as an oil. $^1$H NMR ($CDCl_3$, 300 MHz) 2.88 (s, 3H), 4.24 (d, J=4.5 Hz, 2H), 6.99 (d, J=9 Hz, 1H), 7.13 (dt, J=8.1 Hz, J=2 Hz, 1H), 7.25 (s, 1H); ESIMS found $C_8H_9BrFNO_2S$ m/z 282.0 ($Br^{79}$M+H).

Step 3

A solution of N-(3-bromo-5-fluorobenzyl)methanesulfonamide (CVI) (34.0 g, 102.4 mmol, 1.0 eq) and 4,4,5,5-tetramethyl-2-(4,4,5,5-tetramethyl-1,3,2-dioxaborolan-2-yl)-1,3,2-dioxaborolane (52.02 g, 204.9 mmol, 2.0 eq), KOAc (20.11 g, 204.9 mmol, 2.0 eq) was dissolved in dioxane (20 mL). Then $Pd(dppf)Cl_2$ (7.60 g, 10.2 mmol, 0.1 eq) was added to the mixture. It was stirred at 90° C. for 2 h. Then the solvent was removed to get the residue which was purified by silica gel column (PE:EtOAc=10:1→100% EtOAc) to get N-(3-fluoro-5-(4,4,5,5-tetramethyl-1,3,2-dioxaborolan-2-yl)benzyl)methanesulfonamide (CVII) (30.0 g, crude). $^1$H NMR ($CDCl_3$, 400 MHz) 1.37 (s, 12H), 2.92 (s, 3H), 4.34 (d, J=6.3 Hz, 2H), 7.19 (dt, J=9.3 Hz, J=2.1 Hz, 1H), 7.44 (dd, J=8.7 Hz, J=2.4 Hz, 1H), 7.54 (s, 1H); ESIMS found $C_{14}H_{21}BFNO_4S$ m/z 330.1 (M+H).

Step 4

A solution of N-(3-fluoro-5-(4,4,5,5-tetramethyl-1,3,2-dioxaborolan-2-yl) benzyl)methanesulfonamide (CVII) (6.83 g, 20.75 mmol, 1.2 eq), 4-chloro-3-nitropyridin-2-amine (LXXXI) (3.0 g, 17.29 mmol, 1.0 eq), $Na_2CO_3$ (6.41 g, 60.52 mmol) and $Pd(dppf)Cl_2$ (641.27 mg, 864.50 μmol) in dioxane (40 mL) and $H_2O$ (8 mL) was de-gassed and then heated to 80° C. overnight under $N_2$. TLC (PE:EtOAc=1:1) showed the starting material was consumed completely. The reaction mixture was poured into $H_2O$ (300 mL). The mixture was extracted with EtOAc (3×250 mL). The organic phase was washed with saturated brine (300 mL), dried over anhydrous $NaSO_4$, concentrated in vacuum to give a residue. The crude product was purified by silica gel chromatography (PE:EtOAc=10:1) to give N-(3-(2-amino-3-nitropyridin-4-yl)-5-fluorobenzyl) methanesulfonamide (CVIII) (2.2 g, 6.46 mmol, 37.4% yield) as brown solid. ESIMS found $C_{13}H_{13}FN_4O_4S$ m/z 341.1 (M+H).

Step 5

A solution of N-[[3-(4-amino-3-nitro-2-pyridyl)-5-fluorophenyl]methyl]methanesulfonamide (CVIII) (2.2 g, 6.46 mmol, 1.0 eq), Fe (1.44 g, 25.84 mmol, 4.0 eq) and NH₄Cl (2.8 g, 51.68 mmol, 8.0 eq) was dissolved in MeOH (30 mL). The mixture was stirred at 80° C. for 16 h. The mixture was cooled to room temperature and concentrated in reduced pressure at 60° C. The combined organic phase was washed with saturated brine (100 mL×2), dried over anhydrous Na₂SO₄, filtered and concentrated in vacuo to get crude N-(3-(3,4-diaminopyridin-2-yl)-5-fluorobenzyl) methanesulfonamide (CIX) (1.60 g, 5.16 mmol, 79.8% yield) as brown solid. ¹H NMR (CD₃OD, 400 MHz) 2.96 (s, 3H), 3.37 (s, 2H), 6.53 (d, J=4 Hz, 1H), 7.13 (d, J=8.8 Hz, 1H), 7.20 (d, J=9.2 Hz, 1H), 7.31 (s, 1H), 7.44 (d, J=4 Hz, 1H); ESIMS found C₁₃H₁₅FN₄O₂S m/z 311.1 (M+H).

Example 1

Preparation of N-(5-(3-(7-(3-((2-(Dimethylamino)ethyl) amino)-5-fluorphenyl)-3H-imidazo[4,5-b]pyridin-2-yl)-1H-pyrazolo[3,4-b]pyridin-5-yl)pyridin-3-yl)pentanamide (432) is depicted below in Scheme 21.

Scheme 21

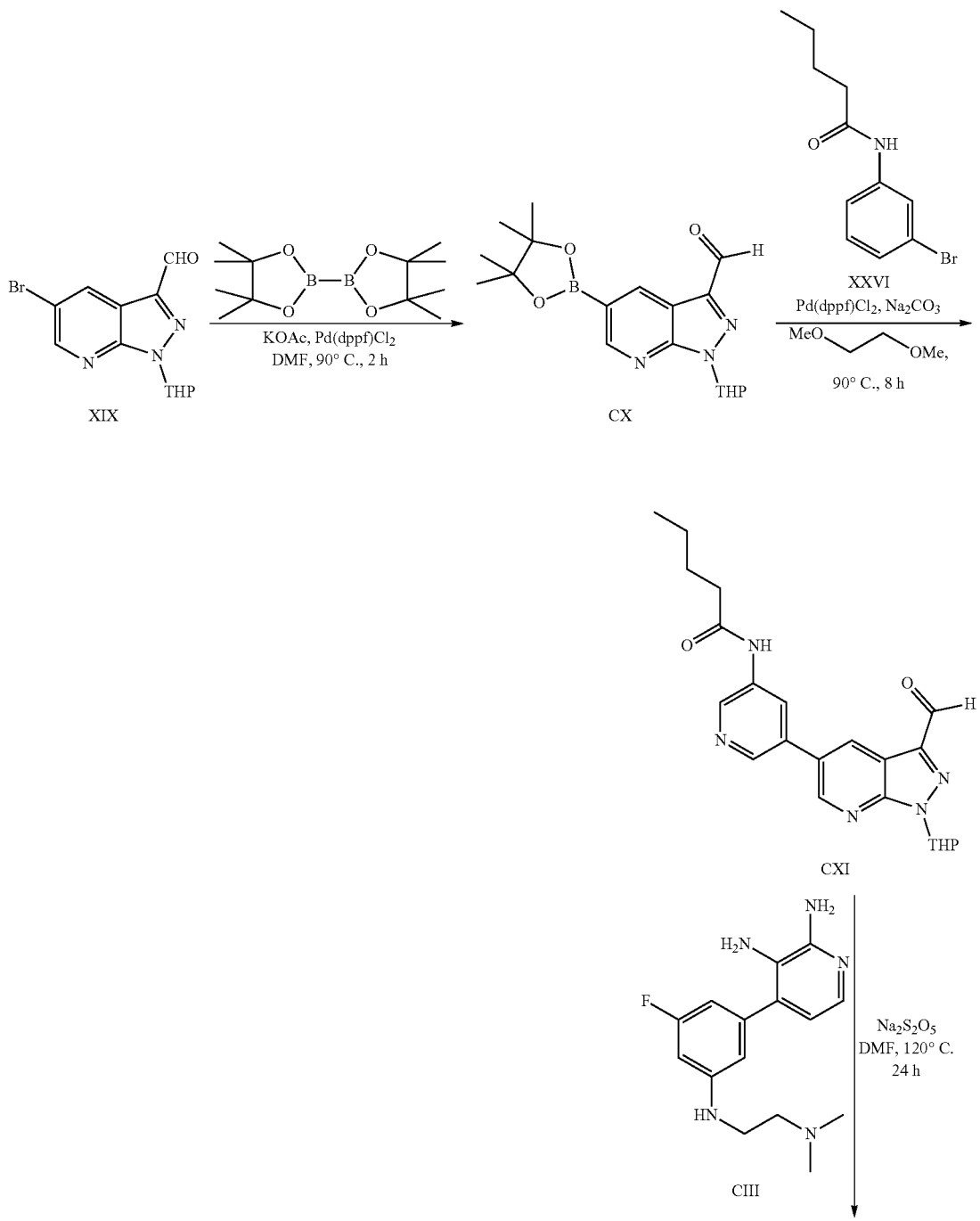

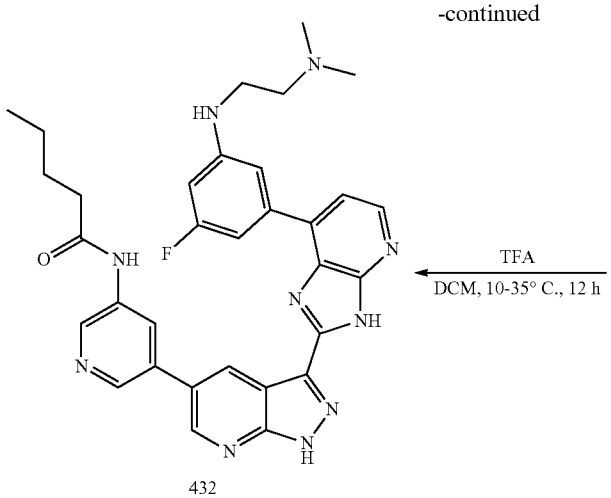

432

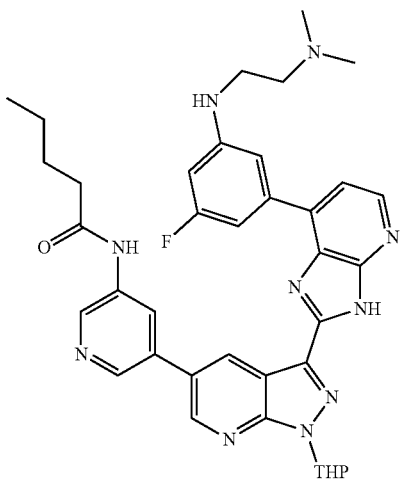

CXII

TFA
DCM, 10-35° C., 12 h

Step 1

A solution of 5-bromo-1-(tetrahydro-pyran-2-yl)-1H-pyrazolo[3,4-b]pyridin-3-yl]-carbaldehyde (XIX) (872 mg, 2.81 mmol, 1.0 eq), bis(pinacolato)diboron (898 mg, 3.37 mmol,), and KOAc (824 mg, 8.4 mmol, 3.0 eq) in dry DMF (40 mL) was purged with argon. $PdCl_2(dppf)_2$ (120 mg, 0.14 mmol, 0.05) was added to the solution and purged again with argon. The solution was heated at 90° C. for 2 h under argon and cooled to the room temperature. The reaction mixture was diluted in water (30 mL) and extracted with DCM (30 mL×3). The combined organic layers were dried over $Na_2SO_4$, filtered and concentrated in vacuo to give 1-(tetrahydro-2H-pyran-2-yl)-5-(4,4,5,5-tetramethyl-1,3,2-dioxaborolan-2-yl)-1H-pyrazolo [3,4-b]pyridine-3-carbaldehyde (CX) which was used for the next step without further purification.

Step 2

A solution of 1-(tetrahydro-2H-pyran-2-yl)-5-(4,4,5,5-tetramethyl-1,3,2-dioxaborolan-2-yl)-1H-pyrazolo [3,4-b]pyridine-3-carbaldehyde (CX) (1.0 g, 2.80 mmol, 1.0 eq), N-(5-bromopyridin-3-yl)pentanamide (XXVI) (720.0 mg, 2.80 mmol, 1.0 eq), Pd(dppf)Cl$_2$ (144 mg, 0.196 mmol, 0.07 eq) and $Na_2CO_3$ (0.89 g, 8.40 mmol, 3.0 eq) in a mixed solvent of 1,2-dimethoxyethane (30 mL) and $H_2O$ (5 mL) was refluxed for 3 h under a nitrogen atmosphere. The reaction mixture was diluted in water (30 mL) and extracted with DCM (30 mL×3). The combined organic layers were dried over $Na_2SO_4$, filtered and concentrated in vacuo, the resultant residue was purified by flash chromatography on silica gel eluting with 100% EtOAc to give the N-(5-(3-formyl-1-(tetrahydro-2H-pyran-2-yl)-1H-pyrazolo[3,4-b]pyridin-5-yl)pyridin-3-yl)pentanamide (CXI) (960 mg, 2.36 mmol, 84.1% for 2 steps) as a yellow solid. $^1$H NMR (CDCl$_3$, 400 MHz) δ ppm 1.00 (t, J=7.6 Hz, 3H), 1.47 (sxt, J=7.6 Hz, 2H), 1.68-1.84 (m, 3H), 1.89 (quin, J=8.8 Hz, 2H), 2.04-2.17 (m, 1H), 2.18-2.31 (m, 1H), 2.50 (t, J=7.2 Hz, 2H), 2.62-2.78 (m, 1H), 3.91 (t, J=10.4 Hz, 1H), 4.21 (d, J=8 Hz, 1H), 6.32 (d, J=10.4 Hz, 1H), 7.39 (s, 1H), 8.52 (s, 1H), 8.64 (s, 1H), 8.79 (s, 1H), 8.89 (d, J=1.6 Hz, 1H), 10.28 (s, 1H); ESIMS found $C_{22}H_{25}N_5O_3$ m/z 408.3 (M+H).

Step 3

A solution of N-(5-(3-formyl-1-(tetrahydro-2H-pyran-2-yl)-1H-pyrazolo[3,4-b]pyridin-5-yl)pyridin-3-yl)pentanamide (CXI) (100.0 mg, 0.25 mmol, 1.0 eq), 4-(3-(2-(dimethylamino)ethylamino)-5-fluorophenyl)pyridine-2,3-diamine (CIII) (71.0 mg, 0.25 mmol, 1.0 eq) and $Na_2S_2O_5$ (56.3 mg, 0.30 mmol, 1.2 eq) in DMF (2 mL) was stirred at 120° C. for 24 h. LC/MS showed the starting material was consumed. Water (5 mL) was added in dropwise and the mixture was filtered. The filtrate was washed by MeOH (0.5 mL) and used for directly for next step without further purification.

Step 4

Crude N-(5-(3-(7-(3-(2-(dimethylamino)ethylamino)-5-fluorophenyl)-3H-imidazo[4,5-b]pyridin-2-yl)-1-(tetrahydro-2H-pyran-2-yl)-1H-pyrazolo[3,4-b] pyridin-5-yl) pyridin-3-yl)pentanamide (CXII) was mixed with in HCl/EtOAc (15 mL) was stirred at 10-35° C. for 12 h. LC/MS showed the starting material was consumed. The mixture was concentrated to give a residue. The residue was purified by pre-HPLC (HCl) to give N-(5-(3-(7-(3-((2-(Dimethylamino)ethyl)amino)-5-fluorophenyl)-3H-imidazo[4,5-b]pyridin-2-yl)-1H-pyrazolo[3,4-b]pyridin-5-yl)pyridin-3-yl) pentanamide (432) (29.6 mg, 0.05 mmol, 24.4% yield for 2 steps) as a white solid. $^1$H NMR (DMSO-d$_6$, 400 MHz) δ ppm 0.92 (t, J=7.34 Hz, 3H), 1.36 (sxt, J=7.36 Hz, 2H), 1.62 (quin, J=7.47 Hz, 2H), 2.43 (t, J=7.40 Hz, 2H), 2.82 (d, J=3.76 Hz, 6H), 3.22-3.30 (m, 3H), 6.60 (d, J=11.17 Hz, 1H), 7.48 (brs, 2H), 7.59 (d, J=5.14 Hz, 1H), 8.45 (d, J=5.15 Hz, 1H), 8.55 (s, 1H), 8.87 (s, 1H), 8.99 (d, J=2.01 Hz, 2H), 9.11 (d, J=2.13 Hz, 1H), 10.06 (brs, 1H), 10.58 (brs, 1H), 14.61 (brs, 1H); ESIMS found for $C_{32}H_{33}FN_{10}O$ m/z 593.3 (M+1).

The following compound was prepared in accordance with the procedure described in the above Example 1.

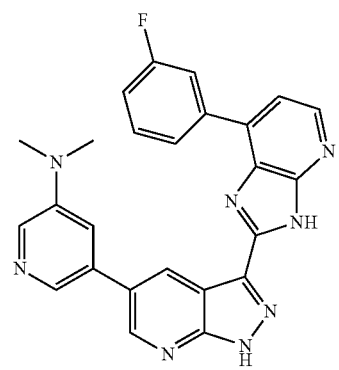

5

5-(3-(7-(3-Fluorophenyl)-3H-imidazo[4,5-b]pyridin-2-yl)-1H-pyrazolo [3,4-b]pyridin-5-yl)-N,N-dimethylpyridin-3-amine 5.

White solid (6.0 mg, 0.01 mmol). $^1$H NMR (CD$_3$OD, 400 MHz) δ ppm 3.27 (s, 6H), 7.47 (td, J=8.63, 2.70 Hz, 1H), 7.75 (td, J=8.06, 5.83 Hz, 1H), 7.80-7.87 (m, 2H), 7.90 (d, J=6.27 Hz, 1H), 8.14 (s, 1H), 8.26 (d, J=2.64 Hz, 1H), 8.48 (s, 1H), 8.69 (d, J=6.27 Hz, 1H), 9.08 (d, J=2.01 Hz, 1H), 9.26 (d, J=2.13 Hz, 1H); ESIMS found for C$_{25}$H$_{19}$FN$_8$ m/z 451.3 (M+1).

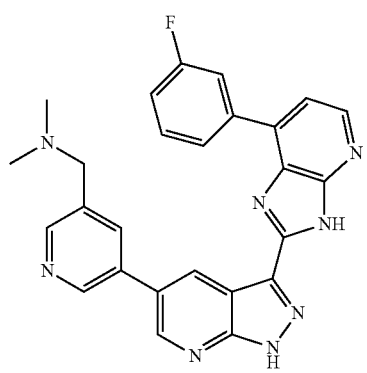

10

1-(5-(3-(7-(3-Fluorophenyl)-3H-imidazo[4,5-b]pyridin-2-yl)-1H-pyrazolo[3,4-b]pyridin-5-yl)pyridin-3-yl)-N,N-dimethylmethanamine 10.

White solid (20.0 mg, 0.04 mmol). $^1$H NMR (DMSO-d$_6$, 400 MHz) δ ppm 2.80 (d, J=4.64 Hz, 6H), 4.49 (d, J=4.89 Hz, 2H), 7.39 (td, J=8.50, 2.70 Hz, 1H), 7.65 (q, J=6.4 Hz, 1H), 7.71 (d, J=5.27 Hz, 1H), 8.20-8.28 (m, 1H), 8.41-8.52 (m, 1H), 8.48 (d, J=5.15 Hz, 1H), 8.73 (brs, 1H), 8.91 (s, 1H), 9.15 (d, J=2.13 Hz, 1H), 9.19 (d, J=2.13 Hz, 1H), 9.24 (s, 1H), 11.13 (brs, 1H), 14.67 (brs, 1H); ESIMS found for C$_{26}$H$_{21}$FN$_8$ m/z 465.1 (M+1).

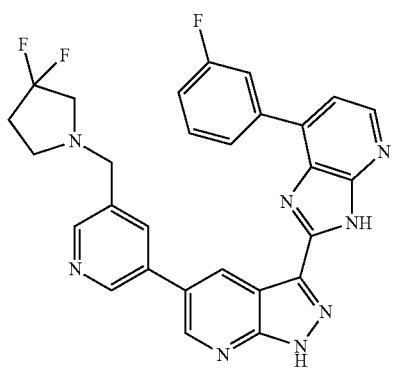

21

5-(5-((3,3-Difluoropyrrolidin-1-yl)methyl)pyridin-3-yl)-3-(7-(3-fluorophenyl)-3H-imidazo[4,5-b]pyridin-2-yl)-1H-pyrazolo[3,4-b]pyridine 21.

White solid (19.0 mg, 0.04 mmol). $^1$H NMR (DMSO-d$_6$, 400 MHz) δ ppm 2.20-2.32 (m, 2H), 2.77 (t, J=6.96 Hz, 2H), 2.96 (t, J=13.30 Hz, 2H), 3.80 (s, 2H), 7.36 (td, J=8.16, 2.51 Hz, 1H), 7.63 (q, J=6.64 Hz, 1H), 7.70 (d, J=3.51 Hz, 1H), 8.16 (s, 1H), 8.27-8.33 (m, 1H), 8.44 (d, J=5.15 Hz, 1H), 8.58 (dd, J=10.29, 1.63 Hz, 1H), 8.62 (d, J=1.76 Hz, 1H), 8.99 (d, J=1.88 Hz, 1H), 9.08 (d, J=2.13 Hz, 1H), 9.13 (d, J=1.63 Hz, 1H), 14.11 (brs, 1H), 14.47 (brs, 1H); ESIMS found for C$_{28}$H$_{21}$F$_3$N$_8$ m/z 527.2 (M+1).

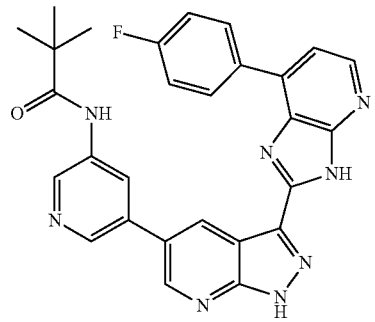

28

N-(5-(3-(7-(4-Fluorophenyl)-3H-imidazo[4,5-b]pyridin-2-yl)-1H-pyrazolo[3,4-b]pyridin-5-yl)pyridin-3-yl)pivalamide 28.

White solid (17.2 mg, 0.03 mmol). $^1$H NMR (DMSO-d$_6$, 400 MHz) δ ppm 1.32 (s, 9H), 7.46 (t, J=8.91 Hz, 2H), 7.63 (d, J=5.14 Hz, 1H), 8.42 (d, J=5.14 Hz, 1H), 8.62 (dd, J=8.78, 5.40 Hz, 2H), 8.70 (s, 1H), 8.76 (d, J=1.88 Hz, 1H), 8.90 (d, J=2.13 Hz, 1H), 9.03-9.06 (m, 1H), 9.06 (s, 1H), 9.68 (s, 1H), 14.02 (s, 1H); ESIMS found for C$_{28}$H$_{23}$FN$_8$O m/z 507.1 (M+1).

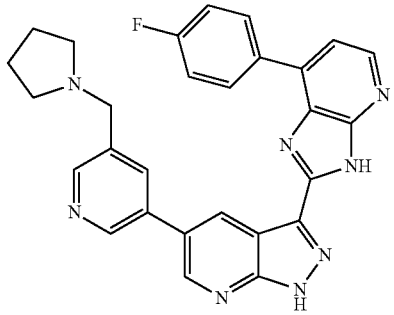

33

3-(7-(4-Fluorophenyl)-3H-imidazo[4,5-b]pyridin-2-yl)-5-(5-(pyrrolidin-1-ylmethyl)pyridin-3-yl)-1H-pyrazolo[3,4-b]pyridine 33.

White solid (9.0 mg, 0.02 mmol). $^1$H NMR (DMSO-d$_6$, 400 MHz) δ ppm 1.86-1.99 (m, 2H), 2.01-2.13 (m, 2H), 3.11-3.23 (m, 2H), 3.42-3.53 (m, 2H), 4.62 (d, J=5.02 Hz, 2H), 7.47 (t, J=8.91 Hz, 2H), 7.65 (d, J=5.40 Hz, 1H), 8.39-8.54 (m, 3H), 9.03 (s, 1H), 9.05 (s, 1H), 9.18 (d, J=1.88 Hz, 2H), 9.32 (d, J=1.63 Hz, 1H), 11.76 (brs, 1H), 14.76 (brs, 1H); ESIMS found for C$_{28}$H$_{23}$FN$_8$ m/z 491.2 (M+1).

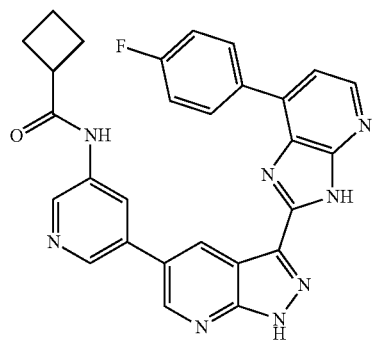

38

N-(5-(3-(7-(4-Fluorophenyl)-3H-imidazo[4,5-b]pyridin-2-yl)-1H-pyrazolo[3,4-b]pyridin-5-yl)pyridin-3-yl)cyclobutanecarboxamide 38.

White solid (22.0 mg, 0.04 mmol). $^1$H NMR (DMSO-d$_6$, 400 MHz) δ ppm 1.80-1.92 (m, 1H), 1.94-2.08 (m, 1H), 2.15-2.26 (m, 2H), 2.27-2.39 (m, 2H), 3.39 (quin, J=8.31 Hz, 2H), 7.49 (t, J=8.91 Hz, 2H), 7.63 (d, J=5.27 Hz, 1H), 8.45 (d, J=5.27 Hz, 1H), 8.54 (brs, 2H), 8.90 (s, 1H), 8.96 (d, J=1.63 Hz, 1H), 8.99 (d, J=1.88 Hz, 1H), 9.07 (d, J=2.13 Hz, 1H), 9.10 (d, J=2.26 Hz, 1H), 10.73 (s, 1H), 14.65 (brs, 1H); ESIMS found for C$_{28}$H$_{21}$FN$_8$O m/z 505.2 (M+1).

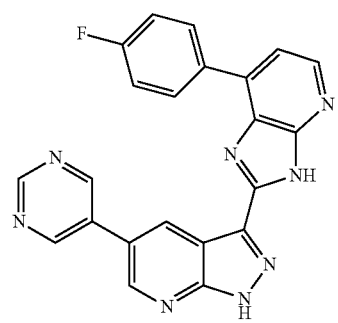

3-(7-(4-Fluorophenyl)-3H-imidazo[4,5-b]pyridin-2-yl)-5-(pyrimidin-5-yl)-1H-pyrazolo[3,4-b]pyridine 44.

White solid (58.2 mg, 0.14 mmol). $^1$H NMR (DMSO-d$_6$, 400 MHz) δ ppm 7.42 (t, J=8.85 Hz, 2H), 7.61 (d, J=5.27 Hz, 1H), 8.44 (d, J=5.15 Hz, 1H), 8.54 (brs, 2H), 9.12 (d, J=2.26 Hz, 1H), 9.19 (d, J=2.13 Hz, 1H), 9.30 (s, 1H), 9.34 (s, 2H), 14.59 (brs, 1H); ESIMS found for C$_{22}$H$_{13}$FN$_8$ m/z 409.0 (M+1).

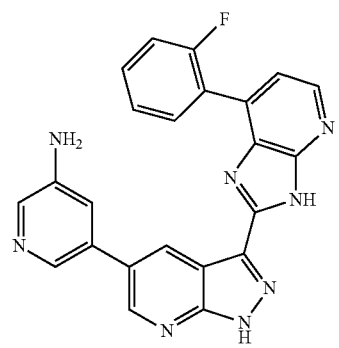

5-(3-(7-(2-Fluorophenyl)-3H-imidazo[4,5-b]pyridin-2-yl)-1H-pyrazolo[3,4-b]pyridin-5-yl)pyridin-3-amine 45.

White solid (24.5 mg, 0.06 mmol). $^1$H NMR (DMSO-d$_6$, 400 MHz) δ ppm 7.41-7.52 (m, 3H), 7.56-7.64 (m, 1H), 7.93-8.17 (m, 1H), 7.99 (s, 1H), 8.11 (d, J=1.76 Hz, 1H), 8.48-8.54 (m, 2H), 9.02 (d, J=4.89 Hz, 2H), 14.71 (brs, 1H); ESIMS found for C$_{23}$H$_{15}$FN$_8$ m/z 423.1 (M+1).

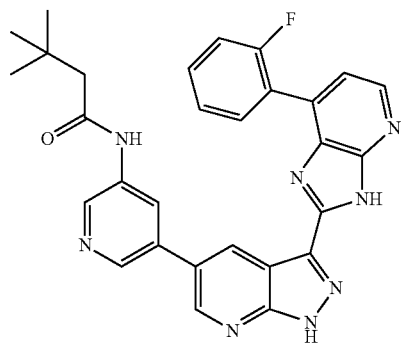

N-(5-(3-(7-(2-Fluorophenyl)-3H-imidazo[4,5-b]pyridin-2-yl)-1H-pyrazolo[3,4-b]pyridin-5-yl)pyridin-3-yl)-3,3-dimethylbutanamide 57.

White solid (27.0 mg, 0.05 mmol). $^1$H NMR (DMSO-d$_6$, 400 MHz) δ ppm 1.08 (s, 9H), 2.30 (s, 2H), 7.38-7.49 (m, 3H), 7.52 (brs, 1H), 8.26 (brs, 1H), 8.45 (brs, 1H), 8.50 (brs, 1H), 8.67 (brs, 1H), 8.77 (brs, 1H), 8.97 (brs, 2H), 10.27 (s, 1H), 14.03 (brs, 1H), 14.52 (brs, 1H); ESIMS found for C$_{29}$H$_{25}$FN$_8$O m/z 521.3 (M+1).

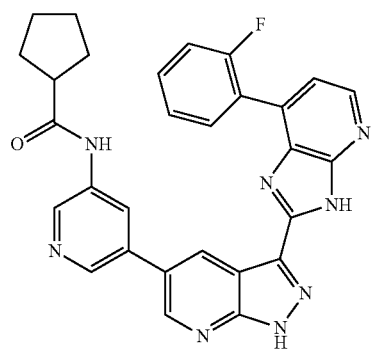

N-(5-(3-(7-(2-Fluorophenyl)-3H-imidazo[4,5-b]pyridin-2-yl)-1H-pyrazolo[3,4-b]pyridin-5-yl)pyridin-3-yl)cyclopentanecarboxamide 61.

White solid (13.0 mg, 0.03 mmol). $^1$H NMR (CD$_3$OD, 400 MHz) δ ppm 1.65-1.76 (m, 2H), 1.76-1.87 (m, 2H), 1.87-1.98 (m, 2H), 2.00-2.10 (m, 2H), 3.00 (quin, J=8.00 Hz, 1H), 7.43-7.56 (m, 2H), 7.73 (q, J=6.27 Hz, 1H), 7.81-7.90 (m, 2H), 8.70 (d, J=6.15 Hz, 1H), 9.03 (brs, 2H), 9.06 (d, J=1.88 Hz, 1H), 9.28 (d, J=1.88 Hz, 1H), 9.34 (brs, 1H); ESIMS found for C$_{29}$H$_{23}$FN$_8$O m/z 519.2 (M+1).

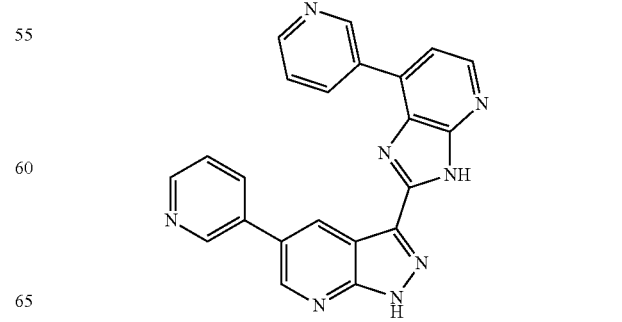

5-(Pyridin-3-yl)-3-(7-(pyridin-3-yl)-3H-imidazo[4,5-b]pyridin-2-yl)-1H-pyrazolo[3,4-b]pyridine 68.

White solid (60.7 mg, 0.16 mmol). $^1$H NMR (DMSO-d$_6$, 400 MHz) δ ppm 7.84 (brs, 1H), 7.96-8.16 (m, 2H), 8.55 (d, J=4.77 Hz, 1H), 8.81 (brs, 1H), 8.88 (brs, 1H), 8.92 (brs, 1H), 9.14 (s, 1H), 9.20 (brs, 1H), 9.24-9.41 (m, 3H), 9.88 (brs, 1H), 14.71 (brs, 1H); ESIMS found for C$_{22}$H$_{14}$N$_8$ m/z 391.0 (M+1).

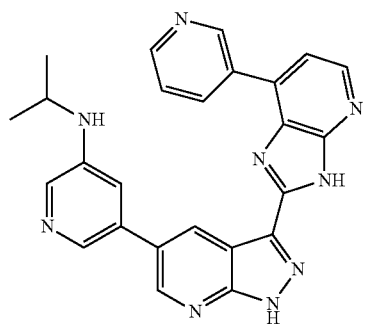

75

N-Isopropyl-5-(3-(7-(pyridin-3-yl)-3H-imidazo[4,5-b]pyridin-2-yl)-1H-pyrazolo[3,4-b]pyridin-5-yl)pyridin-3-amine 75.

White solid (11.0 mg, 0.02 mmol). $^1$H NMR (CD$_3$OD, 400 MHz) δ ppm 1.34 (d, J=6.40 Hz, 6H), 3.87 (spt, J=6.40 Hz, 1H), 7.89 (d, J=5.52 Hz, 1H), 8.02 (s, 1H), 8.09 (d, J=2.26 Hz, 1H), 8.33 (dd, J=7.97, 5.58 Hz, 1H), 8.42 (s, 1H), 8.67 (d, J=5.40 Hz, 1H), 9.00 (d, J=2.01 Hz, 1H), 9.05 (d, J=5.27 Hz, 1H), 9.21 (d, J=2.01 Hz, 1H), 9.39 (d, J=7.91 Hz, 1H), 9.84 (s, 1H); ESIMS found for C$_{25}$H$_{21}$N$_9$ m/z 448.2 (M+1).

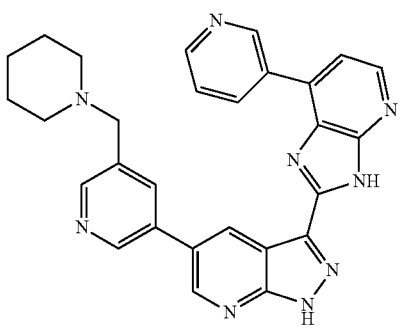

78

5-(5-(Piperidin-1-ylmethyl)pyridin-3-yl)-3-(7-(pyridin-3-yl)-3H-imidazo[4,5-b]pyridin-2-yl)-1H-pyrazolo[3,4-b]pyridine 78.

White solid (9.2 mg, 0.02 mmol). $^1$H NMR (DMSO-d$_6$, 400 MHz) δ ppm 1.34-1.48 (m, 1H), 1.67-1.88 (m, 5H), 2.91-3.06 (m, 2H), 3.36-3.44 (m, 2H), 4.50 (s, 2H), 7.78 (d, J=5.02 Hz, 1H), 7.90 (d, J=3.64 Hz, 1H), 8.53 (d, J=5.02 Hz, 1H), 8.63 (brs, 1H), 8.82-8.89 (m, 2H), 9.07 (brs, 1H), 9.14 (d, J=2.13 Hz, 1H), 9.17 (d, J=2.26 Hz, 1H), 9.20 (d, J=2.13 Hz, 1H), 9.84 (brs, 1H), 10.41 (brs, 1H), 14.64 (s, 1H); ESIMS found for C$_{28}$H$_{25}$N$_9$ m/z 488.2 (M+1).

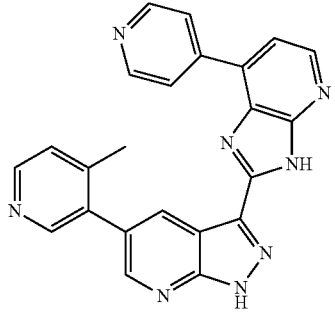

91

5-(4-Methylpyridin-3-yl)-3-(7-(pyridin-4-yl)-3H-imidazo[4,5-b]pyridin-2-yl)-1H-pyrazolo[3,4-b]pyridine 91.

White solid (21.0 mg, 0.05 mmol). $^1$H NMR (CD$_3$OD, 400 MHz) δ ppm 2.71 (s, 3H), 7.97 (d, J=5.65 Hz, 1H), 8.18 (d, J=6.15 Hz, 1H), 8.71 (d, J=5.52 Hz, 1H), 8.80 (d, J=2.01 Hz, 1H), 8.85 (d, J=6.02 Hz, 1H), 8.94-9.00 (m, 3H), 9.08-9.15 (m, 3H); ESIMS found for C$_{23}$H$_{16}$N$_8$ m/z 405.2 (M+1).

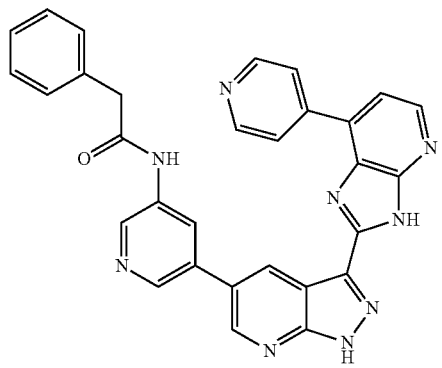

95

2-Phenyl-N-(5-(3-(7-(pyridin-4-yl)-3H-imidazo[4,5-b]pyridin-2-yl)-1H-pyrazolo[3,4-b]pyridin-5-yl)pyridin-3-yl)acetamide 95.

White solid (22.0 mg, 0.04 mmol). $^1$H NMR (DMSO-d$_6$, 400 MHz) δ ppm 3.96 (s, 2H), 7.20-7.26 (m, 1H), 7.32 (t, J=7.34 Hz, 2H), 7.44 (d, J=7.40 Hz, 2H), 7.96 (d, J=5.14 Hz, 1H), 8.60 (d, J=5.27 Hz, 1H), 9.09 (s, 1H), 9.12-9.17 (m, 2H), 9.18 (s, 1H), 9.22 (brs, 3H), 9.26 (brs, 1H), 9.30 (s, 1H), 12.30 (brs, 1H); ESIMS found for C$_{30}$H$_{21}$N$_9$O m/z 524.2 (M+1).

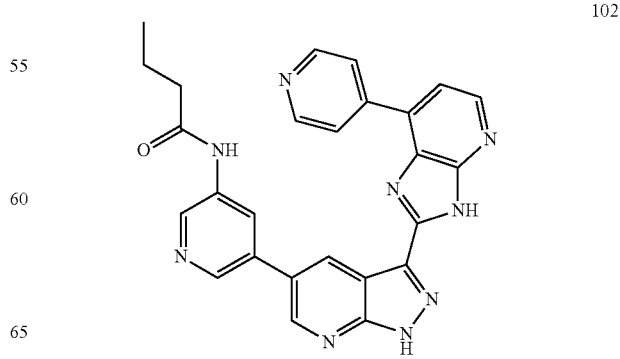

102

N-(5-(3-(7-(Pyridin-4-yl)-3H-imidazo[4,5-b]pyridin-2-yl)-1H-pyrazolo[3,4-b]pyridin-5-yl)pyridin-3-yl)butyramide 102.

White solid (14.0 mg, 0.03 mmol). $^1$H NMR (DMSO-$d_6$, 400 MHz) δ ppm 0.97 (t, J=7.40 Hz, 3H), 1.70 (sxt, J=7.33 Hz, 2H), 2.48 (t, J=7.16 Hz, 2H), 7.93 (d, J=5.27 Hz, 1H), 8.59 (d, J=5.02 Hz, 1H), 8.84 (brs, 1H), 8.90 (brs, 1H), 8.93 (s, 1H), 9.01 (brs, 2H), 9.06-9.11 (m, 3H), 9.12 (d, J=1.63 Hz, 1H), 10.75 (brs, 1H), 14.71 (brs, 1H); ESIMS found for $C_{26}H_{21}N_9O$ m/z 476.1 (M+1).

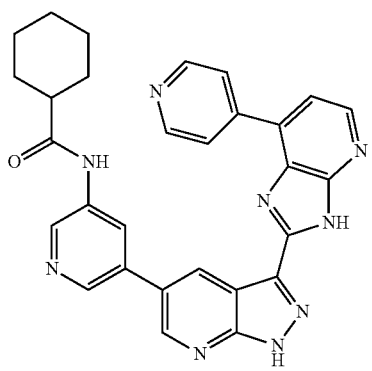

106

N-(5-(3-(7-(Pyridin-4-yl)-3H-imidazo[4,5-b]pyridin-2-yl)-1H-pyrazolo[3,4-b]pyridin-5-yl)pyridin-3-yl)cyclohexanecarboxamide 106.

White solid (20.0 mg, 0.04 mmol). $^1$H NMR (DMSO-$d_6$, 400 MHz) δ ppm 1.19-1.36 (m, 3H), 1.40-1.53 (m, 2H), 1.61-1.70 (m, 1H), 1.73-1.83 (m, 2H), 1.93 (d, J=12.05 Hz, 2H), 2.51-2.58 (m, 1H), 7.93 (d, J=5.14 Hz, 1H), 8.57 (d, J=5.14 Hz, 1H), 9.02 (s, 1H), 9.03-9.08 (m, 2H), 9.08-9.20 (m, 6H), 11.18 (brs, 1H), 14.75 (brs, 1H); ESIMS found for $C_{29}H_{25}N_9O$ m/z 516.1 (M+1).

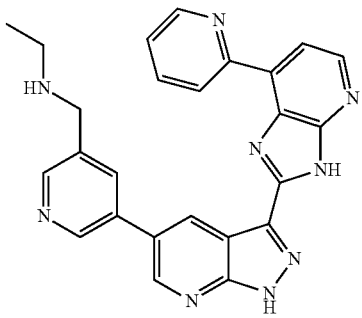

114

N-((5-(3-(7-(Pyridin-2-yl)-3H-imidazo[4,5-b]pyridin-2-yl)-1H-pyrazolo[3,4-b]pyridin-5-yl)pyridin-3-yl)methyl)ethanamine 114.

White solid (32.0 mg, 0.07 mmol). $^1$H NMR (DMSO-$d_6$, 400 MHz) δ ppm 1.30 (t, J=7.22 Hz, 3H), 2.97-3.08 (m, 2H), 4.29-4.38 (m, 2H), 7.56 (dd, J=7.03, 5.02 Hz, 1H), 8.11 (d, J=5.15 Hz, 1H), 8.14 (td, J=7.72, 1.38 Hz, 1H), 8.52 (d, J=5.02 Hz, 1H), 8.82 (brs, 1H), 8.86 (d, J=4.64 Hz, 1H), 8.90 (s, 1H), 9.16 (d, J=2.01 Hz, 1H), 9.20 (brs, 3H), 9.90 (brs, 2H), 14.75 (brs, 1H); ESIMS found for $C_{25}H_{21}N_9$ m/z 448.2 (M+1).

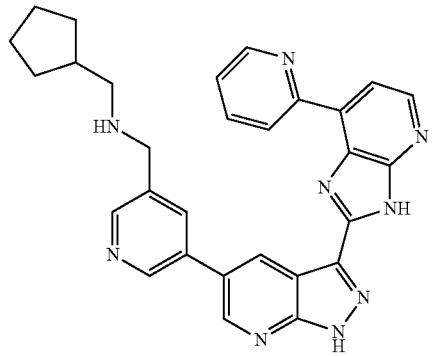

130

1-Cyclopentyl-N-((5-(3-(7-(pyridin-2-yl)-3H-imidazo[4,5-b]pyridin-2-yl)-1H-pyrazolo[3,4-b]pyridin-5-yl)pyridin-3-yl)methyl)methanamine 130.

White solid (33.0 mg, 0.07 mmol). $^1$H NMR (DMSO-$d_6$, 400 MHz) δ ppm 1.22-1.34 (m, 2H), 1.46-1.64 (m, 4H), 1.75-1.86 (m, 2H), 2.28 (spt, J=7.76 Hz, 1H), 2.94-3.02 (m, 2H), 4.40 (t, J=5.40 Hz, 2H), 7.62 (dd, J=7.15, 5.40 Hz, 1H), 8.13 (d, J=5.27 Hz, 1H), 8.23 (td, J=7.84, 1.63 Hz, 1H), 8.57 (d, J=5.27 Hz, 1H), 8.91 (d, J=4.02 Hz, 1H), 8.98 (s, 2H), 9.12 (d, J=4.52 Hz, 1H), 9.19 (d, J=2.01 Hz, 1H), 9.24 (d, J=2.26 Hz, 1H), 9.31 (s, 1H), 9.59 (brs, 2H), 14.76 (brs, 1H); ESIMS found for $C_{29}H_{27}N_9$ m/z 502.3 (M+1).

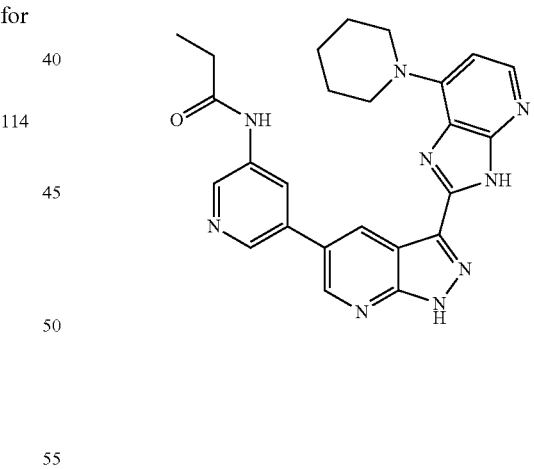

133

N-(5-(3-(7-(Piperidin-1-yl)-3H-imidazo[4,5-b]pyridin-2-yl)-1H-pyrazolo[3,4-b]pyridin-5-yl)pyridin-3-yl)propionamide 133.

White solid (23.0 mg, 0.05 mmol). $^1$H NMR (DMSO-$d_6$, 400 MHz) δ ppm 1.14 (t, J=7.47 Hz, 3H), 1.76 (brs, 6H), 2.47 (q, J=7.64 Hz, 2H), 3.92-4.22 (m, 4H), 6.96 (d, J=7.53 Hz, 1H), 7.98 (brs, 1H), 8.75-8.90 (m, 4H), 9.08 (d, J=2.01 Hz, 1H), 10.84 (s, 1H), 14.67 (brs, 1H), 14.96 (s, 1H); ESIMS found for $C_{25}H_{25}N_9O$ m/z 468.3 (M+1).

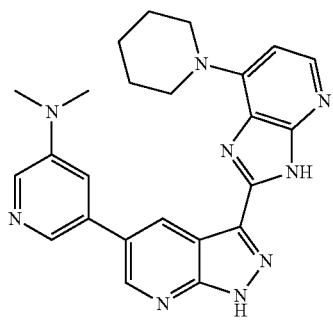

N,N-Dimethyl-5-(3-(7-(piperidin-1-yl)-3H-imidazo[4,5-b]pyridin-2-yl)-1H-pyrazolo[3,4-b]pyridin-5-yl)pyridin-3-amine 139.

White solid (31.0 mg, 0.07 mmol). $^1$H NMR (DMSO-d$_6$, 400 MHz) δ ppm 1H NMR (400 MHz, DMSO-d$_6$) δ 1.76 (brs, 6H), 3.17 (s, 6H), 4.25 (brs, 4H), 6.97 (d, J=7.65 Hz, 1H), 7.99 (brs, 1H), 8.08 (brs, 1H), 8.27 (d, J=2.64 Hz, 1H), 8.52 (s, 1H), 8.96 (d, J=2.01 Hz, 1H), 9.15 (d, J=2.13 Hz, 1H), 14.75 (brs, 1H); ESIMS found for $C_{24}H_{25}N_9$ m/z 440.2 (M+1).

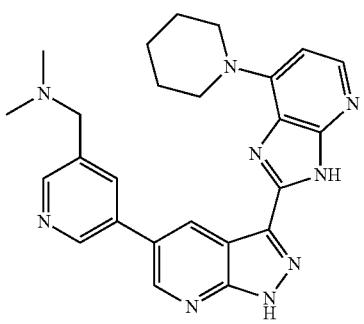

N,N-Dimethyl-1-(5-(3-(7-(piperidin-1-yl)-3H-imidazo[4,5-b]pyridin-2-yl)-1H-pyrazolo[3,4-b]pyridin-5-yl)pyridin-3-yl)methanamine 145.

White solid (13.0 mg, 0.03 mmol). $^1$H NMR (DMSO-d$_6$, 400 MHz) δ ppm 1.76 (brs, 6H), 2.79 (d, J=4.02 Hz, 6H), 4.44 (d, J=3.64 Hz, 2H), 6.97 (d, J=6.90 Hz, 1H), 7.98 (brs, 1H), 8.61 (s, 1H), 8.81 (d, J=1.63 Hz, 1H), 8.93 (brs, 1H), 9.09 (d, J=1.88 Hz, 1H), 9.12 (d, J=2.13 Hz, 1H), 11.13 (brs, 1H), 14.68 (brs, 1H), 14.98 (s, 1H); ESIMS found for $C_{25}H_{27}N_9$ m/z 454.2 (M+1).

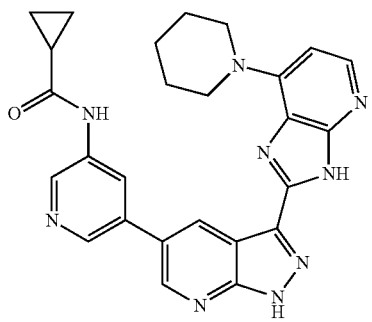

N-(5-(3-(7-(Piperidin-1-yl)-3H-imidazo[4,5-b]pyridin-2-yl)-1H-pyrazolo[3,4-b]pyridin-5-yl)pyridin-3-yl)cyclopropanecarboxamide 151.

White solid (8.0 mg, 0.02 mmol). $^1$H NMR (DMSO-d$_6$, 400 MHz) δ ppm 0.86-0.92 (m, 4H), 1.75 (brs, 6H), 1.86-1.95 (m, 1H), 4.28 (brs, 2H), 6.94 (d, J=7.15 Hz, 1H), 7.96 (brs, 1H), 8.67 (brs, 1H), 8.73 (s, 2H), 8.85 (d, J=2.01 Hz, 1H), 9.06 (d, J=1.51 Hz, 1H), 10.82 (s, 1H), 14.60 (brs, 1H); ESIMS found for $C_{26}H_{25}N_9O$ m/z 480.1 (M+1).

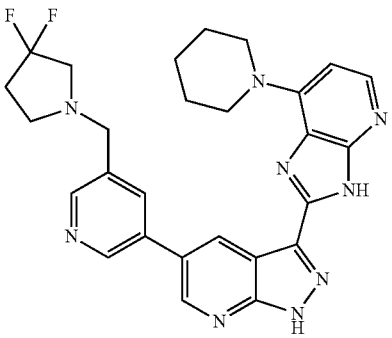

5-(5-((3,3-Difluoropyrrolidin-1-yl)methyl)pyridin-3-yl)-3-(7-(piperidin-1-yl)-3H-imidazo[4,5-b]pyridin-2-yl)-1H-pyrazolo[3,4-b]pyridine 157.

White solid (31.0 mg, 0.06 mmol). $^1$H NMR (DMSO-d$_6$, 400 MHz) δ ppm 1.76 (brs, 6H), 2.56-2.67 (m, 2H), 3.47-3.59 (m, 4H), 3.80-394 (m, 4H), 4.57 (brs, 2H), 6.96 (d, J=7.28 Hz, 1H), 7.98 (brs, 1H), 8.72 (brs, 1H), 8.88 (s, 1H), 8.93 (s, 1H), 9.11 (d, J=1.51 Hz, 1H), 9.14 (d, J=2.13 Hz, 1H), 14.70 (brs, 1H), 14.99 (brs, 1H); ESIMS found for $C_{27}H_{27}F_2N_9$ m/z 516.2 (M+1).

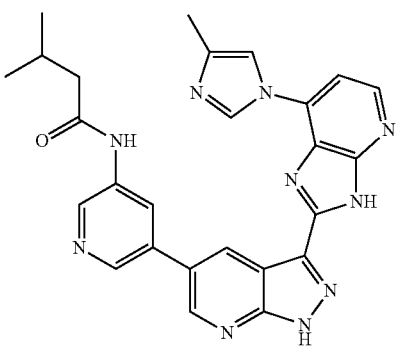

3-Methyl-N-(5-(3-(7-(4-methyl-1H-imidazol-1-yl)-3H-imidazo[4,5-b]pyridin-2-yl)-1H-pyrazolo[3,4-b]pyridin-5-yl)pyridin-3-yl)butanamide 160.

White solid (6.2 mg, 0.01 mmol). $^1$H NMR (DMSO-d$_6$, 400 MHz) δ ppm 0.95 (d, J=6.65 Hz, 6H), 2.13 (non, J=6.78 Hz, 1H), 2.39 (d, J=7.03 Hz, 2H), 2.45 (s, 3H), 7.83 (d, J=5.40 Hz, 1H), 8.54 (d, J=5.40 Hz, 1H), 8.63 (s, 1H), 9.05 (d, J=1.88 Hz, 1H), 9.11 (s, 1H), 9.19 (s, 1H), 9.22 (s, 1H), 9.37 (d, J=1.63 Hz, 1H), 10.24 (d, J=1.13 Hz, 1H), 11.73 (s, 1H); ESIMS found for $C_{26}H_{24}N_{10}O$ m/z 493.2 (M+1).

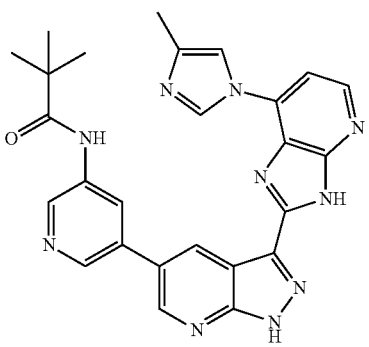

N-(5-(3-(7-(4-Methyl-1H-imidazol-1-yl)-3H-imidazo[4,5-b]pyridin-2-yl)-1H-pyrazolo[3,4-b]pyridin-5-yl)pyridin-3-yl)pivalamide 165.

White solid (6.2 mg, 0.01 mmol). $^1$H NMR (DMSO-d$_6$, 400 MHz) δ ppm 1.30 (s, 9H), 2.42 (s, 3H), 7.81 (d, J=5.27 Hz, 1H), 8.58 (d, J=5.40 Hz, 1H), 8.62 (brs, 1H), 8.72 (brs, 1H), 8.89 (s, 1H), 9.03 (d, J=2.01 Hz, 1H), 9.07 (s, 1H), 9.14 (d, J=1.76 Hz, 1H), 9.88 (s, 1H), 10.12 (brs, 1H), 14.54 (brs, 1H), 14.74 (s, 1H); ESIMS found for $C_{26}H_{24}N_{10}O$ m/z 493.2 (M+1).

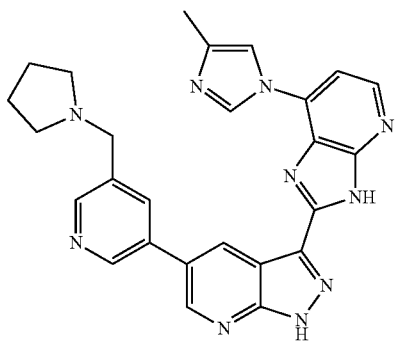

3-(7-(4-Methyl-1H-imidazol-1-yl)-3H-imidazo[4,5-b]pyridin-2-yl)-5-(5-(pyrrolidin-1-ylmethyl)pyridin-3-yl)-1H-pyrazolo[3,4-b]pyridine 171.

White solid (13.0 mg, 0.03 mmol). $^1$H NMR (DMSO-d$_6$, 400 MHz) δ ppm 1.89-1.99 (m, 2H), 2.01-2.11 (m, 2H), 2.48 (s, 3H), 3.03-3.12 (m, 2H), 3.13-3.25 (m, 2H), 4.60 (brs, 2H), 7.83 (d, J=5.40 Hz, 1H), 8.61 (d, J=5.40 Hz, 1H), 8.65 (brs, 1H), 8.79-8.87 (m, 1H), 8.90 (brs, 1H), 9.18 (s, 1H), 9.28 (brs, 2H), 10.27 (brs, 1H), 11.55 (s, 1H), 14.77 (brs, 1H); ESIMS found for $C_{26}H_{24}N_{10}$ m/z 477.1 (M+1).

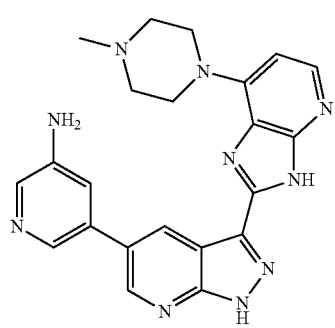

5-(3-(7-(4-Methylpiperazin-1-yl)-3H-imidazo[4,5-b]pyridin-2-yl)-1H-pyrazolo[3,4-b]pyridin-5-yl)pyridin-3-amine 186.

White solid (100.4 mg, 0.24 mmol). $^1$H NMR (DMSO-d$_6$, 400 MHz) δ ppm 2.38 (brs, 3H), 2.64-2.85 (m, 4H), 4.05 (brs, 4H), 5.54 (brs, 2H), 6.58 (d, J=6.15 Hz, 1H), 7.27 (s, 1H), 7.97-8.04 (m, 2H), 8.14 (s, 1H), 8.89 (s, 2H), 14.24 (brs, 1H); ESIMS found for $C_{22}H_{22}N_{10}$ m/z 427.1 (M+1).

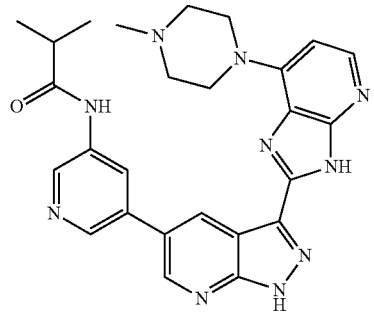

N-(5-(3-(7-(4-Methylpiperazin-1-yl)-3H-imidazo[4,5-b]pyridin-2-yl)-1H-pyrazolo[3,4-b]pyridin-5-yl)pyridin-3-yl)isobutyramide 192.

White solid (14.0 mg, 0.03 mmol). $^1$H NMR (DMSO-d$_6$, 400 MHz) δ ppm 1.18 (d, J=6.78 Hz, 6H), 2.79 (spt, J=6.76 Hz, 1H), 2.86 (brs, 3H), 3.29-3.42 (m, 2H), 3.70 (d, J=10.54 Hz, 2H), 3.84 (brs, 2H), 5.32 (brs, 2H), 7.04 (brs, 1H), 8.17 (brs, 1H), 8.80 (brs, 1H), 8.87 (brs, 1H), 8.89 (brs, 1H), 9.03 (d, J=1.88 Hz, 2H), 10.99 (brs, 1H), 11.52 (brs, 1H), 14.76 (d, J=2.13 Hz, 1H); ESIMS found for $C_{26}H_{28}N_{10}O$ m/z 497.2 (M+1).

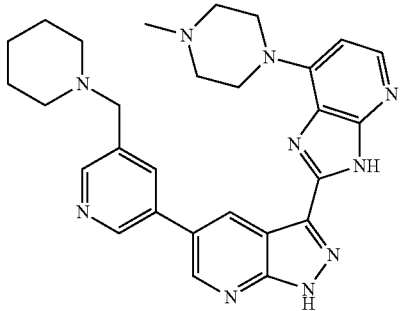

3-(7-(4-Methylpiperazin-1-yl)-3H-imidazo[4,5-b]pyridin-2-yl)-5-(5-(piperidin-1-ylmethyl)pyridin-3-yl)-1H-pyrazolo[3,4-b]pyridine 198.

White solid (10.0 mg, 0.02 mmol). $^1$H NMR (DMSO-d$_6$, 400 MHz) δ ppm 1.35-1.47 (m, 1H), 1.68-1.76 (m, 1H), 1.76-1.92 (m, 4H), 2.83 (brs, 3H), 2.91-3.02 (m, 2H), 3.27-3.43 (m, 4H), 3.65 (d, J=12.05 Hz, 4H), 3.76-3.88 (m, 2H), 4.45 (d, J=3.51 Hz, 2H), 6.97 (brs, 1H), 8.15 (brs, 1H), 8.75 (s, 1H), 8.84 (s, 1H), 8.99 (d, J=1.76 Hz, 1H), 9.15 (d, J=2.13 Hz, 2H), 11.30 (brs, 1H), 11.58 (brs, 1H), 14.66 (brs, 1H); ESIMS found for $C_{28}H_{32}N_{10}$ m/z 509.2 (M+1).

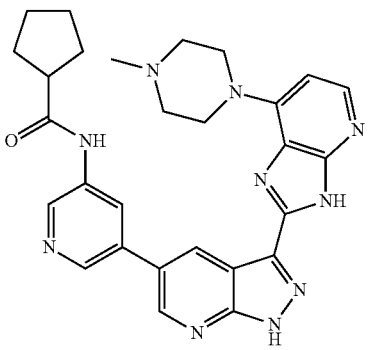

N-(5-(3-(7-(4-Methylpiperazin-1-yl)-3H-imidazo[4,5-b]pyridin-2-yl)-1H-pyrazolo[3,4-b]pyridin-5-yl)pyridin-3-yl)cyclopentanecarboxamide 204.

White solid (11.0 mg, 0.02 mmol). $^1$H NMR (DMSO-d$_6$, 400 MHz) δ ppm 1.52-1.64 (m, 2H), 1.65-1.85 (m, 4H), 1.88-2.00 (m, 2H), 2.85 (s, 3H), 2.93-3.03 (m, 1H), 3.24-3.44 (m, 4H), 3.77-3.99 (m, 2H), 5.31 (brs, 2H), 7.05 (brs, 1H), 8.18 (brs, 1H), 8.80 (brs, 1H), 8.88 (d, J=1.76 Hz, 1H), 8.90 (brs, 1H), 9.02 (d, J=2.01 Hz, 1H), 9.07 (brs, 1H), 11.09 (brs, 1H), 11.53 (brs, 1H), 14.78 (brs, 1H); ESIMS found for C$_{28}$H$_{30}$N$_{10}$O m/z 523.3 (M+1).

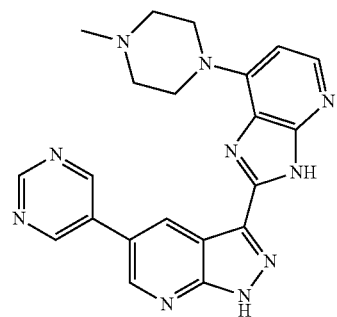

3-(7-(4-Methylpiperazin-1-yl)-3H-imidazo[4,5-b]pyridin-2-yl)-5-(pyrimidin-5-yl)-1H-pyrazolo[3,4-b]pyridine 209.

White solid (27.0 mg, 0.07 mmol). $^1$H NMR (DMSO-d$_6$, 400 MHz) δ ppm 2.83 (d, J=1.00 Hz, 3H), 3.25-3.38 (m, 2H), 3.63 (d, J=11.54 Hz, 2H), 3.77-3.93 (m, 4H), 7.02-7.11 (m, 1H), 8.18 (brs, 1H), 8.96 (s, 1H), 9.11 (d, J=2.01 Hz, 1H), 9.29 (s, 1H), 9.31 (s, 2H), 11.60 (brs, 1H), 14.77 (brs, 1H); ESIMS found for C$_{21}$H$_{20}$N$_{10}$ m/z 413.1 (M+1).

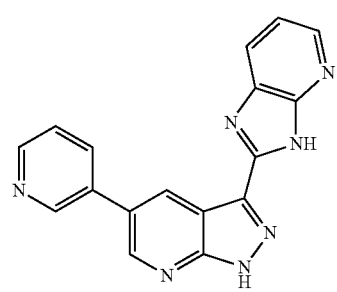

3-(3H-Imidazo[4,5-b]pyridin-2-yl)-5-(pyridin-3-yl)-1H-pyrazolo[3,4-b]pyridine 212.

White solid (41.2 mg, 0.13 mmol). $^1$H NMR (DMSO-d$_6$, 400 MHz) δ ppm 7.53 (dd, J=7.47, 5.21 Hz, 1H), 8.06 (dd, J=7.97, 5.46 Hz, 1H), 8.33 (d, J=7.91 Hz, 1H), 8.56 (d, J=4.27 Hz, 1H), 8.85 (d, J=8.03 Hz, 1H), 8.91 (d, J=5.65 Hz, 1H), 9.15 (q, J=2.09 Hz, 2H), 9.36 (d, J=1.38 Hz, 1H), 14.89 (brs, 1H); ESIMS found for C$_{17}$H$_{11}$N$_7$ m/z 314.0 (M+1).

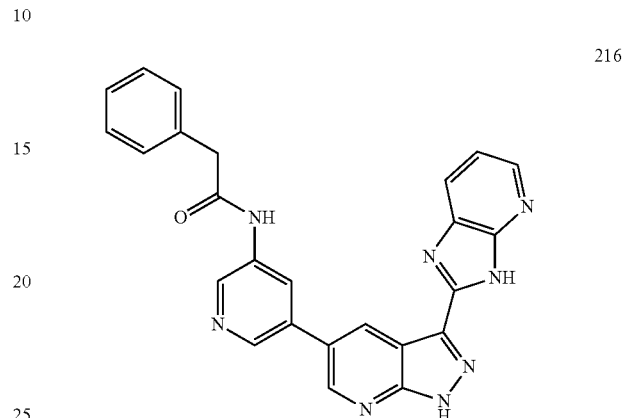

N-(5-(3-(3H-Imidazo[4,5-b]pyridin-2-yl)-1H-pyrazolo[3,4-b]pyridin-5-yl)pyridin-3-yl)-2-phenylacetamide 216.

White solid (9.4 mg, 0.02 mmol). $^1$H NMR (DMSO-d$_6$, 400 MHz) δ ppm 3.78 (s, 2H), 7.24-7.30 (m, 1H), 7.32-7.42 (m, 4H), 7.45 (dd, J=7.53, 5.02 Hz, 1H), 8.23 (d, J=8.66 Hz, 1H), 8.51 (d, J=4.52 Hz, 1H), 8.60 (s, 1H), 8.86 (s, 1H), 8.99 (s, 1H), 9.01 (d, J=2.13 Hz, 1H), 9.04 (d, J=2.13 Hz, 1H), 10.96 (s, 1H), 14.74 (brs, 1H); ESIMS found for C$_{25}$H$_{18}$N$_8$O m/z 447.2 (M+1).

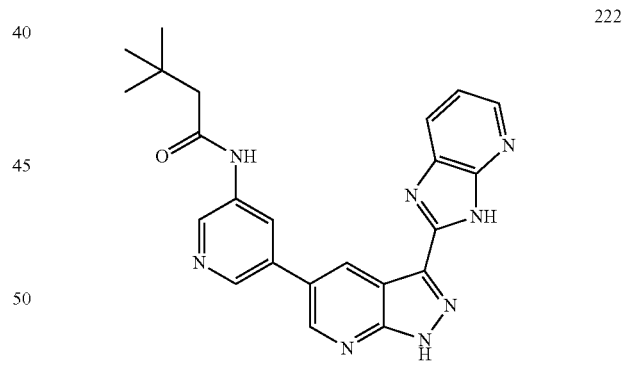

N-(5-(3-(3H-Imidazo[4,5-b]pyridin-2-yl)-1H-pyrazolo[3,4-b]pyridin-5-yl)pyridin-3-yl)-3,3-dimethylbutanamide 222.

White solid (7.0 mg, 0.02 mmol). $^1$H NMR (DMSO-d$_6$, 400 MHz) δ ppm 1.07 (s, 9H), 2.34 (s, 2H), 7.54 (dd, J=7.65, 5.27 Hz, 1H), 8.33 (d, J=7.65 Hz, 1H), 8.56 (d, J=4.89 Hz, 1H), 8.73 (s, 1H), 8.97 (s, 1H), 9.03-9.06 (m, 1H), 9.07 (d, J=2.13 Hz, 1H), 9.14 (s, 1H), 10.90 (brs, 1H), 14.89 (brs, 1H); ESIMS found for C$_{23}$H$_{22}$N$_8$O m/z 427.1 (M+1).

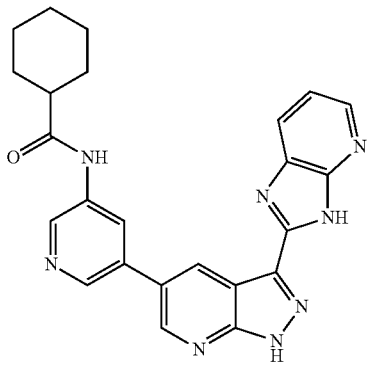

N-(5-(3-(3H-Imidazo[4,5-b]pyridin-2-yl)-1H-pyrazolo[3,4-b]pyridin-5-yl) pyridin-3-yl)cyclohexanecarboxamide 228.

White solid (9.0 mg, 0.02 mmol). $^1$H NMR (DMSO-d$_6$, 400 MHz) δ ppm 1.14-1.37 (m, 3H), 1.45 (qd, J=12.17, 2.13 Hz, 2H), 1.67 (d, J=12.55 Hz, 1H), 1.74-1.82 (m, 2H), 1.89 (d, J=12.55 Hz, 2H), 2.41-2.49 (m, 1H), 7.55 (dd, J=7.97, 5.33 Hz, 1H), 8.34 (d, J=7.91 Hz, 1H), 8.56 (dd, J=5.27, 1.00 Hz, 1H), 8.76 (t, J=1.88 Hz, 1H), 8.97 (d, J=1.76 Hz, 1H), 9.02-9.06 (m, 1H), 9.06 (d, J=2.26 Hz, 1H), 9.11 (d, J=2.01 Hz, 1H), 10.86 (s, 1H), 14.90 (brs, 1H); ESIMS found for C$_{24}$H$_{22}$N$_8$O m/z 439.1 (M+1).

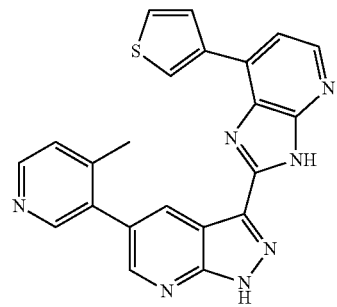

5-(4-Methylpyridin-3-yl)-3-(7-(thiophen-3-yl)-3H-imidazo[4,5-b] pyridin-2-yl)-1H-pyrazolo[3,4-b]pyridine 237.

White solid (20.0 mg, 0.05 mmol). $^1$H NMR (CD$_3$OD, 400 MHz) δ ppm 2.71 (s, 3H), 7.82 (dd, J=5.14, 2.89 Hz, 1H), 7.93 (d, J=4.14 Hz, 1H), 7.98 (d, J=6.27 Hz, 1H), 8.18 (d, J=6.27 Hz, 1H), 8.58 (d, J=6.27 Hz, 1H), 8.65 (brs, 1H), 8.82 (d, J=2.13 Hz, 1H), 8.83-8.87 (m, 1H), 8.97 (s, 1H), 9.09 (d, J=2.26 Hz, 1H); ESIMS found for C$_{22}$H$_{15}$N$_7$S m/z 410.2 (M+1).

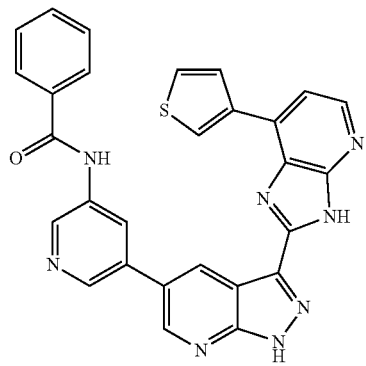

N-(5-(3-(7-(Thiophen-3-yl)-3H-imidazo[4,5-b]pyridin-2-yl)-1H-pyrazolo[3,4-b]pyridin-5-yl)pyridin-3-yl)benzamide 243.

White solid (11.0 mg, 0.02 mmol). $^1$H NMR (DMSO-d$_6$, 400 MHz) δ ppm 7.56-7.63 (m, 2H), 7.64-7.70 (m, 2H), 7.70-7.76 (m, 1H), 8.08 (d, J=7.40 Hz, 2H), 8.21 (brs, 1H), 8.38 (d, J=5.02 Hz, 1H), 8.84 (brs, 1H), 8.89 (brs, 1H), 8.93 (brs, 1H), 9.05 (brs, 1H), 9.10 (s, 1H), 9.18 (s, 1H), 10.73 (s, 1H), 13.98 (brs, 1H); ESIMS found for C$_{28}$H$_{18}$N$_8$OS m/z 515.1 (M+1).

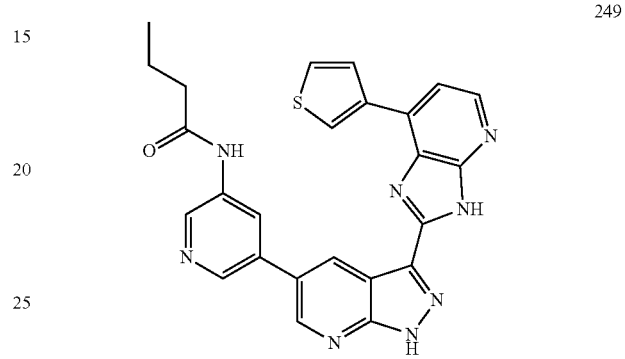

N-(5-(3-(7-(Thiophen-3-yl)-3H-imidazo[4,5-b]pyridin-2-yl)-1H-pyrazolo[3,4-b]pyridin-5-yl)pyridin-3-yl)butyramide 249.

White solid (13.0 mg, 0.03 mmol). $^1$H NMR (DMSO-d$_6$, 400 MHz) δ ppm 0.97 (t, J=7.40 Hz, 3H), 1.70 (sxt, J=7.33 Hz, 2H), 2.45 (t, J=7.28 Hz, 3H), 7.70 (d, J=5.14 Hz, 1H), 7.79 (dd, J=5.02, 3.01 Hz, 1H), 8.20 (d, J=4.52 Hz, 1H), 8.40 (d, J=5.27 Hz, 1H), 8.82 (brs, 1H), 8.91 (d, J=1.63 Hz, 1H), 8.95 (s, 2H), 9.06 (d, J=2.01 Hz, 1H), 9.15 (d, J=2.26 Hz, 1H), 10.71 (brs, 1H), 14.62 (brs, 1H); ESIMS found for C$_{25}$H$_{20}$N$_8$OS m/z 481.1 (M+1).

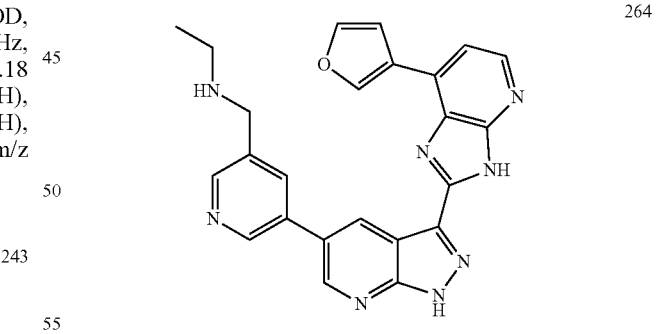

N-((5-(3-(7-(Furan-3-yl)-3H-imidazo[4,5-b]pyridin-2-yl)-1H-pyrazolo [3,4-b]pyridin-5-yl)pyridin-3-yl)methyl)ethanamine 264.

White solid (20.0 mg, 0.05 mmol). $^1$H NMR (DMSO-d$_6$, 400 MHz) δ ppm 1.31 (t, J=7.09 Hz, 3H), 3.07 (q, J=5.02 Hz, 2H), 4.47 (brs, 3H), 7.44 (s, 1H), 7.72 (d, J=5.40 Hz, 1H), 7.95 (s, 1H), 8.44 (d, J=5.27 Hz, 1H), 9.09 (s, 1H), 9.14 (s, 1H), 9.19 (s, 1H), 9.21 (s, 1H), 9.33 (s, 1H), 9.45 (s, 1H), 10.17 (brs, 2H), 14.91 (brs, 1H); ESIMS found for C$_{24}$H$_{20}$N$_8$O m/z 437.2 (M+1).

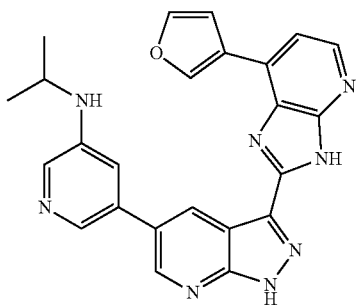

270

5-(3-(7-(Furan-3-yl)-3H-imidazo[4,5-b]pyridin-2-yl)-1H-pyrazolo[3,4-b]pyridin-5-yl)-N-isopropylpyridin-3-amine 270.

White solid (20.0 mg, 0.05 mmol). $^1$H NMR (DMSO-$d_6$, 400 MHz) δ ppm 1.22 (d, J=6.27 Hz, 6H), 3.81 (brs, 1H), 6.39 (brs, 1H), 7.43 (s, 1H), 7.52 (brs, 1H), 7.57 (d, J=5.14 Hz, 1H), 7.90 (t, J=1.63 Hz, 1H), 8.07 (s, 1H), 8.29 (brs, 1H), 8.35 (d, J=5.02 Hz, 1H), 8.97 (s, 1H), 8.99 (s, 1H), 9.08 (s, 1H), 13.93 (brs, 1H), 14.55 (brs, 1H); ESIMS found for $C_{24}H_{20}N_8O$ m/z 437.2 (M+1).

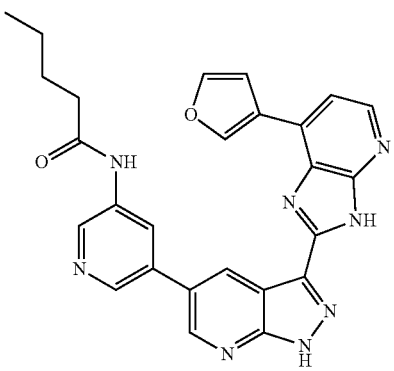

276

N-(5-(3-(7-(Furan-3-yl)-3H-imidazo[4,5-b]pyridin-2-yl)-1H-pyrazolo [3,4-b]pyridin-5-yl)pyridin-3-yl)pentanamide 276.

White solid (20.0 mg, 0.04 mmol). $^1$H NMR (DMSO-$d_6$, 400 MHz) δ ppm 0.92 (t, J=7.34 Hz, 3H), 1.37 (sxt, J=7.52 Hz, 2H), 1.64 (quin, J=7.37 Hz, 2H), 2.43-2.48 (m, 3H), 7.46 (d, J=1.13 Hz, 1H), 7.62 (d, J=5.02 Hz, 1H), 7.90 (s, 1H), 8.39 (d, J=5.27 Hz, 1H), 8.80 (s, 1H), 8.98 (s, 1H), 9.06 (brs, 3H), 9.04 (d, J=2.13 Hz, 1H), 9.14 (d, J=2.01 Hz, 1H), 10.88 (s, 1H), 14.67 (brs, 1H); ESIMS found for $C_{26}H_{22}N_8O_2$ m/z 479.2 (M+1).

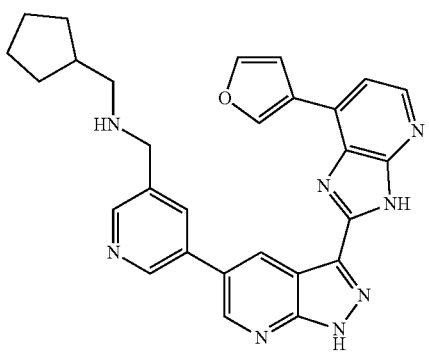

282

1-Cyclopentyl-N-((5-(3-(7-(furan-3-yl)-3H-imidazo[4,5-b]pyridin-2-yl)-1H-pyrazolo[3,4-b]pyridin-5-yl)pyridin-3-yl)methyl)methanamine 282.

White solid (24.9 mg, 0.05 mmol). $^1$H NMR (DMSO-$d_6$, 400 MHz) δ ppm 1.20-1.32 (m, 2H), 1.48-1.65 (m, 4H), 1.76-1.87 (m, 2H), 2.24 (spt, J=7.80 Hz, 1H), 2.95-3.04 (m, 2H), 4.34 (brs, 2H), 7.44 (brs, 1H), 7.57 (d, J=5.02 Hz, 1H), 7.90 (t, J=1.51 Hz, 1H), 8.36 (d, J=5.02 Hz, 1H), 8.58 (s, 1H), 8.80 (d, J=1.76 Hz, 1H), 9.01 (s, 1H), 9.09 (d, J=2.26 Hz, 1H), 9.16 (dd, J=5.02, 1.76 Hz, 4H), 13.95 (brs, 1H), 14.57 (s, 1H); ESIMS found for $C_{28}H_{26}N_8O$ m/z 491.2 (M+1).

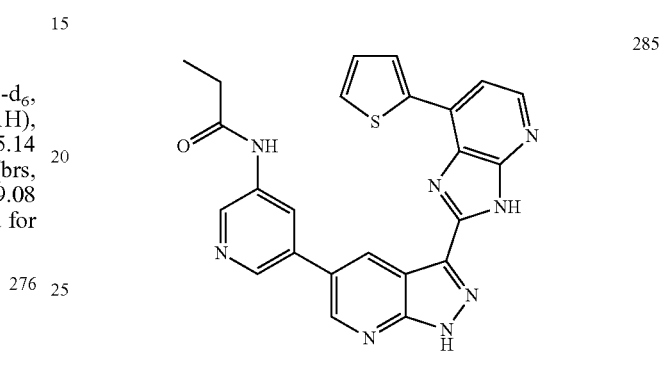

285

N-(5-(3-(7-(Thiophen-2-yl)-3H-imidazo[4,5-b]pyridin-2-yl)-1H-pyrazolo[3,4-b]pyridin-5-yl)pyridin-3-yl)propionamide 285.

White solid (11.0 mg, 0.02 mmol). $^1$H NMR (DMSO-$d_6$, 400 MHz) δ ppm 1.17 (t, J=7.47 Hz, 3H), 7.33 (t, J=4.0 Hz, 1H), 7.68 (d, J=5.02 Hz, 1H), 7.84 (d, J=4.77 Hz, 1H), 8.32-8.39 (m, 2H), 8.88 (brs, 1H), 8.89 (brs, 1H), 8.92 (s, 1H), 9.08 (d, J=2.01 Hz, 1H), 9.27 (d, J=1.88 Hz, 1H), 10.70 (brs, 1H), 14.60 (brs, 1H); ESIMS found for $C_{24}H_{18}N_8OS$ m/z 467.1 (M+1).

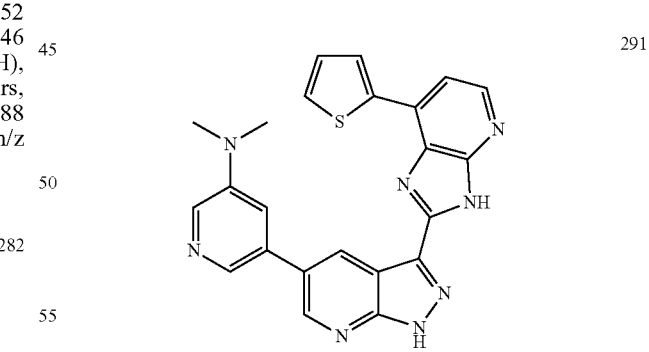

291

N,N-Dimethyl-5-(3-(7-(thiophen-2-yl)-3H-imidazo[4,5-b]pyridin-2-yl)-1H-pyrazolo[3,4-b]pyridin-5-yl)pyridin-3-amine 291.

White solid (12.0 mg, 0.03 mmol). $^1$H NMR (DMSO-$d_6$, 400 MHz) δ ppm 3.20 (brs, 7H), 7.31 (brs, 1H), 7.68 (d, J=4.52 Hz, 1H), 7.85-7.90 (m, 1H), 8.12 (brs, 1H), 8.30 (brs, 1H), 8.37 (brs, 2H), 8.61 (brs, 1H), 9.18 (brs, 1H), 9.34 (brs, 1H), 14.06 (brs, 1H), 14.63 (brs, 1H); ESIMS found for $C_{23}H_{18}N_8S$ m/z 439.1 (M+1).

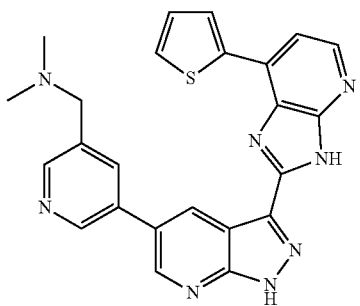

N,N-Dimethyl-1-(5-(3-(7-(thiophen-2-yl)-3H-imidazo[4,5-b]pyridin-2-yl)-1H-pyrazolo[3,4-b]pyridin-5-yl)pyridin-3-yl)methanamine 297.

White solid (12.8 mg, 0.03 mmol). $^1$H NMR (DMSO-$d_6$, 400 MHz) δ ppm 2.82 (d, J=4.64 Hz, 6H), 4.51 (d, J=4.89 Hz, 3H), 7.29-7.35 (m, 1H), 7.68 (d, J=5.27 Hz, 1H), 7.87 (d, J=4.89 Hz, 1H), 8.34-8.41 (m, 2H), 8.75 (brs, 1H), 8.93 (brs, 1H), 9.15 (s, 1H), 9.25 (s, 1H), 9.30 (d, J=2.01 Hz, 1H), 11.14 (brs, 1H), 14.64 (brs, 1H); ESIMS found for $C_{24}H_{20}N_8S$ m/z 453.2 (M+1).

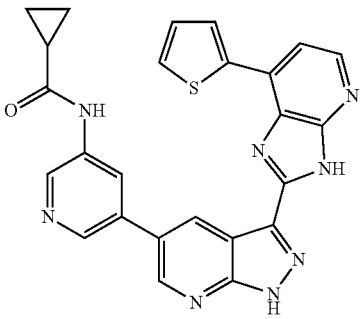

N-(5-(3-(7-(Thiophen-2-yl)-3H-imidazo[4,5-b]pyridin-2-yl)-1H-pyrazolo[3,4-b]pyridin-5-yl)pyridin-3-yl)cyclopropanecarboxamide 303.

White solid (21.0 mg, 0.04 mmol). $^1$H NMR (DMSO-$d_6$, 400 MHz) δ ppm 0.87-0.97 (m, 4H), 1.87-1.96 (m, 1H), 7.31 (dd, J=4.77, 3.89 Hz, 1H), 7.67 (d, J=5.14 Hz, 1H), 7.79 (d, J=4.77 Hz, 1H), 8.30-8.39 (m, 2H), 8.79 (s, 1H), 8.87 (d, J=4.89 Hz, 2H), 9.07 (d, J=2.13 Hz, 1H), 9.25 (d, J=1.88 Hz, 1H), 10.94 (s, 1H), 14.04 (brs, 1H), 14.57 (brs, 1H); ESIMS found for $C_{25}H_{18}N_8OS$ m/z 479.2 (M+1).

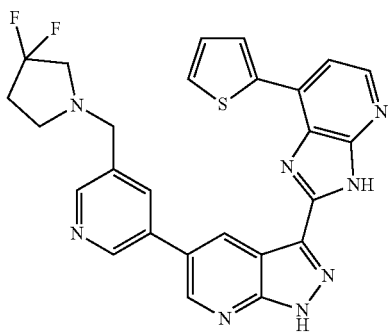

5-(5-((3,3-Difluoropyrrolidin-1-yl)methyl)pyridin-3-yl)-3-(7-(thiophen-2-yl)-3H-imidazo[4,5-b]pyridin-2-yl)-1H-pyrazolo[3,4-b]pyridine 309.

White solid (20.0 mg, 0.04 mmol). $^1$H NMR (DMSO-$d_6$, 400 MHz) δ ppm 2.66 (brs, 2H), 3.71 (brs, 2H), 4.01 (t, J=12.17 Hz, 2H), 4.79 (brs, 2H), 7.33 (t, J=4.08 Hz, 1H), 7.69 (d, J=5.14 Hz, 1H), 7.99 (d, J=4.64 Hz, 1H), 8.30-8.41 (m, 2H), 9.16 (brs, 1H), 9.21 (brs, 2H), 9.27 (s, 1H), 9.35 (brs, 1H), 14.75 (brs, 1H); ESIMS found for $C_{26}H_{20}F_2N_8S$ m/z 515.1 (M+1).

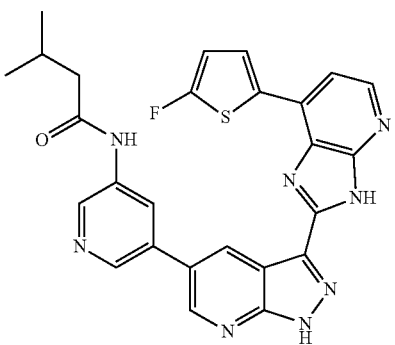

N-(5-(3-(7-(5-Fluorothiophen-2-yl)-3H-imidazo[4,5-b]pyridin-2-yl)-1H-pyrazolo[3,4-b]pyridin-5-yl)pyridin-3-yl)-3-methylbutanamide 312.

White solid (46.8 mg, 0.09 mmol). $^1$H NMR (DMSO-$d_6$, 400 MHz) δ ppm 0.97 (d, J=6.53 Hz, 6H), 2.12 (non, J=6.4 Hz, 1H), 2.30 (d, J=7.15 Hz, 2H), 6.95 (d, J=3.89 Hz, 1H), 7.68 (d, J=5.27 Hz, 1H), 8.00 (t, J=3.64 Hz, 1H), 8.34 (d, J=5.27 Hz, 1H), 8.74 (s, 1H), 8.82 (s, 1H), 8.86 (s, 1H), 9.06 (s, 1H), 9.24 (s, 1H), 10.52 (brs, 1H), 14.06 (brs, 1H), 14.58 (s, 1H); ESIMS found for $C_{26}H_{21}FN_8OS$ m/z 513.2 (M+1).

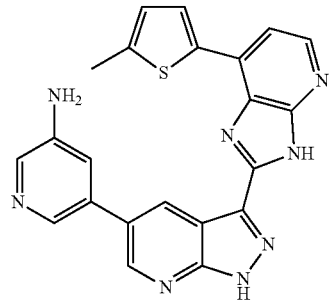

5-(3-(7-(5-Methylthiophen-2-yl)-3H-imidazo[4,5-b]pyridin-2-yl)-1H-pyrazolo[3,4-b]pyridin-5-yl)pyridin-3-amine 339.

White solid (126.0 mg, 0.30 mmol). $^1$H NMR (DMSO-$d_6$, 400 MHz) δ ppm 2.60 (s, 3H), 5.58 (s, 2H), 6.99 (d, J=2.89 Hz, 1H), 7.37 (t, J=2.24 Hz, 1H), 7.62 (d, J=5.15 Hz, 1H), 8.04 (d, J=2.51 Hz, 1H), 8.06 (d, J=3.64 Hz, 1H), 8.25 (d, J=2.01 Hz, 1H), 8.30 (d, J=5.15 Hz, 1H), 8.95 (d, J=2.13 Hz, 1H), 9.32 (d, J=2.26 Hz, 1H), 13.95 (brs, 1H), 14.42 (s, 1H); ESIMS found for $C_{22}H_{16}N_8S$ m/z 425.0 (M+1).

345

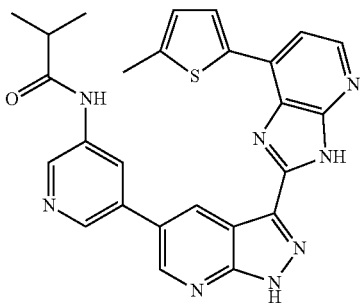

N-(5-(3-(7-(5-Methylthiophen-2-yl)-3H-imidazo[4,5-b]pyridin-2-yl)-1H-pyrazolo[3,4-b]pyridin-5-yl)pyridin-3-yl)isobutyramide 345.

White solid (9.0 mg, 0.02 mmol). $^1$H NMR (DMSO-$d_6$, 400 MHz) δ ppm 1.16 (d, J=6.90 Hz, 6H), 2.54 (s, 3H), 2.67-2.75 (m, 1H), 7.02 (d, J=2.64 Hz, 1H), 7.58 (d, J=5.40 Hz, 1H), 8.14 (d, J=3.76 Hz, 1H), 8.31 (d, J=5.15 Hz, 1H), 8.60 (t, J=2.32 Hz, 1H), 8.77 (d, J=1.88 Hz, 1H), 8.85 (d, J=2.51 Hz, 1H), 9.02 (d, J=2.26 Hz, 1H), 9.32 (d, J=1.88 Hz, 1H), 10.31 (s, 1H), 13.97 (s, 1H), 14.50 (s, 1H); ESIMS found for $C_{26}H_{22}N_8OS$ m/z 495.1 (M+1).

351

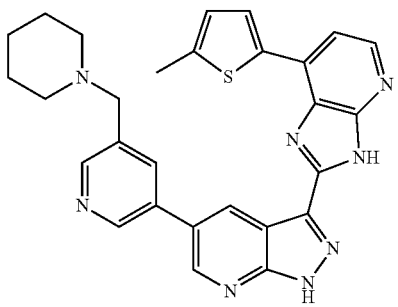

3-(7-(5-Methylthiophen-2-yl)-3H-imidazo[4,5-b]pyridin-2-yl)-5-(5-(piperidin-1-ylmethyl)pyridin-3-yl)-1H-pyrazolo[3,4-b]pyridine 351.

White solid (10.8 mg, 0.02 mmol). $^1$H NMR (DMSO-$d_6$, 400 MHz) δ ppm 1.33-1.46 (m, 1H), 1.66-1.74 (m, 1H), 1.76-1.86 (m, 4H), 2.61 (s, 3H), 2.88-3.01 (m, 2H), 3.42 (d, J=9.79 Hz, 2H), 4.47 (d, J=5.02 Hz, 2H), 7.02 (d, J=3.64 Hz, 1H), 7.62 (d, J=5.40 Hz, 1H), 8.15 (d, J=3.64 Hz, 1H), 8.33 (d, J=5.27 Hz, 1H), 8.75 (brs, 1H), 8.89 (s, 1H), 9.17 (d, J=2.26 Hz, 1H), 9.25 (d, J=2.01 Hz, 1H), 9.41 (d, J=2.13 Hz, 1H), 10.73 (brs, 1H), 14.58 (brs, 1H); ESIMS found for $C_{28}H_{26}N_8S$ m/z 507.3 (M+1).

357

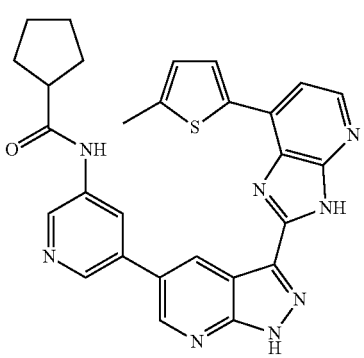

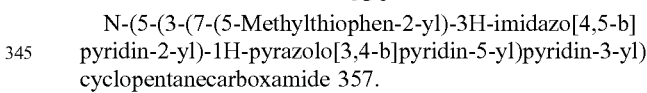

N-(5-(3-(7-(5-Methylthiophen-2-yl)-3H-imidazo[4,5-b]pyridin-2-yl)-1H-pyrazolo[3,4-b]pyridin-5-yl)pyridin-3-yl)cyclopentanecarboxamide 357.

White solid (12.0 mg, 0.02 mmol). $^1$H NMR (DMSO-$d_6$, 400 MHz) δ ppm 1.54-1.84 (m, 6H), 1.87-1.98 (m, 2H), 2.87-2.97 (m, 1H), 7.01 (d, J=1.38 Hz, 1H), 7.59 (d, J=4.77 Hz, 1H), 8.16 (d, J=2.89 Hz, 1H), 8.31 (d, J=4.89 Hz, 1H), 8.85 (brs, 1H), 8.99 (brs, 1H), 9.06 (brs, 1H), 9.12 (brs, 1H), 9.28 (brs, 1H), 10.95 (brs, 1H), 14.64 (brs, 1H); ESIMS found for $C_{28}H_{24}N_8OS$ m/z 521.2 (M+1).

384

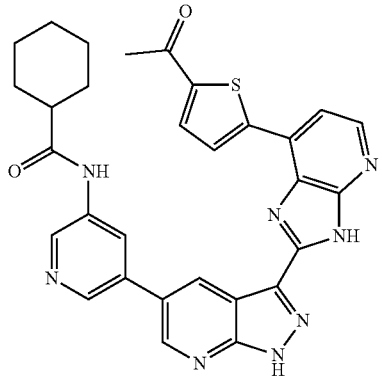

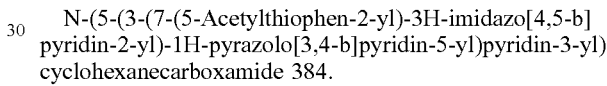

N-(5-(3-(7-(5-Acetylthiophen-2-yl)-3H-imidazo[4,5-b]pyridin-2-yl)-1H-pyrazolo[3,4-b]pyridin-5-yl)pyridin-3-yl)cyclohexanecarboxamide 384.

White solid (17.0 mg, 0.03 mmol). $^1$H NMR (DMSO-$d_6$, 400 MHz) δ ppm 1.19-1.36 (m, 4H), 1.38-1.51 (m, 2H), 1.66 (d, J=10.92 Hz, 1H), 1.77 (d, J=12.92 Hz, 2H), 1.88 (brs, 1H), 2.43-2.48 (m, 1H), 2.56 (s, 3H), 7.76 (d, J=5.27 Hz, 1H), 8.07 (d, J=4.02 Hz, 1H), 8.37-8.46 (m, 2H), 8.90 (s, 1H), 9.07 (d, J=2.13 Hz, 1H), 9.09 (s, 1H), 9.27 (d, J=2.01 Hz, 1H), 9.29 (d, J=1.51 Hz, 1H), 11.03 (s, 1H), 14.71 (brs, 1H); ESIMS found for $C_{30}H_{26}N_8O_2S$ m/z 563.2 (M+1).

393

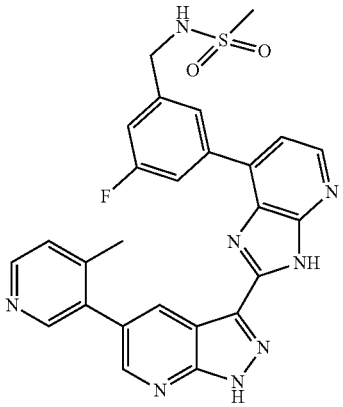

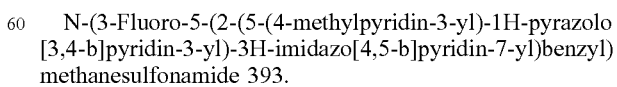

N-(3-Fluoro-5-(2-(5-(4-methylpyridin-3-yl)-1H-pyrazolo[3,4-b]pyridin-3-yl)-3H-imidazo[4,5-b]pyridin-7-yl)benzyl)methanesulfonamide 393.

White solid (17.0 mg, 0.03 mmol). $^1$H NMR (CD$_3$OD, 400 MHz) δ ppm 2.68 (s, 3H), 2.89 (s, 3H), 4.37 (s, 2H), 7.36 (d, J=8.85 Hz, 1H), 7.72 (d, J=5.65 Hz, 1H), 7.85 (d, J=9.42 Hz, 1H), 8.08 (brs, 1H), 8.14 (d, J=6.22 Hz, 1H), 8.54 (d, J=5.46 Hz, 1H), 8.77 (d, J=2.07 Hz, 1H), 8.80 (d, J=6.03

Hz, 1H), 8.92 (s, 1H), 9.08 (d, J=2.07 Hz, 1H); ESIMS found for C<sub>26</sub>H<sub>21</sub>FN<sub>8</sub>O<sub>2</sub>S m/z 529.2 (M+1).

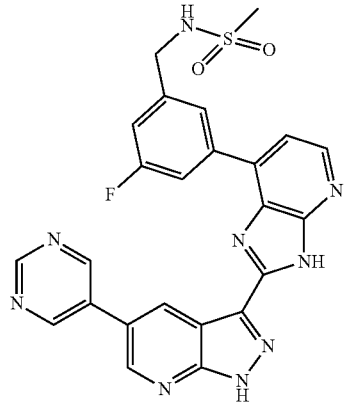

414

N-(3-Fluoro-5-(2-(5-(pyrimidin-5-yl)-1H-pyrazolo[3,4-b]pyridin-3-yl)-3H-imidazo[4,5-b]pyridin-7-yl)benzyl)methanesulfonamide 414.

White solid (26.0 mg, 0.05 mmol). $^1$H NMR (DMSO-d$_6$, 400 MHz) δ ppm 2.93 (s, 3H), 4.33 (d, J=6.15 Hz, 2H), 7.34 (d, J=9.41 Hz, 1H), 7.67 (d, J=5.02 Hz, 1H), 7.83 (t, J=6.27 Hz, 1H), 8.23 (brs, 1H), 8.45 (d, J=5.02 Hz, 1H), 8.78-8.99 (m, 3H), 9.11 (d, J=2.01 Hz, 1H), 9.18 (d, J=1.88 Hz, 1H), 9.27 (s, 1H), 9.32 (s, 2H), 14.12 (brs, 1H), 14.66 (s, 1H); ESIMS found for C$_{24}$H$_{18}$FN$_9$O$_2$S m/z 516.2 (M+1).

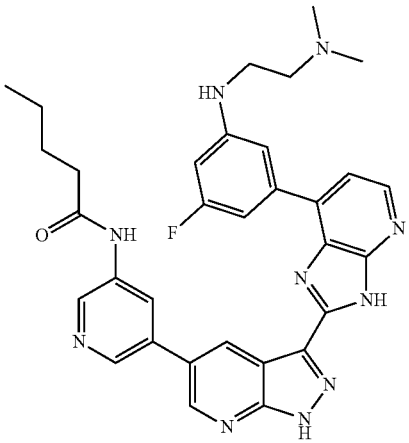

432

N-(5-(3-(7-(3-((2-(Dimethylamino)ethyl)amino)-5-fluorophenyl)-3H-imidazo[4,5-b]pyridin-2-yl)-1H-pyrazolo[3,4-b]pyridin-5-yl)pyridin-3-yl)pentanamide 432.

White solid (29.6 mg, 0.05 mmol). $^1$H NMR (DMSO-d$_6$, 400 MHz) δ ppm 0.92 (t, J=7.34 Hz, 3H), 1.36 (sxt, J=7.36 Hz, 2H), 1.62 (quin, J=7.47 Hz, 2H), 2.43 (t, J=7.40 Hz, 2H), 2.82 (d, J=3.76 Hz, 6H), 3.22-3.30 (m, 3H), 6.60 (d, J=11.17 Hz, 1H), 7.48 (brs, 2H), 7.59 (d, J=5.14 Hz, 1H), 8.45 (d, J=5.15 Hz, 1H), 8.55 (s, 1H), 8.87 (s, 1H), 8.99 (d, J=2.01 Hz, 2H), 9.11 (d, J=2.13 Hz, 1H), 10.06 (brs, 1H), 10.58 (brs, 1H), 14.61 (brs, 1H); ESIMS found for C$_{32}$H$_{33}$FN$_{10}$O m/z 593.3 (M+1).

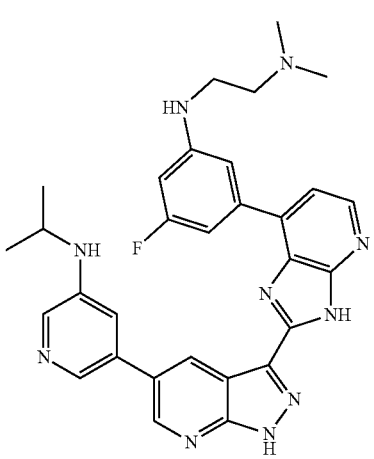

426

N$^1$-(3-Fluoro-5-(2-(5-(5-(isopropylamino)pyridin-3-yl)-1H-pyrazolo [3,4-b]pyridin-3-yl)-3H-imidazo[4,5-b]pyridin-7-yl)phenyl)-N$^2$,N$^2$-dimethylethane-1,2-diamine 426.

White solid (16.0 mg, 0.03 mmol). $^1$H NMR (DMSO-d$_6$, 400 MHz) δ ppm 1.22 (d, J=6.02 Hz, 6H), 2.80 (brs, 6H), 3.23 (brs, 2H), 3.82-3.93 (m, 2H), 6.62 (d, J=11.17 Hz, 1H), 7.34 (brs, 1H), 7.52 (brs, 1H), 7.61 (d, J=4.77 Hz, 1H), 7.96 (brs, 1H), 8.16 (brs, 1H), 8.47 (brs, 1H), 8.50 (brs, 1H), 9.03 (brs, 1H), 9.09 (brs, 1H), 10.56 (brs, 1H), 14.73 (brs, 1H); ESIMS found for C$_{30}$H$_{31}$FN$_{10}$ m/z 551.2 (M+1).

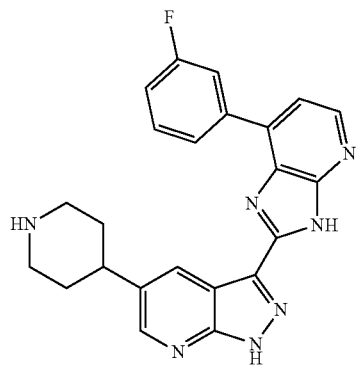

909

3-(7-(3-Fluorophenyl)-3H-imidazo[4,5-b]pyridin-2-yl)-5-(piperidin-4-yl)-1H-pyrazolo[3,4-b]pyridine 909.

Gray solid (4.0 mg, 0.008 mmol). $^1$H NMR (DMSO-d$_6$, 500 MHz) δ ppm 0.85 (br t, J=7.00 Hz, 2H), 1.48 (br s, 1H), 1.90-2.03 (m, 2H), 2.15-2.22 (m, 2H), 3.04-3.12 (m, 1H), 3.43 (br d, J=12.90 Hz, 1H), 7.35-7.43 (m, 1H), 7.71 (br s, 2H), 8.38 (br s, 1H), 8.44 (br d, J=4.67 Hz, 1H), 8.53 (br s, 1H), 8.64 (s, 1H), 8.73 (s, 1H); ESIMS found for C$_{23}$H$_{20}$FN$_7$ m/z 414.3 (M+1).

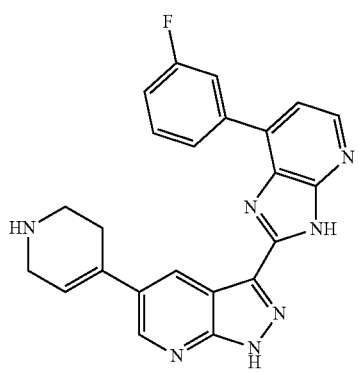

3-(7-(3-Fluorophenyl)-3H-imidazo[4,5-b]pyridin-2-yl)-5-(1,2,3,6-tetrahydropyridin-4-yl)-1H-pyrazolo[3,4-b]pyridine 910.

Yellow solid (7.0 mg, 0.01 mmol). $^1$H NMR (DMSO-d$_6$, 500 MHz) δ ppm 2.60 (br s, 2H), 3.10 (br s, 2H), 3.53 (br s, 2H), 6.48 (br s, 1H), 7.39 (s, 1H), 7.61-7.67 (m, 1H), 7.69 (br s, 1H), 8.24 (br s, 1H), 8.43 (d, J=5.21 Hz, 1H), 8.65 (br s, 1H), 8.88 (s, 1H), 8.89 (s, 1H); ESIMS found for C$_{23}$H$_{18}$FN$_7$ m/z 412.2 (M+1).

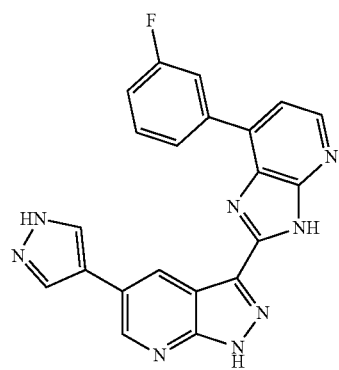

3-(7-(3-Fluorophenyl)-3H-imidazo[4,5-b]pyridin-2-yl)-5-(1H-pyrazol-4-yl)-1H-pyrazolo[3,4-b]pyridine 911.

Black solid (5.6 mg, 0.01 mmol). $^1$H NMR (DMSO-d$_6$, 500 MHz) δ ppm 7.36-7.44 (m, 1H), 7.60-7.75 (m, 3H), 8.27 (br d, J=7.96 Hz, 1H), 8.34 (br s, 1H), 8.43 (d, J=5.21 Hz, 1H), 8.70 (br d, J=11.25 Hz, 1H), 8.98 (d, J=1.65 Hz, 1H), 9.01 (d, J=1.92 Hz, 1H), 13.16 (br s, 1H), 13.98 (s, 1H), 14.31 (s, 1H); ESIMS found for C$_{21}$H$_{13}$FN$_8$ m/z 397.1 (M+1).

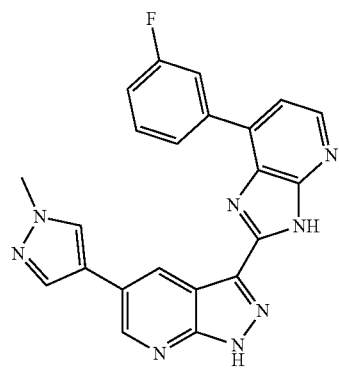

3-(7-(3-Fluorophenyl)-3H-imidazo[4,5-b]pyridin-2-yl)-5-(1-methyl-1H-pyrazol-4-yl)-1H-pyrazolo[3,4-b]pyridine 912.

Orange solid (21.0 mg, 0.05 mmol). $^1$H NMR (DMSO-d$_6$, 500 MHz) δ ppm 3.94 (s, 3H), 7.40 (br t, J=7.55 Hz, 1H), 7.64-7.74 (m, 2H), 7.97 (s, 1H), 8.22-8.30 (m, 2H), 8.43 (d, J=5.21 Hz, 1H), 8.70 (br d, J=11.25 Hz, 1H), 8.95 (br s, 1H), 8.96 (br s, 1H), 13.98 (br s, 1H), 14.32 (br s, 1H); ESIMS found for C$_{22}$H$_{15}$FN$_8$ m/z 411.1 (M+1).

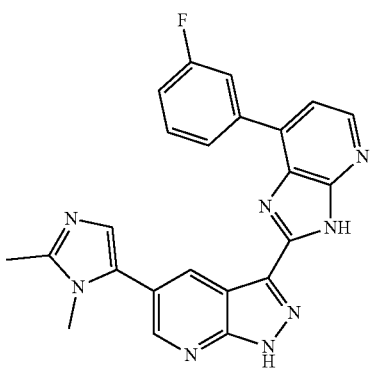

5-(1,2-Dimethyl-1H-imidazol-5-yl)-3-(7-(3-fluorophenyl)-3H-imidazo[4,5-b]pyridin-2-yl)-1H-pyrazolo[3,4-b]pyridine 913.

Yellow solid (1.3 mg, 0.003 mmol). $^1$H NMR (DMSO-d$_6$, 500 MHz) δ ppm 2.42 (s, 3H), 3.66 (s, 3H), 7.09 (s, 1H), 7.33-7.41 (m, 1H), 7.60-7.71 (m, 2H), 8.25 (br d, J=7.68 Hz, 1H), 8.43 (br d, J=5.21 Hz, 1H), 8.49 (br d, J=10.15 Hz, 1H), 8.77 (s, 1H), 8.86 (s, 1H), 14.00 (brs, 1H), 14.46 (brs, 1H); ESIMS found for C$_{23}$H$_{17}$FN$_8$ m/z 425.1 (M+1).

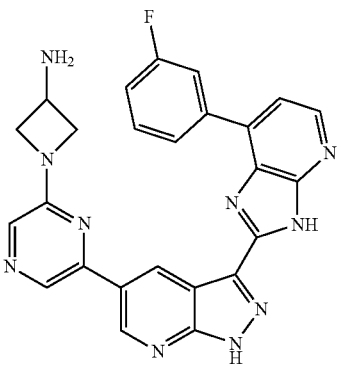

1-(6-(3-(7-(3-Fluorophenyl)-3H-imidazo[4,5-b]pyridin-2-yl)-1H-pyrazolo[3,4-b]pyridin-5-yl)pyrazin-2-yl)azetidin-3-amine 914.

Yellow solid (42.3 mg, 0.09 mmol). $^1$H NMR (DMSO-d$_6$, 500 MHz) δ ppm 3.69-3.78 (m, 2H), 3.92 (br s, 1H), 4.30 (br t, J=7.82 Hz, 2H), 7.30-7.39 (m, 1H), 7.51 (br d, J=4.67 Hz, 1H), 7.58-7.67 (m, 1H), 7.86 (s, 1H), 8.26-8.36 (m, 2H), 8.48 (br d, J=12.62 Hz, 1H), 8.52 (s, 1H), 9.21 (s, 1H), 9.40 (s, 1H); ESIMS found for C$_{25}$H$_{19}$FN$_{10}$ m/z 479.2 (M+H).

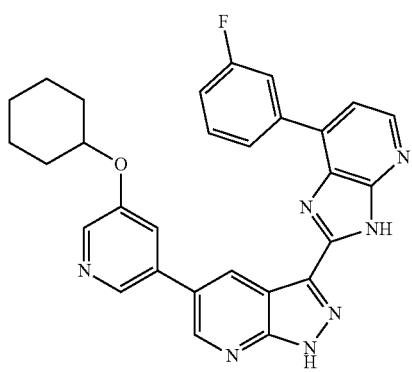

5-(5-(Cyclohexyloxy)pyridin-3-yl)-3-(7-(3-fluorophenyl)-3H-imidazo[4,5-b]pyridin-2-yl)-1H-pyrazolo[3,4-b]pyridine 915.

Brown solid (34 mg, 0.067 mmol, 20.87% yield). $^1$H NMR (DMSO-$d_6$, 500 MHz) δ ppm 1.25-1.36 (m, 1H), 1.36-1.46 (m, 2H), 1.47-1.59 (m, 3H), 1.69-1.79 (m, 2H), 1.95-2.05 (m, 2H), 4.59-4.69 (m, 1H), 7.34 (td, J=8.37, 1.92 Hz, 1H), 7.57-7.66 (m, 1H), 7.70 (d, J=5.21 Hz, 1H), 7.83 (t, J=2.20 Hz, 1H), 8.31 (d, J=7.96 Hz, 1H), 8.37 (d, J=2.47 Hz, 1H), 8.44 (d, J=4.94 Hz, 1H), 8.55 (br d, J=10.98 Hz, 1H), 8.60 (d, J=1.65 Hz, 1H), 9.07 (d, J=1.92 Hz, 1H), 9.12 (d, J=1.92 Hz, 1H), 14.05 (br s, 1H), 14.50 (br s, 1H); ESIMS found for $C_{29}H_{24}FN_7O$ m/z 506.2 (M+1).

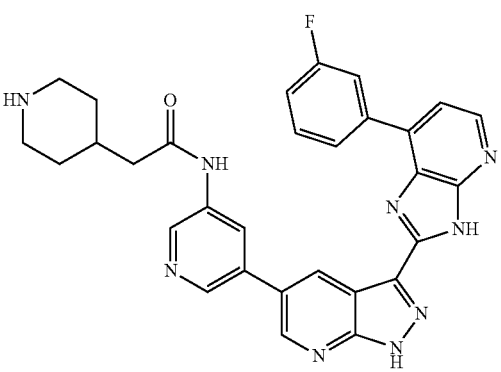

N-(5-(3-(7-(3-Fluorophenyl)-3H-imidazo[4,5-b]pyridin-2-yl)-1H-pyrazolo [3,4-b]pyridin-5-yl)pyridin-3-yl)-2-(piperidin-4-yl)acetamide 917.

Brown solid (25.1 mg, 0.05 mmol). $^1$H NMR (DMSO-$d_6$, 500 MHz) δ ppm 1.28-1.39 (m, 2H), 1.80 (br d, J=13.45 Hz, 2H), 2.37 (br d, J=7.14 Hz, 2H), 2.75 (br t, J=12.90 Hz, 2H), 3.16 (br d, J=13.72 Hz, 1H), 7.29-7.36 (m, 1H), 7.62-7.70 (m, 2H), 8.31 (br s, 1H), 8.43-8.50 (m, 2H), 8.53 (br s, 1H), 8.74 (d, J=1.92 Hz, 1H), 8.80 (s, 1H), 8.99 (d, J=1.92 Hz, 1H), 9.09 (d, J=2.20 Hz, 1H), 10.36 (s, 1H); ESIMS found for $C_{30}H_{26}FN_9O$ m/z 548.1 (M+1).

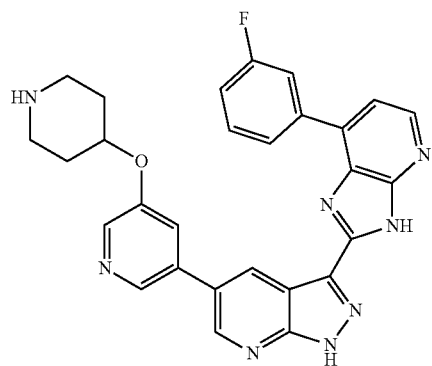

3-(7-(3-Fluorophenyl)-3H-imidazo[4,5-b]pyridin-2-yl)-5-(5-(piperidin-4-yloxy)pyridin-3-yl)-1H-pyrazolo[3,4-b]pyridine 916.

Dark yellow solid (22 mg, 0.041 mmol, 64.8% yield). $^1$H NMR (DMSO-$d_6$, 500 MHz) δ ppm 1.85-1.97 (m, 2H), 2.12-2.22 (m, 2H), 3.11 (ddd, J=12.49, 8.51, 3.43 Hz, 2H), 3.26-3.32 (m, 2H), 4.88-4.97 (m, 1H), 7.37 (td, J=8.44, 2.33 Hz, 1H), 7.59-7.67 (m, 1H), 7.70 (br d, J=4.12 Hz, 1H), 7.93 (t, J=2.20 Hz, 1H), 8.30 (br d, J=8.23 Hz, 1H), 8.42-8.49 (m, 2H), 8.59 (br d, J=9.33 Hz, 1H), 8.68 (d, J=1.65 Hz, 1H), 9.08 (d, J=2.20 Hz, 1H), 9.14 (s, 1H); ESIMS found for $C_{28}H_{23}FN_8O$ m/z 507.2 (M+1).

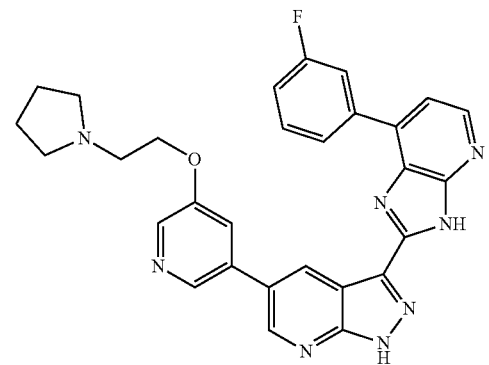

3-(7-(3-Fluorophenyl)-3H-imidazo[4,5-b]pyridin-2-yl)-5-(5-(2-(pyrrolidin-1-yl)ethoxy)pyridin-3-yl)-1H-pyrazolo[3,4-b]pyridine 918.

Beige solid (6.5 mg, 0.012 mmol, 65.2% yield). $^1$H NMR (DMSO-$d_6$, 500 MHz) δ ppm 1.70 (br t, J=3.29 Hz, 4H), 2.56 (br s, 4H), 2.88 (br t, J=5.63 Hz, 2H), 4.29 (t, J=5.76 Hz, 2H), 7.34 (td, J=8.51, 2.47 Hz, 1H), 7.57-7.65 (m, 1H), 7.69 (br d, J=4.67 Hz, 1H), 7.86 (t, J=2.06 Hz, 1H), 8.30 (br d, J=7.68 Hz, 1H), 8.38 (d, J=2.74 Hz, 1H), 8.44 (d, J=5.21 Hz, 1H), 8.55 (br d, J=11.25 Hz, 1H), 8.63 (d, J=1.65 Hz, 1H), 9.08 (d, J=2.20 Hz, 1H), 9.14 (s, 1H), 14.05 (br s, 1H), 14.50 (br s, 1H); ESIMS found for $C_{29}H_{25}FN_8O$ m/z 521.2 (M+1).

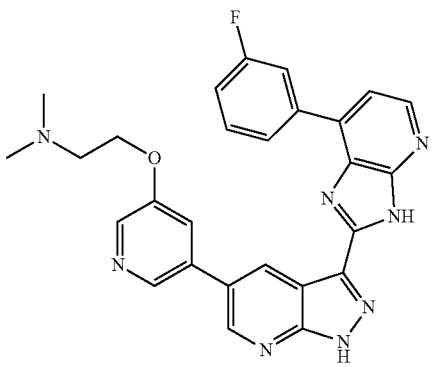

2-((5-(3-(7-(3-Fluorophenyl)-3H-imidazo[4,5-b]pyridin-2-yl)-1H-pyrazolo [3,4-b]pyridin-5-yl)pyridin-3-yl)oxy)-N,N-dimethylethan-1-amine 919.

Yellow solid (4.5 mg, 0.009 mmol). ¹H NMR (DMSO-d₆, 500 MHz) δ ppm 2.25 (s, 6H), 2.71 (t, J=5.63 Hz, 2H), 4.27 (t, J=5.76 Hz, 2H), 7.34 (td, J=8.58, 2.06 Hz, 1H), 7.59-7.66 (m, 1H), 7.69 (br s, 1H), 7.83-7.87 (m, 1H), 8.30 (br s, 1H), 8.38 (d, J=2.74 Hz, 1H), 8.44 (d, J=5.21 Hz, 1H), 8.55 (br d, J=11.80 Hz, 1H), 8.64 (d, J=1.92 Hz, 1H), 9.08 (d, J=2.20 Hz, 1H), 9.14 (s, 1H), 14.02 (br s, 1H), 14.46 (br s, 1H); ESIMS found for C₂₇H₂₃FN₈O m/z 495.2 (M+1).

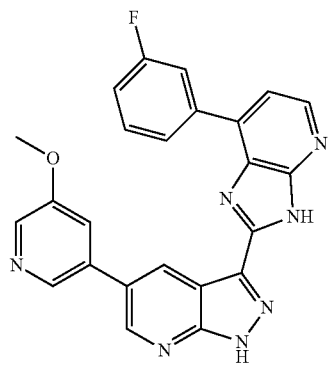

3-(7-(3-Fluorophenyl)-3H-imidazo[4,5-b]pyridin-2-yl)-5-(5-methoxypyridin-3-yl)-1H-pyrazolo[3,4-b]pyridine 920.

Orange solid (2.0 mg, 0.005 mmol). ¹H NMR (DMSO-d₆, 500 MHz) δ ppm 3.97 (s, 3H), 7.35 (td, J=8.37, 2.20 Hz, 1H), 7.57-7.69 (m, 2H), 7.81-7.85 (m, 1H), 8.27 (br s, 1H), 8.39 (d, J=2.74 Hz, 1H), 8.42 (d, J=4.94 Hz, 1H), 8.55 (br s, 1H), 8.64 (d, J=1.65 Hz, 1H), 9.05 (d, J=2.20 Hz, 1H), 9.14 (d, J=2.20 Hz, 1H); ESIMS found for C₂₄H₁₆FN₇O m/z 438.2 (M+1).

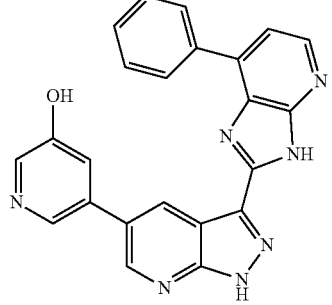

5-(3-(7-(3-Fluorophenyl)-3H-imidazo[4,5-b]pyridin-2-yl)-1H-pyrazolo[3,4-b] pyridin-5-yl)pyridin-3-ol 921.

Yellow solid (8.2 mg, 0.02 mmol). ¹H NMR (DMSO-d₆, 500 MHz) δ ppm 7.36 (td, J=8.78, 2.47 Hz, 1H), 7.56 (t, J=2.20 Hz, 1H), 7.63 (td, J=7.96, 6.31 Hz, 1H), 7.70 (d, J=4.94 Hz, 1H), 8.24 (d, J=2.47 Hz, 1H), 8.33 (d, J=7.68 Hz, 1H), 8.44 (d, J=5.21 Hz, 1H), 8.49-8.56 (m, 2H), 8.99 (d, J=2.47 Hz, 1H), 9.09 (d, J=2.20 Hz, 1H), 10.16 (s, 1H), 14.04 (s, 1H), 14.48 (s, 1H); ESIMS found for C₂₃H₁₄FN₇O m/z 424.1 (M+1).

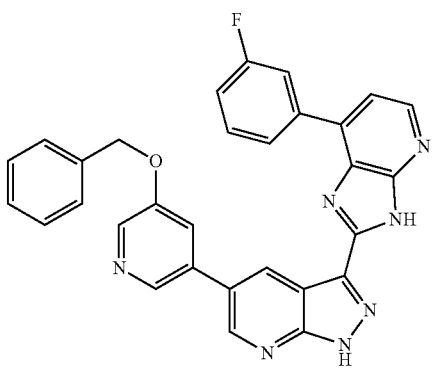

5-(5-(Benzyloxy)pyridin-3-yl)-3-(7-(3-fluorophenyl)-3H-imidazo[4,5-b]pyridin-2-yl)-1H-pyrazolo[3,4-b]pyridine 922.

Brown solid (20 mg, 0.035 mmol, 12.85% yield). ¹H NMR (DMSO-d₆, 500 MHz) δ ppm 5.32 (s, 2H), 7.21-7.30 (m, 1H), 7.35-7.41 (m, 1H), 7.45 (t, J=7.55 Hz, 2H), 7.54 (d, J=7.14 Hz, 2H), 7.58-7.65 (m, 1H), 7.70 (d, J=4.94 Hz, 1H), 7.96 (s, 1H), 8.31 (br d, J=7.68 Hz, 1H), 8.44 (d, J=5.21 Hz, 1H), 8.46 (d, J=2.74 Hz, 1H), 8.56 (br d, J=11.25 Hz, 1H), 8.68 (d, J=1.37 Hz, 1H), 9.09 (d, J=1.92 Hz, 1H), 9.17 (d, J=1.92 Hz, 1H), 14.06 (br s, 1H), 14.51 (br s, 1H); ESIMS found for C₃₀H₂₀FN₇O m/z 514.2 (M+1).

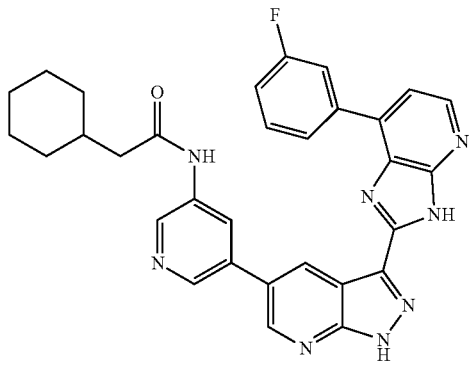

2-Cyclohexyl-N-(5-(3-(7-(3-fluorophenyl)-3H-imidazo[4,5-b]pyridin-2-yl)-1H-pyrazolo[3,4-b]pyridin-5-yl)pyridin-3-yl)acetamide 923.

Amber colored solid (22 mg, 0.038 mmol, 20.97% yield). ¹H NMR (DMSO-d₆, 500 MHz) δ ppm 0.96-1.08 (m, 2H), 1.11-1.31 (m, 3H), 1.63 (br d, J=12.08 Hz, 1H), 1.68 (br d, J=12.90 Hz, 2H), 1.75 (br d, J=12.35 Hz, 2H), 1.82 (ddd, J=10.63, 7.07, 3.70 Hz, 1H), 2.29 (d, J=7.14 Hz, 2H), 7.29 (br t, J=7.55 Hz, 1H), 7.61-7.68 (m, 1H), 7.70 (br s, 1H), 8.36 (br s, 1H), 8.44 (d, J=5.21 Hz, 1H), 8.49 (br d, J=9.33 Hz, 1H), 8.55 (br s, 1H), 8.72 (d, J=1.92 Hz, 1H), 8.79 (s, 1H), 8.99 (d, J=2.20 Hz, 1H), 9.08 (d, J=1.92 Hz, 1H), 10.27 (s, 1H), 14.07 (br s, 1H), 14.51 (br s, 1H); ESIMS found for $C_{31}H_{27}FN_8O$ m/z 547.3 (M+1).

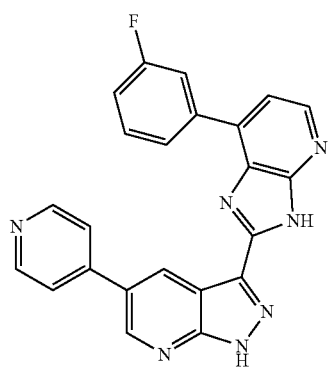

924

3-(7-(3-Fluorophenyl)-3H-imidazo[4,5-b]pyridin-2-yl)-5-(pyridin-4-yl)-1H-pyrazolo[3,4-b]pyridine 924.

Brown solid (25.0 mg, 0.06 mmol). $^1$H NMR (DMSO-d$_6$, 500 MHz) δ ppm 7.39 (td, J=8.37, 2.20 Hz, 1H), 7.62-7.69 (m, 1H), 7.72 (d, J=5.21 Hz, 1H), 7.91 (d, J=6.04 Hz, 2H), 8.27 (d, J=7.96 Hz, 1H), 8.45 (d, J=5.21 Hz, 1H), 8.66 (br d, J=11.53 Hz, 1H), 8.74 (d, J=6.04 Hz, 2H), 9.15 (d, J=2.20 Hz, 1H), 9.28 (d, J=2.20 Hz, 1H), 14.08 (br s, 1H), 14.53 (s, 1H); ESIMS found for $C_{23}H_{14}FN_7$ m/z 408.1 (M+1).

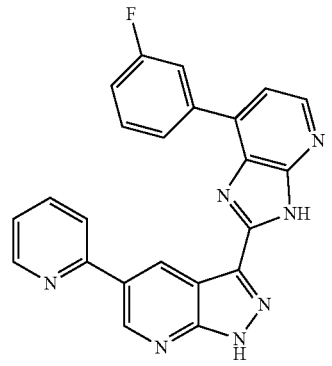

925

3-(7-(3-Fluorophenyl)-3H-imidazo[4,5-b]pyridin-2-yl)-5-(pyridin-2-yl)-1H-pyrazolo[3,4-b]pyridine 925.

Dark brown solid (15 mg, 0.033 mmol, 10.86% yield). $^1$H NMR (DMSO-d$_6$, 500 MHz) δ ppm 7.35-7.43 (m, 1H), 7.46 (br t, J=6.04 Hz, 1H), 7.64-7.76 (m, 2H), 7.94-8.04 (m, 1H), 8.16 (br d, J=9.06 Hz, 1H), 8.32 (br d, J=9.88 Hz, 1H), 8.45 (d, J=7.14 Hz, 1H), 8.63 (br d, J=11.25 Hz, 1H), 8.78 (br d, J=4.12 Hz, 1H), 9.40 (s, 1H), 9.62 (s, 1H), 14.07 (br s, 1H), 14.47 (br s, 1H); ESIMS found for $C_{23}H_{14}FN_7$ m/z 408.1 (M+1).

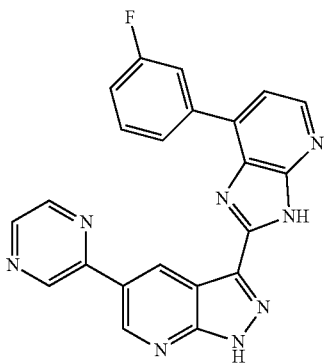

926

3-(7-(3-Fluorophenyl)-3H-imidazo[4,5-b]pyridin-2-yl)-5-(pyrazin-2-yl)-1H-pyrazolo[3,4-b]pyridine 926.

Brown solid (10 mg, 0.023 mmol, 7.16% yield). $^1$H NMR (DMSO-d$_6$, 500 MHz) δ ppm 7.40 (br t, J=8.23 Hz, 1H), 7.62-7.70 (m, 1H), 7.71 (br d, J=4.67 Hz, 1H), 8.32 (br d, J=7.41 Hz, 1H), 8.45 (br d, J=4.94 Hz, 1H), 8.60 (br d, J=10.98 Hz, 1H), 8.71 (d, J=2.20 Hz, 1H), 8.82 (s, 1H), 9.45 (d, J=2.20 Hz, 2H), 9.66 (s, 1H), 14.09 (br s, 1H), 14.56 (br s, 1H); ESIMS found for $C_{22}H_{13}FN_8$ m/z 409.1 (M+1).

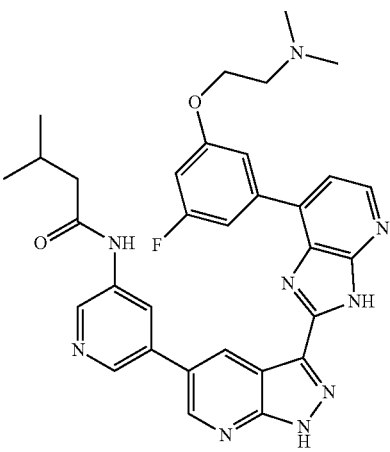

1234

N-(5-(3-(7-(3-(2-(Dimethylamino)ethoxy)-5-fluorophenyl)-3H-imidazo[4,5-b] pyridin-2-yl)-1H-pyrazolo[3,4-b]pyridin-5-yl)pyridin-3-yl)-3-methylbutanamide 1234.

Orange solid (8.8 mg, 0.015 mmol, 10.6% yield). $^1$H NMR (DMSO-d$_6$, 500 MHz) δ 0.97 (d, J=6.59 Hz, 6H), 2.04-2.17 (m, 7H), 2.27 (d, J=7.14 Hz, 2H), 2.43 (br s, 2H), 4.10 (br t, J=5.49 Hz, 2H), 6.93 (br d, J=10.43 Hz, 1H), 7.71 (br d, J=4.94 Hz, 1H), 7.96 (br d, J=10.98 Hz, 1H), 8.03 (br s, 1H), 8.39-8.47 (m, 1H), 8.69 (s, 1H), 8.86 (d, J=2.20 Hz, 1H), 8.96 (s, 1H), 9.04 (d, J=2.20 Hz, 1H), 10.26 (s, 1H), 14.06 (br s, 1H), 14.52 (br s, 1H); ESIMS found for $C_{32}H_{32}FN_9O_2$ m/z 594.3 (M+1).

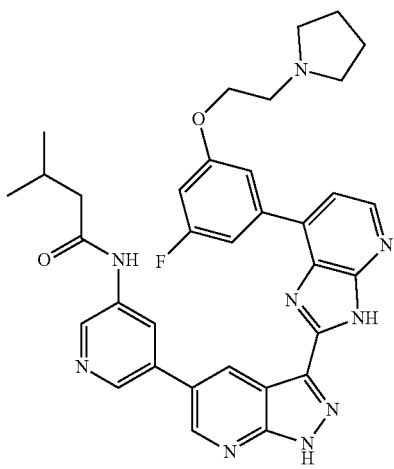

N-(5-(3-(7-(3-Fluoro-5-(2-(pyrrolidin-1-yl)ethoxy)phenyl)-3H-imidazo[4,5-b]pyridin-2-yl)-1H-pyrazolo[3,4-b]pyridin-5-yl)pyridin-3-yl)-3-methylbutanamide 1278.

Yellow solid (5.4 mg, 8.71 μmol, 13.63% yield). $^1$H NMR (DMSO-d$_6$, 500 MHz) δ ppm 0.97 (d, J=6.59 Hz, 6H), 1.59 (br s, 4H), 2.12 (td, J=13.45, 6.59 Hz, 1H), 2.27 (br d, J=7.14 Hz, 2H), 2.38 (br s, 4H), 2.57 (br s, 2H), 4.12 (br t, J=5.76 Hz, 2H), 6.92 (br d, J=10.15 Hz, 1H), 7.69 (br s, 1H), 7.95 (br s, 1H), 8.06 (br s, 1H), 8.41 (br d, J=4.94 Hz, 1H), 8.43 (br s, 1H), 8.68 (s, 1H), 8.86 (d, J=1.92 Hz, 1H), 8.95 (s, 1H), 9.04 (s, 1H), 10.26 (s, 1H), 14.02 (brs, 1H), 14.42 (brs, 1H); ESIMS found for C$_{34}$H$_{34}$FN$_9$O$_2$ m/z 620.3 (M+1).

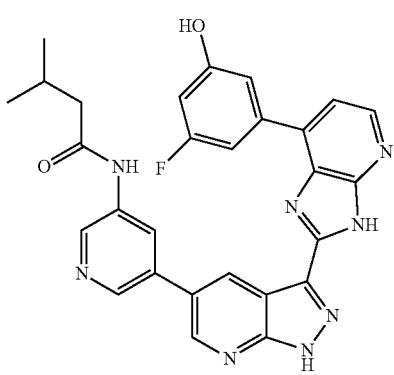

N-(5-(3-(7-(3-Fluoro-5-hydroxyphenyl)-3H-imidazo[4,5-b]pyridin-2-yl)-1H-pyrazolo[3,4-b]pyridin-5-yl)pyridin-3-yl)-3-methylbutanamide 1322.

Yellow solid (5.4 mg, 10.33 μmol, 9.22% yield). $^1$H NMR (DMSO-d$_6$, 500 MHz) δ ppm 0.98 (d, J=6.86 Hz, 6H), 2.08-2.18 (m, 1H), 2.28 (d, J=7.14 Hz, 2H), 6.67 (br d, J=10.43 Hz, 1H), 7.59 (br s, 1H), 7.75 (br s, 1H), 7.88 (br s, 1H), 8.39-8.45 (m, 2H), 8.74 (d, J=1.92 Hz, 1H), 8.86 (d, J=2.20 Hz, 1H), 8.98 (d, J=1.92 Hz, 1H), 9.11 (s, 1H), 10.12 (s, 1H), 10.22 (br s, 1H), 14.03 (br s, 1H), 14.52 (s, 1H); ESIMS found for C$_{28}$H$_{23}$FN$_8$O$_2$ m/z 523.2 (M+1).

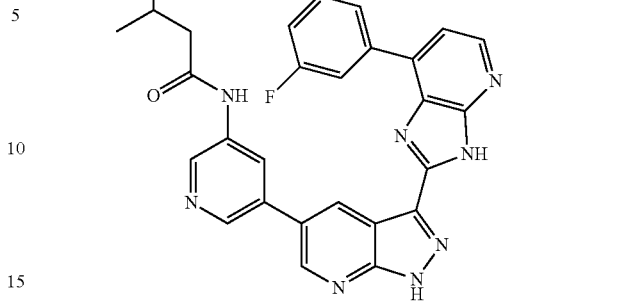

N-(5-(3-(7-(3-Fluoro-5-methoxyphenyl)-3H-imidazo[4,5-b]pyridin-2-yl)-1H-pyrazolo[3,4-b]pyridin-5-yl)pyridin-3-yl)-3-methylbutanamide 1366.

Yellow solid (19.8 mg, 0.037 mmol, 31.8% yield). $^1$H NMR (DMSO-d$_6$, 500 MHz) δ ppm 0.97 (br d, J=6.59 Hz, 6H), 2.11 (dt, J=13.38, 6.90 Hz, 1H), 2.28 (br d, J=7.14 Hz, 2H), 3.83 (s, 3H), 6.92 (br d, J=10.70 Hz, 1H), 7.68 (br s, 1H), 7.92 (br s, 1H), 8.11 (br s, 1H), 8.41 (br d, J=4.94 Hz, 1H), 8.44 (br s, 1H), 8.70 (s, 1H), 8.85 (s, 1H), 8.94 (s, 1H), 9.07 (s, 1H), 10.26 (s, 1H); ESIMS found for C$_{29}$H$_{25}$FN$_8$O$_2$ m/z 537.2 (M+1).

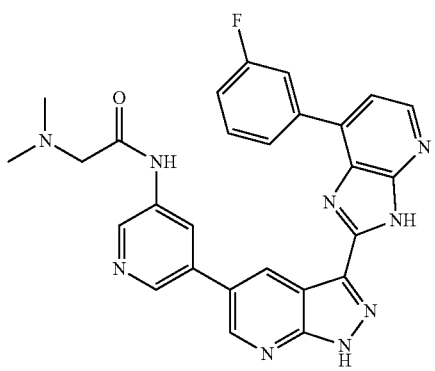

2-(Dimethylamino)-N-(5-(3-(7-(3-fluorophenyl)-3H-imidazo[4,5-b]pyridin-2-yl)-1H-pyrazolo[3,4-b]pyridin-5-yl)pyridin-3-yl)acetamide 1409.

Brown solid (5.3 mg, 0.01 mmol). $^1$H NMR (DMSO-d$_6$, 500 MHz) δ ppm 2.34 (s, 6H), 3.18 (s, 2H), 7.28-7.35 (m, 1H), 7.62-7.67 (m, 1H), 7.70 (br s, 1H), 8.34 (br s, 1H), 8.44 (br d, J=4.94 Hz, 1H), 8.50 (br s, 1H), 8.59 (br s, 1H), 8.75 (d, J=2.20 Hz, 1H), 8.95 (s, 1H), 9.01 (d, J=2.20 Hz, 1H), 9.11 (s, 1H), 10.12 (br s, 1H), 14.04 (brs, 1H), 14.49 (brs, 1H); ESIMS found for C$_{27}$H$_{22}$FN$_9$O m/z 508.1 (M+1).

Example 2

The screening assay for Wnt activity is described as follows. Reporter cell lines can be generated by stably transducing cancer cell lines (e.g., colon cancer) or primary cells (e.g., IEC-6 intestinal cells) with a lentiviral construct that includes a Wnt-responsive promoter driving expression of the firefly luciferase gene.

SW480 colon carcinoma cells were transduced with a lentiviral vector expressing luciferase with a human Sp5 promoter consisting of a sequence of eight TCF/LEF binding sites. SW480 cells stably expressing the Sp5-Luc reporter gene and a hygromycin resistance gene were selected by treatment with 150 μg/ml of hygromycin for 7 days. These stably transduced SW480 cells were expanded in cell culture and used for all further screening activities. For Sp5-Luc reporter gene assays, the cells were plated at 10,000 cells/well in 96-well plates with growth medium containing 10% fetal calf serum and incubated overnight at 37° C. and 5% $CO_2$. Each compound was dissolved in DMSO as a 10 mM stock in standard j-vials and used to prepare compound source plates in dose-response format with 3-fold serial dilutions and a 10 mM top concentration. Compound transfer from serially diluted source plates to assay plates containing the cells was accomplished using a pintool (Multimek 96, Beckman equipped with V&P Scientific FP1S50H pins) based liquid handling protocol. This protocol used a slotted pin to transfer 50 nl of compound from a source plate well to an assay plate well containing 50 μl of cells in growth medium. The 1000-fold dilution resulted in a final DMSO concentration of 0.1% on the cells in each well. Control wells received 50 nl of DMSO treatment for normalization and calculating $IC_{50}$ values. The treated cells were incubated at 37° C. and 5% $CO_2$ for an additional forty-two hours. Following incubation, the growth medium was removed and 50 μl of BrightGlo luminescence reagent (Promega) was added to each well of the 96-well assay plates. The plates were placed on an orbital shaker for 5 min and then luminescence was quantified on the Victor3 (Perkin Elmer) plate reader. Readings were normalized to DMSO only treated cells, and normalized activities were utilized for $IC_{50}$ calculations using the dose-response log (inhibitor) vs. response -variable slope (four parameters) nonlinear regression feature available in GraphPad Prism 5.0 or 6.0. Table 2 shows the measured activity for selected compounds of Formula I as described herein.

TABLE 2

| Compound | $IC_{50}$ (μM) |
| --- | --- |
| 5 | 0.1723 |
| 10 | >10 |
| 21 | 0.0358 |
| 28 | 0.0423 |
| 33 | 0.1438 |
| 38 | 0.0115 |
| 44 | 0.3773 |
| 45 | 0.0037 |
| 57 | 0.1181 |
| 61 | 0.0420 |
| 68 | >10 |
| 75 | 0.0454 |
| 78 | >10 |
| 91 | >10 |
| 102 | 2.3830 |
| 106 | >10 |
| 114 | >10 |
| 130 | 0.6328 |
| 133 | 0.0366 |
| 139 | 0.3845 |
| 145 | 2.7970 |
| 151 | 0.2470 |
| 157 | 4.2110 |
| 160 | 0.0083 |
| 165 | >10 |
| 171 | 0.2762 |
| 186 | >10 |
| 192 | >10 |
| 198 | >10 |
| 204 | 0.3125 |
| 209 | >10 |
| 212 | 0.2145 |

TABLE 2-continued

| Compound | $IC_{50}$ (μM) |
| --- | --- |
| 216 | 0.7509 |
| 222 | 0.1919 |
| 228 | >10 |
| 237 | 0.0216 |
| 243 | 0.0330 |
| 249 | 0.0027 |
| 264 | >10 |
| 270 | 0.0443 |
| 276 | 0.0081 |
| 282 | >10 |
| 285 | 0.0033 |
| 291 | 0.0438 |
| 297 | >10 |
| 303 | 0.0077 |
| 309 | 0.0380 |
| 312 | 0.0270 |
| 339 | 0.0026 |
| 351 | >10 |
| 357 | 0.0080 |
| 384 | >10 |
| 393 | 0.0206 |
| 414 | >10 |
| 426 | 0.1288 |
| 432 | 0.0217 |
| 909 | >10 |
| 910 | >10 |
| 911 | 0.030 |
| 912 | 0.221 |
| 913 | 0.066 |
| 914 | 1.023 |
| 915 | >10 |
| 916 | >10 |
| 917 | >10 |
| 918 | >10 |
| 919 | >10 |
| 920 | 1.050 |
| 921 | 0.027 |
| 922 | >10 |
| 923 | >10 |
| 924 | >10 |
| 925 | >10 |
| 926 | >10 |
| 1234 | 1.130 |
| 1278 | 0.890 |
| 1322 | 0.395 |
| 1366 | 0.125 |
| 1409 | 3.990 |

Example 3

The above synthesized compounds were screened using primary human mesenchymal stem cells (hMSCs) to determine their ability to induce chondrogenesis (process by which cartilage is developed).

Human Mesenchymal Stem Cell Culture:

Primary human mesenchymal stem cells (hMSCs) were purchased from Lonza (Walkersville, Md.) and expanded in Mesenchymal Stem Cell Growth Media (Lonza). Cells between passage 3 and 6 were used for the experiments.

Compound Screening:

Each compound was dissolved in DMSO as a 10 mM stock and used to prepare compound source plates. Serial dilution (1:3, 6-point dose-response curves from 2700 nM to 10 nM) and compound transfer was performed using the ECHO 550 (Labcyte, Sunnyvale, Calif.) into 96-well clear bottom assay plates (Greiner Bio-One) with appropriate DMSO backfill for a final DMSO concentration of 0.03%. hMSCs were plated at 20,000 cells/well in 250 μL/well Incomplete Chondrogenic Induction Medium (Lonza; DMEM, dexamethasone, ascorbate, insulin-transferrin-selenium [ITS supplement], gentamycin-amphotericin [GA- 1000], sodium pyruvate, proline and L-glutamine). TGF-β3 (10 ng/mL) was used as a positive control for differentiation while negative control wells were treated with 75 nL DMSO for normalization and calculating $EC_{50}$ values. Cells were incubated at 37° C. and 5% $CO_2$ for 6 days. To image chondrogenic nodules, the cells were fixed using 4% formaldehyde (Electron Microscopy Sciences), and stained with 2 µg/mL Rhodamine B (Sigma-Aldrich) and 20 µM Nile Red (Sigma-Aldrich) [Johnson K., et. al, A Stem Cell-Based Approach to Cartilage Repair, *Science*, (2012), 336(6082). 717-721]. The nodules imaged (4 images per well at 4× magnification) by excitation at 531 nm and emission at 625 nm and quantified using the CellInsight CX5 (Thermo Scientific). Number of nodules in each well was normalized to the average of 3 DMSO treated wells on the same plate using Excel (Microsoft Inc.). The normalized averages (fold change over DMSO) of 3 replicate wells for each compound concentration were calculated. Due to solubility limitations of some of the compounds, curve fitting was incomplete leading to inaccurate $EC_{50}$ determinations.

Using TGF-β3 as a positive control, the concentration of test compounds required to induce equivalent levels of chondrogenesis is reported. In addition, the maximum activity of each compound and the respective dose that each compound reached maximum chondrogenesis activity is reported. Table 3 shows the activity of selected compounds as provided herein.

TABLE 3

| Compound | Conc (nM) of Max. activity | Max. Activity as % TGF-β3 activity | Conc (nM) of 100% TGF-β3 activity |
|---|---|---|---|
| 38 | 300 | N/A | 48.6 |
| 45 | 300 | 300 | 59.9 |
| 75 | 30 | N/A | 58.5 |
| 133 | 2700 | 300 | 316.9 |
| 160 | 2700 | N/A | 26.8 |
| 249 | 300 | N/A | 31.9 |
| 285 | 2700 | N/A | 48.9 |
| 339 | 300 | N/A | 43.2 |
| 393 | 100 | 100 | 140.1 |
| 432 | 300 | N/A | 57.0 |
| 911 | 300 | 100 | 110.4 |
| 913 | 900 | 300 | 117.0 |

Example 4

The above synthesized compounds were screened using primary human fibroblasts (derived from IPF patients) treated with TGF-β1 to determine their ability to inhibit the fibrotic process.

Human Fibroblast Cell Culture:

Primary human fibroblasts derived from IPF patients (LL29 cells) [[1]Xiaoqiu Liu, et. al., "Fibrotic Lung Fibroblasts Show Blunted Inhibition by cAMP Due to Deficient cAMP Response Element-Binding Protein Phosphorylation", *Journal of Pharmacology and Experimental Therapeutics* (2005), 315(2), 678-687; [2]Watts, K. L., et. al., "RhoA signaling modulates cyclin D1 expression in human lung fibroblasts; implications for idiopathic pulmonary fibrosis", *Respiratory Research* (2006), 7(1), 88] were obtained from American Type Culture Collection (ATCC) and expanded in F12 medium supplemented with 15% Fetal Bovine Serum and Penicillin/Streptomycin.

Compound Screening:

Each compound was dissolved in DMSO as a 10 mM stock and used to prepare compound source plates. Serial dilution (1:2, 11-point dose-response curves from 10 µM to 1.87 nM) and compound transfer was performed using the ECHO 550 (Labcyte, Sunnyvale, Calif.) into 384-well clear bottom assay plates (Greiner Bio-One) with appropriate DMSO backfill for a final DMSO concentration of 0.1%. LL29 cells were plated at 1,500 cells/well in 80 µl/well F12 medium supplemented with 1% Fetal Bovine Serum. One hour after addition of the cells, TGF-β1 (Peprotech; 20 ng/mL) was added to the plates to induce fibrosis (ref. 1 and 2 above). Wells treated with TGF-β1 and containing DMSO were used as controls. Cells were incubated at 37° C. and 5% $CO_2$ for 4 days. Following incubation for 4 days, SYTOX green nucleic acid stain (Life Technologies [Thermo Fisher Scientific]) was added to the wells at a final concentration of 1 uM and incubated at room temperature for 30 min. Cells were then fixed using 4% formaldehyde (Electron Microscopy Sciences), washed 3 times with PBS followed by blocking and permeabilization using 3% Bovine Serum Albumin (BSA; Sigma) and 0.3% Triton X-100 (Sigma) in PBS. Cells were then stained with antibody specific to α-smooth muscle actin (αSMA; Abcam) (ref. 1 and 2 above) in 3% Bovine Serum Albumin (BSA; Sigma) and 0.3% Triton X-100 (Sigma) in PBS, and incubated overnight at 4° C. Cells were then washed 3 times with PBS, followed by incubation with Alexa Flor-647 conjugated secondary antibody (Life Technologies [Thermo Fisher Scientific]) and DAPI at room temperature for 1 hour. Cells were then washed 3 times with PBS and plates were sealed for imaging. αSMA staining was imaged by excitation at 630 nm and emission at 665 nm and quantified using the Compartmental Analysis program on the CellInsight CX5 (Thermo Scientific). Dead or apoptotic cells were excluded from analysis based on positive SYTOX green staining. % of total cells positive for αSMA were counted in each well and normalized to the average of 11 wells treated with TGF-β1 on the same plate using Dotmatics' Studies Software. The normalized averages (fold change over untreated) of 3 replicate wells for each compound concentration were used to create dose-responses curves and $EC_{50}$ values were calculated using non-linear regression curve fit in the Dotmatics' Studies Software. The $EC_{50}$ values are reported.

Table 4 shows the activity of selected compounds as provided herein.

TABLE 4

| Compound | Inhibition of fibrosis $EC_{50}$ (nM) |
|---|---|
| 10 | 2.550 |
| 28 | 0.026 |
| 33 | 7.802 |
| 38 | 0.118 |
| 45 | 0.009 |
| 61 | 0.587 |
| 68 | 9.990 |
| 78 | 9.990 |
| 91 | 9.990 |
| 102 | 9.990 |
| 106 | 9.990 |
| 114 | 9.990 |
| 130 | 0.009 |
| 133 | 0.853 |
| 139 | 9.990 |
| 145 | 1.442 |
| 151 | 0.414 |
| 157 | 0.009 |

TABLE 4-continued

| Compound | Inhibition of fibrosis EC$_{50}$ (nM) |
|---|---|
| 165 | 9.990 |
| 171 | 0.009 |
| 186 | 9.990 |
| 192 | 0.009 |
| 198 | 3.036 |
| 212 | 0.501 |
| 216 | 9.990 |
| 228 | 0.009 |
| 237 | 0.282 |
| 243 | 0.113 |
| 249 | 0.035 |
| 264 | 0.009 |
| 270 | 0.786 |
| 282 | 9.990 |
| 285 | 0.009 |
| 297 | 9.990 |
| 303 | 9.990 |
| 312 | 0.189 |
| 339 | 0.040 |
| 351 | 9.990 |
| 357 | 1.390 |
| 384 | 9.990 |
| 393 | 0.674 |
| 414 | 9.990 |
| 426 | 0.287 |
| 909 | 9.990 |
| 910 | 9.990 |
| 911 | 0.029 |
| 912 | 0.118 |
| 913 | 0.216 |
| 916 | 0.009 |
| 919 | 0.009 |
| 920 | 0.009 |
| 921 | 0.164 |
| 924 | 9.990 |
| 925 | 9.990 |
| 926 | 0.013 |
| 1409 | 0.009 |

What is claimed is:

1. A method of treating a disorder selected from the group consisting of: skin fibrosis; scleroderma; progressive systemic fibrosis; muscle fibrosis; glomerulosclerosis; glomerulonephritis; hypertrophic scar formation; uterine fibrosis; renal fibrosis; cirrhosis of the liver; liver fibrosis; adhesions occurring in the abdomen, pelvis, spine or tendons; chronic obstructive pulmonary disease; fibrosis following myocardial infarction; pulmonary fibrosis; idiopathic pulmonary fibrosis (IPF); fibrosis and scarring associated with diffuse/interstitial lung disease; central nervous system fibrosis; fibrosis following stroke; fibrosis associated with neurodegenerative disorders selected from the group consisting of Alzheimer's Disease and multiple sclerosis, fibrosis associated with proliferative vitreoretinopathy (PVR); restenosis; endometriosis; ischemic disease; and radiation fibrosis in a subject, the method comprising administering to the subject a therapeutically effective amount of a compound of Formula I, or a pharmaceutically acceptable salt thereof:

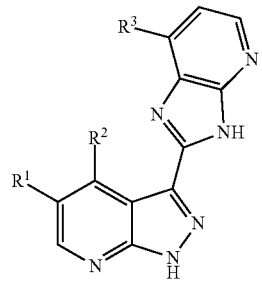

wherein:
R$^1$ is selected from the group consisting of -pyridinyl(R$^4$)q, -pyrazinyl(R$^4$)q, -pyrazolyl(R$^4$)q, -imidazolyl(R$^4$)q and -heterocyclyl(R$^5$)$_h$;
R$^2$ is selected from the group consisting of H and halide;
R$^3$ is selected from the group consisting of H, -heteroaryl (R$^6$)$_q$, -heterocyclyl(R$^7$)$_h$, and -aryl(R$^8$)$_k$;
each R$^4$ is one substituent attached to the heteroaryl and is independently selected from the group consisting of halide, —(C$_{1-4}$ alkylene)$_p$heterocyclyl(R$^9$)$_h$, —(C$_{1-4}$ alkylene)$_p$carbocyclyl(R$^{10}$)$_j$, —(C$_{1-4}$ alkylene)$_p$aryl (R$^{11}$)$_k$, —NHC(=O)R$^{12}$, —NR$^{13}$R$^{14}$, —(C$_{1-6}$ alkylene)NR$^{15}$R$^{16}$, and —OR$^{22}$;
each R$^5$ is one substituent attached to the heterocyclyl and is independently selected from the group consisting of —(C$_{1-4}$ alkyl), halide, —CF$_3$, and —CN;
each R$^6$ is one substituent attached to the heteroaryl and is independently selected from the group consisting of —(C$_{1-6}$ alkyl), halide, —CF$_3$, —OCH$_3$, —CN, and —C(=O)R$^{17}$;
each R$^7$ is one substituent attached to the heterocyclyl and is independently selected from the group consisting of —(C$_{1-6}$ alkyl), halide, —CF$_3$, —CN, and —OCH$_3$;
each R$^8$ is one substituent attached to the aryl and is independently selected from the group consisting of —(C$_{1-6}$ alkyl), halide, —CF$_3$, —CN, —OCH$_3$, —(C$_{1-6}$ alkylene)$_p$NHSO$_2$R$^{17}$, —NR$^{13}$(C$_{1-6}$ alkylene) NR$^{13}$R$^{14}$, —(C$_{1-6}$ alkylene)$_p$NR$^{13}$R$^{14}$, and —OR$^{25}$;
each R$^9$ is one substituent attached to the heterocyclyl and is independently selected from the group consisting of amino, —(C$_{1-4}$ alkyl), halide, —CF$_3$, and —CN;
each R$^{10}$ is one substituent attached to the carbocyclyl and is independently selected from the group consisting of —(C$_{1-4}$ alkyl), halide, —CF$_3$, and —CN;
each R$^{11}$ is one substituent attached to the aryl and is independently selected from the group consisting of —(C$_{1-4}$ alkyl), halide, —CF$_3$, and —CN;
each R$^{12}$ is independently selected from the group consisting of -heteroaryl(R's)$_q$, -aryl(R$^{19}$)$_k$, —CH$_2$aryl (R$^{19}$)$_k$, —CH$_2$carbocyclyl(R$^{20}$)$_j$, —(C$_{1-4}$ alkylene) NR$^{23}$R$^{24}$, and —CH$_2$heterocyclyl(R$^{21}$)$_h$;
each R$^{13}$ is independently selected from the group consisting of H and —(C$_{1-6}$ alkyl);
each R$^{14}$ is independently selected from the group consisting of H, —(C$_{1-6}$ alkyl), —CH$_2$aryl(R$^{19}$)$_k$, and —CH$_2$carbocyclyl(R$^{20}$)$_j$;
each R$^{15}$ is independently selected from the group consisting of H and —(C$_{1-6}$ alkyl);
each R$^{16}$ is independently selected from the group consisting of Me, —CH$_2$aryl(R$^{19}$)$_k$, and —CH$_2$carbocyclyl (R$^{20}$)$_j$;
each R$^{17}$ is a —(C$_{1-6}$ alkyl);

each $R^{18}$ is one substituent attached to the heteroaryl and is independently selected from the group consisting of —($C_{1-4}$ alkyl), halide, —$CF_3$, and —CN;
each $R^{19}$ is one substituent attached to the aryl and is independently selected from the group consisting of —($C_{1-4}$ alkyl), halide, —$CF_3$, and —CN;
each $R^{20}$ is one substituent attached to the carbocyclyl and is independently selected from the group consisting of —($C_{1-4}$ alkyl), halide, —$CF_3$, and —CN;
each $R^{21}$ is one substituent attached to the heterocyclyl and is independently selected from the group consisting of —($C_{1-4}$ alkyl), halide, —$CF_3$, and —CN;
$R^{22}$ is selected from the group consisting of H, —($C_{1-6}$ alkyl), —($C_{1-4}$ alkylene)$_p$heterocyclyl($R^{21}$)$_h$, —($C_{1-4}$ alkylene)$_p$carbocyclyl($R^{20}$)$_j$, —($C_{1-4}$ alkylene)$_p$aryl ($R^{19}$)$_k$, and —($C_{1-6}$ alkylene)$_p$NR$^{23}$R$^{24}$;
each $R^{23}$ is independently selected from the group consisting of H and —($C_{1-6}$ alkyl);
each $R^{24}$ is independently selected from the group consisting of H and —($C_{1-6}$ alkyl);
$R^{25}$ is selected from the group consisting of H, —($C_{1-6}$ alkyl), —($C_{1-4}$ alkylene)$_p$heterocyclyl($R^{21}$)$_h$, and —($C_{1-6}$ alkylene)$_p$NR$^{23}$R$^{24}$;
each p is independently 0 or 1;
each q is independently 0 to 4;
each h is independently 0 to 10;
each k is independently 0 to 5; and
each j is independently 0 to 12.

2. The method of claim 1, wherein $R^1$ is selected from the group consisting of -pyridinyl($R^4$)$_q$, -pyrazinyl($R^4$)q, -pyrazolyl($R^4$)q, and -imidazolyl($R^4$)q.

3. The method of claim 2, wherein $R^1$ is pyridinyl($R^4$)$_q$.

4. The method of claim 3, wherein $R^4$ is selected from the group consisting of $CH_2$heterocyclyl($R^9$)$_h$, —NHC(=O)$R^{12}$, —NR$^{13}$R$^{14}$, —CH$_2$NR$^{15}$R$^{16}$, and —OR$^{22}$.

5. The method of claim 4, wherein $R^3$, is -phenyl($R^8$)$_k$.

6. The method of claim 5, wherein each $R^8$ is independently selected from the group consisting of halide and —$CH_2NHSO_2R^{17}$.

7. The method of claim 4, wherein $R^3$ is selected from the group consisting of -pyridinyl($R^6$)$_q$, -imidazolyl($R^6$)$_q$, -furanyl($R^6$)$_q$, and -thiophenyl($R^6$)$_q$.

8. The method of claim 7, wherein q is 1 and $R^6$ is selected from the group consisting of halide, —($C_{1-3}$ alkyl), and —C(=O)$R^{17}$.

9. The method of claim 4, wherein $R^3$ is selected from the group consisting of -piperidinyl($R^7$)$_h$, -morpholinyl($R^7$)$_h$, and -piperazinyl($R^7$)$_h$.

10. The method of claim 9, wherein each $R^7$ is independently selected from the group consisting of a halide and —($C_{1-3}$ alkyl).

11. A method of treating a disorder selected from the group consisting of: skin fibrosis; scleroderma; progressive systemic fibrosis; muscle fibrosis; glomerulosclerosis; glomerulonephritis; hypertrophic scar formation; uterine fibrosis; renal fibrosis; cirrhosis of the liver; liver fibrosis; adhesions occurring in the abdomen, pelvis, spine or tendons; chronic obstructive pulmonary disease; fibrosis following myocardial infarction; pulmonary fibrosis; idiopathic pulmonary fibrosis (IPF); fibrosis and scarring associated with diffuse/interstitial lung disease; central nervous system fibrosis; fibrosis following stroke; fibrosis associated with neurodegenerative disorders selected from the group consisting of Alzheimer's Disease and multiple sclerosis, fibrosis associated with proliferative vitreoretinopathy (PVR); restenosis; endometriosis; ischemic disease; and radiation fibrosis in a subject, the method comprising administering to the subject a therapeutically effective amount of a compound of Formula I, or a pharmaceutically acceptable salt thereof:

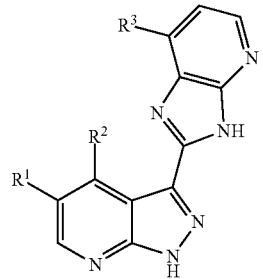

I wherein:
$R^1$ is selected from the group consisting of -heteroaryl ($R^4$)$_q$ and -heterocyclyl($R^5$)$_h$;
$R^2$ is selected from the group consisting of H and halide;
$R^3$ is selected from the group consisting of -heteroaryl ($R^6$)$_q$, -heterocyclyl($R^7$)$_h$, and -aryl($R^8$)$_k$, with the proviso that heteroaryl does not include pyridinyl and imidazolyl;
each $R^4$ is one substituent attached to the heteroaryl and is independently selected from the group consisting of halide, —($C_{1-6}$ alkyl), —($C_{1-4}$ alkylene)$_p$heterocyclyl ($R^9$)$_h$, —($C_{1-4}$ alkylene)$_p$carbocyclyl($R^{10}$)$_j$, —($C_{1-4}$ alkylene)$_p$aryl($R^{11}$)$_k$, —NHC(=O)$R^{12}$, —NR$^{13}$R$^{14}$, —($C_{1-6}$ alkylene)NR$^{15}$R$^{16}$, and —OR$^{22}$;
each $R^5$ is one substituent attached to the heterocyclyl and is independently selected from the group consisting of —($C_{1-4}$ alkyl), halide, —$CF_3$, and —CN;
each $R^6$ is one substituent attached to the heteroaryl and is independently selected from the group consisting of —($C_{1-6}$ alkyl), halide, —$CF_3$, —$OCH_3$, —CN, and —C(=O)$R^{17}$;
each $R^7$ is one substituent attached to the heterocyclyl and is independently selected from the group consisting of —($C_{1-6}$ alkyl), halide, —$CF_3$, —CN, and —$OCH_3$;
each $R^8$ is one substituent attached to the aryl and is independently selected from the group consisting of —($C_{1-6}$ alkyl), —$CF_3$, —CN, —$OCH_3$, —($C_{1-6}$ alkylene)$_p$NHSO$_2$R$^{17}$, —NR$^{13}$($C_{1-6}$ alkylene)NR$^{13}$R$^{14}$, —($C_{1-6}$ alkylene)$_p$NR$^{13}$R$^{14}$, and —OR$^{25}$;
each $R^9$ is one substituent attached to the heterocyclyl and is independently selected from the group consisting of amino, —($C_{1-4}$ alkyl), halide, —$CF_3$, and —CN;
each $R^{10}$ is one substituent attached to the carbocyclyl and is independently selected from the group consisting of —($C_{1-4}$ alkyl), halide, —$CF_3$, and —CN;
each $R^{11}$ is one substituent attached to the aryl and is independently selected from the group consisting of —($C_{1-4}$ alkyl), halide, —$CF_3$, and —CN;
each $R^{12}$ is independently selected from the group consisting of —($C_{1-9}$ alkyl), -heteroaryl($R^{18}$)$_q$, -aryl($R^{19}$)$_k$, —CH$_2$aryl($R^{19}$)$_k$, -carbocyclyl($R^{20}$)$_j$, —CH$_2$carbocyclyl($R^{20}$)$_j$, —($C_{1-4}$ alkylene)NR$^{23}$R$^{24}$, and —CH$_2$heterocyclyl($R^{21}$)$_h$;
each $R^{13}$ is independently selected from the group consisting of H and —($C_{1-6}$ alkyl);
each $R^{14}$ is independently selected from the group consisting of H, —($C_{1-6}$ alkyl), —CH$_2$aryl($R^{19}$)$_k$, and —CH$_2$carbocyclyl($R^{20}$)$_j$;
each $R^{15}$ is independently selected from the group consisting of H and —($C_{1-6}$ alkyl);

each R$^{16}$ is independently selected from the group consisting of H, —(C$_{1-6}$ alkyl), —CH$_2$aryl(R$^{19}$)$_k$, and —CH$_2$carbocyclyl(R$^{20}$);

each R$^{17}$ is a —(C$_{1-6}$ alkyl);

each R$^{18}$ is one substituent attached to the heteroaryl and is independently selected from the group consisting of —(C$_{1-4}$ alkyl), halide, —CF$_3$, and —CN;

each R$^{19}$ is one substituent attached to the aryl and is independently selected from the group consisting of —(C$_{1-4}$ alkyl), halide, —CF$_3$, and —CN;

each R$^{20}$ is one substituent attached to the carbocyclyl and is independently selected from the group consisting of —(C$_{1-4}$ alkyl), halide, —CF$_3$, and —CN;

each R$^{21}$ is one substituent attached to the heterocyclyl and is independently selected from the group consisting of —(C$_{1-4}$ alkyl), halide, —CF$_3$, and —CN;

R$^{22}$ is selected from the group consisting of H, —(C$_{1-6}$ alkyl), —(C$_{1-4}$ alkylene)$_p$heterocyclyl(R$^{21}$)$_h$, —(C$_{1-4}$ alkylene)$_p$carbocyclyl(R$^{20}$)$_j$, —(C$_{1-4}$ alkylene)$_p$aryl(R$^{19}$)$_k$, and —(C$_{1-6}$ alkylene)$_p$NR$^{23}$R$^{24}$;

each R$^{23}$ is independently selected from the group consisting of H and —(C$_{1-6}$ alkyl);

each R$^{24}$ is independently selected from the group consisting of H and —(C$_{1-6}$ alkyl);

R$^{25}$ is selected from the group consisting of H, —(C$_{1-6}$ alkyl), —(C$_{1-4}$ alkylene)$_p$heterocyclyl(R$^{21}$)$_h$, and —(C$_{1-6}$ alkylene)$_p$NR$^{23}$R$^{24}$;

each p is independently 0 or 1;
each q is independently 0 to 4;
each h is independently 0 to 10;
each k is independently 0 to 5; and
each j is independently 0 to 12.

12. The method of claim 11, wherein R$^1$ is selected from the group consisting of -pyridinyl(R$^4$)$_q$, -pyrimidinyl(R$^4$)$_q$, -pyrazolyl(R$^4$)$_q$, and -imidazolyl(R$^4$)$_q$.

13. The method of claim 12, wherein R$^4$ is selected from the group consisting of —(C$_{1-3}$ alkyl), —CH$_2$heterocyclyl(R$^9$)$_h$, —NHC(=O)R$^{12}$, —NR$^{13}$R$^{14}$, —CH$_2$NR$^{15}$R$^{16}$, and —OR$^{22}$.

14. The method of claim 13, wherein R$^3$ is -phenyl(R$^8$)$_k$.

15. The method of claim 13, wherein R$^3$ is selected from the group consisting of -furanyl(R$^6$)$_q$ and -thiophenyl(R$^6$)$_q$.

16. The method of claim 15, wherein q is 1 and R$^6$ is selected from the group consisting of halide, —(C$_{1-3}$ alkyl), and —C(=O)R$^{17}$.

17. The method of claim 13, wherein R$^3$ is selected from the group consisting of -piperidinyl(R$^7$)$_h$, -morpholinyl(R$^7$)$_h$, and -piperazinyl(R$^7$)$_h$.

18. The method of claim 17, wherein each R$^7$ is independently selected from the group consisting of a halide and —(C$_{1-3}$ alkyl).

19. The method of claim 1, wherein the compound of Formula I is selected from the group consisting of:

5-(3-(7-(3-fluorophenyl)-3H-imidazo[4,5-b]pyridin-2-yl)-1H-pyrazolo[3,4-b]pyridin-5-yl)pyridin-3-amine [1];

3-(7-(3-fluorophenyl)-3H-imidazo[4,5-b]pyridin-2-yl)-5-(pyridin-3-yl)-1H-pyrazolo[3,4-b]pyridine [2];

5-(3-(7-(3-fluorophenyl)-3H-imidazo[4,5-b]pyridin-2-yl)-1H-pyrazolo[3,4-b]pyridin-5-yl)-N,N-dimethyl-pyridin-3-amine [5];

N-(5-(3-(7-(3-fluorophenyl)-3H-imidazo[4,5-b]pyridin-2-yl)-1H-pyrazolo[3,4-b]pyridin-5-yl)pyridin-3-yl)-2-phenylacetamide [7];

N-(5-(3-(7-(3-fluorophenyl)-3H-imidazo[4,5-b]pyridin-2-yl)-1H-pyrazolo[3,4-b]pyridin-5-yl)pyridin-3-yl)benzamide [8];

5-(3-(7-(3-fluorophenyl)-3H-imidazo[4,5-b]pyridin-2-yl)-1H-pyrazolo[3,4-b]pyridin-5-yl)-N-isopropylpyridin-3-amine [9];

1-(5-(3-(7-(3-fluorophenyl)-3H-imidazo[4,5-b]pyridin-2-yl)-1H-pyrazolo[3,4-b]pyridin-5-yl)pyridin-3-yl)-N,N-dimethylmethanamine [10];

3-(7-(3-fluorophenyl)-3H-imidazo[4,5-b]pyridin-2-yl)-5-(5-(pyrrolidin-1-ylmethyl)pyridin-3-yl)-1H-pyrazolo[3,4-b]pyridine [11];

3-(7-(3-fluorophenyl)-3H-imidazo[4,5-b]pyridin-2-yl)-5-(5-(piperidin-1-ylmethyl)pyridin-3-yl)-1H-pyrazolo[3,4-b]pyridine [12];

N-benzyl-1-(5-(3-(7-(3-fluorophenyl)-3H-imidazo[4,5-b]pyridin-2-yl)-1H-pyrazolo[3,4-b]pyridin-5-yl)pyridin-3-yl)methanamine [19];

1 cyclopentyl-N-((5-(3-(7-(3-fluorophenyl)-3H-imidazo[4,5-b]pyridin-2-yl)-1H-pyrazolo[3,4-b]pyridin-5-yl)pyridin-3-yl)methyl)methanamine [20];

5-(5-((3,3-difluoropyrrolidin-1-yl)methyl)pyridin-3-yl)-3-(7-(3-fluorophenyl)-3H-imidazo[4,5-b]pyridin-2-yl)-1H-pyrazolo[3,4-b]pyridine [21];

5-(3-(7-(4-fluorophenyl)-3H-imidazo[4,5-b]pyridin-2-yl)-1H-pyrazolo[3,4-b]pyridin-5-yl)pyridin-3-amine [23];

3-(7-(4-fluorophenyl)-3H-imidazo[4,5-b]pyridin-2-yl)-5-(pyridin-3-yl)-1H-pyrazolo[3,4-b]pyridine [24];

5-(3-(7-(4-fluorophenyl)-3H-imidazo[4,5-b]pyridin-2-yl)-1H-pyrazolo[3,4-b]pyridin-5-yl)-N,N-dimethyl-pyridin-3-amine [27];

N-(5-(3-(7-(4-fluorophenyl)-3H-imidazo[4,5-b]pyridin-2-yl)-1H-pyrazolo[3,4-b]pyridin-5-yl)pyridin-3-yl)-2-phenylacetamide [29];

N-(5-(3-(7-(4-fluorophenyl)-3H-imidazo[4,5-b]pyridin-2-yl)-1H-pyrazolo[3,4-b]pyridin-5-yl)pyridin-3-yl)benzamide [30];

5-(3-(7-(4-fluorophenyl)-3H-imidazo[4,5-b]pyridin-2-yl)-1H-pyrazolo[3,4-b]pyridin-5-yl)-N-isopropylpyridin-3-amine [31];

1-(5-(3-(7-(4-fluorophenyl)-3H-imidazo[4,5-b]pyridin-2-yl)-1H-pyrazolo[3,4-b]pyridin-5-yl)pyridin-3-yl)-N,N-dimethylmethanamine [32];

3-(7-(4-fluorophenyl)-3H-imidazo[4,5-b]pyridin-2-yl)-5-(5-(pyrrolidin-1-ylmethyl)pyridin-3-yl)-1H-pyrazolo[3,4-b]pyridine [33];

3-(7-(4-fluorophenyl)-3H-imidazo[4,5-b]pyridin-2-yl)-5-(5-(piperidin-11-ylmethyl)pyridin-3-yl)-1H-pyrazolo[3,4-b]pyridine [34];

N-benzyl-1-(5-(3-(7-(4-fluorophenyl)-3H-imidazo[4,5-b]pyridin-2-yl)-1H-pyrazolo[3,4-b]pyridin-5-yl)pyridin-3-yl)methanamine [41];

1-cyclopentyl-N-((5-(3-(7-(4-fluorophenyl)-3H-imidazo[4,5-b]pyridin-2-yl)-1H-pyrazolo[3,4-b]pyridin-5-yl)pyridin-3-yl)methyl)methanamine [42];

5-(5-((3,3-difluoropyrrolidin-1-yl)methyl)pyridin-3-yl)-3-(7-(4-fluorophenyl)-3H-imidazo[4,5-b]pyridin-2-yl)-1H-pyrazolo[3,4-b]pyridine [43];

5-(3-(7-(2-fluorophenyl)-3H-imidazo[4,5-b]pyridin-2-yl)-1H-pyrazolo[3,4-b]pyridin-5-yl)pyridin-3-amine [45];

3-(7-(2-fluorophenyl)-3H-imidazo[4,5-b]pyridin-2-yl)-5-(pyridin-3-yl)-1H-pyrazolo[3,4-b]pyridine [46];

5-(3-(7-(2-fluorophenyl)-3H-imidazo[4,5-b]pyridin-2-yl)-1H-pyrazolo[3,4-b]pyridin-5-yl)-N,N-dimethyl-pyridin-3-amine [49];

N-(5-(3-(7-(2-fluorophenyl)-3H-imidazo[4,5-b]pyridin-2-yl)-1H-pyrazolo[3,4-b]pyridin-5-yl)pyridin-3-yl)-2-phenylacetamide [51];

N-(5-(3-(7-(2-fluorophenyl)-3H-imidazo[4,5-b]pyridin-2-yl)-1H-pyrazolo[3,4-b]pyridin-5-yl)pyridin-3-yl)benzamide [52];

5-(3-(7-(2-fluorophenyl)-3H-imidazo[4,5-b]pyridin-2-yl)-1H-pyrazolo[3,4-b]pyridin-5-yl)-N-isopropylpyridin-3-amine [53];

1-(5-(3-(7-(2-fluorophenyl)-3H-imidazo[4,5-b]pyridin-2-yl)-1H-pyrazolo[3,4-b]pyridin-5-yl)pyridin-3-yl)-N,N-dimethylmethanamine [54];

3-(7-(2-fluorophenyl)-3H-imidazo[4,5-b]pyridin-2-yl)-5-(5-(pyrrolidin-1-ylmethyl) pyridin-3-yl)-1H-pyrazolo[3,4-b]pyridine [55];

3-(7-(2-fluorophenyl)-3H-imidazo[4,5-b]pyridin-2-yl)-5-(5-(piperidin-1-ylmethyl) pyridin-3-yl)-1H-pyrazolo[3,4-b]pyridine [56];

N-benzyl-1-(5-(3-(7-(2-fluorophenyl)-3H-imidazo[4,5-b]pyridin-2-yl)-1H-pyrazolo[3,4-b]pyridin-5-yl)pyridin-3-yl)methanamine [63];

1-cyclopentyl-N-((5-(3-(7-(2-fluorophenyl)-3H-imidazo[4,5-b]pyridin-2-yl)-1H-pyrazolo[3,4-b]pyridin-5-yl)pyridin-3-yl)methyl)methanamine [64];

5-(5-((3,3-difluoropyrrolidin-1-yl)methyl)pyridin-3-yl)-3-(7-(2-fluorophenyl)-3H-imidazo[4,5-b]pyridin-2-yl)-1H-pyrazolo[3,4-b]pyridine [65];

5-(3-(7-(pyridin-3-yl)-3H-imidazo[4,5-b]pyridin-2-yl)-1H-pyrazolo[3,4-b]pyridin-5-yl)pyridin-3-amine [67];

5-(pyridin-3-yl)-3-(7-(pyridin-3-yl)-3H-imidazo[4,5-b]pyridin-2-yl)-1H-pyrazolo[3,4-b]pyridine [68];

N,N-dimethyl-5-(3-(7-(pyridin-3-yl)-3H-imidazo[4,5-b]pyridin-2-yl)-1H-pyrazolo[3,4-b]pyridin-5-yl)pyridin-3-amine [71];

2-phenyl-N-(5-(3-(7-(pyridin-3-yl)-3H-imidazo[4,5-b]pyridin-2-yl)-1H-pyrazolo[3,4-b]pyridin-5-yl)pyridin-3-yl)acetamide [73];

N-(5-(3-(7-(pyridin-3-yl)-3H-imidazo[4,5-b]pyridin-2-yl)-1H-pyrazolo[3,4-b]pyridin-5-yl)pyridin-3-yl)benzamide [74];

N-isopropyl-5-(3-(7-(pyridin-3-yl)-3H-imidazo[4,5-b]pyridin-2-yl)-1H-pyrazolo[3,4-b]pyridin-5-yl)pyridin-3-amine [75];

N,N-dimethyl-1-(5-(3-(7-(pyridin-3-yl)-3H-imidazo[4,5-b]pyridin-2-yl)-1H-pyrazolo[3,4-b]pyridin-5-yl)pyridin-3-yl)methanamine [76];

3-(7-(pyridin-3-yl)-3H-imidazo[4,5-b]pyridin-2-yl)-5-(5-(pyrrolidin-1-ylmethyl)pyridin-3-yl)-1H-pyrazolo[3,4-b]pyridine [77];

5-(5-(piperidin--ylmethyl)pyridin-3-yl)-3-(7-(pyridin-3-yl)-3H-imidazo[4,5-b]pyridin-2-yl)-1H-pyrazolo[3,4-b]pyridine [78];

N-benzyl-1-(5-(3-(7-(pyridin-3-yl)-3H-imidazo[4,5-b]pyridin-2-yl)-1H-pyrazolo[3,4-b]pyridin-5-yl)pyridin-3-yl)methanamine [85];

1-cyclopentyl-N-((5-(3-(7-(pyridin-3-yl)-3H-imidazo[4,5-b]pyridin-2-yl)-1H-pyrazolo[3,4-b]pyridin-5-yl)pyridin-3-yl)methyl)methanamine [86];

5-(5-((3,3-difluoropyrrolidin-1-yl)methyl)pyridin-3-yl)-3-(7-(pyridin-3-yl)-3H-imidazo[4,5-b]pyridin-2-yl)-1H-pyrazolo[3,4-b]pyridine [87];

5-(3-(7-(pyridin-4-yl)-3H-imidazo[4,5-b]pyridin-2-yl)-1H-pyrazolo[3,4-b]pyridin-5-yl)pyridin-3-amine [89];

5-(pyridin-3-yl)-3-(7-(pyridin-4-yl)-3H-imidazo[4,5-b]pyridin-2-yl)-1H-pyrazolo[3,4-b]pyridine [90];

N,N-dimethyl-5-(3-(7-(pyridin-4-yl)-3H-imidazo[4,5-b]pyridin-2-yl)-1H-pyrazolo[3,4-b]pyridin-5-yl)pyridin-3-amine [93];

2-phenyl-N-(5-(3-(7-(pyridin-4-yl)-3H-imidazo[4,5-b]pyridin-2-yl)-1H-pyrazolo[3,4-b]pyridin-5-yl)pyridin-3-yl)acetamide [95];

N-(5-(3-(7-(pyridin-4-yl)-3H-imidazo[4,5-b]pyridin-2-yl)-1H-pyrazolo[3,4-b]pyridin-5-yl)pyridin-3-yl)benzamide [96];

N-isopropyl-5-(3-(7-(pyridin-4-yl)-3H-imidazo[4,5-b]pyridin-2-yl)-1H-pyrazolo[3,4-b]pyridin-5-yl)pyridin-3-amine [97];

N,N-dimethyl-1-(5-(3-(7-(pyridin-4-yl)-3H-imidazo[4,5-b]pyridin-2-yl)-1H-pyrazolo[3,4-b]pyridin-5-yl)pyridin-3-yl)methanamine [98];

3-(7-(pyridin-4-yl)-3H-imidazo[4,5-b]pyridin-2-yl)-5-(5-(pyrrolidin-1-ylmethyl)pyridin-3-yl)-1H-pyrazolo[3,4-b]pyridine [99];

5-(5-(piperidin-1-ylmethyl)pyridin-3-yl)-3-(7-(pyridin-4-yl)-3H-imidazo[4,5-b]pyridin-2-yl)-1H-pyrazolo[3,4-b]pyridine [100];

N-benzyl-1-(5-(3-(7-(pyridin-4-yl)-3H-imidazo[4,5-b]pyridin-2-yl)-1H-pyrazolo[3,4-b]pyridin-5-yl)pyridin-3-yl)methanamine [107];

1-cyclopentyl-N-((5-(3-(7-(pyridin-4-yl)-3H-imidazo[4,5-b]pyridin-2-yl)-1H-pyrazolo[3,4-b]pyridin-5-yl)pyridin-3-yl)methyl)methanamine [108];

5-(5-((3,3-difluoropyrrolidin-1-yl)methyl)pyridin-3-yl)-3-(7-(pyridin-4-yl)-3H-imidazo[4,5-b]pyridin-2-yl)-1H-pyrazolo[3,4-b]pyridine [109];

5-(3-(7-(pyridin-2-yl)-3H-imidazo[4,5-b]pyridin-2-yl)-1H-pyrazolo[3,4-b]pyridin-5-yl)pyridin-3-amine [111];

3-(7-(pyridin-2-yl)-3H-imidazo[4,5-b]pyridin-2-yl)-5-(pyridin-3-yl)-1H-pyrazolo[3,4-b]pyridine [112];

N,N-dimethyl-5-(3-(7-(pyridin-2-yl)-3H-imidazo[4,5-b]pyridin-2-yl)-1H-pyrazolo[3,4-b]pyridin-5-yl)pyridin-3-amine [115];

2-phenyl-N-(5-(3-(7-(pyridin-2-yl)-3H-imidazo[4,5-b]pyridin-2-yl)-1H-pyrazolo[3,4-b]pyridin-5-yl)pyridin-3-yl)acetamide [117];

N-(5-(3-(7-(pyridin-2-yl)-3H-imidazo[4,5-b]pyridin-2-yl)-1H-pyrazolo[3,4-b]pyridin-5-yl)pyridin-3-yl)benzamide [118];

N-isopropyl-5-(3-(7-(pyridin-2-yl)-3H-imidazo[4,5-b]pyridin-2-yl)-1H-pyrazolo[3,4-b]pyridin-5-yl)pyridin-3-amine [119];

N,N-dimethyl-1-(5-(3-(7-(pyridin-2-yl)-3H-imidazo[4,5-b]pyridin-2-yl)-1H-pyrazolo[3,4-b]pyridin-5-yl)pyridin-3-yl)methanamine [120];

3-(7-(pyridin-2-yl)-3H-imidazo[4,5-b]pyridin-2-yl)-5-(5-(pyrrolidin-1-ylmethyl)pyridin-3-yl)-1H-pyrazolo[3,4-b]pyridine [121];

5-(5-(piperidin-1-ylmethyl)pyridin-3-yl)-3-(7-(pyridin-2-yl)-3H-imidazo[4,5-b]pyridin-2-yl)-1H-pyrazolo[3,4-b]pyridine [122];

N-benzyl-1-(5-(3-(7-(pyridin-2-yl)-3H-imidazo[4,5-b]pyridin-2-yl)-1H-pyrazolo[3,4-b]pyridin-5-yl)pyridin-3-yl)methanamine [129];

1-cyclopentyl-N-((5-(3-(7-(pyridin-2-yl)-3H-imidazo[4,5-b]pyridin-2-yl)-1H-pyrazolo[3,4-b]pyridin-5-yl)pyridin-3-yl)methyl)methanamine [130];

5-(5-((3,3-difluoropyrrolidin-1-yl)methyl)pyridin-3-yl)-3-(7-(pyridin-2-yl)-3H-imidazo[4,5-b]pyridin-2-yl)-1H-pyrazolo[3,4-b]pyridine [131];

5-(3-(7-(piperidin-1-yl)-3H-imidazo[4,5-b]pyridin-2-yl)-1H-pyrazolo[3,4-b]pyridin-5-yl)pyridin-3-amine [135];

3-(7-(piperidin-1-yl)-3H-imidazo[4,5-b]pyridin-2-yl)-5-(pyridin-3-yl)-1H-pyrazolo[3,4-b]pyridine [136];

N,N-dimethyl-5-(3-(7-(piperidin-1-yl)-3H-imidazo[4,5-b]pyridin-2-yl)-1H-pyrazolo[3,4-b]pyridin-5-yl)pyridin-3-amine [139];

2-phenyl-N-(5-(3-(7-(piperidin-1-yl)-3H-imidazo[4,5-b]pyridin-2-yl)-1H-pyrazolo[3,4-b]pyridin-5-yl)pyridin-3-yl)acetamide [142];

N-(5-(3-(7-(piperidin-1-yl)-3H-imidazo[4,5-b]pyridin-2-yl)-1H-pyrazolo[3,4-b]pyridin-5-yl)pyridin-3-yl)benzamide [143];

N-isopropyl-5-(3-(7-(piperidin-1-yl)-3H-imidazo[4,5-b]pyridin-2-yl)-1H-pyrazolo[3,4-b]pyridin-5-yl)pyridin-3-amine [144];

N,N-dimethyl-1-(5-(3-(7-(piperidin-1-yl)-3H-imidazo[4,5-b]pyridin-2-yl)-1H-pyrazolo[3,4-b]pyridin-5-yl)pyridin-3-yl)methanamine [145];

3-(7-(piperidin-1-yl)-3H-imidazo[4,5-b]pyridin-2-yl)-5-(5-(pyrrolidin-1-ylmethyl)pyridin-3-yl)-1H-pyrazolo[3,4-b]pyridine [146];

3-(7-(piperidin-1-yl)-3H-imidazo[4,5-b]pyridin-2-yl)-5-(5-(piperidin-1-ylmethyl)pyridin-3-yl)-1H-pyrazolo[3,4-b]pyridine [147];

N-benzyl-1-(5-(3-(7-(piperidin-1-yl)-3H-imidazo[4,5-b]pyridin-2-yl)-1H-pyrazolo[3,4-b]pyridin-5-yl)pyridin-3-yl)methanamine [155];

1-cyclopentyl-N-((5-(3-(7-(piperidin-1-yl)-3H-imidazo[4,5-b]pyridin-2-yl)-1H-pyrazolo[3,4-b]pyridin-5-yl)pyridin-3-yl)methyl)methanamine [156];

5-(5-((3,3-difluoropyrrolidin-1-yl)methyl)pyridin-3-yl)-3-(7-(piperidin-1-yl)-3H-imidazo[4,5-b]pyridin-2-yl)-1H-pyrazolo[3,4-b]pyridine [157];

5-(3-(7-(4-methyl-1H-imidazol-1-yl)-3H-imidazo[4,5-b]pyridin-2-yl)-1H-pyrazolo[3,4-b]pyridin-5-yl)pyridin-3-amine [161];

3-(7-(4-methyl-1H-imidazol-1-yl)-3H-imidazo[4,5-b]pyridin-2-yl)-5-(pyridin-3-yl)-1H-pyrazolo[3,4-b]pyridine [162];

N,N-dimethyl-5-(3-(7-(4-methyl-1H-imidazol-1-yl)-3H-imidazo[4,5-b]pyridin-2-yl)-1H-pyrazolo[3,4-b]pyridin-5-yl)pyridin-3-amine [164];

N-(5-(3-(7-(4-methyl-1H-imidazol-1-yl)-3H-imidazo[4,5-b]pyridin-2-yl)-1H-pyrazolo[3,4-b]pyridin-5-yl)pyridin-3-yl)-2-phenylacetamide [167];

N-(5-(3-(7-(4-methyl-1H-imidazol-1-yl)-3H-imidazo[4,5-b]pyridin-2-yl)-1H-pyrazolo[3,4-b]pyridin-5-yl)pyridin-3-yl)benzamide [168];

N-isopropyl-5-(3-(7-(4-methyl-1H-imidazol-1-yl)-3H-imidazo[4,5-b]pyridin-2-yl)-1H-pyrazolo[3,4-b]pyridin-5-yl)pyridin-3-amine [169];

N,N-dimethyl-1-(5-(3-(7-(4-methyl-1H-imidazol-1-yl)-3H-imidazo[4,5-b]pyridin-2-yl)-1H-pyrazolo[3,4-b]pyridin-5-yl)pyridin-3-yl)methanamine [170];

3-(7-(4-methyl-1H-imidazol-1-yl)-3H-imidazo[4,5-b]pyridin-2-yl)-5-(5-(pyrrolidin-1-ylmethyl)pyridin-3-yl)-1H-pyrazolo[3,4-b]pyridine [171];

3-(7-(4-methyl-1H-imidazol-1-yl)-3H-imidazo[4,5-b]pyridin-2-yl)-5-(5-(piperidin-1-ylmethyl)pyridin-3-yl)-1H-pyrazolo[3,4-b]pyridine [172];

N-benzyl-1-(5-(3-(7-(4-methyl-1H-imidazol-1-yl)-3H-imidazo[4,5-b]pyridin-2-yl)-1H-pyrazolo[3,4-b]pyridin-5-yl)pyridin-3-yl)methanamine [180];

1-cyclopentyl-N-((5-(3-(7-(4-methyl-1H-imidazol-1-yl)-3H-imidazo[4,5-b]pyridin-2-yl)-1H-pyrazolo[3,4-b]pyridin-5-yl)pyridin-3-yl)methyl)methanamine [181];

5-(5-((3,3-difluoropyrrolidin-1-yl)methyl)pyridin-3-yl)-3-(7-(4-methyl-1H-imidazol-1-yl)-3H-imidazo[4,5-b]pyridin-2-yl)-1H-pyrazolo[3,4-b]pyridine [182];

5-(3-(7-(4-methylpiperazin-1-yl)-3H-imidazo[4,5-b]pyridin-2-yl)-1H-pyrazolo[3,4-b]pyridin-5-yl)pyridin-3-amine [186];

3-(7-(4-methylpiperazin-1-yl)-3H-imidazo[4,5-b]pyridin-2-yl)-5-(pyridin-3-yl)-1H-pyrazolo[3,4-b]pyridine [187];

3-(7-(4-methylpiperazin-1-yl)-3H-imidazo[4,5-b]pyridin-2-yl)-5-(4-methylpyridin-3-yl)-1H-pyrazolo[3,4-b]pyridine [188];

N,N-dimethyl-5-(3-(7-(4-methylpiperazin-1-yl)-3H-imidazo[4,5-b]pyridin-2-yl)-1H-pyrazolo[3,4-b]pyridin-5-yl)pyridin-3-amine [190];

N-(5-(3-(7-(4-methylpiperazin-1-yl)-3H-imidazo[4,5-b]pyridin-2-yl)-1H-pyrazolo[3,4-b]pyridin-5-yl)pyridin-3-yl)-2-phenylacetamide [193];

N-(5-(3-(7-(4-methylpiperazin-1-yl)-3H-imidazo[4,5-b]pyridin-2-yl)-1H-pyrazolo[3,4-b]pyridin-5-yl)pyridin-3-yl)benzamide [194];

N-isopropyl-5-(3-(7-(4-methylpiperazin-1-yl)-3H-imidazo[4,5-b]pyridin-2-yl)-1H-pyrazolo[3,4-b]pyridin-5-yl)pyridin-3-amine [195];

N,N-dimethyl-1-(5-(3-(7-(4-methylpiperazin-1-yl)-3H-imidazo[4,5-b]pyridin-2-yl)-1H-pyrazolo[3,4-b]pyridin-5-yl)pyridin-3-yl)methanamine [196];

3-(7-(4-methylpiperazin-1-yl)-3H-imidazo[4,5-b]pyridin-2-yl)-5-(5-(pyrrolidin-1-ylmethyl)pyridin-3-yl)-1H-pyrazolo[3,4-b]pyridine [197]; and 3-(7-(4-methylpiperazin-1-yl)-3H-imidazo[4,5-b]pyridin-2-yl)-5-(5-(piperidin-1-ylmethyl)pyridin-3-yl)-1H-pyrazolo[3,4-b]pyridine [198]; or a pharmaceutically acceptable salt thereof.

20. The method of claim 1, wherein the compound of Formula I is selected from the group consisting of:

N-benzyl-1-(5-(3-(7-(4-methylpiperazin-1-yl)-3H-imidazo[4,5-b]pyridin-2-yl)-1H-pyrazolo[3,4-b]pyridin-5-yl)pyridin-3-yl)methanamine [206];

1-cyclopentyl-N-((5-(3-(7-(4-methylpiperazin-1-yl)-3H-imidazo[4,5-b]pyridin-2-yl)-1H-pyrazolo[3,4-b]pyridin-5-yl)pyridin-3-yl)methyl)methanamine [207];

5-(5-((3,3-difluoropyrrolidin-1-yl)methyl)pyridin-3-yl)-3-(7-(4-methylpiperazin-1-yl)-3H-imidazo [4,5-b]pyridin-2-yl)-1H-pyrazolo[3,4-b]pyridine [208];

5-(3-(3H-imidazo[4,5-b]pyridin-2-yl)-1H-pyrazolo[3,4-b]pyridin-5-yl)pyridin-3-amine [211];

3-(3H-imidazo[4,5-b]pyridin-2-yl)-5-(pyridin-3-yl)-1H-pyrazolo[3,4-b]pyridine [212];

5-(3-(3H-imidazo[4,5-b]pyridin-2-yl)-1H-pyrazolo[3,4-b]pyridin-5-yl)-N,N-dimethylpyridin-3-amine [214];

N-(5-(3-(3H-imidazo[4,5-b]pyridin-2-yl)-1H-pyrazolo[3,4-b]pyridin-5-yl)pyridin-3-yl)-2-phenylacetamide [216];

N-(5-(3-(3H-imidazo[4,5-b]pyridin-2-yl)-1H-pyrazolo[3,4-b]pyridin-5-yl)pyridin-3-yl)benzamide [217];

5-(3-(3H-imidazo[4,5-b]pyridin-2-yl)-1H-pyrazolo[3,4-b]pyridin-5-yl)-N-isopropylpyridin-3-amine [218];

1-(5-(3-(3H-imidazo[4,5-b]pyridin-2-yl)-1H-pyrazolo[3,4-b]pyridin-5-yl)pyridin-3-yl)-N,N-dimethylmethanamine [219];

3-(3H-imidazo[4,5-b]pyridin-2-yl)-5-(5-(pyrrolidin-1-ylmethyl)pyridin-3-yl)-1H-pyrazolo[3,4-b]pyridine [220];

3-(3H-imidazo[4,5-b]pyridin-2-yl)-5-(5-(piperidin-1-ylmethyl)pyridin-3-yl)-1H-pyrazolo[3,4-b]pyridine [221];

1-(5-(3-(3H-imidazo[4,5-b]pyridin-2-yl)-1H-pyrazolo[3,4-b]pyridin-5-yl)pyridin-3-yl)-N-benzylmethanamine [229];

1-(5-(3-(3H-imidazo[4,5-b]pyridin-2-yl)-1H-pyrazolo[3,4-b]pyridin-5-yl)pyridin-3-yl)-N-(cyclopentylmethyl)methanamine [230];

5-(5-((3,3-difluoropyrrolidin-1-yl)methyl)pyridin-3-yl)-3-(3H-imidazo[4,5-b]pyridin-2-yl)-1H-pyrazolo[3,4-b]pyridine [231];

5-(3-(7-(thiophen-3-yl)-3H-imidazo[4,5-b]pyridin-2-yl)-1H-pyrazolo[3,4-b]pyridin-5-yl)pyridin-3-amine [235];

5-(pyridin-3-yl)-3-(7-(thiophen-3-yl)-3H-imidazo[4,5-b]pyridin-2-yl)-1H-pyrazolo[3,4-b]pyridine [236];

N,N-dimethyl-5-(3-(7-(thiophen-3-yl)-3H-imidazo[4,5-b]pyridin-2-yl)-1H-pyrazolo[3,4-b]pyridin-5-yl)pyridin-3-amine [239];

2-phenyl-N-(5-(3-(7-(thiophen-3-yl)-3H-imidazo[4,5-b]pyridin-2-yl)-1H-pyrazolo[3,4-b]pyridin-5-yl)pyridin-3-yl)acetamide [242];

N-(5-(3-(7-(thiophen-3-yl)-3H-imidazo[4,5-b]pyridin-2-yl)-1H-pyrazolo[3,4-b]pyridin-5-yl)pyridin-3-yl)benzamide [243];

N-isopropyl-5-(3-(7-(thiophen-3-yl)-3H-imidazo[4,5-b]pyridin-2-yl)-1H-pyrazolo[3,4-b]pyridin-5-yl)pyridin-3-amine [244];

N,N-dimethyl-1-(5-(3-(7-(thiophen-3-yl)-3H-imidazo[4,5-b]pyridin-2-yl)-1H-pyrazolo[3,4-b]pyridin-5-yl)pyridin-3-yl)methanamine [245];

5-(5-(pyrrolidin-1-ylmethyl)pyridin-3-yl)-3-(7-(thiophen-3-yl)-3H-imidazo[4,5-b]pyridin-2-yl)-1H-pyrazolo[3,4-b]pyridine [246];

5-(5-(piperidin-1-ylmethyl)pyridin-3-yl)-3-(7-(thiophen-3-yl)-3H-imidazo[4,5-b]pyridin-2-yl)-1H-pyrazolo[3,4-b]pyridine [247];

N-benzyl-1-(5-(3-(7-(thiophen-3-yl)-3H-imidazo[4,5-b]pyridin-2-yl)-1H-pyrazolo[3,4-b]pyridin-5-yl)pyridin-3-yl)methanamine [255];

1-cyclopentyl-N-((5-(3-(7-(thiophen-3-yl)-3H-imidazo[4,5-b]pyridin-2-yl)-1H-pyrazolo[3,4-b]pyridin-5-yl)pyridin-3-yl)methyl)methanamine [256];

5-(5-((3,3-difluoropyrrolidin-1-yl)methyl)pyridin-3-yl)-3-(7-(thiophen-3-yl)-3H-imidazo[4,5-b]pyridin-2-yl)-1H-pyrazolo[3,4-b]pyridine [257];

5-(3-(7-(furan-3-yl)-3H-imidazo[4,5-b]pyridin-2-yl)-1H-pyrazolo[3,4-b]pyridin-5-yl)pyridin-3-amine [261];

3-(7-(furan-3-yl)-3H-imidazo[4,5-b]pyridin-2-yl)-5-(pyridin-3-yl)-1H-pyrazolo[3,4-b]pyridine [262];

5-(3-(7-(furan-3-yl)-3H-imidazo[4,5-b]pyridin-2-yl)-1H-pyrazolo[3,4-b]pyridin-5-yl)-N,N-dimethylpyridin-3-amine [265];

N-(5-(3-(7-(furan-3-yl)-3H-imidazo[4,5-b]pyridin-2-yl)-1H-pyrazolo[3,4-b]pyridin-5-yl)pyridin-3-yl)-2-phenylacetamide [268];

N-(5-(3-(7-(furan-3-yl)-3H-imidazo[4,5-b]pyridin-2-yl)-1H-pyrazolo[3,4-b]pyridin-5-yl)pyridin-3-yl)benzamide [269];

5-(3-(7-(furan-3-yl)-3H-imidazo[4,5-b]pyridin-2-yl)-1H-pyrazolo[3,4-b]pyridin-5-yl)-N-isopropylpyridin-3-amine [270];

1-(5-(3-(7-(furan-3-yl)-3H-imidazo[4,5-b]pyridin-2-yl)-1H-pyrazolo[3,4-b]pyridin-5-yl)pyridin-3-yl)-N,N-dimethylmethanamine [271];

3-(7-(furan-3-yl)-3H-imidazo[4,5-b]pyridin-2-yl)-5-(5-(pyrrolidin-1-ylmethyl)pyridin-3-yl)-1H-pyrazolo[3,4-b]pyridine [272];

3-(7-(furan-3-yl)-3H-imidazo[4,5-b]pyridin-2-yl)-5-(5-(piperidin-1-ylmethyl)pyridin-3-yl)-1H-pyrazolo[3,4-b]pyridine [273];

N-benzyl-1-(5-(3-(7-(furan-3-yl)-3H-imidazo[4,5-b]pyridin-2-yl)-1H-pyrazolo[3,4-b]pyridin-5-yl)pyridin-3-yl)methanamine [281];

1-cyclopentyl-N-((5-(3-(7-(furan-3-yl)-3H-imidazo[4,5-b]pyridin-2-yl)-1H-pyrazolo[3,4-b]pyridin-5-yl)pyridin-3-yl)methyl)methanamine [282];

5-(5-((3,3-difluoropyrrolidin-1-yl)methyl)pyridin-3-yl)-3-(7-(furan-3-yl)-3H-imidazo[4,5-b]pyridin-2-yl)-1H-pyrazolo[3,4-b]pyridine [283];

5-(3-(7-(thiophen-2-yl)-3H-imidazo[4,5-b]pyridin-2-yl)-1H-pyrazolo[3,4-b]pyridin-5-yl)pyridin-3-amine [287];

5-(pyridin-3-yl)-3-(7-(thiophen-2-yl)-3H-imidazo[4,5-b]pyridin-2-yl)-1H-pyrazolo[3,4-b]pyridine [288];

N,N-dimethyl-5-(3-(7-(thiophen-2-yl)-3H-imidazo[4,5-b]pyridin-2-yl)-1H-pyrazolo[3,4-b]pyridin-5-yl)pyridin-3-amine [291];

2-phenyl-N-(5-(3-(7-(thiophen-2-yl)-3H-imidazo[4,5-b]pyridin-2-yl)-1H-pyrazolo[3,4-b]pyridin-5-yl)pyridin-3-yl)acetamide [294];

N-(5-(3-(7-(thiophen-2-yl)-3H-imidazo[4,5-b]pyridin-2-yl)-1H-pyrazolo[3,4-b]pyridin-5-yl)pyridin-3-yl)benzamide [295];

N-isopropyl-5-(3-(7-(thiophen-2-yl)-3H-imidazo[4,5-b]pyridin-2-yl)-1H-pyrazolo[3,4-b]pyridin-5-yl)pyridin-3-amine [296];

N,N-dimethyl-1-(5-(3-(7-(thiophen-2-yl)-3H-imidazo[4,5-b]pyridin-2-yl)-1H-pyrazolo[3,4-b]pyridin-5-yl)pyridin-3-yl)methanamine [297];

5-(5-(pyrrolidin-1-ylmethyl)pyridin-3-yl)-3-(7-(thiophen-2-yl)-3H-imidazo[4,5-b]pyridin-2-yl)-1H-pyrazolo[3,4-b]pyridine [298];

5-(5-(piperidin-1-ylmethyl)pyridin-3-yl)-3-(7-(thiophen-2-yl)-3H-imidazo[4,5-b]pyridin-2-yl)-1H-pyrazolo[3,4-b]pyridine [299];

N-benzyl-1-(5-(3-(7-(thiophen-2-yl)-3H-imidazo[4,5-b]pyridin-2-yl)-1H-pyrazolo[3,4-b]pyridin-5-yl)pyridin-3-yl)methanamine [307];

1-cyclopentyl-N-((5-(3-(7-(thiophen-2-yl)-3H-imidazo[4,5-b]pyridin-2-yl)-1H-pyrazolo[3,4-b]pyridin-5-yl)pyridin-3-yl)methyl)methanamine [308];

5-(5-((3,3-difluoropyrrolidin-1-yl)methyl)pyridin-3-yl)-3-(7-(thiophen-2-yl)-3H-imidazo[4,5-b]pyridin-2-yl)-1H-pyrazolo[3,4-b]pyridine [309];

5-(3-(7-(5-fluorothiophen-2-yl)-3H-imidazo[4,5-b]pyridin-2-yl)-1H-pyrazolo[3,4-b]pyridin-5-yl)pyridin-3-amine [313];

3-(7-(5-fluorothiophen-2-yl)-3H-imidazo[4,5-b]pyridin-2-yl)-5-(pyridin-3-yl)-1H-pyrazolo[3,4-b]pyridine [314];

5-(3-(7-(5-fluorothiophen-2-yl)-3H-imidazo[4,5-b]pyridin-2-yl)-1H-pyrazolo[3,4-b]pyridin-5-yl)-N,N-dimethylpyridin-3-amine [317];

N-(5-(3-(7-(5-fluorothiophen-2-yl)-3H-imidazo[4,5-b]pyridin-2-yl)-1H-pyrazolo[3,4-b]pyridin-5-yl)pyridin-3-yl)-2-phenylacetamide [320];

N-(5-(3-(7-(5-fluorothiophen-2-yl)-3H-imidazo[4,5-b]pyridin-2-yl)-1H-pyrazolo[3,4-b]pyridin-5-yl)pyridin-3-yl)benzamide [321];

5-(3-(7-(5-fluorothiophen-2-yl)-3H-imidazo[4,5-b]pyridin-2-yl)-1H-pyrazolo[3,4-b]pyridin-5-yl)-N-isopropylpyridin-3-amine [322];

1-(5-(3-(7-(5-fluorothiophen-2-yl)-3H-imidazo[4,5-b]pyridin-2-yl)-1H-pyrazolo[3,4-b]pyridin-5-yl)pyridin-3-yl)-N,N-dimethylmethanamine [323];

3-(7-(5-fluorothiophen-2-yl)-3H-imidazo[4,5-b]pyridin-2-yl)-5-(5-(pyrrolidin-1-ylmethyl)pyridin-3-yl)-1H-pyrazolo[3,4-b]pyridine [324];

3-(7-(5-fluorothiophen-2-yl)-3H-imidazo[4,5-b]pyridin-2-yl)-5-(5-(piperidin-1l-ylmethyl)pyridin-3-yl)-1H-pyrazolo[3,4-b]pyridine [325];

N-benzyl-1-(5-(3-(7-(5-fluorothiophen-2-yl)-3H-imidazo[4,5-b]pyridin-2-yl)-1H-pyrazolo[3,4-b]pyridin-5-yl)pyridin-3-yl)methanamine [333];

1-cyclopentyl-N-((5-(3-(7-(5-fluorothiophen-2-yl)-3H-imidazo[4,5-b]pyridin-2-yl)-1H-pyrazolo[3,4-b]pyridin-5-yl)pyridin-3-yl)methyl)methanamine [334];

5-(5-((3,3-difluoropyrrolidin-1-yl)methyl)pyridin-3-yl)-3-(7-(5-fluorothiophen-2-yl)-3H-imidazo[4,5-b]pyridin-2-yl)-1H-pyrazolo[3,4-b]pyridine [335];

5-(3-(7-(5-methylthiophen-2-yl)-3H-imidazo[4,5-b]pyridin-2-yl)-1H-pyrazolo[3,4-b]pyridin-5-yl)pyridin-3-amine [339];

3-(7-(5-methylthiophen-2-yl)-3H-imidazo[4,5-b]pyridin-2-yl)-5-(pyridin-3-yl)-1H-pyrazolo[3,4-b]pyridine [340];

N,N-dimethyl-5-(3-(7-(5-methylthiophen-2-yl)-3H-imidazo[4,5-b]pyridin-2-yl)-1H-pyrazolo[3,4-b]pyridin-5-yl)pyridin-3-amine [343];

N-(5-(3-(7-(5-methylthiophen-2-yl)-3H-imidazo[4,5-b]pyridin-2-yl)-1H-pyrazolo[3,4-b]pyridin-5-yl)pyridin-3-yl)-2-phenylacetamide [346];

N-(5-(3-(7-(5-methylthiophen-2-yl)-3H-imidazo[4,5-b]pyridin-2-yl)-1H-pyrazolo[3,4-b]pyridin-5-yl)pyridin-3-yl)benzamide [347];

N-isopropyl-5-(3-(7-(5-methylthiophen-2-yl)-3H-imidazo[4,5-b]pyridin-2-yl)-1H-pyrazolo[3,4-b]pyridin-5-yl)pyridin-3-amine [348];

N,N-dimethyl-1-(5-(3-(7-(5-methylthiophen-2-yl)-3H-imidazo[4,5-b]pyridin-2-yl)-1H-pyrazolo[3,4-b]pyridin-5-yl)pyridin-3-yl)methanamine [349];

3-(7-(5-methylthiophen-2-yl)-3H-imidazo[4,5-b]pyridin-2-yl)-5-(5-(pyrrolidin-1-ylmethyl)pyridin-3-yl)-1H-pyrazolo[3,4-b]pyridine [350];

3-(7-(5-methylthiophen-2-yl)-3H-imidazo[4,5-b]pyridin-2-yl)-5-(5-(piperidin-1-ylmethyl)pyridin-3-yl)-1H-pyrazolo[3,4-b]pyridine [351];

N-benzyl-1-(5-(3-(7-(5-methylthiophen-2-yl)-3H-imidazo[4,5-b]pyridin-2-yl)-1H-pyrazolo[3,4-b]pyridin-5-yl)pyridin-3-yl)methanamine [359];

1-cyclopentyl-N-((5-(3-(7-(5-methylthiophen-2-yl)-3H-imidazo[4,5-b]pyridin-2-yl)-1H-pyrazolo[3,4-b]pyridin-5-yl)pyridin-3-yl)methyl)methanamine [360];

5-(5-((3,3-difluoropyrrolidin-1-yl)methyl)pyridin-3-yl)-3-(7-(5-methylthiophen-2-yl)-3H-imidazo [4,5-b]pyridin-2-yl)-1H-pyrazolo[3,4-b]pyridine [361];

1-(5-(2-(5-(5-aminopyridin-3-yl)-1H-pyrazolo[3,4-b]pyridin-3-yl)-3H-imidazo[4,5-b]pyridin-7-yl)thiophen-2-yl)ethanone [365];

1-(5-(2-(5-(pyridin-3-yl)-1H-pyrazolo[3,4-b]pyridin-3-yl)-3H-imidazo[4,5-b]pyridin-7-yl)thiophen-2-yl)ethanone [366];

1-(5-(2-(5-(5-(dimethylamino)pyridin-3-yl)-1H-pyrazolo[3,4-b]pyridin-3-yl)-3H-imidazo[4,5-b]pyridin-7-yl)thiophen-2-yl)ethanone [369];

N-(5-(3-(7-(5-acetylthiophen-2-yl)-3H-imidazo[4,5-b]pyridin-2-yl)-1H-pyrazolo[3,4-b]pyridin-5-yl)pyridin-3-yl)-2-phenylacetamide [372];

N-(5-(3-(7-(5-acetylthiophen-2-yl)-3H-imidazo[4,5-b]pyridin-2-yl)-1H-pyrazolo[3,4-b]pyridin-5-yl)pyridin-3-yl)benzamide [373];

1-(5-(2-(5-(5-(isopropylamino)pyridin-3-yl)-1H-pyrazolo[3,4-b]pyridin-3-yl)-3H-imidazo[4,5-b]pyridin-7-yl)thiophen-2-yl)ethanone [374];

1-(5-(2-(5-(5-((dimethylamino)methyl)pyridin-3-yl)-1H-pyrazolo[3,4-b]pyridin-3-yl)-3H-imidazo[4,5-b]pyridin-7-yl)thiophen-2-yl)ethanone [375];

1-(5-(2-(5-(5-(pyrrolidin-1-ylmethyl)pyridin-3-yl)-1H-pyrazolo[3,4-b]pyridin-3-yl)-3H-imidazo[4,5-b]pyridin-7-yl)thiophen-2-yl)ethanone [376];

1-(5-(2-(5-(5-(piperidin-1-ylmethyl)pyridin-3-yl)-1H-pyrazolo[3,4-b]pyridin-3-yl)-3H-imidazo[4,5-b]pyridin-7-yl)thiophen-2-yl)ethanone [377];

1-(5-(2-(5-(5-((benzylamino)methyl)pyridin-3-yl)-1H-pyrazolo[3,4-b]pyridin-3-yl)-3H-imidazo[4,5-b]pyridin-7-yl)thiophen-2-yl)ethanone [385];

1-(5-(2-(5-(5-(((cyclopentylmethyl)amino)methyl)pyridin-3-yl)-1H-pyrazolo[3,4-b]pyridin-3-yl)-3H-imidazo[4,5-b]pyridin-7-yl)thiophen-2-yl)ethan-1-one [386];

1-(5-(2-(5-(5-((3,3-difluoropyrrolidin-1-yl)methyl)pyridin-3-yl)-1H-pyrazolo[3,4-b]pyridin-3-yl)-3H-imidazo[4,5-b]pyridin-7-yl)thiophen-2-yl)ethanone [387];

N-(3-(2-(5-(5-aminopyridin-3-yl)-1H-pyrazolo[3,4-b]pyridin-3-yl)-3H-imidazo[4,5-b]pyridin-7-yl)-5-fluorobenzyl)methanesulfonamide [391];

N-(3-fluoro-5-(2-(5-(pyridin-3-yl)-1H-pyrazolo[3,4-b]pyridin-3-yl)-3H-imidazo[4,5-b]pyridin-7-yl)benzyl)methanesulfonamide [392];

N-(3-(2-(5-(5-(dimethylamino)pyridin-3-yl)-1H-pyrazolo[3,4-b]pyridin-3-yl)-3H-imidazo[4,5-b]pyridin-7-yl)-5-fluorobenzyl)methanesulfonamide [395];

N-(5-(3-(7-(3-fluoro-5-(methylsulfonamidomethyl)phenyl)-3H-imidazo[4,5-b]pyridin-2-yl)-1H-pyrazolo[3,4-b]pyridin-5-yl)pyridin-3-yl)-2-phenylacetamide [398];

N-(5-(3-(7-(3-fluoro-5-(methylsulfonamidomethyl)phenyl)-3H-imidazo[4,5-b]pyridin-2-yl)-1H-pyrazolo[3,4-b]pyridin-5-yl)pyridin-3-yl)benzamide [399];

N-(3-fluoro-5-(2-(5-(5-(isopropylamino)pyridin-3-yl)-1H-pyrazolo[3,4-b]pyridin-3-yl)-3H-imidazo[4,5-b]pyridin-7-yl)benzyl)methanesulfonamide [400];

N-(3-(2-(5-(5-((dimethylamino)methyl)pyridin-3-yl)-1H-pyrazolo[3,4-b]pyridin-3-yl)-3H-imidazo[4,5-b]pyridin-7-yl)-5-fluorobenzyl)methanesulfonamide [401];

N-(3-fluoro-5-(2-(5-(5-(pyrrolidin-1-ylmethyl)pyridin-3-yl)-1H-pyrazolo[3,4-b]pyridin-3-yl)-3H-imidazo [4,5-b]pyridin-7-yl)benzyl)methanesulfonamide [402];

N-(3-fluoro-5-(2-(5-(5-(piperidin-1-ylmethyl)pyridin-3-yl)-1H-pyrazolo[3,4-b]pyridin-3-yl)-3H-imidazo [4,5-b]pyridin-7-yl)benzyl)methanesulfonamide [403];

N-(3-(2-(5-(5-((benzylamino)methyl)pyridin-3-yl)-1H-pyrazolo[3,4-b]pyridin-3-yl)-3H-imidazo[4,5-b]pyridin-7-yl)-5-fluorobenzyl)methanesulfonamide [411];

N-(3-(2-(5-(5-(((cyclopentylmethyl)amino)methyl)pyridin-3-yl)-1H-pyrazolo[3,4-b]pyridin-3-yl)-3H-imidazo[4,5-b]pyridin-7-yl)-5-fluorobenzyl)methanesulfonamide [412];

N-(3-(2-(5-(5-((3,3-difluoropyrrolidin-1-yl)methyl)pyridin-3-yl)-1H-pyrazolo[3,4-b]pyridin-3-yl)-3H-imidazo[4,5-b]pyridin-7-yl)-5-fluorobenzyl)methanesulfonamide [413];

N-(3-(2-(5-(5-aminopyridin-3-yl)-1H-pyrazolo[3,4-b]pyridin-3-yl)-3H-imidazo[4,5-b]pyridin-7-yl)-5-fluorophenyl)-$N^2,N^2$-dimethylethane-1,2-diamine [417];

N-(3-fluoro-5-(2-(5-(pyridin-3-yl)-1H-pyrazolo[3,4-b]pyridin-3-yl)-3H-imidazo[4,5-b]pyridin-7-yl)phenyl)-$N^2,N^2$-dimethylethane-1,2-diamine [418];

N-(3-(2-(5-(5-(dimethylamino)pyridin-3-yl)-1H-pyrazolo [3,4-b]pyridin-3-yl)-3H-imidazo[4,5-b]pyridin-7-yl)-5-fluorophenyl)-$N^2$,$N^2$-dimethylethane-1,2-diamine [421];

N-(5-(3-(7-(3-((2-(dimethylamino)ethyl)amino)-5-fluorophenyl)-3H-imidazo[4,5-b]pyridin-2-yl)-1H-pyrazolo[3,4-b]pyridin-5-yl)pyridin-3-yl)-2-phenylacetamide [424];

N-(5-(3-(7-(3-((2-(dimethylamino)ethyl)amino)-5-fluorophenyl)-3H-imidazo[4,5-b]pyridin-2-yl)-1H-pyrazolo[3,4-b]pyridin-5-yl)pyridin-3-yl)benzamide [425];

N-(3-fluoro-5-(2-(5-(5-(isopropylamino)pyridin-3-yl)-1H-pyrazolo[3,4-b]pyridin-3-yl)-3H-imidazo [4,5-b]pyridin-7-yl)phenyl)-$N^2$,$N^2$-dimethylethane-1,2-diamine [426];

N-(3-(2-(5-(5-(((dimethylamino)methyl)pyridin-3-yl)-1H-pyrazolo[3,4-b]pyridin-3-yl)-3H-imidazo[4,5-b]pyridin-7-yl)-5-fluorophenyl)-$N^2$,$N^2$-dimethylethane-1,2-diamine [427];

$N^1$-(3-fluoro-5-(2-(5-(5-(pyrrolidin-1-ylmethyl)pyridin-3-yl)-1H-pyrazolo[3,4-b]pyridin-3-yl)-3H-imidazo [4,5-b]pyridin-7-yl)phenyl)-$N^2$,$N^2$-dimethylethane-1,2-diamine [428];

$N^1$-(3-fluoro-5-(2-(5-(5-(piperidin-1-ylmethyl)pyridin-3-yl)-1H-pyrazolo[3,4-b]pyridin-3-yl)-3H-imidazo [4,5-b]pyridin-7-yl)phenyl)-$N^2$,$N^2$-dimethylethane-1,2-diamine [429];

$N^1$-(3-(2-(5-(5-((benzylamino)methyl)pyridin-3-yl)-1H-pyrazolo[3,4-b]pyridin-3-yl)-3H-imidazo[4,5-b]pyridin-7-yl)-5-fluorophenyl)-$N^2$,$N^2$-dimethylethane-1,2-diamine [437];

$N^1$-(3-(2-(5-(5-(((cyclopentylmethyl)amino)methyl)pyridin-3-yl)-1H-pyrazolo[3,4-b]pyridin-3-yl)-3H-imidazo [4,5-b]pyridin-7-yl)-5-fluorophenyl)-$N^2$,$N^2$-dimethylethane-1,2-diamine [438]; and $N^1$-(3-(2-(5-(5-((3,3-difluoropyrrolidin-1-yl)methyl)pyridin-3-yl)-1H-pyrazolo[3,4-b]pyridin-3-yl)-3H-imidazo [4,5-b]pyridin-7-yl)-5-fluorophenyl)-$N^2$,$N^2$-dimethylethane-1,2-diamine [439]; or a pharmaceutically acceptable salt thereof.

21. The method of claim 1, wherein the compound of Formula I is selected from the group consisting of:

3-(7-(3-fluorophenyl)-3H-imidazo[4,5-b]pyridin-2-yl)-5-(piperidin-4-yl)-1H-pyrazolo[3,4-b]pyridine [909];

3-(7-(3-fluorophenyl)-3H-imidazo[4,5-b]pyridin-2-yl)-5-(1,2,3,6-tetrahydropyridin-4-yl)-1H-pyrazolo[3,4-b]pyridine [910];

3-(7-(3-fluorophenyl)-3H-imidazo[4,5-b]pyridin-2-yl)-5-(1H-pyrazol-4-yl)-1H-pyrazolo[3,4-b]pyridine [911];

1-(6-(3-(7-(3-fluorophenyl)-3H-imidazo[4,5-b]pyridin-2-yl)-1H-pyrazolo[3,4-b]pyridin-5-yl)pyrazin-2-yl)azetidin-3-amine [914];

5-(5-(cyclohexyloxy)pyridin-3-yl)-3-(7-(3-fluorophenyl)-3H-imidazo[4,5-b]pyridin-2-yl)-1H-pyrazolo[3,4-b]pyridine [915];

3-(7-(3-fluorophenyl)-3H-imidazo[4,5-b]pyridin-2-yl)-5-(5-(piperidin-4-yloxy)pyridin-3-yl)-1H-pyrazolo[3,4-b]pyridine [916];

N-(5-(3-(7-(3-fluorophenyl)-3H-imidazo[4,5-b]pyridin-2-yl)-1H-pyrazolo[3,4-b]pyridin-5-yl)pyridin-3-yl)-2-(piperidin-4-yl)acetamide [917];

3-(7-(3-fluorophenyl)-3H-imidazo[4,5-b]pyridin-2-yl)-5-(5-(2-(pyrrolidin-1-yl)ethoxy)pyridin-3-yl)-1H-pyrazolo[3,4-b]pyridine [918];

2-((5-(3-(7-(3-fluorophenyl)-3H-imidazo[4,5-b]pyridin-2-yl)-1H-pyrazolo[3,4-b]pyridin-5-yl)pyridin-3-yl)oxy)-N,N-dimethylethan-1-amine [919];

3-(7-(3-fluorophenyl)-3H-imidazo[4,5-b]pyridin-2-yl)-5-(5-methoxypyridin-3-yl)-1H-pyrazolo[3,4-b]pyridine [920];

5-(3-(7-(3-fluorophenyl)-3H-imidazo[4,5-b]pyridin-2-yl)-1H-pyrazolo[3,4-b]pyridin-5-yl)pyridin-3-ol [921];

5-(5-(benzyloxy)pyridin-3-yl)-3-(7-(3-fluorophenyl)-3H-imidazo[4,5-b]pyridin-2-yl)-1H-pyrazolo[3,4-b]pyridine [922];

2-cyclohexyl-N-(5-(3-(7-(3-fluorophenyl)-3H-imidazo[4,5-b]pyridin-2-yl)-1H-pyrazolo[3,4-b]pyridin-5-yl)pyridin-3-yl)acetamide [923];

3-(7-(3-fluorophenyl)-3H-imidazo[4,5-b]pyridin-2-yl)-5-(pyridin-4-yl)-1H-pyrazolo[3,4-b]pyridine [924];

3-(7-(3-fluorophenyl)-3H-imidazo[4,5-b]pyridin-2-yl)-5-(pyridin-2-yl)-1H-pyrazolo[3,4-b]pyridine [925];

3-(7-(3-fluorophenyl)-3H-imidazo[4,5-b]pyridin-2-yl)-5-(pyrazin-2-yl)-1H-pyrazolo[3,4-b]pyridine [926];

3-(7-(4-fluorophenyl)-3H-imidazo[4,5-b]pyridin-2-yl)-5-(piperidin-4-yl)-1H-pyrazolo[3,4-b]pyridine [927];

3-(7-(4-fluorophenyl)-3H-imidazo[4,5-b]pyridin-2-yl)-5-(1,2,3,6-tetrahydropyridin-4-yl)-1H-pyrazolo[3,4-b]pyridine [928];

3-(7-(4-fluorophenyl)-3H-imidazo[4,5-b]pyridin-2-yl)-5-(1H-pyrazol-4-yl)-1H-pyrazolo[3,4-b]pyridine [929];

1-(6-(3-(7-(4-fluorophenyl)-3H-imidazo[4,5-b]pyridin-2-yl)-1H-pyrazolo[3,4-b]pyridin-5-yl)pyrazin-2-yl)azetidin-3-amine [932];

5-(5-(cyclohexyloxy)pyridin-3-yl)-3-(7-(4-fluorophenyl)-3H-imidazo[4,5-b]pyridin-2-yl)-1H-pyrazolo[3,4-b]pyridine [933];

3-(7-(4-fluorophenyl)-3H-imidazo[4,5-b]pyridin-2-yl)-5-(5-(piperidin-4-yloxy)pyridin-3-yl)-1H-pyrazolo[3,4-b]pyridine [934];

N-(5-(3-(7-(4-fluorophenyl)-3H-imidazo[4,5-b]pyridin-2-yl)-1H-pyrazolo[3,4-b]pyridin-5-yl)pyridin-3-yl)-2-(piperidin-4-yl)acetamide [935];

3-(7-(4-fluorophenyl)-3H-imidazo[4,5-b]pyridin-2-yl)-5-(5-(2-(pyrrolidin-1-yl)ethoxy)pyridin-3-yl)-1H-pyrazolo[3,4-b]pyridine [936];

2-((5-(3-(7-(4-fluorophenyl)-3H-imidazo[4,5-b]pyridin-2-yl)-1H-pyrazolo[3,4-b]pyridin-5-yl)pyridin-3-yl)oxy)-N,N-dimethylethan-1-amine [937];

3-(7-(4-fluorophenyl)-3H-imidazo[4,5-b]pyridin-2-yl)-5-(5-methoxypyridin-3-yl)-1H-pyrazolo[3,4-b]pyridine [938];

5-(3-(7-(4-fluorophenyl)-3H-imidazo[4,5-b]pyridin-2-yl)-1H-pyrazolo[3,4-b]pyridin-5-yl)pyridin-3-ol [939];

5-(5-(benzyloxy)pyridin-3-yl)-3-(7-(4-fluorophenyl)-3H-imidazo[4,5-b]pyridin-2-yl)-1H-pyrazolo[3,4-b]pyridine [940];

2-cyclohexyl-N-(5-(3-(7-(4-fluorophenyl)-3H-imidazo[4,5-b]pyridin-2-yl)-1H-pyrazolo[3,4-b]pyridin-5-yl)pyridin-3-yl)acetamide [941];

3-(7-(4-fluorophenyl)-3H-imidazo[4,5-b]pyridin-2-yl)-5-(pyridin-4-yl)-1H-pyrazolo[3,4-b]pyridine [942];

3-(7-(4-fluorophenyl)-3H-imidazo[4,5-b]pyridin-2-yl)-5-(pyridin-2-yl)-1H-pyrazolo[3,4-b]pyridine [943];

3-(7-(4-fluorophenyl)-3H-imidazo[4,5-b]pyridin-2-yl)-5-(pyrazin-2-yl)-1H-pyrazolo[3,4-b]pyridine [944];

3-(7-(2-fluorophenyl)-3H-imidazo[4,5-b]pyridin-2-yl)-5-(piperidin-4-yl)-1H-pyrazolo[3,4-b]pyridine [945];

3-(7-(2-fluorophenyl)-3H-imidazo[4,5-b]pyridin-2-yl)-5-(1,2,3,6-tetrahydropyridin-4-yl)-1H-pyrazolo[3,4-b]pyridine [946];

3-(7-(2-fluorophenyl)-3H-imidazo[4,5-b]pyridin-2-yl)-5-(1H-pyrazol-4-yl)-1H-pyrazolo[3,4-b]pyridine [947];

1-(6-(3-(7-(2-fluorophenyl)-3H-imidazo[4,5-b]pyridin-2-yl)-1H-pyrazolo[3,4-b]pyridin-5-yl)pyrazin-2-yl)azetidin-3-amine [950];

5-(5-(cyclohexyloxy)pyridin-3-yl)-3-(7-(2-fluorophenyl)-3H-imidazo[4,5-b]pyridin-2-yl)-1H-pyrazolo[3,4-b]pyridine [951];

3-(7-(2-fluorophenyl)-3H-imidazo[4,5-b]pyridin-2-yl)-5-(5-(piperidin-4-yloxy)pyridin-3-yl)-1H-pyrazolo[3,4-b]pyridine [952];

N-(5-(3-(7-(2-fluorophenyl)-3H-imidazo[4,5-b]pyridin-2-yl)-1H-pyrazolo[3,4-b]pyridin-5-yl)pyridin-3-yl)-2-(piperidin-4-yl)acetamide [953];

3-(7-(2-fluorophenyl)-3H-imidazo[4,5-b]pyridin-2-yl)-5-(5-(2-(pyrrolidinn-1-yl)ethoxy)pyridin-3-yl)-1H-pyrazolo[3,4-b]pyridine [954];

2-((5-(3-(7-(2-fluorophenyl)-3H-imidazo[4,5-b]pyridin-2-yl)-1H-pyrazolo[3,4-b]pyridin-5-yl)pyridin-3-yl)oxy)-N,N-dimethylethan-1-amine [955];

3-(7-(2-fluorophenyl)-3H-imidazo[4,5-b]pyridin-2-yl)-5-(5-methoxypyridin-3-yl)-1H-pyrazolo[3,4-b]pyridine [956];

5-(3-(7-(2-fluorophenyl)-3H-imidazo[4,5-b]pyridin-2-yl)-1H-pyrazolo[3,4-b]pyridin-5-yl)pyridin-3-ol [957];

5-(5-(benzyloxy)pyridin-3-yl)-3-(7-(2-fluorophenyl)-3H-imidazo[4,5-b]pyridin-2-yl)-1H-pyrazolo[3,4-b]pyridine [958];

2-cyclohexyl-N-(5-(3-(7-(2-fluorophenyl)-3H-imidazo[4,5-b]pyridin-2-yl)-1H-pyrazolo[3,4-b]pyridin-5-yl)pyridin-3-yl)acetamide [959];

3-(7-(2-fluorophenyl)-3H-imidazo[4,5-b]pyridin-2-yl)-5-(pyridin-4-yl)-1H-pyrazolo[3,4-b]pyridine [960];

3-(7-(2-fluorophenyl)-3H-imidazo[4,5-b]pyridin-2-yl)-5-(pyridin-2-yl)-1H-pyrazolo[3,4-b]pyridine [961];

3-(7-(2-fluorophenyl)-3H-imidazo[4,5-b]pyridin-2-yl)-5-(pyrazin-2-yl)-1H-pyrazolo[3,4-b]pyridine [962];

5-(piperidin-4-yl)-3-(7-(pyridin-3-yl)-3H-imidazo[4,5-b]pyridin-2-yl)-1H-pyrazolo[3,4-b]pyridine [963];

3-(7-(pyridin-3-yl)-3H-imidazo[4,5-b]pyridin-2-yl)-5-(1,2,3,6-tetrahydropyridin-4-yl)-1H-pyrazolo[3,4-b]pyridine [964];

5-(1H-pyrazol-4-yl)-3-(7-(pyridin-3-yl)-3H-imidazo[4,5-b]pyridin-2-yl)-1H-pyrazolo[3,4-b]pyridine [965];

1-(6-(3-(7-(pyridin-3-yl)-3H-imidazo[4,5-b]pyridin-2-yl)-1H-pyrazolo[3,4-b]pyridin-5-yl)pyrazin-2-yl)azetidin-3-amine [968];

5-(5-(cyclohexyloxy)pyridin-3-yl)-3-(7-(pyridin-3-yl)-3H-imidazo[4,5-b]pyridin-2-yl)-1H-pyrazolo[3,4-b]pyridine [969];

5-(5-(piperidin-4-yloxy)pyridin-3-yl)-3-(7-(pyridin-3-yl)-3H-imidazo[4,5-b]pyridin-2-yl)-1H-pyrazolo[3,4-b]pyridine [970];

2-(piperidin-4-yl)-N-(5-(3-(7-(pyridin-3-yl)-3H-imidazo[4,5-b]pyridin-2-yl)-1H-pyrazolo[3,4-b]pyridin-5-yl)pyridin-3-yl)acetamide [971];

3-(7-(pyridin-3-yl)-3H-imidazo[4,5-b]pyridin-2-yl)-5-(5-(2-(pyrrolidin-1-yl)ethoxy)pyridin-3-yl)-1H-pyrazolo[3,4-b]pyridine [972];

N,N-dimethyl-2-((5-(3-(7-(pyridin-3-yl)-3H-imidazo[4,5-b]pyridin-2-yl)-1H-pyrazolo[3,4-b]pyridin-5-yl)pyridin-3-yl)oxy)ethan-1-amine [973];

5-(5-methoxypyridin-3-yl)-3-(7-(pyridin-3-yl)-3H-imidazo[4,5-b]pyridin-2-yl)-1H-pyrazolo[3,4-b]pyridine [974];

5-(3-(7-(pyridin-3-yl)-3H-imidazo[4,5-b]pyridin-2-yl)-1H-pyrazolo[3,4-b]pyridin-5-yl)pyridin-3-ol [975];

5-(5-(benzyloxy)pyridin-3-yl)-3-(7-(pyridin-3-yl)-3H-imidazo[4,5-b]pyridin-2-yl)-1H-pyrazolo[3,4-b]pyridine [976];

2-cyclohexyl-N-(5-(3-(7-(pyridin-3-yl)-3H-imidazo[4,5-b]pyridin-2-yl)-1H-pyrazolo[3,4-b]pyridin-5-yl)pyridin-3-yl)acetamide [977];

3-(7-(pyridin-3-yl)-3H-imidazo[4,5-b]pyridin-2-yl)-5-(pyridin-4-yl)-1H-pyrazolo[3,4-b]pyridine [978];

5-(pyridin-2-yl)-3-(7-(pyridin-3-yl)-3H-imidazo[4,5-b]pyridin-2-yl)-1H-pyrazolo[3,4-b]pyridine [979];

5-(pyrazin-2-yl)-3-(7-(pyridin-3-yl)-3H-imidazo[4,5-b]pyridin-2-yl)-1H-pyrazolo[3,4-b]pyridine [980];

5-(piperidin-4-yl)-3-(7-(pyridin-4-yl)-3H-imidazo[4,5-b]pyridin-2-yl)-1H-pyrazolo[3,4-b]pyridine [981];

3-(7-(pyridin-4-yl)-3H-imidazo[4,5-b]pyridin-2-yl)-5-(1,2,3,6-tetrahydropyridin-4-yl)-1H-pyrazolo[3,4-b]pyridine [982];

5-(1H-pyrazol-4-yl)-3-(7-(pyridin-4-yl)-3H-imidazo[4,5-b]pyridin-2-yl)-1H-pyrazolo[3,4-b]pyridine [983];

1-(6-(3-(7-(pyridin-4-yl)-3H-imidazo[4,5-b]pyridin-2-yl)-1H-pyrazolo[3,4-b]pyridin-5-yl)pyrazin-2-yl)azetidin-3-amine [986];

5-(5-(cyclohexyloxy)pyridin-3-yl)-3-(7-(pyridin-4-yl)-3H-imidazo[4,5-b]pyridin-2-yl)-1H-pyrazolo[3,4-b]pyridine [987];

5-(5-(piperidin-4-yloxy)pyridin-3-yl)-3-(7-(pyridin-4-yl)-3H-imidazo[4,5-b]pyridin-2-yl)-1H-pyrazolo[3,4-b]pyridine [988];

2-(piperidin-4-yl)-N-(5-(3-(7-(pyridin-4-yl)-3H-imidazo[4,5-b]pyridin-2-yl)-1H-pyrazolo[3,4-b]pyridin-5-yl)pyridin-3-yl)acetamide [989];

3-(7-(pyridin-4-yl)-3H-imidazo[4,5-b]pyridin-2-yl)-5-(5-(2-(pyrrolidin-1-yl)ethoxy)pyridin-3-yl)-1H-pyrazolo[3,4-b]pyridine [990];

N,N-dimethyl-2-((5-(3-(7-(pyridin-4-yl)-3H-imidazo[4,5-b]pyridin-2-yl)-1H-pyrazolo[3,4-b]pyridin-5-yl)pyridin-3-yl)oxy)ethan-1-amine [991];

5-(5-methoxypyridin-3-yl)-3-(7-(pyridin-4-yl)-3H-imidazo[4,5-b]pyridin-2-yl)-1H-pyrazolo[3,4-b]pyridine [992];

5-(3-(7-(pyridin-4-yl)-3H-imidazo[4,5-b]pyridin-2-yl)-1H-pyrazolo[3,4-b]pyridin-5-yl)pyridin-3-ol [993];

5-(5-(benzyloxy)pyridin-3-yl)-3-(7-(pyridin-4-yl)-3H-imidazo[4,5-b]pyridin-2-yl)-1H-pyrazolo[3,4-b]pyridine [994];

2-cyclohexyl-N-(5-(3-(7-(pyridin-4-yl)-3H-imidazo[4,5-b]pyridin-2-yl)-1H-pyrazolo[3,4-b]pyridin-5-yl)pyridin-3-yl)acetamide [995];

5-(pyridin-4-yl)-3-(7-(pyridin-4-yl)-3H-imidazo[4,5-b]pyridin-2-yl)-1H-pyrazolo[3,4-b]pyridine [996];

5-(pyridin-2-yl)-3-(7-(pyridin-4-yl)-3H-imidazo[4,5-b]pyridin-2-yl)-1H-pyrazolo[3,4-b]pyridine [997];

5-(pyrazin-2-yl)-3-(7-(pyridin-4-yl)-3H-imidazo[4,5-b]pyridin-2-yl)-1H-pyrazolo[3,4-b]pyridine [998];

5-(piperidin-4-yl)-3-(7-(pyridin-2-yl)-3H-imidazo[4,5-b]pyridin-2-yl)-1H-pyrazolo[3,4-b]pyridine [999]; and 3-(7-(pyridin-2-yl)-3H-imidazo[4,5-b]pyridin-2-yl)-5-(1,2,3,6-tetrahydropyridin-4-yl)-1H-pyrazolo[3,4-b]pyridine [1000]; or a pharmaceutically acceptable salt thereof.

22. The compound of claim 1, wherein the compound of Formula I is selected from the group consisting of:

5-(1H-pyrazol-4-yl)-3-(7-(pyridin-2-yl)-3H-imidazo[4,5-b]pyridin-2-yl)-1H-pyrazolo[3,4-b]pyridine [1001];

1-(6-(3-(7-(pyridin-2-yl)-3H-imidazo[4,5-b]pyridin-2-yl)-1H-pyrazolo[3,4-b]pyridin-5-yl)pyrazin-2-yl)azetidin-3-amine [1004];

5-(5-(cyclohexyloxy)pyridin-3-yl)-3-(7-(pyridin-2-yl)-3H-imidazo[4,5-b]pyridin-2-yl)-1H-pyrazolo[3,4-b]pyridine [1005];

5-(5-(piperidin-4-yloxy)pyridin-3-yl)-3-(7-(pyridin-2-yl)-3H-imidazo[4,5-b]pyridin-2-yl)-1H-pyrazolo[3,4-b]pyridine [1006];

2-(piperidin-4-yl)-N-(5-(3-(7-(pyridin-2-yl)-3H-imidazo[4,5-b]pyridin-2-yl)-1H-pyrazolo[3,4-b]pyridin-5-yl)pyridin-3-yl)acetamide [1007];

3-(7-(pyridin-2-yl)-3H-imidazo[4,5-b]pyridin-2-yl)-5-(5-(2-(pyrrolidin-1-yl)ethoxy)pyridin-3-yl)-1H-pyrazolo[3,4-b]pyridine [1008];

N,N-dimethyl-2-((5-(3-(7-(pyridin-2-yl)-3H-imidazo[4,5-b]pyridin-2-yl)-1H-pyrazolo[3,4-b]pyridin-5-yl)pyridin-3-yl)oxy)ethan-1-amine [1009];

5-(5-methoxypyridin-3-yl)-3-(7-(pyridin-2-yl)-3H-imidazo[4,5-b]pyridin-2-yl)-1H-pyrazolo[3,4-b]pyridine [1010];

5-(3-(7-(pyridin-2-yl)-3H-imidazo[4,5-b]pyridin-2-yl)-1H-pyrazolo[3,4-b]pyridin-5-yl)pyridin-3-ol [1011];

5-(5-(benzyloxy)pyridin-3-yl)-3-(7-(pyridin-2-yl)-3H-imidazo[4,5-b]pyridin-2-yl)-1H-pyrazolo[3,4-b]pyridine [1012];

2-cyclohexyl-N-(5-(3-(7-(pyridin-2-yl)-3H-imidazo[4,5-b]pyridin-2-yl)-1H-pyrazolo[3,4-b]pyridin-5-yl)pyridin-3-yl)acetamide [1013];

3-(7-(pyridin-2-yl)-3H-imidazo[4,5-b]pyridin-2-yl)-5-(pyridin-4-yl)-1H-pyrazolo[3,4-b]pyridine [1014];

5-(pyridin-2-yl)-3-(7-(pyridin-2-yl)-3H-imidazo[4,5-b]pyridin-2-yl)-1H-pyrazolo[3,4-b]pyridine [1015];

5-(pyrazin-2-yl)-3-(7-(pyridin-2-yl)-3H-imidazo[4,5-b]pyridin-2-yl)-1H-pyrazolo[3,4-b]pyridine [1016];

3-(7-(piperidin-1-yl)-3H-imidazo[4,5-b]pyridin-2-yl)-5-(piperidin-4-yl)-1H-pyrazolo[3,4-b]pyridine [1017];

3-(7-(piperidin-1-yl)-3H-imidazo[4,5-b]pyridin-2-yl)-5-(1,2,3,6-tetrahydropyridin-4-yl)-1H-pyrazolo[3,4-b]pyridine [1018];

3-(7-(piperidin-1-yl)-3H-imidazo[4,5-b]pyridin-2-yl)-5-(1H-pyrazol-4-yl)-1H-pyrazolo[3,4-b]pyridine [1019];

5-(1-methyl-1H-pyrazol-4-yl)-3-(7-(piperidin-1-yl)-3H-imidazo[4,5-b]pyridin-2-yl)-1H-pyrazolo[3,4-b]pyridine [1020];

5-(1,2-dimethyl-1H-imidazol-5-yl)-3-(7-(piperidin-1-yl)-3H-imidazo[4,5-b]pyridin-2-yl)-1H-pyrazolo[3,4-b]pyridine [1021];

1-(6-(3-(7-(piperidin-1-yl)-3H-imidazo[4,5-b]pyridin-2-yl)-1H-pyrazolo[3,4-b]pyridin-5-yl)pyrazin-2-yl)azetidin-3-amine [1022];

5-(5-(cyclohexyloxy)pyridin-3-yl)-3-(7-(piperidin-1-yl)-3H-imidazo[4,5-b]pyridin-2-yl)-1H-pyrazolo[3,4-b]pyridine [1023];

3-(7-(piperidin-1-yl)-3H-imidazo[4,5-b]pyridin-2-yl)-5-(5-(piperidin-4-yloxy)pyridin-3-yl)-1H-pyrazolo[3,4-b]pyridine [1024];

N-(5-(3-(7-(piperidin-1-yl)-3H-imidazo[4,5-b]pyridin-2-yl)-1H-pyrazolo[3,4-b]pyridin-5-yl)pyridin-3-yl)-2-(piperidin-4-yl)acetamide [1025];

3-(7-(piperidin-1-yl)-3H-imidazo[4,5-b]pyridin-2-yl)-5-(5-(2-(pyrrolidin-1-yl)ethoxy)pyridin-3-yl)-1H-pyrazolo[3,4-b]pyridine [1026];

N,N-dimethyl-2-((5-(3-(7-(piperidin-1-yl)-3H-imidazo[4,5-b]pyridin-2-yl)-1H-pyrazolo[3,4-b]pyridin-5-yl)pyridin-3-yl)oxy)ethan-1-amine [1027];

5-(5-methoxypyridin-3-yl)-3-(7-(piperidin-1-yl)-3H-imidazo[4,5-b]pyridin-2-yl)-1H-pyrazolo[3,4-b]pyridine [1028];

5-(3-(7-(piperidin-1-yl)-3H-imidazo[4,5-b]pyridin-2-yl)-1H-pyrazolo[3,4-b]pyridin-5-yl)pyridin-3-ol [1029];

5-(5-(benzyloxy)pyridin-3-yl)-3-(7-(piperidin-1-yl)-3H-imidazo[4,5-b]pyridin-2-yl)-1H-pyrazolo[3,4-b]pyridine [1030];

2-cyclohexyl-N-(5-(3-(7-(piperidin-1-yl)-3H-imidazo[4,5-b]pyridin-2-yl)-1H-pyrazolo[3,4-b]pyridin-5-yl)pyridin-3-yl)acetamide [1031];

3-(7-(piperidin-1-yl)-3H-imidazo[4,5-b]pyridin-2-yl)-5-(pyridin-4-yl)-1H-pyrazolo[3,4-b]pyridine [1032];

3-(7-(piperidin-1-yl)-3H-imidazo[4,5-b]pyridin-2-yl)-5-(pyridin-2-yl)-1H-pyrazolo[3,4-b]pyridine [1033];

3-(7-(piperidin-1-yl)-3H-imidazo[4,5-b]pyridin-2-yl)-5-(pyrazin-2-yl)-1H-pyrazolo[3,4-b]pyridine [1034];

3-(7-(4-methyl-1H-imidazol-1-yl)-3H-imidazo[4,5-b]pyridin-2-yl)-5-(piperidin-4-yl)-1H-pyrazolo[3,4-b]pyridine [1035];

3-(7-(4-methyl-1H-imidazol-1-yl)-3H-imidazo[4,5-b]pyridin-2-yl)-5-(1,2,3,6-tetrahydropyridin-4-yl)-1H-pyrazolo[3,4-b]pyridine [1036];

3-(7-(4-methyl-1H-imidazol-1-yl)-3H-imidazo[4,5-b]pyridin-2-yl)-5-(1H-pyrazol-4-yl)-1H-pyrazolo[3,4-b]pyridine [1037];

1-(6-(3-(7-(4-methyl-1H-imidazol-1-yl)-3H-imidazo[4,5-b]pyridin-2-yl)-1H-pyrazolo[3,4-b]pyridin-5-yl)pyrazin-2-yl)azetidin-3-amine [1040];

5-(5-(cyclohexyloxy)pyridin-3-yl)-3-(7-(4-methyl-1H-imidazol-1-yl)-3H-imidazo[4,5-b]pyridin-2-yl)-1H-pyrazolo[3,4-b]pyridine [1041];

3-(7-(4-methyl-1H-imidazol-1-yl)-3H-imidazo[4,5-b]pyridin-2-yl)-5-(5-(piperidin-4-yloxy)pyridin-3-yl)-1H-pyrazolo[3,4-b]pyridine [1042];

N-(5-(3-(7-(4-methyl-1H-imidazol-1-yl)-3H-imidazo[4,5-b]pyridin-2-yl)-1H-pyrazolo[3,4-b]pyridin-5-yl)pyridin-3-yl)-2-(piperidin-4-yl)acetamide [1043];

3-(7-(4-methyl-1H-imidazol-1-yl)-3H-imidazo[4,5-b]pyridin-2-yl)-5-(5-(2-(pyrrolidin-1-yl)ethoxy)pyridin-3-yl)-1H-pyrazolo[3,4-b]pyridine [1044];

N,N-dimethyl-2-((5-(3-(7-(4-methyl-1H-imidazol-1-yl)-3H-imidazo[4,5-b]pyridin-2-yl)-1H-pyrazolo[3,4-b]pyridin-5-yl)pyridin-3-yl)oxy)ethan-1-amine [1045];

5-(5-methoxypyridin-3-yl)-3-(7-(4-methyl-1H-imidazol-1-yl)-3H-imidazo[4,5-b]pyridin-2-yl)-1H-pyrazolo[3,4-b]pyridine [1046];

5-(3-(7-(4-methyl-1H-imidazol-1-yl)-3H-imidazo[4,5-b]pyridin-2-yl)-1H-pyrazol-yl)-[3,4-b]pyridin-5-yl)pyridin-3-ol [1047];

5-(5-(benzyloxy)pyridin-3-yl)-3-(7-(4-methyl-1H-imidazol-1-yl)-3H-imidazo[4,5-b]pyridin-2-yl)-1H-pyrazolo[3,4-b]pyridine [1048];

2-cyclohexyl-N-(5-(3-(7-(4-methyl-1H-imidazol-1-yl)-3H-imidazo[4,5-b]pyridin-2-yl)-1H-pyrazolo[3,4-b]pyridin-5-yl)pyridin-3-yl)acetamide [1049];

3-(7-(4-methyl-1H-imidazol-1-yl)-3H-imidazo[4,5-b]pyridin-2-yl)-5-(pyridin-4-yl)-1H-pyrazolo[3,4-b]pyridine [1050];

3-(7-(4-methyl-1H-imidazol-1-yl)-3H-imidazo[4,5-b]pyridin-2-yl)-5-(pyridin-2-yl)-1H-pyrazolo[3,4-b]pyridine [1051];

3-(7-(4-methyl-1H-imidazol-1-yl)-3H-imidazo[4,5-b]pyridin-2-yl)-5-(pyrazin-2-yl)-1H-pyrazolo[3,4-b]pyridine [1052];

3-(7-(4-methylpiperazin-1-yl)-3H-imidazo[4,5-b]pyridin-2-yl)-5-(piperidin-4-yl)-1H-pyrazolo[3,4-b]pyridine [1053];

3-(7-(4-methylpiperazin-1-yl)-3H-imidazo[4,5-b]pyridin-2-yl)-5-(1,2,3,6-tetrahydropyridin-4-yl)-1H-pyrazolo[3,4-b]pyridine [1054];

3-(7-(4-methylpiperazin-1-yl)-3H-imidazo[4,5-b]pyridin-2-yl)-5-(1H-pyrazol-4-yl)-1H-pyrazolo[3,4-b]pyridine [1055];

1-(6-(3-(7-(4-methylpiperazin-1-yl)-3H-imidazo[4,5-b]pyridin-2-yl)-1H-pyrazolo[3,4-b]pyridin-5-yl)pyrazin-2-yl)azetidin-3-amine [1058];

5-(5-(cyclohexyloxy)pyridin-3-yl)-3-(7-(4-methylpiperazin-1-yl)-3H-imidazo[4,5-b]pyridin-2-yl)-1H-pyrazolo[3,4-b]pyridine [1059];

3-(7-(4-methylpiperazin-1-yl)-3H-imidazo[4,5-b]pyridin-2-yl)-5-(5-(piperidin-4-yloxy)pyridin-3-yl)-1H-pyrazolo[3,4-b]pyridine [1060];

N-(5-(3-(7-(4-methylpiperazin-1-yl)-3H-imidazo[4,5-b]pyridin-2-yl)-1H-pyrazolo[3,4-b]pyridin-5-yl)pyridin-3-yl)-2-(piperidin-4-yl)acetamide [1061];

3-(7-(4-methylpiperazin-1-yl)-3H-imidazo[4,5-b]pyridin-2-yl)-5-(5-(2-(pyrrolidin-1-yl)ethoxy)pyridin-3-yl)-1H-pyrazolo[3,4-b]pyridine [1062];

N,N-dimethyl-2-((5-(3-(7-(4-methylpiperazin-1-yl)-3H-imidazo[4,5-b]pyridin-2-yl)-1H-pyrazolo[3,4-b]pyridin-5-yl)pyridin-3-yl)oxy)ethan-1-amine [1063];

5-(5-methoxypyridin-3-yl)-3-(7-(4-methylpiperazin-1-yl)-3H-imidazo[4,5-b]pyridin-2-yl)-1H-pyrazolo[3,4-b]pyridine [1064];

5-(3-(7-(4-methylpiperazin-1-yl)-3H-imidazo[4,5-b]pyridin-2-yl)-1H-pyrazolo[3,4-b]pyridin-5-yl)pyridin-3-ol [1065];

5-(5-(benzyloxy)pyridin-3-yl)-3-(7-(4-methylpiperazin-1-yl)-3H-imidazo[4,5-b]pyridin-2-yl)-1H-pyrazolo[3,4-b]pyridine [1066];

2-cyclohexyl-N-(5-(3-(7-(4-methylpiperazin-1-yl)-3H-imidazo[4,5-b]pyridin-2-yl)-1H-pyrazolo[3,4-b]pyridin-5-yl)pyridin-3-yl)acetamide [1067];

3-(7-(4-methylpiperazin-1-yl)-3H-imidazo[4,5-b]pyridin-2-yl)-5-(pyridin-4-yl)-1H-pyrazolo[3,4-b]pyridine [1068];

3-(7-(4-methylpiperazin-1-yl)-3H-imidazo[4,5-b]pyridin-2-yl)-5-(pyridin-2-yl)-1H-pyrazolo[3,4-b]pyridine [1069];

3-(7-(4-methylpiperazin-1-yl)-3H-imidazo[4,5-b]pyridin-2-yl)-5-(pyrazin-2-yl)-1H-pyrazolo[3,4-b]pyridine [1070];

3-(3H-imidazo[4,5-b]pyridin-2-yl)-5-(piperidin-4-yl)-1H-pyrazolo[3,4-b]pyridine [1071];

3-(3H-imidazo[4,5-b]pyridin-2-yl)-5-(1,2,3,6-tetrahydropyridin-4-yl)-1H-pyrazolo[3,4-b]pyridine [1072];

3-(3H-imidazo[4,5-b]pyridin-2-yl)-5-(1H-pyrazol-4-yl)-1H-pyrazolo[3,4-b]pyridine [1073];

1-(6-(3-(3H-imidazo[4,5-b]pyridin-2-yl)-1H-pyrazolo[3,4-b]pyridin-5-yl)pyrazin-2-yl)azetidin-3-amine [1076];

5-(5-(cyclohexyloxy)pyridin-3-yl)-3-(3H-imidazo[4,5-b]pyridin-2-yl)-1H-pyrazolo[3,4-b]pyridine [1077];

3-(3H-imidazo[4,5-b]pyridin-2-yl)-5-(5-(piperidin-4-yloxy)pyridin-3-yl)-1H-pyrazolo[3,4-b]pyridine [1078];

N-(5-(3-(3H-imidazo[4,5-b]pyridin-2-yl)-1H-pyrazolo[3,4-b]pyridin-5-yl)pyridin-3-yl)-2-(piperidin-4-yl)acetamide [1079];

3-(3H-imidazo[4,5-b]pyridin-2-yl)-5-(5-(2-(pyrrolidin-1-yl)ethoxy)pyridin-3-yl)-1H-pyrazolo[3,4-b]pyridine [1080];

2-((5-(3-(3H-imidazo[4,5-b]pyridin-2-yl)-1H-pyrazolo[3,4-b]pyridin-5-yl)pyridin-3-yl)oxy)-N,N-dimethylethan-1-amine [1081];

3-(3H-imidazo[4,5-b]pyridin-2-yl)-5-(5-methoxypyridin-3-yl)-1H-pyrazolo[3,4-b]pyridine [1082];

5-(3-(3H-imidazo[4,5-b]pyridin-2-yl)-1H-pyrazolo[3,4-b]pyridin-5-yl)pyridin-3-ol [1083];

5-(5-(benzyloxy)pyridin-3-yl)-3-(3H-imidazo[4,5-b]pyridin-2-yl)-1H-pyrazolo[3,4-b]pyridine [1084];

N-(5-(3-(3H-imidazo[4,5-b]pyridin-2-yl)-1H-pyrazolo[3,4-b]pyridin-5-yl)pyridin-3-yl)-2-cyclohexylacetamide [1085];

3-(3H-imidazo[4,5-b]pyridin-2-yl)-5-(pyridin-4-yl)-1H-pyrazolo[3,4-b]pyridine [1086];

3-(3H-imidazo[4,5-b]pyridin-2-yl)-5-(pyridin-2-yl)-1H-pyrazolo[3,4-b]pyridine [1087];

3-(3H-imidazo[4,5-b]pyridin-2-yl)-5-(pyrazin-2-yl)-1H-pyrazolo[3,4-b]pyridine [1088];

5-(piperidin-4-yl)-3-(7-(thiophen-3-yl)-3H-imidazo[4,5-b]pyridin-2-yl)-1H-pyrazolo[3,4-b]pyridine [1089];

5-(1,2,3,6-tetrahydropyridin-4-yl)-3-(7-(thiophen-3-yl)-3H-imidazo[4,5-b]pyridin-2-yl)-1H-pyrazolo[3,4-b]pyridine [1090];

5-(1H-pyrazol-4-yl)-3-(7-(thiophen-3-yl)-3H-imidazo[4,5-b]pyridin-2-yl)-1H-pyrazolo[3,4-b]pyridine [1091];

1-(6-(3-(7-(thiophen-3-yl)-3H-imidazo[4,5-b]pyridin-2-yl)-1H-pyrazolo[3,4-b]pyridin-5-yl)pyrazin-2-yl)azetidin-3-amine [1094];

5-(5-(cyclohexyloxy)pyridin-3-yl)-3-(7-(thiophen-3-yl)-3H-imidazo[4,5-b]pyridin-2-yl)-1H-pyrazolo[3,4-b]pyridine [1095];

5-(5-(piperidin-4-yloxy)pyridin-3-yl)-3-(7-(thiophen-3-yl)-3H-imidazo[4,5-b]pyridin-2-yl)-1H-pyrazolo[3,4-b]pyridine [1096];

2-(piperidin-4-yl)-N-(5-(3-(7-(thiophen-3-yl)-3H-imidazo[4,5-b]pyridin-2-yl)-1H-pyrazolo[3,4-b]pyridin-5-yl)pyridin-3-yl)acetamide [1097];

5-(5-(2-(pyrrolidin-1-yl)ethoxy)pyridin-3-yl)-3-(7-(thiophen-3-yl)-3H-imidazo[4,5-b]pyridin-2-yl)-1H-pyrazolo[3,4-b]pyridine [1098];

N,N-dimethyl-2-((5-(3-(7-(thiophen-3-yl)-3H-imidazo[4,5-b]pyridin-2-yl)-1H-pyrazolo[3,4-b]pyridin-5-yl)pyridin-3-yl)oxy)ethan-1-amine [1099];

5-(5-methoxypyridin-3-yl)-3-(7-(thiophen-3-yl)-3H-imidazo[4,5-b]pyridin-2-yl)-1H-pyrazolo[3,4-b]pyridine [1100];

5-(3-(7-(thiophen-3-yl)-3H-imidazo[4,5-b]pyridin-2-yl)-1H-pyrazolo[3,4-b]pyridin-5-yl)pyridin-3-ol [1101];

5-(5-(benzyloxy)pyridin-3-yl)-3-(7-(thiophen-3-yl)-3H-imidazo[4,5-b]pyridin-2-yl)-1H-pyrazolo[3,4-b]pyridine [1102];

2-cyclohexyl-N-(5-(3-(7-(thiophen-3-yl)-3H-imidazo[4,5-b]pyridin-2-yl)-1H-pyrazolo[3,4-b]pyridin-5-yl)pyridin-3-yl)acetamide [1103];

5-(pyridin-4-yl)-3-(7-(thiophen-3-yl)-3H-imidazo[4,5-b]pyridin-2-yl)-1H-pyrazolo[3,4-b]pyridine [1104];

5-(pyridin-2-yl)-3-(7-(thiophen-3-yl)-3H-imidazo[4,5-b]pyridin-2-yl)-1H-pyrazolo[3,4-b]pyridine [1105];

5-(pyrazin-2-yl)-3-(7-(thiophen-3-yl)-3H-imidazo[4,5-b]pyridin-2-yl)-1H-pyrazolo[3,4-b]pyridine [1106];

3-(7-(furan-3-yl)-3H-imidazo[4,5-b]pyridin-2-yl)-5-(piperidin-4-yl)-1H-pyrazolo[3,4-b]pyridine [1107];

3-(7-(furan-3-yl)-3H-imidazo[4,5-b]pyridin-2-yl)-5-(1,2,3,6-tetrahydropyridin-4-yl)-1H-pyrazolo[3,4-b]pyridine [1108];

3-(7-(furan-3-yl)-3H-imidazo[4,5-b]pyridin-2-yl)-5-(1H-pyrazol-4-yl)-1H-pyrazolo[3,4-b]pyridine [1109];

1-(6-(3-(7-(furan-3-yl)-3H-imidazo[4,5-b]pyridin-2-yl)-1H-pyrazolo[3,4-b]pyridin-5-yl)pyrazin-2-yl)azetidin-3-amine [1112];

5-(5-(cyclohexyloxy)pyridin-3-yl)-3-(7-(furan-3-yl)-3H-imidazo[4,5-b]pyridin-2-yl)-1H-pyrazolo[3,4-b]pyridine [1113];

3-(7-(furan-3-yl)-3H-imidazo[4,5-b]pyridin-2-yl)-5-(5-(piperidin-4-yloxy)pyridin-3-yl)-1H-pyrazolo[3,4-b]pyridine [1114];

N-(5-(3-(7-(furan-3-yl)-3H-imidazo[4,5-b]pyridin-2-yl)-1H-pyrazolo[3,4-b]pyridin-5-yl)pyridin-3-yl)-2-(piperidin-4-yl)acetamide [1115];

3-(7-(furan-3-yl)-3H-imidazo[4,5-b]pyridin-2-yl)-5-(5-(2-(pyrrolidin-1-yl)ethoxy)pyridin-3-yl)-1H-pyrazolo[3,4-b]pyridine [1116];

2-((5-(3-(7-(furan-3-yl)-3H-imidazo[4,5-b]pyridin-2-yl)-1H-pyrazolo[3,4-b]pyridin-5-yl)pyridin-3-yl)oxy)-N,N-dimethylethan-1-amine [1117];

3-(7-(furan-3-yl)-3H-imidazo[4,5-b]pyridin-2-yl)-5-(5-methoxypyridin-3-yl)-1H-pyrazolo[3,4-b]pyridine [1118];

5-(3-(7-(furan-3-yl)-3H-imidazo[4,5-b]pyridin-2-yl)-1H-pyrazolo[3,4-b]pyridin-5-yl)pyridin-3-ol [1119];

5-(5-(benzyloxy)pyridin-3-yl)-3-(7-(furan-3-yl)-3H-imidazo[4,5-b]pyridin-2-yl)-1H-pyrazolo[3,4-b]pyridine [1120];

2-cyclohexyl-N-(5-(3-(7-(furan-3-yl)-3H-imidazo[4,5-b]pyridin-2-yl)-1H-pyrazolo[3,4-b]pyridin-5-yl)pyridin-3-yl)acetamide [1121];

3-(7-(furan-3-yl)-3H-imidazo[4,5-b]pyridin-2-yl)-5-(pyridin-4-yl)-1H-pyrazolo[3,4-b]pyridine [1122];

3-(7-(furan-3-yl)-3H-imidazo[4,5-b]pyridin-2-yl)-5-(pyridin-2-yl)-1H-pyrazolo[3,4-b]pyridine [1123];

3-(7-(furan-3-yl)-3H-imidazo[4,5-b]pyridin-2-yl)-5-(pyrazin-2-yl)-1H-pyrazolo[3,4-b]pyridine [1124];

5-(piperidin-4-yl)-3-(7-(thiophen-2-yl)-3H-imidazo[4,5-b]pyridin-2-yl)-1H-pyrazolo[3,4-b]pyridine [1125];

5-(1,2,3,6-tetrahydropyridin-4-yl)-3-(7-(thiophen-2-yl)-3H-imidazo[4,5-b]pyridin-2-yl)-1H-pyrazolo[3,4-b]pyridine [1126];

5-(1H-pyrazol-4-yl)-3-(7-(thiophen-2-yl)-3H-imidazo[4,5-b]pyridin-2-yl)-1H-pyrazolo[3,4-b]pyridine [1127];

1 (6-(3-(7-(thiophen-2-yl)-3H-imidazo[4,5-b]pyridin-2-yl)-1H-pyrazolo[3,4-b]pyridin-5-yl)pyrazin-2-yl)azetidin-3-amine [1130];

5-(5-(cyclohexyloxy)pyridin-3-yl)-3-(7-(thiophen-2-yl)-3H-imidazo[4,5-b]pyridin-2-yl)-1H-pyrazolo [3,4-b]pyridine [1131];

5-(5-(piperidin-4-yloxy)pyridin-3-yl)-3-(7-(thiophen-2-yl)-3H-imidazo[4,5-b]pyridin-2-yl)-1H-pyrazolo[3,4-b]pyridine [1132];

2-(piperidin-4-yl)-N-(5-(3-(7-(thiophen-2-yl)-3H-imidazo[4,5-b]pyridin-2-yl)-1H-pyrazolo[3,4-b]pyridin-5-yl)pyridin-3-yl)acetamide [1133];

5-(5-(2-(pyrrolidin-1-yl)ethoxy)pyridin-3-yl)-3-(7-(thiophen-2-yl)-3H-imidazo[4,5-b]pyridin-2-yl)-1H-pyrazolo[3,4-b]pyridine [1134];

N,N-dimethyl-2-((5-(3-(7-(thiophen-2-yl)-3H-imidazo[4,5-b]pyridin-2-yl)-1H-pyrazolo[3,4-b]pyridin-5-yl)pyridin-3-yl)oxy)ethan-1-amine [1135];

5-(5-methoxypyridin-3-yl)-3-(7-(thiophen-2-yl)-3H-imidazo[4,5-b]pyridin-2-yl)-1H-pyrazolo[3,4-b]pyridine [1136];

5-(3-(7-(thiophen-2-yl)-3H-imidazo[4,5-b]pyridin-2-yl)-1H-pyrazolo[3,4-b]pyridin-5-yl)pyridin-3-ol [1137];

5-(5-(benzyloxy)pyridin-3-yl)-3-(7-(thiophen-2-yl)-3H-imidazo[4,5-b]pyridin-2-yl)-1H-pyrazolo[3,4-b]pyridine [1138];

2-cyclohexyl-N-(5-(3-(7-(thiophen-2-yl)-3H-imidazo[4,5-b]pyridin-2-yl)-1H-pyrazolo[3,4-b]pyridin-5-yl)pyridin-3-yl)acetamide [1139];

5-(pyridin-4-yl)-3-(7-(thiophen-2-yl)-3H-imidazo[4,5-b]pyridin-2-yl)-1H-pyrazolo[3,4-b]pyridine [1140];

5-(pyridin-2-yl)-3-(7-(thiophen-2-yl)-3H-imidazo[4,5-b]pyridin-2-yl)-1H-pyrazolo[3,4-b]pyridine [1141];

5-(pyrazin-2-yl)-3-(7-(thiophen-2-yl)-3H-imidazo[4,5-b]pyridin-2-yl)-1H-pyrazolo[3,4-b]pyridine [1142];

3-(7-(5-fluorothiophen-2-yl)-3H-imidazo[4,5-b]pyridin-2-yl)-5-(piperidin-4-yl)-1H-pyrazolo[3,4-b]pyridine [1143];

3-(7-(5-fluorothiophen-2-yl)-3H-imidazo[4,5-b]pyridin-2-yl)-5-(1,2,3,6-tetrahydropyridin-4-yl)-1H-pyrazolo[3,4-b]pyridine [1144];

3-(7-(5-fluorothiophen-2-yl)-3H-imidazo[4,5-b]pyridin-2-yl)-5-(1H-pyrazol-4-yl)-1H-pyrazolo[3,4-b]pyridine [1145];

1-(6-(3-(7-(5-fluorothiophen-2-yl)-3H-imidazo[4,5-b]pyridin-2-yl)-1H-pyrazolo[3,4-b]pyridin-5-yl)pyrazin-2-yl)azetidin-3-amine [1148];

5-(5-(cyclohexyloxy)pyridin-3-yl)-3-(7-(5-fluorothiophen-2-yl)-3H-imidazo[4,5-b]pyridin-2-yl)-1H-pyrazolo[3,4-b]pyridine [1149];

3-(7-(5-fluorothiophen-2-yl)-3H-imidazo[4,5-b]pyridin-2-yl)-5-(5-(piperidin-4-yloxy)pyridin-3-yl)-1H-pyrazolo[3,4-b]pyridine [1150];

N-(5-(3-(7-(5-fluorothiophen-2-yl)-3H-imidazo[4,5-b]pyridin-2-yl)-1H-pyrazolo[3,4-b]pyridin-5-yl)pyridin-3-yl)-2-(piperidin-4-yl)acetamide [1151];

3-(7-(5-fluorothiophen-2-yl)-3H-imidazo[4,5-b]pyridin-2-yl)-5-(5-(2-(pyrrolidin-1-yl)ethoxy)pyridin-3-yl)-1H-pyrazolo[3,4-b]pyridine [1152];

2-((5-(3-(7-(5-fluorothiophen-2-yl)-3H-imidazo[4,5-b]pyridin-2-yl)-1H-pyrazolo[3,4-b]pyridin-5-yl)pyridin-3-yl)oxy)-N,N-dimethylethan-1-amine [1153];

3-(7-(5-fluorothiophen-2-yl)-3H-imidazo[4,5-b]pyridin-2-yl)-5-(5-methoxypyridin-3-yl)-1H-pyrazolo[3,4-b]pyridine [1154];

5-(3-(7-(5-fluorothiophen-2-yl)-3H-imidazo[4,5-b]pyridin-2-yl)-1H-pyrazolo[3,4-b]pyridin-5-yl)pyridin-3-ol [1155];

5-(5-(benzyloxy)pyridin-3-yl)-3-(7-(5-fluorothiophen-2-yl)-3H-imidazo[4,5-b]pyridin-2-yl)-1H-pyrazolo[3,4-b]pyridine [1156];

2-cyclohexyl-N-(5-(3-(7-(5-fluorothiophen-2-yl)-3H-imidazo[4,5-b]pyridin-2-yl)-1H-pyrazolo[3,4-b]pyridin-5-yl)pyridin-3-yl)acetamide [1157];

3-(7-(5-fluorothiophen-2-yl)-3H-imidazo[4,5-b]pyridin-2-yl)-5-(pyridin-4-yl)-1H-pyrazolo[3,4-b]pyridine [1158];

3-(7-(5-fluorothiophen-2-yl)-3H-imidazo[4,5-b]pyridin-2-yl)-5-(pyridin-2-yl)-1H-pyrazolo[3,4-b]pyridine [1159];

3-(7-(5-fluorothiophen-2-yl)-3H-imidazo[4,5-b]pyridin-2-yl)-5-(pyrazin-2-yl)-1H-pyrazolo[3,4-b]pyridine [1160];

3-(7-(5-methylthiophen-2-yl)-3H-imidazo[4,5-b]pyridin-2-yl)-5-(piperidin-4-yl)-1H-pyrazolo[3,4-b]pyridine [1161];

3-(7-(5-methylthiophen-2-yl)-3H-imidazo[4,5-b]pyridin-2-yl)-5-(1,2,3,6-tetrahydropyridin-4-yl)-1H-pyrazolo[3,4-b]pyridine [1162];

3-(7-(5-methylthiophen-2-yl)-3H-imidazo[4,5-b]pyridin-2-yl)-5-(1H-pyrazol-4-yl)-1H-pyrazolo[3,4-b]pyridine [1163];
1-(6-(3-(7-(5-methylthiophen-2-yl)-3H-imidazo[4,5-b]pyridin-2-yl)-1H-pyrazolo[3,4-b]pyridin-5-yl)pyrazin-2-yl)azetidin-3-amine [1166];
5-(5-(cyclohexyloxy)pyridin-3-yl)-3-(7-(5-methylthiophen-2-yl)-3H-imidazo[4,5-b]pyridin-2-yl)-1H-pyrazolo[3,4-b]pyridine [1167];
3-(7-(5-methylthiophen-2-yl)-3H-imidazo[4,5-b]pyridin-2-yl)-5-(5-(piperidin-4-yloxy)pyridin-3-yl)-1H-pyrazolo[3,4-b]pyridine [1168];
N-(5-(3-(7-(5-methylthiophen-2-yl)-3H-imidazo[4,5-b]pyridin-2-yl)-1H-pyrazolo[3,4-b]pyridin-5-yl)pyridin-3-yl)-2-(piperidin-4-yl)acetamide [1169];
3-(7-(5-methylthiophen-2-yl)-3H-imidazo[4,5-b]pyridin-2-yl)-5-(5-(2-(pyrrolidin-1-yl)ethoxy)pyridin-3-yl)-1H-pyrazolo[3,4-b]pyridine [1170];
N,N-dimethyl-2-((5-(3-(7-(5-methylthiophen-2-yl)-3H-imidazo[4,5-b]pyridin-2-yl)-1H-pyrazolo[3,4-b]pyridin-5-yl)pyridin-3-yl)oxy)ethan-1-amine [1171];
5-methoxypyridin-3-yl)-3-(7-(5-methylthiophen-2-yl)-3H-imidazo[4,5-b]pyridin-2-yl)-1H-pyrazolo[3,4-b]pyridine [1172];
5-(3-(7-(5-methylthiophen-2-yl)-3H-imidazo[4,5-b]pyridin-2-yl)-1H-pyrazolo[3,4-b]pyridin-5-yl)pyridin-3-ol [1173];
5-(5-(benzyloxy)pyridin-3-yl)-3-(7-(5-methylthiophen-2-yl)-3H-imidazo[4,5-b]pyridin-2-yl)-1H-pyrazolo[3,4-b]pyridine [1174];
2-cyclohexyl-N-(5-(3-(7-(5-methylthiophen-2-yl)-3H-imidazo[4,5-b]pyridin-2-yl)-1H-pyrazolo[3,4-b]pyridin-5-yl)pyridin-3-yl)acetamide [1175];
3-(7-(5-methylthiophen-2-yl)-3H-imidazo[4,5-b]pyridin-2-yl)-5-(pyridin-4-yl)-1H-pyrazolo[3,4-b]pyridine [1176];
3-(7-(5-methylthiophen-2-yl)-3H-imidazo[4,5-b]pyridin-2-yl)-5-(pyridin-2-yl)-1H-pyrazolo[3,4-b]pyridine [1177];
3-(7-(5-methylthiophen-2-yl)-3H-imidazo[4,5-b]pyridin-2-yl)-5-(pyrazin-2-yl)-1H-pyrazolo[3,4-b]pyridine [1178];
1-(5-(2-(5-(piperidin-4-yl)-1H-pyrazolo[3,4-b]pyridin-3-yl)-3H-imidazo[4,5-b]pyridin-7-yl)thiophen-2-yl)ethan-1-one [1179];
1-(5-(2-(5-(1,2,3,6-tetrahydropyridin-4-yl)-1H-pyrazolo[3,4-b]pyridin-3-yl)-3H-imidazo[4,5-b]pyridin-7-yl)thiophen-2-yl)ethan-1-one [1180];
1-(5-(2-(5-(1H-pyrazol-4-yl)-1H-pyrazolo[3,4-b]pyridin-3-yl)-3H-imidazo[4,5-b]pyridin-7-yl)thiophen-2-yl)ethan-1-one [1181];
1-(5-(2-(5-(6-(3-aminoazetidin-1-yl)pyrazin-2-yl)-1H-pyrazolo[3,4-b]pyridin-3-yl)-3H-imidazo [4,5-b]pyridin-7-yl)thiophen-2-yl)ethan-1-one [1184];
1-(5-(2-(5-(5-(cyclohexyloxy)pyridin-3-yl)-1H-pyrazolo[3,4-b]pyridin-3-yl)-3H-imidazo[4,5-b]pyridin-7-yl)thiophen-2-yl)ethan-1-one [1185];
1-(5-(2-(5-(5-(piperidin-4-yloxy)pyridin-3-yl)-1H-pyrazolo[3,4-b]pyridin-3-yl)-3H-imidazo[4,5-b]pyridin-7-yl)thiophen-2-yl)ethan-1-one [1186];
N-(5-(3-(7-(5-acetylthiophen-2-yl)-3H-imidazo[4,5-b]pyridin-2-yl)-1H-pyrazolo[3,4-b]pyridin-5-yl)pyridin-3-yl)-2-(piperidin-4-yl)acetamide [1187];
1-(5-(2-(5-(5-(2-(pyrrolidin-1-yl)ethoxy)pyridin-3-yl)-1H-pyrazolo[3,4-b]pyridin-3-yl)-3H-imidazo [4,5-b]pyridin-7-yl)thiophen-2-yl)ethan-1-one [1188];
1-(5-(2-(5-(5-(2-(dimethylamino)ethoxy)pyridin-3-yl)-1H-pyrazolo[3,4-b]pyridin-3-yl)-3H-imidazo [4,5-b]pyridin-7-yl)thiophen-2-yl)ethan-1-one [1189];
1-(5-(2-(5-(5-methoxypyridin-3-yl)-1H-pyrazolo[3,4-b]pyridin-3-yl)-3H-imidazo[4,5-b]pyridin-7-yl)thiophen-2-yl)ethan-1-one [1190];
1-(5-(2-(5-(5-hydroxypyridin-3-yl)-1H-pyrazolo[3,4-b]pyridin-3-yl)-3H-imidazo[4,5-b]pyridin-7-yl)thiophen-2-yl)ethan-1-one [1191];
1-(5-(2-(5-(5-(benzyloxy)pyridin-3-yl)-1H-pyrazolo[3,4-b]pyridin-3-yl)-3H-imidazo[4,5-b]pyridin-7-yl)thiophen-2-yl)ethan-1-one [1192];
N-(5-(3-(7-(5-acetylthiophen-2-yl)-3H-imidazo[4,5-b]pyridin-2-yl)-1H-pyrazolo[3,4-b]pyridin-5-yl)pyridin-3-yl)-2-cyclohexylacetamide [1193];
1-(5-(2-(5-(pyridin-4-yl)-1H-pyrazolo[3,4-b]pyridin-3-yl)-3H-imidazo[4,5-b]pyridin-7-yl)thiophen-2-yl)ethan-1-one [1194];
1-(5-(2-(5-(pyridin-2-yl)-1H-pyrazolo[3,4-b]pyridin-3-yl)-3H-imidazo[4,5-b]pyridin-7-yl)thiophen-2-yl)ethan-1-one [1195];
1-(5-(2-(5-(pyrazin-2-yl)-1H-pyrazolo[3,4-b]pyridin-3-yl)-3H-imidazo[4,5-b]pyridin-7-yl)thiophen-2-yl)ethan-1-one [1196];
N-(3-fluoro-5-(2-(5-(piperidin-4-yl)-1H-pyrazolo[3,4-b]pyridin-3-yl)-3H-imidazo[4,5-b]pyridin-7-yl)benzyl)methanesulfonamide [1197];
N-(3-fluoro-5-(2-(5-(1,2,3,6-tetrahydropyridin-4-yl)-1H-pyrazolo[3,4-b]pyridin-3-yl)-3H-imidazo [4,5-b]pyridin-7-yl)benzyl)methanesulfonamide [1198]; and
N-(3-(2-(5-(1H-pyrazol-4-yl)-1H-pyrazolo[3,4-b]pyridin-3-yl)-3H-imidazo[4,5-b]pyridin-7-yl)-5-fluorobenzyl)methanesulfonamide [1199]; or a pharmaceutically acceptable salt thereof.

23. The method of claim 1, wherein the compound of Formula I is selected from the group consisting of:
N-(3-(2-(5-(6-(3-aminoazetidin-1-yl)pyrazin-2-yl)-1H-pyrazolo[3,4-b]pyridin-3-yl)-3H-imidazo[4,5-b]pyridin-7-yl)-5-fluorobenzyl)methanesulfonamide [1202];
N-(3-(2-(5-(5-(cyclohexyloxy)pyridin-3-yl)-1H-pyrazolo[3,4-b]pyridin-3-yl)-3H-imidazo[4,5-b]pyridin-7-yl)-5-fluorobenzyl)methanesulfonamide [1203];
N-(3-fluoro-5-(2-(5-(5-(piperidin-4-yloxy)pyridin-3-yl)-1H-pyrazolo[3,4-b]pyridin-3-yl)-3H-imidazo [4,5-b]pyridin-7-yl)benzyl)methanesulfonamide [1204];
N-(5-(3-(7-(3-fluoro-5-(methylsulfonamidomethyl)phenyl)-3H-imidazo[4,5-b]pyridin-2-yl)-1H-pyrazolo[3,4-b]pyridin-5-yl)pyridin-3-yl)-2-(piperidin-4-yl)acetamide [1205];
N-(3-fluoro-5-(2-(5-(5-(2-(pyrrolidin-1-yl)ethoxy)pyridin-3-yl)-1H-pyrazolo[3,4-b]pyridin-3-yl)-3H-imidazo[4,5-b]pyridin-7-yl)benzyl)methanesulfonamide [1206];
N-(3-(2-(5-(5-(2-(dimethylamino)ethoxy)pyridin-3-yl)-1H-pyrazolo[3,4-b]pyridin-3-yl)-3H-imidazo [4,5-b]pyridin-7-yl)-5-fluorobenzyl)methanesulfonamide [1207];
N-(3-fluoro-5-(2-(5-(5-methoxypyridin-3-yl)-1H-pyrazolo[3,4-b]pyridin-3-yl)-3H-imidazo[4,5-b]pyridin-7-yl)benzyl)methanesulfonamide [1208];
N-(3-fluoro-5-(2-(5-(5-hydroxypyridin-3-yl)-1H-pyrazolo[3,4-b]pyridin-3-yl)-3H-imidazo[4,5-b]pyridin-7-yl)benzyl)methanesulfonamide [1209];
N-(3-(2-(5-(5-(benzyloxy)pyridin-3-yl)-1H-pyrazolo[3,4-b]pyridin-3-yl)-3H-imidazo[4,5-b]pyridin-7-yl)-5-fluorobenzyl)methanesulfonamide [1210];

2-cyclohexyl-N-(5-(3-(7-(3-fluoro-5-(methylsulfonamidomethyl)phenyl)-3H-imidazo[4,5-b]pyridin-2-yl)-1H-pyrazolo[3,4-b]pyridin-5-yl)pyridin-3-yl)acetamide [1211];

N-(3-fluoro-5-(2-(5-(pyridin-4-yl)-1H-pyrazolo[3,4-b]pyridin-3-yl)-3H-imidazo[4,5-b]pyridin-7-yl)benzyl)methanesulfonamide [1212];

N-(3-fluoro-5-(2-(5-(pyridin-2-yl)-1H-pyrazolo[3,4-b]pyridin-3-yl)-3H-imidazo[4,5-b]pyridin-7-yl)benzyl)methanesulfonamide [1213];

N-(3-fluoro-5-(2-(5-(pyrazin-2-yl)-1H-pyrazolo[3,4-b]pyridin-3-yl)-3H-imidazo[4,5-b]pyridin-7-yl)benzyl)methanesulfonamide [1214];

$N^1$-(3-fluoro-5-(2-(5-(piperidin-4-yl)-1H-pyrazolo[3,4-b]pyridin-3-yl)-3H-imidazo[4,5-b]pyridin-7-yl)phenyl)-$N^2,N^2$-dimethylethane-1,2-diamine [1215];

$N^1$-(3-fluoro-5-(2-(5-(1,2,3,6-tetrahydropyridin-4-yl)-1H-pyrazolo[3,4-b]pyridin-3-yl)-3H-imidazo [4,5-b]pyridin-7-yl)phenyl)-$N^2,N^2$-dimethylethane-1,2-diamine [1216];

$N^1$-(3-(2-(5-(1H-pyrazol-4-yl)-1H-pyrazolo[3,4-b]pyridin-3-yl)-3H-imidazo[4,5-b]pyridin-7-yl)-5-fluorophenyl)-$N^2,N^2$-dimethylethane-1,2-diamine [1217];

$N^1$-(3-(2-(5-(6-(3-aminoazetidin-1-yl)pyrazin-2-yl)-1H-pyrazolo[3,4-b]pyridin-3-yl)-3H-imidazo [4,5-b]pyridin-7-yl)-5-fluorophenyl)-$N^2,N^2$-dimethylethane-1,2-diamine [1220];

$N^1$-(3-(2-(5-(5-(cyclohexyloxy)pyridin-3-yl)-1H-pyrazolo[3,4-b]pyridin-3-yl)-3H-imidazo [4,5-b]pyridin-7-yl)-5-fluorophenyl)-$N^2,N^2$-dimethylethane-1,2-diamine [1221];

$N^1$-(3-fluoro-5-(2-(5-(5-(piperidin-4-yloxy)pyridin-3-yl)-1H-pyrazolo[3,4-b]pyridin-3-yl)-3H-imidazo [4,5-b]pyridin-7-yl)phenyl)-$N^2,N^2$-dimethylethane-1,2-diamine [1222];

N-(5-(3-(7-(3-((2-(dimethylamino)ethyl)amino)-5-fluorophenyl)-3H-imidazo[4,5-b]pyridin-2-yl)-1H-pyrazolo[3,4-b]pyridin-5-yl)pyridin-3-yl)-2-(piperidin-4-yl)acetamide [1223];

$N^1$-(3-fluoro-5-(2-(5-(5-(2-(pyrrolidin-1-yl)ethoxy)pyridin-3-yl)-1H-pyrazolo[3,4-b]pyridin-3-yl)-3H-imidazo [4,5-b]pyridin-7-yl)phenyl)-$N^2,N^2$-dimethylethane-1,2-diamine [1224];

$N^1$-(3-(2-(5-(5-(2-(dimethylamino)ethoxy)pyridin-3-yl)-1H-pyrazolo[3,4-b]pyridin-3-yl)-3H-imidazo [4,5-b]pyridin-7-yl)-5-fluorophenyl)-$N^2,N^2$-dimethylethane-1,2-diamine [1225];

$N^1$-(3-fluoro-5-(2-(5-(5-methoxypyridin-3-yl)-1H-pyrazolo[3,4-b]pyridin-3-yl)-3H-imidazo [4,5-b]pyridin-7-yl)phenyl)-$N^2,N^2$-dimethylethane-1,2-diamine [1226];

5-(3-(7-(3-((2-(dimethylamino)ethyl)amino)-5-fluorophenyl)-3H-imidazo[4,5-b]pyridin-2-yl)-1H-pyrazolo[3,4-b]pyridin-5-yl)pyridin-3-ol [1227];

$N^1$-(3-(2-(5-(5-(benzyloxy)pyridin-3-yl)-1H-pyrazolo[3,4-b]pyridin-3-yl)-3H-imidazo[4,5-b]pyridin-7-yl)-5-fluorophenyl)-$N^2,N^2$-dimethylethane-1,2-diamine [1228];

2-cyclohexyl-N-(5-(3-(7-(3-((2-(dimethylamino)ethyl)amino)-5-fluorophenyl)-3H-imidazo [4,5-b]pyridin-2-yl)-1H-pyrazolo[3,4-b]pyridin-5-yl)pyridin-3-yl)acetamide [1229];

$N^1$-(3-fluoro-5-(2-(5-(pyridin-4-yl)-1H-pyrazolo[3,4-b]pyridin-3-yl)-3H-imidazo[4,5-b]pyridin-7-yl)phenyl)-$N^2,N^2$-dimethylethane-1,2-diamine [1230];

$N^1$-(3-fluoro-5-(2-(5-(pyridin-2-yl)-1H-pyrazolo[3,4-b]pyridin-3-yl)-3H-imidazo[4,5-b]pyridin-7-yl)phenyl)-$N^2,N^2$-dimethylethane-1,2-diamine [1231];

$N^1$-(3-fluoro-5-(2-(5-(pyrazin-2-yl)-1H-pyrazolo[3,4-b]pyridin-3-yl)-3H-imidazo[4,5-b]pyridin-7-yl)phenyl)-$N^2,N^2$-dimethylethane-1,2-diamine [1232];

5-(3-(7-(3-(2-(dimethylamino)ethoxy)-5-fluorophenyl)-3H-imidazo[4,5-b]pyridin-2-yl)-1H-pyrazolo[3,4-b]pyridin-5-yl)pyridin-3-amine [1235];

2-(3-fluoro-5-(2-(5-(pyridin-3-yl)-1H-pyrazolo[3,4-b]pyridin-3-yl)-3H-imidazo[4,5-b]pyridin-7-yl)phenoxy)-N,N-dimethylethan-1-amine [1236];

5-(3-(7-(3-(2-(dimethylamino)ethoxy)-5-fluorophenyl)-3H-imidazo[4,5-b]pyridin-2-yl)-1H-pyrazolo[3,4-b]pyridin-5-yl)-N,N-dimethylpyridin-3-amine [1239];

N-(5-(3-(7-(3-(2-(dimethylamino)ethoxy)-5-fluorophenyl)-3H-imidazo[4,5-b]pyridin-2-yl)-1H-pyrazolo[3,4-b]pyridin-5-yl)pyridin-3-yl)-2-phenylacetamide [1242];

N-(5-(3-(7-(3-(2-(dimethylamino)ethoxy)-5-fluorophenyl)-3H-imidazo[4,5-b]pyridin-2-yl)-1H-pyrazolo[3,4-b]pyridin-5-yl)pyridin-3-yl)benzamide [1243];

5-(3-(7-(3-(2-(dimethylamino)ethoxy)-5-fluorophenyl)-3H-imidazo[4,5-b]pyridin-2-yl)-1H-pyrazolo[3,4-b]pyridin-5-yl)-N-isopropylpyridin-3-amine [1244];

2-(3-(2-(5-(5-((dimethylamino)methyl)pyridin-3-yl)-1H-pyrazolo[3,4-b]pyridin-3-yl)-3H-imidazo [4,5-b]pyridin-7-yl)-5-fluorophenoxy)-N,N-dimethylethan-1-amine [1245];

2-(3-fluoro-5-(2-(5-(5-(pyrrolidin-1-ylmethyl)pyridin-3-yl)-1H-pyrazolo[3,4-b]pyridin-3-yl)-3H-imidazo [4,5-b]pyridin-7-yl)phenoxy)-N,N-dimethylethan-1-amine [1246];

2-(3-fluoro-5-(2-(5-(5-(piperidin-1-ylmethyl)pyridin-3-yl)-1H-pyrazolo[3,4-b]pyridin-3-yl)-3H-imidazo [4,5-b]pyridin-7-yl)phenoxy)-N,N-dimethylethan-1-amine [1247];

2-(3-(2-(5-(5-((benzylamino)methyl)pyridin-3-yl)-1H-pyrazolo[3,4-b]pyridin-3-yl)-3H-imidazo[4,5-b]pyridin-7-yl)-5-fluorophenoxy)-N,N-dimethylethan-1-amine [1255];

2-(3-(2-(5-(5-(((cyclopentylmethyl)amino)methyl)pyridin-3-yl)-1H-pyrazolo[3,4-b]pyridin-3-yl)-3H-imidazo[4,5-b]pyridin-7-yl)-5-fluorophenoxy)-N,N-dimethylethan-1-amine [1256];

2-(3-(2-(5-(5-((3,3-difluoropyrrolidin-1-yl)methyl)pyridin-3-yl)-1H-pyrazolo[3,4-b]pyridin-3-yl)-3H-imidazo[4,5-b]pyridin-7-yl)-5-fluorophenoxy)-N,N-dimethylethan-1-amine [1257];

2-(3-fluoro-5-(2-(5-(pyrimidin-5-yl)-1H-pyrazolo[3,4-b]pyridin-3-yl)-3H-imidazo[4,5-b]pyridin-7-yl)phenoxy)-N,N-dimethylethan-1-amine [1258];

2-(3-fluoro-5-(2-(5-(pyridin-2-yl)-1H-pyrazolo[3,4-b]pyridin-3-yl)-3H-imidazo[4,5-b]pyridin-7-yl)phenoxy)-N,N-dimethylethan-1-amine [1259];

2-(3-fluoro-5-(2-(5-(piperidin-4-yl)-1H-pyrazolo[3,4-b]pyridin-3-yl)-3H-imidazo[4,5-b]pyridin-7-yl)phenoxy)-N,N-dimethylethan-1-amine [1260];

2-(3-fluoro-5-(2-(5-(1,2,3,6-tetrahydropyridin-4-yl)-1H-pyrazolo[3,4-b]pyridin-3-yl)-3H-imidazo [4,5-b]pyridin-7-yl)phenoxy)-N,N-dimethylethan-1-amine [1261];

2-(3-(2-(5-(1H-pyrazol-4-yl)-1H-pyrazolo[3,4-b]pyridin-3-yl)-3H-imidazo[4,5-b]pyridin-7-yl)-5-fluorophenoxy)-N,N-dimethylethan-1-amine [1262];

1-(6-(3-(7-(3-(2-(dimethylamino)ethoxy)-5-fluorophenyl)-3H-imidazo[4,5-b]pyridin-2-yl)-1H-pyrazolo[3,4-b]pyridin-5-yl)pyrazin-2-yl)azetidin-3-amine [1265];

2-(3-(2-(5-(5-(cyclohexyloxy)pyridin-3-yl)-1H-pyrazolo[3,4-b]pyridin-3-yl)-3H-imidazo[4,5-b]pyridin-7-yl)-5-fluorophenoxy)-N,N-dimethylethan-1-amine [1266];

2-(3-fluoro-5-(2-(5-(5-(piperidin-4-yloxy)pyridin-3-yl)-1H-pyrazolo[3,4-b]pyridin-3-yl)-3H-imidazo [4,5-b]pyridin-7-yl)phenoxy)-N,N-dimethylethan-1-amine [1267];

N-(5-(3-(7-(3-(2-(dimethylamino)ethoxy)-5-fluorophenyl)-3H-imidazo[4,5-b]pyridin-2-yl)-1H-pyrazolo[3,4-b]pyridin-5-yl)pyridin-3-yl)-2-(piperidin-4-yl)acetamide [1268];

2-(3-fluoro-5-(2-(5-(5-(2-(pyrrolidin-1-yl)ethoxy)pyridin-3-yl)-1H-pyrazolo[3,4-b]pyridin-3-yl)-3H-imidazo[4,5-b]pyridin-7-yl)phenoxy)-N,N-dimethylethan-1-amine [1269];

2-((5-(3-(7-(3-(2-(dimethylamino)ethoxy)-5-fluorophenyl)-3H-imidazo[4,5-b]pyridin-2-yl)-1H-pyrazolo[3,4-b]pyridin-5-yl)pyridin-3-yl)oxy)-N,N-dimethylethan-1-amine [1270];

2-(3-fluoro-5-(2-(5-(5-methoxypyridin-3-yl)-1H-pyrazolo[3,4-b]pyridin-3-yl)-3H-imidazo[4,5-b]pyridin-7-yl)phenoxy)-N,N-dimethylethan-1-amine [1271];

5-(3-(7-(3-(2-(dimethylamino)ethoxy)-5-fluorophenyl)-3H-imidazo[4,5-b]pyridin-2-yl)-1H-pyrazolo[3,4-b]pyridin-5-yl)pyridin-3-ol [1272];

2-(3-(2-(5-(5-(benzyloxy)pyridin-3-yl)-1H-pyrazolo[3,4-b]pyridin-3-yl)-3H-imidazo[4,5-b]pyridin-7-yl)-5-fluorophenoxy)-N,N-dimethylethan-1-amine [1273];

2-cyclohexyl-N-(5-(3-(7-(3-(2-(dimethylamino)ethoxy)-5-fluorophenyl)-3H-imidazo[4,5-b]pyridin-2-yl)-1H-pyrazolo[3,4-b]pyridin-5-yl)pyridin-3-yl)acetamide [1274];

2-(3-fluoro-5-(2-(5-(pyridin-4-yl)-1H-pyrazolo[3,4-b]pyridin-3-yl)-3H-imidazo[4,5-b]pyridin-7-yl)phenoxy)-N,N-dimethylethan-1-amine [1275];

2-(3-fluoro-5-(2-(5-(pyrazin-2-yl)-1H-pyrazolo[3,4-b]pyridin-3-yl)-3H-imidazo[4,5-b]pyridin-7-yl)phenoxy)-N,N-dimethylethan-1-amine [1276];

5-(3-(7-(3-fluoro-5-(2-(pyrrolidin-1-yl)ethoxy)phenyl)-3H-imidazo[4,5-b]pyridin-2-yl)-1H-pyrazolo[3,4-b]pyridin-5-yl)pyridin-3-amine [1279];

3-(7-(3-fluoro-5-(2-(pyrrolidin-1-yl)ethoxy)phenyl)-3H-imidazo[4,5-b]pyridin-2-yl)-5-(pyridin-3-yl)-1H-pyrazolo[3,4-b]pyridine [1280];

5-(3-(7-(3-fluoro-5-(2-(pyrrolidin-1-yl)ethoxy)phenyl)-3H-imidazo[4,5-b]pyridin-2-yl)-1H-pyrazolo[3,4-b]pyridin-5-yl)-N,N-dimethylpyridin-3-amine [1283];

N-(5-(3-(7-(3-fluoro-5-(2-(pyrrolidin-1-yl)ethoxy)phenyl)-3H-imidazo[4,5-b]pyridin-2-yl)-1H-pyrazolo[3,4-b]pyridin-5-yl)pyridin-3-yl)-2-phenylacetamide [1286];

N-(5-(3-(7-(3-fluoro-5-(2-(pyrrolidin-1-yl)ethoxy)phenyl)-3H-imidazo[4,5-b]pyridin-2-yl)-1H-pyrazolo[3,4-b]pyridin-5-yl)pyridin-3-yl)benzamide [1287];

5-(3-(7-(3-fluoro-5-(2-(pyrrolidin-1-yl)ethoxy)phenyl)-3H-imidazo[4,5-b]pyridin-2-yl)-1H-pyrazolo[3,4-b]pyridin-5-yl)-N-isopropylpyridin-3-amine [1288];

1-(5-(3-(7-(3-fluoro-5-(2-(pyrrolidin-1-yl)ethoxy)phenyl)-3H-imidazo[4,5-b]pyridin-2-yl)-1H-pyrazolo[3,4-b]pyridin-5-yl)pyridin-3-yl)-N,N-dimethylmethanamine [1289];

3-(7-(3-fluoro-5-(2-(pyrrolidin-1-yl)ethoxy)phenyl)-3H-imidazo[4,5-b]pyridin-2-yl)-5-(5-(pyrrolidin-1-ylmethyl)pyridin-3-yl)-1H-pyrazolo[3,4-b]pyridine [1290];

3-(7-(3-fluoro-5-(2-(pyrrolidin-1-yl)ethoxy)phenyl)-3H-imidazo[4,5-b]pyridin-2-yl)-5-(5-(piperidin-1-ylmethyl)pyridin-3-yl)-1H-pyrazolo[3,4-b]pyridine [1291];

N-benzyl-1-(5-(3-(7-(3-fluoro-5-(2-(pyrrolidin-1-yl)ethoxy)phenyl)-3H-imidazo[4,5-b]pyridin-2-yl)-1H-pyrazolo[3,4-b]pyridin-5-yl)pyridin-3-yl)methanamine [1299];

1-cyclopentyl-N-((5-(3-(7-(3-fluoro-5-(2-(pyrrolidin-1-yl)ethoxy)phenyl)-3H-imidazo[4,5-b]pyridin-2-yl)-1H-pyrazolo[3,4-b]pyridin-5-yl)pyridin-3-yl)methyl)methanamine [1300];

5-(5-((3,3-difluoropyrrolidin-1-yl)methyl)pyridin-3-yl)-3-(7-(3-fluoro-5-(2-(pyrrolidin-1-yl)ethoxy)phenyl)-3H-imidazo[4,5-b]pyridin-2-yl)-1H-pyrazolo[3,4-b]pyridine [1301];

3-(7-(3-fluoro-5-(2-(pyrrolidin-1-yl)ethoxy)phenyl)-3H-imidazo[4,5-b]pyridin-2-yl)-5-(pyrimidin-5-yl)-1H-pyrazolo[3,4-b]pyridine [1302];

3-(7-(3-fluoro-5-(2-(pyrrolidin-1-yl)ethoxy)phenyl)-3H-imidazo[4,5-b]pyridin-2-yl)-5-(pyridin-2-yl)-1H-pyrazolo[3,4-b]pyridine [1303];

3-(7-(3-fluoro-5-(2-(pyrrolidin-1-yl)ethoxy)phenyl)-3H-imidazo[4,5-b]pyridin-2-yl)-5-(piperidin-4-yl)-1H-pyrazolo[3,4-b]pyridine [1304];

3-(7-(3-fluoro-5-(2-(pyrrolidin-1-yl)ethoxy)phenyl)-3H-imidazo[4,5-b]pyridin-2-yl)-5-(1,2,3,6-tetrahydropyridin-4-yl)-1H-pyrazolo[3,4-b]pyridine [1305];

3-(7-(3-fluoro-5-(2-(pyrrolidin-1-yl)ethoxy)phenyl)-3H-imidazo[4,5-b]pyridin-2-yl)-5-(H-pyrazol-4-yl)-1H-pyrazolo[3,4-b]pyridine [1306];

1-(6-(3-(7-(3-fluoro-5-(2-(pyrrolidin-1-yl)ethoxy)phenyl)-3H-imidazo[4,5-b]pyridin-2-yl)-1H-pyrazolo[3,4-b]pyridin-5-yl)pyrazin-2-yl)azetidin-3-amine [1309];

5-(5-(cyclohexyloxy)pyridin-3-yl)-3-(7-(3-fluoro-5-(2-(pyrrolidin-1-yl)ethoxy)phenyl)-3H-imidazo[4,5-b]pyridin-2-yl)-1H-pyrazolo[3,4-b]pyridine [1310];

3-(7-(3-fluoro-5-(2-(pyrrolidin-1-yl)ethoxy)phenyl)-3H-imidazo[4,5-b]pyridin-2-yl)-5-(5-(piperidin-4-yloxy)pyridin-3-yl)-1H-pyrazolo[3,4-b]pyridine [1311];

N-(5-(3-(7-(3-fluoro-5-(2-(pyrrolidin-1-yl)ethoxy)phenyl)-3H-imidazo[4,5-b]pyridin-2-yl)-1H-pyrazolo[3,4-b]pyridin-5-yl)pyridin-3-yl)-2-(piperidin-4-yl)acetamide [1312];

3-(7-(3-fluoro-5-(2-(pyrrolidin-1-yl)ethoxy)phenyl)-3H-imidazo[4,5-b]pyridin-2-yl)-5-(5-(2-(pyrrolidin-1-yl)ethoxy)pyridin-3-yl)-1H-pyrazolo[3,4-b]pyridine [1313];

2-((5-(3-(7-(3-fluoro-5-(2-(pyrrolidin-1-yl)ethoxy)phenyl)-3H-imidazo[4,5-b]pyridin-2-yl)-1H-pyrazolo[3,4-b]pyridin-5-yl)pyridin-3-yl)oxy)-N,N-dimethylethan-1-amine [1314];

3-(7-(3-fluoro-5-(2-(pyrrolidin-1-yl)ethoxy)phenyl)-3H-imidazo[4,5-b]pyridin-2-yl)-5-(5-methoxypyridin-3-yl)-1H-pyrazolo[3,4-b]pyridine [1315];

5-(3-(7-(3-fluoro-5-(2-(pyrrolidin-1-yl)ethoxy)phenyl)-3H-imidazo[4,5-b]pyridin-2-yl)-1H-pyrazolo[3,4-b]pyridin-5-yl)pyridin-3-ol [1316];

5-(5-(benzyloxy)pyridin-3-yl)-3-(7-(3-fluoro-5-(2-(pyrrolidin-1-yl)ethoxy)phenyl)-3H-imidazo [4,5-b]pyridin-2-yl)-1H-pyrazolo[3,4-b]pyridine [1317];

2-cyclohexyl-N-(5-(3-(7-(3-fluoro-5-(2-(pyrrolidin-1-yl)ethoxy)phenyl)-3H-imidazo[4,5-b]pyridin-2-yl)-1H-pyrazolo[3,4-b]pyridin-5-yl)pyridin-3-yl)acetamide [1318];

3-(7-(3-fluoro-5-(2-(pyrrolidin-1-yl)ethoxy)phenyl)-3H-imidazo[4,5-b]pyridin-2-yl)-5-(pyridin-4-yl)-1H-pyrazolo[3,4-b]pyridine [1319];

3-(7-(3-fluoro-5-(2-(pyrrolidin-1-yl)ethoxy)phenyl)-3H-imidazo[4,5-b]pyridin-2-yl)-5-(pyrazin-2-yl)-1H-pyrazolo[3,4-b]pyridine [1320];

3-(2-(5-(5-aminopyridin-3-yl)-1H-pyrazolo[3,4-b]pyridin-3-yl)-3H-imidazo[4,5-b]pyridin-7-yl)-5-fluorophenol [1323];

3-fluoro-5-(2-(5-(pyridin-3-yl)-1H-pyrazolo[3,4-b]pyridin-3-yl)-3H-imidazo[4,5-b]pyridin-7-yl)phenol [1324];

3-(2-(5-(5-(dimethylamino)pyridin-3-yl)-1H-pyrazolo[3,4-b]pyridin-3-yl)-3H-imidazo[4,5-b]pyridin-7-yl)-5-fluorophenol [1327];

N-(5-(3-(7-(3-fluoro-5-hydroxyphenyl)-3H-imidazo[4,5-b]pyridin-2-yl)-1H-pyrazolo[3,4-b]pyridin-5-yl)pyridin-3-yl)-2-phenylacetamide [1330];

N-(5-(3-(7-(3-fluoro-5-hydroxyphenyl)-3H-imidazo[4,5-b]pyridin-2-yl)-1H-pyrazolo[3,4-b]pyridin-5-yl)pyridin-3-yl)benzamide [1331];

3-fluoro-5-(2-(5-(5-(isopropylamino)pyridin-3-yl)-1H-pyrazolo[3,4-b]pyridin-3-yl)-3H-imidazo[4,5-b]pyridin-7-yl)phenol [1332];

3-(2-(5-(5-((dimethylamino)methyl)pyridin-3-yl)-1H-pyrazolo[3,4-b]pyridin-3-yl)-3H-imidazo[4,5-b]pyridin-7-yl)-5-fluorophenol [1333];

3-fluoro-5-(2-(5-(5-(pyrrolidin-1-ylmethyl)pyridin-3-yl)-1H-pyrazolo[3,4-b]pyridin-3-yl)-3H-imidazo [4,5-b]pyridin-7-yl)phenol [1334];

3-fluoro-5-(2-(5-(5-(piperidin-1-ylmethyl)pyridin-3-yl)-1H-pyrazolo[3,4-b]pyridin-3-yl)-3H-imidazo [4,5-b]pyridin-7-yl)phenol [1335];

3-(2-(5-(5-((benzylamino)methyl)pyridin-3-yl)-1H-pyrazolo[3,4-b]pyridin-3-yl)-3H-imidazo[4,5-b]pyridin-7-yl)-5-fluorophenol [1343];

3-(2-(5-(5-(((cyclopentylmethyl)amino)methyl)pyridin-3-yl)-1H-pyrazolo[3,4-b]pyridin-3-yl)-3H-imidazo[4,5-b]pyridin-7-yl)-5-fluorophenol [1344];

3-(2-(5-(5-((3,3-difluoropyrrolidin-1-yl)methyl)pyridin-3-yl)-1H-pyrazolo[3,4-b]pyridin-3-yl)-3H-imidazo[4,5-b]pyridin-7-yl)-5-fluorophenol [1345];

3-fluoro-5-(2-(5-(pyrimidin-5-yl)-1H-pyrazolo[3,4-b]pyridin-3-yl)-3H-imidazo[4,5-b]pyridin-7-yl)phenol [1346];

3-fluoro-5-(2-(5-(pyridin-2-yl)-1H-pyrazolo[3,4-b]pyridin-3-yl)-3H-imidazo[4,5-b]pyridin-7-yl)phenol [1347];

3-fluoro-5-(2-(5-(piperidin-4-yl)-1H-pyrazolo[3,4-b]pyridin-3-yl)-3H-imidazo[4,5-b]pyridin-7-yl)phenol [1348];

3-fluoro-5-(2-(5-(1,2,3,6-tetrahydropyridin-4-yl)-1H-pyrazolo[3,4-b]pyridin-3-yl)-3H-imidazo [4,5-b]pyridin-7-yl)phenol [1349];

3-(2-(5-(1H-pyrazol-4-yl)-1H-pyrazolo[3,4-b]pyridin-3-yl)-3H-imidazo[4,5-b]pyridin-7-yl)-5-fluorophenol [1350];

3-(2-(5-(6-(3-aminoazetidin-1-yl)pyrazin-2-yl)-1H-pyrazolo[3,4-b]pyridin-3-yl)-3H-imidazo[4,5-b]pyridin-7-yl)-5-fluorophenol [1353];

3-(2-(5-(5-(cyclohexyloxy)pyridin-3-yl)-1H-pyrazolo[3,4-b]pyridin-3-yl)-3H-imidazo[4,5-b]pyridin-7-yl)-5-fluorophenol [1354];

3-fluoro-5-(2-(5-(5-(piperidin-4-yloxy)pyridin-3-yl)-1H-pyrazolo[3,4-b]pyridin-3-yl)-3H-imidazo [4,5-b]pyridin-7-yl)phenol [1355];

N-(5-(3-(7-(3-fluoro-5-hydroxyphenyl)-3H-imidazo[4,5-b]pyridin-2-yl)-1H-pyrazolo[3,4-b]pyridin-5-yl)pyridin-3-yl)-2-(piperidin-4-yl)acetamide [1356];

3-fluoro-5-(2-(5-(5-(2-(pyrrolidin-1-yl)ethoxy)pyridin-3-yl)-1H-pyrazolo[3,4-b]pyridin-3-yl)-3H-imidazo [4,5-b]pyridin-7-yl)phenol [1357];

3-(2-(5-(5-(2-(dimethylamino)ethoxy)pyridin-3-yl)-1H-pyrazolo[3,4-b]pyridin-3-yl)-3H-imidazo[4,5-b]pyridin-7-yl)-5-fluorophenol [1358];

3-fluoro-5-(2-(5-(5-methoxypyridin-3-yl)-1H-pyrazolo[3,4-b]pyridin-3-yl)-3H-imidazo[4,5-b]pyridin-7-yl)phenol [1359];

5-(3-(7-(3-fluoro-5-hydroxyphenyl)-3H-imidazo[4,5-b]pyridin-2-yl)-1H-pyrazolo[3,4-b]pyridin-5-yl)pyridin-3-ol [1360];

3-(2-(5-(5-(benzyloxy)pyridin-3-yl)-1H-pyrazolo[3,4-b]pyridin-3-yl)-3H-imidazo[4,5-b]pyridin-7-yl)-5-fluorophenol [1361];

2-cyclohexyl-N-(5-(3-(7-(3-fluoro-5-hydroxyphenyl)-3H-imidazo[4,5-b]pyridin-2-yl)-1H-pyrazolo[3,4-b]pyridin-5-yl)pyridin-3-yl)acetamide [1362];

3-fluoro-5-(2-(5-(pyridin-4-yl)-1H-pyrazolo[3,4-b]pyridin-3-yl)-3H-imidazo[4,5-b]pyridin-7-yl)phenol [1363];

3-fluoro-5-(2-(5-(pyrazin-2-yl)-1H-pyrazolo[3,4-b]pyridin-3-yl)-3H-imidazo[4,5-b]pyridin-7-yl)phenol [1364];

5-(3-(7-(3-fluoro-5-methoxyphenyl)-3H-imidazo[4,5-b]pyridin-2-yl)-1H-pyrazolo[3,4-b]pyridin-5-yl)pyridin-3-amine [1367];

3-(7-(3-fluoro-5-methoxyphenyl)-3H-imidazo[4,5-b]pyridin-2-yl)-5-(pyridin-3-yl)-1H-pyrazolo[3,4-b]pyridine [1368];

5-(3-(7-(3-fluoro-5-methoxyphenyl)-3H-imidazo[4,5-b]pyridin-2-yl)-1H-pyrazolo[3,4-b]pyridin-5-yl)-N,N-dimethylpyridin-3-amine [1371];

N-(5-(3-(7-(3-fluoro-5-methoxyphenyl)-3H-imidazo[4,5-b]pyridin-2-yl)-1H-pyrazolo[3,4-b]pyridin-5-yl)pyridin-3-yl)-2-phenylacetamide [1374];

N-(5-(3-(7-(3-fluoro-5-methoxyphenyl)-3H-imidazo[4,5-b]pyridin-2-yl)-1H-pyrazolo[3,4-b]pyridin-5-yl)pyridin-3-yl)benzamide [1375];

5-(3-(7-(3-fluoro-5-methoxyphenyl)-3H-imidazo[4,5-b]pyridin-2-yl)-1H-pyrazolo[3,4-b]pyridin-5-yl)-N-isopropylpyridin-3-amine [1376];

1-(5-(3-(7-(3-fluoro-5-methoxyphenyl)-3H-imidazo[4,5-b]pyridin-2-yl)-1H-pyrazolo[3,4-b]pyridin-5-yl)pyridin-3-yl)-N,N-dimethylmethanamine [1377];

3-(7-(3-fluoro-5-methoxyphenyl)-3H-imidazo[4,5-b]pyridin-2-yl)-5-(5-(pyrrolidin-1-ylmethyl)pyridin-3-yl)-1H-pyrazolo[3,4-b]pyridine [1378];

3-(7-(3-fluoro-5-methoxyphenyl)-3H-imidazo[4,5-b]pyridin-2-yl)-5-(5-(piperidin-1-ylmethyl)pyridin-3-yl)-1H-pyrazolo[3,4-b]pyridine [1379];

N-benzyl-1-(5-(3-(7-(3-fluoro-5-methoxyphenyl)-3H-imidazo[4,5-b]pyridin-2-yl)-1H-pyrazolo[3,4-b]pyridin-5-yl)pyridin-3-yl)methanamine [1387];

1-cyclopentyl-N-((5-(3-(7-(3-fluoro-5-methoxyphenyl)-3H-imidazo[4,5-b]pyridin-2-yl)-1H-pyrazolo[3,4-b]pyridin-5-yl)pyridin-3-yl)methyl)methanamine [1388];

5-(5-((3,3-difluoropyrrolidin-1-yl)methyl)pyridin-3-yl)-3-(7-(3-fluoro-5-methoxyphenyl)-3H-imidazo[4,5-b]pyridin-2-yl)-1H-pyrazolo[3,4-b]pyridine [1389];

3-(7-(3-fluoro-5-methoxyphenyl)-3H-imidazo[4,5-b]pyridin-2-yl)-5-(pyrimidin-5-yl)-1H-pyrazolo[3,4-b]pyridine [1390];

3-(7-(3-fluoro-5-methoxyphenyl)-3H-imidazo[4,5-b]
pyridin-2-yl)-5-(pyridin-2-yl)-1H-pyrazolo[3,4-b]pyri-
dine [1391];
3-(7-(3-fluoro-5-methoxyphenyl)-3H-imidazo[4,5-b]
pyridin-2-yl)-5-(piperidin-4-yl)-1H-pyrazolo[3,4-b]
pyridine [1392];
3-(7-(3-fluoro-5-methoxyphenyl)-3H-imidazo[4,5-b]
pyridin-2-yl)-5-(1,2,3,6-tetrahydropyridin-4-yl)-1H-
pyrazolo[3,4-b]pyridine [1393];
3-(7-(3-fluoro-5-methoxyphenyl)-3H-imidazo[4,5-b]
pyridin-2-yl)-5-(1H-pyrazol-4-yl)-1H-pyrazolo[3,4-b]
pyridine [1394];
1-(6-(3-(7-(3-fluoro-5-methoxyphenyl)-3H-imidazo[4,5-
b]pyridin-2-yl)-1H-pyrazolo[3,4-b]pyridin-5-yl)
pyrazin-2-yl)azetidin-3-amine [1397];
5-(5-(cyclohexyloxy)pyridin-3-yl)-3-(7-(3-fluoro-5-
methoxyphenyl)-3H-imidazo[4,5-b]pyridin-2-yl)-1H-
pyrazolo[3,4-b]pyridine [1398];
3-(7-(3-fluoro-5-methoxyphenyl)-3H-imidazo[4,5-b]
pyridin-2-yl)-5-(5-(piperidin-4-yloxy)pyridin-3-yl)-
1H-pyrazolo[3,4-b]pyridine [1399]; and
N-(5-(3-(7-(3-fluoro-5-methoxyphenyl)-3H-imidazo[4,5-
b]pyridin-2-yl)-1H-pyrazolo[3,4-b]pyridin-5-yl)pyri-
din-3-yl)-2-(piperidin-4-yl)acetamide [1400]; or a
pharmaceutically acceptable salt thereof.

24. The method of claim 1, wherein the compound of Formula I is selected from the group consisting of:
3-(7-(3-fluoro-5-methoxyphenyl)-3H-imidazo[4,5-b]
pyridin-2-yl)-5-(5-(2-(pyrrolidin-1-yl)ethoxy)pyridin-
3-yl)-1H-pyrazolo[3,4-b]pyridine [1401];
2-((5-(3-(7-(3-fluoro-5-methoxyphenyl)-3H-imidazo[4,
5-b]pyridin-2-yl)-1H-pyrazolo[3,4-b]pyridin-5-yl)
pyridin-3-yl)oxy)-N,N-dimethylethan-1-amine [1402];
3-(7-(3-fluoro-5-methoxyphenyl)-3H-imidazo[4,5-b]
pyridin-2-yl)-5-(5-methoxypyridin-3-yl)-1H-pyrazolo
[3,4-b]pyridine [1403];
5-(3-(7-(3-fluoro-5-methoxyphenyl)-3H-imidazo[4,5-b]
pyridin-2-yl)-1H-pyrazolo[3,4-b]pyridin-5-yl)pyridin-
3-ol [1404];
5-(5-(benzyloxy)pyridin-3-yl)-3-(7-(3-fluoro-5-methoxy-
phenyl)-3H-imidazo[4,5-b]pyridin-2-yl)-1H-pyrazolo
[3,4-b]pyridine [1405];
2-cyclohexyl-N-(5-(3-(7-(3-fluoro-5-methoxyphenyl)-
3H-imidazo[4,5-b]pyridin-2-yl)-1H-pyrazolo[3,4-b]
pyridin-5-yl)pyridin-3-yl)acetamide [1406];
3-(7-(3-fluoro-5-methoxyphenyl)-3H-imidazo[4,5-b]
pyridin-2-yl)-5-(pyridin-4-yl)-1H-pyrazolo[3,4-b]pyri-
dine [1407];
3-(7-(3-fluoro-5-methoxyphenyl)-3H-imidazo[4,5-b]
pyridin-2-yl)-5-(pyrazin-2-yl)-1H-pyrazolo [3,4-b]
pyridine [1408];
2-(dimethylamino)-N-(5-(3-(7-(3-fluorophenyl)-3H-imi-
dazo[4,5-b]pyridin-2-yl)-1H-pyrazolo[3,4-b]pyridin-5-
yl)pyridin-3-yl)acetamide [1409];
2-(dimethylamino)-N-(5-(3-(7-(4-fluorophenyl)-3H-imi-
dazo[4,5-b]pyridin-2-yl)-1H-pyrazolo[3,4-b]pyridin-5-
yl)pyridin-3-yl)acetamide [1410];
2-(dimethylamino)-N-(5-(3-(7-(2-fluorophenyl)-3H-imi-
dazo[4,5-b]pyridin-2-yl)-1H-pyrazolo[3,4-b]pyridin-5-
yl)pyridin-3-yl)acetamide [1411];
2-(dimethylamino)-N-(5-(3-(7-(pyridin-3-yl)-3H-imi-
dazo[4,5-b]pyridin-2-yl)-1H-pyrazolo[3,4-b]pyridin-5-
yl)pyridin-3-yl)acetamide [1412];
2-(dimethylamino)-N-(5-(3-(7-(pyridin-4-yl)-3H-imi-
dazo[4,5-b]pyridin-2-yl)-1H-pyrazolo[3,4-b]pyridin-5-
yl)pyridin-3-yl)acetamide [1413];
2-(dimethylamino)-N-(5-(3-(7-(pyridin-2-yl)-3H-imi-
dazo[4,5-b]pyridin-2-yl)-1H-pyrazolo[3,4-b]pyridin-5-
yl)pyridin-3-yl)acetamide [1414];
2-(dimethylamino)-N-(5-(3-(7-(piperidin-1-yl)-3H-imi-
dazo[4,5-b]pyridin-2-yl)-1H-pyrazolo[3,4-b]pyridin-5-
yl)pyridin-3-yl)acetamide [1415];
2-(dimethylamino)-N-(5-(3-(7-(4-methyl-1H-imidazol-1-
yl)-3H-imidazo[4,5-b]pyridin-2-yl)-1H-pyrazolo [3,4-
b]pyridin-5-yl)pyridin-3-yl)acetamide [1416];
2-(dimethylamino)-N-(5-(3-(7-(4-methylpiperazin-1-yl)-
3H-imidazo[4,5-b]pyridin-2-yl)-1H-pyrazolo [3,4-b]
pyridin-5-yl)pyridin-3-yl)acetamide [1417];
N-(5-(3-(3H-imidazo[4,5-b]pyridin-2-yl)-1H-pyrazolo[3,
4-b]pyridin-5-yl)pyridin-3-yl)-2-(dimethylamino)acet-
amide [1418];
2-(dimethylamino)-N-(5-(3-(7-(thiophen-3-yl)-3H-imi-
dazo[4,5-b]pyridin-2-yl)-1H-pyrazolo[3,4-b]pyridin-5-
yl)pyridin-3-yl)acetamide [1419];
2-(dimethylamino)-N-(5-(3-(7-(furan-3-yl)-3H-imidazo
[4,5-b]pyridin-2-yl)-1H-pyrazolo[3,4-b]pyridin-5-yl)
pyridin-3-yl)acetamide [1420];
2-(dimethylamino)-N-(5-(3-(7-(thiophen-2-yl)-3H-imi-
dazo[4,5-b]pyridin-2-yl)-1H-pyrazolo[3,4-b]pyridin-5-
yl)pyridin-3-yl)acetamide [1421];
2-(dimethylamino)-N-(5-(3-(7-(5-fluorothiophen-2-yl)-
3H-imidazo[4,5-b]pyridin-2-yl)-1H-pyrazolo[3,4-b]
pyridin-5-yl)pyridin-3-yl)acetamide [1422];
2-(dimethylamino)-N-(5-(3-(7-(5-methylthiophen-2-yl)-
3H-imidazo[4,5-b]pyridin-2-yl)-1H-pyrazolo[3,4-b]
pyridin-5-yl)pyridin-3-yl)acetamide [1423];
N-(5-(3-(7-(5-acetylthiophen-2-yl)-3H-imidazo[4,5-b]
pyridin-2-yl)-1H-pyrazolo[3,4-b]pyridin-5-yl)pyridin-
3-yl)-2-(dimethylamino)acetamide [1424];
2-(dimethylamino)-N-(5-(3-(7-(3-fluoro-5-(methylsulfo-
namidomethyl)phenyl)-3H-imidazo [4,5-b]pyridin-2-
yl)-1H-pyrazolo[3,4-b]pyridin-5-yl)pyridin-3-yl)acet-
amide [1425];
2-(dimethylamino)-N-(5-(3-(7-(3-((2-(dimethylamino)
ethyl)amino)-5-fluorophenyl)-3H-imidazo[4,5-b]pyri-
din-2-yl)-1H-pyrazolo[3,4-b]pyridin-5-yl)pyridin-3-
yl)acetamide [1426];
2-(dimethylamino)-N-(5-(3-(7-(3-(2-(dimethylamino)
ethoxy)-5-fluorophenyl)-3H-imidazo[4,5-b]pyridin-2-
yl)-1H-pyrazolo[3,4-b]pyridin-5-yl)pyridin-3-yl)acet-
amide [1427];
2-(dimethylamino)-N-(5-(3-(7-(3-fluoro-5-(2-(pyrroli-
din-1-yl)ethoxy)phenyl)-3H-imidazo[4,5-b]pyridin-2-
yl)-1H-pyrazolo[3,4-b]pyridin-5-yl)pyridin-3-yl)acet-
amide [1428];
2-(dimethylamino)-N-(5-(3-(7-(3-fluoro-5-hydroxyphe-
nyl)-3H-imidazo[4,5-b]pyridin-2-yl)-1H-pyrazolo[3,4-
b]pyridin-5-yl)pyridin-3-yl)acetamide [1429];
2-(dimethylamino)-N-(5-(3-(7-(3-fluoro-5-methoxyphe-
nyl)-3H-imidazo[4,5-b]pyridin-2-yl)-1H-pyrazolo[3,4-
b]pyridin-5-yl)pyridin-3-yl)acetamide [1430];
4-(2-(5-(pyridin-3-yl)-1H-pyrazolo[3,4-b]pyridin-3-yl)-
3H-imidazo[4,5-b]pyridin-7-yl)morpholine [1431];
3-(7-(4,4-difluoropiperidin-1-yl)-3H-imidazo[4,5-b]pyri-
din-2-yl)-5-(pyridin-3-yl)-1H-pyrazolo[3,4-b]pyridine
[1432];
3-(7-(1-methylpiperidin-4-yl)-3H-imidazo[4,5-b]pyridin-
2-yl)-5-(pyridin-3-yl)-1H-pyrazolo[3,4-b]pyridine
[1433];
4-(2-(5-(5-fluoropyridin-3-yl)-1H-pyrazolo[3,4-b]pyri-
din-3-yl)-3H-imidazo[4,5-b]pyridin-7-yl)morpholine
[1434];

5-(5-fluoropyridin-3-yl)-3-(7-(4-methylpiperazin-1-yl)-3H-imidazo[4,5-b]pyridin-2-yl)-1H-pyrazolo[3,4-b]pyridine [1435];

3-(7-(4,4-difluoropiperidin-1-yl)-3H-imidazo[4,5-b]pyridin-2-yl)-5-(5-fluoropyridin-3-yl)-1H-pyrazolo[3,4-b]pyridine [1436];

5-(5-fluoropyridin-3-yl)-3-(7-(1-methylpiperidin-4-yl)-3H-imidazo[4,5-b]pyridin-2-yl)-1H-pyrazolo[3,4-b]pyridine [1437];

5-(5-fluoropyridin-3-yl)-3-(7-(piperidin-1-yl)-3H-imidazo[4,5-b]pyridin-2-yl)-1H-pyrazolin[3,4-b]pyridine [1438];

4-(2-(5-(1-cyclopropyl-1H-pyrazol-4-yl)-1H-pyrazolo[3,4-b]pyridin-3-yl)-3H-imidazo[4,5-b]pyridin-7-yl)morpholine [1442];

5-(1-cyclopropyl-1H-pyrazol-4-yl)-3-(7-(4-methylpiperazin-1-yl)-3H-imidazo[4,5-b]pyridin-2-yl)-1H-pyrazolo[3,4-b]pyridine [1443];

5-(1-cyclopropyl-1H-pyrazol-4-yl)-3-(7-(4,4-difluoropiperidin-1-yl)-3H-imidazo[4,5-b]pyridin-2-yl)-1H-pyrazolo[3,4-b]pyridine [1444];

5-(1-cyclopropyl-1H-pyrazol-4-yl)-3-(7-(1-methylpiperidin-4-yl)-3H-imidazo[4,5-b]pyridin-2-yl)-1H-pyrazolo[3,4-b]pyridine [1445]; and 5-(1-cyclopropyl-1H-pyrazol-4-yl)-3-(7-(piperidin-1-yl)-3H-imidazo[4,5-b]pyridin-2-yl)-1H-pyrazolo[3,4-b]pyridine [1446]; or a pharmaceutically acceptable salt thereof.

25. The method of claim 11, wherein the compound of Formula I is selected from the group consisting of:

N-(5-(3-(7-(piperidin-1-yl)-3H-imidazo[4,5-b]pyridin-2-yl)-1H-pyrazolo[3,4-b]pyridin-5-yl)pyridin-3-yl)propionamide [133];

3-methyl-N-(5-(3-(7-(piperidin-1-yl)-3H-imidazo[4,5-b]pyridin-2-yl)-1H-pyrazolo[3,4-b]pyridin-5-yl)pyridin-3-yl)butanamide [134];

5-(4-methylpyridin-3-yl)-3-(7-(piperidin-1-yl)-3H-imidazo[4,5-b]pyridin-2-yl)-1H-pyrazolo[3,4-b]pyridine [137];

N-(5-(3-(7-(piperidin-1-yl)-3H-imidazo[4,5-b]pyridin-2-yl)-1H-pyrazolo[3,4-b]pyridin-5-yl)pyridin-3-yl)pivalamide [140];

N-(5-(3-(7-(piperidin-1-yl)-3H-imidazo[4,5-b]pyridin-2-yl)-1H-pyrazolo[3,4-b]pyridin-5-yl)pyridin-3-yl)isobutyramide [141];

3,3-dimethyl-N-(5-(3-(7-(piperidin-1-yl)-3H-imidazo[4,5-b]pyridin-2-yl)-1H-pyrazolo[3,4-b]pyridin-5-yl)pyridin-3-yl)butanamide [148];

N-(5-(3-(7-(piperidin-1-yl)-3H-imidazo[4,5-b]pyridin-2-yl)-1H-pyrazolo[3,4-b]pyridin-5-yl)pyridin-3-yl)butyramide [149];

N-(5-(3-(7-(piperidin-1-yl)-3H-imidazo[4,5-b]pyridin-2-yl)-1H-pyrazolo[3,4-b]pyridin-5-yl)pyridin-3-yl)pentanamide [150];

N-(5-(3-(7-(piperidin-1-yl)-3H-imidazo[4,5-b]pyridin-2-yl)-1H-pyrazolo[3,4-b]pyridin-5-yl)pyridin-3-yl)cyclopropanecarboxamide [151];

N-(5-(3-(7-(piperidin-1-yl)-3H-imidazo[4,5-b]pyridin-2-yl)-1H-pyrazolo[3,4-b]pyridin-5-yl)pyridin-3-yl)cyclobutanecarboxamide [152];

N-(5-(3-(7-(piperidin-1-yl)-3H-imidazo[4,5-b]pyridin-2-yl)-1H-pyrazolo[3,4-b]pyridin-5-yl)pyridin-3-yl)cyclopentanecarboxamide [153];

N-(5-(3-(7-(piperidin-1-yl)-3H-imidazo[4,5-b]pyridin-2-yl)-1H-pyrazolo[3,4-b]pyridin-5-yl)pyridin-3-yl)cyclohexanecarboxamide [154];

3-(7-(piperidin-1-yl)-3H-imidazo[4,5-b]pyridin-2-yl)-5-(pyrimidin-5-yl)-1H-pyrazolo[3,4-b]pyridine [158];

N-(5-(3-(7-(4-methylpiperazin-1-yl)-3H-imidazo[4,5-b]pyridin-2-yl)-1H-pyrazolo[3,4-b]pyridin-5-yl)pyridin-3-yl)propionamide [184];

3-methyl-N-(5-(3-(7-(4-methylpiperazin-1-yl)-3H-imidazo[4,5-b]pyridin-2-yl)-1H-pyrazolo[3,4-b]pyridin-5-yl)pyridin-3-yl)butanamide [185];

N-(5-(3-(7-(4-methylpiperazin-1-yl)-3H-imidazo[4,5-b]pyridin-2-yl)-1H-pyrazolo[3,4-b]pyridin-5-yl)pyridin-3-yl)pivalamide [191];

N-(5-(3-(7-(4-methylpiperazin-1-yl)-3H-imidazo[4,5-b]pyridin-2-yl)-1H-pyrazolo[3,4-b]pyridin-5-yl)pyridin-3-yl)isobutyramide [192];

3,3-dimethyl-N-(5-(3-(7-(4-methylpiperazin-1-yl)-3H-imidazo[4,5-b]pyridin-2-yl)-1H-pyrazolo[3,4-b]pyridin-5-yl)pyridin-3-yl)butanamide [199];

N-(5-(3-(7-(4-methylpiperazin-1-yl)-3H-imidazo[4,5-b]pyridin-2-yl)-1H-pyrazolo[3,4-b]pyridin-5-yl)pyridin-3-yl)butyramide [200];

N-(5-(3-(7-(4-methylpiperazin-1-yl)-3H-imidazo[4,5-b]pyridin-2-yl)-1H-pyrazolo[3,4-b]pyridin-5-yl)pyridin-3-yl)pentanamide [201];

N-(5-(3-(7-(4-methylpiperazin-1-yl)-3H-imidazo[4,5-b]pyridin-2-yl)-1H-pyrazolo[3,4-b]pyridin-5-yl)pyridin-3-yl)cyclopropanecarboxamide [202];

N-(5-(3-(7-(4-methylpiperazin-1-yl)-3H-imidazo[4,5-b]pyridin-2-yl)-1H-pyrazolo[3,4-b]pyridin-5-yl)pyridin-3-yl)cyclobutanecarboxamide [203];

N-(5-(3-(7-(4-methylpiperazin-1-yl)-3H-imidazo[4,5-b]pyridin-2-yl)-1H-pyrazolo[3,4-b]pyridin-5-yl)pyridin-3-yl)cyclopentanecarboxamide [204];

N-(5-(3-(7-(4-methylpiperazin-1-yl)-3H-imidazo[4,5-b]pyridin-2-yl)-1H-pyrazolo[3,4-b]pyridin-5-yl)pyridin-3-yl)cyclohexanecarboxamide [205];

3-(7-(4-methylpiperazin-1-yl)-3H-imidazo[4,5-b]pyridin-2-yl)-5-(pyrimidin-5-yl)-1H-pyrazolo[3,4-b]pyridine [209];

N-(5-(3-(7-(thiophen-3-yl)-3H-imidazo[4,5-b]pyridin-2-yl)-1H-pyrazolo[3,4-b]pyridin-5-yl)pyridin-3-yl)propionamide [233];

3-methyl-N-(5-(3-(7-(thiophen-3-yl)-3H-imidazo[4,5-b]pyridin-2-yl)-1H-pyrazolo[3,4-b]pyridin-5-yl)pyridin-3-yl)butanamide [234];

5-(4-methylpyridin-3-yl)-3-(7-(thiophen-3-yl)-3H-imidazo[4,5-b]pyridin-2-yl)-1H-pyrazolo[3,4-b]pyridine [237];

N-(5-(3-(7-(thiophen-3-yl)-3H-imidazo[4,5-b]pyridin-2-yl)-1H-pyrazolo[3,4-b]pyridin-5-yl)pyridin-3-yl)pivalamide [240];

N-(5-(3-(7-(thiophen-3-yl)-3H-imidazo[4,5-b]pyridin-2-yl)-1H-pyrazolo[3,4-b]pyridin-5-yl)pyridin-3-yl)isobutyramide [241];

3,3-dimethyl-N-(5-(3-(7-(thiophen-3-yl)-3H-imidazo[4,5-b]pyridin-2-yl)-1H-pyrazolo[3,4-b]pyridin-5-yl)pyridin-3-yl)butanamide [248];

N-(5-(3-(7-(thiophen-3-yl)-3H-imidazo[4,5-b]pyridin-2-yl)-1H-pyrazolo[3,4-b]pyridin-5-yl)pyridin-3-yl)butyramide [249];

N-(5-(3-(7-(thiophen-3-yl)-3H-imidazo[4,5-b]pyridin-2-yl)-1H-pyrazolo[3,4-b]pyridin-5-yl)pyridin-3-yl)pentanamide [250];

N-(5-(3-(7-(thiophen-3-yl)-3H-imidazo[4,5-b]pyridin-2-yl)-1H-pyrazolo[3,4-b]pyridin-5-yl)pyridin-3-yl)cyclopropanecarboxamide [251];

N-(5-(3-(7-(thiophen-3-yl)-3H-imidazo[4,5-b]pyridin-2-yl)-1H-pyrazolo[3,4-b]pyridin-5-yl)pyridin-3-yl)cyclobutanecarboxamide [252];
N-(5-(3-(7-(thiophen-3-yl)-3H-imidazo[4,5-b]pyridin-2-yl)-1H-pyrazolo[3,4-b]pyridin-5-yl)pyridin-3-yl)cyclopentanecarboxamide [253];
N-(5-(3-(7-(thiophen-3-yl)-3H-imidazo[4,5-b]pyridin-2-yl)-1H-pyrazolo[3,4-b]pyridin-5-yl)pyridin-3-yl)cyclohexanecarboxamide [254];
5-(pyrimidin-5-yl)-3-(7-(thiophen-3-yl)-3H-imidazo[4,5-b]pyridin-2-yl)-1H-pyrazolo[3,4-b]pyridine [258];
N-(5-(3-(7-(furan-3-yl)-3H-imidazo[4,5-b]pyridin-2-yl)-1H-pyrazolo[3,4-b]pyridin-5-yl)pyridin-3-yl)propionamide [259];
N-(5-(3-(7-(furan-3-yl)-3H-imidazo[4,5-b]pyridin-2-yl)-1H-pyrazolo[3,4-b]pyridin-5-yl)pyridin-3-yl)-3-methylbutanamide [260];
3-(7-(furan-3-yl)-3H-imidazo[4,5-b]pyridin-2-yl)-5-(4-methylpyridin-3-yl)-1H-pyrazolo[3,4-b]pyridine [263];
N-(5-(3-(7-(furan-3-yl)-3H-imidazo[4,5-b]pyridin-2-yl)-1H-pyrazolo[3,4-b]pyridin-5-yl)pyridin-3-yl)pivalamide [266];
N-(5-(3-(7-(furan-3-yl)-3H-imidazo[4,5-b]pyridin-2-yl)-1H-pyrazolo[3,4-b]pyridin-5-yl)pyridin-3-yl)isobutyramide [267];
N-(5-(3-(7-(furan-3-yl)-3H-imidazo[4,5-b]pyridin-2-yl)-1H-pyrazolo[3,4-b]pyridin-5-yl)pyridin-3-yl)-3,3-dimethylbutanamide [274];
N-(5-(3-(7-(furan-3-yl)-3H-imidazo[4,5-b]pyridin-2-yl)-1H-pyrazolo[3,4-b]pyridin-5-yl)pyridin-3-yl)butyramide [275];
N-(5-(3-(7-(furan-3-yl)-3H-imidazo[4,5-b]pyridin-2-yl)-1H-pyrazolo[3,4-b]pyridin-5-yl)pyridin-3-yl)pentanamide [276];
N-(5-(3-(7-(furan-3-yl)-3H-imidazo[4,5-b]pyridin-2-yl)-1H-pyrazolo[3,4-b]pyridin-5-yl)pyridin-3-yl)cyclopropanecarboxamide [277];
N-(5-(3-(7-(furan-3-yl)-3H-imidazo[4,5-b]pyridin-2-yl)-1H-pyrazolo[3,4-b]pyridin-5-yl)pyridin-3-yl)cyclobutanecarboxamide [278];
N-(5-(3-(7-(furan-3-yl)-3H-imidazo[4,5-b]pyridin-2-yl)-1H-pyrazolo[3,4-b]pyridin-5-yl)pyridin-3-yl)cyclopentanecarboxamide [279];
N-(5-(3-(7-(furan-3-yl)-3H-imidazo[4,5-b]pyridin-2-yl)-1H-pyrazolo[3,4-b]pyridin-5-yl)pyridin-3-yl)cyclohexanecarboxamide [280];
3-(7-(furan-3-yl)-3H-imidazo[4,5-b]pyridin-2-yl)-5-(pyrimidin-5-yl)-1H-pyrazolo[3,4-b]pyridine 12841;
N-(5-(3-(7-(thiophen-2-yl)-3H-imidazo[4,5-b]pyridin-2-yl)-1H-pyrazolo[3,4-b]pyridin-5-yl)pyridin-3-yl)propionamide [285];
3-methyl-N-(5-(3-(7-(thiophen-2-yl)-3H-imidazo[4,5-b]pyridin-2-yl)-1H-pyrazolo[3,4-b]pyridin-5-yl)pyridin-3-yl)butanamide [286];
S -(4-methylpyridin-3-yl)-3-(7-(thiophen-2-yl)-3H-imidazo[4,5-b]pyridin-2-yl)-1H-pyrazolo[3,4-b]pyridine [289];
N-(5-(3-(7-(thiophen-2-yl)-3H-imidazo[4,5-b]pyridin-2-yl)-1H-pyrazolo[3,4-b]pyridin-5-yl)pyridin-3-yl)pivalamide [292];
N-(5-(3-(7-(thiophen-2-yl)-3H-imidazo[4,5-b]pyridin-2-yl)-1H-pyrazolo[3,4-b]pyridin-5-yl)pyridin-3-yl)isobutyramide [293];
3,3-dimethyl-N-(5-(3-(7-(thiophen-2-yl)-3H-imidazo[4,5-b]pyridin-2-yl)-1H-pyrazolo[3,4-b]pyridin-5-yl)pyridin-3-yl)butanamide [300];
N-(5-(3-(7-(thiophen-2-yl)-3H-imidazo[4,5-b]pyridin-2-yl)-1H-pyrazolo[3,4-b]pyridin-5-yl)pyridin-3-yl)butyramide [301];
N-(5-(3-(7-(thiophen-2-yl)-3H-imidazo[4,5-b]pyridin-2-yl)-1H-pyrazolo[3,4-b]pyridin-5-yl)pyridin-3-yl)pentanamide [302];
N-(5-(3-(7-(thiophen-2-yl)-3H-imidazo[4,5-b]pyridin-2-yl)-1H-pyrazolo[3,4-b]pyridin-5-yl)pyridin-3-yl)cyclopropanecarboxamide [303];
N-(5-(3-(7-(thiophen-2-yl)-3H-imidazo[4,5-b]pyridin-2-yl)-1H-pyrazolo[3,4-b]pyridin-5-yl)pyridin-3-yl)cyclobutanecarboxamide [304];
N-(5-(3-(7-(thiophen-2-yl)-3H-imidazo[4,5-b]pyridin-2-yl)-1H-pyrazolo[3,4-b]pyridin-5-yl)pyridin-3-yl)cyclopentanecarboxamide [305];
N-(5-(3-(7-(thiophen-2-yl)-3H-imidazo[4,5-b]pyridin-2-yl)-1H-pyrazolo[3,4-b]pyridin-5-yl)pyridin-3-yl)cyclohexanecarboxamide [306];
5-(pyrimidin-5-yl)-3-(7-(thiophen-2-yl)-3H-imidazo[4,5-b]pyridin-2-yl)-1H-pyrazolo[3,4-b]pyridine [310];
N-(5-(3-(7-(5-fluorothiophen-2-yl)-3H-imidazo[4,5-b]pyridin-2-yl)-1H-pyrazolo[3,4-b]pyridin-5-yl)pyridin-3-yl)propionamide [311];
N-(5-(3-(7-(5-fluorothiophen-2-yl)-3H-imidazo[4,5-b]pyridin-2-yl)-1H-pyrazolo[3,4-b]pyridin-5-yl)pyridin-3-yl)-3-methylbutanamide [312];
3-(7-(5-fluorothiophen-2-yl)-3H-imidazo[4,5-b]pyridin-2-yl)-5-(4-methylpyridin-3-yl)-1H-pyrazolo[3,4-b]pyridine [315];
N-(5-(3-(7-(5-fluorothiophen-2-yl)-3H-imidazo[4,5-b]pyridin-2-yl)-1H-pyrazolo[3,4-b]pyridin-5-yl)pyridin-3-yl)pivalamide [318];
N-(5-(3-(7-(5-fluorothiophen-2-yl)-3H-imidazo[4,5-b]pyridin-2-yl)-1H-pyrazolo[3,4-b]pyridin-5-yl)pyridin-3-yl)isobutyramide [319];
N-(5-(3-(7-(5-fluorothiophen-2-yl)-3H-imidazo[4,5-b]pyridin-2-yl)-1H-pyrazolo[3,4-b]pyridin-5-yl)pyridin-3-yl)-3,3-dimethylbutanamide [326];
N-(5-(3-(7-(5-fluorothiophen-2-yl)-3H-imidazo[4,5-b]pyridin-2-yl)-1H-pyrazolo[3,4-b]pyridin-5-yl)pyridin-3-yl)butyramide [327];
N-(5-(3-(7-(5-fluorothiophen-2-yl)-3H-imidazo[4,5-b]pyridin-2-yl)-1H-pyrazolo[3,4-b]pyridin-5-yl)pyridin-3-yl)pentanamide [328];
N-(5-(3-(7-(5-fluorothiophen-2-yl)-3H-imidazo[4,5-b]pyridin-2-yl)-1H-pyrazolo[3,4-b]pyridin-5-yl)pyridin-3-yl)cyclopropanecarboxamide [329];
N-(5-(3-(7-(5-fluorothiophen-2-yl)-3H-imidazo[4,5-b]pyridin-2-yl)-1H-pyrazolo[3,4-b]pyridin-5-yl)pyridin-3-yl)cyclobutanecarboxamide [330];
N-(5-(3-(7-(5-fluorothiophen-2-yl)-3H-imidazo[4,5-b]pyridin-2-yl)-1H-pyrazolo[3,4-b]pyridin-5-yl)pyridin-3-yl)cyclopentanecarboxamide [331];
N-(5-(3-(7-(5-fluorothiophen-2-yl)-3H-imidazo[4,5-b]pyridin-2-yl)-1H-pyrazolo[3,4-b]pyridin-5-yl)pyridin-3-yl)cyclohexanecarboxamide [332];
3-(7-(5-fluorothiophen-2-yl)-3H-imidazo[4,5-b]pyridin-2-yl)-5-(pyrimidin-5-yl)-1H-pyrazolo[3,4-b]pyridine [336];
N-(5-(3-(7-(5-methylthiophen-2-yl)-3H-imidazo[4,5-b]pyridin-2-yl)-1H-pyrazolo[3,4-b]pyridin-5-yl)pyridin-3-yl)propionamide [337];
3-methyl-N-(5-(3-(7-(5-methyhthiophen-2-yl)-3H-imidazo[4,5-b]pyridin-2-yl)-1H-pyrazolo[3,4-b]pyridin-5-yl)pyridin-3-yl)butanamide [338];

5-(4-methylpyridin-3-yl)-3-(7-(5-methylthiophen-2-yl)-3H-imidazo[4,5-b]pyridin-2-yl)-1H-pyrazolo[3,4-b]pyridine [341];

N-(5-(3-(7-(5-methylthiophen-2-yl)-3H-imidazo[4,5-b]pyridin-2-yl)-1H-pyrazolo[3,4-b]pyridin-5-yl)pyridin-3-yl)pivalamide [344];

N-(5-(3-(7-(5-methylthiophen-2-yl)-3H-imidazo[4,5-b]pyridin-2-yl)-1H-pyrazolo[3,4-b]pyridin-5-yl)pyridin-3-yl)isobutyramide [345];

3,3-dimethyl-N-(5-(3-(7-(5-methylthiophen-2-yl)-3H-imidazo[4,5-b]pyridin-2-yl)-1H-pyrazolo[3,4-b]pyridin-5-yl)pyridin-3-yl)butanamide [352];

N-(5-(3-(7-(5-methylthiophen-2-yl)-3H-imidazo[4,5-b]pyridin-2-yl)-1H-pyrazolo[3,4-b]pyridin-5-yl)pyridin-3-yl)butyramide [353];

N-(5-(3-(7-(5-methylthiophen-2-yl)-3H-imidazo[4,5-b]pyridin-2-yl)-1H-pyrazolo[3,4-b]pyridin-5-yl)pyridin-3-yl)pentanamide [354];

N-(5-(3-(7-(5-methylthiophen-2-yl)-3H-imidazo[4,5-b]pyridin-2-yl)-1H-pyrazolo[3,4-b]pyridin-5-yl)pyridin-3-yl)cyclopropanecarboxamide [355];

N-(5-(3-(7-(5-methylthiophen-2-yl)-3H-imidazo[4,5-b]pyridin-2-yl)-1H-pyrazolo[3,4-b]pyridin-5-yl)pyridin-3-yl)cyclobutanecarboxamide [356];

N-(5-(3-(7-(5-methylthiophen-2-yl)-3H-imidazo[4,5-b]pyridin-2-yl)-1H-pyrazolo[3,4-b]pyridin-5-yl)pyridin-3-yl)cyclopentanecarboxamide [357];

N-(5-(3-(7-(5-methylthiophen-2-yl)-3H-imidazo[4,5-b]pyridin-2-yl)-1H-pyrazolo[3,4-b]pyridin-5-yl)pyridin-3-yl)cyclohexanecarboxamide [358];

3-(7-(5-methylthiophen-2-yl)-3H-imidazo[4,5-b]pyridin-2-yl)-5-(pyrimidin-5-yl)-1H-pyrazolo[3,4-b]pyridine [362];

N-(5-(3-(7-(5-acetylthiophen-2-yl)-3H-imidazo[4,5-b]pyridin-2-yl)-1H-pyrazolo[3,4-b]pyridin-5-yl)pyridin-3-yl)propionamide [363];

N-(5-(3-(7-(5-acetylthiophen-2-yl)-3H-imidazo[4,5-b]pyridin-2-yl)-1H-pyrazolo[3,4-b]pyridin-5-yl)pyridin-3-yl)-3-methylbutanamide [364];

1-(5-(2-(5-(4-methylpyridin-3-yl)-1H-pyrazolo[3,4-b]pyridin-3-yl)-3H-imidazo[4,5-b]pyridin-7-yl)thiophen-2-yl)ethanone [367];

N-(5-(3-(7-(5-acetylthiophen-2-yl)-3H-imidazo[4,5-b]pyridin-2-yl)-1H-pyrazolo[3,4-b]pyridin-5-yl)pyridin-3-yl)pivalamide [370];

N-(5-(3-(7-(5-acetylthiophen-2-yl)-3H-imidazo[4,5-b]pyridin-2-yl)-1H-pyrazolo[3,4-b]pyridin-5-yl)pyridin-3-yl)isobutyramide [371];

N-(5-(3-(7-(5-acetylthiophen-2-yl)-3H-imidazo[4,5-b]pyridin-2-yl)-1H-pyrazolo[3,4-b]pyridin-5-yl)pyridin-3-yl)-3,3-dimethylbutanamide [378];

N-(5-(3-(7-(5-acetylthiophen-2-yl)-3H-imidazo[4,5-b]pyridin-2-yl)-1H-pyrazolo[3,4-b]pyridin-5-yl)pyridin-3-yl)butyramide [379];

N-(5-(3-(7-(5-acetylthiophen-2-yl)-3H-imidazo[4,5-b]pyridin-2-yl)-1H-pyrazolo[3,4-b]pyridin-5-yl)pyridin-3-yl)pentanamide [380];

N-(5-(3-(7-(5-acetylthiophen-2-yl)-3H-imidazo[4,5-b]pyridin-2-yl)-1H-pyrazolo[3,4-b]pyridin-5-yl)pyridin-3-yl)cyclopropanecarboxamide [381];

N-(5-(3-(7-(5-acetylthiophen-2-yl)-3H-imidazo[4,5-b]pyridin-2-yl)-1H-pyrazolo[3,4-b]pyridin-5-yl)pyridin-3-yl)cyclobutanecarboxamide [382];

N-(5-(3-(7-(5-acetylthiophen-2-yl)-3H-imidazo[4,5-b]pyridin-2-yl)-1H-indazol-5-yl)pyridin-3-yl)cyclopentanecarboxamide [383];

N-(5-(3-(7-(5-acetylthiophen-2-yl)-3H-imidazo[4,5-b]pyridin-2-yl)-1H-pyrazolo[3,4-b]pyridin-5-yl)pyridin-3-yl)cyclohexanecarboxamide [384];

1-(5-(2-(5-(pyrimidin-5-yl)-1H-pyrazolo[3,4-b]pyridin-3-yl)-3H-imidazo[4,5-b]pyridin-7-yl)thiophen-2-yl)ethanone [388];

5-(1-methyl-1H-pyrazol-4-yl)-3-(7-(piperidin-1-yl)-3H-imidazo[4,5-b]pyridin-2-yl)-1H-pyrazolo[3,4-b]pyridine [1020];

5-(1,2-dimethyl-1H-imidazol-5-yl)-3-(7-(piperidin-1-yl)-3H-imidazo[4,5-b]pyridin-2-yl)-1H-pyrazolo[3,4-b]pyridine [1021];

5-(1-methyl-1H-pyrazol-4-yl)-3-(7-(4-methylpiperazin-1-yl)-3H-imidazo[4,5-b]pyridin-2-yl)-1H-pyrazolo[3,4-b]pyridine [1056];

5-(1,2-dimethyl-1H-imidazol-5-yl)-3-(7-(4-methylpiperazin-1-yl)-3H-imidazo[4,5-b]pyridin-2-yl)-1H-pyrazolo[3,4-b]pyridine [1057];

5-(1-methyl-1H-pyrazol-4-yl)-3-(7-(thiophen-3-yl)-3H-imidazo[4,5-b]pyridin-2-yl)-1H-pyrazolo[3,4-b]pyridine [1092];

5-(1,2-dimethyl-1H-imidazol-5-yl)-3-(7-(thiophen-3-yl)-3H-imidazo[4,5-b]pyridin-2-yl)-1H-pyrazolo[3,4-b]pyridine [1093];

3-(7-(furan-3-yl)-3H-imidazo[4,5-b]pyridin-2-yl)-5-(1-methyl-1H-pyrazol-4-yl)-1H-pyrazolo[3,4-b]pyridine [1110];

5-(1,2-dimethyl-1H-imidazol-5-yl)-3-(7-(furan-3-yl)-3H-imidazo[4,5-b]pyridin-2-yl)-1H-pyrazolo [3,4-b]pyridine [1111];

5-(1-methyl-1H-pyrazol-4-yl)-3-(7-(thiophen-2-yl)-3H-imidazo[4,5-b]pyridin-2-yl)-1H-pyrazolo[3,4-b]pyridine [1128];

5-(1,2-dimethyl-1H-imidazol-5-yl)-3-(7-(thiophen-2-yl)-3H-imidazo[4,5-b]pyridin-2-yl)-1H-pyrazolo[3,4-b]pyridine [1129];

3-(7-(5-fluorothiophen-2-yl)-3H-imidazo[4,5-b]pyridin-2-yl)-5-(1-methyl-1H-pyrazol-4-yl)-1H-pyrazolo[3,4-b]pyridine [1146];

5-(1,2-dimethyl-1H-imidazol-5-yl)-3-(7-(5-fluorothiophen-2-yl)-3H-imidazo[4,5-b]pyridin-2-yl)-1H-pyrazolo[3,4-b]pyridine [1147];

5-(1-methyl-1H-pyrazol-4-yl)-3-(7-(5-methylthiophen-2-yl)-3H-imidazo[4,5-b]pyridin-2-yl)-1H-pyrazolo[3,4-b]pyridine [1164];

5-(1,2-dimethyl-1H-imidazol-5-yl)-3-(7-(5-methylthiophen-2-yl)-3H-imidazo[4,5-b]pyridin-2-yl)-1H-pyrazolo[3,4-b]pyridine [1165];

1-(5-(2-(5-(1-methyl-1H-pyrazol-4-yl)-1H-pyrazolo[3,4-b]pyridin-3-yl)-3H-imidazo[4,5-b]pyridin-7-yl)thiophen-2-yl)ethan-1-one [1182];

1-(5-(2-(5-(1,2-dimethyl-1H-imidazol-5-yl)-1H-pyrazolo[3,4-b]pyridin-3-yl)-3H-imidazo[4,5-b]pyridin-7-yl)thiophen-2-yl)ethan-1-one [1183];

4-(2-(5-(1-methyl-1H-pyrazol-4-yl)-1H-pyrazolo[3,4-b]pyridin-3-yl)-3H-imidazo[4,5-b]pyridin-7-yl)morpholine [1439];

3-(7-(4,4-difluoropiperidin-1-yl)-3H-imidazo[4,5-b]pyridin-2-yl)-5-(1-methyl-1H-pyrazol-4-yl)-1H-pyrazolo[3,4-b]pyridine [1440]; and 5-(1-methyl-1H-pyrazol-4-yl)-3-(7-(1-methylpiperidin-4-yl)-3H-imidazo[4,5-b]pyridin-2-yl)-1H-pyrazolo[3,4-b]pyridine [1441]; or a pharmaceutically acceptable salt thereof.

26. A compound or pharmaceutically acceptable salt thereof having the structure of:

N-((5-(3-(7-(3-fluorophenyl)-3H-imidazo[4,5-b]pyridin-2-yl)-1H-pyrazolo[3,4-b]pyridin-5-yl) pyridin-3-yl)methyl)ethanamine [4];

3-(7-(3-fluorophenyl)-3H-imidazo[4,5-b]pyridin-2-yl)-5-(pyrimidin-5-yl)-1H-pyrazolo[3,4-b]pyridine [22];

N-((5-(3-(7-(4-fluorophenyl)-3H-imidazo[4,5-b]pyridin-2-yl)-1H-pyrazolo[3,4-b]pyridin-5-yl)pyridin-3-yl)methyl)ethanamine [26];

3-(7-(4-fluorophenyl)-3H-imidazo[4,5-b]pyridin-2-yl)-5-(pyrimidin-5-yl)-1H-pyrazolo[3,4-b]pyridine [44];

N-((5-(3-(7-(2-fluorophenyl)-3H-imidazo[4,5-b]pyridin-2-yl)-1H-pyrazolo[3,4-b]pyridin-5-yl)pyridin-3-yl)methyl)ethanamine [48];

3-(7-(2-fluorophenyl)-3H-imidazo[4,5-b]pyridin-2-yl)-5-(pyrimidin-5-yl)-1H-pyrazolo[3,4-b]pyridine [66];

N-((5-(3-(7-(pyridin-3-yl)-3H-imidazo[4,5-b]pyridin-2-yl)-1H-pyrazolo[3,4-b]pyridin-5-yl)pyridin-3-yl)methyl)ethanamine [70];

3-(7-(pyridin-3-yl)-3H-imidazo[4,5-b]pyridin-2-yl)-5-(pyrimidin-5-yl)-1H-pyrazolo[3,4-b]pyridine [88];

N-((5-(3-(7-(pyridin-4-yl)-3H-imidazo[4,5-b]pyridin-2-yl)-1H-pyrazolo[3,4-b]pyridin-5-yl)pyridin-3-yl)methyl)ethanamine [92];

3-(7-(pyridin-4-yl)-3H-imidazo[4,5-b]pyridin-2-yl)-5-(pyrimidin-5-yl)-1H-pyrazolo[3,4-b]pyridine [110];

N-((5-(3-(7-(pyridin-2-yl)-3H-imidazo[4,5-b]pyridin-2-yl)-1H-pyrazolo[3,4-b]pyridin-5-yl)pyridin-3-yl)methyl)ethanamine [114];

3-(7-(pyridin-2-yl)-3H-imidazo[4,5-b]pyridin-2-yl)-5-(pyrimidin-5-yl)-1H-pyrazolo[3,4-b]pyridine [132];

N-((5-(3-(7-(piperidin-1-yl)-3H-imidazo[4,5-b]pyridin-2-yl)-1H-pyrarazolo[3,4-b]pyridin-5-yl)pyridin-3-yl)methyl)ethanamine [138];

N-(5-(3-(7-(4-methyl-1H-imidazol-1-yl)-3H-imidazo[4,5-b]pyridin-2-yl)-1H-pyrazolo[3,4-b]pyridin-5-yl)pyridin-3-yl)propionamide [159];

3-methyl-N-(5-(3-(7-(4-methyl-1H-imidazol-1-yl)-3H-imidazo[4,5-b]pyridin-2-yl)-1H-pyrazolo[3,4-b]pyridin-5-yl)pyridin-3-yl)butanamide [160];

N-(5-(3-(7-(4-methyl-1H-imidazol-1-yl)-3H-imidazo[4,5-b]pyridin-2-yl)-1H-pyrazolo[3,4-b]pyridin-5-yl)pyridin-3-yl)pivalamide [165];

N-(5-(3-(7-(4-methyl-1H-imidazol-1-yl)-3H-imidazo[4,5-b]pyridin-2-yl)-1H-pyrazolo[3,4-b]pyridin-5-yl)pyridin-3-yl)isobutyramide [166];

3,3-dimethyl-N-(5-(3-(7-(4-methyl-1H-imidazol-1-yl)-3H-imidazo[4,5-b]pyridin-2-yl)-1H-pyrazolo[3,4-b]pyridin-5-yl)pyridin-3-yl)butanamide [173];

N-(5-(3-(7-(4-methyl-1H-imidazol-1-yl)-3H-imidazo[4,5-b]pyridin-2-yl)-1H-pyrazolo[3,4-b]pyridin-5-yl)pyridin-3-yl)butyramide [174];

N-(5-(3-(7-(4-methyl-1H-imidazol-1-yl)-3H-imidazo[4,5-b]pyridin-2-yl)-1H-pyrazolo[3,4-b]pyridin-5-yl)pyridin-3-yl)pentanamide [175];

N-(5-(3-(7-(4-methyl-1H-imidazol-1-yl)-3H-imidazo[4,5-b]pyridin-2-yl)-1H-pyrazolo[3,4-b]pyridin-5-yl)pyridin-3-yl)cyclopropanecarboxamide [176];

N-(5-(3-(7-(4-methyl-1H-imidazol-1-yl)-3H-imidazo[4,5-b]pyridin-2-yl)-1H-pyrazolo[3,4-b]pyridin-5-yl)pyridin-3-yl)cyclobutanecarboxamide [177];

N-(5-(3-(7-(4-methyl-1H-imidazol-1-yl)-3H-imidazo[4,5-b]pyridin-2-yl)-1H-pyrazolo[3,4-b]pyridin-5-yl)pyridin-3-yl)cyclopentanecarboxamide [178];

N-(5-(3-(7-(4-methyl-1H-imidazol-1-yl)-3H-imidazo[4,5-b]pyridin-2-yl)-1H-pyrazolo[3,4-b]pyridin-5-yl)pyridin-3-yl)cyclohexanecarboxamide [179];

3-(7-(4-methyl-1H-imidazol-1-yl)-3H-imidazo[4,5-b]pyridin-2-yl)-5-(pyrimidin-5-yl)-1H-pyrazolo[3,4-b]pyridine [183];

N-((5-(3-(7-(4-methylpiperazin-1-yl)-3H-imidazo[4,5-b]pyridin-2-yl)-1H-pyrazolo[3,4-b]pyridin-5-yl)pyridin-3-yl)methyl)ethanamine [189];

N-((5-(3-(3H-imidazo[4,5-b]pyridin-2-yl)-1H-pyrazolo[3,4-b]pyridin-5-yl)pyridin-3-yl)methyl)ethanamine [213];

N-(5-(3-(3H-imidazo[4,5-b]pyridin-2-yl)-1H-pyrazolo[3,4-b]pyridin-5-yl)pyridin-3-yl)cyclopropanecarboxamide [225];

N-(5-(3-(3H-imidazo[4,5-b]pyridin-2-yl)-1H-pyrazolo[3,4-b]pyridin-5-yl)pyridin-3-yl)cyclobutanecarboxamide [226];

N-(5-(3-(3H-imidazo[4,5-b]pyridin-2-yl)-1H-pyrazolo[3,4-b]pyridin-5-yl)pyridin-3-yl)cyclopentanecarboxamide [227];

N-(5-(3-(3H-imidazo[4,5-b]pyridin-2-yl)-1H-pyrazolo[3,4-b]pyridin-5-yl)pyridin-3-yl)cyclohexanecarboxamide [228];

3-(3H-imidazo[4,5-b]pyridin-2-yl)-5-(pyrimidin-5-yl)-1H-pyrazolo[3,4-b]pyridine [232];

N-((5-(3-(7-(thiophen-3-yl)-3H-imidazo[4,5-b]pyridin-2-yl)-1H-pyrazolo[3,4-b]pyridin-5-yl)pyridin-3-yl)methyl)ethanamine [238];

N-((5-(3-(7-(furan-3-yl)-3H-imidazo[4,5-b]pyridin-2-yl)-1H-pyrazolo[3,4-b]pyridin-5-yl)pyridin-3-yl)methyl)ethanamine [264];

N-((5-(3-(7-(thiophen-2-yl)-3H-imidazo[4,5-b]pyridin-2-yl)-1H-pyrazolo[3,4-b]pyridin-5-yl)pyridin-3-yl)methyl)ethanamine [290];

N-((5-(3-(7-(5-fluorothiophen-2-yl)-3H-imidazo[4,5-b]pyridin-2-yl)-1H-pyrazolo[3,4-b]pyridin-5-yl)pyridin-3-yl)methyl)ethanamine [316];

N-((5-(3-(7-(5-methylthiophen-2-yl)-3H-imidazo[4,5-b]pyridin-2-yl)-1H-pyrazolo[3,4-b]pyridin-5-yl)pyridin-3-yl)methyl)ethanamine [342];

1-(5-(2-(5-(5-((ethylamino)methyl)pyridin-3-yl)-1H-pyrazolo[3,4-b]pyridin-3-yl)-3H-imidazo [4,5-b]pyridin-7-yl)thiophen-2-yl)ethanone [368];

N-(5-(3-(7-(3-fluoro-5-(methylsulfonamidomethyl)phenyl)-3H-imidazo[4,5-b]pyridin-2-yl)-1H-pyrazolo[3,4-b]pyridin-5-yl)pyridin-3-yl)propionamide [389];

N-(5-(3-(7-(3-fluoro-5-(methylsulfonamidomethyl)phenyl)-3H-imidazo[4,5-b]pyridin-2-yl)-1H-pyrazolo[3,4-b]pyridin-5-yl)pyridin-3-yl)-3-methylbutanamide [390];

N-(3-fluoro-5-(2-(5-(4-methylpyridin-3-yl)-1H-pyrazolo[3,4-b]pyridin-3-yl)-3H-imidazo[4,5-b]pyridin-7-yl)benzyl)methane sulfonamide [393];

N-(3-(2-(5-(5-((ethylamino)methyl)pyridin-3-yl)-1H-pyrazolo[3,4-b]pyridin-3-yl)-3H-imidazo [4,5-b]pyridin-7-yl)-5-fluorobenzyl)methanesulfonamide [394];

N-(5-(3-(7-(3-fluoro-5-(methylsulfonamidomethyl)phenyl)-3H-imidazo[4,5-b]pyridin-2-yl)-1H-pyrazolo[3,4-b]pyridin-5-yl)pyridin-3-yl)pivalamide [396];

N-(5-(3-(7-(3-fluoro-5-(methylsulfonamidomethyl)phenyl)-3H-imidazo[4,5-b]pyridin-2-yl)-1H-pyrazolo[3,4-b]pyridin-5-yl)pyridin-3-yl)isobutyramide [397];

N-(5-(3-(7-(3-fluoro-5-(methylsulfonamidomethyl)phenyl)-3H-imidazo[4,5-b]pyridin-2-yl)-1H-pyrazolo[3,4-b]pyridin-5-yl)pyridin-3-yl)-3,3-dimethylbutanamide [404];

N-(5-(3-(7-(3-fluoro-5-(methylsulfonamidomethyl)phenyl)-3H-imidazo[4,5-b]pyridin-2-yl)-1H-pyrazolo[3,4-b]pyridin-5-yl)pyridin-3-yl)butyramide [405];

N-(5-(3-(7-(3-fluoro-5-(methylsulfonamidomethyl)phenyl)-3H-imidazo[4,5-b]pyridin-2-yl)-1H-pyrazolo[3,4-b]pyridin-5-yl)pyridin-3-yl)pentanamide [406];

N-(5-(3-(7-(3-fluoro-5-(methylsulfonamidomethyl)phenyl)-3H-imidazo[4,5-b]pyridin-2-yl)-1H-pyrazolo[3,4-b]pyridin-5-yl)pyridin-3-yl)cyclopropanecarboxamide [407];

N-(5-(3-(7-(3-fluoro-5-(methylsulfonamidomethyl)phenyl)-3H-imidazo[4,5-b]pyridin-2-yl)-1H-pyrazolo[3,4-b]pyridin-5-yl)pyridin-3-yl)cyclobutanecarboxamide [408];

N-(5-(3-(7-(3-fluoro-5-(methylsulfonamidomethyl)phenyl)-3H-imidazo[4,5-b]pyridin-2-yl)-1H-pyrazolo[3,4-b]pyridin-5-yl)pyridin-3-yl)cyclopentanecarboxamide [409];

N-(5-(3-(7-(3-fluoro-5-(methylsulfonamidomethyl)phenyl)-3H-imidazo[4,5-b]pyridin-2-yl)-1H-pyrazolo[3,4-b]pyridin-5-yl)pyridin-3-yl)cyclohexanecarboxamide [410];

N-(3-fluoro-5-(2-(5-(pyrimidin-5-yl)-1H-pyrazolo[3,4-b]pyridin-3-yl)-3H-imidazo[4,5-b]pyridin-7-yl)benzyl)methanesulfonamide [414];

N-(5-(3-(7-(3-((2-(dimethylamino)ethyl)amino)-5-fluorophenyl)-3H-imidazo[4,5-b]pyridin-2-yl)-1H-pyrazolo[3,4-b]pyridin-5-yl)pyridin-3-yl)propionamide [415];

N-(5-(3-(7-(3-((2-(dimethylamino)ethyl)amino)-5-fluorophenyl)-3H-imidazo[4,5-b]pyridin-2-yl)-1H-pyrazolo[3,4-b]pyridin-5-yl)pyridin-3-yl)-3-methylbutanamide [416];

$N^1$-(3-fluoro-5-(2-(5-(4-methylpyridin-3-yl)-1H-pyrazolo[3,4-b]pyridin-3-yl)-3H-imidazo[4,5-b]pyridin-7-yl)phenyl)-$N^2$,$N^2$-dimethylethane-1,2-diamine [419];

$N^1$-(3-(2-(5-(5-((ethylamino)methyl)pyridin-3-yl)-1H-pyrazolo[3,4-b]pyridin-3-yl)-3H-imidazo[4,5-b]pyridin-7-yl)-5-fluorophenyl)-$N^2$,$N^2$-dimethylethane-1,2-diamine [420];

N-(5-(3-(7-(3-((2-(dimethylamino)ethyl)amino)-5-fluorophenyl)-3H-imidazo[4,5-b]pyridin-2-yl)-1H-pyrazolo[3,4-b]pyridin-5-yl)pyridin-3-yl)pivalamide [422];

N-(5-(3-(7-(3-((2-(dimethylamino)ethyl)amino)-5-fluorophenyl)-3H-imidazo[4,5-b]pyridin-2-yl)-1H-pyrazolo[3,4-b]pyridin-5-yl)pyridin-3-yl)isobutyramide [423];

N-(5-(3-(7-(3-((2-(dimethylamino)ethyl)amino)-5-fluorophenyl)-3H-imidazo[4,5-b]pyridin-2-yl)-1H-pyrazolo[3,4-b]pyridin-5-yl)pyridin-3-yl)-3,3-dimethylbutanamide [430];

N-(5-(3-(7-(3-((2-(dimethylamino)ethyl)amino)-5-fluorophenyl)-3H-imidazo[4,5-b]pyridin-2-yl)-1H-pyrazolo[3,4-b]pyridin-5-yl)pyridin-3-yl)butyramide [431];

N-(5-(3-(7-(3-((2-(dimethylamino)ethyl)amino)-5-fluorophenyl)-3H-imidazo[4,5-b]pyridin-2-yl)-1H-pyrazolo[3,4-b]pyridin-5-yl)pyridin-3-yl)pentanamide [432];

N-(5-(3-(7-(3-((2-(dimethylamino)ethyl)amino)-5-fluorophenyl)-3H-imidazo[4,5-b]pyridin-2-yl)-1H-pyrazolo[3,4-b]pyridin-5-yl)pyridin-3-yl)cyclopropanecarboxamide [433];

N-(5-(3-(7-(3-((2-(dimethylamino)ethyl)amino)-5-fluorophenyl)-3H-imidazo[4,5-b]pyridin-2-yl)-1H-pyrazolo[3,4-b]pyridin-5-yl)pyridin-3-yl)cyclobutanecarboxamide [434];

N-(5-(3-(7-(3-((2-(dimethylamino)ethyl)amino)-5-fluorophenyl)-3H-imidazo[4,5-b]pyridin-2-yl)-1H-pyrazolo[3,4-b]pyridin-5-yl)pyridin-3-yl)cyclopentanecarboxamide [435];

N-(5-(3-(7-(3-((2-(dimethylamino)ethyl)amino)-5-fluorophenyl)-3H-imidazo[4,5-b]pyridin-2-yl)-1H-pyrazolo[3,4-b]pyridin-5-yl)pyridin-3-yl)cyclohexanecarboxamide [436];

$N^1$-(3-fluoro-5-(2-(5-(pyrimidin-5-yl)-1H-pyrazolo[3,4-b]pyridin-3-yl)-3H-imidazo[4,5-b]pyridin-7-yl)phenyl)-$N^2$,$N^2$-dimethylethane-1,2-diamine [440]

3-(7-(3-fluorophenyl)-3H-imidazo[4,5-b]pyridin-2-yl)-5-(1-methyl-1H-pyrazol-4-yl)-1H-pyrazolo[3,4-b]pyridine [912];

5-(1,2-dimethyl-1H-imidazol-5-yl)-3-(7-(3-fluorophenyl)-3H-imidazo[4,5-b]pyridin-2-yl)-1H-pyrazolo[3,4-b]pyridine [913];

3-(7-(4-fluorophenyl)-3H-imidazo[4,5-b]pyridin-2-yl)-5-(1-methyl-1H-pyrazol-4-yl)-1H-pyrazolo[3,4-b]pyridine [930];

5-(1,2-dimethyl-1H-imidazol-5-yl)-3-(7-(4-fluorophenyl)-3H-imidazo[4,5-b]pyridin-2-yl)-1H-pyrazolo[3,4-b]pyridine [931];

3-(7-(2-fluorophenyl)-3H-imidazo[4,5-b]pyridin-2-yl)-5-(1-methyl-1H-pyrazol-4-yl)-1H-pyrazolo[3,4-b]pyridine [948];

5-(1,2-dimethyl-1H-imidazol-5-yl)-3-(7-(2-fluorophenyl)-3H-imidazo[4,5-b]pyridin-2-yl)-1H-pyrazolo[3,4-b]pyridine [949];

5-(1-methyl-1H-pyrazol-4-yl)-3-(7-(pyridin-3-yl)-3H-imidazo[4,5-b]pyridin-2-yl)-1H-pyrazolo[3,4-b]pyridine [966];

5-(1,2-dimethyl-1H-imidazol-5-yl)-3-(7-(pyridin-3-yl)-3H-imidazo[4,5-b]pyridin-2-yl)-1H-pyrazolo[3,4-b]pyridine [967];

5-(1-methyl-1H-pyrazol-4-yl)-3-(7-(pyridin-4-yl)-3H-imidazo[4,5-b]pyridin-2-yl)-1H-pyrazol[3,4-b]pyridine [984];

5-(1,2-dimethyl-1H-imidazol-5-yl)-3-(7-(pyridin-4-yl)-3H-imidazo[4,5-b]pyridin-2-yl)-1H-pyrazolo[3,4-b]pyridine [985];

5-(1-methyl-1H-pyrazol-4-yl)-3-(7-(pyridin-2-yl)-3H-imidazo[4,5-b]pyridin-2-yl)-1H-pyrazol[3,4-b]pyridine [1002];

5-(1,2-dimethyl-1H-imidazol-5-yl)-3-(7-(pyridin-2-yl)-3H-imidazo[4,5-b]pyridin-2-yl)-1H-pyrazolo[3,4-b]pyridine [1003];

3-(7-(4-methyl-1H-imidazol-1-yl)-3H-imidazo[4,5-b]pyridin-2-yl)-5-(1-methyl-1H-pyrazol-4-yl)-1H-pyrazolo[3,4-b]pyridine [1038];

5-(1,2-dimethyl-1H-imidazol-5-yl)-3-(7-(4-methyl-1H-imidazol-1-yl)-3H-imidazo[4,5-b]pyridin-2-yl)-1H-pyrazolo[3,4-b]pyridine [1039];

3-(3H-imidazo[4,5-b]pyridin-2-yl)-5-(1-methyl-1H-pyrazol-4-yl)-1H-pyrazolo[3,4-b]pyridine [1074];

5-(1,2-dimethyl-1H-imidazol-5-yl)-3-(3H-imidazo[4,5-b]pyridin-2-yl)-1H-pyrazolo[3,4-b]pyridine [1075];

N-(3-fluoro-5-(2-(5-(1-methyl-1H-pyrazol-4-yl)-1H-pyrazolo[3,4-b]pyridin-3-yl)-3H-imidazo[4,5-b]pyridin-7-yl)benzyl)methanesulfonamide [1200];

N-(3-(2-(5-(1,2-dimethyl-1H-imidazol-5-yl)-1H-pyrazolo[3,4-b]pyridin-3-yl)-3H-imidazo[4,5-b]pyridin-7-yl)-5-fluorobenzyl)methanesulfonamide [1201];

$N^1$-(3-fluoro-5-(2-(5-(1-methyl-1H-pyrazol-4-yl)-1H-pyrazolo[3,4-b]pyridin-3-yl)-3H-imidazo[4,5-b]pyridin-7-yl)phenyl)-$N^2$,$N^2$-dimethylethane-1,2-diamine [1218];

$N^1$-(3-(2-(5-(1,2-dimethyl-1H-imidazol-5-yl)-1H-pyrazolo[3,4-b]pyridin-3-yl)-3H-imidazo[4,5-b]pyridin-7-yl)-5-fluorophenyl)-$N^2$,$N^2$-dimethylethane-1,2-diamine [1219];

N-(5-(3-(7-(3-(2-(dimethylamino)ethoxy)-5-fluorophenyl)-3H-imidazo[4,5-b]pyridin-2-yl)-1H-pyrazolo[3,4-b]pyridin-5-yl)pyridin-3-yl)propionamide [1233];

N-(5-(3-(7-(3-(2-(dimethylamino)ethoxy)-5-fluorophenyl)-3H-imidazo[4,5-b]pyridin-2-yl)-1H-pyrazolo[3,4-b]pyridin-5-yl)pyridin-3-yl)-3-methylbutanamide [1234];

2-(3-fluoro-5-(2-(5-(4-methylpyridin-3-yl)-1H-pyrazolo[3,4-b]pyridin-3-yl)-3H-imidazo[4,5-b]pyridin-7-yl)phenoxy)-N,N-dimethylethan-1-amine [1237];

2-(3-(2-(5-(5-((ethylamino)methyl)pyridin-3-yl)-1H-pyrazolo[3,4-b]pyridin-3-yl)-3H-imidazo[4,5-b]pyridin-7-yl)-5-fluorophenoxy)-N,N-dimethylethan-1-amine [1238];

N-(5-(3-(7-(3-(2-(dimethylamino)ethoxy)-5-fluorophenyl)-3H-imidazo[4,5-b]pyridin-2-yl)-1H-pyrazolo[3,4-b]pyridin-5-yl)pyridin-3-yl)pivalamide [1240];

N-(5-(3-(7-(3-(2-(dimethylamino)ethoxy)-5-fluorophenyl)-3H-imidazo[4,5-b]pyridin-2-yl)-1H-pyrazolo[3,4-b]pyridin-5-yl)pyridin-3-yl)isobutyramide [1241];

N-(5-(3-(7-(3-(2-(dimethylamino)ethoxy)-5-fluorophenyl)-3H-imidazo[4,5-b]pyridin-2-yl)-1H-pyrazolo[3,4-b]pyridin-5-yl)pyridin-3-yl)-3,3-dimethylbutanamide [1248];

N-(5-(3-(7-(3-(2-(dimethylamino)ethoxy)-5-fluorophenyl)-3H-imidazo[4,5-b]pyridin-2-yl)-1H-pyrazolo[3,4-b]pyridin-5-yl)pyridin-3-yl)butyramide [1249];

N-(5-(3-(7-(3-(2-(dimethylamino)ethoxy)-5-fluorophenyl)-3H-imidazo[4,5-b]pyridin-2-yl)-1H-pyrazolo[3,4-b]pyridin-5-yl)pyridin-3-yl)pentanamide [1250];

N-(5-(3-(7-(3-(2-(dimethylamino)ethoxy)-5-fluorophenyl)-3H-imidazo[4,5-b]pyridin-2-yl)-1H-pyrazolo[3,4-b]pyridin-5-yl)pyridin-3-yl)cyclopropanecarboxamide [1251];

N-(5-(3-(7-(3-(2-(dimethylamino)ethoxy)-5-fluorophenyl)-3H-imidazo[4,5-b]pyridin-2-yl)-1H-pyrazolo[3,4-b]pyridin-5-yl)pyridin-3-yl)cyclobutanecarboxamide [1252];

N-(5-(3-(7-(3-(2-(dimethylamino)ethoxy)-5-fluorophenyl)-3H-imidazo[4,5-b]pyridin-2-yl)-1H-pyrazolo[3,4-b]pyridin-5-yl)pyridin-3-yl)cyclopentanecarboxamide [1253];

N-(5-(3-(7-(3-(2-(dimethylamino)ethoxy)-5-fluorophenyl)-3H-imidazo[4,5-b]pyridin-2-yl)-1H-pyrazolo[3,4-b]pyridin-5-yl)pyridin-3-yl)cyclohexanecarboxamide [1254];

2-(3-fluoro-5-(2-(5-(1-methyl-1H-pyrazol-4-yl)-1H-pyrazolo[3,4-b]pyridin-3-yl)-3H-imidazo[4,5-b]pyridin-7-yl)phenoxy)-N,N-dimethylethan-1-amine [1263];

2-(3-(2-(5-(1,2-dimethyl-1H-imidazol-5-yl)-1H-pyrazolo[3,4-b]pyridin-3-yl)-3H-imidazo[4,5-b]pyridin-7-yl)-5-fluorophenoxy)-N,N-dimethylethan-1-amine [1264];

N-(5-(3-(7-(3-fluoro-5-(2-(pyrrolidin-1-yl)ethoxy)phenyl)-3H-imidazo[4,5-b]pyridin-2-yl)-1H-pyrazolo[3,4-b]pyridin-5-yl)pyridin-3-yl)propionamide [1277];

N-(5-(3-(7-(3-fluoro-5-(2-(pyrrolidin-1-yl)ethoxy)phenyl)-3H-imidazo[4,5-b]pyridin-2-yl)-1H-pyrazolo[3,4-b]pyridin-5-yl)pyridin-3-yl)-3-methylbutanamide [1278];

3-(7-(3-fluoro-5-(2-(pyrrolidin-1-yl)ethoxy)phenyl)-3H-imidazo[4,5-b]pyridin-2-yl)-5-(4-methylpyridin-3-yl)-1H-pyrazolo[3,4-b]pyridine [1281];

N-((5-(3-(7-(3-fluoro-5-(2-(pyrrolidin-1-yl)ethoxy)phenyl)-3H-imidazo[4,5-b]pyridin-2-yl)-1H-pyrazolo[3,4-b]pyridin-5-yl)pyridin-3-yl)methyl)ethanamine [1282];

N-(5-(3-(7-(3-fluoro-5-(2-(pyrrolidin-1-yl)ethoxy)phenyl)-3H-imidazo[4,5-b]pyridin-2-yl)-1H-pyrazolo[3,4-b]pyridin-5-yl)pyridin-3-yl)pivalamide [1284];

N-(5-(3-(7-(3-fluoro-5-(2-(pyrrolidin-1-yl)ethoxy)phenyl)-3H-imidazo[4,5-b]pyridin-2-yl)-1H-pyrazolo[3,4-b]pyridin-5-yl)pyridin-3-yl)isobutyramide [1285];

N-(5-(3-(7-(3-fluoro-5-(2-(pyrrolidin-1-yl)ethoxy)phenyl)-3H-imidazo[4,5-b]pyridin-2-yl)-1H-pyrazolo[3,4-b]pyridin-5-yl)pyridin-3-yl)-3,3-dimethylbutanamide [1292];

N-(5-(3-(7-(3-fluoro-5-(2-(pyrrolidin-1-yl)ethoxy)phenyl)-3H-imidazo[4,5-b]pyridin-2-yl)-1H-pyrazolo[3,4-b]pyridin-5-yl)pyridin-3-yl)butyramide [1293];

N-(5-(3-(7-(3-fluoro-5-(2-(pyrrolidin-1-yl)ethoxy)phenyl)-3H-imidazo[4,5-b]pyridin-2-yl)-1H-pyrazolo[3,4-b]pyridin-5-yl)pyridin-3-yl)pentanamide [1294];

N-(5-(3-(7-(3-fluoro-5-(2-(pyrrolidin-1-yl)ethoxy)phenyl)-3H-imidazo[4,5-b]pyridin-2-yl)-1H-pyrazolo[3,4-b]pyridin-5-yl)pyridin-3-yl)cyclopropanecarboxamide [1295];

N-(5-(3-(7-(3-fluoro-5-(2-(pyrrolidin-1-yl)ethoxy)phenyl)-3H-imidazo[4,5-b]pyridin-2-yl)-1H-pyrazolo[3,4-b]pyridin-5-yl)pyridin-3-yl)cyclobutanecarboxamide [1296];

N-(5-(3-(7-(3-fluoro-5-(2-(pyrrolidin-1-yl)ethoxy)phenyl)-3H-imidazo[4,5-b]pyridin-2-yl)-1H-pyrazolo[3,4-b]pyridin-5-yl)pyridin-3-yl)cyclopentanecarboxamide [1297];

N-(5-(3-(7-(3-fluoro-5-(2-(pyrrolidin-1-yl)ethoxy)phenyl)-3H-imidazo[4,5-b]pyridin-2-yl)-1H-pyrazolo[3,4-b]pyridin-5-yl)pyridin-3-yl)cyclohexanecarboxamide [1298];

3-(7-(3-fluoro-5-(2-(pyrrolidin-1-yl)ethoxy)phenyl)-3H-imidazo[4,5-b]pyridin-2-yl)-5-(1-methyl-1H-pyrazol-4-yl)-1H-pyrazolo[3,4-b]pyridine [1307];

5-(1,2-dimethyl-1H-imidazol-5-yl)-3-(7-(3-fluoro-5-(2-(pyrrolidin-1-yl)ethoxy)phenyl)-3H-imidazo[4,5-b]pyridin-2-yl)-1H-pyrazolo[3,4-b]pyridine [1308];

N-(5-(3-(7-(3-fluoro-5-hydroxyphenyl)-3H-imidazo[4,5-b]pyridin-2-yl)-1H-pyrazolo[3,4-b]pyridin-5-yl)pyridin-3-yl)propionamide [1321];

N-(5-(3-(7-(3-fluoro-5-hydroxyphenyl)-3H-imidazo[4,5-b]pyridin-2-yl)-1H-pyrazolo[3,4-b]pyridin-5-yl)pyridin-3-yl)-3-methylbutanamide [1322];

3-fluoro-5-(2-(5-(4-methylpyridin-3-yl)-1H-pyrazolo[3,4-b]pyridin-3-yl)-3H-imidazo[4,5-b]pyridin-7-yl)phenol [1325];

3-(2-(5-(5-((ethylamino)methyl)pyridin-3-yl)-1H-pyrazolo[3,4-b]pyridin-3-yl)-3H-imidazo[4,5-b]pyridin-7-yl)-5-fluorophenol [1326];

N-(5-(3-(7-(3-fluoro-5-hydroxyphenyl)-3H-imidazo[4,5-b]pyridin-2-yl)-1H-pyrazolo[3,4-b]pyridin-5-yl)pyridin-3-yl)pivalamide [1328];

N-(5-(3-(7-(3-fluoro-5-hydroxyphenyl)-3H-imidazo[4,5-b]pyridin-2-yl)-1H-pyrazolo[3,4-b]pyridin-5-yl)pyridin-3-yl)isobutyramide [1329];

N-(5-(3-(7-(3-fluoro-5-hydroxyphenyl)-3H-imidazo[4,5-b]pyridin-2-yl)-1H-pyrazolo[3,4-b]pyridin-5-yl)pyridin-3-yl)-3,3-dimethylbutanamide [1336];

N-(5-(3-(7-(3-fluoro-5-hydroxyphenyl)-3H-imidazo[4,5-b]pyridin-2-yl)-1H-pyrazolo[3,4-b]pyridin-5-yl)pyridin-3-yl)butyramide [1337];

N-(5-(3-(7-(3-fluoro-5-hydroxyphenyl)-3H-imidazo[4,5-b]pyridin-2-yl)-1H-pyrazolo[3,4-b]pyridin-5-yl)pyridin-3-yl)pentanamide [1338];

N-(5-(3-(7-(3-fluoro-5-hydroxyphenyl)-3H-imidazo[4,5-b]pyridin-2-yl)-1H-pyrazolo[3,4-b]pyridin-5-yl)pyridin-3-yl)cyclopropanecarboxamide [1339];

N-(5-(3-(7-(3-fluoro-5-hydroxyphenyl)-3H-imidazo[4,5-b]pyridin-2-yl)-1H-pyrazolo[3,4-b]pyridin-5-yl)pyridin-3-yl)cyclobutanecarboxamide [1340];

N-(5-(3-(7-(3-fluoro-5-hydroxyphenyl)-3H-imidazo[4,5-b]pyridin-2-yl)-1H-pyrazolo[3,4-b]pyridin-5-yl)pyridin-3-yl)cyclopentanecarboxamide [1341];

N-(5-(3-(7-(3-fluoro-5-hydroxyphenyl)-3H-imidazo[4,5-b]pyridin-2-yl)-1H-pyrazolo[3,4-b]pyridin-5-yl)pyridin-3-yl)cyclohexanecarboxamide [1342];

3-fluoro-5-(2-(5-(1-methyl-1H-pyrazol-4-yl)-1H-pyrazolo[3,4-b]pyridin-3-yl)-3H-imidazo[4,5-b]pyridin-7-yl)phenol [1351];

3-(2-(5-(1,2-dimethyl-1H-imidazol-5-yl)-1H-pyrazolo[3,4-b]pyridin-3-yl)-3H-imidazo[4,5-b]pyridin-7-yl)-5-fluorophenol [1352];

N-(5-(3-(7-(3-fluoro-5-methoxyphenyl)-3H-imidazo[4,5-b]pyridin-2-yl)-1H-pyrazolo[3,4-b]pyridin-5-yl)pyridin-3-yl)propionamide [1365];

N-(5-(3-(7-(3-fluoro-5-methoxyphenyl)-3H-imidazo[4,5-b]pyridin-2-yl)-1H-pyrazolo[3,4-b]pyridin-5-yl)pyridin-3-yl)-3-methylbutanamide [1366];

3-(7-(3-fluoro-5-methoxyphenyl)-3H-imidazo[4,5-b]pyridin-2-yl)-5-(4-methylpyridin-3-yl)-1H-pyrazolo[3,4-b]pyridine [1369];

N-((5-(3-(7-(3-fluoro-5-methoxyphenyl)-3H-imidazo[4,5-b]pyridin-2-yl)-1H-pyrazolo[3,4-b]pyridin-5-yl)pyridin-3-yl)methyl)ethanamine [1370];

N-(5-(3-(7-(3-fluoro-5-methoxyphenyl)-3H-imidazo[4,5-b]pyridin-2-yl)-1H-pyrazolo[3,4-b]pyridin-5-yl)pyridin-3-yl)pivalamide [1372];

N-(5-(3-(7-(3-fluoro-5-methoxyphenyl)-3H-imidazo[4,5-b]pyridin-2-yl)-1H-pyrazolo[3,4-b]pyridin-5-yl)pyridin-3-yl)isobutyramide [1373];

N-(5-(3-(7-(3-fluoro-5-methoxyphenyl)-3H-imidazo[4,5-b]pyridin-2-yl)-1H-pyrazolo[3,4-b]pyridin-5-yl)pyridin-3-yl)-3,3-dimethylbutanamide [1380];

N-(5-(3-(7-(3-fluoro-5-methoxyphenyl)-3H-imidazo[4,5-b]pyridin-2-yl)-1H-pyrazolo[3,4-b]pyridin-5-yl)pyridin-3-yl)butyramide [1381];

N-(5-(3-(7-(3-fluoro-5-methoxyphenyl)-3H-imidazo[4,5-b]pyridin-2-yl)-1H-pyrazolo[3,4-b]pyridin-5-yl)pyridin-3-yl)pentanamide [1382];

N-(5-(3-(7-(3-fluoro-5-methoxyphenyl)-3H-imidazo[4,5-b]pyridin-2-yl)-1H-pyrazolo[3,4-b]pyridin-5-yl)pyridin-3-yl)cyclopropanecarboxamide [1383];

N-(5-(3-(7-(3-fluoro-5-methoxyphenyl)-3H-imidazo[4,5-b]pyridin-2-yl)-1H-pyrazolo[3,4-b]pyridin-5-yl)pyridin-3-yl)cyclobutanecarboxamide [1384];

N-(5-(3-(7-(3-fluoro-5-methoxyphenyl)-3H-imidazo[4,5-b]pyridin-2-yl)-1H-pyrazolo[3,4-b]pyridin-5-yl)pyridin-3-yl)cyclopentanecarboxamide [1385];

N-(5-(3-(7-(3-fluoro-5-methoxyphenyl)-3H-imidazo[4,5-b]pyridin-2-yl)-1H-pyrazolo[3,4-b]pyridin-5-yl)pyridin-3-yl)cyclohexanecarboxamide [1386];

3-(7-(3-fluoro-5-methoxyphenyl)-3H-imidazo[4,5-b]pyridin-2-yl)-5-(1-methyl-1H-pyrazol-4-yl)-1H-pyrazolo[3,4-b]pyridine [1395]; and 5-(1,2-dimethyl-1H-imidazol-5-yl)-3-(7-(3-fluoro-5-methoxyphenyl)-3H-imidazo[4,5-b]pyridin-2-yl)-1H-pyrazolo[3,4-b]pyridine [1396]; or a pharmaceutically acceptable salt thereof.

27. The method of claim 1, wherein the fibrotic disorder is a skin fibrosis.

28. The method of claim 1, wherein the fibrotic disorder is scleroderma.

29. The method of claim 1, wherein the fibrotic disorder is pulmonary fibrosis.

30. The method of claim 1, wherein the fibrotic disorder is renal fibrosis.

31. The method of claim 1, wherein the fibrotic disorder is idiopathic pulmonary fibrosis (IPF).

32. The method of claim 1, wherein the fibrotic disorder is cirrhosis of the liver.

33. The method of claim 1, wherein the fibrotic disorder is liver fibrosis.

34. The method of claim 1, wherein the subject is a human.

\* \* \* \* \*

UNITED STATES PATENT AND TRADEMARK OFFICE
CERTIFICATE OF CORRECTION

PATENT NO. : 10,526,347 B2  
APPLICATION NO. : 16/162155  
DATED : January 7, 2020  
INVENTOR(S) : KC et al.

Page 1 of 2

It is certified that error appears in the above-identified patent and that said Letters Patent is hereby corrected as shown below:

In the Claims

Column 498, Line 16-17, in Claim 1, delete "$(R^4)q$," and insert -- $(R^4)_q$, --, therefor.

Column 498, Line 17, in Claim 1, delete "$(R^4)q$," and insert -- $(R^4)_q$, --, therefor.

Column 498, Line 17, in Claim 1, delete "$(R^4)q$," and insert -- $(R^4)_q$, --, therefor.

Column 498, Line 17, in Claim 1, delete "$(R^4)q$" and insert -- $(R^4)_q$ --, therefor.

Column 498, Line 54, in Claim 1, delete "$(R's)_q$," and insert -- $(R^{18})_q$. --, therefor.

Column 499, Line 30, in Claim 2, delete "$(R^4)q$," and insert -- $(R^4)_q$, --, therefor.

Column 499, Line 31, in Claim 2, delete "$(R^4)q$," and insert -- $(R^4)_q$, --, therefor.

Column 499, Line 31, in Claim 2, delete "$(R^4)q$." and insert -- $(R^4)_q$. --, therefor.

Column 501, Line 3, in Claim 11, delete "$(R^{20})$;" and insert -- $(R^{20})_j$; --, therefor.

Column 510, Line 62, in Claim 20, delete "N" and insert -- $N^1$ --, therefor.

Column 510, Line 65, in Claim 20, delete "N" and insert -- $N^1$ --, therefor.

Column 511, Line 1, in Claim 20, delete "N" and insert -- $N^1$ --, therefor.

Column 511, Line 12, in Claim 20, delete "N" and insert -- $N^1$ --, therefor.

Column 511, Line 16, in Claim 20, delete "N" and insert -- $N^1$ --, therefor.

Signed and Sealed this  
Ninth Day of June, 2020

Andrei Iancu  
*Director of the United States Patent and Trademark Office*

CERTIFICATE OF CORRECTION (continued)
U.S. Pat. No. 10,526,347 B2

Column 513, Approximately Line 15, in Claim 21, delete "(pyrrolidinn" and insert -- (pyrrolidin --, therefor.

Column 516, Line 48, in Claim 22, delete "pyrazol-yl)-" and insert -- pyrazolo --, therefor.

Column 526, Line 31, in Claim 23, delete "(H" and insert -- (1H --, therefor.

Column 531, Line 11, in Claim 24, delete "pyrazolin" and insert -- pyrazolo --, therefor.

Column 533, Line 49, in Claim 25, delete "12841;" and insert -- [284]; --, therefor.

Column 533, Line 56, in Claim 25, delete "S –(" and insert -- 5-( --, therefor.

Column 534, Line 65, in Claim 25, delete "methyhthiophen" and insert -- methylthiophen --, therefor.

Column 540, Line 33, in Claim 26, delete "pyrazol" and insert -- pyrazolo --, therefor.

Column 540, Line 39, in Claim 26, delete "pyrazol" and insert -- pyrazolo --, therefor.